(12) United States Patent
Bovet

(10) Patent No.: US 12,419,264 B2
(45) Date of Patent: Sep. 23, 2025

(54) MODULATING SUGAR AND AMINO ACID CONTENT IN A PLANT (SULTR3)

(71) Applicant: PHILIP MORRIS PRODUCTS S.A., Neuchatel (CH)

(72) Inventor: Lucien Bovet, La Chaux-de-Fonds (CH)

(73) Assignee: Philip Morris Products S.A., Neuchatel (CH)

( * ) Notice: Subject to any disclaimer, the term of this patent is extended or adjusted under 35 U.S.C. 154(b) by 265 days.

(21) Appl. No.: 17/765,746

(22) PCT Filed: Sep. 28, 2020

(86) PCT No.: PCT/EP2020/077055
§ 371 (c)(1),
(2) Date: Mar. 31, 2022

(87) PCT Pub. No.: WO2021/063863
PCT Pub. Date: Apr. 8, 2021

(65) Prior Publication Data
US 2023/0200344 A1  Jun. 29, 2023

(30) Foreign Application Priority Data
Oct. 1, 2019 (EP) ..................................... 19200856

(51) Int. Cl.
*A01H 6/82* (2018.01)
*A24B 3/10* (2006.01)
*C12N 15/82* (2006.01)

(52) U.S. Cl.
CPC ............... *A01H 6/823* (2018.05); *A24B 3/10* (2013.01); *C12N 15/8245* (2013.01); *C12N 15/8251* (2013.01)

(58) Field of Classification Search
None
See application file for complete search history.

(56) References Cited

U.S. PATENT DOCUMENTS 10,925,293 B2  2/2021  Petrie

FOREIGN PATENT DOCUMENTS

| CN | 104087599 | 10/2014 |
|---|---|---|
| RU | 2636344 | 11/2017 |
| WO | WO 00/04154 | 1/2000 |
| WO | WO 2013/179211 | 12/2013 |

OTHER PUBLICATIONS

Ding et al 2016 BMC Genomics 17:373-pp. 1-19 (Year: 2016).*
Office Action issued in China for Application No. 202080069172.8 dated Aug. 10, 2023 (11 pages). English translation included.
Predicted: Sulfate transporter 3.1 like [Nicotiana sylvestris], Genbank accession No. XP 009778206.1, Oct. 21, 2014.
Chen, Z., "SULTR3s function in chloroplast sulfate uptake and affect ABA biosynthesis and the stress response", Plant Physiol., vol. 180, No. 1, pp. 593-604, May 31, 2019.
Office Action issued in Russia for Application No. 2021122150/10 dated Dec. 12, 2023 (8 pages). English translation included.
Zhong et al., Expression of a Mutant Form of Cellulose Synthase AtCesA7 Causes Dominant Negative Effect on Cellulose Biosynthesis, Plant Physiology, 2003, V.132, pp. 786-795 (Abstract).
PCT Search Report and Written Opinion for Application No. PCT/EP2020/077055 dated Oct. 14, 2020 (11 pages).
Extended European Search Report for Application No. 19200856.3 dated Feb. 14, 2020 (6 pages).
Database Geneseq [Online] May 23, 2000, "Soybean Sulphate Permease-1.", XP002797277, retrieved from EBI Accession No. GSP: AAY44942.
Yiqiong Ding et al., "Identification and Functional Characterization of the Sulfate Transporter Gene GmSULTR1;2b in Soybean", BMC Genomics, vol. 17, May 20, 2016.
Ning Yuan et al., "Heterologous Expression of a Rice miR395 Gene in Niotiana Tabacum Impairs Sulfate Homeostasis", Scientific Reports, vol. 6, No. 1, Jun. 28, 2016.

* cited by examiner

*Primary Examiner* — Brent T Page
(74) *Attorney, Agent, or Firm* — Mueting Raasch Group

(57) ABSTRACT

There is described herein a plant cell (i) a polynucleotide comprising, consisting or consisting essentially of a sequence having at least 60% sequence identity to SEQ ID NO: 1 (NtSULTR3;1A-S), SEQ ID NO: 3 (NtSULTR3;1A-T), SEQ ID NO: 5 (NtSULTR3;1B-S), SEQ ID NO: 7 (NtSULTR3;1B-T), SEQ ID NO: 15 (NtSULTR3;3-T), SEQ ID NO: 17 (NtSULTR3;4A-S), SEQ ID NO: 19 (NtSULTR3;4A-T) or SEQ ID NO: 23 (NtSULTR3;4B-T); (ii) a polypeptide encoded by the polynucleotide set forth in (i); (iii) a polypeptide comprising, consisting or consisting essentially of a sequence having at least 87% sequence identity to SEQ ID NO: 2 (NtSULTR3;1A-S) or at least 87% sequence identity to SEQ ID NO: 4 (NtSULTR3;1A-T) or at least 87% sequence identity to SEQ ID NO: 6 (NtSULTR3;1B-S), or at least 88% sequence identity to SEQ ID NO: 8 (NtSULTR3;1B-T), or at least 70% sequence identity to SEQ ID NO: 16 (NtSULTR3;3-T), or at least 84% sequence identity to SEQ ID NO: 18 (NtSULTR3;4A-S) or at least 79% sequence identity to SEQ ID NO: 20 (NtSULTR3;4A-T); or at least 87% sequence identity to SEQ ID NO: 24 (NtSULTR3;4B-T); or (iv) a construct, vector or expression vector comprising the isolated polynucleotide set forth in (i), wherein said plant cell comprises at least one modification which modulates (a) the expression or activity of the polynucleotide or (b) the expression or activity of the polynucleotide the polypeptide, as compared to a control plant cell in which the expression or activity of the polynucleotide or polypeptide has not been modified.

19 Claims, 6 Drawing Sheets

Specification includes a Sequence Listing.

MODULATING SUGAR AND AMINO ACID CONTENT IN A PLANT (SULTR3)

CROSS-REFERENCE TO RELATED APPLICATIONS

This application is a U.S. National Stage Application of International Application No. PCT/EP2020/077055 filed Sep. 28, 2020, which was published in English on Apr. 8, 2021, as International Publication No. WO 2021/063863 A1. International Application No. PCT/EP2020/077055 claims priority to European Application No. 19200856.3 filed Oct. 1, 2019.

FIELD OF THE INVENTION

The present invention relates to plant cells and the like with modulated expression or activity of chloroplast sulphate transporters (SULTR3).

BACKGROUND

To manufacture tobacco products, different types of tobaccos are mixed at various ratios to create blends with certain flavour characteristics. Flue-cured tobacco (for example, Virginia) is the most widely grown tobacco and is characterised by a high ratio of sugar to nitrogen but it has a limited flavour profile. Other tobacco types—such as air-cured (for example, Burley, Maryland and Galpao) or fire-cured (for example, Dark) tobacco types—offer alternative flavour profiles. These different flavour profiles are important in the production of blended tobacco products.

The flavour characteristics are the result of particular flavour compounds or the precursors for these compounds that are present at certain levels in tobacco plants. By way of example, altered content of sugars in cured tobacco can result in a different flavour and aroma perception of the tobacco. In aerosol and smoke, glucose and to a lesser extent fructose may generate Amadori compounds via the Maillard reaction. This can result in bready, nutty or popcorn-like flavours.

However, since the varieties of tobacco for commercial production are limited, this means that the opportunities to develop tobacco products with different flavour and aroma profiles are also limited. This equally applies to the manufacture of reconstituted tobacco material that is used in heated tobacco sticks in reduced risk products.

There remains a need in the art to improve the opportunities to create tobacco that offers new flavours and sensory experiences for consumers, whilst still retaining commercially acceptable yields and traits. The present invention seeks to address this and other needs.

SUMMARY OF THE INVENTION

Polynucleotide and polypeptide sequences of SULTR3 from *Nicotiana tabacum* are disclosed herein. Whilst many different genes are believed to be probable sulphate transporters in plants based on structural identity, the point at which these genes become active in their function as sulphate transporters in plants is not typically known. In particular, very little is known about sulphate transporter gene expression in tobacco, especially during curing. The present inventors have now identified certain NtSULTR3 polynucleotides involved in sulphate transport in plants that are functionally expressed during curing. Surprisingly, it is observed that modulating the expression of these certain NtSULTR3 genes or the activity of the protein encoded thereby can change the pool of reducing sugars (such as glucose or fructose, or a combination thereof), non-reducing sugars (such as sucrose), free amino acids (such as glutamine, glutamic acid or aspartic acid, or a combination of two or more thereof), and optionally asparagine, generated during leaf curing. It is unexpected that changes to certain sulphate transporter genes can lead to changes in the levels of sugars or free amino acids and optionally asparagine generated during leaf curing. Advantageously, this now provides the opportunity to create tobacco blends with new flavour and aroma characteristics. This can also result in a different flavour or sensory perception of the aerosol or smoke generated upon heating the tobacco blend. Likewise, liquid extracts obtained from the tobacco can have a different flavour or sensory perception. Modifying the sugar-amino acid balance may also impact the release of acrylamide in aerosol and smoke.

Fourteen chloroplast sulfate transporter polynucleotide sequences from *Nicotiana tabacum* are described, including NtSULTR3;1A-S (SEQ ID NO: 1), NtSULTR3;1A-T (SEQ ID NO: 3), NtSULTR3;1B-S (SEQ ID NO: 5), NtSULTR3;1B-T (SEQ ID NO: 7), NtSULTR3;2-S (SEQ ID NO: 9), NtSULTR3;2-T (SEQ ID NO: 11), NtSULTR3;3-S (SEQ ID NO: 13), NtSULTR3;3-T (SEQ ID NO: 15), NtSULTR3;4A-S (SEQ ID NO: 17), NtSULTR3;4A-T (SEQ ID NO: 19), NtSULTR3;4B-S (SEQ ID NO: 21), NtSULTR3;4B-T (SEQ ID NO: 23), NtSULTR3;5-S (SEQ ID NO: 25) and NtSULTR3;5-T (SEQ ID NO: 27) are disclosed. NtSULTR3;1A-S (SEQ ID NO: 1), NtSULTR3;1A-T (SEQ ID NO: 3), NtSULTR3;1B-S (SEQ ID NO: 5), NtSULTR3;1B-T (SEQ ID NO: 7), NtSULTR3;3-T (SEQ ID NO: 15), NtSULTR3;4A-S (SEQ ID NO: 17), NtSULTR3;4A-T (SEQ ID NO: 19) and NtSULTR3;4B-T (SEQ ID NO: 23) are, in particular, shown to be expressed during curing. NtSULTR3;1A-S (SEQ ID NO: 1), NtSULTR3;1A-T (SEQ ID NO: 3) and NtSULTR3;3-T (SEQ ID NO: 15) are, in particular, shown to play a role in sugar and amino acid metabolism during curing.

Modifications to the expression or activity of one or more SULTR3s can be combined together with modifications to the expression or activity of one or more SUSs to further modulate the levels of sugars and free amino acids in cured leaves. In particular, modulating both SULTR3 and SUS in a plant cell may modulate the levels of reducing sugars in cured leaves to a greater extent than modulating either SULTR3 or SUS in a plant cell. NtSUS1-S (SEQ ID NO: 30), NtSUS1-T (SEQ ID NO: 32), NtSUS2-S (SEQ ID NO: 34), NtSUS2-T (SEQ ID NO: 36), NtSUS3-S (SEQ ID NO: 38), NtSUS3-T (SEQ ID NO: 40), NtSUS4-S (SEQ ID NO: 42), NtSUS4-T (SEQ ID NO: 44), NtSUS5-S (SEQ ID NO: 46), NtSUS5-T (SEQ ID NO: 48), NtSUS6-S (SEQ ID NO: 50) and NtSUS6-T (SEQ ID NO: 52) are disclosed. NtSUS2-S, (SEQ ID NO: 34), NtSUS2-T (SEQ ID NO: 36), NtSUS3-S (SEQ ID NO: 38), NtSUS3-T (SEQ ID NO: 40), NtSUS4-S (SEQ ID NO: 42) and NtSUS4-T (SEQ ID NO: 44) may play a role in (reducing) sugar metabolism during curing. NtSUS2-S SEQ ID NO: 34), NtSUS3-S (SEQ ID NO: 38), NtSUS3-T (SEQ ID NO: 40) and NtSUS4-S (SEQ ID NO: 42), in particular, may play a role in sugar metabolism during curing.

In one aspect, there is provided a plant cell comprising: (i) a polynucleotide comprising, consisting or consisting essentially of a sequence having at least 60% sequence identity to SEQ ID NO: 1 (NtSULTR3;1A-S), SEQ ID NO: 3 (NtSULTR3;1A-T), SEQ ID NO: 5 (NtSULTR3;1B-S), SEQ ID NO: 7 (NtSULTR3;1B-T), SEQ ID NO: 15 (NtSULTR3;3-

T), SEQ ID NO: 17 (NtSULTR3;4A-S), SEQ ID NO: 19 (NtSULTR3;4A-T) or SEQ ID NO: 23 (NtSULTR3;4B-T); (ii) a polypeptide encoded by the polynucleotide set forth in (i); (iii) a polypeptide comprising, consisting or consisting essentially of a sequence having at least 87% sequence identity to SEQ ID NO: 2 (NtSULTR3;1A-S) or at least 87% sequence identity to SEQ ID NO: 4 (NtSULTR3;1A-T) or at least 87% sequence identity to SEQ ID NO: 6 (NtSULTR3; 1B-S), or at least 88% sequence identity to SEQ ID NO: 8 (NtSULTR3;1B-T), or at least 70% sequence identity to SEQ ID NO: 16 (NtSULTR3;3-T), or at least 84% sequence identity to SEQ ID NO: 18 (NtSULTR3;4A-S) or at least 63% or at least 79% sequence identity to SEQ ID NO: 20 (NtSULTR3;4A-T); or at least 87% sequence identity to SEQ ID NO: 24 (NtSULTR3;4B-T); or (iv) a construct, vector or expression vector comprising the isolated polynucleotide set forth in (i), wherein said plant cell comprises at least one modification which modulates (a) the expression or activity of the polynucleotide or (b) the expression or activity of the polynucleotide the polypeptide, as compared to a control plant cell in which the expression or activity of the polynucleotide or polypeptide has not been modified.

Suitably, the plant cell comprises: (i) a polynucleotide comprising, consisting or consisting essentially of a sequence having at least 60% sequence identity to SEQ ID NO: 1 (NtSULTR3;1A-S) or SEQ ID NO: 3 (NtSULTR3; 1A-T); (ii) a polypeptide encoded by the polynucleotide set forth in (i); (iii) a polypeptide comprising, consisting or consisting essentially of a sequence having at least 87% sequence identity to SEQ ID NO: 2 (NtSULTR3;1A-S), or at least 87% sequence identity to SEQ ID NO: 4 (NtSULTR3;1A-T); or (iv) a construct, vector or expression vector comprising the isolated polynucleotide set forth in (i).

Suitably, the modulated expression or modulated activity modulates the levels of glucose, fructose and sucrose in cured leaf of a plant comprising the plant cell as compared to the levels of glucose, fructose and sucrose in a control cured leaf.

Suitably, the levels of glucose are reduced by at least about 77%, at least about 69% and at least about 60%, respectively, as compared to a control cured leaf. Suitably, the levels of fructose are reduced by at least about 77%, at least about 69% and at least about 60%, respectively, as compared to a control cured leaf. Suitably, the levels of sucrose are reduced by at least about 77%, at least about 69% and at least about 60%, respectively, as compared to a control cured leaf. Suitably, the levels of glucose, fructose and sucrose are reduced by at least about 77%, at least about 69% and at least about 60%, respectively, as compared to a control cured leaf. For example, the levels of glucose, fructose or sucrose or a combination of one or more thereof are reduced by at least about 80%, at least about 75% at least about 70% or at least about 65%.

Suitably, the modulated expression or modulated activity modulates the levels of free amino acids, glutamine, glutamate and aspartate in cured leaf of a plant comprising the plant cell as compared to the levels of free amino acids, glutamine, glutamate and aspartate in a control cured leaf.

Suitably, the levels of free amino acids are increased by at least about 1.5 times, by at least about 2.3 times, by at least about 2.4 times and by at least about 1.5 times, respectively, as compared to a control cured leaf. Suitably, the levels of glutamine are increased by at least about 1.5 times, by at least about 2.3 times, by at least about 2.4 times and by at least about 1.5 times, respectively, as compared to a control cured leaf. Suitably, the levels of glutamate are increased by at least about 1.5 times, by at least about 2.3 times, by at least about 2.4 times and by at least about 1.5 times, respectively, as compared to a control cured leaf. Suitably, the levels of aspartate are increased by at least about 1.5 times, by at least about 2.3 times, by at least about 2.4 times and by at least about 1.5 times, respectively, as compared to a control cured leaf. Suitably, the levels of free amino acids, glutamine, glutamate and aspartate are increased by at least about 1.5 times, by at least about 2.3 times, by at least about 2.4 times and by at least about 1.5 times, respectively, as compared to a control cured leaf. Suitably, the cured leaf is from a mid-position leaf on a plant.

Suitably, there is a negligible impact on the phenotype of a plant comprising the plant cell. For example, the phenotype of the plant may be unchanged.

Suitably, the at least one modification is at least one modification in the plant cell's genome, or at least one modification in the construct, vector or expression vector, or at least one transgenic modification.

Suitably, the at least one modification is a genetic mutation in the polynucleotide.

Suitably, the plant is *Nicotiana tabacum*.

Suitably, the plant cell further comprises: (i) at least one modification in a NtSUS polynucleotide or polypeptide encoded thereby, suitably, wherein the NtSUS polynucleotide or polypeptide encoded thereby is selected from the group consisting of NtSUS2-T, NtSUS3-S, NtSUS3-T, NtSUS4-S, NtSUS4-T or a combination of two or more thereof, more suitably, wherein the NtSUS polynucleotide or polypeptide encoded thereby is selected from the group consisting of NtSUS2-S, NtSUS3-S, NtSUS3-T and NtSUS4-S or a combination of two or more thereof; or (ii) further comprising at least one modification in a CLC-Nt2 polynucleotide or polypeptide encoded thereby or a NtCLCe polynucleotide or polypeptide encoded thereby, or a combination thereof; or (iii) a combination of (i) and (ii).

In a further aspect, there is provided a plant or part thereof comprising the plant cell described herein.

In a further aspect, there is provided plant material, cured plant material, or homogenized plant material, derived or obtained from the plant or part thereof as described herein; suitably, wherein the plant material is selected from the group consisting of biomass, seed, stem, flowers, or leaves or a combination of two or more thereof; Suitably, the cured plant material is selected from the group consisting of flue-cured plant material, sun-cured plant material or air-cured plant material or a combination of two or more thereof.

In a further aspect, there is provided a tobacco product comprising the plant cell as described herein, the part of the plant as described herein or the plant material as described herein.

In a further aspect, there is provided a method for producing the plant as described herein, comprising the steps of: (a) providing a plant cell comprising at least one modification as described herein; and (b) propagating the plant cell into a plant.

Suitably, in step (a) the at least one modification is introduced by genome editing; suitably, wherein the genome editing is selected from CRISPR-mediated genome editing, zinc finger nuclease-mediated mutagenesis, chemical or radiation mutagenesis, homologous recombination, oligonucleotide-directed mutagenesis and meganuclease-mediated mutagenesis; or wherein in step (a) the at least one modification is introduced using an interference polynucleotide or by introducing at least one mutation or a combination thereof.

In a further aspect, there is provided a method for producing cured plant material with altered levels of glucose, fructose and sucrose and altered levels of free amino acids, glutamine, glutamate and aspartate as compared to control plant material, comprising the steps of: (a) providing a plant or part thereof or the plant material as described herein; (b) harvesting the plant material therefrom; and (c) curing the plant material.

In a further aspect, there is provided a method of producing a liquid tobacco extract, the method comprising the steps of: (a) preparing tobacco starting material from a plant or part thereof containing a plant cell comprising at least one modification which modulates the expression or activity of NtSULTR3 as described herein; (b) heating the tobacco starting material at a suitable extraction temperature; (c) collecting the volatile compounds released from the tobacco starting material during heating; and (d) combining the collected volatile compounds released from the tobacco starting material and forming a liquid tobacco extract.

In a further aspect, there is provided a method of producing a liquid tobacco extract, the method comprising the steps of: (a) preparing a first tobacco starting material from a plant or part thereof containing a plant cell comprising at least one modification which modulates the expression or activity of NtSULTR3 as described herein; (b) preparing a second tobacco starting material from a plant or part thereof containing a plant cell comprising: (i) at least one modification in a NtSUS polynucleotide or polypeptide encoded thereby, suitably, wherein the NtSUS polynucleotide or polypeptide encoded thereby is selected from the group consisting of NtSUS2-T, NtSUS3-S, NtSUS3-T, NtSUS4-S, NtSUS4-T or a combination of two or more thereof, more suitably, wherein the NtSUS polynucleotide or polypeptide encoded thereby is selected from the group consisting of NtSUS2-S, NtSUS3-S, NtSUS3-T and NtSUS4-S or a combination of two or more thereof; or (ii) comprising at least one modification in a CLC-Nt2 polynucleotide or polypeptide encoded thereby or a NtCLCe polynucleotide or polypeptide encoded thereby, or a combination thereof; or (iii) a combination of (i) and (ii); (c) heating the first tobacco starting material at a first extraction temperature; (d) heating the second tobacco starting material at a second extraction temperature; (e) collecting the volatile compounds released from the first tobacco starting materials and second tobacco starting materials during heating; and (f) combining the collected volatile compounds released from the first and second tobacco starting materials and forming a liquid tobacco extract from the combined volatile compounds.

In a further aspect, there is provided a liquid tobacco extract produced, obtained or obtainable by the method described above.

Some Advantages

Advantageously, modifying the sugar-amino acid balance in tobacco may impact the release of acrylamide (a carcinogenic compound resulting from the interaction of glucose (fructose) with asparagine) upon heating in aerosol and smoke.

Advantageously, reconstituted tobacco material of heated tobacco sticks requires reducing sugars for proper cast leaf preparation. The present disclosure may impact the content and the balance of the sugars thereby affecting cast leaf preparation.

Advantageously, non-genetically modified plants can be created which may be more acceptable to consumers.

Advantageously, the present disclosure is not restricted to the use of EMS mutant plants.

The disclosure may be applied to various plant varieties or crops. Usually, senescing leaves (source leaves) produce sucrose as a source of carbon and asparagine as assimilated nitrogen resources for sink leaves and seeds. Therefore sucrose and asparagine has to be transported first from parenchymal (photosynthetic) senescing leaf cells to the phloem and then to upper sink tissues. Manipulating one or more NtSULTR3 polynucleotides or the polypeptides encoded thereby may impact the level of reducing sugars, non-reducing sugars and free amino acids.

Advantageously, the present disclosure can be combined together with modulating the expression of other genes—such as NtSUS or the polypeptide encoded thereby, as described herein

DETAILED DESCRIPTION

Figure 1:
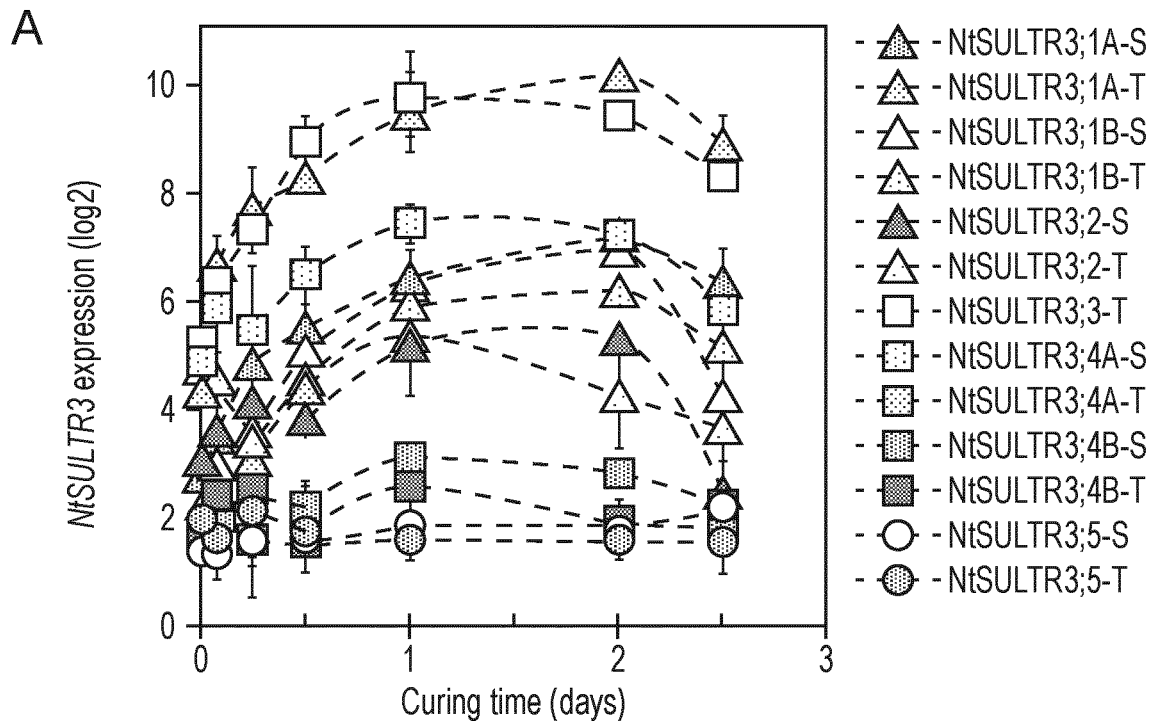
FIG. 1 is a graph and a table showing the expression of NtSULTR3 during a Virginia flue-curing time course. Gene expression is analyzed using Tobarray-Affymetrix chips during 2.5 days of curing (A) and using RNAseq in green, ripe and after 48 h curing (B).

Section headings as used in this disclosure are for organisation purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. The materials, methods, and examples disclosed herein are illustrative only and not intended to be limiting.

The terms "comprise(s)," "include(s)," "having," "has," "can," "contain(s)," and variants thereof are intended to be open-ended transitional phrases, terms, or words that do not preclude the possibility of additional acts or structures.

The singular forms "a," "and" and "the" include plural references unless the context clearly dictates otherwise.

The present disclosure contemplates other embodiments "comprising," "consisting of" and "consisting essentially of" the embodiments or elements presented herein, whether explicitly set forth or not.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used throughout the specification and the claims, the following terms have the following meanings:

"Coding sequence" or "polynucleotide encoding" means the nucleotides (RNA or DNA molecule) that comprise a polynucleotide which encodes a polypeptide. The coding sequence can further include initiation and termination signals operably linked to regulatory elements including a promoter and polyadenylation signal capable of directing expression in the cells of an individual or mammal to which the polynucleotide is administered. The coding sequence may be codon optimized.

"Complement" or "complementary" can mean Watson-Crick (for example, A-T/U and C-G) or Hoogsteen base pairing between nucleotides or nucleotide analogues. "Complementarity" refers to a property shared between two polynucleotides, such that when they are aligned antiparallel to each other, the nucleotide bases at each position will be complementary.

"Construct" refers to a double-stranded, recombinant polynucleotide fragment comprising one or more polynucleotides. The construct comprises a "template strand" base-paired with a complementary "sense or coding strand." A given construct can be inserted into a vector in two possible orientations, either in the same (or sense) orientation or in the reverse (or antisense) orientation with respect to the orientation of a promoter positioned within a vector—such as an expression vector.

The term "control" in the context of a control plant or control plant cells means a plant or plant cells in which the expression, function or activity of one or more genes or polypeptides has not been modified (for example, increased or decreased) and so it can provide a comparison with a plant in which the expression, function or activity of the same one or more genes or polypeptides has been modified. A "control plant" is a plant that is substantially equivalent to a test plant or modified plant in all parameters with the exception of the test parameters. For example, when referring to a plant into which a polynucleotide has been introduced, a control plant is an equivalent plant into which no such polynucleotide has been introduced. A control plant can be an equivalent plant into which a control polynucleotide has been introduced. In such instances, the control polynucleotide is one that is expected to result in little or no phenotypic effect on the plant. The control plant may comprise an empty vector. The control plant may correspond to a wild-type plant. The control plant may be a null segregant wherein the T1 segregant no longer possesses the transgene.

The term "decrease" or "decreased", refers to a reduction of from about 10% to about 99%, or a reduction of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or, or at least 150%, or at least 200% more of a quantity or a function—such as polypeptide function, transcriptional function, or polypeptide expression. The term "decreased," or the phrase "a decreased amount" can refer to a quantity or a function that is less than what would be found in a plant or a product from the same variety of plant processed in the same manner, which has not been modified. Thus, in some contexts, a wild-type plant of the same variety that has been processed in the same manner is used as a control by which to measure whether a reduction in quantity is obtained.

"Donor DNA" or "donor template" refers to a double-stranded DNA fragment or molecule that includes at least a portion of the gene of interest. The donor DNA may encode a functional polypeptide.

"Endogenous gene or polypeptide" refers to a gene or polypeptide that originates from the genome of an organism and has not undergone a change, such as a loss, gain, or exchange of genetic material. An endogenous gene undergoes normal gene transmission and gene expression. An endogenous polypeptide undergoes normal expression.

"Enhancer sequences" refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms including increasing transcriptional efficiency, stabilization of mature mRNA and translational enhancement.

"Expression" refers to the production of a functional product. For example, expression of a polynucleotide fragment may refer to transcription of the polynucleotide fragment (for example, transcription resulting in mRNA or functional RNA) and may include translation of mRNA into a precursor or mature polypeptide. "Overexpression" refers to the production of a gene product in transgenic organisms that exceeds levels of production in a null segregating (or non-transgenic) organism from the same experiment.

"Functional" describes a polypeptide that has biological function or activity. A "functional gene" refers to a gene transcribed to mRNA, which is translated to a functional or active polypeptide.

"Genetic construct" refers to DNA or RNA molecules that comprise a polynucleotide that encodes a polypeptide. The coding sequence can include initiation and termination signals operably linked to regulatory elements including a promoter and polyadenylation signal capable of directing expression.

"Genome editing" generally refers to the process by which genomic nucleic acid in a cell is altered. This can be by removing, inserting or replacing one or more nucleotides in the genomic nucleic acid, for example. Endonucleases can be used to create specific breaks or nicks at defined locations in the genome and are further described herein.

The terms "homology" or "similarity" refer to the degree of sequence similarity between two polypeptides or between two polynucleotide molecules compared by sequence alignment. The degree of homology between two discrete polynucleotides being compared is a function of the number of identical, or matching, nucleotides at comparable positions. Homology or similarity can be determined across the full length of a subject sequence.

"Identical" or "identity" in the context of two or more polynucleotides or polypeptides means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be determined manually or by using a computer sequence algorithm such as ClustalW, ClustalX, BLAST, FASTA or Smith-Waterman. Suitable parameters for ClustalW maybe as follows: For polynucleotide alignments: Gap Open Penalty=15.0, Gap Extension Penalty=6.66, and Matrix=Identity. For polypeptide alignments: Gap Open Penalty=10. o, Gap Extension Penalty=0.2, and Matrix=Gonnet. For DNA and Protein alignments: ENDGAP=−1, and GAPDIST=4.

The term "increase" or "increased" refers to an increase of from about 10% to about 99%, or an increase of at least 10%, at least 20%, at least 25%, at least 30%, at least 40%, at least 50%, at least 60%, at least 70%, at least 75%, at least 80%, at least 90%, at least 95%, at least 98%, at least 99%, at least 100%, at least 150%, or at least 200% or more or more of a quantity or a function or an activity, such as but not limited to one or more of polypeptide function or activity, transcriptional function or activity, and polypeptide expression. The term "increased," or the phrase "an increased amount" can refer to a quantity or a function or an activity in a plant or a product generated from the plant that is more than what would be found in a plant or a product from the same variety of plant processed in the same manner, which has not been modified. Thus, in some contexts, a wild-type plant of the same variety that has been processed in the same manner is used as a control by which to measure whether an increase in quantity is obtained.

The term "inhibit" or "inhibited" refers to a reduction of from about 98% to about 100%, or a reduction of at least 98%, at least 99%, but particularly of 100%, of a quantity or a function or an activity, such as but not limited to one or more of polypeptide function or activity, transcriptional function or activity, and polypeptide expression.

The term "introduced" means providing a polynucleotide (for example, a construct) or polypeptide into a cell. Introduced includes reference to the incorporation of a polynucleotide into a eukaryotic cell where the polynucleotide may be incorporated into the genome of the cell, and includes reference to the transient provision of a polynucleotide or polypeptide to the cell. Introduced includes reference to stable or transient transformation methods, as well as sexually crossing. Thus, "introduced" in the context of inserting a polynucleotide (for example, a recombinant construct/expression construct) into a cell, means "transfection" or "transformation" or "transduction" and includes reference to the incorporation of a polynucleotide into a eukaryotic cell where the polynucleotide may be incorporated into the genome of the cell (for example, chromosome, plasmid, plastid or mitochondrial DNA), converted into an autonomous replicon, or transiently expressed (for example, transfected mRNA).

The terms "isolated" or "purified" refer to material that is substantially or essentially free from components that normally accompany it as found in its native state. Purity and homogeneity are typically determined using analytical chemistry techniques such as polyacrylamide gel electrophoresis or high performance liquid chromatography. A polypeptide that is the predominant species present in a preparation is substantially purified. In particular, an isolated polynucleotide is separated from open reading frames that flank the desired gene and encode polypeptides other than the desired polypeptide. The term "purified" denotes that a polynucleotide or polypeptide gives rise to essentially one band in an electrophoretic gel. Particularly, it means that the polynucleotide or polypeptide is at least 85% pure, more preferably at least 95% pure, and most preferably at least 99% pure. Isolated polynucleotides may be purified from a host cell in which they naturally occur. Conventional polynucleotide purification methods known to skilled artisans may be used to obtain isolated polynucleotides. The term also embraces recombinant polynucleotides and chemically synthesized polynucleotides.

"Liquid tobacco extract" describes the direct product of an extraction process carried out on a tobacco starting material. The extraction process for producing the liquid tobacco extract can comprise heating the tobacco starting material under specific heating conditions and collecting the volatile compounds generated. The liquid tobacco extract can contain a mixture of compounds that have derived from the tobacco starting material and have been removed during the extraction process, typically in combination with a liquid carrier or solvent.

"Modulate" or "modulating" refers to causing or facilitating a qualitative or quantitative change, alteration, or modification in a process, pathway, function or activity of interest.

Without limitation, such a change, alteration, or modification may be an increase or decrease in the relative process, pathway, function or activity of interest. For example, gene expression or polypeptide expression or polypeptide function or activity can be modulated. Typically, the relative change, alteration, or modification will be determined by comparison to a control.

The term 'non-naturally occurring' describes an entity—such as a polynucleotide, a genetic mutation, a polypeptide, a plant, a plant cell and plant material—that is not formed by nature or that does not exist in nature. Such non-naturally occurring entities or artificial entities may be made, synthesized, initiated, modified, intervened, or manipulated by methods described herein or that are known in the art. Such non-naturally occurring entities or artificial entities may be made, synthesized, initiated, modified, intervened, or manipulated by man. Thus, by way of example, a non-naturally occurring plant, a non-naturally occurring plant cell or non-naturally occurring plant material may be made using traditional plant breeding techniques—such as backcrossing—or by genetic manipulation technologies—such as antisense RNA, interfering RNA, meganuclease and the like. By way of further example, a non-naturally occurring plant, a non-naturally occurring plant cell or non-naturally occurring plant material may be made by introgression of or by transferring one or more genetic mutations (for example one or more polymorphisms) from a first plant or plant cell into a second plant or plant cell (which may itself be naturally occurring), such that the resulting plant, plant cell or plant material or the progeny thereof comprises a genetic constitution (for example, a genome, a chromosome or a segment thereof) that is not formed by nature or that does not exist in nature. The resulting plant, plant cell or plant material is thus artificial or non-naturally occurring. Accordingly, an artificial or non-naturally occurring plant or plant cell may be made by modifying a genetic sequence in a first naturally occurring plant or plant cell, even if the resulting genetic sequence occurs naturally in a second plant or plant cell that comprises a different genetic background from the first plant or plant cell. In certain embodiments, a mutation is not a naturally occurring mutation that exists naturally in a polynucleotide or a polypeptide—such as a gene or a polypeptide. Differences in genetic background can be detected by phenotypic differences or by molecular biology techniques known in the art—such as polynucleotide sequencing, presence or absence of genetic markers (for example, microsatellite RNA markers).

"Oligonucleotide" or "polynucleotide" means at least two nucleotides covalently linked together. The depiction of a single strand also defines the sequence of the complementary strand. Thus, a polynucleotide also encompasses the complementary strand of a depicted single strand. Many variants of a polynucleotide may be used for the same purpose as a given polynucleotide. Thus, a polynucleotide also encompasses substantially identical polynucleotides and complements thereof. A single strand provides a probe that may hybridize to a given sequence under stringent hybridization conditions. Thus, a polynucleotide also encompasses a probe that hybridizes under stringent hybridization conditions. Polynucleotides may be single stranded or double stranded, or may contain portions of both double stranded and single stranded sequence. The polynucleotide may be DNA, both genomic and cDNA, RNA, or a hybrid, where the polynucleotide may contain combinations of deoxyribo- and ribo-nucleotides, and combinations of bases including uracil, adenine, thymine, cytosine, guanine, inosine, xanthine hypoxanthine, isocytosine and isoguanine. Polynucleotides may be obtained by chemical synthesis methods or by recombinant methods.

The specificity of single-stranded DNA to hybridize complementary fragments is determined by the "stringency" of the reaction conditions (Sambrook et al., Molecular Cloning and Laboratory Manual, Second Ed., Cold Spring Harbor (1989)). To hybridize under "stringent conditions" describes hybridization protocols in which polynucleotides at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH, and polynucleotide concentration) at which 50% of the probes complementary to the given sequence hybridize to the given sequence at equilibrium. Since the given sequences are generally present at excess, at Tm, 50% of the probes are occupied at equilibrium.

Stringent conditions typically comprise: (1) low ionic strength and high temperature washes, for example 15 mM sodium chloride, 1.5 mM sodium citrate, 0.1% sodium dodecyl sulfate, at 50° C.; (2) a denaturing agent during hybridization, for example, 50% (v/v) formamide, 0.1% bovine serum albumin, 0.1% Ficoll, 0.1% polyvinylpyrrolidone, 50 mM sodium phosphate buffer (750 mM sodium chloride, 75 mM sodium citrate; pH 6.5), at 42° C.; or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 µg/mL), 0.1% SDS, and 10% dextran sulfate at 42° C., with a wash at 42° C. in 0.2×SSC (sodium chloride/sodium citrate) and 50% formamide at 55° C., followed by a high-stringency wash consisting of 0.1×SSC containing EDTA at 55° C. Suitably, the conditions are such that sequences at least about 65%, 70%, 75%, 85%, 90%, 95%, 98%, or 99% homologous to each other typically remain hybridized to each other.

"Moderately stringent conditions" use washing solutions and hybridization conditions that are less stringent, such that a polynucleotide will hybridize to the entire, fragments, derivatives, or analogs of the polynucleotide. One example comprises hybridization in 6×SSC, 5×Denhardt's solution, 0.5% SDS and 100 µg/mL denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions have been described (see Ausubel et al., Current Protocols in Molecular Biology, Volumes 1-3, John Wiley & Sons, Inc., Hoboken, N.J. (1993); Kriegler, Gene Transfer and Expression: A Laboratory Manual, Stockton Press, New York, N.Y. (1990); Perbal, A Practical Guide to Molecular Cloning, 2nd edition, John Wiley & Sons, New York, N.Y. (1988)).

"Low stringent conditions" use washing solutions and hybridization conditions that are less stringent than those for moderate stringency, such that a polynucleotide will hybridize to the entire, fragments, derivatives, or analogs of the polynucleotide. A non-limiting example of low stringency hybridization conditions includes hybridization in 35% formamide, 5×SSC, 50 mM Tris HCl (pH 7.5), 5 mM EDTA, 0.02% PVP, 0.02% Ficoll, 0.2% BSA, 100 µg/mL denatured salmon sperm DNA, 10% (wt/vol) dextran sulfate at 40° C., followed by one or more washes in 2×SSC, 25 mM Tris HCl (pH 7.4), 5 mM EDTA, and 0.1% SDS at 50° C. Other conditions of low stringency, such as those for cross-species hybridizations, are well-described (see Ausubel et al., 1993; Kriegler, 1990).

"Operably linked" means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function. "Operably linked" refers to the association of polynucleotide fragments in a single fragment so that the function of one is regulated by the other. For example, a promoter is operably linked with a polynucleotide fragment when it is capable of regulating the transcription of that polynucleotide fragment.

The term "plant" refers to any plant at any stage of its life cycle or development, and its progenies. In one embodiment, the plant is a tobacco plant, which refers to a plant belonging to the genus *Nicotiana*. The term includes reference to whole plants, plant organs, plant tissues, plant propagules, plant seeds, plant cells and progeny of same. Plant cells include, without limitation, cells from seeds, suspension cultures, embryos, meristematic regions, callus tissue, leaves, roots, shoots, gametophytes, sporophytes, pollen, and microspores. Suitable species, cultivars, hybrids and varieties of tobacco plant are described herein.

"Plant material" includes leaf, root, sepal, root tip, petal, flower, shoot, stem, seed and stalk. Plant material can be viable or non-viable plant material.

"Polynucleotide", "polynucleotide sequence" or "polynucleotide fragment" are used interchangeably herein and refer to a polymer of RNA or DNA that is single- or double-stranded, optionally containing synthetic, non-natural or altered nucleotide bases. The polynucleotides of the present disclosure are set forth in the accompanying sequence listing.

"Polypeptide" or "polypeptide sequence" refer to a polymer of amino acids in which one or more amino acid residues is an artificial chemical analogue of a corresponding naturally occurring amino acid, as well as to naturally occurring polymers of amino acids. The terms are also inclusive of modifications including, but not limited to, glycosylation, lipid attachment, sulfation, gamma-carboxylation of glutamic acid residues, hydroxylation and ADP-ribosylation. The polypeptides of the present disclosure are set forth in the accompanying sequence listing.

"Promoter" means a synthetic or naturally-derived molecule which is capable of conferring, activating or enhancing expression of a polynucleotide in a cell. The term refers to a polynucleotide element/sequence, typically positioned upstream and operably-linked to a double-stranded polynucleotide fragment. Promoters can be derived entirely from regions proximate to a native gene of interest, or can be composed of different elements derived from different native promoters or synthetic polynucleotide segments. A promoter may comprise one or more specific transcriptional regulatory sequences to further enhance expression, to alter spatial expression or to alter temporal expression. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents.

"Tissue-specific promoter" and "tissue-preferred promoter" as used interchangeably herein refer to a promoter that is expressed predominantly but not necessarily exclusively in one tissue or organ, but that may also be expressed in one specific cell. A "developmentally regulated promoter" refers to a promoter whose function is determined by developmental events. A "constitutive promoter" refers to a promoter that causes a gene to be expressed in most cell types at most times. An "inducible promoter" selectively express an operably linked DNA sequence in response to the presence of an endogenous or exogenous stimulus, for example by chemical compounds (chemical inducers) or in response to environmental, hormonal, chemical, or developmental signals. Examples of inducible or regulated promoters include promoters regulated by light, heat, stress, flooding or drought, pathogens, phytohormones, wounding, or chemicals such as ethanol, jasmonate, salicylic acid, or safeners.

"Recombinant" refers to an artificial combination of two otherwise separated segments of sequence—such as by chemical synthesis or by the manipulation of isolated segments of polynucleotides by genetic engineering techniques. The term also includes reference to a cell or vector, that has been modified by the introduction of a heterologous polynucleotide or a cell derived from a cell so modified, but does not encompass the alteration of the cell or vector by naturally occurring events (for example, spontaneous mutation, natural transformation or transduction or transposition) such as those occurring without deliberate human intervention).

"Recombinant construct" refers to a combination of polynucleotides that are not normally found together in nature. Accordingly, a recombinant construct may comprise regulatory sequences and coding sequences that are derived from different sources, or regulatory sequences and coding sequences derived from the same source, but arranged in a manner different than that normally found in nature. The recombinant construct can be a recombinant DNA construct.

"Regulatory sequences" and "regulatory elements" as used interchangeably herein refer to polynucleotide sequences located upstream (5 non-coding sequences), within, or downstream (3' non-coding sequences) of a coding sequence, and which influence the transcription, RNA processing or stability, or translation of the associated coding sequence. Regulatory sequences include promoters, translation leader sequences, introns, and polyadenylation recognition sequences. The terms "regulatory sequence" and "regulatory element" are used interchangeably herein.

The term "tobacco" is used in a collective sense to refer to tobacco crops (for example, a plurality of tobacco plants grown in the field and not hydroponically grown tobacco), tobacco plants and parts thereof, including but not limited to, roots, stems, leaves, flowers, and seeds prepared or obtained, as described herein. It is understood that "tobacco" includes *Nicotiana tabacum* plants and products thereof.

The term "tobacco products" refers to consumer tobacco products, including but not limited to, smoking materials (for example, cigarettes, cigars, and pipe tobacco), snuff, chewing tobacco, gum, and lozenges, as well as components, materials and ingredients for manufacture of consumer tobacco products. Suitably, these tobacco products are manufactured from tobacco leaves and stems harvested from tobacco and cut, dried, cured or fermented according to conventional techniques in tobacco preparation.

"Transcription terminator", "termination sequences", or "terminator" refers to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Transgenic" refers to any cell, cell line, callus, tissue, plant part or plant, the genome of which has been altered by the presence of a heterologous polynucleotide, such as a recombinant construct, including those initial transgenic events as well as those created by sexual crosses or asexual propagation from the initial transgenic event. The term does not encompass the alteration of the genome (chromosomal or extra-chromosomal) by conventional plant breeding methods or by naturally occurring events—such as random cross-fertilization, non-recombinant viral infection, non-recombinant bacterial transformation, non-recombinant transposition, or spontaneous mutation.

"Transgenic plant" refers to a plant which comprises within its genome one or more heterologous polynucleotides, that is, a plant that contains recombinant genetic material not normally found therein and which has been introduced into the plant in question (or into progenitors of the plant) by human manipulation. For example, the heterologous polynucleotide can be stably integrated within the genome such that the polynucleotide is passed on to successive generations. The heterologous polynucleotide can be integrated into the genome alone or as part of a recombinant construct. The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant or tree and parts of the plant or tree, for instance grains, seeds, flowers, leaves, roots, fruit, pollen, stems and the like. Each heterologous polynucleotide may confer a different trait to the transgenic plant.

"Transgene" refers to a gene or genetic material containing a gene sequence that has been isolated from one organism and is introduced into a different organism. This non-native segment of DNA may retain the ability to produce RNA or polypeptide in the transgenic organism, or it may alter the normal function of the transgenic organism's genetic code.

"Variant" with respect to a polynucleotide means: (i) a portion or fragment of a polynucleotide; (ii) the complement of a polynucleotide or portion thereof; (iii) a polynucleotide that is substantially identical to a polynucleotide of interest or the complement thereof; or (iv) a polynucleotide that hybridizes under stringent conditions to the polynucleotide of interest, complement thereof, or a polynucleotide substantially identical thereto.

"Variant" with respect to a peptide or polypeptide means a peptide or polypeptide that differs in sequence by the insertion, deletion, or conservative substitution of amino acids, but retain at least one biological function or activity. Variant may also mean a polypeptide that retains at least one biological function or activity. A conservative substitution of an amino acid, that is, replacing an amino acid with a different amino acid of similar properties (for example, hydrophilicity, degree and distribution of charged regions) is recognized in the art as typically involving a minor change.

The term "variety" refers to a population of plants that share constant characteristics which separate them from other plants of the same species. While possessing one or more distinctive traits, a variety is further characterized by a very small overall variation between individuals within that variety. A variety is often sold commercially.

"Vector" refers to a polynucleotide vehicle that comprises a combination of polynucleotide components for enabling the transport of polynucleotides, polynucleotide constructs and polynucleotide conjugates and the like. A vector may be a viral vector, bacteriophage, bacterial artificial chromosome or yeast artificial chromosome. A vector may be a DNA or RNA vector. Suitable vectors include episomes capable of extra-chromosomal replication such as circular, double-stranded nucleotide plasmids; linearized double-stranded nucleotide plasmids; and other vectors of any origin. An "expression vector" is a polynucleotide vehicle that comprises a combination of polynucleotide components for enabling the expression of polynucleotide(s), polynucleotide constructs and polynucleotide conjugates and the like. Suitable expression vectors include episomes capable of extra-chromosomal replication such as circular, double-stranded nucleotide plasmids; linearized double-stranded nucleotide plasmids; and other functionally equivalent expression vectors of any origin. An expression vector comprises at least a promoter positioned upstream and operably-linked to a polynucleotide, polynucleotide constructs or polynucleotide conjugate, as defined below.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and polypeptide and polynucleotide chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. Polynucleotides

An isolated polynucleotide is disclosed comprising, consisting or consisting essentially of a sequence having at least 60% sequence identity to any of the sequences described herein, including any of polynucleotides shown in the sequence listing. Suitably, the isolated polynucleotide comprises, consists or consists essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99% or 100% sequence identity thereto.

Suitably, the polynucleotide(s) described herein encode an active polypeptide that has at least about 50%, 60%, 70%, 80%, 90%, 95%, 96%, 97%, 98%, 99%, 100% or more of the function or activity of the polypeptide(s) shown in the sequence listing.

In one embodiment, there is provided an isolated NtSULTR3 polynucleotide comprising, consisting or consisting essentially of a polynucleotide having at least 60% sequence identity to: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25 or SEQ ID NO: 27; suitably, SEQ ID NO: 1, SEQ ID NO: 3, SEQ ID NO: 5, SEQ ID NO: 7, SEQ ID NO: 15, SEQ ID NO: 17, SEQ ID NO: 19 or SEQ ID NO: 23; more suitably, SEQ ID NO: 1 or SEQ ID NO: 3.

In another embodiment, there is provided an isolated NtSUS polynucleotide comprising, consisting or consisting essentially of a polynucleotide having at least 60% sequence identity to: SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44; SEQ ID NO: 46, SEQ ID NO: 48, SEQ ID NO: 50 or SEQ ID NO: 52; suitably, SEQ ID NO: 34, SEQ ID NO: 36, SEQ ID NO: 38, SEQ ID NO: 40, SEQ ID NO: 42 or SEQ ID NO: 44; more suitably, SEQ ID NO: 34, SEQ ID NO: 38, SEQ ID NO: 40 or SEQ ID NO: 42.

Suitably, the isolated NtSULTR3 polynucleotide comprises, consists or consist essentially of a sequence having at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to: SEQ ID NO: 1, SEQ ID NO:

3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25 or SEQ ID NO: 27; suitably, SEQ ID NO: 1, SEQ ID NO: 3, SEQ ID NO: 5, SEQ ID NO: 7, SEQ ID NO: 15, SEQ ID NO: 17, SEQ ID NO: 19 or SEQ ID NO: 23; more suitably, SEQ ID NO: 1 or SEQ ID NO: 3.

Suitably, the isolated NtSUS polynucleotide comprises, consists or consist essentially of a sequence having at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to: SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44; SEQ ID NO: 46, SEQ ID NO: 48, SEQ ID NO: 50 or SEQ ID NO: 52; suitably, SEQ ID NO: 34, SEQ ID NO: 36, SEQ ID NO: 38, SEQ ID NO: 40, SEQ ID NO: 42 or SEQ ID NO: 44; more suitably, SEQ ID NO: 34, SEQ ID NO: 38, SEQ ID NO: 40 or SEQ ID NO: 42.

Suitably, the isolated NtSULTR3 polynucleotide comprises, consists or consist essentially of a sequence having at least about 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25 or SEQ ID NO: 27; suitably, SEQ ID NO: 1, SEQ ID NO: 3, SEQ ID NO: 5, SEQ ID NO: 7, SEQ ID NO: 15, SEQ ID NO: 17, SEQ ID NO: 19 or SEQ ID NO: 23; more suitably, SEQ ID NO: 1 or SEQ ID NO: 3.

Suitably, the isolated NtSUS polynucleotide comprises, consists or consist essentially of a sequence having at least about 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to: SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44; SEQ ID NO: 46, SEQ ID NO: 48, SEQ ID NO: 50 or SEQ ID NO: 52; suitably, SEQ ID NO: 34, SEQ ID NO: 36, SEQ ID NO: 38, SEQ ID NO: 40, SEQ ID NO: 42 or SEQ ID NO: 44; more suitably, SEQ ID NO: 34, SEQ ID NO: 38, SEQ ID NO: 40 or SEQ ID NO: 42.

Suitably, the isolated NtSULTR3 polynucleotide comprises, consists or consist essentially of a sequence having at least about 95%, 96%, 97%, 98%, 99%, 99.1%, 99.2%, 99.3%, 99.4%, 99.5%, 99.6%, 99.7%, 99.8%, 99.9% or 100% sequence identity to: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25 or SEQ ID NO: 27; suitably, SEQ ID NO: 1, SEQ ID NO: 3, SEQ ID NO: 5, SEQ ID NO: 7, SEQ ID NO: 15, SEQ ID NO: 17, SEQ ID NO: 19 or SEQ ID NO: 23; more suitably, SEQ ID NO: 1 or SEQ ID NO: 3.

Suitably, the isolated NtSUS polynucleotide comprises, consists or consist essentially of a sequence having at least about 95%, 96%, 97%, 98%, 99%, 99.1%, 99.2%, 99.3%, 99.4%, 99.5%, 99.6%, 99.7%, 99.8%, 99.9% or 100% sequence identity to: SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44; SEQ ID NO: 46, SEQ ID NO: 48, SEQ ID NO: 50 or SEQ ID NO: 52; suitably, SEQ ID NO: 34, SEQ ID NO: 36, SEQ ID NO: 38, SEQ ID NO: 40, SEQ ID NO: 42 or SEQ ID NO: 44; more suitably, SEQ ID NO: 34, SEQ ID NO: 38, SEQ ID NO: 40 or SEQ ID NO: 42.

In another embodiment, there is provided NtSULTR3 polynucleotides comprising, consisting or consisting essentially of polynucleotides with substantial homology (that is, sequence similarity) or substantial identity to: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25 or SEQ ID NO: 27;

suitably, SEQ ID NO: 1, SEQ ID NO: 3, SEQ ID NO: 5, SEQ ID NO: 7, SEQ ID NO: 15, SEQ ID NO: 17, SEQ ID NO: 19 or SEQ ID NO: 23; more suitably, SEQ ID NO: 1 or SEQ ID NO: 3.

In another embodiment, there is provided NtSUS polynucleotides comprising, consisting or consisting essentially of polynucleotides with substantial homology (that is, sequence similarity) or substantial identity to: SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44; SEQ ID NO: 46, SEQ ID NO: 48, SEQ ID NO: 50 or SEQ ID NO: 52; suitably, SEQ ID NO: 34, SEQ ID NO: 36, SEQ ID NO: 38, SEQ ID NO: 40, SEQ ID NO: 42 or SEQ ID NO: 44; more suitably, SEQ ID NO: 34, SEQ ID NO: 38, SEQ ID NO: 40 or SEQ ID NO: 42.

In another embodiment, there is provided fragments of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25 or SEQ ID NO: 27 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25 or SEQ ID NO: 27.

In another embodiment, there is provided fragments of SEQ ID NO: 1, SEQ ID NO: 3, SEQ ID NO: 5, SEQ ID NO: 7, SEQ ID NO: 15, SEQ ID NO: 17, SEQ ID NO: 19 or SEQ ID NO: 23 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO: 1, SEQ ID NO: 3, SEQ ID NO: 5, SEQ ID NO: 7, SEQ ID NO: 15, SEQ ID NO: 17, SEQ ID NO: 19 or SEQ ID NO: 23.

In another embodiment, there is provided fragments of SEQ ID NO: 1 or SEQ ID NO: 3 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO: 1 or SEQ ID NO: 3.

In another embodiment, there is provided fragments of SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44; SEQ ID NO: 46, SEQ ID NO: 48, SEQ ID NO: 50 or SEQ ID NO: 52 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44; SEQ ID NO: 46, SEQ ID NO: 48, SEQ ID NO: 50 or SEQ ID NO: 52.

In another embodiment, there is provided fragments of SEQ ID NO: 34, SEQ ID NO: 36, SEQ ID NO: 38, SEQ ID NO: 40, SEQ ID NO: 42 or SEQ ID NO: 44 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO: 34, SEQ ID NO: 36, SEQ ID NO: 38, SEQ ID NO: 40, SEQ ID NO: 42 or SEQ ID NO: 44.

In another embodiment, there is provided fragments of SEQ ID NO: 34, SEQ ID NO: 38, SEQ ID NO: 40 or SEQ ID NO: 42 with substantial homology (that is, sequence similarity) or substantial identity thereto that have at least about 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO: 34, SEQ ID NO: 38, SEQ ID NO: 40 or SEQ ID NO: 42.

In another embodiment, there is provided NtSULTR3 polynucleotides comprising a sufficient or substantial degree of identity or similarity to: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25 or SEQ ID NO: 27 that encode a polypeptide that functions as chloroplast sulphate transporter; suitably, a sufficient or substantial degree of identity or similarity to SEQ ID NO: 1, SEQ ID NO: 3, SEQ ID NO: 5, SEQ ID NO: 7, SEQ ID NO: 15, SEQ ID NO: 17, SEQ ID NO: 19 or SEQ ID NO: 23 that encode a polypeptide that functions as chloroplast sulphate transporter; more suitably, a sufficient or substantial degree of identity or similarity to SEQ ID NO: 1 or SEQ ID NO: 3 that encode a polypeptide that functions as chloroplast sulphate transporter.

In another embodiment, there is provided NtSUS polynucleotides comprising a sufficient or substantial degree of identity or similarity to: SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44; SEQ ID NO: 46, SEQ ID NO: 48, SEQ ID NO: 50 or SEQ ID NO: 52 that encode a polypeptide that functions as an SUS; suitably, a sufficient or substantial degree of identity or similarity to SEQ ID NO: 34, SEQ ID NO: 36, SEQ ID NO: 38, SEQ ID NO: 40, SEQ ID NO: 42 or SEQ ID NO: 44 that encode a polypeptide that functions as an SUS; more suitably, a sufficient or substantial degree of identity or similarity to SEQ ID NO: 34, SEQ ID NO: 38, SEQ ID NO: 40 or SEQ ID NO: 42 that encode a polypeptide that functions as an SUS.

In another embodiment, there is provided a polymer of NtSULTR3 polynucleotides which comprises, consists or consists essentially of a polynucleotide designated herein as: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25 or SEQ ID NO: 27; suitably, SEQ ID NO: 1, SEQ ID NO: 3, SEQ ID NO: 5, SEQ ID NO: 7, SEQ ID NO: 15, SEQ ID NO: 17, SEQ ID NO: 19 or SEQ ID NO: 23; more suitably, SEQ ID NO: 1 or SEQ ID NO: 3.

In another embodiment, there is provided a polymer of NtSUS polynucleotides which comprises, consists or consists essentially of a polynucleotide designated herein as: SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44; SEQ ID NO: 46, SEQ ID NO: 48, SEQ ID NO: 50 or SEQ ID NO: 52; suitably, SEQ ID NO: 34, SEQ ID NO: 36, SEQ ID NO: 38, SEQ ID NO: 40, SEQ ID NO: 42 or SEQ ID NO: 44; more suitably, SEQ ID NO: 34, SEQ ID NO: 38, SEQ ID NO: 40 or SEQ ID NO: 42.

Suitably, the polynucleotides described herein encode members of the SULTR3 family that have chloroplast sulphate transporter activity or the SUS family that have SUS activity.

A polynucleotide can include a polymer of nucleotides, which may be unmodified or modified deoxyribonucleic acid (DNA) or ribonucleic acid (RNA). Accordingly, a polynucleotide can be, without limitation, a genomic DNA, complementary DNA (cDNA), mRNA, or antisense RNA or a fragment(s) thereof. Moreover, a polynucleotide can be single-stranded or double-stranded DNA, DNA that is a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid. Generally, polynucleotides can be assembled from isolated or cloned fragments of cDNA, genomic DNA, oligonucleotides, or individual nucleotides, or a combination of the foregoing. Although the polynucleotides described herein are shown as DNA sequences, they include their corresponding RNA sequences, and their complementary (for example, completely complementary) DNA or RNA sequences, including the reverse complements thereof.

Fragments of a polynucleotide may range from at least about 25 nucleotides, about 50 nucleotides, about 75 nucleotides, about 100 nucleotides about 150 nucleotides, about 200 nucleotides, about 250 nucleotides, about 300 nucleotides, about 400 nucleotides, about 500 nucleotides, about 600 nucleotides, about 700 nucleotides, about 800 nucleotides, about 900 nucleotides, about 1000 nucleotides, about 1100 nucleotides, about 1200 nucleotides, about 1300 nucleotides or about 1400 nucleotides and up to the full-length polynucleotide encoding the polypeptides described herein.

A polynucleotide will generally contain phosphodiester bonds, although in some cases, polynucleotide analogues are included that may have alternate backbones, comprising, for example, phosphoramidate, phosphorothioate, phosphorodithioate, or O-methylphophoroamidite linkages; and peptide polynucleotide backbones and linkages. Other analogue polynucleotides include those with positive backbones; non-ionic backbones, and non-ribose backbones. Modifications of the ribose-phosphate backbone may be done for a variety of reasons, for example, to increase the stability and half-life of such molecules in physiological environments or as probes on a biochip. Mixtures of naturally occurring polynucleotides and analogues can be made; alternatively, mixtures of different polynucleotide analogues, and mixtures of naturally occurring polynucleotides and analogues may be made.

A variety of polynucleotide analogues are known, including, for example, phosphoramidate, phosphorothioate, phosphorodithioate, O-methylphophoroamidite linkages and peptide polynucleotide backbones and linkages. Other analogue polynucleotides include those with positive backbones, non-ionic backbones and non-ribose backbones. Polynucleotides containing one or more carbocyclic sugars are also included.

Other analogues include peptide polynucleotides which are peptide polynucleotide analogues.

Among the uses of the disclosed polynucleotides, and fragments thereof, is the use of fragments as probes in hybridisation assays or primers for use in amplification assays. Such fragments generally comprise at least about 10, 11, 12, 13, 14, 15, 16, 17, 18, 19 or 20 or more contiguous nucleotides of a DNA sequence. In other embodiments, a DNA fragment comprises at least about 10, 15, 20, 30, 40, 50 or 60 or more contiguous nucleotides of a DNA sequence. Thus, in one aspect, there is also provided a method for detecting a polynucleotide comprising the use of the probes or primers or both.

The basic parameters affecting the choice of hybridization conditions and guidance for devising suitable conditions are described by Sambrook, J., E. F. Fritsch, and T. Maniatis (1989, Molecular Cloning: A Laboratory Manual, Cold Spring Harbor Laboratory Press, Cold Spring Harbor, N.Y.). Using knowledge of the genetic code in combination with the polypeptide sequences described herein, sets of degenerate oligonucleotides can be prepared. Such oligonucleotides are useful as primers, for example, in polymerase chain reactions (PCR), whereby DNA fragments are isolated and amplified.

One way of achieving moderately and high stringent conditions are described herein. At least one modification (for example, mutation) can be included in one or more of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25 or SEQ ID NO: 27; suitably, at least one modification (for example, mutation) can be included in one or more of SEQ ID NO: 1, SEQ ID NO: 3, SEQ ID NO: 5, SEQ ID NO: 7, SEQ ID NO: 15, SEQ ID NO: 17, SEQ ID NO: 19 or SEQ ID NO: 23; more suitably, at least one modification (for example, mutation) can be included in one or more of SEQ ID NO: 1 or SEQ ID NO: 3.

At least one modification (for example, mutation) can be included in one or more of SEQ ID NO: 1, SEQ ID NO: 3, SEQ ID NO: 5, SEQ ID NO: 7, SEQ ID NO: 15, SEQ ID NO: 17, SEQ ID NO: 19 or SEQ ID NO: 23 and at least one or more further modifications (for example, mutations) can be included in one or more of SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44; SEQ ID NO: 46, SEQ ID NO: 48, SEQ ID NO: 50 or SEQ ID NO: 52.

At least one modification (for example, mutation) can be included in one or more of SEQ ID NO: 1, SEQ ID NO: 3, SEQ ID NO: 5, SEQ ID NO: 7, SEQ ID NO: 15, SEQ ID NO: 17, SEQ ID NO: 19 or SEQ ID NO: 23 and at least one modification (for example, mutation) can be included in one or more of SEQ ID NO: 34, SEQ ID NO: 36, SEQ ID NO: 38, SEQ ID NO: 40, SEQ ID NO: 42 and SEQ ID NO: 44, more suitably, one or more of SEQ ID NO: 34, SEQ ID NO: 38, SEQ ID NO: 40 and SEQ ID NO: 42.

At least one modification (for example, mutation) can be included in one or more of SEQ ID NO: 1, SEQ ID NO: 3, SEQ ID NO: 5, SEQ ID NO: 7, SEQ ID NO: 15, SEQ ID NO: 17, SEQ ID NO: 19 or SEQ ID NO: 23 and at least one modification (for example, mutation) can be included in one or more of SEQ ID NO: 34, SEQ ID NO: 36, SEQ ID NO: 38, SEQ ID NO: 40, SEQ ID NO: 42 and SEQ ID NO: 44 whereas no modification(s) (for example, mutation(s)) are included in one or more of SEQ ID NO: 30, SEQ ID NO: 32, SEQ ID NO: 46, SEQ ID NO: 48, SEQ ID NO: 50, SEQ ID NO: 52, more suitably, and at least one modification (for example, mutation) can be included in one or more of SEQ ID NO: 34, SEQ ID NO: 38, SEQ ID NO: 40 and SEQ ID NO: 42 whereas no modification(s) (for example, mutation(s)) are included in one or more of SEQ ID NO: 30, SEQ ID NO: 32, SEQ ID NO: 36, and SEQ ID NO: 44, SEQ ID NO: 46, SEQ ID NO: 48, SEQ ID NO: 50, SEQ ID NO: 52.

At least one modification (for example, mutation) can be included in one or more of SEQ ID NO: 1 or SEQ ID NO: 3 and at least one or more further modifications (for example, mutations) can be included in one or more of SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 44; SEQ ID NO: 46, SEQ ID NO: 48, SEQ ID NO: 50 or SEQ ID NO: 52.

At least one modification (for example, mutation) can be included in one or more of SEQ ID NO: 1 or SEQ ID NO: 3 and at least one modification (for example, mutation) can be included in one or more of SEQ ID NO: 34, SEQ ID NO: 36, SEQ ID NO: 38, SEQ ID NO: 40, SEQ ID NO: 42 and SEQ ID NO: 44, more suitably, one or more of SEQ ID NO: 34, SEQ ID NO: 38, SEQ ID NO: 40 and SEQ ID NO: 42.

At least one modification (for example, mutation) can be included in one or more of SEQ ID NO: 1 or SEQ ID NO: 3 and at least one modification (for example, mutation) can be included in one or more of SEQ ID NO: 34, SEQ ID NO: 36, SEQ ID NO: 38, SEQ ID NO: 40, SEQ ID NO: 42 and SEQ ID NO: 44 whereas no modification(s) (for example, mutation(s)) are included in one or more of SEQ ID NO: 30, SEQ ID NO: 32, SEQ ID NO: 46, SEQ ID NO: 48, SEQ ID NO: 50, SEQ ID NO: 52, more suitably, and at least one modification (for example, mutation) can be included in one or more of SEQ ID NO: 34, SEQ ID NO: 38, SEQ ID NO: 40 and SEQ ID NO: 42 whereas no modification(s) (for example, mutation(s)) are included in one or more of SEQ ID NO: 30, SEQ ID NO: 32, SEQ ID NO: 36, and SEQ ID NO: 44, SEQ ID NO: 46, SEQ ID NO: 48, SEQ ID NO: 50, SEQ ID NO: 52.

3. Polypeptides

There is also provided an isolated polypeptide comprising, consisting or consisting essentially of a polypeptide having at least 60% sequence identity to any of the polypeptide described herein, including any of the polypeptides shown in the sequence listing. Suitably, the isolated polypeptide comprises, consists or consists essentially of a sequence having at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity thereto. There is also provided a NtSULTR3 polypeptide comprising, consisting or consisting essentially of a sequence having at least 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 2, SEQ ID NO: 4, SEQ ID NO: 6, SEQ ID NO: 8, SEQ ID NO: 10, SEQ ID NO:12, SEQ ID NO: 14, SEQ ID NO: 16, SEQ ID NO:18, SEQ ID NO: 20, SEQ ID NO: 22, SEQ ID NO: 24, SEQ ID NO: 26 and SEQ ID NO: 28.

There is also provided a NtSULTR3 polypeptide comprising, consisting or consisting essentially of a sequence having at least 80%, 81%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 2, SEQ ID NO: 4, SEQ ID NO: 6, SEQ ID NO: 8, SEQ ID NO: 10, SEQ ID NO:12, SEQ ID NO: 14, SEQ ID NO: 16, SEQ ID NO:18, SEQ ID NO: 20, SEQ ID NO: 22, SEQ ID NO: 24, SEQ ID NO: 26 and SEQ ID NO: 28.

There is also provided a NtSULTR3 polypeptide comprising, consisting or consisting essentially of a sequence having at least 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 2, SEQ ID NO: 4, SEQ ID NO: 6, SEQ ID NO: 8, SEQ ID NO: 10, SEQ ID NO:12, SEQ ID NO: 14, SEQ ID NO: 16, SEQ ID NO:18, SEQ ID NO: 20, SEQ ID NO: 22, SEQ ID NO: 24, SEQ ID NO: 26 and SEQ ID NO: 28.

There is also provided a NtSULTR3 polypeptide encoded by SEQ ID NO: 2, SEQ ID NO: 4, SEQ ID NO: 6, SEQ ID NO: 8, SEQ ID NO: 10, SEQ ID NO:12, SEQ ID NO: 14, SEQ ID NO: 16, SEQ ID NO:18, SEQ ID NO: 20, SEQ ID NO: 22, SEQ ID NO: 24, SEQ ID NO: 26 and SEQ ID NO: 28.

The NtSULTR3 polypeptide can include sequences comprising a sufficient or substantial degree of identity or similarity to SEQ ID NO: 2, SEQ ID NO: 4, SEQ ID NO: 6, SEQ ID NO: 8, SEQ ID NO: 10, SEQ ID NO:12, SEQ ID NO: 14, SEQ ID NO: 16, SEQ ID NO:18, SEQ ID NO: 20, SEQ ID NO: 22, SEQ ID NO: 24, SEQ ID NO: 26 and SEQ ID NO: 28 to function as a chloroplast sulphate transporter.

There is also provided a NtSUS polypeptide comprising, consisting or consisting essentially of a sequence having at least 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 31, SEQ ID NO: 33, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51 or SEQ ID NO: 53.

There is also provided a NtSUS polypeptide comprising, consisting or consisting essentially of a sequence having at least 80%, 81%, 81%, 82%, 83%, 84%, 85%, 86%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to: SEQ ID NO: 31, SEQ ID NO: 33, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51 or SEQ ID NO: 53; or more suitably, SEQ ID NO: 35, SEQ ID NO: 37, SEQ ID NO: 39, SEQ ID NO: 41, SEQ ID NO: 43 or SEQ ID NO: 45; or more suitably, SEQ ID NO: 35, SEQ ID NO: 39, SEQ ID NO: 41 or SEQ ID NO: 43.

There is also provided a NtSUS polypeptide comprising, consisting or consisting essentially of a sequence having at least 95% 96%, 97%, 98%, 99%, 99.1%, 99.2%, 99.3%, 99.4%, 99.5%, 99.6%, 99.7%, 99.8%, 99.9% or 100% sequence identity to: SEQ ID NO: 31, SEQ ID NO: 33, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51; or SEQ ID NO: 53; suitably, SEQ ID NO: 35, SEQ ID NO: 37, SEQ ID NO: 39, SEQ ID NO: 41, SEQ ID NO: 43 or SEQ ID NO: 45; more suitably, SEQ ID NO: 35, SEQ ID NO: 39, SEQ ID NO: 41 or SEQ ID NO: 43.

There is also disclosed a polypeptide comprising, consisting or consisting essentially of a sequence having at least 88% sequence identity to SEQ ID NO: 2 or SEQ ID NO: 4; 81% sequence identity to SEQ ID NO: 2 or SEQ ID NO: 4 and SEQ ID NO: 6 or SEQ ID NO: 8; or 69% sequence identity to SEQ ID NO: 2 or SEQ ID NO: 4 and SEQ ID NO: 6 or SEQ ID NO: 8 and SEQ ID NO: 10 or SEQ ID NO: 12.

There is also provided a NtSUS polypeptide encoded by: SEQ ID NO: 31, SEQ ID NO: 33, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51 or SEQ ID NO: 53; suitably, SEQ ID NO: 35, SEQ ID NO: 37, SEQ ID NO: 39, SEQ ID NO: 41, SEQ ID NO: 43 or SEQ ID NO: 45; more suitably, SEQ ID NO: 35, SEQ ID NO: 39, SEQ ID NO: 41 or SEQ ID NO: 43.

The NtSUS polypeptide can include sequences comprising a sufficient or substantial degree of identity or similarity to SEQ ID NO: 31, SEQ ID NO: 33, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51 or SEQ ID NO: 53 to function as a SUS; suitably, SEQ ID NO: 35, SEQ ID NO: 37, SEQ ID NO: 39, SEQ ID NO: 41, SEQ ID NO: 43 or SEQ ID NO: 45 to function as a SUS; more suitably, SEQ ID NO: 35, SEQ ID NO: 39, SEQ ID NO: 41 or SEQ ID NO: 43 to function as a SUS.

The fragments of the polypeptide(s) typically retain some or all of the function or activity of the full length sequence—such as chloroplast sulphate transporter activity or SUS activity. Fragments of a polypeptide may range from at least about 25 amino acids, about 50 amino acids, about 75 amino acids, about 100 amino acids about 150 amino acids, about 200 amino acids, about 250 amino acids, about 300 amino acids, about 400 amino acids, about 500 amino acids, and up to the full-length polypeptide described herein.

The polypeptides also include mutants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally provided that they still have some or all of their function or activity. Suitably, this function or activity is modulated.

A deletion refers to removal of one or more amino acids from a polypeptide. An insertion refers to one or more amino acid residues being introduced into a predetermined site in a polypeptide. Insertions may comprise intra-sequence insertions of single or multiple amino acids. A substitution refers to the replacement of amino acids of the polypeptide with other amino acids having similar properties (such as similar hydrophobicity, hydrophilicity, antigenicity, propensity to form or break a-helical structures or β-sheet structures). Amino acid substitutions are typically of single residues, but may be clustered depending upon functional constraints placed upon the polypeptide and may range from about 1 to about 10 amino acids. The amino acid substitutions are preferably conservative amino acid substitutions as described below. Amino acid substitutions, deletions or insertions can be made using peptide synthetic techniques—such as solid phase peptide synthesis or by recombinant DNA manipulation. Methods for the manipulation of DNA sequences to produce substitution, insertion or deletion variants of a polypeptide are well known in the art. The variant may have alterations which produce a silent change and result in a functionally equivalent polypeptide. Deliberate amino acid substitutions may be made on the basis of similarity in polarity, charge, solubility, hydrophobicity, hydrophilicity and the amphipathic nature of the residues as long as the secondary binding of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. Conservative substitutions may be made, for example according to the Table below. Amino acids in the same block in the second column and preferably in the same line in the third column may be substituted for each other:

| ALIPHATIC | Non-polar | Gly Ala Pro |
| --- | --- | --- |
| | | Ile Leu Val |
| | Polar - uncharged | Cys Ser Thr Met |
| | | Asn Gly |
| | Polar - charged | Asp Glu |
| | | Lys Arg |
| AROMATIC | | His Phe TrpTyr |

The polypeptide may be a mature polypeptide or an immature polypeptide or a polypeptide derived from an immature polypeptide. Polypeptides may be in linear form or cyclized using known methods. Polypeptides typically comprise at least 10, at least 20, at least 30, or at least 40 contiguous amino acids.

At least one modification (for example, mutation) can be included in one or more of SEQ ID NO: 2, SEQ ID NO: 4, SEQ ID NO: 6, SEQ ID NO: 8, SEQ ID NO: 10, SEQ ID NO:12, SEQ ID NO: 14, SEQ ID NO: 16, SEQ ID NO:18, SEQ ID NO: 20, SEQ ID NO: 22, SEQ ID NO: 24, SEQ ID NO: 26 and SEQ ID NO: 28.

At least one modification (for example, mutation) can be included in one or more of SEQ ID NO: 2, SEQ ID NO: 4, SEQ ID NO: 6, SEQ ID NO: 8, SEQ ID NO: 16, SEQ ID NO:18, SEQ ID NO: 20 and SEQ ID NO: 24.

At least one modification (for example, mutation) can be included in one or more of SEQ ID NO: 2 and SEQ ID NO: 4.

At least one modification (for example, mutation) can be included in one or more of SEQ ID NO: 2, SEQ ID NO: 4, SEQ ID NO: 6, SEQ ID NO: 8, SEQ ID NO: 10, SEQ ID NO:12, SEQ ID NO: 14, SEQ ID NO: 16, SEQ ID NO:18, SEQ ID NO: 20, SEQ ID NO: 22, SEQ ID NO: 24, SEQ ID NO: 26 and SEQ ID NO: 28 and optionally at least one or more further modifications (for example, mutations) can be included in one or more of SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51 or SEQ ID NO: 53, suitably, in one or more of SEQ ID NO: 35, SEQ ID NO: 37, SEQ ID NO: 39, SEQ ID NO: 41, SEQ ID NO: 43 and SEQ ID NO: 45, or more suitably, in one or more of SEQ ID NO: 35, SEQ ID NO: 39, SEQ ID NO: 41 or SEQ ID NO: 43.

At least one modification (for example, mutation) can be included in one or more of SEQ ID NO: 2, SEQ ID NO: 4, SEQ ID NO: 6, SEQ ID NO: 8, SEQ ID NO: 16, SEQ ID NO:18, SEQ ID NO: 20 and SEQ ID NO: 24 and optionally at least one or more further modifications (for example, mutations) can be included in one or more of SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51 or SEQ ID NO: 53, suitably, in one or more of SEQ ID NO: 35, SEQ ID NO: 37, SEQ ID NO: 39, SEQ ID NO: 41, SEQ ID NO: 43 and SEQ ID NO: 45, or more suitably, in one or more of SEQ ID NO: 35, SEQ ID NO: 39, SEQ ID NO: 41 or SEQ ID NO: 43.

At least one modification (for example, mutation) can be included in one or more of SEQ ID NO: 2 and SEQ ID NO: 4 and optionally at least one or more further modifications (for example, mutations) can be included in one or more of SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51 or SEQ ID NO: 53, suitably, in one or more of SEQ ID NO: 35, SEQ ID NO: 37, SEQ ID NO: 39, SEQ ID NO: 41, SEQ ID NO: 43 and SEQ ID NO: 45, or more suitably, in one or more of SEQ ID NO: 35, SEQ ID NO: 39, SEQ ID NO: 41 or SEQ ID NO: 43.

At least one modification (for example, mutation) can be included in one or more of SEQ ID NO: 2, SEQ ID NO: 4, SEQ ID NO: 6, SEQ ID NO: 8, SEQ ID NO: 10, SEQ ID NO:12, SEQ ID NO: 14, SEQ ID NO: 16, SEQ ID NO:18, SEQ ID NO: 20, SEQ ID NO: 22, SEQ ID NO: 24, SEQ ID NO: 26 and SEQ ID NO: 28 and at least one modification (for example, mutation) can be included in one or more of SEQ ID NO: 35, SEQ ID NO: 37, SEQ ID NO: 39, SEQ ID NO: 41, SEQ ID NO: 43 and SEQ ID NO: 45, whereas no modification(s) (for example, mutation(s)) are included in one or more of SEQ ID NO: 31, SEQ ID NO: 33, SEQ ID NO: 47, SEQ ID NO: 49, SEQ ID NO: 51 and SEQ ID NO: 53, more suitably, at least one modification (for example, mutation) can be included in one or more of SEQ ID NO: 35, SEQ ID NO: 39, SEQ ID NO: 41 and SEQ ID NO: 43, whereas no modification(s) (for example, mutation(s)) are included in one or more of SEQ ID NO: 31, SEQ ID NO: 33, SEQ ID NO: 37, and SEQ ID NO: 45, SEQ ID NO: 47, SEQ ID NO: 49, SEQ ID NO: 51 and SEQ ID NO: 53.

At least one modification (for example, mutation) can be included in one or more of SEQ ID NO: 2, SEQ ID NO: 4, SEQ ID NO: 6, SEQ ID NO: 8, SEQ ID NO: 16, SEQ ID NO:18, SEQ ID NO: 20 and SEQ ID NO: 24 and at least one modification (for example, mutation) can be included in one or more of SEQ ID NO: 35, SEQ ID NO: 37, SEQ ID NO: 39, SEQ ID NO: 41, SEQ ID NO: 43 and SEQ ID NO: 45, whereas no modification(s) (for example, mutation(s)) are included in one or more of SEQ ID NO: 31, SEQ ID NO: 33, SEQ ID NO: 47, SEQ ID NO: 49, SEQ ID NO: 51 and SEQ ID NO: 53, more suitably, at least one modification (for example, mutation) can be included in one or more of SEQ ID NO: 35, SEQ ID NO: 39, SEQ ID NO: 41 and SEQ ID NO: 43, whereas no modification(s) (for example, mutation(s)) are included in one or more of SEQ ID NO: 31, SEQ ID NO: 33, SEQ ID NO: 37, and SEQ ID NO: 45, SEQ ID NO: 47, SEQ ID NO: 49, SEQ ID NO: 51 and SEQ ID NO: 53.

At least one modification (for example, mutation) can be included in one or more of SEQ ID NO: 2 and SEQ ID NO: 4 and at least one modification (for example, mutation) can be included in one or more of SEQ ID NO: 35, SEQ ID NO: 37, SEQ ID NO: 39, SEQ ID NO: 41, SEQ ID NO: 43 and SEQ ID NO: 45, whereas no modification(s) (for example, mutation(s)) are included in one or more of SEQ ID NO: 31, SEQ ID NO: 33, SEQ ID NO: 47, SEQ ID NO: 49, SEQ ID NO: 51 and SEQ ID NO: 53, more suitably, at least one modification (for example, mutation) can be included in one or more of SEQ ID NO: 35, SEQ ID NO: 39, SEQ ID NO: 41 and SEQ ID NO: 43, whereas no modification(s) (for example, mutation(s)) are included in one or more of SEQ ID NO: 31, SEQ ID NO: 33, SEQ ID NO: 37, and SEQ ID NO: 45, SEQ ID NO: 47, SEQ ID NO: 49, SEQ ID NO: 51 and SEQ ID NO: 53.

4. Modifying Plants a. Transformation

Recombinant constructs can be used to transform plants or plant cells in order to modulate polypeptide expression, function or activity. A recombinant polynucleotide construct can comprise a polynucleotide encoding one or more polynucleotides as described herein, operably linked to a regulatory region suitable for expressing the polypeptide. Thus, a polynucleotide can comprise a coding sequence that encodes the polypeptide as described herein. Plants or plant cells in which polypeptide expression, function or activity are modulated can include mutant, non-naturally occurring, transgenic, man-made or genetically engineered plants or plant cells. Suitably, the transgenic plant or plant cell comprises a genome that has been altered by the stable integration of recombinant DNA. Recombinant DNA includes DNA which has been genetically engineered and constructed outside of a cell and includes DNA containing naturally occurring DNA or cDNA or synthetic DNA. A transgenic plant can include a plant regenerated from an originally-transformed plant cell and progeny transgenic plants from later generations or crosses of a transformed plant. Suitably, the transgenic modification alters the expression or function or activity of the polynucleotide or the polypeptide described herein as compared to a control plant.

The polypeptide encoded by a recombinant polynucleotide can be a native polypeptide, or can be heterologous to the cell. In some cases, the recombinant construct contains a polynucleotide that modulates expression, operably linked to a regulatory region. Examples of suitable regulatory regions are described herein.

Vectors containing recombinant polynucleotide constructs such as those described herein are also provided. Suitable vector backbones include, for example, those routinely used in the art such as plasmids, viruses, artificial chromosomes, bacterial artificial chromosomes, yeast artificial chromosomes, or bacteriophage artificial chromosomes. Suitable expression vectors include, without limitation, plasmids and viral vectors derived from, for example, bacteriophage, baculoviruses, and retroviruses. Numerous vectors and expression systems are commercially available.

The vectors can include, for example, origins of replication, scaffold attachment regions or markers. A marker gene can confer a selectable phenotype on a plant cell. For example, a marker can confer biocide resistance, such as resistance to an antibiotic (for example, kanamycin, G418, bleomycin, or hygromycin), or an herbicide (for example, glyphosate, chlorsulfuron or phosphinothricin). In addition, an expression vector can include a tag sequence designed to facilitate manipulation or detection (for example, purification or localization) of the expressed polypeptide. Tag sequences, such as luciferase, beta-glucuronidase, green fluorescent polypeptide, glutathione S-transferase, polyhistidine, c-myc or hemagglutinin sequences typically are expressed as a fusion with the encoded polypeptide. Such tags can be inserted anywhere within the polypeptide, including at either the carboxyl or amino terminus.

A plant or plant cell can be transformed by having the recombinant polynucleotide integrated into its genome to become stably transformed. The plant or plant cell described herein can be stably transformed. Stably transformed cells typically retain the introduced polynucleotide with each cell division. A plant or plant cell can be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions. A number of methods are available in the art for transforming a plant cell including biolistics, gene gun techniques, *Agrobacterium*-mediated transformation, viral vector-mediated transformation, freeze-thaw method, microparticle bombardment, direct DNA uptake, sonication, microinjection, plant virus-mediated transfer, and electroporation.

If a cell or cultured tissue is used as the recipient tissue for transformation, plants can be regenerated from transformed cultures if desired, by techniques known to those skilled in the art.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a polynucleotide can be modulated in a similar manner. Some suitable regulatory regions initiate transcription only, or predominantly, in certain cell types. Methods for identifying and characterizing regulatory regions in plant genomic DNA are known in the art.

Exemplary promoters include tissue-specific promoters recognized by tissue-specific factors present in different tissues or cell types (for example, root-specific promoters, shoot-specific promoters, xylem-specific promoters), or present during different developmental stages, or present in response to different environmental conditions. Suitable promoters include constitutive promoters that can be activated in most cell types without requiring specific inducers. Examples of promoters that can be used to control polypeptide expression include the cauliflower mosaic virus 35S (CaMV/35S), SSU, OCS, lib4, usp, STLS1, B33, nos or ubiquitin- or phaseolin-promoters. Persons skilled in the art are capable of generating multiple variations of recombinant promoters. Tissue-specific promoters are transcriptional control elements that are only active in particular cells or tissues at specific times during plant development, such as in vegetative tissues or reproductive tissues. Examples of tissue-specific promoters under developmental control include promoters that can initiate transcription only (or primarily only) in certain tissues, such as vegetative tissues, for example, roots or leaves, or reproductive tissues, such as fruit, ovules, seeds, pollen, pistols, flowers, or any embryonic tissue. Reproductive tissue-specific promoters may be, for example, anther-specific, ovule-specific, embryo-specific, endosperm-specific, integument-specific, seed and seed coat-specific, pollen-specific, petal-specific, sepal-specific, or combinations thereof.

Exemplary leaf-specific promoters include pyruvate, orthophosphate dikinase (PPDK) promoter from C4 plant (maize), cab-m1Ca+2 promoter from maize, the *Arabidopsis thaliana* myb-related gene promoter (Atmyb5), the ribulose biphosphate carboxylase (RBCS) promoters (for example, the tomato RBCS 1, RBCS2 and RBCS3A genes expressed in leaves and light-grown seedlings, RBCS1 and RBCS2 expressed in developing tomato fruits or ribulose bisphosphate carboxylase promoter expressed almost exclusively in mesophyll cells in leaf blades and leaf sheaths at high levels).

Exemplary senescence-specific promoters include a tomato promoter active during fruit ripening, senescence and abscission of leaves, a maize promoter of gene encoding a cysteine protease, the promoter of 82E4 and the promoter of SAG genes. Exemplary anther-specific promoters can be used. Exemplary root-preferred promoters known to persons skilled in the art may be selected. Exemplary seed-preferred promoters include both seed-specific promoters (those promoters active during seed development such as promoters of seed storage polypeptides) and seed-germinating promoters (those promoters active during seed germination).

Examples of inducible promoters include promoters responsive to pathogen attack, anaerobic conditions, elevated temperature, light, drought, cold temperature, or high salt concentration. Pathogen-inducible promoters include those from pathogenesis-related polypeptides (PR polypeptides), which are induced following infection by a pathogen (for example, PR polypeptides, SAR polypeptides, beta-1,3-glucanase, chitinase).

In addition to plant promoters, other suitable promoters may be derived from bacterial origin for example, the octopine synthase promoter, the nopaline synthase promoter and other promoters derived from Ti plasmids, or may be derived from viral promoters (for example, 35S and 19S RNA promoters of cauliflower mosaic virus (CaMV), constitutive promoters of tobacco mosaic virus, cauliflower mosaic virus (CaMV) 19S and 35S promoters, or figwort mosaic virus 35S promoter).

b. Mutation

A plant or plant cell comprising at least one mutation in one or more polynucleotides or polypeptides as described herein is disclosed, wherein said mutation results in modulated function or activity of NtSULTR3 or the polypeptide(s) encoded thereby or modulated function or activity of NtSULTR3 and NtSUS or the polypeptides encoded thereby. Combinations of such mutations are discussed herein.

There is provided a method for modulating the level of a NtSULTR3 polypeptide or a NtSULTR3 polypeptide and a NtSUS polypeptide in a (cured) plant or in (cured) plant material said method comprising introducing into the genome of said plant one or more mutations that modulate expression of at least one NtSULTR3 gene or at least one NtSULTR3 gene and at least one NtSUS gene, wherein said at least one gene is selected from any of the sequences according to the present disclosure.

There is also provided a method for identifying a plant with modulated levels of reducing sugars, said method comprising screening a polynucleotide sample from a plant of interest for the presence of one or more mutations in the sequences according to the present disclosure—such as NtSULTR3 or NtSULTR3 and NtSUS or a combination thereof, and optionally correlating the identified mutation(s) with mutation(s) that are known to modulate levels of reducing sugars.

There is also disclosed a plant or plant cell that is heterozygous or homozygous for one or more mutations in a NtSULTR3 gene or a NtSULTR3 gene and a NtSUS gene according to the present disclosure, wherein said mutation results in modulated expression of the gene or function or activity of the NtSULTR3 polypeptide or the NtSULTR3 and NtSUS polypeptides encoded thereby.

A number of approaches can be used to combine mutations in one plant including sexual crossing. A plant having one or more favourable heterozygous or homozygous mutations in a gene according to the present disclosure that modulates expression of the gene or the function or activity of the polypeptide encoded thereby can be crossed with a plant having one or more favourable heterozygous or homozygous mutations in one or more other genes that modulate expression thereof or the function or activity of the polypeptide encoded thereby. In one embodiment, crosses are made in order to introduce one or more favourable heterozygous or homozygous mutations within gene according to the present disclosure within the same plant.

The function or activity of one or more polypeptides of the present disclosure in a plant is increased or decreased if the function or activity is lower or higher than the function or activity of the same polypeptide(s) in a plant that has not been modified to inhibit the function or activity of that polypeptide and which has been cultured, harvested and cured using the same protocols.

In some embodiments, the mutation(s) is introduced into a plant or plant cell using a mutagenesis approach, and the introduced mutation is identified or selected using methods known to those of skill in the art—such as Southern blot analysis, DNA sequencing, PCR analysis, or phenotypic analysis. Mutations that impact gene expression or that interfere with the function of the encoded polypeptide can be determined using methods that are well known in the art. Insertional mutations in gene exons usually result in null-mutants. Mutations in conserved residues can be particularly effective in inhibiting the metabolic function of the encoded polypeptide. It will be appreciated, for example, that a mutation in one or more of the highly conserved regions would likely alter polypeptide function, while a mutation outside of those highly conserved regions would likely have little to no effect on polypeptide function. In addition, a mutation in a single nucleotide can create a stop codon, which would result in a truncated polypeptide and, depending on the extent of truncation, loss of function.

Methods for obtaining mutant polynucleotides and polypeptides are also disclosed. Any plant of interest, including a plant cell or plant material can be genetically modified by various methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other equivalent methods.

Mutations in the polynucleotides and polypeptides described herein can include man-made mutations or synthetic mutations or genetically engineered mutations. Mutations in the polynucleotides and polypeptides described herein can be mutations that are obtained or obtainable via a process which includes an in vitro or an in vivo manipulation step. Mutations in the polynucleotides and polypeptides described herein can be mutations that are obtained or obtainable via a process which includes intervention by man. The function or activity of the mutant polypeptide variant may be higher, lower or about the same as the unmutated polypeptide.

Methods that introduce a mutation randomly in a polynucleotide can include chemical mutagenesis and radiation mutagenesis. Chemical mutagenesis involves the use of exogenously added chemicals—such as mutagenic, teratogenic, or carcinogenic organic compounds—to induce mutations. Mutagens that create primarily point mutations and short deletions, insertions, missense mutations, simple sequence repeats, transversions or transitions, including chemical mutagens or radiation, may be used to create the mutations. Mutagens include ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)amino-propylamino]acridine dihydrochloride and formaldehyde.

Spontaneous mutations in the locus that may not have been directly caused by the mutagen are also contemplated provided that they result in the desired phenotype. Suitable mutagenic agents can also include, for example, ionising radiation—such as X-rays, gamma rays, fast neutron irradiation and UV radiation. The dosage of the mutagenic chemical or radiation is determined experimentally for each type of plant tissue such that a mutation frequency is obtained that is below a threshold level characterized by lethality or reproductive sterility. Any method of plant polynucleotide preparation known to those of skill in the art may be used to prepare the plant polynucleotide for mutation screening.

The mutation process may include one or more plant crossing steps.

After mutation, screening can be performed to identify mutations that create premature stop codons or otherwise non-functional genes. After mutation, screening can be performed to identify mutations that create functional genes that are capable of being expressed at increased or decreased levels. Screening of mutants can be carried out by sequencing, or by the use of one or more probes or primers specific to the gene or polypeptide. Specific mutations in polynucleotides can also be created that can result in modulated gene expression, modulated stability of mRNA, or modulated stability of polypeptide. Such plants are referred to herein as "non-naturally occurring" or "mutant" plants. Typically, the mutant or non-naturally occurring plants will include at least a portion of foreign or synthetic or man-made nucleotide (for example, DNA or RNA) that was not present in the plant before it was manipulated. The foreign nucleotide may be a single nucleotide, two or more nucleotides, two or more contiguous nucleotides or two or more non-contiguous nucleotides—such as at least 10, 20, 30, 40, 50, 100, 200, 300, 400, 500, 600, 700, 800, 900, 1000, 1100, 1200, 1300, 1400 or 1500 or more contiguous or non-contiguous nucleotides.

c. Transgenics and Genome Editing

Sequence-specific polynucleotides that can interfere with the transcription of one or more endogenous gene(s); sequence-specific polynucleotides that can interfere with the translation of RNA transcripts (for example, double-stranded RNAs, siRNAs, ribozymes); sequence-specific polypeptides that can interfere with the stability of one or more polypeptides; sequence-specific polynucleotides that can interfere with the enzymatic function of one or more polypeptides or the binding function of one or more polypeptides with respect to substrates or regulatory polypeptides; antibodies that exhibit specificity for one or more polypeptides; small molecule compounds that can interfere with the stability of one or more polypeptides or the enzymatic function of one or more polypeptides or the binding function of one or more polypeptides; zinc finger polypeptides that bind one or more polynucleotides; and meganucleases that have function towards one or more polynucleotides can be used to modulate the expression or function or activity of one or more of the polynucleotides or polypeptides described herein. Genome editing technologies are well known in the art and are discussed further below.

d. Zinc Finger Nucleases

Zinc finger polypeptides can be used to modulate the expression or function or activity of one or more of the NtSULTR3 or NtSULTR3 and NtSUS polynucleotides described herein. The use of zinc finger nucleases is described in Nature Rev. Genet. (2010) 11 (9): 636-646).

e. Meganucleases

Meganucleases, such as I-CreI, can be used to modulate the expression or function or activity of one or more of the NtSULTR3 or NtSULTR3 and NtSUS polynucleotides described herein. The use of meganucleases is described in *Curr Gene Ther*. (2011) February; 11(1):11-27 and *Int J Mol Sci*. (2019) 20(16), 4045.

f. TALENs

Transcription activator-like effector nucleases (TALENs) can be used to modulate the expression or function or activity of one or more of NtSULTR3 or NtSULTR3 and NtSUS polynucleotides described herein. The use of TALENs is described in Nature Rev. *Mol. Cell Biol.* (2013) 14: 49-55 and *Int J Mol Sci*. (2019) 20(16), 4045.

g. CRISPR

The CRISPR system can be used to modulate the expression or function or activity of one or more of the NtSULTR3 or NtSULTR3 and NtSUS polynucleotides described herein and is a preferred method. This technology is described in, for example, *Plant Methods* (2016) 12:8; *Front Plant Sci*. (2016) 7: 506; Biotechnology Advances (2015) 33, 1, p 41-52; *Acta Pharmaceutica Sinica B* (2017) 7, 3, p 292-302; *Curr. Op. in Plant Biol*. (2017) 36, 1-8 and *Int J Mol Sci* (2019) 20(16), 4045. As is well known in the art, the CRISPR editing system generally includes two components: a CRISPR-associated endonuclease (Cas) (for example, Cas9) and a guide RNA (gRNA). Cas forms a double stranded DNA break at a site in the genome that is defined by the sequence of a gRNA molecule bound to Cas. The location at which Cas breaks the DNA is defined by the unique sequence of the gRNA that is bound to it. gRNA is a specifically designed RNA sequence that recognizes the target DNA region of interest and directs the Cas nuclease there for editing. It has two sections: (i) a tracr RNA, which serves as a binding scaffold for the Cas nuclease; and (ii) crispr RNA (crRNA), a 17-20 nucleotide sequence complementary to the target DNA. The exact region of the DNA to be targeted will depend on the specific application. For example, to activate or repress a target polynucleotide, gRNAs can be targeted to the promoter driving expression of the target polynucleotide. Methods for designing gRNAs are well known in the art, including Chop Chop Harvard.

The application of Cas9-based genome editing in *Arabidopsis* and tobacco is described in, for example, *Methods Enzymol.* (2014) 546:459-72 and *Plant Physiol Biochem.* (2018) 131:37-46. CRISPR technology has been widely implemented in plants (see, for example, WO2015/189693).

In addition to Cas9, other RNA-guided nucleases for use in the CRISPR system have been described, including, CasI, CasIB, Cas2, Cas3, Cas4, Cas5, Cas6, Cas7, Cas8, CasIO, CpfI, CsyI, Csy2, Csy3, CseI, Cse2, CscI, Csc2, Csa5, Csn2, Csm2, Csm3, Csm4, Csm5, Csm6, CmrI, Cmr3, Cmr4, Cmr5, Cmr6, CsbI, Csb2, Csb3, Csx17, Csx14, CsxIO, Csx16, CsaX, Csx3, CsxI, Csx15, CsfI, Csf2, Csf3 and Csf4. In certain embodiments, the use of Cas9 is preferred.

The present disclosure further provides a CRISPR based genome editing system comprising an RNA-guided nuclease and a gRNA, where the CRISPR based genome editing system modulates the activity of one or more of the polynucleotides described herein. The present disclosure also provides a method of cleaving one or more polynucleotides in a plant cell, comprising introducing a gRNA and an RNA-guided nuclease into the plant cell, wherein the gRNA acts in association with the RNA-guided nuclease to create a strand break in one or more of the polynucleotides described herein. A CRISPR construct is also disclosed comprising: (i) a polynucleotide encoding a CRISPR-associated endonuclease; and (ii) a gRNA including a polynucleotide sequence (typically of about 17-20 nucleotides) complementary to the DNA of the polynucleotide as described herein that is to be targeted.

h. Antisense Modification

Antisense technology is another well-known method that can be used to modulate the expression or activity of one or more NtSULTR3 polypeptides or one or more NtSULTR3 and NtSUS polypeptides. See, for example, Gene (1988) 10; 72(1-2):45-50.

i. Mobile Genetic Elements

Alternatively, genes can be targeted for inactivation by introducing transposons (for example, IS elements) into the genomes of plants of interest. See, for example, *Cytology and Genetics* (2006) 40(4):68-81.

j. Ribozymes

Alternatively, NtSULTR3 or NtSULTR3 and NtSUS polynucleotides can be targeted for inactivation by introducing ribozymes derived from a number of small circular RNAs that are capable of self-cleavage and replication in plants. See, for example, FEMS Microbiology Reviews (1999) 23, 3, 257-275.

5. Plants

The mutant or non-naturally occurring plants or plant cells can have any combination of one or more modifications (for example, mutations) in one or more of NtSULTR3 or NtSULTR3 and NtSUS or the polypeptides encoded thereby which result in modulated expression or function or activity of those polynucleotides or their polynucleotide products. For example, the mutant or non-naturally occurring plants or plant cells may have a single modification in a single NtSULTR3 polynucleotide or polypeptide or a single NtSULTR3 polynucleotide or polypeptide and a single NtSUS polynucleotide or polypeptide; multiple modifications in a single NtSULTR3 polynucleotide or polypeptide or a single NtSULTR3 and a single NtSUS polynucleotide or polypeptide; a single modification in two or more or three or more or four or more NtSULTR3 polynucleotides or polypeptides or NtSULTR3 and NtSUS polynucleotides or polypeptides; or multiple modifications in two or more or three or more or four or more NtSULTR3 or NtSULTR3 and NtSUS polynucleotides or polypeptides. By way of further example, the mutant or non-naturally occurring plants or plant cells may have one or more modifications in a specific portion of NtSULTR3 or NtSULTR3 and NtSUS polynucleotide(s) or polypeptide(s)—such as in a region of NtSULTR3 or NtSULTR3 and NtSUS that encodes an active site of the NtSULTR3 or NtSUS polypeptide or a portion thereof. By way of further example, the mutant or non-naturally occurring plants or plant cells may have one or more modifications in a region outside of one or more NtSULTR3 or NtSULTR3 and NtSUS polynucleotide(s) or polypeptide(s)—such as in a region upstream or downstream of the NtSULTR3 or NtSULTR3 and NtSUS polynucleotide(s) it regulates provided that they modulate the function or expression of the NtSULTR3 or NtSULTR3 and NtSUS p(s). Upstream elements can include promoters, enhancers or transcription factors. Some elements—such as enhancers—can be positioned upstream or downstream of the gene it regulates. The element(s) need not be located near to the gene that it regulates since some elements have been found located several hundred thousand base pairs upstream or downstream of the gene that it regulates. The mutant or non-naturally occurring plants or plant cells may have one or more modifications located within the first 100 nucleotides of the gene(s), within the first 200 nucleotides of the gene(s), within the first 300 nucleotides of the gene(s), within the first 400 nucleotides of the gene(s), within the first 500 nucleotides of the gene(s), within the first 600 nucleotides of the gene(s), within the first 700 nucleotides of the gene(s), within the first 800 nucleotides of the gene(s), within the first 900 nucleotides of the gene(s), within the first 1000 nucleotides of the gene(s), within the first 1100 nucleotides of the gene(s), within the first 1200 nucleotides of the gene(s), within the first 1300 nucleotides of the gene(s), within the first 1400 nucleotides of the gene(s) or within the first 1500 nucleotides of the gene(s). The mutant or non-naturally occurring plants or plant cells may have one or more modifications located within the first, second, third, fourth, fifth, sixth, seventh, eighth, ninth, tenth, eleventh, twelfth, thirteenth, fourteenth or fifteenth set of 100 nucleotides of the gene(s) or combinations thereof. Mutant or non-naturally occurring plants or plant cells (for example, mutant, non-naturally occurring or transgenic plants or plant cells and the like, as described herein) comprising the mutant polypeptide variants are disclosed.

In one embodiment, seeds from plants are mutagenised and then grown into first generation mutant plants. The first generation plants are then allowed to self-pollinate and seeds from the first generation plant are grown into second generation plants, which are then screened for mutations in their loci. Though the mutagenized plant material can be screened for mutations, an advantage of screening the second generation plants is that all somatic mutations correspond to germline mutations. One of skill in the art would understand that a variety of plant materials, including but not limited to, seeds, pollen, plant tissue or plant cells, may be mutagenised in order to create the mutant plants. However, the type of plant material mutagenised may affect when the plant polynucleotide is screened for mutations. For example, when pollen is subjected to mutagenesis prior to pollination of a non-mutagenized plant the seeds resulting from that pollination are grown into first generation plants. Every cell of the first generation plants will contain mutations created in the pollen; thus these first generation plants may then be screened for mutations instead of waiting until the second generation.

6. Preparation of Modified Plants, Screening, and Crossing

Prepared NtSULTR3 or NtSULTR3 and NtSUS polynucleotides from individual plants, plant cells, or plant material can optionally be pooled in order to expedite screening for mutations in the population of plants originating from the mutagenized plant tissue, cells or material. One or more subsequent generations of plants, plant cells or plant material can be screened. The size of the optionally pooled group is dependent upon the sensitivity of the screening method used.

After the samples are optionally pooled, they can be subjected to polynucleotide-specific amplification techniques, such as PCR. Any one or more primers or probes specific to the gene or the sequences immediately adjacent to the gene may be utilized to amplify the sequences within the optionally pooled sample. Suitably, the one or more primers or probes are designed to amplify the regions of the locus where useful mutations are most likely to arise. Most preferably, the primer is designed to detect mutations within regions of the polynucleotide. Additionally, it is preferable for the primer(s) and probe(s) to avoid known polymorphic sites in order to ease screening for point mutations. To facilitate detection of amplification products, the one or more primers or probes may be labelled using any conventional labelling method. Primer(s) or probe(s) can be designed based upon the sequences described herein using methods that are well understood in the art.

To facilitate detection of amplification products, the primer(s) or probe(s) may be labelled using any conventional labelling method. These can be designed based upon the sequences described herein using methods that are well understood in the art.

Polymorphisms may be identified by means known in the art and some have been described in the literature.

In some embodiments, a plant may be regenerated or grown from the plant, plant tissue or plant cell. Any suitable methods for regenerating or growing a plant from a plant cell or plant tissue may be used, such as, without limitation, tissue culture or regeneration from protoplasts. Suitably, plants may be regenerated by growing transformed plant cells on callus induction media, shoot induction media or root induction media. See, for example, McCormick et al., *Plant Cell Reports* 5:81-84 (1986). These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. Thus, "transformed seeds" refers to seeds that contain the nucleotide construct stably integrated into the plant genome.

Accordingly, in a further aspect there is provided a method of preparing a mutant plant. The method involves providing at least one cell of a plant comprising a NtSULTR3 or NtSULTR3 and NtSUS gene encoding a functional polynucleotide described herein (or any combination thereof as described herein). Next, the at least one cell of the plant is treated under conditions effective to modulate the function of the polynucleotide(s). The at least one mutant plant cell is then propagated into a mutant plant, where the mutant plant has modulated levels of NtSULTR3 or NtSULTR3 and NtSUS polypeptide(s) described herein (or any combination thereof as described herein) as compared to that of a control plant. In one embodiment of this method of making a mutant plant, the treating step involves subjecting the at least one cell to a chemical mutagenising agent as described above and under conditions effective to yield at least one mutant plant cell. In another embodiment of this method, the treating step involves subjecting the at least one cell to a radiation source under conditions effective to yield at least one mutant plant cell. The term "mutant plant" includes mutant plants in which the genotype is modified as compared to a control plant, suitably by means other than genetic engineering or genetic modification.

In certain embodiments, the mutant plant, mutant plant cell or mutant plant material may comprise one or more mutations that have occurred naturally in another plant, plant cell or plant material and confer a desired trait. This mutation can be incorporated (for example, introgressed) into another plant, plant cell or plant material (for example, a plant, plant cell or plant material with a different genetic background to the plant from which the mutation was derived) to confer the trait thereto. Thus by way of example, a mutation that occurred naturally in a first plant may be introduced into a second plant—such as a second plant with a different genetic background to the first plant. The skilled person is therefore able to search for and identify a plant carrying naturally in its genome one or more mutant alleles of the genes described herein which confer a desired trait. The mutant allele(s) that occurs naturally can be transferred to the second plant by various methods including breeding, backcrossing and introgression to produce a lines, varieties or hybrids that have one or more mutations in the genes described herein. The same technique can also be applied to the introgression of one or more non-naturally occurring mutation(s) from a first plant into a second plant. Plants showing a desired trait may be screened out of a pool of mutant plants. Suitably, the selection is carried out utilising the knowledge of the polynucleotide as described herein. Consequently, it is possible to screen for a genetic trait as compared to a control. Such a screening approach may involve the application of conventional amplification or hybridization techniques as discussed herein. Thus, a further aspect of the present disclosure relates to a method for identifying a mutant plant comprising the steps of: (a) providing a sample comprising one or more NtSULTR3 or NtSULTR3 and NtSUS polynucleotide(s) from a plant; and (b) determining the sequence of the polynucleotide(s), wherein a difference in the sequence of the polynucleotide(s) as compared to the polynucleotide(s) of a control plant is indicative that said plant is a mutant plant. In another aspect there is provided a method for identifying a mutant plant which accumulates increased or decreased levels of reducing sugars, non-reducing sugars and free amino acids compared to a control plant comprising the steps of: (a) providing a sample from a plant to be screened; (b) determining if said sample comprises one or more mutations in one or more NtSULTR3 or NtSULTR3 and NtSUS polynucleotides described herein; and (c) determining the level of at least one reducing sugar, at least one non-reducing sugar and at least one free amino acid. Suitably the level of the at least one reducing sugar, non-reducing sugar and free amino acid is determined in cured leaves. In another aspect, there is provided a method for preparing a mutant plant which has increased or decreased levels of at least one reducing sugar, at least one non-reducing sugar and at least one free amino acid as compared to a control plant comprising the steps of: (a) providing a sample from a first plant; (b) determining if said sample comprises one or more mutations in one or more NtSULTR3 or NtSULTR3 and NtSUS polynucleotides described herein that result in modulated levels of the at least one reducing sugar, at least one non-reducing sugar and at least one free amino acid; and (c) transferring the one or more mutations into a second plant. Suitably the level of the at least one reducing sugar is determined in cured leaves. The mutation(s) can be transferred into the second plant using various methods that are known in the art—such as by genetic engineering, genetic manipulation, introgression, plant breeding, backcrossing and the like. In one embodiment, the first plant is a naturally occurring plant. In one embodiment, the second plant has a different genetic background to the first plant. In another aspect there is provided a method for preparing a mutant plant which has increased or decreased levels of at least one reducing sugar, at least one non-reducing sugar and at least one free amino acid as compared to a control plant comprising the steps of: (a) providing a sample from a first plant; (b) determining if said sample comprises one or more mutations in one or more of the NtSULTR3 or NtSULTR3 and NtSUS polynucleotides described herein that results in modulated levels of the at least one reducing sugar, at least one non-reducing sugar and at least one free amino acid; and (c) introgressing the one or more mutations from the first plant into a second plant. Suitably the level of the at least one reducing sugar, at least one non-reducing sugar and at least one free amino acid is determined in cured leaves. In one embodiment, the step of introgressing comprises plant breeding, optionally including backcrossing and the like. In one embodiment, the first plant is a naturally occurring plant. In one embodiment, the second plant has a different genetic background to the first plant. In one embodiment, the first plant is not a cultivar or an elite cultivar. In one embodiment, the second plant is a cultivar or an elite cultivar. A further aspect relates to a mutant plant (including a cultivar or elite cultivar mutant plant) obtained or obtainable by the methods described herein. In certain embodiments, the mutant plant may have one or more mutations localised only to a specific region of the plant—such as within the sequence of the one or more NtSULTR3 or NtSULTR3 and NtSUS polynucleotide(s) described herein. According to this embodiment, the remaining genomic sequence of the mutant plant will be the same or substantially the same as the plant prior to the mutagenesis.

In certain embodiments, the mutant plants may have one or more mutations localised in more than one genomic region of the plant—such as within the sequence of one or more of the NtSULTR3 or NtSULTR3 and NtSUS polynucleotides described herein and in one or more further regions of the genome. According to this embodiment, the remaining genomic sequence of the mutant plant will not be the same or will not be substantially the same as the plant prior to the mutagenesis. In certain embodiments, the mutant plants may not have one or more mutations in one or more, two or more, three or more, four or more or five or more exons of the NtSULTR3 or NtSULTR3 and NtSUS polynucleotide(s) described herein; or may not have one or more mutations in one or more, two or more, three or more, four or more or five or more introns of the NtSULTR3 or NtSULTR3 and NtSUS polynucleotide(s) described herein; or may not have one or more mutations in a promoter of the NtSULTR3 or NtSULTR3 and NtSUS polynucleotide(s) described herein; or may not have one or more mutations in the 3' untranslated region of the NtSULTR3 or NtSULTR3 and NtSUS polynucleotide(s) described herein; or may not have one or more mutations in the 5' untranslated region of the NtSULTR3 or NtSULTR3 and NtSUS polynucleotide(s) described herein; or may not have one or more mutations in the coding region of the NtSULTR3 or NtSULTR3 and NtSUS polynucleotide(s) described herein; or may not have one or more mutations in the non-coding region of the NtSULTR3 or NtSULTR3 and NtSUS polynucleotide(s) described herein; or any combination of two or more, three or more, four or more, five or more; or six or more thereof parts thereof.

In a further aspect there is provided a method of identifying a plant, a plant cell or plant material comprising a mutation in a gene encoding a NtSULTR3 or NtSULTR3 and NtSUS polynucleotide described herein comprising: (a) subjecting a plant, a plant cell or plant material to mutagenesis; (b) obtaining a sample from said plant, plant cell or plant material or descendants thereof; and (c) determining the polynucleotide sequence of the NtSULTR3 or NtSULTR3 and NtSUS gene(s) or a variant or a fragment thereof, wherein a difference in said sequence is indicative of one or more mutations therein. This method also allows the selection of plants having mutation(s) that occur(s) in genomic regions that affect the expression of the NtSULTR3 or NtSULTR3 and NtSUS gene in a plant cell, such as a transcription initiation site, a start codon, a region of an intron, a boundary of an exon-intron, a terminator, or a stop codon.

7. Plant Families, Species, Varieties, Seeds, and Tissue Culture

Plants suitable for use in the present disclosure include monocotyledonous and dicotyledonous plants and plant cell systems. Plants suitable for use in the present disclosure include members of the genera *Camellia*, *Cannabis* and *Nicotiana*. Suitable species of *Camellia* and *Cannabis* may include *Camellia sinensis* (tea), *Cannabis sativa*, *Cannabis indica* and *Cannabis ruderalis*.

Various embodiments are directed to mutant tobacco, non-naturally occurring tobacco or transgenic tobacco plants or plant cells. The disclosed compositions and methods can be applied to any species of the genus *Nicotiana*, including *N. rustica* and *N. tabacum* (for example, LA B21, LN KY171, TI 1406, Basma, Galpao, Perique, Beinhart 1000-1, and Petico). Other species include *N. acaulis, N. acuminata, N. africana, N. alata, N. ameghinoi, N. amplexicaulis, N. arentsii, N. attenuata, N. azambujae, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N. x sanderae*. In one embodiment, the plant is *N. tabacum*.

The use of tobacco cultivars and elite tobacco cultivars is also contemplated herein. The transgenic, non-naturally occurring or mutant plant may therefore be a tobacco variety or elite tobacco cultivar that comprises one or more transgenes, or one or more genetic mutations or a combination thereof. The genetic mutation(s) (for example, one or more polymorphisms) can be mutations that do not exist naturally in the individual tobacco variety or tobacco cultivar (for example, elite tobacco cultivar) or can be genetic mutation(s) that do occur naturally provided that the mutation does not occur naturally in the individual tobacco variety or tobacco cultivar (for example, elite tobacco cultivar).

Particularly useful *Nicotiana tabacum* varieties include Burley type, dark type, flue-cured type, and Oriental type tobaccos. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC, 'Perique' tobacco, PVHO3, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B13P, Xanthi (Mitchell-Mor), Bel-W3, 79-615, Samsun Holmes NN, KTRDC number 2 Hybrid 49, Burley 21, KY8959, KY9, MD 609, PG01, PG04, PO1, PO2, PO3, RG11, RG 8, VA509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpao Comum, HB04P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

Embodiments are also directed to compositions and methods for producing mutant plants, non-naturally occurring plants, hybrid plants, or transgenic plants that have been modified to modulate the expression or function of one or more NtSULTR3 or NtSULTR3 and NtSUS polynucleotide(s) described herein (or any combination thereof as described herein). Advantageously, the mutant plants, non-naturally occurring plants, hybrid plants, or transgenic plants that are obtained may be similar or substantially the same in overall appearance to control plants. Various phenotypic characteristics such as degree of maturity, number of leaves per plant, stalk height, leaf insertion angle, leaf size (width and length), internode distance, and lamina-midrib ratio can be assessed by field observations.

One aspect relates to a seed of a mutant plant, a non-naturally occurring plant, a hybrid plant or a transgenic plant described herein. Preferably, the seed is a tobacco seed. A further aspect relates to pollen or an ovule of a mutant plant, a non-naturally occurring plant, a hybrid plant or a transgenic plant that is described herein. In addition, there is provided a mutant plant, a non-naturally occurring plant, a hybrid plant or a transgenic plant as described herein which further comprises a polynucleotide conferring male sterility.

Also provided is a tissue culture of regenerable cells of the mutant plant, non-naturally occurring plant, hybrid plant, or transgenic plant or a part thereof as described herein, which culture regenerates plants capable of expressing all the morphological and physiological characteristics of the parent. The regenerable cells include cells from leaves, pollen, embryos, cotyledons, hypocotyls, roots, root tips, anthers, flowers and a part thereof, ovules, shoots, stems, stalks, pith and capsules or callus or protoplasts derived therefrom.

The plant material that is described herein can be cured tobacco material—such as cured tobacco material from Virginia type or Oriental type. Cured tobacco material can be flue cured or sun-cured or air cured tobacco material.

The CORESTA recommendation for tobacco curing is described in: CORESTA Guide No 17, April 2016, Sustainability in Leaf Tobacco Production.

8. Modulating Sugar and Amino Acid Content

The mutant, transgenic or non-naturally occurring plants or parts thereof of the present disclosure exhibit modulated sugar and amino acid content in cured leaves, suitably, fully cured leaves. Suitably, the cured leaves are taken from mid-position leaves of a plant. Suitably, the mutant, transgenic or non-naturally occurring plants or parts thereof have substantially the same visual appearance as the control plant.

Part of the plant of the present disclosure (for example, the cured leaves) can have decreased levels of the at least one reducing sugar of at least 50% therein, decreased levels of the at least one non-reducing sugar of at least 50% therein and increased levels of the at least one free amino acid of at least 1.5 times therein as compared to a control plant in which the expression or the function of said NtSULTR3 or NtSULTR3 and NtSUS polypeptide(s) has not been modulated. For example, the part of the plant (for example, the cured leaves) has decreased levels of the at least one reducing sugar of at least 60% therein, decreased levels of the at least one non-reducing sugar of at least 60% therein and increased levels of the at least one free amino acid of at least 1.5 times. By way of further example, the part of the plant (for example, the cured leaves) has decreased levels of the at least one reducing sugar of at least 69% therein, decreased levels of the at least one non-reducing sugar of at least 60% therein and increased levels of the at least one free amino acid of at least 1.5 times.

In certain embodiments, the levels of glucose and fructose are reduced by at least about 55% or more—such as at least about 60% or more, or at least about 65% or more and the level of sucrose is reduced by at least about 55% or more—such as at least about 60% or more as compared to a control plant.

In certain embodiments, the level of glucose is reduced by at least 55% or more, or at least 65% or more, or at least 70% or more, or at least 75% or more, or at least 77% or more and the level of fructose is reduced by at least about 55% or more, or at least 60% or more, or at least 65% or more, or at least 69% or more and the level of sucrose is reduced by about 55% or more, or at least about 60% or more as compared to a control plant.

In certain embodiments, the level of glucose is reduced by at least 75% or more, the level of fructose is reduced by at least about 65% or more and the level of sucrose is reduced by about 55% or more as compared to a control plant.

In certain embodiments, the level of glucose is reduced by at least 77% or more, the level of fructose is reduced by at least about 69% or more and the level of sucrose is reduced by about 60% or more as compared to a control plant.

In certain embodiments, the levels of at least one free amino acid are increased by at least 1.5 times therein as compared to a control plant. In certain embodiments, the levels of glutamine, glutamate and aspartate are increased by at least 2 times therein as compared to a control plant. In certain embodiments, the levels of glutamine, glutamate and aspartate are increased by at least 2.3 times, at least 2.4 times and at least 2 times, respectively, as compared to a control plant.

In certain embodiments, the level of glucose is reduced by at least 75% or more, the level of fructose is reduced by at least about 65% or more, the level of sucrose is reduced by about 55% or more and the levels of glutamine, glutamate and aspartate are increased by at least 2 times as compared to a control plant.

In certain embodiments, the level of glucose is reduced by at least 77% or more, the level of fructose is reduced by at least about 69% and the level of sucrose is reduced by about 60% and the levels of glutamine, glutamate and aspartate are increased by at least 2.3 times, at least 2.4 times and at least 2 times, respectively, as compared to a control plant.

The amount of asparagine may be increased by at least about 1.5 times as compared to a control plant.

Part of the plant of the present disclosure (for example, the cured leaves) can have increased levels of the at least one reducing sugar, increased levels of the at least one non-reducing sugar and decreased levels of the at least one free amino acid as compared to a control plant in which the expression or the function of said NtSULTR3 or NtSULTR3 and NtSUS polynucleotides or polypeptides encoded thereby has not been modulated.

A further aspect, relates to cured plant material—such as cured leaf or cured tobacco—derived or derivable from the mutant, non-naturally occurring or transgenic plant or cell as described herein, wherein the levels of at least one reducing sugar and at least one non-reducing sugar and free amino acids is modulated as discussed above as compared to a control. The amount of asparagine may be modulated as compared to a control plant.

A still further aspect, relates to cured plant material—such as cured leaf or cured tobacco—derived or derivable from the mutant, non-naturally occurring or transgenic plant or cell as described herein, wherein the levels of glucose, fructose and sucrose and the levels of glutamine, glutamate and aspartate are modulated as discussed above as compared to a control. The amount of asparagine may be modulated as compared to a control plant.

Embodiments are also directed to compositions and methods for producing the mutant, non-naturally occurring or transgenic plants or plant cells described herein with modulated levels of at least one reducing sugar and at least one non-reducing sugar and free amino acids as discussed above. The amount of asparagine may be modulated as compared to a control plant.

In one embodiment, the phenotype of the mutant, non-naturally occurring or transgenic plant is substantially the same as the control plant. In one embodiment, the leaf weight of the mutant, non-naturally occurring or transgenic plant is substantially the same as the control plant. In one embodiment, the leaf number of the mutant, non-naturally occurring or transgenic plant is substantially the same as the control plant. In one embodiment, the leaf weight and the leaf number of the mutant, non-naturally occurring or transgenic plant is substantially the same as the control plant. In one embodiment, the stalk height of the mutant, non-naturally occurring or transgenic plants is substantially the same as the control plants at, for example, one, two or three or more months after field transplant or 10, 20, 30 or 36 or more days after topping. For example, the stalk height of the mutant, non-naturally occurring or transgenic plants is not less than the stalk height of the control plants. In another embodiment, the chlorophyll content of the mutant, non-naturally occurring or transgenic plants is substantially the same as the control plants. In another embodiment, the stalk height of the mutant, non-naturally occurring or transgenic plants is substantially the same as the control plants and the chlorophyll content of the mutant, non-naturally occurring or transgenic plants is substantially the same as the control plants. In other embodiments, the size or form or number or colouration of the leaves of the mutant, non-naturally occurring or transgenic plants is substantially the same as the control plants.

In another aspect, there is provided a method for modulating the amount of at least one reducing sugar and at least one non-reducing sugar and at least one free amino acid in at least a part of a plant (for example, the leaves—such as cured leaves), comprising the steps of: (i) modulating the expression or function of an one or more of the NtSULTR3 or NtSULTR3 and NtSUS polypeptides described herein (or any combination thereof as described herein), suitably, wherein the NtSULTR3 or NtSULTR3 and NtSUS polypeptide(s) is encoded by the corresponding NtSULTR3 or NtSULTR3 and NtSUS polynucleotides described herein; (ii) measuring the level of the at least one reducing sugar (for example, glucose and fructose) and at least one non-reducing sugar (for example, sucrose) and at least one free amino acid (for example, glutamine, glutamate and aspartate)—in at least a part (for example, the leaves—such as cured leaves—or tobacco or in smoke) of the mutant, non-naturally occurring or transgenic plant obtained in step (i); and (iii) identifying a mutant, non-naturally occurring or transgenic plant in which the level of the at least at least one reducing sugar and at least one non-reducing sugar and at least one free amino acid has been modulated in comparison to a control plant.

In another aspect, there is provided a method for modulating the amount of at least one reducing sugar and at least one non-reducing sugar and at least one free amino acid in at least a part of cured plant material—such as cured leaf—comprising the steps of: (i) modulating the expression or function of an one or more of the NtSULTR3 or NtSULTR3 and NtSUS polypeptides (or any combination thereof as described herein), suitably, wherein the NtSULTR3 or NtSULTR3 and NtSUS polypeptide(s) is encoded by the corresponding NtSULTR3 or NtSULTR3 and NtSUS polynucleotides described herein; (ii) harvesting plant material—such as one or more of the leaves—and curing for a period of time; (iii) measuring the level of the at least one reducing sugar (for example, glucose and fructose), at least one non-reducing sugar (for example, sucrose) and at least one free amino acid (for example, glutamine, glutamate and aspartate)—in at least a part of the cured plant material obtained in step (ii) or during step (ii); and (iv) identifying cured plant material in which the level of the at least one reducing sugar and at least one non-reducing sugar and at least one free amino acid has been modulated in comparison to a control plant.

An increase in expression as compared to the control may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200%, 300%, 500%, 1000% or more, which includes an increase in transcriptional function or NtSULTR3 or NtSULTR3 and NtSUS polynucleotide expression or NtSULTR3 or NtSULTR3 and NtSUS polypeptide expression or a combination thereof.

An increase in function or activity as compared to a control may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200%, 300%, 500%, 1000% or more, which includes an increase in transcriptional function or NtSULTR3 or NtSULTR3 and NtSUS polynucleotide expression or NtSULTR3 or NtSULTR3 and NtSUS polypeptide expression or a combination thereof.

A decrease in expression as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a decrease in transcriptional function or NtSULTR3 or NtSULTR3 and NtSUS polynucleotide expression or NtSULTR3 or NtSULTR3 and NtSUS polypeptide expression or a combination thereof.

A decrease in function or activity as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a decrease in transcriptional function or NtSULTR3 or NtSULTR3 and NtSUS polynucleotide expression or NtSULTR3 or NtSULTR3 and NtSUS polypeptide expression or a combination thereof.

Polynucleotides and recombinant constructs described herein can be used to modulate the expression or function or activity of the NtSULTR3 or NtSULTR3 and NtSUS polynucleotides or NtSULTR3 or NtSULTR3 and NtSUS polypeptides described herein in a plant species of interest, suitably tobacco.

A number of polynucleotide based methods can be used to increase gene expression in plants and plant cells. By way of example, a construct, vector or expression vector that is compatible with the plant to be transformed can be prepared which comprises the gene of interest together with an upstream promoter that is capable of overexpressing the gene in the plant or plant cell. Exemplary promoters are described herein. Following transformation and when grown under suitable conditions, the promoter can drive expression in order to modulate the levels of NtSULTR3 or NtSULTR3 and NtSUS in the plant, or in a specific tissue thereof. In one exemplary embodiment, a vector carrying one or more NtSULTR3 or NtSULTR3 and NtSUS polynucleotides described herein (or any combination thereof as described herein) is generated to overexpress the gene in a plant or plant cell. The vector carries a suitable promoter—such as the cauliflower mosaic virus CaMV 35S promoter—upstream of the transgene driving its constitutive expression in all tissues of the plant. The vector also carries an antibiotic resistance gene in order to confer selection of the transformed calli and cell lines.

The expression of sequences from promoters can be enhanced by including expression control sequences, which are well known in the art. Signals associated with senescence and signals which are active during the curing procedure are specifically indicated.

Various embodiments are therefore directed to methods for modulating the expression level of one or more NtSULTR3 or NtSULTR3 and NtSUS polynucleotides described herein (or any combination thereof as described herein) by integrating multiple copies of the NtSULTR3 or NtSULTR3 and NtSUS polynucleotide into a plant genome, comprising: transforming a plant cell host with an expression vector that comprises a promoter operably-linked to one or more NtSULTR3 or NtSULTR3 and NtSUS polynucleotides described herein. The polypeptide encoded by a recombinant polynucleotide can be a native polypeptide, or can be heterologous to the cell.

In one embodiment, the plant for use in the present disclosure is a plant that is flue-cured as such plants have a high reducing sugar content (greater than about 14% dry weight when field grown at the end of curing). Mutant, transgenic or non-naturally occurring plants or parts thereof that are flue-cured can have a reducing sugar content that is less than about 14% dry weight when field grown at the end of curing—such as less than about 10% dry weight when field grown at the end of curing, or less than about 5% dry weight when field grown at the end of curing, or less than about 1% dry weight when field grown at the end of curing.

In one embodiment, the plant of use in the present disclosure is a plant that is sun-cured as such plants have a reducing sugar content (greater than about 6.8% dry weight when field grown at the end of curing). Mutant, transgenic or non-naturally occurring plants or parts thereof that are sun-cured can have a reducing sugar content that is less than about 5% dry weight when field grown at the end of curing—such as less than about 2.5% dry weight when field grown at the end of curing, or less than about 1% dry weight when field grown at the end of curing.

In one embodiment, the plant of use in the present disclosure is a plant that is air-cured. Such plants have a reducing sugar content of greater than about 1.7% dry weight when field grown at the end of curing. Mutant, transgenic or non-naturally occurring plants or parts thereof that are sun-cured can have a reducing sugar content that is less than about 1.5% dry weight when field grown at the end of curing—such as less than about 1% dry weight when field grown at the end of curing, or less than about 0.5% dry weight when field grown at the end of curing.

In certain embodiments, the use of plants that are flue-cured or sun-cured is preferred.

9. Breeding

A plant carrying a mutant allele of one or more NtSULTR3 or NtSULTR3 and NtSUS polynucleotides described herein (or any combination thereof as described herein) can be used in a plant breeding program to create useful lines, varieties and hybrids. In particular, the mutant allele can be introgressed into the commercially important varieties described above. Thus, methods for breeding plants are provided, that comprise crossing a mutant plant, a non-naturally occurring plant or a transgenic plant as described herein with a plant comprising a different genetic identity. The method may further comprise crossing the progeny plant with another plant, and optionally repeating the crossing until a progeny with the desirable genetic traits or genetic background is obtained. One purpose served by such breeding methods is to introduce a desirable genetic trait into other varieties, breeding lines, hybrids or cultivars, particularly those that are of commercial interest. Another purpose is to facilitate stacking of genetic modifications of different genes in a single plant variety, lines, hybrids or cultivars. Intraspecific as well as interspecific matings are contemplated. The progeny plants that arise from such crosses, also referred to as breeding lines, are examples of non-naturally occurring plants of the disclosure.

In one embodiment, a method is provided for producing a non-naturally occurring plant comprising: (a) crossing a mutant or transgenic plant with a second plant to yield progeny tobacco seed; (b) growing the progeny tobacco seed, under plant growth conditions, to yield the non-naturally occurring plant. The method may further comprises: (c) crossing the previous generation of non-naturally occurring plant with itself or another plant to yield progeny tobacco seed; (d) growing the progeny tobacco seed of step (c) under plant growth conditions, to yield additional non-naturally occurring plants; and (e) repeating the crossing and growing steps of (c) and (d) multiple times to generate further generations of non-naturally occurring plants. The method may optionally comprises prior to step (a), a step of providing a parent plant which comprises a genetic identity that is characterized and that is not identical to the mutant or transgenic plant. In some embodiments, depending on the breeding program, the crossing and growing steps are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate generations of non-naturally occurring plants. Backcrossing is an example of such a method wherein a progeny is crossed with one of its parents or another plant genetically similar to its parent, in order to obtain a progeny plant in the next generation that has a genetic identity which is closer to that of one of the parents. Techniques for plant breeding, particularly plant breeding, are well known and can be used in the methods of the disclosure. The disclosure further provides non-naturally occurring plants produced by these methods. Certain embodiments exclude the step of selecting a plant.

In some embodiments of the methods described herein, lines resulting from breeding and screening for variant genes are evaluated in the field using standard field procedures. Control genotypes including the original unmutagenized parent are included and entries are arranged in the field in a randomized complete block design or other appropriate field design. For tobacco, standard agronomic practices are used, for example, the tobacco is harvested, weighed, and sampled for chemical and other common testing before and during curing. Statistical analyses of the data are performed to confirm the similarity of the selected lines to the parental line. Cytogenetic analyses of the selected plants are optionally performed to confirm the chromosome complement and chromosome pairing relationships.

DNA fingerprinting, single nucleotide polymorphism, microsatellite markers, or similar technologies may be used in a marker-assisted selection (MAS) breeding program to transfer or breed mutant alleles of a gene into other tobaccos, as described herein. For example, a breeder can create segregating populations from hybridizations of a genotype containing a mutant allele with an agronomically desirable genotype. Plants in the F2 or backcross generations can be screened using a marker developed from a genomic sequence or a fragment thereof, using one of the techniques listed herein. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

According to the disclosure, in a breeding program, successful crosses yield F1 plants that are fertile. Selected F1 plants can be crossed with one of the parents, and the first backcross generation plants are self-pollinated to produce a population that is again screened for variant gene expression (for example, the null version of the gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant gene expression. In some embodiments, a plant population in the F2 generation is screened for variant gene expression, for example, a plant is identified that fails to express a polypeptide due to the absence of the gene according to standard methods, for example, by using a PCR method with primers based upon the polynucleotide sequence information for the polynucleotide(s) described herein (or any combination thereof as described herein).

Hybrid tobacco varieties can be produced by preventing self-pollination of female parent plants (that is, seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting F1 seed is harvested.

Varieties and lines described herein can be used to form single-cross tobacco F1 hybrids. In such embodiments, the plants of the parent varieties can be grown as substantially homogeneous adjoining populations to facilitate natural cross-pollination from the male parent plants to the female parent plants. The F1 seed formed on the female parent plants is selectively harvested by conventional means. One also can grow the two parent plant varieties in bulk and harvest a blend of F1 hybrid seed formed on the female parent and seed formed upon the male parent as the result of self-pollination. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed.

A population of mutant, non-naturally occurring or transgenic plants can be screened or selected for those members of the population that have a desired trait or phenotype. For example, a population of progeny of a single transformation event can be screened for those plants having a desired level of expression or function of the polypeptide(s) encoded thereby. Physical and biochemical methods can be used to identify expression or activity levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme function of polypeptides and polynucleotides; and polypeptide gel electrophoresis, Western blots, immunoprecipitation, and enzyme-linked immunoassays to detect polypeptides. Other techniques such as in situ hybridization, enzyme staining, and immunostaining and enzyme assays also can be used to detect the presence or expression, function or activity of NtSULTR3 or NtSULTR3 and NtSUS polypeptides or polynucleotides.

Mutant, non-naturally occurring or transgenic plant cells and plants are described herein comprising one or more recombinant polynucleotides, one or more polynucleotide constructs, one or more double-stranded RNAs, one or more conjugates or one or more vectors/expression vectors.

10. Modification of Other Genes

Without limitation, the plants and parts thereof described herein can be modified either before or after the expression, function or activity of the one or more NtSULTR3 or NtSULTR3 and NtSUS polynucleotides or NtSULTR3 or NtSULTR3 and NtSUS polypeptides according to the present disclosure have been modulated.

One or more of the following further genetic modifications can be present in the mutant, non-naturally occurring or transgenic plants and parts thereof.

One or more genes that are involved in the conversion of nitrogenous metabolic intermediates can be modified resulting in lower levels of at least one tobacco-specific nitrosamine (TSNA). Non-limiting examples of such genes include those encoding nicotine demethylase—such as CYP82E4, CYP82E5 and CYP82E10 as described in WO2006/091194, WO2008/070274, WO2009/064771 and WO2011/088180—and nitrate reductase, as described in WO2016/046288.

One or more genes that are involved in heavy metal uptake or heavy metal transport can be modified resulting in lower heavy metal content. Non-limiting examples include genes in the family of multidrug resistance associated polypeptides, the family of cation diffusion facilitators (CDF), the family of Zrt-Irt-like polypeptides (ZIP), the family of cation exchangers (CAX), the family of copper transporters (COPT), the family of heavy-metal ATPases (for example, HMAs, as described in WO2009/074325 and WO2017/129739), the family of homologs of natural resistance-associated macrophage polypeptides (NRAMP), and other members of the family of ATP-binding cassette (ABC) transporters (for example, MRPs), as described in WO2012/028309, which participate in transport of heavy metals—such as cadmium.

Other exemplary modifications can result in plants with modulated expression or function of isopropylmalate synthase which results in a change in sucrose ester composition which can be used to alter favour profile (see WO2013/029799).

Other exemplary modifications can result in plants with modulated expression or function of threonine synthase in which levels of methional can be modulated (see WO2013/029800).

Other exemplary modifications can result in plants with modulated expression or function of one or more of neoxanthin synthase, lycopene beta cyclase and 9-cis-epoxycarotenoid dioxygenase to modulate beta-damascenone content to alter flavour profile (see WO2013/064499).

Other exemplary modifications can result in plants with modulated expression or function of members of the CLC family of chloride channels to modulate nitrate levels therein (see WO2014/096283 and WO2015/197727).

Other exemplary modifications can result in plants with modulated expression or function of one or more asparagine synthetases to modulate levels of asparagine in leaf and modulated levels of acrylamide in aerosol produced upon heating or combusting the leaf (see WO2017/129739).

Other exemplary modifications can result in plants with modulated protease activity during curing (see WO2016/009006).

Other exemplary modifications can result in plants having reduced nitrate levels by altering the gene expression of nitrate reductase (for example, Nia2) or the activity of the protein encoded thereby (see WO2016/046288).

Other exemplary modifications can result in plants having modified alkaloid levels by altering the gene expression of putative ABC-2 transporters NtABCGI-T and NtABCGI-S or the activity of the protein encoded thereby (see WO2019/086609) Other exemplary modifications can result in plants having modulated time to flowering by altering the gene expression of genes encoding Terminal Flower 1 (TFL1) or the activity of the protein encoded thereby (see WO2018/114641).

Other exemplary modifications can result in plants with modulated expression or function of one or more asparagine synthetases to modulate levels of asparagine in leaf and modulated levels of acrylamide in aerosol produced upon heating or combusting the leaf (see WO2017/042162).

Examples of other modifications include modulating herbicide tolerance, for example, glyphosate is an active ingredient of many broad spectrum herbicides. Glyphosate resistant transgenic plants have been developed by transferring the aroA gene (a glyphosate EPSP synthetase from *Salmonella typhimurium* and *E. coli*). Sulphonylurea resistant plants have been produced by transforming the mutant ALS (acetolactate synthetase) gene from *Arabidopsis*. OB polypeptide of photosystem II from mutant *Amaranthus hybridus* has been transferred in to plants to produce atrazine resistant transgenic plants; and bromoxynil resistant transgenic plants have been produced by incorporating the bxn gene from the bacterium *Klebsiella pneumoniae*.

Another exemplary modification results in plants that are resistant to insects. *Bacillus thuringiensis* (Bt) toxins can provide an effective way of delaying the emergence of Bt-resistant pests, as recently illustrated in broccoli where pyramided cry1Ac and cry1C Bt genes controlled diamondback moths resistant to either single polypeptide and significantly delayed the evolution of resistant insects.

Another exemplary modification results in plants that are resistant to diseases caused by pathogens (for example, viruses, bacteria, fungi). Plants expressing the Xa21 gene (resistance to bacterial blight) with plants expressing both a Bt fusion gene and a chitinase gene (resistance to yellow stem borer and tolerance to sheath) have been engineered.

Another exemplary modification results in altered reproductive capability, such as male sterility.

Another exemplary modification results in plants that are tolerant to abiotic stress (for example, drought, temperature, salinity), and tolerant transgenic plants have been produced by transferring acyl glycerol phosphate enzyme from *Arabidopsis*; genes coding mannitol dehydrogenase and sorbitol dehydrogenase which are involved in synthesis of mannitol and sorbitol improve drought resistance.

Another exemplary modification results in plants in which the activity of one or more nicotine N-demethylases is modulated such that the levels of nornicotine and metabolites of nornicotine—that are formed during curing can be modulated (see WO2015169927).

Other exemplary modifications can result in plants with improved storage polypeptides and oils, plants with enhanced photosynthetic efficiency, plants with prolonged shelf life, plants with enhanced carbohydrate content, and plants resistant to fungi. Transgenic plants in which the expression of S-adenosyl-L-methionine (SAM) or cystathionine gamma-synthase (CGS) has been modulated are also contemplated.

One or more genes that are involved in the nicotine synthesis pathway can be modified resulting in plants or parts of plants that when cured, produce modulated levels of nicotine.

The nicotine synthesis genes can be selected from the group consisting of: A622, BBLa, BBLb, JRE5L1, JRE5L2, MATE1, MATE 2, MPO1, MPO2, MYC2a, MYC2b, NBB1, nic1, nic2, NUP1, NUP2, PMT1, PMT2, PMT3, PMT4 and QPT or a combination of one or more thereof.

One or more genes that are involved in controlling the amount of one or more alkaloids can be modified resulting in plants or parts of plants that produce modulated levels of alkaloid.

Alkaloid level controlling genes can be selected from the group consisting of; BBLa, BBLb, JRE5L1, JRE5L2, MATE1, MATE 2, MYC2a, MYC2b, nic1, nic2, NUP1 and NUP2 or a combination of two or more thereof.

One or more such traits may be introgressed into the mutant, non-naturally occurring or transgenic plants from another cultivar or may be directly transformed into it.

Various embodiments provide mutant plants, non-naturally occurring plants or transgenic plants, as well as biomass in which the expression level of one or more polynucleotides according to the present disclosure are modulated to thereby modulate the level of polypeptide(s) encoded thereby.

11. Consumable Products

Parts of the plants described herein, particularly the leaf lamina and midrib of such plants, can be incorporated into or used in making various consumable products including but not limited to aerosol forming materials, aerosol forming devices, smoking articles, smokable articles, smokeless products, medicinal or cosmetic products, intravenous preparations, tablets, powders, and tobacco products. Examples of aerosol forming materials include tobacco compositions, tobaccos, tobacco extract, cut tobacco, cut filler, cured tobacco, expanded tobacco, homogenized tobacco, reconstituted tobacco, and pipe tobaccos. Smoking articles and smokable articles are types of aerosol forming devices. Examples of smoking articles or smokable articles include cigarettes, cigarillos, and cigars. Examples of smokeless products comprise chewing tobaccos, and snuffs. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or a slurry, deposited on, mixed in, surrounded by, or otherwise combined with other ingredients in any format, such as flakes, films, tabs, foams, or beads. The term 'smoke' is used to describe a type of aerosol that is produced by smoking articles, such as cigarettes, or by combusting an aerosol forming material.

In one embodiment, there is also provided cured plant material from the mutant, transgenic and non-naturally occurring plants described herein. Processes of curing green tobacco leaves are known by those having skills in the art and include without limitation air-curing, fire-curing, flue-curing and sun-curing as described herein.

In another embodiment, there is described tobacco products including tobacco-containing aerosol forming materials comprising plant material—such as leaves, preferably cured leaves—from the mutant tobacco plants, transgenic tobacco plants or non-naturally occurring tobacco plants described herein. The tobacco products described herein can be a blended tobacco product which may further comprise unmodified tobacco.

12. Products and Methods for Crop Management and Agriculture

The mutant, non-naturally occurring or transgenic plants may have other uses in, for example, agriculture.

The disclosure also provides methods for producing seeds comprising cultivating the mutant plant, non-naturally occurring plant, or transgenic plant described herein, and collecting seeds from the cultivated plants. Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the package that describes the nature of the seeds therein.

Compositions, methods and kits for genotyping plants for identification, selection, or breeding can comprise a means of detecting the presence of a NtSULTR3 or NtSULTR3 and NtSUS polynucleotide(s) in a sample of polynucleotide. Accordingly, a composition is described comprising one or more primers for specifically amplifying at least a portion of one or more of the NtSULTR3 or NtSULTR3 and NtSUS polynucleotides and optionally one or more probes and optionally one or more reagents for conducting the amplification or detection.

Accordingly, gene specific oligonucleotide primers or probes comprising about 10 or more contiguous polynucleotides corresponding to the NtSULTR3 or NtSULTR3 and NtSUS polynucleotide(s) described herein are disclosed. Said primers or probes may comprise or consist of about 15, 20, 25, 30, 40, 45 or 50 more contiguous polynucleotides that hybridise (for example, specifically hybridise) to the NtSULTR3 or NtSULTR3 and NtSUS polynucleotide(s) described herein. In some embodiments, the primers or probes may comprise or consist of about 10 to 50 contiguous nucleotides, about 10 to 40 contiguous nucleotides, about 10 to 30 contiguous nucleotides or about 15 to 30 contiguous nucleotides that may be used in sequence-dependent methods of gene identification (for example, Southern hybridization) or isolation (for example, in situ hybridization of bacterial colonies or bacteriophage plaques) or gene detection (for example, as one or more amplification primers in amplification or detection). The one or more specific primers or probes can be designed and used to amplify or detect a part or all of the polynucleotide(s). By way of specific example, two primers may be used in a PCR protocol to amplify a polynucleotide fragment. The PCR may also be performed using one primer that is derived from a polynucleotide sequence and a second primer that hybridises to the sequence upstream or downstream of the polynucleotide sequence—such as a promoter sequence, the 3' end of the mRNA precursor or a sequence derived from a vector. Examples of thermal and isothermal techniques useful for in vitro amplification of polynucleotides are well known in the art. The sample may be or may be derived from a plant, a plant cell or plant material or a tobacco product made or derived from the plant, the plant cell or the plant material as described herein.

In a further aspect, there is also provided a method of detecting a NtSULTR3 or NtSULTR3 and NtSUS polynucleotide(s) described herein (or any combination thereof as described herein) in a sample comprising the step of: (a) providing a sample comprising, or suspected of comprising, a polynucleotide; (b) contacting said sample with one or more primers or one or more probes for specifically detecting at least a portion of the NtSULTR3 or NtSULTR3 and NtSUS polynucleotide(s); and (c) detecting the presence of an amplification product, wherein the presence of an amplification product is indicative of the presence of the NtSULTR3 or NtSULTR3 and NtSUS polynucleotide(s) in the sample. In a further aspect, there is also provided the use of one or more primers or probes for specifically detecting at least a portion of the NtSULTR3 or NtSULTR3 and NtSUS polynucleotide(s). Kits for detecting at least a portion of the NtSULTR3 or NtSULTR3 and NtSUS polynucleotide(s) are also provided which comprise one or more primers or probes for specifically detecting at least a portion of the NtSULTR3 or NtSULTR3 and NtSUS polynucleotide(s). The kit may comprise reagents for polynucleotide amplification—such as PCR—or reagents for probe hybridization-detection technology—such as Southern Blots, Northern Blots, in-situ hybridization, or microarray. The kit may comprise reagents for antibody binding-detection technology such as Western Blots, ELISAs, SELDI mass spectrometry or test strips. The kit may comprise reagents for DNA sequencing. The kit may comprise reagents and instructions for using the kit.

In some embodiments, a kit may comprise instructions for one or more of the methods described. The kits described may be useful for genetic identity determination, phylogenetic studies, genotyping, haplotyping, pedigree analysis or plant breeding particularly with co-dominant scoring.

The present disclosure also provides a method of genotyping a plant, a plant cell or plant material comprising a NtSULTR3 or NtSULTR3 and NtSUS polynucleotide as described herein. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. The specific method of genotyping may employ any number of molecular marker analytic techniques including amplification fragment length polymorphisms (AFLPs). AFLPs are the product of allelic differences between amplification fragments caused by polynucleotide variability. Thus, the present disclosure further provides a means to follow segregation of one or more genes or polynucleotides as well as chromosomal sequences genetically linked to these genes or polynucleotides using such techniques as AFLP analysis.

13. Tobacco Extracts

There is also disclosed herein methods of producing a liquid tobacco extract and a liquid tobacco extract produced by the method(s).

A specific extraction temperature is selected for the tobacco starting material(s), preferably based on at least the reducing sugar content and optionally the nicotine content of the tobacco starting material(s). The extraction temperature(s) are typically selected from within the range of about 100 degrees Celsius to about 160 degrees Celsius. The duration of the heating step may optionally be controlled to provide a degree of control over the composition of the extract derived from the tobacco starting material(s). Suitably, the tobacco starting material(s) is heated at the extraction temperature for at least about 90 minutes, more suitably at least about 120 minutes. The heating step is typically carried out in an inert atmosphere. Suitably, a flow of an inert gas—such as nitrogen—is passed through the starting tobacco material during the heating step. The volatile tobacco compounds are released into the flow of inert gas during the heating step such that the inert gas acts as a carrier for the volatile components. The flow of inert gas can be at a flow rate of at least about 25 litres per minute, more suitably at least about 30 litres per minute. A relatively high flow rate of inert gas may advantageously improve the efficiency of extraction from the tobacco starting material. Optionally, the heating step may be carried out under vacuum. Suitable heating methods for carrying out the heating of the tobacco starting material are known to the skilled person and include: dry distillation, hydrodistillation, vacuum distillation, flash distillation and thin film hydrodistillation.

Where the volatile compounds are collected by absorption in a liquid solvent the step of forming the liquid tobacco extract can comprise drying the solution of the volatile compounds in the liquid solvent in order to concentrate the solution. Drying may be carried out using any suitable means, including but not limited to desiccation, molecular sieves, freeze drying, phase separation, distillation, membrane permeation, controlled crystallisation of water and filtering, reverse hygroscopicity, ultracentrifugation, liquid chromatography, reverse osmosis or chemical drying.

The liquid tobacco extract is particularly suitable for producing a composition or formulation or gel composition, for use in an aerosol-generating system. An aerosol-generating system comprising the composition or formulation or gel composition is disclosed. In such an aerosol-generating system, the composition or formulation or gel is typically heated within an aerosol-generating device—such as a device comprising a heater element that interacts with the composition or formulation or gel incorporating the liquid tobacco extract to produce an aerosol. During use, volatile compounds are released by heat transfer and entrained in air drawn through the aerosol generating device. As the released compounds cool they condense to form an aerosol that is inhaled by the consumer.

The invention is further described in the Examples below, which are provided to describe the invention in further detail. These examples, which set forth a preferred mode presently contemplated for carrying out the invention, are intended to illustrate and not to limit the invention.

EXAMPLES

Example 1—Materials & Methods

DNA Extraction and Plant Genotyping

Leaf samples are extracted using the BioSprint 96 (Qiagen, Hilden, Germany) together with the BioSprint 96 DNA plant kit (Qiagen, Hilden, Germany). DNA samples are used in a TaqMan reaction in order to determine the plant genotype. Taqman is carried out using the ABI PRISM 7900HT Sequence Detection System (Applied Biosystems, Life Technologies, Foster City, CA, USA) and TaqMan Fast Advanced Master Mix (Applied Biosystems, Foster City, CA, USA).

Measuring Free Amino Acid Content

Amino acid content can be measured using various methods that are known in the art. One such method is Method MP 1471 rev 5 2011, Resana, Italy: Chelab Silliker S.r.I, Mérieux NutriSciences Company. For amino acid determination in cured plant leaves, after mid-rib removal, cured lamina are dried at 40° C. for 2-3 days, if required. Tobacco material is then ground in fine powder (~100 uM) before the analysis of amino acid content. Another method for measuring amino acid content in plant material is described in UNI EN ISO 13903:2005. The measurement of free amino acid content can be performed according to UNI EN ISO 13903:2005.

Measuring Reducing Sugar Content

Reducing sugar content can be measured using a segmented-flow colorimetric method developed for analysis of tobacco samples as adapted by Skalar Instrument Co (West Chester, PA) and described in *Tobacco Science* 20: 139-144 (1976). The measurement of reducing sugar content is also described in Coresta Recommended Method 38, CRM38, CRM and ISO 15154: 2003. For reducing sugar determination in cured leaves, after mid-rib removal, cured lamina are dried at 40° C. for 2-3 days, if required. Tobacco material is then ground in fine powder (~100 uM) before the analyses of reducing sugars. The measurement of reducing sugar content is performed according to ISO 15154: 2003.

Example 2—Analysis of Expression of NtSULTR Genes

Table 1 shows that NtSULTR3;3-T is expressed in whole plant tissues, particularly in petal. Interestingly, the copy NtSULTR3;3-S is not expressed in Virginia tobacco, but is expressed in some other tobaccos—such as TN90. Apparently, the NtSULTR3;3-S genomic sequence is either not identified in the Virginia genome or altered in Virginia and dark tobacco (Sierro et al. (2014) *Nat Commun.* May 8; 5:3833, see Tables 3 & 4). NtSULTR3;3-S genomic and polypeptide sequences are deduced from a TN90 sequencing library. The other SULTR3 genes expressed in petal are NtSULTR3;1A-S, NtSULTR3;1A-T and NtSULTR3;1B-S. NtSULTR3;4A-T is apparently more specific to stem. NtSULTR3;2-S is expressed in sepal and root. Interestingly, several SULTR3 genes are not or poorly expressed in green leaves, namely NtSULTR3;1A-S, NtSULTR3;1A-T, NtSULTR3;3-S, NtSULTR3;4A-S, NtSULTR3;4B-S, NtSULTR3;4B-T, NtSULTR3;5-S and NtSULTR3;5-T.

Example 3—Expression of NtSULTR Genes During Curing

During Virginia (flue-cured) tobacco curing, reducing sugars, glucose and fructose, increase in the yellowing leaf by a factor ~3, reaching a maximum level after one or two days of curing following leaf harvest. Free amino acids also increase by a factor ~4 after one or two days of curing. This indicates that leaf yellowing activities impact the production of sugars, reducing sugars and free amino acids. Among all NtSULTR3 transcripts, NtSULTR3;1A-S and NtSULTR3;3-T expression increases by a factor close to 3 (in log 2) after 2 days of curing (transcriptomic data from Affymetric Tobarray chips, see FIG. 1A). This suggests that the expression of these two genes may activate the chloroplast import of sulfate during the early phase of curing. RNAseq data (see FIG. 1B) confirm the data presented in FIG. 1A. Other SULTR3 genes (log 2>3) may also play a role in the transport of sulfate into the chloroplast during curing, principally NtSULTR3;1A-T, NtSULTR3;1B-S, NtSULTR3;1B-T, NtSULTR3;4A-S and NtSULTR3;4A-T.

Example 4—Sulphate Levels During Curing

Figure 2:
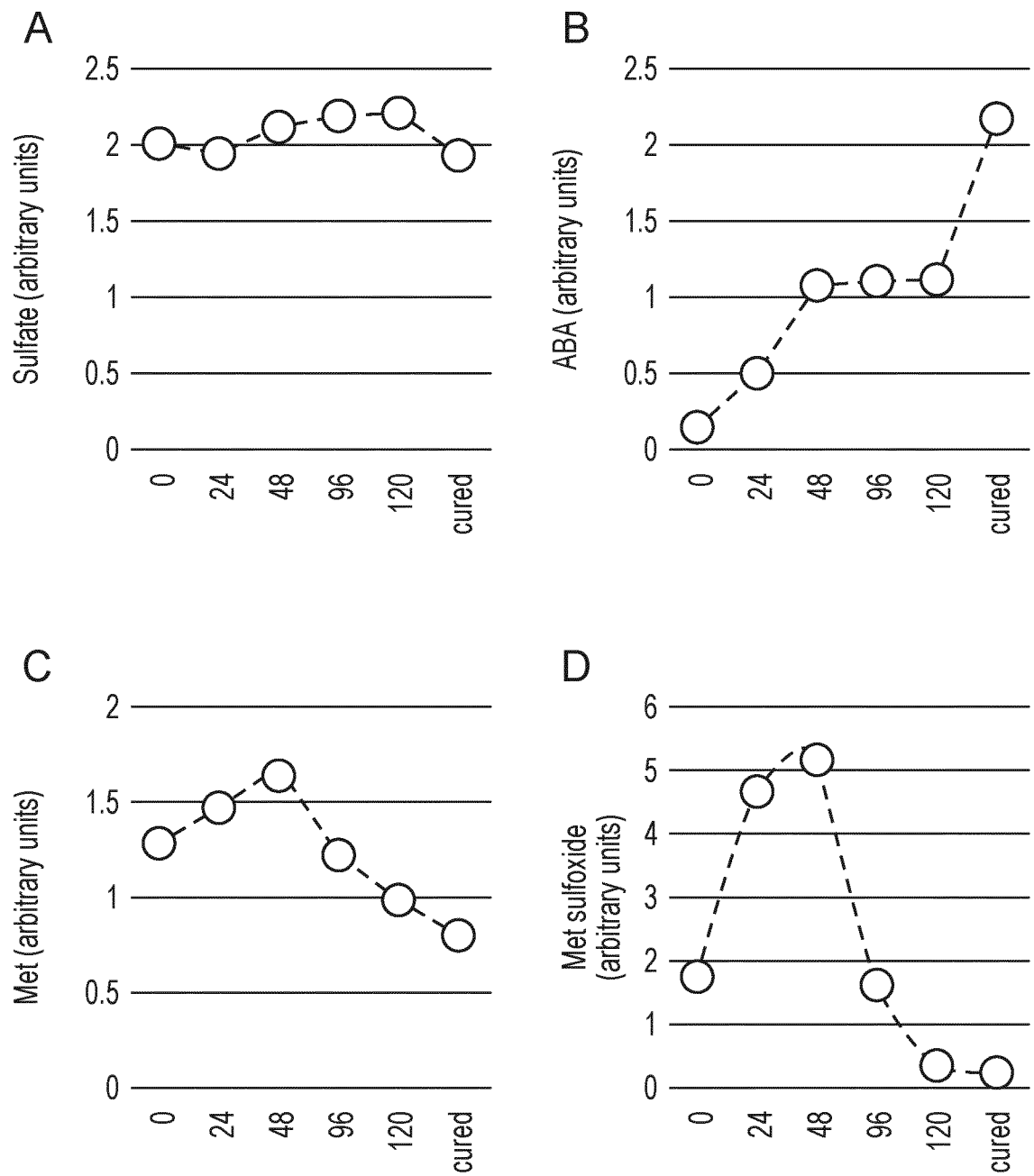
FIG. 2 is a series of graphs showing variation of sulfate (A), abscisic acid (ABA)(B), methionine (Met, C) and methionine sulfoxide (Met sulfoxide, D) during the curing-time course of a dark tobacco. No specific concentration values are available within such metabolomic data (arbitrary units).

Metabolomic data collected from a curing-time course of a dark tobacco (lyophilized leaf lamina material) shows that the major pool of sulfate is not affected during the yellowing phase, thereby suggesting that a small part of the total sulfate pool is reduced during curing (see FIG. 2A). On the other hand, ABA as a known marker of leaf senescence increase during the curing time-course (see FIG. 2B). After 48 h, 30% more methionine and three times more methionine sulfoxide are detected in the leaf lamina tissues (see FIGS. 2C and 2D). Methionine sulfoxide is a degradation product of methionine resulting from ROS activities. ROS activities are known to increase during leaf senescence (see Jajic et al. (2015) *Plants* 4:393-411. doi:10.3390/plants4030393).

Example 5—Expression of SULTR3 and SAG12 During Curing

In the same samples (dark, air-cured tobacco), frozen leaf lamina material is also used to isolate RNA and analyze the expression of SULTR3 genes and SAG12. SAG12 is a transcriptional marker of leaf senescence which is 60× more expressed after 96 h leaf yellowing. Simultaneously, NtSULTR3;1A-S, which is the major SULTR3 expressed genes during leaf curing (see FIG. 1), undergoes about 20 times more expression after 96 h curing (see Table 2). As observed previously in FIG. 1, other members of the SULTR3 family are also expressed during leaf curing, including NtSULTR3;1A-T, NtSULTR3;1B-S, NtSULTR3;1B-T, NtSULTR3;3-T, NtSULTR3;4A-S, NtSULTR3;4A-T and NtSULTR3;4B-T.

Example 6—Silencing of NtSULTR3;1A-S and NtSULTR3;1A-T

Figure 3:
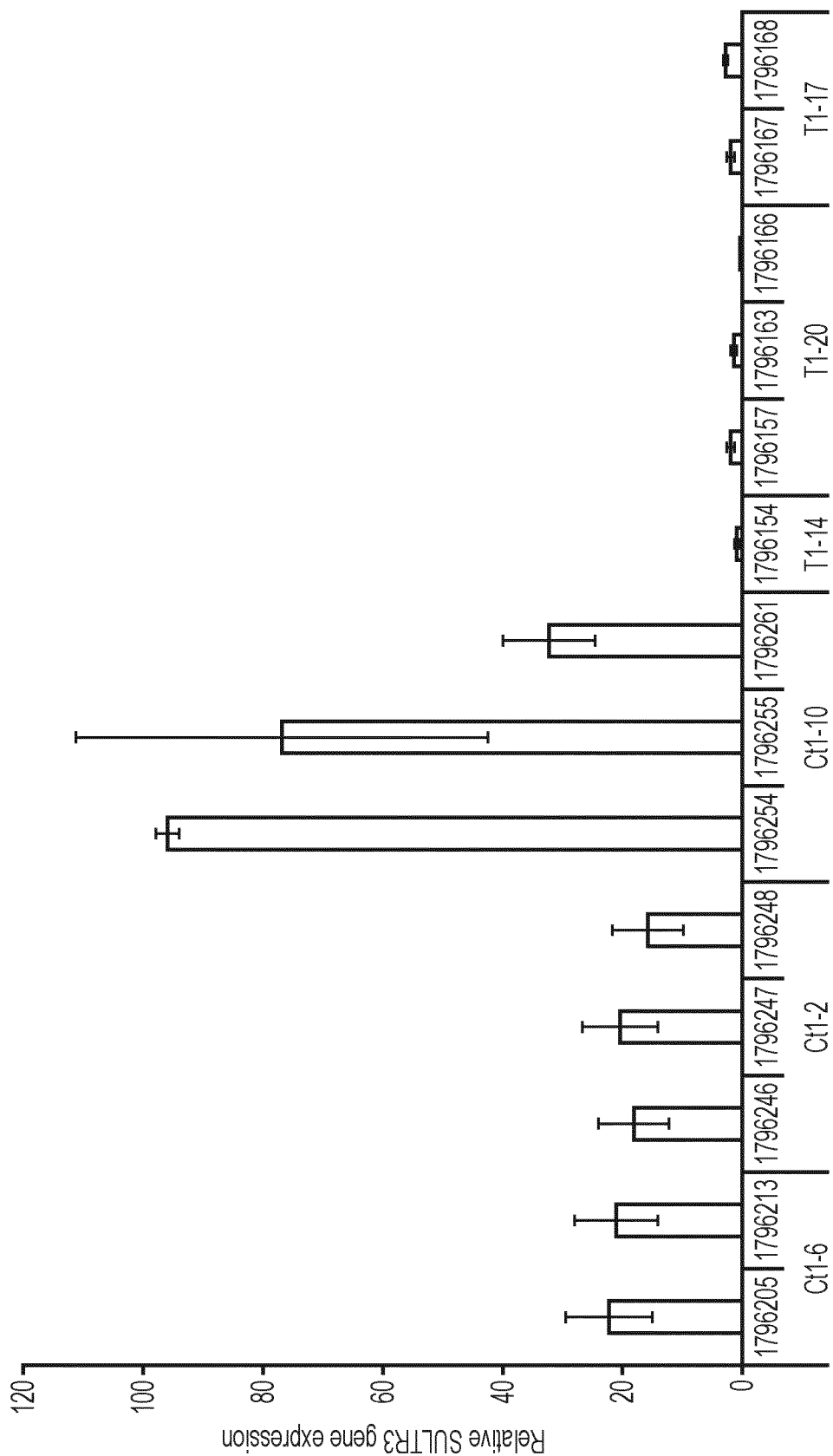
FIG. 3 is graph showing silencing of NtSULTR3;1A-S and NtSULTR3;1A-T using a GATEWAY vector and measurement of expression in Virginia tobacco leaf after 48 h curing using qPCR. T1-14, T1-20 and T1-17 are anti-NtSULTR3;1A transgenic lines and CT1-6, CT1-2 and CT1-10 correspond to control lines that are not silenced.

As the major SULTR3 induced gene during leaf curing, the silencing of NtSULTR3;1A (both S and T copies, SEQ ID NO: 1 and 3) is investigated in flue-cured tobacco to determine whether NtSULTR3;1A genes contribute to change reducing sugars and free amino acid levels in cured tobacco leaves. A specific DNA fragment of the coding sequence of both NtSULTR3;1A-S and NtSULTR3;1A-T is cloned with the strong constitutive *Mirabilis* Mosaic Virus (MMV) promoter in a GATEWAY vector. The gene fragment of NtSULTR3;1A is flanked between MMV and the 3' nos terminator sequence of the nopaline synthase gene of *Agrobacterium tumefaciens*. The tobacco line K326 is transformed using standard *Agrobacterium*-mediated transformation protocols. Independent T1 plant leaves and their respective control lines are analyzed by qPCR after 48 h curing to confirm the silencing of NtSULTR3;1A (see FIG. 3).

Example 7—Analysis of Glucose, Fructose and Sucrose Levels in NtSULTR3;1A-S and NtSULTR3;1A-T Silenced Plants The mid-position leaves of the controls and transgenic 35S:NtSULTR3;1A-RNAi lines are collected at maturation and subjected to flue-curing. The sugars (glucose, fructose and sucrose) are analyzed in fully cured leaves (see FIG. 4).

Figure 4:
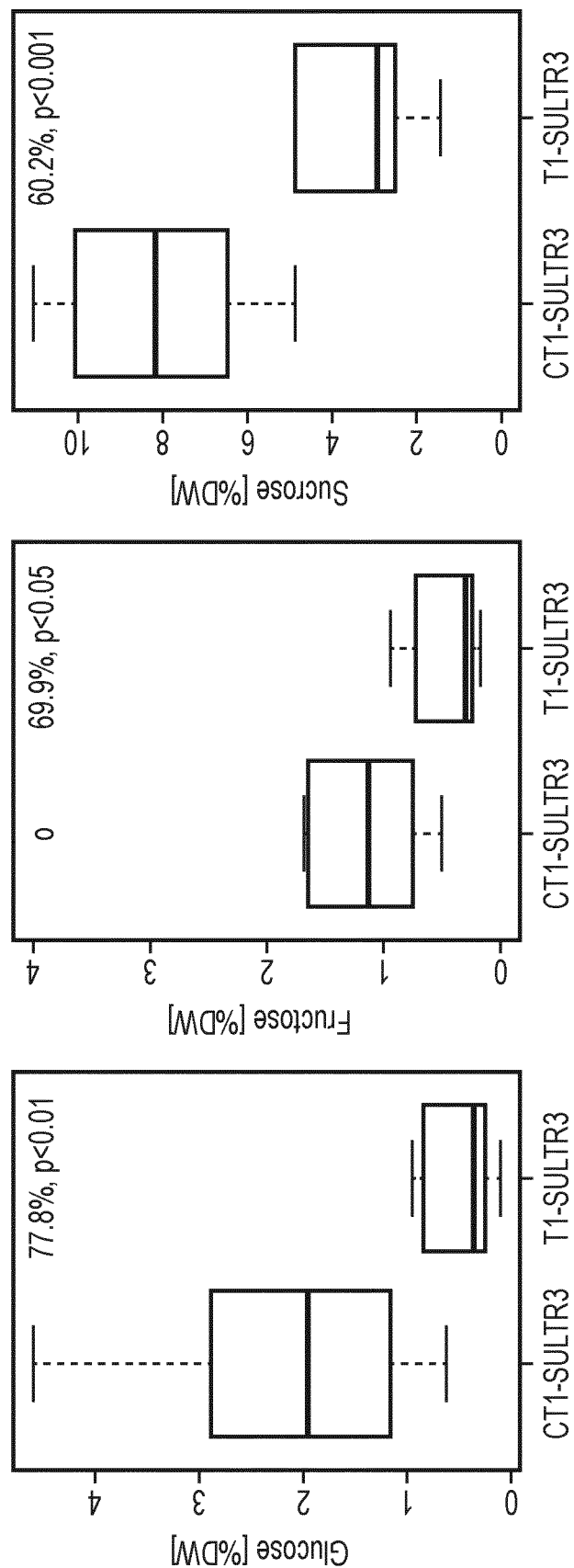
FIG. 4 shows sugar (glucose, fructose and sucrose) levels in 35S:NtSULTR3;1A-RNAi lines (T1-SULTR3) and control (CT1-SULTR3) cured leaves (CT1, n=8; and T1, n=6). Box plots are presented as well as T-test statistical analyses.

The data presented in FIG. 4 show a strong and significant reduction of glucose, fructose and sucrose in the anti-NtSULTR3;1A plants. The level of glucose, fructose and sucrose is reduced by 77%, 69% and 60%, respectively. No impact on visual plant fitness and chlorophyll degradation is observed in anti-NtSULTR3;1A plants cultivated under a greenhouse environment.

Figure 5:
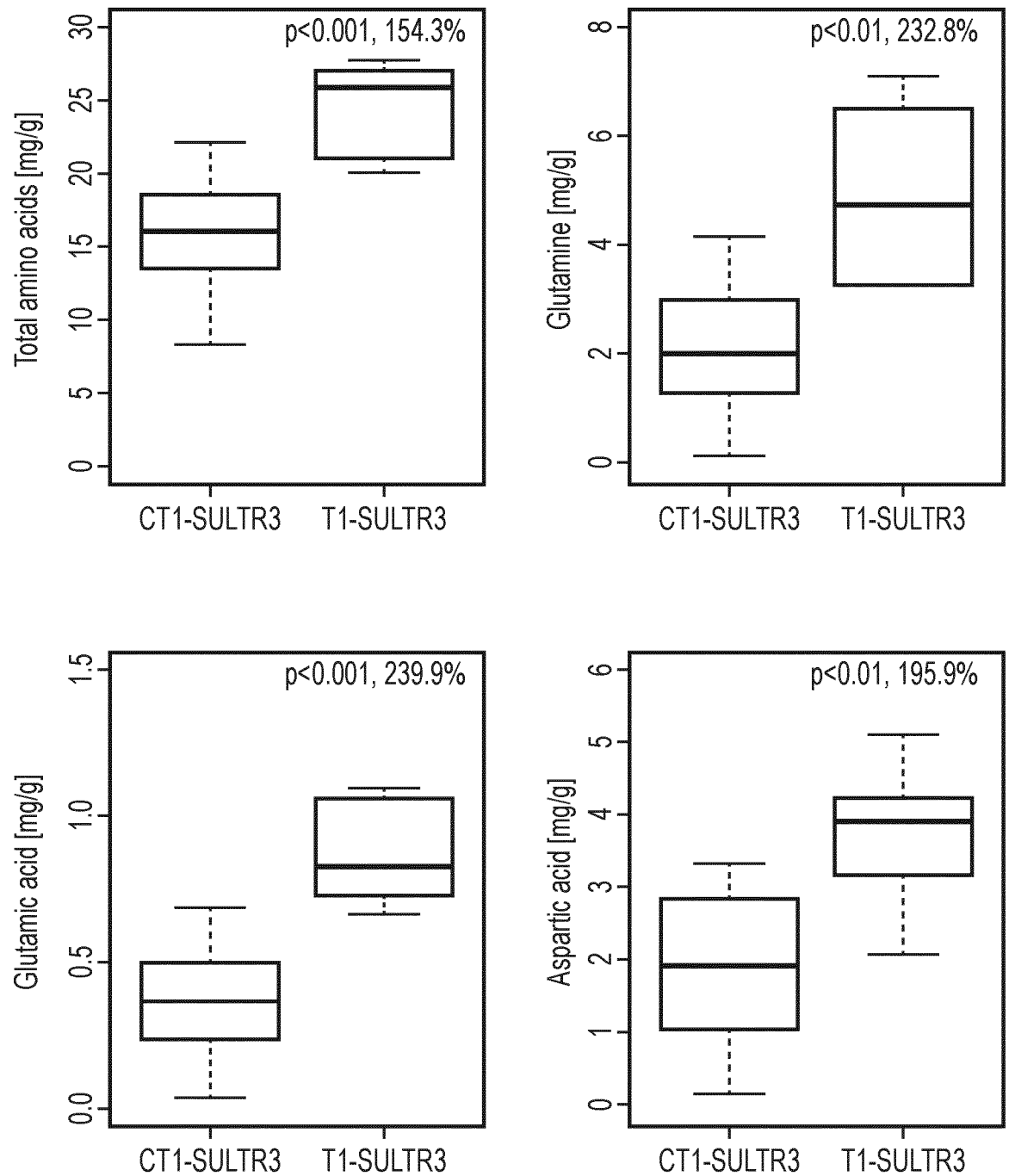
FIG. 5 shows free amino acids content in 35S:NtSULTR3; 1A-RNAi lines (T1-SULTR3) and control (CT1-SULTR3) cured leaves (CT1, n=8; and T1, n=6). Box plots are presented as well as T-test statistical analyses.
Figure 6:
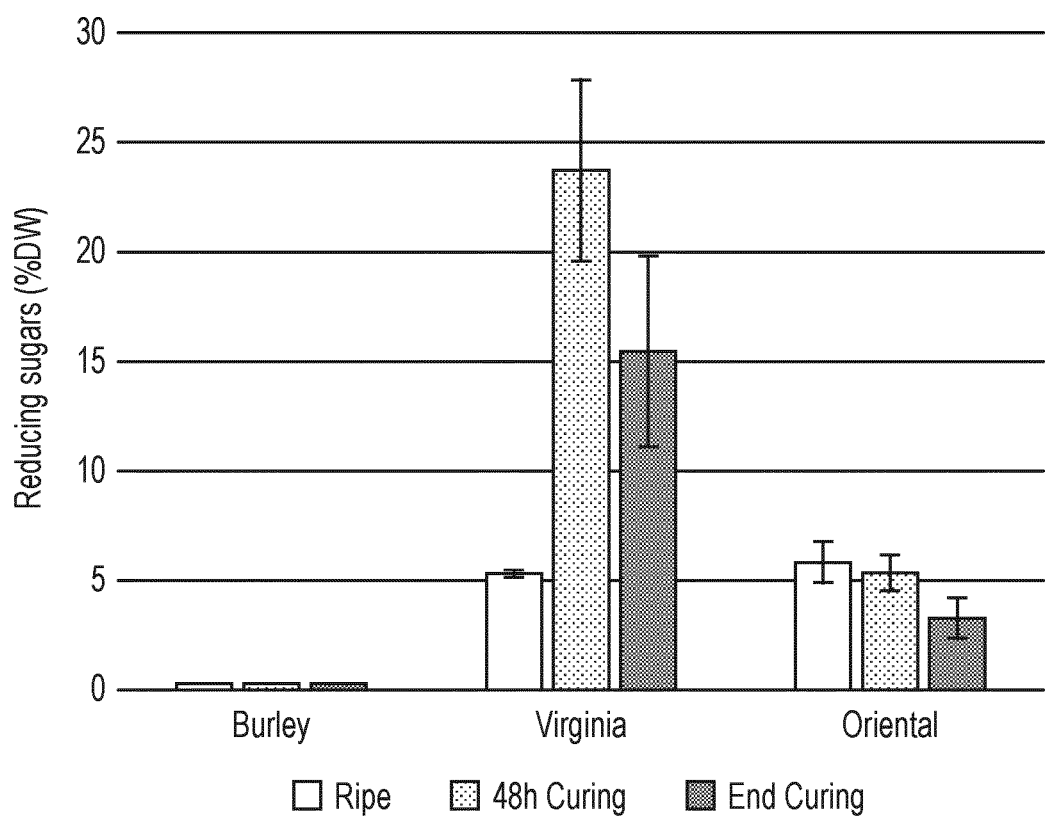
FIG. 6 is a bar graph showing the content per variety of reducing sugars after harvest (ripe), after two days of curing (48 hours curing) and at the end of curing in Burley, Virginia and Oriental tobacco.

Example 8—Analysis of Free Amino Acid Levels in NtSULTR3;1A-S and NtSULTR3;1A-T Silenced Plants The total free amino acids (left panel) are analyzed in fully cured leaves. The data presented in FIG. 5 shows a strong and significant increase of free amino acids in the cured anti-NtSULTR3;1A compared to control plants, which is concomitant to the decrease of sugars (FIG. 4). The major amino acids increasing during the curing of anti-NtSULTR3;1A plants are glutamine, glutamate and aspartate. Free amino acids, glutamine, glutamate and aspartate are about 1.5, 2.3, 2.4 and 2 times more elevated in 35S:NtSULTR3;1A-RNAi lines, respectively. It has to be noticed that asparagine also significantly increases (1.5×) compared to control plants, but with a limited significance (P<0.05, n=6) level).

Example 9—Identification of SUS Genes after Curing in Burley, Virginia and Oriental Tobacco Leaf To identify key functions contributing to sucrose metabolism during early curing time of Burley, Virginia and Oriental tobacco leaf, an overrepresentation analysis for the function of genes up-regulated in cured leaves after 48 hours curing, as compared to the ripe leaves at harvest (log 2 fold change >2, adjusted p-value<0.05) is performed in Burley, Virginia and Oriental tobacco. Genes involved in the production of reducing sugars and that are active after 48 hours curing independently of the curing types and tobacco varieties are identified. Tobacco genes involved in the production of reducing sugars are identified.

The key genes directly involved in the production of reducing sugars during early curing in leaves belong to the gene family of SUS. SUS is likely a key enzyme to drive the accumulation of reducing sugars in cured detached leaves.

The tobacco genome is found to have 12 NtSUS gene products distributed in 6 families with one S and one T copy from each ancestor: NtSUS1-S, NtSUS1-T, NtSUS2-S, NtSUS2-T, NtSUS3-S, NtSUS3-T, NtSUS4-S, NtSUS4-T, NtSUS5-S, NtSUS5-T, NtSUS6-S and NtSUS6-T.

SUS transcripts are from the genomic sequences NtSUS2-S, NtSUS3-S, NtSUS3-T and NtSUS4-S. These genes are up-regulated during leaf curing (senescence), as shown in Table 3. This confirms that S copies are particularly involved in the chemical modification of early cured leaves and in this particular case the increase of glucose and fructose.

Although low amounts of reducing sugar levels are found in cured leaves of Burley, compared to Virginia and Oriental, NtSUS genes are nevertheless activated in Burley (see Table 3), likely as a constitutive response to also ensure available carbon source for amino acid synthesis during the early curing phase.

In both Burley (BU) and Virginia (FC), NtSUS1-S and NtSUS1-T, which are not expressed during early curing (see Table 3), are particularly expressed in root and stem, indicating a possible specific function in these tissues to deliver carbohydrates for cell wall synthesis or supply carbon resources under anoxia (see Table 4). On the other hand, NtSUS3-S, NtSUS3-T, NtSUS4-S, which are induced during early leaf curing, are also expressed in all organs, whereas NtSUS2-S and NtSUS2-T are mainly expressed in immature flowers and petals. NtSUS5-S, NtSUS5-T, NtSUS6-S and NtSUS6-T are expressed at low levels in all the analysed plant tissues (see Table 4).

To increase the pool of reducing sugars in cured leaves, overexpression of NtSUS2-S, NtSUS3-S, NtSUS3-T or NtSUS4-S, or a combination of one or more thereof, using a senescence induced promoter like SAG12 or E4 might be considered (the use of a constitutive promoter may strongly change plant metabolism). On the other hand, knocking-out NtSUS2-S, NtSUS3-S, NtSUS3-T or NtSUS4-S, or a combination of one or more thereof, may contribute to reduce the content of reducing sugars in cured leaves.

Example 10—Silencing of NtSUS Expression in Virginia Tobacco Leaf

The silencing of NtSUS in Burley tobacco is investigated to determine if these genes contribute to decreasing reducing sugar content in cured Virginia tobacco leaves. A specific DNA fragment within the coding sequence of both NtSUS is cloned with the strong constitutive *Mirabilis* Mosaic Virus (MMV) promoter in a GATEWAY vector. The NtSUS gene fragment is flanked between MMV and the 3' nos terminator sequence of the nopaline synthase gene of *Agrobacterium tumefaciens*.

To enable the selection of low reducing sugar content plants, independent TO plant leaves and respective control lines are analyzed after 60 h curing to determine the impact on reducing sugar content. The best TO lines displaying the lowest level of reducing sugar are selected. Seeds are harvested from these best TO lines. T1 progeny are assayed by qPCR to determine the efficiency of the NtSUS silencing events in relation to decreasing reducing sugar content.

Manipulating NtSUS genes (for example, with either a constitutive promotor or a specific senescence promotor—such as SAG12 or E4) may change the chemistry of tobacco cured leaves. Similarly knocking-out NtSUS genes using a genome editing strategy—such as CRISPR or mutant selection may change amino acid leaf chemistry of the main varieties of commercial tobacco.

Example 11—Producing a Liquid Tobacco Extract from a NtSULTR3 Modified Tobacco Plant and a NtSUS Modified Tobacco Plant Each Having Modulated Reducing Sugar Content A first tobacco starting material is prepared from cured leaves of a NtSULTR3 modified tobacco plant and a second tobacco starting material is prepared from cured leaves of a NtSUS modified tobacco plant according to the present disclosure. The tobacco material is cut to form tobacco shreds having dimensions of about 2.5 millimetres by about 2.5 millimetres and the tobacco shreds are loaded into an extraction chamber, without compression. The tobacco starting material is heated within the extraction chamber. During heating, a flow of nitrogen is passed through the extraction chamber at a flow rate of about 40 litres per minute. For each tobacco starting material, the volatile compounds released during the heating step are collected by absorption into a liquid solvent formed of propylene glycol, at minus 10 degrees Celsius and with agitation of 750 rpm. The solution of propylene glycol with the collected volatile compounds is dried in a desiccation process to reduce the moisture level of the solution to approximately 15 percent. Concentrated solutions of collected volatiles from the tobacco starting materials are collected.

A combined liquid tobacco extract can be prepared. For each of the tobacco starting materials processed as described above, the first tobacco starting material is heated at a temperature and for a period time that is different to the second tobacco starting material. For each tobacco starting material, the volatile compounds released during the heating step are collected and dried. The resultant concentrated solutions of collected volatiles from the first and second tobacco starting materials can be combined at a defined ratio to produce a liquid tobacco extract.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

TABLE 2

Expression of SULTR3 genes during the curing time-course of a dark tobacco.

|  | 0 | 24 | 48 | 96 | 120 |
|---|---|---|---|---|---|
| NtSULTR3; 1A-S | 5.14 | 14.68 | 18.25 | 94.5 | 111.29 |
| NtSULTR3; 1A-T | 0.28 | 1.9 | 2.53 | 31.07 | 13.69 |
| NtSULTR3; 1B-S | 0.47 | 4.71 | 4.85 | 22.94 | 26.97 |
| NtSULTR3; 1B-T | 0.47 | 1.43 | 0.74 | 5.65 | 13.29 |
| NtSUTR3-3_S | 0.12 | 0.26 | 0.14 | 0.01 | 0.14 |
| NtSULTR3; 2-T | 0.03 | 0.04 | 0.24 | 0.12 | 0.79 |
| NtSULTR3; 3-S | 0 | 0 | 0 | 0 | 0 |
| NtSULTR3; 3-T | 3.5 | 8.88 | 15.14 | 12.21 | 20.84 |
| NtSULTR3; 4A-S | 14.07 | 27.76 | 29.98 | 8.46 | 22.16 |
| NtSULTR3; 4A-T | 14.84 | 14.54 | 18.25 | 3.62 | 6.52 |
| NtSULTR3; 4B-S | 0.03 | 0.05 | 0.04 | 0.15 | 0.07 |
| NtSULTR3; 4B-T | 0.2 | 0.23 | 0.32 | 1.16 | 2.67 |
| NtSULTR3; 5-S | 0.1 | 0.13 | 0.1 | 0.17 | 0.25 |
| NtSULTR3; 5-T | 0.1 | 0.05 | 0.09 | 0.15 | 0.12 |
| SAG12 | 14.17 | 71.47 | 231.54 | 840 | 426.63 |

TABLE 1

Expression of NtSULTR3 genes in root, stem, mid-leaf, immature flower, sepal, and petal of Virginia plants grown in the field (RNAseq, FPKM).

|  | NtSULTR3; 1A-S | NtSULTR3; 1A-T | NtSULTR3; 1B-S | NtSULTR3; 1B-T | NtSUTR3; 2-S | NtSULTR3; 2-T | NtSULTR3; 3-S |
|---|---|---|---|---|---|---|---|
| Immature Flower | 0.05 | 0.6 | 1.75 | 1.95 | 34.41 | 9.39 | 0 |
| Petal | 20.27 | 68.71 | 38.13 | 2.02 | 2.11 | 0.8 | 0.05 |
| Sepal | 0.37 | 2.6 | 8.72 | 7.02 | 61.45 | 14.82 | 0.01 |
| Lower Leaf | 0.19 | 0.13 | 4.41 | 4.58 | 2.12 | 1.83 | 0 |
| Middle Leaf | 0.02 | 1.07 | 3.88 | 3.27 | 6.26 | 3.89 | 0.01 |
| Upper Leaf | 0.08 | 0.47 | 4.26 | 4 | 2.31 | 1.73 | 0.02 |
| Stem | 4.35 | 0.07 | 9.26 | 3.69 | 0.21 | 4.41 | 0 |
| Root | 16.93 | 11.91 | 0.83 | 1.91 | 49.72 | 37.56 | 0.03 |

|  | NtSULTR3; 3-T | NtSULTR3; 4A-S | NtSULTR3; 4A-T | NtSULTR3; 4B-S | NtSULTR3; 4B-T | NtSULTR3; 5-S | NtSULTR3; 5-T |
|---|---|---|---|---|---|---|---|
| Immature Flower | 17.41 | 1.11 | 2.28 | 0.5 | 0.87 | 1.28 | 0.98 |
| Petal | 90.09 | 0.05 | 0.03 | 0.05 | 0.03 | 1.12 | 0.4 |
| Sepal | 63.26 | 11.59 | 4.71 | 0.26 | 1.52 | 1.47 | 0.11 |
| Lower Leaf | 20.71 | 0.2 | 0.13 | 0.01 | 0.11 | 1 | 0.06 |
| Middle Leaf | 18.55 | 1.38 | 4.53 | 0.22 | 0.43 | 1.17 | 0.29 |
| Upper Leaf | 24.43 | 0.74 | 1.94 | 0 | 0.3 | 1.01 | 1.03 |
| Stem | 18.45 | 10.02 | 34.9 | 1.78 | 2.53 | 2.38 | 1.66 |
| Root | 41.42 | 3.65 | 4.17 | 0.37 | 0.64 | 1.4 | 2.19 |

SEQUENCE LISTING

SEQ ID NO: 1 Polynucleotide sequence of NtSULTR3; 1A-S
atgggtaacaaggactatgagtacccagcatcaatgaatggggagagcagaaaaacacagccagtggaaatcccaccaccacaacctttttta
agtctctaaaaaacacagttaaagaaacttttgtttcctgatgatccacttagacaattcaagaatcagccaccacgcaagaaattcatacttgg
acttcagtatttgtttccaatctttgaatggggtcctcgttacaccttggatttcttcaaatcggaccttattgctgggatcactatagccagt
ctcgccattcctcagggaattagctatgcaaaacttgccaatttgccacctatacttggcctctgtaagtcacaacgttactctatgtttata
tatattataatggtggtgtacgtgagtgcacctcaattactttccataatcattatagagatgaattcaaactttaaatttgatgggtttaatt
aatctttacgtgctcactactgaacctggtgcactcttgcaattatggattcagattttaaaaactttagcaatttttttaatttgtactttgc
tacatgaaaaaggtatgaggtcgatttgaacccactgactatatacattacaatttacatgtgcttccgcttactagcacaagtacaggataac
tatgtcaagaatttccttaatgtgtgaggcgtggttaattagttaattacgtgataacttatgggtttgttggttattctgatgacagattcca
gcttgttccgccattagtctacgcagtaatgggcagttcaagagatttagcagttgggacagttgctgtagcatcacttctcattagttcaat
gttaggggacgaagttaatccaattgagaatccaacacttatcttcatcttgcgttcacggccacattcttttccggaatgtttgaagcagct
cttggaattttcaggttagtatatatatacagtagaataatatactataaatgaaagggtgtactacataaattgggtcatcagatgaactatg
ttttaatcgtttgattatgactatgtctttttgttagaataaggaacgattaaggtaagttgatggtaacgttaattgggggaaataattttgc
atgcaggcttggatttatagtggattttctatctcatgcaacaatagttgggtcatgggtggagcagccacagttgtgatacttcagcagcta
aaagggatacttggtcttgaccattttactcagtccaccgatgtcatttccgtcttgcgttctgtttttacccaaacgcacgaggtatatatat
aaatgttagtgttaaaatggcccaaatatgataatataatgtgatattatccgctttgcgataagtccgtatttttttctcaaaaggaaattcaa
ctcgttataagtattttttttttctacttttgcatattattggacttttgttcacatacacgtacccaacaaaccggctcatagacaggctaagaca
ataagccgggctcccacatcacactccgtatttccacataatatgatattgtcgcttttagttaagcctgcacggttttcacaccattaagaatt
ccaagctccttataatagttttttctctacttttttatgtgatacttttgttcgcacacaccaacaataacttattattgatgtattttaatttgtt
gtaacatataacttatcttatttttcacgtgttctcttcccgcccccaaccccttacaacatctgcgactattttccgtgcaaggctatagcc
ttgttttcttgaatattaattttgaaaagcaagtattattgttcgattctcattaacttctcttttcgttttagttgaatcttcaagaggatta
gttttttttaattttaattaattaatatggttatgactttgcttatggttaatgacaaaaataattgcagtggcgatgggaaagtgcggtgct
gggtttctgtttcctttctacctgctgggttctagattccttgtaagttacaaccaactttgatctattcaaacttgaatagtaccataaaat
caattattaaagagtctaaattttatgcatgtgatataagaaatattttataaaatcgagttatttattaaaataaataaggagttgggtcata
tatacaataaatctctgcactataactgctgctcttaattttagttataatgaaatgcatgcatgcagagcaaaagagaccgaagttgttctg
gatatcagcaatggctccattgatgtccgtcatactgggaaccattttttgtctatttcacgcacgctgaaaaacatggcgttcaagtggtatgt
cctttaattaattatgttttcttaatttctagaaggtgtataatagaagttacaatcctatttggcttaaagatttcaatttgactggtgagct
actatactaaattagaccactgttcacaacataaacactatggtgggtgggggtgatgtgatatttctgctatttggattactgcatttgtgag
tgtttaatttgggtgtgattcttgtggttttgagtattgcacacgttcgtttgatatagacgacctaccaatgccatgattgactgataattaa
atgtttcaaggacactggcccagcgtatttgctgttggcattatctttgcccatttaaaaatagacatttctagatgatggttttcttcgtcct
agaagttactcaattttacattaaacactatatgacaatgaaattgagatagaacaaagtttgaattactgtagtcgatgattcatttgttgaa
atatattatggtattaatgttagaccgggtttagttatgaaaatttccattactgaataccatctggcatatatcttactcccaccgttcact
ttcacttgtgagccaaaatacattttcacttttttacttgtccaatataccaaattaagagaaagacggtctttttttttttcgttttaccctatt
attaattacacatttcccaaatcatttctcaaaacttttttgaaatgttattattattatgataaaattacaaaatacatacttcatttgtttt
tttcttaaagagagtgcaaagtcaaaagcgaacgactaaaaatgaatggatggagtagttaaagtccaaaaacatgatgtcggaattaaaaatg
taacctaatggttacatatagaggtggcaaaatggttaaaagaaaacagttatccacccatattatccatcaaaatatgggttggataatgaac
catttaaaaacgggtcgaatatgactattgaaccatattatgcacttaggaaatggttaaccaaatggataaccaatggataataatgtattta
acttttacatttgtaaagcctcaaatttggagttcctcaagtttggaaaattaggaattctctcataagtgatcatatttaagaagccgtagata
atatggatatcaatattaccccccggataaacccgtttttatcgtctcaaatacggatcggatcggtatcaatttatccatttttaaattaccc
gttttgacccgctcgtatccgacccgcgcatttgccaccccagttcatatataactttattccacgtaactttggtgtagtttcaatccaattaa
tggtttgatacaattcggaagtcctctcttctttttgtaattttttctttctactactcccctccgtttcatattaaatgagttactttccttttta
gtctgttccaaaacaaatgacatatttctaaattaggaaataattcaaacttttaaactctttcatttacccatttaccattaatgagaagctt
ttatagccacacaaatgtcatggccccacaaacctttttaccccttaagcttttaagaccacaagtttcaaaaatctttttcttttttcgtaaa
cttcgtgcggagtcaaaactacctcatctcatctaatatgaaacggagggagtattatatatgagccatcccaccaaaatagttatgtgat
aatttattttgtaactgcacacatataattagacataatgtgaaaaacatgactaattggatggttaattatgaaaatattatgaacagattggaaa
gctgaagaaagggctaaatccagtgtcaataatggatttgtcatttggagcaccttatgtttcaacatctatcaaaactggcataatcacgggt
gtcgtatctcttgctgtaagctttcacttttcccatacttgacccttgtcatgaagatatgatctcatatgtcgagagacaatgtaattaaat
gtataagtacacatacaagtagtgcaattaacctagtgtaagtttaagtcattcataaaattactttgattggggacatgataggaaggaata
gcagtggggagaagctttgcaatgttcaagaattaccatatagatgcaaaagagattgatcgcttttggaatgatgaacatcgttggctctt
gcacttcctgctacctcactactggtatatatttttccttattctcttttcaaatttgtctttctaattacctgaaacagcgggaaaaacaatggc
ccattagttggattagtcaacatctgattgtatggaccatcatgtcgggacacacataaaggtagcaaataaatgcagaaagagacggaatatc
tacataacaaagtagtggtaatagatgcagagtaacaacttaaaaaagacagaaaaaaaaaaggtttcatgatttgttgtcagatttgaccag
ctatacagtgtttagttaactaaaacatattaatgttaataatataagattattaattcgcaaccatagcagagaagaagacacaatcataaat
ataatgtagagttaaaaagtaaggaagcgtaccattcaattccactgacacaatagcagttgacgattaagcctgatgccaacttcca
cgatccactagctacacgctctcacactcgaaagaacttgacttatgggacgtctaccattaccacatattcaagagacagaatacgatagggt
ttctaatgcctaggtaacgggggttggcctctatttataaaattgcatatccatcacaggtcaattgttatgggtctcacttatccacaca
catagtatttaatattagacatttatttatccatcatttgggtcacgtcaccatcctttcaggctataaccaattaatataagttcaaattcc
aacaaataacactatattttcagataatttatatgctaggatttaagttatacacacttgcaatgtaaatagtgttgttctatcaatgtattttt
gactgtttggtgtattacttgccaatttgtttcatgttactcatatagtcttaccttttaatgatcttttaaagtggttaatgtcaaatattttat
attgtcagtacataaaatttgaagtcattttatatttcctgaacaaggtgctaatcagaaaagtgaaagtgcaggtccatttcgcgatcagc
agtgaacttcaacgcaggatgtaaaacagcagtatcaaacatagtaatggcgctggcagtaatggtgacactgttggtgctgacgccattgttc
cattacactccattagtggtcttatcatccattataattctgcaatgctcggactcatcgactataatgctgcaattcacctctggcacgtcg
acaaatttgatttcctggtgtgcataagtgcatacctggcgtcgtctttgccagtgtcgaaattggcttagtcattgctgtacgtatccctta
atttctagtaactactattttccatctgttcggaataaatacaaggagattcgaaacgcaatatatgttgcaccaataatttgaccctta
gccaaattaactttttgaacccttttgtcacacactagaattttttttttcttatattaaagggggatccaacatttttatatataacaaaaaat
tattttttattttttgcacaatataattttttccacaaaggatattcaattgaatccccttatttctatctagctccgccttgtcggttcctt
ctaaattgtcttttaaagtttctgcacaattcatttaatagccttaatcataaaagtatttatctaaaatactatttatatctccgttaatgtt
ttttgattaaattaacactctactaactggagcggaatggtggattccgtaaaaataacttttttattttttctaagatatcaaatattttgatac
aaattcagtttggatacaacaactaaaattatatattggaaaaattccactttgttattactaatggactagtagtaactaggaagctaagcagg
tggtttccaattaattaatcaagatttagctcttagtcaggttggtttatcgttgctgtcctgctaagggtatgtcttgtagcaaggccaagaacgtt
agtacttggtaacataccagattctaagatctatagaaatgttgagcaatacacaaaacacagacactgttccgggtgttctcatacttgacctt
ggtgcacccatttactttgccaatgctagctacttaagagagaggtaatttaaattgtatactatatatctaactacacaaatatgtatatata
ctaataattaagcgctaattatgtgctctgcttcacttttataggatctcaagatggatcgacgacgaggaagacaagttaaattcttccgga
gagacattgcaatatgtaatacttgatatgggaggtcagttaacttctcctatgtctacaatcttatagtttgacaaggacatgctaaaacgat
ttttgtaattttaactagttatagtaggtttcattctcttttcgaggtgactacatcatggttgatatgaagaattatatggtgctaaatatt

SEQUENCE LISTING

```
gtatattatcagtacgtacgtataactaaaactcgtgctaaaattctatatatgatgggcagctgtaggcaacattgatactagcggaattagc
atgctagaagaggtcaagaagaatcttgatagaagagatctcaaggtttgccctaactattatatatcctacacgttaaatgatatattggaag
ttatgaagtgataattaatcctttaatttgcaacaacatagtaatggtgtgctttaattcttgtggggtattgtagcttgtgctggcaaatc
caggggcagaggtaatgaagaagctgaacaagtccaaattcatagagacaataggacaggaatggatatttctaactgtgggggaggcagtgga
atcatgcaattatatgcttcactcctgcaaaccaaaatctgccatagatggttcatttagcaataacgtttga
```

SEQ ID NO: 2 Polypeptide sequence of NtSULTR3; 1A-S
```
MGNKDYEYPASMNGESRKTQPVEIPPPQPFFKSLKNTVKETLFPDDPLRQFKNQPPRKKFILGLQYLFPIFEWGPRYTLDFFKSDLIAGITIAS
LAIPQGISYAKLANLPPILGLYSSFVPPLVYAVMGSSRDLAVGTVAVASLLISSMLGDEVNPIENPTLYLHLAFTATFFSGMFEAALGIFRLGF
IVDFLSHATIVGFMGGAATVVILQQLKGILGLDHFTQSTDVISVLRSVFTQTHEWRWESAVLGFCFLFYLLGSRFLSQKRPKLFWISAMAPLMS
VILGTIFVYFTHAEKHGVQVIGKLKKGLNPVSIMDLSFGAPYVSTSIKTGIITGVVSLAEGIAVGRSFAMFKNYHIDGNKEMIAFGMMNIVGSC
TSCYLTTGANQKSESAGPFSRSAVNFNAGCKTAVSNIVMALAVMVTLLVLTPLFHYTPLVVLSSIIISAMLGLIDYNAAIHLWHVDKFDFLVCI
SAYLGVVFASVEIGLVIAVGLSLLRVLLFVARPRTLVLGNIPDSKIYRNVEQYTNTDTVPGVLILDLGAPIYFANASYLRERISRWIDDEEDKL
NSSGETLQYVILDMGAVGNIDTSGISMLEEVKKNLDRRDLKLVLANPGAEVMKKLNKSKFIETIGQEWIFLTVGEAVESCNYMLHSCKPKSAID
GSFSNNV
```

SEQ ID NO: 3 Polynucleotide sequence of NtSULTR3; 1A-T
```
atgggtaacaaggactatgagtaccatcatcaatgaatggggagagcagaaaaacacacgcagtggaaatcccaccaccacaacctttttca
agtctctaaagaacacagttaaagaaactttgttccctgatgatccacttaggcaattcaagaatcagccacctcgcaagaaattcatacttgg
acttcagtatatcttttccaatctttgaatgggtcctcgttacacctggattttgctggggatcactatagccagt
ctcgccattcctcaggggaattagctatgcaaaacttgccaatttgccacctatacttggcctctgtaagtcacagtataacgttattctgtgtt
ttattataatggtggtgtacgtgagtgagtgcacctcaattagttcgttggatatcattatgtagacgaattaaaatttaaatttggcgggtt
caattttttacttgctcaccactgaacctggtgcactcttgcaattatgaactatacattacaatttacatgtgcttccgcttaccagcacaagt
acatgataactatgtcaggaaattcctaatgtttgtatcttaatctcccaaaatcctaacaagcttctagtaggggattggagcagtgtgaggc
gtagctagtacgtgataacttatgggttgttggttattctgatgacagattccagcttgttccgccactagtctacgcagtaatgggagg
tcaagagacttagcagttgggacagttgctgttgcgtcacttctaattagttcaatgctagggggacgaagtaaatccaactgataatccaacac
tttatcttcatcttgccttcacagccacattcttttccggaatatttgaagcagctcttggaattttcaggttagtatatacagtagaatatac
tataattaaatgaaagtgtgctacatatataaattgggtcagtgaactagtatgttttaatcgtttgatgattatgactgtcttttttgttaga
ataagttgatggtaatgctagttgggtaaataattttttacatgcaggctgggattcatagtggattttctatcacatgcaacaatagttgggtt
catgggtggagcagccacagttgttatacttcagcagctaaaagggatacttggtcttcaccattttactcagtccactgatgtcatttccgtc
ttgcgttctgttttacccaaacgcatgaggtatatataaatgtgattcgctttgtgttaagtttgcacgattttttccttaaagaaaatccaac
tcattataagtgtttttttacattttgtgttggacttttgttcacatgtacgcccaaacaacctggctcgtatacaggctaagacaataagtc
gggcccccacttcatacctcgttatctccacatagtatgatattgtcgttttaggttaagctctacaattttcacccctattaaaattattcaa
cttttaacaagtaattttttttctacttttctcatgtgagacttttgattacatacaccaacaatagctatcatggatgtatttaatttgtcgt
aacatataacttatcttatttttacgtgtgctctcgccccccaagcccctacaattctgcgactctttcgataatggatatgtattttccgt
gcaagactatagtcttgttttcttgaatatatttatttttaaaaagcaaatattattgttcgattctcactaacttcttttcttttttttttcct
tgagaataaaaattctactgttaccgtacaattttagttgaacctttcacgaggattagttttattctatttttttttattttaattaattaatgt
ggtttctgactttgcttatggttaatgataaaaataattgcagtggcgatggcaaagtgcggtgctgggttttctgtttcctttttctacctgctg
gggtctagattccttgtaagttacaaccaacctttgacctattcaaacatatatgaatagtaccatgaaagcaaattttttaaggagtataaattt
tatgcatggtgttaaaagaaatattttatatgttcgagttataattttattattaaagtaattaggattgagttatataccaatttaaagaattt
ttacactataactattgctcgttgtaatggaaatgcatgcatgcagagccaaaaaagcaaagttgttttgaatatcagcaatggctccattg
atgtccgtcatactgggaactattttgtctatttcacgcacgctgaaaaacacggcgttcaagtggtatgtccttttaattaatttttgttttct
taatttcaagaaggtgtataattaaattacatctatttggcttaaaagatttcaatatgactggtgagctactaaattagtctactgttcacaa
cacaaacactatggtgggtgatgtgatatttctgctatttggattactgcatttggagtgtttaatttgggttttgattcttgtggtttgagt
attgcacacgttcgtttgatatagacagacctaccaatgccatgctgactgacattttactgacacactggcccagcaaatttgctg
ttggcattatctttgcccatttaaggagacacattctctaggtgatagttttcttcgtcctcagaagttactcaattaacattaacaaaatatgaca
atgaaattgagatagaacaaagtttgaattattgtagtcgatgattcatttttgtgaaatatattatggtagttttagactgggttaagttata
gaaaatttcattactgaataccatctggcatatatgttacttgtcacatctactaaaaatacattttcacttttacttgttactataccaaa
tcaagacaaagataatcttttttctttttttgttttaccctttactcattaattactctttcctaaatttctttcctcaagacttttttgaaatgtta
ttattattatgagtaaaatttataaaatacatacttcatacatttttttcttaaggagggtacaaaattaaaaagtgaacaactaaaaatgaacaaa
tggaatatttcaagtccaaaaacatgatgtcggaattaaaaatgcaacctaatggttacatataactttattcaacgtaactttagtgtagttt
caatccaattaatggtttgatacaatcgaaagtcgtcttcttttttgtaattttttctttctactattatatgagccatccccaccaaaatag
gcatgtgataagttatttgtgactgcacatataattagacatcatgtgaaaaacatgactaaatggatggttaattatgtggattatgaacaga
ttggagagctgaagaaagggttaaatccagtgtcaataatggattttgtcatttggagcacccttatctttcaacagctatcaaaactggcatagt
cacgggtgttgtatctcttgctgtaagctttcactattcccatacttgaccttttgcgcaaaactaatttctcttttacggctctataagcaag
caccttagacatgaaattgtttcaagtaatggagattttcttaggttcaaatctagtgattttaaatatgattaatatgacttataatgtcccg
agttataattcaataatcttttcaactacattaccattcaattaccatccaaccgccccattaactactaagctgataaagttgaagattttctta
gacttatcatgaagatatctcatgtccagtgacaatgtaaatgtataagtagacaattagtgcaattaacctactgtaacttaactcattcat
aaaactttgatttggggacgtgacaggaaggaatagcagtggggagaagctttgcaatgttcaagaactaccatatagatggcaacaaagagat
gatcgctttggaatgatgaacatcgtcggctcgtgcacttcctgctacctcactactggtatatattttccttattctctttcaaatttgttt
ttgaattacctgaaacagcgggaaaaacaatgccccattaattggattaatcaacatctgtccatcatgtccggagcacccagtatacacat
aaaagtgcaaataaagtagtggttaatacatgcagattaacagcttcaagaaaaaaaaaggtttcatgattttgttgtcagatta
gaccagctacagtgttttaattaactaaaatataataatgttaactatactatatttcagataattttatatactaggattttaaattatacacact
cagttttattattctatcaatgtattttggctgtttgggcatgacatatctactccagcttacagaggatatgatccttgataggcaggtttg
tgggttgggaattaggatagaaggttagtagctagacatgcgtgtctccttctcatgcgggtagcattaatattaatctcttatcttcgtagct
tcttatccgcagatttcttttgctatactatgttgtttctttcgctttgattattctatcacctatccctttatctggctgttattactattt
gttgtgtctgcctcttttaaattttctttgagcccgggtgatctatcgaaaaacaacctctcaacttttcacaaaggtcagggtaaggtttgcgt
atattctaccttccccaaacccctacttggtggggattacactgggtgttgtcgtagtatttttggccgtttggtgtattacttgccaattgttt
catgttactaatatagacttatcttcaattgtctttttaagtgatttttattgagtaaatacttttacattgccattatacaaaattttaagctca
tttatatatcatgaacaagctggtaatcagaaaagtgaaagtgcaggtccatttttcgcgatcggcagtgaacttcaacgcaggatgcaaaacag
cagtatcaaacatagtaatggcgctggcagtaatggtgacactgttggtgctaactccattgttccattacactccattagtggtcttatcatc
cattaaatttctgcaatgttcagaatcatcgactataatgctgactccaccataatgctgcaacaaattttgattttcttggtctgcattagt
gcttacttggcgtcgtctttgccagtgtcgaaattggctagtcattgctgctacgtatccctttaattctagtaactaatatttcattcgatt
caggtgggagtcaggaattttatgatgagattcagaaagatacttaaatattacctagaatttgaccctgtgaccaaaatcaacttttga
acccccttgccattaattatattcctattaatataagggattcaaccatttatatataacataaaaactcttttttaatttgcacatcatagtttt
gggcaaaagaaattcaattgaatccccttatttctacctagctccacccttgtcagtccgtattaactgtcttttaaggttttttgcacaattct
taagaaaagaatttaatagccttaatcataacgtttcataatttaatcaacactctactaactagagcagaagtggtagattccaaaaaaaaaa
```

SEQUENCE LISTING

```
aaaaatacttttgcgtttctaaaatatcaaacattttgaagcaaattcagtttggatagaacaattaaaaattatacattggaaaaatccgtt
ctgttattactaatagactagtagtaactaggaaggggggaagaaacgagtacttgtcaactaagcaggtggtttccaattaatcaagatttaat
agcgtaaacttttaatgcaaatgcaggttgctttatcgttgctaaggtgttgctatttgtagcaagaccaagaatgttagtgcttggtaacat
ccccgattctaagatctacagaaatgttgagcaatacacaaacacagacactgttccgggcgttctcatacttgaccttggtgcacccatttac
tttgccaatgcaagctacttaagagagaggtaatttgaaactgtactacatatgtaactacacatcttcgaacatgtagatgcaaagttaacac
taattctgagttctgtttcactttttataggatctcaagatggatcgacgacgaggaagacaagttaaattcttcaggagagacgttgcaatat
gttatacttgatatgggaggtcagttaacttgtcctatatatgtttatgatcttgaaatttgacaatttcttatccaagtaaaaaagaaacaag
gatgtgctaaaaagatttaagttatatacgtataaataatgtttacattatcagtgtttattacgttctcattctattttataggttaccaa
ttgttgtgttgattttacctgatagtgctaatatagtacttagaacttaaactcagtgctaaaattctttatatgatgggcagccgtaggcaac
attgatactagcggaattagcatgctagaagaggtcaagaagaatcttgatagaagatctcaaggtttgactcttattaatatcctcagtac
atgttaaaaatctattggaagttatcaagtgctaataaattcttttgcaacaaaactgtaacatatattattgtgggattgtagcttgtgctggc
aaatccagggcgcagaggtaatgaagaagctgaacaagtccaatttcatagagacaataggacaggaatggatatttctaactgtggggaggct
gtggaatcatgcaattacatgcttcactcctgcaaaccaaagtcttccacagatggttcatttagcaacaacgtttga SEQ ID NO: 4 Polypeptide sequence of NtSULTR3; 1A-T
MGNKDYEYPSSMNGESRKTHAVEIPPPQPFFKSLKNTVKETLFPDDPLRQFKNQPPRKKFILGLQYIFPIFEWGPRYTLDFFKSDLIAGITIAS
LAIPQGISYAKLANLPPILGLYSSFVPPLVYAVMGSSRDLAVGTVAVASLLISSMLGDEVNPTDNPTLYLHLAFTATFFSGIFEAALGIFRLGF
IVDFLSHATIVGFMGGAATVVILQQLKGILGLHHFTQSTDVISVLRSVFTQTHESQKRPKLFWISAMAPLMSVILGTIFVYFTHAEKHGVQVIG
ELKKGLNPVSIMDLSFGAPYLSTAIKTGIVTGVVSLAEGIAVGRSFAMFKNYHIDGNKEMIAFGMMNIVGSCTSCYLTTEDMILDRQVCGLGIR
IEGCKTAVSNIVMALAVMVTLLVLTPLFHYTPLVVLSSIIISAMFGLIDYNAAIHLWHVDKFDFLVCISAYFGVVFASVEIGLVIAVALSLLRV
LLFVARPRMLVLGNIPDSKIYRNVEQYTNTDTVPGVLILDLGAPIYFANASYLRERISRWIDDEEDKLNSSGETLQYVILDMGAVGNIDTSGIS
MLEEVKKNLDRRDLKLVLANPGAEVMKKLNKSNFIETIGQEWIFLTVGEAVESCNYMLHSCKPKSSTDGSFSNNV SEQ ID NO: 5 Polynucleotide sequence of NtSULTR3; 1B-S
atgggtaatgcagattatgagtacccatcaataatgaatggagagagcacaggcataggcatacatagagtggaaatcccaccaccacagcctt
ttttcaaatcactaaagaatacagtgaaagaaactttatttccagatgatcccctaggcaattcaagaaccaaacacccctagaaaattcat
acttggtgtgcagtatttctttccaattttttgaatgggggttctcgttacaattttggttcttcaaatctgatcttattgctggaattaccata
gctagtcttgctattcctcagggaataagctatgcaaaacttgccaacttgccacctattctggactatgtaagtcttgataatttattcagt
caactctcatatcatgttgaagtgtacatgcgatcatttcatctaaaacaaatgatgtgtatacacagttcaaaaccttaaacacagcaact
catatctttagtagttttgcagtagccgatgttgcatatatatagttaacgggtcaactgcaccgttaacaacaacaagaaaccaagtatag
ttcacaagtgggtctgggagggtagcatatacgtagaccttaccccttagcttgaaggtagtgaggttgtttcccatagacttttggctcaag
caactgcaccgttaacaacaacaagaaaccaatatagtcctgcaagtgggtctggggaaaggtggcgtgaccttacctctagcttgaaggtag
tgaggttgtttcccgtagaccctcagctcaagcaactgcaccgttaactaaagtgaaaaactaacctaaaatttaaaaagatattgaagtttgaacg
taaaatttcaaaaatgaaatatgtttaataataagaatctaaaggttgaattcatcaatttaaatcctggattcgctatttttgtgttttgca
gattcaagctttgttccacctttagttatgcaataatgggcagttcaagagatttggcagtgggcacagttgctgttggatcgcttctaatgg
cttctatgataggaaatgaagtaaatgcaactgagaatccagcactgtatcttcatcttgcgtttactgccacattcttcgctggactatttga
attagctcttggattttttcaggtcattgtctctatttcttgttagtacgttcttagtttacaatatcgcttatactaaaatagtttgagccgaa
gaagcaagcagcagtgcattacttttagggtaagctgtctacgtcacactccttggaatgcggccttttccccgaatccggcatgaacgcggaatg
gcttttacaccgggctgtctcagtttgagcttaattaatttatggttaattaattttgtaggctgggattatttgtggatttctatcacatgc
aaccatgtaggattatgggaggagcagctacagtggtgatactacagcagctaaagggaatacttggtcttgaacattttacacatgctaca
gatgttgtctctgtcttgcgttctgtctttaccccaaattcaccaggtaatttttttttttttactctatcaagttacttgaaaatctattaaataa
tattctgtaacaagtatgctttgttaacctacatacataaattatagtaacaccttaagtaacctgttatagctagtaaaactataatatagtataa
ataaatttaaatctagtgaaagctcccattctttcgacagaatagatggtaaatatttttcagttactgattgattcttaatttgttcctttt
toggttaaagtttgaagagaaatgttttttttgtttgtaatagtaactttctgatgctaaactttattattattttattttttttacattttact
tttttggttcgtttcgttttctccaccccttttttagcccgtggaaaaaactcattagtagtacaaatcatgagattgagttgaactaaagttat
tattgaagagtaaaattttttggattttagttacacactttttatccccttttgatttatttgtttgtttattactccgagtacttatatttgttact
ttctttaaatatactctaatgatggttaattggttaaaataactgcagtggcgatgggaaagtgcggtgctaggattttgtttccttttctacc
tgatgatggcaaaatttttttgtaagtatacacactgactttgacctttttgaaatgcgaatagtatccacaagtcaaaagcagtctactatcaaa
agtggataccctttagacttataatgctcaattaagctttcctatcttcctcaaataattcataccttaaatttaagaccttaaatttgcttaatttctta
ctctttcgaaattattatgactgatattgacttttgctcctcgatttaacctaccccactccgaaaatgccaacaatcttaaaagcaatgtcttct
atttaaagtttatgaattatgatttatcacataatcgatattattactgagttcgtaattagatatttatacttatttaaaaaaaattctaata
taaatataatatttaagtaaaagtgattgggtccggcccatcctacgagaataagctagctccatttctgctcgtcagagggaaaatttatata
tttttctcgtgagaaaagaaaattaacttttatatttttgttaataggaaaactactagtagtattctacaactttatagaaaagaatagagaagag
tgtagtttaaaaaagttgctaatatatgcatgcatgcagagccaaaagagaccgaagcgttttgattttcagcaatggcgccattgacgtccg
tcatattgggaactattcttgtttatctcacccacgctgaaaaacacggtgttgcagtggttaagaaaaaaatttcattaatagtaaatttaatct
attatagcaagtaaactgtcttattttttcatcttactaatatagaagttaaattcgcgtgttagcttaagctcttaaattcaaggacttcattc
aacttctgaattactcctactagtttactacagtataagaacataaatcctacctagctccaacaatctcatatttcctaccccattgaattctct
ttttagacatactataactcctatctagtaactttgcggtttaagtacccctagatgtttgtttgggcaaacaacggcaacaataacggtccagt
aaaatctcactaataaggtctggggagtatagtgtgtacgcagactttaccctaccgctataggtagaggctattccgaaagacactcggc
tcaagaagacgaaaaagaatatatcagcaccatcaataaaaagtatggaacaataacaacgtcaccagacagggacaaacaacctactagtg
ccaaaattggttatccatgatattctacgtttattagctgttcatattccttattggtgaattttaaagagacacttttgattgatagcttcat
ttgtcttaataaaattgggtcaagttgacacttaaagacaaacaagacgaagggtgaaataaaaagttttttattttgtgtatacgtac
tttgtcggtcacggaaaaaaaagtagtagtgctatgagaacttttagcataacaagactttttgtgaatagtttagacctcacacagtataaagaa
ttttcaccgcatttaattactacaaaaataactataggcaactatccataacaacttagatttgtaacctcaaaacataaagcatgtcacatgc
atactcaacaagctaagtttagcgcataattttcttcacactgtcagtgcgcgtatgacctatagatcacgggttcgaattataaaatcattca
ttaatatttatatcagatgtagattgtctgcatcaataacccattaagatgcggccctttcccgaaccttgcgagaacgcgtgattactttgtgc
accggattgccctttagtacacatagtaaagtcgtatgcagaagatgttgtatcttaggagagatgttgtgataattgtggatgcttata
ttatccatcaatcattggattcttataattatgtgaatgaaaaattggaacagataggggagctgaagaaagggttaaatcctccgtcaataat
ggatctgtcatttgggtcggcctatatgacaactgctatcaaaacaggaatagtcacgggtgtcatttctcttgctgtaagcactcgatctgct
ttccaatctcaacctttgtcctcttctgctgcaattcctgctacttgcattacttttctctagctaatgttcttttttttacaatttcaaga
acaagcatacaaacatgtgtgcatggacggatcttgataatgttcaccgctttgaatacaatattagagtacagaacttatatttatttcttc
gtccctcatttttacttatccactataaaagtataaatttcattttctttgtcgtttagcaaagaaagaagaacaatctttttttttcaatg
tgattaggaggtcacgggttcgagccgcgaaaatagctcttgcagaaatgtagggtaaagttggtacgatagaccttgtgttccgggccta
cccgacccgcgcatacgagaattagtgcactgggtgctctttactttcatatcattaactgctcattcccaaattattttcccagatt
ttttgaaatgctataattattataggtaaaatagtagaacacatattttaattttttttcttaaagaaagtacaacgttaaagtggacaac
taataaaattgaacggagaaagtcattaattgtaactatatcataattggatgcttattgggacttctttggcgacgatatataaatcactag
agaatttggccgcgcttcgcgcgattatataaaagaactataataaattttgtgattttataataaaactaaattcaatctgatcaaataaaca
```

-continued

SEQUENCE LISTING accaaaaatagataaatataatttaggaagtcatggtctactcttgaggtaaccctagagcaaaaattacaaagaatcatcctcaaggttgat
tttatatatatacacacgtgtgtgtgcacgacgcagatgtttttcaaatattttttcttagtttataatattttacttttttagaactgcggt
taattatttaaattgtacaatggttagttttactttgttgtttaatatacatatatatttatctagataaatatatctggcgaaataatttttc
ttctactcatttgatatatgtattgtttaaatccttaattagagagtcgaatattattttgcgaaaggtttctccattgttctttattttccttg
ttctctcttccttcctttcttgttcatttcttccctcttttgttcttttctacattttcacccactaaccactacttcatctagaactttttga
aaatgttactttttgtaaaataatcaagtcaattcctcttttgcttcctcttaattttctgcgaaacaataatagattctctttttttcctgaaa
tagctcctccgaacaatcataaatgcaatcattttcattttcgaatatattcagcaaaaattttttggggcaattttaattgccacctattgtcat
tattacaatcatttcactcttccttttggacagaagaaaacatacatatatagaaaattgatatgaaaagaaataaaaaaagaaataaagtata
caaatgttcgtatcactgcatatctctgaatgaactctttttttttaaatactataacctcatttttactttgtaatgaggcatacgaagcacaa
aaccttcataattatatagtaatacacaagtaagttgtatgcatttattatacgtttcaaaatacaactgcaataaagcagaattgctcactga
aattaacttcattttcaagaaaaatcatattatatataaaaatactcactacagatattagtgtcattccccttacaagaatatataaatataat
aacgtaagaatcattatgtaatataattatgagtgtgcttttgaaaaactgaacttttgtagagatcaaagattaaagagtccctaaaaagata
gagtaagtccatatccgagaaatttagatggaaagaaagaagccaaaaagaagaaccatattaagagaaaatttgaaaactttattttcatgca
accatttaaagtaggaatgtgaaagctcattttccaaaccatattctttacgttcatgctctgctgggcgttacgttatttccattcttcaaaa
gcaccactttgaaattcttcccatctcaatgagtttctgtttcttccagcactaaagtagttgctttgtttctccttttgggaatcaagccaac
gtacatcttttaatggaaaggagaagtggagaagtaatatgagtagactggtagactggtgaggataagaacttggctgagaagccattgttggaagca
tgtgtatatcgatctgacgtgatgtgtaaccctttagtaaaagacaattctttttacacattttgaattgttgcacaactatatttgttattta
taaactgcagtgattgcgaggctccataaatgaggaatatggatggctgaaacggtaacatccattcatttgacagtttcttttattaattgac
atgaagagacacgacttttgggcttttttaaagcaaaataaataaagtaaaaattgagaaagtatgaaaaggcccccaaaaatttgagaaaataaa
taaatatgattcttggcttttagagaagtgccaagtcatcttcttctatccctctttttatagatatagattagtaaaattgcaatgatagtat
aacatttttatacaatatcagtgtacataactccttgtcacatgtatgaatcaaaattctataaaattgtgtatgaactttgaaggcaactttca
atgcactgtaaacttacaagtatatagacaataagtgtatttcgtatacttataattgcattatgtggcaaagaatttttttagtggatttga
aactctctataacactgcactaaaattaaatccttaatttattgatatggacaggaaggaatagcagtagggagaagttttgcaatgttcaa
gaattaccatatagatggaaacaaagagatgattgcttttggaatgacgataattgttggctcctgcacctcctgctacctcactactggtacg
ttcctacatactactatagtatatcatatttgacttggttatatttctcttttctcttttatttccttttatgggccgaaagttgatgtggatt
actctcatttcccatttgggcccataccacgtgattgtatgctccgcatacctactaacaataaaagaagaaaaagaaaaagcaaaaaaaaaa
aagagagaaagagagaaagaaaagcttaaaattaatgggatagagactggaaaagagggaaacgtaattatactatattatatgggaaggaaaat
actaaaaaatggagggggtggaaggtaagaaaagagtgggggttggctaggttgtgaaatgcatatattttcaacaaagtgtaacgagtttgagt
cgtattatgtgtaaataaaggggtattatgttattgataattccttgtcgataaaaaaaaaatgaaaataagaaagaatgaggaattgacaata
aggacatttcaagtttttagcaaattaacattacattaaacgtaaatttatggagtagtttagtcaaataagtttaaaagagcaaatgtgaat
aggtcagtgttttcgaaaagactaacactactacattacctaaaaaataattacatacaactgtccacaatatgtggcattagaaacttgaaaa
ataagacagttaacctataataagaagtaaaaatactgatagtgtaaaaattatttatactgcagggccattctcgcgatcagcagtgaatt
ttaacgcaggatgcaaaactgcagtatcaaacattgtcatggcgttggcagtgatggtgacattgtgttgctaacgccattgttccacttcac
tcccctcgtcgtcctgtcctccattatcatctccgccatgctcggcctcattgattataatgcagccattcatctctggcatgtcgacaaattc
gacttcttggtctgcatcagtgcttacattggcgttgtctttgccaacattgagattggcttagtcttagccgtaagtatccttatgttctat
gcactaacagtgtaaaaaaaaatttacagtatcaaatttgaccgataattatatggttgacttataaaaatgttgtttaatggaaatgcaggta
ggattatcgttgctaagggtgttacttttttatagcaaggcaaggacgttagtacttggtaatatcccagattctatgatatacagaaatgttg
agcattacccaaatacaaacaactctccaggcgttctcattcttgacattggagccctatttacttcgctaattctagctatttaagagaacg
gtaattagtattttgataactgtagtgtctatatcagtttgcagacacctcgactaattatggttaactcaattcttgttataggatctcaagg
tggattgacgaagaggaagacaagttaaaatcttcaggagaaacaacattgcagtatgttatacttgatatgggaggttagttaatttatgcag
tctctataatttcttcatcactcagtttattttttttgaaaataacaataaaacattttaaacgtagcacaagaacatataagataggattttaatta
cattgacagctaaaattctttgattggcagctgtgggaaatatcgatacaagtggaattagcatgcttgaagaagtcaagaaaaatcttgatag
aagagattacaaggttgggctcttgtttttccaatttcttctcttgaaacaatttcactatatcactgatgttactgcttagttgatactgctcct
tttcattttgtccttgggccgagggtatccaaaaaatagcctctctacctttacaggcaaggtagggataaggtctgcgtacatattaccctcc
ccaaattatgctgggtatgttattgttgttgtcattccaagttataaagacagactgcaccataaagtacatctataagataggatttaaatta
catacactaaaagtactgtaaaaaaaaattccaacgatcagtgttttataacttattatagcaggtaacttgccttattttcagattactaatc
ctgctttttatggccagtcagtgtatagaagttaaacttgtgtaacatatggtggtttttttttttttttttgtggcaatgcagcttgtgtt
ggcaaatccaggagcagaggtgatgaaaaagttgaacaagtccaaatttattgagacattaggacaagaatggatctttctaacagtagggaa
gctgtgggagcatgcaatttcatgcttcattcctgcaaaccaaaatctacaacagatgaggcatcccaaaaatggagcaacaacgtttga SEQ ID NO: 6 Polypeptide sequence of NtSULTR3; 1B-S
MGNADYEYPSIMNGESTGIGIHRVEIPPPQPFFKSLKNTVKETLFPDDPLRQFKNQTPLRKFILGVQYFFPIFEWGSRYNFGFFKSDLIAGITI
ASLAIPQGISYAKLANLPPILGLYSSFVPPLVYAIMGSSRDLAVGTVAVGSLLMASMIGNEVNATENPALYLHLAFTATFFAGLFELALGFFRL
GFIVDFLSHATIVGFMGGAATVVILQQLKGILGLEHFTHATDVVSVLRSVFTQIHQWRWESAVLGFCFLFYLMMAKFFSQKRPKLFWISAMAPL
TSVILGTILVYLTHAEKHGVAVIGELKKGLNPPSIMDLSFGGSAYMTTAIKTGIVTGVISLAEGIAVGRSFAMFKNYHIDGNKEMIAFGMMNIVG
SCTSCYLTTGPFSRSAVNFNAGCKTAVSNIVMALAVMVTLLLLTPLFHFTPLVVLSSIIISAMLGLIDYNAAIHLWHVDKFDFLVCISAYIGVV
FANIEIGLVLAVGLSLLRVLLFIARPRTLVLGNIPDSMIYRNVEHYPNTNNVPGVLILDIGAPIYFANSSYLRERISRWIDEEEDKLKSSGETT
LQYVILDMGAVGNIDTSGISMLEEVKKNLDRRDYKLVLANPGAEVMKKLNKSKFIETLGQEWIFLTVGEAVGACNFMLHSCKPKSTTDEASQKW
SNNV SEQ ID NO: 7 Polynucleotide sequence of NtSULTR3; 1B-T
atgaatggagaaagcgcagggacaggcatacatagagtggaaatcccaccaccaccaaccttttttcaagtcactaaagaatacagtgaaggaaa
ctttatttccagatgatcccccttaggcaattcaagaaccaaacacccccttcgaaaattcatacttggtcttcagtatttcttcccaattttga
atggggttctcgttacaattttgggttcttcaaatctgatcttattgctggaattaccatagctagtcttgctattcctcagggaataagctat
gcaaaacttgccaacttgccacctattcttggcctatgtgagtcttgatataattattttttgtcggctctaatatcatgttaaagtgtgtaatc
atttcatccaaaacttatgaggtgatatacacagttcaaccaccttaaatacaacaactcatgtcttttagtagttttggagtagcgcatgttgca
tatagttaacgggttcaagtgcactaaaactttaaaaaaaaatattagactttttgaacgtaaaattttttaaaaaataaaatgttcaataatatg
aatctaagggttgaatccatctaatttacatagatccgctattttttgtgttttgcagattcaagcttgttccaccattagtgtacgcaataat
gggcagttcaagagatttggcagtggggacagttgctgttggatcgcttctaatggcttctatgataggaaatgaagttaatgcaactgagaat
ccagcactttatcttcatcttgcttttcactgccacattctttgctggattatttgaattagctcttggatttttcaggttagtgtctctatttc
atgttagtacgttcttaatttactatatcgcctgtactaaaatagtttgagccaaggaagcagctatcgatgctggcattagggtaggttggtc
tacgtcaccactcgttgggtgcgaccccttcccgaactctacgtgaatgcggaatgctgcatcggggatgcttcaattttagcttaattaatttt
atggttaattaatctttcaggctgggatttatagtggattttctatcacatgcaaccatagtaggattttatgggaggagcagctacagtggtga
tactacagcagctaaagggaatacttggtcttgaacattttactcatgccacagatgttgtctctgcttacgttctgtctttacccaaactca
gcaggtaaatttttttttactctatcatgttacttgaaaatctattataaataattattctgtaacaagtatgctttgttaacctatataaatta
tggagtaatatcataagtaaatttgttatggcaagtaaattaaactatattataatataaaagaaatttaaatctagtaaaagcttctattccttt
cgacaaaataaaatggtaattgttttcagtacttgttatttctcttctttcttctcttttcggttaaaagttaaaatagaagtgcttttttcgtgt SEQ ID NO: 8 Polypeptide sequence of NtSULTR3;1B-T
MGNADYEYPSIMNGESAGTGIHRVEIPPPQPFFKSLKNTVKETLFPDDPLRQFKNQTPLRKFILGLQYFFPIFEWGSRYNFGFFKSDLIAGITI
ASLAIPQGISYAKLANLPPILGLYSSFVPPLVYAIMGSSRDLAVGTVAVGSLLMASMIGNEVNATENPALYLHLAFTATFFAGLFELALGFFRL
GFIVDFLSHATIVGFMGGAATVVILQQLKGILGLEHFTHATDVVSVLRSVFTQTQQSQKRPKLFWISAMAPLTSVILGTILVYVTHAEKHGVAV

```
IGELKKGLNPPSIMDLSFGSAYMTTAIKTGIVTGVISLAEGIAVGRSFAMFKNYHIDGNKEMIAFGMMNIVGSCTSCYLTTGPFSRSAVNFNAG
CKTAVSNIVMALAVMVTLLLLTPLFHFTPLVVLSSIIISAMLGLIDYNAAIHLWHVDKFDFLVCISAYIGVVFANIEIGLVLAVGLSLLRVLLF
IARPRTLVLGNIPDSMIYRNVEHYPNTNNVPGVLILDIGAPIYFANSSYLRERISRWIDEEEDKLKFSGETTLQYVILDMGAVGNIDTSGISML
EEVKKNLDRRDYKLVLANPGAEVMKKLNKSKFIETLGQEWIFLTVGEAVGACNFMLHSCKPKSTTDDASQKWSNNV

SEQ ID NO: 9 Polynucleotide sequence of NtSULTR3;2-S
atgggtaatgctcactttgatgatcaatattcacatcaaaaggtagaaatcccagcaccaaagccattcttgaagacactcaaatcttgtgtga
agaaacactatttcctgatgacccctttaggaaattcaagaaccagtcacttaccaagaaacttgctttgggtttgcagtattttgtccccat
cctcgattgggctcctcgctatacgtttcaacttttcaaagctgattttattgctggaatcacaattgctagtcttgctgttcctcaagggata
agctatgctggtttggctaacttgcctccagttattggactttgtaagttactatttatataaatatacatgaattaatccatcaaatatcttt
gaaatatactcgaaatcatgcatctagctttggacatggaactagtacatacacaaggctagcctctttccaactagtcctctagtctttaaaata
tactatatgaatttgacttttatgcacctgcaatgtcaagcaaattaggcagataatcctgcaggtctaggtaaaaaaaattatatcgtatca
gtatatttttacaagttaaacacttaaaatatacataactataattgtgattataaaggtattacgtgtcttgatatgtaagttacaaatgatac
gtacgtcgagtccatagcctgagcgcacgtacatggcacaataaagttactagtccagatttagttaaatagaagttttcattgtgttgatct
gataaatatattttggaaatgcagattcaagctttgtgccaccgatggtatatgcgatgttgggaagttcgaagcatttggcaataggaaatgt
ggcagttccatcgcttctcatttctgcaatgcttggccgagtcgttaatcctcacgataatcccaagcttatcttcagttggtatttactgct
actttctttgctggagttttccaagcttccttaggcttgttaaggtcagaagtcttcattttttttcgttagatttagtgtcgagtcaaattgca
acggcagtagacctaattaatttgtattttatctgatggtgatataggctaggattcatagtggacttttctatcgcatgcaacaatattgggt
tcatgggaggagcagccacagtagtgtgcttacagcagctgaaaggaattcttggacttgttcatttcacccatgaaactgatattgtcagtgt
catgcgctccatctttagccaattacaccaggttccttccactatctcattttattttttaaatctttttttctcaaaataataagttatacttag
cctccaatattttacgtacggtcttttcttttttctttcttatacgttttttgttaattattttgctacagtggagatgggaaagtggagtcctagg
ttgttgttttctcttcttcctcttgttgaccagatattttgtaagtaaattaattaattttaaatttatactcgctttcggcagatttgttacg
tatttatagtttataaataaatatgtcactattgtgttatatccgtaaattaatcatgatactatccattaagcatgtgatacaattgtagact
tccttcaccttaagattaactcatactcgtgtataacatcttctaatgattcctagaattgttttcaccatattttcaattgctaataacctca
ttaattatttcataccattatcttcagttcaagttcactagattaatttactaatggacttgttttatttattgtgtggtgtaattcctatacca
gagcaaaagaagccagcttttcttctggataagttgtatggcgcctctaacatctgtgatcttgggaagtgttcttgtttatttcacccatgct
gaaaaaaatggggttcaagtggtaattaatttctccacagtcgaaattaaatttatatctttatatttcactgccaaattttatttttttattttc
tatacatgatgtgaatataatttatggtgagtgaccagtgacgtccacatgttggtccccttagtatgatatcgattaacttttttctagcgatgt
ttgtattaattataagacagtacgtacatgcggctaacctgtgaatatgtttggactttttgttggattttaattttctcagattgggcacttgaa
aaaagggataaatccaccatcgtattctgaactggcatttagctcgcagtatcttacaactgccattaagactggaatcgtcactggtgtcatc
gccatggctgtaagtacaatatgtctccaattgttaatttattttttatttacttttttatctgtcatactaattcggattcggtcttagacttttc
tgatttatataagattctcatgacctcattctatagtctggaagatacttgggtcaaaaaggttagaaaagaaaaaaaatagacgggaataaat
gttcataaattatgcttgaagaaactaattaaaatagtgatatacttcttgtctctttgtcattttatcgtacacacggcaatatattggtgac
tagctcatagactacaactagcagcttttagttaaagaattaactatatacataaatttattcttacattattgatgtacataagttaaactct
ttaaattcctctttgtgcttttttttgattctgaatttttatataaatgtggtatatgtcagacacaccaacttgtttaggactgcgaagttgtgc
ttgttatatatatatatatatatatatatatatatatatatatatatatatatatatacacatgaagaataacagttggcgtatatta
tttattgcttacctattttaaccgatgaaattaaacaatacaggaaggaatagcagttggaaggagtttcgccatagtggagaactatcacatt
gatgggaaacaaagaaatgattgcctttgggatgatgaacattgctggttcttgcacctcttgctacttaaccacaggtactctttcactcaaaa
ctaacatctctcagtccactcaattacttaaattaaaattagttggtgaatgtatagtatatgtataatttatattaatatatgtgttattagt
gtataatctaattataccggctagaaaagtgacactgaaactaaacagctatttgtgtaaagatcccattttttttccttcaagtttctagag
atgggagtgaacaattgaaaacataattaagtaaaattgcttttttagattaagttgtaaatgagatggtcatataattcaacat
aatcatgagttctcgtctcaccaccacacattacgagaattttcacgaaaaaagaatttaggctcacaactaggggtgtgctgaacacattctt
taatttagttgtctgtttgctaattttcttctaatattaacatctttttttcctttttcaggaccattttcacgtacggcagtgaatttca
atgcaggatgcaagacagcagtgtccaacatagtaatggcaacagcagtgatgataacattgttgttgctaacaccattgttccattacacacc
cctgttgtgctttcctccattataatttcagccatgctaggcatcattgactataagtcgtatccaccttggaaagttgacaaatacgat
ttcctcgtttgcattagttccttcattggagttgtctttggtagcgttgaagttggcctaatagtcgcggtaagtagcatacattttaatagg
atttaaaaatctttctgcgcactcagcttaattttaattttatgataactatgttcgtgtgtgattcaggtggcaatgtcttttacttaggat
acttctctttgtagcaaggccaaagacatttgtcttaggtaaaataccaaactccatgacctatagaaacactgaacaatattcagcagcaagc
agtgttcctggaattctcatcatacacattgatgccccaatctattttgcaaatgcaaagttatttgagggaaaggtaactacaacacccacatt
ttcatctcaatttagtgattgatgacttcaacacaatagttagtcacttttatatcgatgggtcttgaaatatcttaggatttcaagatggat
agatgaagaagaagagaagcaaaggactttatctgagattgagctgcaatatgtcatattggatatgagtggtaagtgttaattcaagataaaa
aaaacttcgggttttttttttcttttttaatagttaatgttttactgctgacatcaatcctcttaaatgcagctgttggaaacatcgatacaagt
ggaattagtatgcttgaggaagtgaagagaaatgcagataggcagatctgctaaaggtacaaatatctgacaaattattagtagtgaaacatcata
ttaccatttatagttgtctctacgggaacagttcagtgattaataaaccacaactcgaacttttagtatcacgagcttgaattcagtgacatctt
gtccactactacccagttgatttccttttttctttttctttttttattcaattgttcaatttgtagcttttattggcaaatcctgagggaagt
gatgaagaagctggataagtcaaatttcattgacacaattgggaaggaatggatctatttaacagttggggaggctgttaatgcatgcaattat
attcttcacacttgcaagtttcaatccaagagaattgaatcttcaacaatcccagacgataacgtatga SEQ ID NO: 10 Polypeptide sequence of NtSULTR3;2-S
MGNAHFDDQYSHQKVEIPAPKPFLKTLKSCVKETLFPDDPFRKFKNQSLTKKLALGLQYFVPILDWAPRYTFQLFKADFIAGITIASLAVPQGI
SYAGLANLPPVIGLYSSFVPPMVYAMLGSSKHLAIGNVAVPSLLISAMLGRVVNPHDNPKLYLQLVFTATFFAGVFQASLGLLRLGFIVDFLSH
ATILGFMGGAATVVCLQQLKGILGLVHFTHETDIVSVMRSIFSQLHQWRWESGVLGCCFLFFLLLTRYFSKKKPAFFWISCMAPLTSVILGSVL
VYFTHAEKNGVQVIGHLKKGINPPSYSELAFSSQYLTTAIKTGIVTGVIAMAEGIAVGRSFAIVENYHIDGNKEMIAFGMMNIAGSCTSCYLTT
GPFSRTAVNFNAGCKTAVSNIVMATAVMITLLLLTPLFHYTPLVVLSSIIISAMLGIIDYNAAIHLWKVDKYDFLVCISSFIGVVFGSVEVGLI
VAVAMSLLRILLFVARPKTFVLGKIPNSMTYRNTEQYSAASSVPGILIIHIDAPIYFANASYLRERISRWIDEEEEKQRTLSEIELQYVILDMS
AVGNIDTSGISMLEEVKRNADRRCLKLLLANPGGEVMKKLDKSNFIDTIGKEWIYLTVGEAVNACNYILHTCKFQSKRIESSTIPDDNV SEQ ID NO: 11 Polynucleotide sequence of NtSULTR3;2-T
atcactttatctaaaactatccctctgaaactctgagtactcttcatttataatcttgacccttactctatatttattgtataaatttcataac
cttcttagagaagtgcacccttccatttaatgaaatttctctattaattttctcattttcccatttcacatatttacttggatacgtacctatc
acaaaatctcacctattttcatcagaatcttatccaactcacttttctccatcttttggacagtaacacttactgtcaccttccatcaaattc
caagtcattagtaagtttacttgtttgatattaagtagttttgtgatctccctttagattatatatgtccatattttacctataaatttagt
cagcccaaagtctctagtcaaggaaaaatattcaacacaagtactgttacatttccatttcattctctcttctttagaagttattctttttcattt
caactcaattaccaagtggagtagtactagttgtttggtagctgtcttttttgaaagttgatggaaacataaataggaggaaaggaaccacaga
catttttgcattccaaaccattctcattaattagaccaaaatggaaccaaataatgagaacagagttatagacataacagcaatggagtacaca
aagttgtttctccacctcatagaagcacctttcaaaaactcaaaaacaggcttaaggaaaccttttttcctgatgacccttacgtcaattcaa
aggtcagccattgaaacagaagctaattcttggtgctcagtatgttttttcccatactagaatggggtcctaattacagcttcaagttgttcaaa
```

-continued

SEQUENCE LISTING

```
tctgatataatctctggcctcaccattgctagccttgcaattcctcaggttggttctttttttgtctcaggcctaaccctttcttgattttgt
cttttaaagttatggtaatttcctcttttactattgccactttgctaactctttcctttttttcttttggcagggaattagctatgcaaaact
agctaacttacctccaattgttggcctttgtacgtgttttcattgtcatcgtgcaatttattttttcattttttaatttgttgggggtacttaag
taacttttttttttctttcattttgctttggagtgtagattcaagttttgttcctcctcttgtttatgctgttcttggaagctcaaggg atct
tgcagtagggccagtttcaattgcatcacttgttttaggatcaatgctaagagaagtggtgtccccaactaaagatccaatcttgttccttcaa
cttgctttctcttctactttctttgctggccttttccaagcttctttaggcttttttgaggtaattcccactttttttatttcattcttctcaat
tacaaattacaaaggaggtgccaaggttcgaggacgagctgcaccccagggtgtaatgcatatagcccacgctaatacaagtattagtgcttg
tttccacggctcgaattcgtgacttataggtcacgcggagacaaacatatcgttgttcccaggcttccctctactattacctaaaaaagaaaa
agggtaattacaagtgtaagatccatttttagtaatctattttttttgatattttttgggaaattgcagactcggttttattattgattttctttc
aaaagcaacactgattggattcatggctggagctgctgttatagtgtcactgcagcaacttaagagtcttcttggaatcacaaattttaccaag
caaatggcgatagtccctgttttaagttctgttttccatagaactaatgaggttactactgtcttttttaaccctctcttatgtactattgtatg
taaatgtaactgatatattacttttaatttccttctttggcattatataaaactaaattgtctttagtcttcagcttttggagcaaattca
gagaattgtatttgtctgtgtcttttctacatttggattataagaatattcacgtgctgacttggctttcgatgccatcatgtgaattcaagat
tcttaaaatcaagtactaatttctcccccatttgttgatttgttttacaaattttgatgtggataagttcattataatgtaaatcgtctaaa
aaggtgattacgatctgataataattgattgtagaaaaacaaataatagcaattttaatggtgttgtagaatgagaaacatgtagtcaacaagaa
aaaatgttgaccaatctagcatattataagctagtaatgcaccgaatttttttataatttcttccaaaatagtttgacaaaaattaattcttta
ttaactattgaaactttataatagacatccacacacacccttctaatttttcaatttgagttagactacattcaagtcaaggcagccaagggtttg
agtgtttgaccttatgatgttatgttttttttttttttaccccgtcacttttggatcttactaatttgggagtaacatgcttcctcttaaaggc
gactctattttcaagactacaaacccgagagcatgtttatcactttgaggggcttaactgaaatagtaacattttatatggtatatatgcagtg
gtcttggcaaactatactaatggcattctgcttcttggtgttcctccctattgaactagccagacacattgtaagtgctcttttccagtttgtttttct
ttcttcacttttaaaatgtaaggaaaagtcatatttagttgacgtaatttactgaattctaaatgcaaaagtcattatatagttcacaattaag
tacgtaataatgtattgactgtggtttcaaagttttgttgcacaatagataagttcgaatttcttaaattccttaccaattagtagaaaggaaa
gatgtcctatactatattacctttcgggagacatttctaagttctaaccattttttcgaatctgcaaactgtgcatttttcatgttctttgtaaa
tctctatatattttttgaatgaaaatttaataataacttttaaaaattggttaactagtaaataaaagacatagacatccataatcttaaga
aaatttgtaactgatatcatgactcatgagagaaaaatacttaatactttgacttacaaacatttttctttctgttttttgggatgaacatttt
ttatacagtcaaacatctctataatagtcttatttgtaccgaattgtttagctcttatcgcgcaatgatgttatagtgaacatatattataac
atagcatgaaaattagttccataaaaaagttgaatttataagtgaatggttgttatatagtgatattgttatagaaaatctcactgtatatc
ttgttattaacatgacaaacttttgggtgcagagcatgagaaagccaaactattttggggtttcagcaggagccccctcttctttctgtcattat
ctctacacttctggtctttgcaatgaaaggtcaaaagcatggtatcagcattgtatgtttctaaaccaagaaaattatctatacttctaagt
tctaatatctattactactatatttctaaatcttatatttatgtaattatttttccttttgtcttttggtagattggcaaattacaagaaggg t
tgaaccctccttcatgaacatgttacatttcagtggaagctacttgggacttgtaatcaaaactggaattgtcactggcatcctttcacttac
tgtaatttttttctcttttacctatctttttatgaaaaaggaaaagaactcaaattatgattttggaatataacatctataaataatgactata
aagctcatagcaggcactaatatcttagacacaaagaaaacttaggacccgtttgtccataaatcttttttttccgaatttttaaaaaaaaata
tgtttatccataaaaattttgaaagttttttgaagatttttttgaaaatgagtttttttccaaatttttgggagaaacttttttcccccactcacaaaac
tgcaatattttttcaagtgaaatgtatgttcaaacataattttcaaatttcaaataccattttcaacttaactccaaatagtatttgttttca
aaattacaattttttatatccaaacggctacttaatgtgttgtgtaaaaaaaaattaggaaggaattgcagtggggaggacttttgctgcttta
aagaactaccaagtggatggaaacaaagagatgattgctattggggtcatgaacatagttggttcctcaacttcctgctatgtcacaactggta
caataaaccttcaacagtttagaatttctaaaactgtttgttgcttttatttttcactgttttcttgagccaagggtctatcggaaacaatctctc
tacctttaaaggtaggggtaaggtctatgtgcacattaccttccccagacatcacttgtggaattacactgggtttgtttgttgttgatgtag
aatctctaaaactgcagaatcctttaaatgtaactctacattttcaggtgcattctctaggtcagcagtgaatcacaatgcaggaagcaaaact
gcagtttctaacatagtaatggcagtgacagtaatggtgacacttcctttcctaatgccccctcttccaatatactccaagtgtgtgctcggag
ccataatcgtcactgctgtcgttggcctaatcgacatcccagctgcttaccaaatctggaagatcgataaattcgatttcctagtcttgttatg
tgcattcttcggagtcatcttcattctgttcagaatggtcttgccattgcagtaagctccctctcaagttccttttccttttttcttaacagtc
tctccacctgcacaaggtaggggtaagactgcgtacacactaccctcccccacccccacttgtgggattatactgggtatgttgttgttgttacgt
tacttggtttttgacttttcttttataatgaattttcagattggaatatcaattttaaaaggtgttgctgcaaattacaaggcccaaaacagtaatg
ttaggaaatatacctggtactgggatttatagaaatcttgatcattataaggaggctatgagtgttcctggttttctcatttttaagtattgaag
ctccaatcaactttgccaatgcaacttatcttaaagaaaggttagtattagttgaactgctgcattgaccattctatctttcattttcttctt
ttttctcttttccatatttatttaggtcttttttatttgccccgaaaaaaaggattcaagatggatagaagactacgatgcagagggagaaa
aaaacaagaaagagtcggggcttagatttgtggtccttgatttgtctggtaagttcatagagacgcttctcaatattgtcatttattcccaattt
ggcataactggcaaagttgttgtcatgtgaccaggaggtcacaggttcgagccgtgaaaataatatcttcagaaatgcaggataagattcgt
acaataaatcattgtggtccggctcttctccgggtcccgcgcatagtggaagtttagtgcaccgggctgcccttaccccctacttttagataata
ccaagaaacagtcaggacatcaagaaattcccataaataaaacaaattaatttcaacttgaaaagtgattgtggcttgttttttattcttcagc
tgtgactgccattgatacaagtggagtctcattgttcaaggattttgagtatggcaatggaaaggaaaaggccttgaggcaagtgtactttagctt
ttagaagaccattttgttttctatttattctgatattatgtgagtatttattcttaatgattttggcattgcagtttgtattggtgaatcca
ataggagaagtactggaaaaattacagagggctgatgaaactaaagtatgatgagaccagattgccttttttaacagtcgaagaagcagtag
cttcactttcctcaacaataaaatatcaaataccagacaatgtttga
```

SEQ ID NO: 12 Polypeptide sequence of NtSULTR3; 2-T
MGNADFDDQYSHQKVEIPPPKPFLKTLKSCVKETLFPDDPFRKFKKQPLTKKLTLGLQYFVPILDWAPRYTFQLFKADFIAGITIASLAVPQGI
SYAGLANLPPVIGLYSSFVPPMVYAMLGSSKHLAIGNVAVPSLLISAMLGRVVNPHDNPKLYLQLVFTATFFAGVFQASLGLLRLGFIVDFLSH
ATILGFMGGAATVVCLQQLKGILGLVHFTHETEDIVSVMRSIFSLFHQWRWESGVLGCCFLFFLLLTRYFSKKKPAFFWISCMAPLTSVILGSVL
VYFTHAEKNGVQVIGHLKKGINPPSYSELAFSSQYLTTAIKTGIVTGVIAMAEGIAVGRSFAIVENYHIDGNKEMIAFGMMNIAGSCTSCYLTT
GPFSRTAVNFNAGCKTAASNIVMATAVMITLLLLTPLFHYTPLVVLSSIIISAMLGIIDYNAAIHLWKVDKYDFLVCICSFIGVVFSSVEVGLI
VAVAMSLLRILLFVARPKTFVLGKIPNSMTYRNTEQYSAASRVPGVLIIHIDAPIYFANASYLRERISRWIEEEEEEEEEKQRTSTEIELQYV
ILDMSAVGNIDTSGISMLEEVKRNADRRCLKLVLANPGGEVMKKLDKSNFIDKIGKEWIYLTVGEAVNACNYILHTCKFQSERIESSTIPDDNV SEQ ID NO: 13 Polynucleotide sequence of NtSULTR3; 3-S
```
atggaaccaaataatgagaatagagtttatagacataacagcaatggaggtacacaaagttgtttctccaccccatagaagcactttccaaaaac
tcaaaaataggcttaaagaaacctttttcccctgatgaccccttacgtcaattcaaaggtcagccattaaaacagaagctagttcttggtgctca
gtatgttttttcctactctagaatggggtcctaattacagcttcaagttgttcaaatctgatatagtctctggcctcaccattgctagccttgca
attcctcaggttggttcttttttttgtatcttattgatggtactgttatattgcctcttttcctcctcttgagtcgagggttttttcggaaacag
cctctcatcgctcgggtaggggtaaagttttgtgtacacactaacctcccccaccccattagtagatttcactggtcgtcgttgttgttgg
tctttttatcgtctcaggcctaaccattttcttgattttgtcttctaaagttatgaattttcttcactattgttacttgctaactctttc
ccttcttttctttcttctttttggcagggaattagctatgcaaaactagctaacttacctccaattgttggctttgtgagtgttttcattgt
catcatgcattttttttgttggggtacttaagtaattaacttttttttttaatttgcttttggaaagtagattcaagttttgttcctcctct
tgtttatgctgttcttggaagttcaagggatcttgcagtagggccagtttcaattgcatcacttgttttaggatcaatgttgagagaagtggtg
tccccaactaaagatccaatcttgttccttcaacttgcttctcttctactttcttttgctggccttttccaagctcttttaggcttttttgaggt
```

SEQUENCE LISTING

```
attcccactttttttatttcattcttctgaagtacaaattccctaaaaggaaaaaaaaatggacagttcggtgcacaaggtatcatgtgttcac
ccagggcccggaaaagggtcgaactccaagggggtgtgatgtatatacagaggcgtacccaggatttgaaggtcgctggtgcacttttggttca
accaaaatctgctttgtatataggtatccacactattttctaaagacataacatggagttttttgccgaacttagtgtgccggt
gaccoctctacctattgtataggtccgcctctgtgtatatagcctactcttatacaagtattagtggttacgtccacggctcgaactcgcgaca
tacgaatcacacggagaccattttatccttactccaaggcttcctactatgattacctaaaaagaaaaaggacaattacaagtgtagatattgg
ttttggttagtaatctatttttttttaatattttttgggaaattgcagactgggttttattattgattttctttcaaaagcaacactgattggatt
catggctggagctgctgttatagtgtcactgcagcaactcaagagtcttcttggtatcacaaatttttaccaagcaaatggcgatagtccctgtt
ctaagttctgttttccacagaactaatgaggttattactgtcttttttaccctcttcttatctactattgtatgtaaatgtaactgataattata
cttttctcttcttggaattatataaaactaaatttgtctttagttttcagcttttttggagcaaattcagagaattgtatttgtctgtgtcttttt
ctacatttggattataagaatattcacgtgctgacttggctttcgattgccatcatgtgaattcaagattcttaaaatcaagtactaattgtct
ccccatttgttattatttttattttaatttaacaaattttgatgtggataagttcattatcatgcaaaatcgtctaaaaagttgattaga
atctgaaaataattgattgtagaaaaacaaataatagcaatttaatggtgtgtgaatggaaacatgtagtcaacaagaaaaaatgttgacc
agtgtagcatatatattataagctagtaatgcaccgaatttttaaaaattttcttccaaaattgtttgacaaaaattaattctttattaagtatg
gaaactttataaaatacatccccacaaaccttctaattctcaatttgagttgactacattcaagtcaaggcagtcaagggcttgagtgtttgac
ctcatgatgtccaaaaagtttttaaagcaattcggagagaaaaaaaaaggtgcttcactttaatgttttattttttatatttcatcatgtccga
cctgtgagttcgagtcttcccaagagcaaggtgggaagttcttggagggaagatgcggggggtctatttggaaacagtctctctcacccctaggg
taggggtaaggtctgcgtacacactatcctccccagaccacactaaatgggattatactgggttgttgttgttgttgttgtatactccctctaa
agatgactccatttacaagactacaaatccaaagcatatttatctctttgagggggcttaactgaaataataaaggaaaatgacattatataat
cgcttttaaaataataataataaaaataatgtatattttttttttttgtatatataacattttatatggtatatatgcagtggtcttggcaaac
tatactaatggcattctgcttcttggggttctcctattgaccagacacattgtaagtgctcttttccactttttgtttttttccttttttttttc
tttcttcacttttgttatagtgaatatattataacatagcatgaatattcgttacacaaaagctctgaccttttataagaaaatgattgttatata
acgatactattataaaaatgtctaacggtatatcttggtattatcatgataaatttgggtgcagagcatgagaaagccaaaactattttggata
tcagcaggagccctcttctttctgtcattatctctacacttctggtatttgcaatgaaaggtcagaagcatggtatcagcattgtaagtttct
aaaccccaaggaaattcatctatactttaatatctattatattttctaaaccttgatattatgtaattattttcctttgtcattgtagatt
ggcaaattacaagaagggttgaaccctcctcatggaacatgttacatttcagtggaagctacttgggacttgtaatcaaaactggaattatca
ctggcatcctttcacttactgtaatttttttttttttctcttttacctatcttttttatgaaaaggaaaagaactcaaattatgagttttggaa
tataacatccataaataatgactataaagctcatagcaggctctaatatcttagacacagaaaacttaggacctgtttgtccatatcctttt
ttccttctttttttcggaacttttttaaaaaaaatgtgtttgtccataaaattttggaagttttggaaaatgtttgtcgaaaataaattttcaaaa
accaataagttttccccgcttcaaaactgcaatattttattcaaacataattttaatttcaaatattattttttcaacttaactccaatatta
ttattattattattattatttttcaaaactttacagttttttatgtccaaacgcctacttaatgtgttgtgttaaaaaaaaaaaaaaatag
gaaggaattgcagtggggaggactttttgctgctttaaagaactaccaagtggatggaaacaaagagatgattgctattggggtcatgaacatag
ttggttcctcaacttcctgctatgtcacaactggtacataaatctttcaacattttagaatttctaaaactgttttgtttgcttttattttcactg
tttcttgagccgatggtctatcggaaacaatctctctacgtttagaaggtaggagtaaagtctgcgtacacattaccctcccccaaacccacctt
gtgtgattacactgggtttgttattgttacagtagaatttctaaaactgcaaacatgtgttaaatgtaactctaaattttcaggtgcattctc
taggtcagcagtgaatcataatgcaggaagcaaaactgcagtttctaacatagtaatggcagtgacagtgatggtgacactccttttcctaatg
cctctcttccaatatactcccaatgttgtgctcggagccatcatcgtcactgctgttgttggcctgatcgacgtcccagctgcttaccaaatct
ggaagatcgataaattcgatttcctagtcttgttatgtgcattcttcggagtcgatcttcatctctgttcaaaatggtcttgccattgcagtaag
ctccctctcaagttccttttcgttttttcttaacagtctctccgcttgcacaaggtagggggtaagggtgcgtacacaccactctcctcagatcc
cacttgtggaattatacgggggtatattgttgttacgttacttggttttttgacttttcttttataatgaatttcagattggaatatcaatttaaa
ggtgttgctgcaaattacaaggccaaaacagtaatgttaggaaatatacctgggactggaatttatagaaatcttgatcattataaagaggct
atgagtgttcctggttttctcattttaagtattgaagctccaatcaactttgccaatctatcttaaagaaaggttagtactagttgaac
tgctgcattgaccattctgtcattcatttttttttttttttttctcttccatatttatttaggtattttttattgccaaaaaaaggattt
caagatggatagaagactatgatgcagagggaggaaaaaacaagaaacagtcagggcttagatttgtggtccttgatttgtctggtaagttcat
agagacatggttctcaatattgtcatttaatcccaatttggcgtaattggtaaagttgctgccatgtgactaagtggtcacgggttcgagccat
ggaaacagcctcctgcagaaatgcagcgtaaggttgtgtacataaacctctgtgtgccggtctttccctggacctttgcgcatagcgggagctt
agtgcaccgggctgcccttcccccctactttggataataccaagaaacagtcaggacatcaagaaattcccacaaatgaaaacaaattaattta
ccaagaaacagtcaggacatcaagaaattcccacaaatgaaaacaaactaatttcaacttgacaagtaattgtggattgttttttttaatcttcag
ctgtgactgccattgatacaagtggagtctcattgttcaaggatttgagtatggcaatgaaaagaaaggctttgaggtaagtgtactttagct
tttagagtcactatttctttccaacaacaacaacaacaacccagtaaatcccacttagtggggtcgtagtgtgtacgcagac
cttaccctaccctagggtagagagactgtttccaaatagaccccggcatccttccctccaagaacttcccacctgtcttggagagactcg
aactcacagcctttccttccctccaacaatccactatttctttccaaatgaagtcaaaatcctcaagaccattttgttttctatttattctgat
attatgtgagtatttatttccttaatgattttggcattgcagtttgtattggtgaatccaataggagaagtactggaaaaattacagagggctg
atgaaactaaagatatgatgagaccagattgcctcttttaacagtcgaagaagcagtagcttcactttcctcaacaataaaataccaaatacc
agacaatgtttga
```

SEQ ID NO: 14 Polypeptide sequence of NtSULTR3;3-S
MEPNNENRVIDITAMEVHKVVSPPHRSTFQKLKNRLKETFFPDDPLRQFKGQPLKQKLVLGAQYVFPILEWGPNYSFKLFKSDIVSGLTIASLA
IPQGISYAKLANLPPIVGLYSSFVPPLVYAVLGSSRDLAVGPVSIASLVLGSMLREVVSPTKDPILFLQLAFSSTFFAGLFQASLGFLRLGFII
DFLSKATLGIFMAGAAVIVSLQQLKSLLGITNFTKQMAIVPVLSSVFHRTNEWSWQTILMAFCFLGPLLLTRHISMRKPKLFWISAGAPLLSVI
ISTLLVFAMKGQKHGISIIGKLQEGLNPPSWNMLHFSGSYLGLVIKTGIITGILSLTEGIAVGRTFAALKNYQVDGNKEMIAIGVMNIVGSSTS
CYVTTGAFSRSAVNHNAGSKTAVSNIVMAVTVMVTLLFLMPLFQYTPNVVLGAIIVTAVVGLIDVPAAYQIWKIDKFDFLVLLCAFFGVIFISV
QNGLAIAIGISILKVLLQITRPKTVMLGNIPGTGIYRNLDHYKEAMSVPGFLILSIEAPINFANATYLKERISRWIEDYDAEGGKNKKQSGLRF
VVLDLSAVTAIDTSGVSLFKDLSMAMEKKGFEFVLVNPIGEVLEKLQRADETKDMMRPDCLFLTVEEAVASLSSTIKYQIPDNV SEQ ID NO: 15 Polynucleotide sequence of NtSULTR3;3-T
atgaaccaaataatgagaacagagttatagacataacagcaatggaggtacacaaagttgtttctccacctcatagaagcacctttcaaaaac
tcaaaaacaggcttaaggaaaccttttttcctgatgacgtcaattcaaaggtcagccattgaaacagaagctaattcttggtgctca
gtatgttttttcccatactagaatggggtcctaattacagcttcaagttgttcaaatctgatataatctctggcctcaccattgctagccttgca
attcctcaggttggttctttttttgtctcaggcctaaaccctttcttgattttttgtcttttaaagttatgtaattttcctctttactattgcca
ctttgctaactcttttccttttttctttttggcagggaattagctatgcaaaactagctaacttacctccaattgttggcctttgtacgtgttt
tcattgtcatcgtgcaattattttttcattttttaatttgttgggggtacttaagtaacttttttttttcttttcattgctttggagtgtag
attcaagttttgttcctctcttgttttatgctgttcttggaagctcaagggatcttgcagtaggggccagtcttcaattgcatcacttgtttagg
atcaatgctaagagaagtggtgtccccaactaaagatccaatcttgttccttcaacttgcttttctcttctacttctttgctgcccttttccaa
gcttcttaggcttttttgaggtaatttcccacttttttttattttcattcttctcaatttaaaattacaaaggaggtgcacaaggttcgaggacgag
ctgcaccccagggtgtaatgcatatagcccacgctaatacaagtattagtgcttgttccacggctcgaattcgtgacttataggtcacgcgga
gacaaacatatcgttgttcccaggcttcccttctactattacctaaaaaagaaaagggtaattacaagtgtaagatccattttagtaatctat
ttttttttgatattttttgggaaattgcagactcggttttattattgattttctttcaaaagcaacactgattggattcatggctggagctgctgt
```

```
tatagtgtcactgcagcaacttaagagtcttcttggaatcacaaattttaccaagcaaatggcgatagtccctgttttaagttctgttttccat
agaactaatgaggttactactgtcttttttaaccctctcttatgtactattgtatgtaaatgtaactgataattatactttaattttcctttctt
ggcattatataaaactaaatttgtctttagtcttcagcttttttggagcaaattcagagaattgtatttgtctgtgtcttttctacattttggatt
ataagaatattcacgtgctgacttggctttcgatgccatcatgtgaattcaagattcttaaaatcaagtactaattttctccccatttgttgat
ttgttttttacaaattttgatgtggataagttcattataatgtaaaatcgtctcaaaaaggtgattacgatctgataataattgattgtagaaaa
caaataatagcaatttaatggtgttgtagaatgagaaacatgtagtcaacaagaaaaaatgttgaccaatctagcatattataagctagtaatg
caccgaattttttttataatttcttccaaaatagtttgacaaaaattaattcttttattaactattgaaacttttataatagacatccacacacacc
ttctaattttcaattgagttagactacattcaagtcaaggcagccaaggggtttgagtgtttgaccttatgatgttatgtttttttttttttta
ccccgtcacttttggatcttactaatttgggagtaacatgcttcctcttaaaggcgactctattttcaagactacaaacccgagagcatgttta
tcactttgaggggcttaactgaaatagtaacattttatatggtatatatgcagtggtcttggcaaactatactaatggcattctgcttcttggt
gttcctcctattgaccagacacattgtaagtgctcttttccagttttgttttttcttcttcactttttaaaatgtaaggaaaagtcatatttagt
tgacgtaatttactgaattctaaatgcaaaagtcattatatagtttcacaattaagtacgtaataatgtattgactgtgttttcaaagttttgtt
gcacaatagataagttcgaatttcttaaattccttaccaattagtagaaaggaaagatgtcctatactatattacctttcgggagacatttcta
agttctaaccatttttcgaatctgcaaactgtgcattttttcatgttcttttgtaaatctctatatattttttgaatgaaaatttaataataactttt
aaaaattggttaactagataatctgaaataaagaaacataaccataatcttaagaaaatttgtaactgatatcatagactcatgagagaaaaat
acttaatacttttgacttacaaacattttctttctgttttttgggatgaacattttttatacagtcaaacatctctataatagtcttatttgtac
cgaattgttttagctcttatcgcgcaatgatgttatagtgaacatatattataacatagcatgaaaattagttccataaaaaaagttgaattt
atagtgaatggttgttatatagtgatattgttatagaaaaatctcactgtatatcttgttattaacatgacaaacttttgggtgcagagcatga
gaaagccaaagctattttgggtttcagcaggagccctcttctttctgtcattatctctacacttctggtctttgcaatgaaaggtcaaaagca
tggtatcagcattgtatgttttctaaacccaagaaaattatctatcatctcaagttctaatatctattactactatatttctaaatcttttatat
ttatgtaattattttttccttttgtcttttggtagattggcaaattacaagaaggttgaacctcccttcatggaacatgttacatttcagtggaa
gctacttgggacttgtaatcaaaactggaattgtcactggcatcctttcacttactgtaatttttttctcttttacctatctttttatgaaaaa
ggaaaagaactcaaattatgattttggaatataacatctataaataatgactataaagctcatagcaggcactaatatctttagacacaaagaa
aacttaggacccgtttgtccataaatcttttttccgaatttttaaaaaaaaaatgtttaatccataaattttgaaagtttttgaagattttt
tgaaaatgagttttttccaaattttgggagaaacttttttccccactcacaaaactgcaataattttttcaagtgaaatgtatgttcaaacataa
ttttcaaatttcaaataccattttttcaacttaactccaaatagtatttgttttcaaaattacaattttttatatccaaacggctacttaatgtgt
tgtgtaaaaaaaaaattaggaaggaattgcagtggggaggacttttgctgctttaaagaactaccaagtggatggaaacaaagagatgattgct
attggggtcatgaacatagttggttcctcaacttcctgctatgtcacaactggtacaataaaacctttcaacagtttagaatttctaaaactgtt
tgttgctttattttcactgtttcttgagccaagggtctatcggaaacaatctctctaccttttaaaaggtagggggtaaggtctatgtgcacatta
cctcccccagacatcacttgtggaattacactgggttgttttgttgttgatgtagaatctctaaaactgcagaatccttttaaatgtaactctac
attttcaggtgcattctctaggtcagcagtgaatcacaatgcaggaagcaaaactgcagtttctaacatagtaatggcagtgacagtaatggtg
acactccttttcctaatgcccctcttccaatatactcccaatgttgtgctcggagccataatcgtcactgctgtcgttggcctaatcgacatcc
cagctgcttaccaaatctggaagatcgataaattcgatttcctagtcttgttatgtgcattcttcggagtgcatcttcatttctgttcagaatgg
tcttgccattgcagtaagctccctctcaagttcctttcctttttttcttaacagtctctccacctgcacaaggtaggggtaagactgcgtacaca
ctaccctccccaccccacttgtgggattatactgggtatgttgttgttgttacgttacttggttttttgactttcttttataatgaatttcagat
tggaatatcaattttaaaggtgttgctgcaaattacaaggcccaaaacagtaatgttaggaaatatacctggtactgggatttatagaaatctt
gatcattataaggaggctatgagtgttcctggtttctctcattttaagtattgaagctccaatgccaatgcaacttatcttaaagaaa
ggttagtattagttgaactgctgcattgaccattctatctttcattttttcttcttttttttcttcttttccatatttattaggtcttttttattg
ccccgaaaaaaaaggatttcaagatggatagaagactacgatgcagagggagaaaaaacaagaaagagtcggggcttagatttgtggtccttg
atttgtctggtaagttcatagagacgttctcaatattgtcatttattcccaatttggcataactggcaaagttgttgtcatgtgaccaggaggt
cacaggttcgagccgtgaaaataaatatcttgcagaaatgcaggataaggattgcgtacaaataaatcattgtggtccggcctcttctccgggtccg
cgcatagtggaagtttagtgcaccgggctgcccttaccccctactttagataataccaagaaacagtcaggacatcaagaaatttcccataaata
aaacaaattaatttcaacttgaaaagtgattgtggcttgttttttattcttcagctgtgactgccattgatacaagtggagtctcattgttcaa
ggatttgagtatggcaatgaaaagaaaggccttgaggcaagtgtactttagcttttagaagaccattttgttttctatttattctgatattat
gtgagtatttatttccttaatgattttggcattgcagtttgtattggtgaatccaataggagaagtactggaaaaattacagagggctgatgaa
actaaagatatgatgagaccagattgccttttttttaacagtcgaagaagcagtagcttcacttttcctcaacaataaaatatcaaataccagaca
atgtttga
```

SEQ ID NO: 16: Polypeptide sequence of NtSULTR3; 3-T
MEPNNENRVIDITAMEVHKVVSPPHRSTFQKLKNRLKETFFPDDPLRQFKGQPLKQKLILGAQYVFPILEWGPNYSFKLFKSDIISGLTIASLA
IPQGISYAKLANLPPIVGLYSSFVPPLVYAVLGSSRDLAVGPVSIASLVLGSMLREVVSPTKDPILFLQLAFSSTFFAGLFQASLGFLRLGFII
DFLSKATLIGFMAGAAVIVSLQQLKSLLGITNFTKQMAIVPVLSSVFHRTNEWSWQTILMAFCFLVFLLLTRHISMRKPKLFWVSAGAPLLSVI
ISTLLVFAMKGQKHGISIIGKLQEGLNPPSWNMLHFSGSYLGLVTKGIVTGILSLTEGIAVGRTFAALKNYQVDGNKEMIAIGVMNIVGSSTS
CYVTTGAFSRSAVNHNAGSKTAVSNIVMAVTVMVTLLFLMPLFQYTPNVVLGAIIVTAVVGLIDIPAAYQIWKIDKFDFLVLLCAFFGVIFISV
QNGLAIAIGISILKVLLQITRPKTVMLGNIPGTGIYRNLDHYKEAMSVPGFLILSIEAPINFANATYLKERISRWIEDYDAEGEKNKKESGLRF
VVLDLSAVTAIDTSGVSLFKDLSMAMEKKGLEFVLVNPIGEVLEKLQRADETKDMMRPDCLFLTVEEAVASLSSTIKYQIPDNV SEQ ID NO: 17 Polynucleotide sequence of NtSULTR3; 4A-S
```
atgggattaagttcaaacagggtagaagatttatcaggccatgcatgcaatgaaacaattgtcacaatctctactactactactacagaat
tacaaatatcaagtaatccaccatttgaagtacacagagtttgcttaccaccacacaaaaccacccttcaaaaacttaggcaaaggttgttgga
agtatttttcccagatgatccactgcacaaattcaagaaccaaacatggttaatgaagttggttttgggtcttcagttttttcttccctgttttt
gagtggggtcctcagtataatcttaaactactaagggctgatataattttcgggctcacaattgctagccttgctatcccacaaggaattagct
atgcaaaacttgctcaatttgccaccctattgttggcttatgtaagtaaataaccacacttgtcattttcttctttaaaatctaatttgctttga
tcccttaattttagaatgtgaattttgatttttaagtgataaattgttcgttttttatcatttactaacaattttttgtcagttgtattggaatg
aaatggggcagaatagagctgaattgatgtaaaatacatatagccaactccaactcgtttgggggttgaagcataattattgaataaggttttt
ccatagttaaaaccagttgttaattaatcaatattttgataattaattttaattcttaagtttaaaaatcggttaagattatgaaaatttatctg
gggtctactggtctattcattgaaggcagaggtgcatgcaagattataagatcagtggatatgaatattgttgtcttttgtgaattgcgacatg
cagtttcagacttcctataaaatacataattctagaaatttccgcatatatatgtaatttgagtaaaaaatgatgcacccgctgtttgtaaagt
atacagtctatgttgaagagtaaatgtgtgcttaatcgaatacgtactttacttattttgtaaataaaaatcacactatattcaatatagtta
tttactaatctaagagtggaaatattaatggatatgatgatgcagattcaagctttgtgccaccattgatctattcagtttggggagttcgaa
acacttagcagttggtccggtctcgatagcttcacttgttatgggcacaatgctgagtgaagcagttcttacactgaagagcctgttctttac
cttcagttggcttttacagctaccctttttgccggactgtttccaggcttcactagggttttcaggtattaatttctcttgaagcaagaaact
tacacaattaggtcacttaaaaggtagttaatactgccattaactctggataacctggaataaattataagtaaccttctatgaaatgttaa
attacattgaccctgtcagttgataactaagtccatatgttagtcgttctcatccacttgaaaattggtgcaaaagttgttaagtcgactt
tctaatggactcgttatttttattcaactaaaaagagaggaataatttataattctagcataacattcccccattccaccatcaaagttaccgt
taattaagtaatggactacagtagctaagtggaaacaaacttttggaaagatatcccaaaagaatcatttagaaacatttgggcacttccactaa
aaacagcaagaaaacagagaagaaacatggaaagggacagaggattttttacgcgccatataaaactggactctagattttttatgcacaatatga
```

-continued

SEQUENCE LISTING

```
aactaacaaatatagctggtgaaaagaaaaagatttcaaggttgacataatgacttttgttactcttattttgtttgatcactcccaaagctt
tcgactttacaattctaatgtttatgtaataacttgaccaagagtatgcatctctgtctttagccatataaccacagtgttaaacttttaaaga
tgtcacatgaccataagtcaagagagaatttgaattttgcatagcattcaaatgcttacatttccggactatccttcttggccacacttgatc
gctattattgacttttatgtatcaatattgcgttacttctaaattagttgggtcggctatattaatcctgtatacccactccattttatgcgag
tccatttcattctatctttatgttttaagtaatctaaggtcctcaaagatttactttcaagaattaaaacttttttgccatgtgtttatattta
ttttagagctcggttagttcaaatgtcaagcgacttaaagtttatggtttgcaggttaggatttatcattgattttctgtcgaaggcgactttg
gttggcttcatggctggtgcagcagtcattgtttcattgcaacaactgaaagggttgttagggatagtagtccacttcacaagccagatgcaaataa
ttcctgttttgtcttctgttttccagcacaaagatgaagtaagaaaagcttcttttttcaatattgaactcctctaagatataagattgtggaaa
aattaactatgtttgtgcactgatgcaaatcattatttagtaatttaactcttctatatctctaccttacccggtagggtaaggtcttatat
gcactaccctccccaaactccacatgtgggattagactgggtcttttgttgttgttgttgtaactcttctatatctatttgcagtggtctt
ggcaaaccattgttatgggtgtctgttttctcgccttcctactgaccactcggcaaattgtaagtgtttggtttatttcagaacataatattct
gactaatattcatctctgtgttcattttctaactaaagatttgaattttctgctgtgattacagagcaccaggaacccaaaactttttctggctt
tcagcagcatctccgttggcctcggttattctctcaactctggtagtcgcgctccttaagtcgaatgctcatggcattcaaactgtaagtaaaa
ttcatcagctcttacctccattcgtagttttagctatgttgctcggactctccgaaaatgtcgtcgggtgtatgttggatcctccaaaattagt
gtattttaaaggatccaacacgggtgtggcagtattttggagagtccgccaacataggtttttgacagaataaaactgaaaatatctttggt
ttattgcagattggacacctgcaaaagggtctaaatccaccctcattgaacatgttatatctaagtggtccttatctgcctcttgccatcaaaa
ctggcattgtttccggaatcttagcgctaacagtaagtcacttgagactattacaagcaattggccgtagaaatataaagaagcgctttgggtt
tgacattttcattgacctgcaggaagggattgcagtaggaagaacatttgctgctttaaggaattaccaaattgacggcaacaaagaaatgatg
gcgattggacttatgaacatggctggctcttgttcttcgtgctatgttacaacaggtacccgcctcattggcctgttttccccgataagtaaga
ttaactcttttttttaaccagctaatatttgatttacagggtcattttctcgatcagcagtaaattacaacgctggggcacaaacagtctttca
aacataataatggcaacagctgtgctaatcactttgttatttctaatgccactgttctattacacccccattgtcatcttggctgcaattatta
taacagcagttattggcctaattgattatcaagctgctttccggttatgaaagttgacaagctcgacttcttggcttgcttgtgttcattttt
tggtgttctttttcatctcagtgcctctcggcctagccatagcagtaagcatctcctcaaaaatcacatcttatagtacgactttcttttgatgtc
tcctccttgtacctaacattttctacttctgcttgtgaaacttttaggttggagtttcggtttttaagatcctcttgcatgtaacaaggccaaat
actagtgtcctgggcaatattcctggaactcaagtatatcaaaacttaagcagatatagaacagctgttagaattccttcttccttatcctcg
ctgttgaggctcctatctacttttgcaaattctacctacctaaaagagaggttagttcaaacttcaaacacagagtgcagattcagtattttgct
tttcgccaacttcaattaa
```

SEQ ID NO 18: Polypeptide sequence of NtSULTR3; 4A-S
MGLSSNRVEDLSGHACNETIVTISTTTTTELQISSNPPFEVHRVCLPPHKTTLQKLRQRLLEVFFPDDPLHKFKNQTWLMKLVLGLQFFFPVF
EWGPQYNLKLLRADIISGLTIASLAIPQGISYAKLANLPPIVGLYSSFVPPLIYSVLGSSKHLAVGPVSIASLVMGTMLSEAVSYTEEPVLYLQ
LAFTATLFAGLFQASLGFFRLGFIIDFLSKATLVGFMAGAAVIVSLQQLKGLLGIVHFTSQMQIIPVLSSVFQHKDEWSWQTIVMGVCFLAFLL
TTRQISTRNPKLFWLSAASPLASVILSTLVVALLKSNAHGIQTIGHLQKGLNPPSLNMLYLSGPYLPLAIKTGIVSGILALTEGIAVGRTFAAL
RNYQIDGNKEMMAIGLMNMAGSCSSCYVTTGSFSRSAVNYNAGAQTVFSNIIMATAVLITLLFLMPLFYYTPIVILAAIIITAVIGLIDYQAAF
RLWKVDKLDFLACLCSFFGVLFISVPLGLAIAVGVSVFKILLHVTRPNTSVLGNIPGTQVYQNLSRYRTAVRIPSFLILAVEAPIYFANSTYLK
ERLVQTSNTECRFSILLFANFN SEQ ID NO: 19: Polynucleotide sequence of NtSULTR3; 4A-T
```
atgggactaagttcaaacagagtagaagatttatctggccatgcatgcaatgaaacaattatcacaatctctactactagtacagaattacaca
tatcaaataatcaaccatttgaagtacacagagtttgcttaccaccacacaaaactacccttcaaaaactcaggcaaaggctattggaaatatt
tttcccagatgatccacttcacaaattcaagaaccaaacatggttaatgaagttggttttgggtcttcaattttttcttcccagtttttgagtgg
ggtcctcagtataatcttaaactactaagggcagatgtaatttctggactcacaattgctagccttgctatcccacagggaattagctatgcaa
agcttgctaatttgccacctattgttgggctatgtaagtaaatgatcacacttgttatttcttctttaaaatctaatttgcttttgatcccttt
aatttagaatatgaatttgtttttaagtgatagaattgttcgttttatcggttactaacaatcttttttctgttgtattggcttaaccggtga
aaacagcctcttgcaaagatttaggctaaggttgcgtacaaatatacctttgtgttccggctcttcccggaccgcgcaatagcggaagcttagt
gcacggctgccttttcctattggaatgaaatggtgcagaatagagctgaattgatataaaatgcataatagccaactccaagtagtttcgggtt
gaagcataattattgattgataaggggtttctcattgttaaaaccagttgttaatcagtcaatatttggtaatttatttttaagtttaaagatcc
gttaagttaatggaaatttatcaagggtctactggtctattaattgaaggtagaggcgcatgcaagcttataaaatccgtgggtatgaaatatt
gttgtacctacatattcttttgcgaatttgtcacagtgcattttcagacttcctataaaatataattttatgggaaatttctgtatatatatat
atatatatatatgtaattttagtaaaaaatgatttcgctgtttgtaaagtatacattctatgttgaagagtaaatgtgtgcttaatcgacta
cggtgatttactaatttcttgtgctttgcaatatcttttgtaaataaaaatcaaactacatccaatctagatatctactaatctaagagttg
aaatattaatggatatgatgatgcagattcaagctttgtgccaccattgatctattcagtatggggagttcgaaacacttagcagttggtccg
gtctcgatagcttcacttgttatgggcacaatgctgagtgaagcagtttctttatactgaagaacctgttctttacctcagttggcttttacag
ctacccttttttgccggactgtttcagtcttcactcggttttttcaggtatattctattaaaactttaagttctatgccaccgacatgtcacttaa
aaagtaattacaactgattctataaataaacgttattgttaactctagtaacatcctataacaagttaaattgcactgaaatatatttttaggg
tgtcagtgtatataacttaaatttcttttgacgtaatggttctcattcactcgaaaattcgtgcagcgtttaatttgactttctaatatttaaag
agaaagtaaaagaggaggaataattagcttaacattccccattccaccatcaacgttaccgttaatttagtaatggactacagtagctaagt
ggaaacaaacttttggaaagatatccaaaagaatcatttagaaacatttgggcacttccactaaaaacagcaagaaaacagagaaaatgcatgg
aaagggacagaggatgttatgcaccatataaaactggactctggctttttatgcacagtatgaaactaacaaatacagctggagaaaaagaata
aaaattcaaggtacataatgtaattacagaaatttgcttttcaaaatcttccttgagccgaggatctatcagaaagaagatctattgttgttg
ttgttgctgcttttcaaaatctccgcattcctatattaaactatttgttctaagtataatcttatgcctgtagcctagtattcagattttgca
actctattttgttttacaaatcccattatttcaacttacaactttgcagagtattcaaatgcatatattttcaggactatccttcttgg
ccacactagtcaattttcattgcaaaattattgacttctatttcatcaatcgtgcatggatatatcaattctagcaaatttgaaatagatcagg
atcgctggatggctgaaatgtagtaggtgaatctgctaattctaaattagttgggtcggctatatgaatcttgtatatcatttcaattgaatgc
gagtccatttcattctaactttgtgtttagagtaaactatggttctcaaaactttactttcaagaaataaaatttgcttccaagtgctcactg
attcggtttatttagaactcagttagttcaaatggaaatgcactaaaagttcatggtttgcaggttaggatttatcattgattttctgtcgaa
ggcgacttggttgggtcatggctggtgcagcagtcattgtttcattgcaacaactgaaagggttgttagggatagtccacttcacaagccag
atgcaaatagttcctgttttgtcttctgttttccagcacaaaatgaggtaaaaagaagcttctttgtcgatattgaacttcttttgagatataa
gatagtggaaaaacaactatctttgtcaactgatgcaaatcattatttagtagttttactcctctatatctatttgcagtggtcttggcaaac
cattgttatgggcgtttgttttctcgcctttctgctgacgactaggcaaattgtaagtgtttgttttatggcagaacataatattctgattaat
attcatctcttttgttcattttctaactaaagatttgaattttcttctgtaattacagagcaccaggaacccaaaactttttctggctttcagca
gcatctccgttggcctcggttattctctcaactctggtagtgaccctcccttaagtcgaatgctcatggtattcaaactgtaagtaaaattcatc
agctttacctccatccatagttttagctatgttgctcggactctctgaaaatgtcgccgggtgcatgctggatcctccaaaatagtatatttt
taaaggatccaacacgggtacggcagtattttggagagtccgccaacataggtttttagacagaatgaaactgaaaatatctttggtttgcaga
ttggacacctgcaaaagggtctaaatccgcctcattgaacatgttgtatctaagtggtccttatctgcctcttgccattaaaactggcattgt
ttccggaatcttagcgttaacagtaagtcacttgagacgattacaagcaattggccgtagaaatataacgaagcgctttgtgtttgacattttc
attgacctgcaggaagggattgcagtaggaagaacatttgctgctttaaagaattaccaagttgatggcaacaaagaaatgatggcgattggac
```

SEQUENCE LISTING tcatgaatatggctggctcttgttcttcctgctatgttacaacaggtacccgcctcattggcctgttgttcgcgataagattaactcttttta
accagcaaatatttgatttacaggttcattttctcgatcagcagtaaattacaacgctggggcacaaacggtcgtttcaaacataataatggca
acagctgtgttaatcaccttgttgtttctaatgccactgttctattacaccccccattgtcatcttggctgcaattattataacagcagttattg
gcctaattgattatcaagctgcttccggttatggaaagttgacaagctcgatttcttggcttgcttgtgtcgtttttggtgttcttttcat
ctcagtgcctctcggcctagccattgcagtaagcatctcctcaaatatcacatcttatagtaccacttacttttgatatctcctccttgtaccta
acattttctacttctgctcgtgaaatttcaggttggagtttcggttttaagatcctattgcatgttacaaggcccaatactagtgtcctgggc
aatattcctggaactcaagtatatcaaaacttaagtagatatagaacagctgttagaatttccttcttccttatccttgctgttgaggctccta
tctacttttgcaaattctacctacttaaaagaaaggttagttcaaacatagggtacagatttttgtattttgcttttagccaacttcaactaattt
gttaagattattacacagttttatttactcaaaattcacattttgtaactgtaggatattgagatggattcgcgaagaggaagagtggatagta
gccaacaaagaaactgcaatcaaatgtgtaataatcgacatgacaggtcagttgaaaaaaaaagtgacatttactcatcttctgttttactgg
cagttctcaacatgttgagtaacaaaattatgtcttgcttcaccagctgtgtcgtccatagactcaagtggcatcgacacaatatgtgaactac
gaaagacactggataaacgatctcttaaggtaaatccgtcagccacataaaagatgtttcttgtttcccttcactagtcaaaatatttcttac
aaaatttgttttccttttttcttttcctttcacgtgaaatctttgattttttgttggtgtagcttgtgatggcaaatccaggtgggaatgttat
ggaaaaactgcatcaatctaacactctcgacgcctttggattaaatggaatatatctaacagtttctgaagctgtggctgatatctcatctttg
tggaagtctgaacctgaatcatcaatataa SEQ ID NO: 20: Polypeptide sequence of NtSULTR3; 4A-T
MGLSSNRVEDLSGHACNETIITISTTSTELHISNNQPFEVHRVCLPPHKTTLQKLRQRLLEIFFPDDPLHKFKNQTWLMKLVLGLQFFFPVFEW
GPQYNLKLLRADVISGLTIASLAIPQGISYAKLANLPPIVGLYSSFVPPLIYSVLGSSKHLAVGPVSIASLVMGTMLSEAVSYTEEPVLYLQLA
FTATLFAGLFQSSLGFFRLGFIIDFLSKATLVGFMAGAAVIVSLQQLKGLLGISHFTSQMQIVPVLSSVFQHKNEWSWQTIVMGVCFLAFLLTT
RQISTRNPKLFWLSAASPLASVILSTLVVTLLKSKAHGIQTIGHLQKGLNPPSLNMLYLSGPYLPLAIKTGIVSGILALTEGIAVGRTFAALKN
YQVDGNKEMMAIGLMNMAGSCSSCYVTTGSFSRSAVNYNAGAQTVVSNIIMATAVLITLLFLMPLFYYTPIVILAAIIITAVIGLIDYQAAFRL
WKVDKLDFLACLCSFFGVLFISVPLGLAIAVGVSVFKILLHVTRPNTSVLGNIPGTQVYQNLSRYRTAVRIPSFLILAVEAPIYFANSTYLKER
ILRWIREEEEWIVANKETAIKCVIIDMTAVSSIDSSGIDTICELRKTLDKRSLKLVMANPGGNVMEKLHQSNTLDAFGLNGIYLTVSEAVADIS
SLWKSEPESSI SEQ ID NO: 21: Polynucleotide sequence of NtSULTR3; 4B-S
atgacattaaattcaattaaagtggaagattcgtcatgcaatgcaacagaaggagagtcggcaacgtcgtcgtcaatgcaatcctcaggtgtac
ataaggtttgtttgccgccgtacagaaccacttttcagaaactccggcaacggttgtcggagattttctttcccgacgatccacttcataagtt
caagaagcaaacagggttgaggaaatttgtttgggtcttcagtttttcttccctgttttgaatgggtcctctgtacagtttcaaactttta
aggtctgatataatctctggcctcaccattgctagccttgctatccctcaaggaattagttatgctaaacttgccaatttgcctcccattattg
ggtatgtaagtgccactcttttatctttctttttcttcttccctgtgatggtcgccactaaaaccgtcgaggggtgtcaattaaacagcct
tctctccaaagttacacggtatatatatatatatgccaaatattacttcttgtacgttcaccctaacgaaatttccttggttcgccaaccc
ttacttttgtgacgactaaggtgatggtcgcataaagtcaccatgaaaagttctcatttctagtagtgttaccgcaaatgattgccactaaat
ctatcactatttgcaaccattaggtagtaaattcactgaaaaattatattgtatatatatatgtcaaagatgactatttatatatgtatatata
aaatcttgattacctttagtggaattccttcttttgctcgtgtacttttgtggcaactaaggttagtggaattccttctttttgctcgtgtact
ttttgtggcaactaaggttattgacacgtagagtcatcactaaaaatttcattttgtagagttaactaaattatggagtagtaattaattaaag
gtgatatggattttttgtgacacagattcaagctttgtgccaccattaatctattcaattttgggaagttcaagcacttagcagttggtccagt
atctatagcctcactagtgatgggaacaatgttaagccaagcagtttcatacagccaagagccaattctataccttcaacttgctttcacagca
acactttttgctggattgttgcaagcttcattgggggtttttcaggtataatactctgttcatgaactttttttgtattacttacattttttcaa
cttcttttctcattattcataaagaatagaatagaattattccagcaaattttttcatccactatcaatgtttctgttaattaaagttaatgc
tgtaatgtagcatatagcaaagtggaaacaaactttttagaaaaagatataccaacaaattcatttagaaacactgagaccttttgctgaaaaa
atggtgcttatcgaaaaagaaagaatagaaaggaaaaggttgttcactccaaggtagacaaactgaaactaaagatatttacctacactttt
cagaatcttatggttaaagcagtaagtatattttgaaaaatattttcctcaaattttacctcaccaagaattatcagcatatgaaacctatgca
ctaatgtcatatagccttggtggtaaaaaaattcaagtatttaattcataaattcaagagattttgaattccatctgagggaggtcacgaaac
tcattttgtttgtcataacaatctatatgtgtaaagtaattacttgattgtcacacataagattagatcaacatgctcaaactgatctgctct
tatgatttacaaattattggcttctgctgaatttcagcagtttaatcgcaaggaaattgacttaaattccatgacttgcaggttaggattcatc
attgattttctctcaaaggcgactctactagggttcatggctggtgcagcggtcattgtctctttgcaacaactgaaaggattgctagggatat
ctcacttcacaaaccagatgcaaatagttcctgttttgtcttctgttttcacgcaccaaagatgaggttagaagtttcctccaatgttgtgctct
tttgaggtaatattgaaggcataaaattgccgttgtaactctgcaacatcttttcgcagtgtcttggcaaaccattgttaggtgttagttt
tctcatcttcttgctggcgacaaggcaaatcgtaagttttggtttatgtggatgagaaagttttttcttcatgttcatctccttattgatcat
tttctaattaatgtcagagtactaggaaaccgaaacttttctggatttcagcagcagctccgttagtatccgttattctctcaactatcatagt
tttcctacttaaatccaagactattcagactgtgagtaacatgcatcgttttcatccttaaatttagacggaaaagactaaagattc
ttttattgtagattggacacctaccaaagggatttaatccaccatcattgaacatgttacattttagtggccctcatatcgctcttgctatcaa
aattggcattataactggagtcttatctctcacagtaagtgaatactaactactactaccagcattttattcctcaaagaaagaaaggaggag
atttgtgatcgacatagctctgcaggaagggatagcggtaggaaggacatttgctgctatgcaaaattaccaagttgacggtaacaaagaaatg
atagctatcggacttatgaacatggctggctcttgtgcttcctgctttgtcactacaggtacgacctaagcaatactcttattcttagttgtaa
ctaaagctgctaagttttcctctttctcttattccatgtgaaattcaatttttgcagggtcattttctcgatctgctgtaaattacaatgctgga
gcaaaaactgtcgtttcaaatataataatggcgcaactgtgcttatcacccctgctgtttctcatgccgttgttccattacaccccctaacctca
tcttggcagcaattatcataacagcagtgatcggcctaattgattatcaagctgcattccgtttatggaaagttgacaaactagattttgtggc
ttgcttgtcttcctttttggtgtccttttcatctcagtgcctcttggcctagcaattgcagtaagcttctcctcataaatctcaatcctctca
tgccttgaaatatctacttctcatgtctaatatatttctaatatttgttgttcatgaaaaaatttcaggttggtgttcagttttcaagatcct
attgcacgttacacggccaaatactaatgtcttgggtcacattcctggtactcaatcattttcaaagcctaagcagatatagcacagctgttagg
gttccttcttttccttatcatagctgttgaggctccttttctattttgcaaattctacctacctacaagaaaggtaagttaggtttaactttcatc
gataacaagtgaaattgtaaagtttttaaatatttgctacatcagagttgtatcaagcaattgtaattacaggacattgagatggattcgggaa
gaggaagagaggatagaagtcaaaagtgaaactgcaatcaaatgtgtaattcttgacatgacaggtggttgaaaaagaaaacaacatcctctc
atgttttcttcttagtaatctactcgtctagtaacgaaatagtggggttttccttctgcagctgtgacagctatagacactagtgcattga
tacaatgtttgaactcagaaggatacttgagaaaagatcactgaaggtaaatatactgtcaattatattgtgtcaagcttttatttgcagaatt
gcgttatcctttcctttcttgctcgtttatgctttgatgtattctgcttcagctcgtgctggcaaatccggttgaaacgttatggaaaagctg
cataactcgcatgctcttgaggcctttggattagacggattatatctaacagtttctgaagctgtggcggatatttcatcttcttggaagcctg
aagcctga SEQ ID NO 22: Polypeptide sequence of NtSULTR3; 4B-S
MTLNSIKVEDSSCNATEGESATSSSMQSSGVHKVCLPPYRTTFQKLRQRLSEIFFPDDPLHKFKKQTGLRKFVLGLQFFFPVFEWGPLYSFKLL
RSDIISGLTIASLAIPQGISYAKLANLPPIIGLYSSFVPPLIYSILGSSRHLAVGPVSIASLVMGTMLSQAVSYSQEPILYLQLAFTATLFAGL
LQASLGFFRLGFIIDFLSKATLLGFMAGAAVIVSLQQLKGLLGISHFTNQMQIVPVLSSVFTHKDEWSWQTIVMGVSFLIFLLATRQISTRKPK
LFWISAAAPLVSVILSTIIVFLLKSKTIQTIGHLPKGINPPSLNMLHFSGPHIALAIKIGIITGVLSLTEGIAVGRTFAAMQNYQVDGNKEMIA -continued

SEQUENCE LISTING

```
IGLMNMAGSCASCFVTTGSFSRSAVNYNAGAKTVVSNIIMAATVLITLLFLMPLFHYTPNLILAAIIITAVIGLIDYQAAFRLWKVDKLDFVAC
LSSFFGVLFISVPLGLAIAVGSVFKILLHVTRPNTNVLGYIPGTQSFQSLSRYSTAVRVPSFLIIAVEAPFYFANSTYLQERTLRWIREEEER
IEVKRETAIKCVILDMTAVTAIDTSGIDTICELRRILEKRSLKLVLANPVGNVMEKLHNSHALEAFGLDGLYLTVSEAVADISSSWKPEA

SEQ ID NO: 23 Polynucleotide sequence of NtSULTR3; 4B-T
atgacattaaattcaattaaagtggaagattcgtcatgcaatgcaacagaaacagaagcggtaacgtcttcgtcaatgcaatcctcaggtgtac
ataaggtttgtttgccgccgtacagaaccacttttcagaaactccggcaacggttgtcggagattttcttttcccgacgatccacttcacaagtt
caagaaccaaacggggttgaggaaatttgttttgggtcttcagttttttcttccctgtttttgaatggggtcctctgtacagtttcaaacttgta
aggtctgatataatctctggcctcaccattgctagccttgctattcctcaaggaattagttatgctaaacttgccaatttgcctcccattattg
ggttatgtaagtgccactcttttatcttttcttttcttctttctattttaacatgatagtcgccactaaaaccggggagtaacagctttag
ctgaaaaattatactatatatatatatatgccaaatattacctttcgtacgttcacccttaacgaaattccttttggttcgccaaccccttactct
ttgtgacgactaaggcaatggtcgcataaagtcgccatgaaatattctcattctctggtcaaggagtagtaaattgaacaacattcaccgaaaaa
ttatactgtgtatatatatgtcaaatgactatttatacatgtatatataaaatcttttgaataccctttaacaaaattccttcttttgctcgtg
cgtggaacccttacttttgtggcgactaaggttattgacgcgtagagtcgtcactaaaaatttcatttcttgtagtgttaactaaattatggag
taagtaattaattaaaggtggaatggattttttgtgaaacagattcaagctttgtgccgccattaatatattcaatttggaagttcaagacac
ttagcagttggtccagtatctatagcatccactagtgatgggaacaatgttaagccaagcagtttcatacagccaagagccaattctataccttc
aacttgcttttcacagcaacactttttgctggattgttgcaagcttcattgggtttttcaggtatagtactctgttcatgaactttttgtatta
cattttttattgtgtataaacagtgttacactaagttctttttttcctcatttctttacttcatgaagaatagaattgctctagcaaactttc
ccattcccaatatcaatgttactgttaattaaagttaatgctataatgtagcagatagcaaagtagaaacaaacttttagaaaaagatatacca
acagaatcatttaaaaacattgggaacatttgctgagaattcgaaaaaaaaagaagaaaaaggtacagatgattttttggaaaaagaatagaa
aggaaaaggttgttgattccaaggttgacaaaatgaaactaaatatatttacctgcacttttcagaatctcaattaaccagtaaggcagtaatc
atattttgaaaaatattttcctcaaattttacctgaccaagaattatcaacatatgagacctatgcactaatgtcatatagccttgatggtaaa
aatttcaagttagtaactcataaatcaggagtatttgtttccccggggggagatcatgaaactgtttgattttcacttgtgactttgtatgtc
ataacaatctatacttgtaaagtaatcacttgattttcacacataagattagtcctccaaactgatttgctcttatgatttacgaattattggg
ttctgctgaatttactgcagtttaatcataaggaaattgacttaaattccatgacttgcaggttaggattcatcattgattttctctcgaaggc
gactctactagggttcatggctggtcagcggtcattgtctcttgcaacaactgaaaggattgctagggatatcccacttacaaaccagatg
caaatagttcctgttttgtcttctgttttcacgcacaaagatgaggttagaagtttcctccaacattgtgctcttctgagataatattgaaggc
ataaaattgtcattgtaactctgcaacatctgtttgcagtggtcttggcaaaccattgttatgggtgttagttttctcatcttcttgctggcta
caaggcaaatcgtaagttttggttatgtgaatgagaaagtttttgcttcatgttcatctcctcttattgatcattttctaattaatgacagagt
actaggaaaccgaaactttctggattcagcagcagctccgttagtatccgttattctctcaactatcatagttttcctacttaaatccaaga
ctattcagactgtgagtaacatgcatcatttctagtttcatcccttaaatttaggcggaaaagactaaagattcttttgttgtagattggacac
ctaccaaaggggataaatccaccatcattgaacatgttacattttagtggcctcatctcgctcttgctatcaaaactggcattgtaactggag
tcttatcgctcacagtaagtgaatactaactactaccagcattttattcctcaaagaaagaaaaagaggagatttgtgatcgacatagcc
tgcaggaagggatagcggtaggaaggacatttgctgctatgcaaaattaccaagttgacggtaacaaagaaatgatagctatcggacttatgaa
catggctggctcttgtgcttcctgctttgtcactacaggtacaacccaagcaacactcttattcttagttgtaactaaagctgctaagtttcc
tcttactcttattccaactaaaattcaattttgcaggatcattttctcgatctgctgtaaattacaatgctggagcaaaaactgtcgtttcaaa
tataataatggcggcaactgtgcttatcaccctgctgtttctcatgccgctgttccattacacccctaacctcatcttggcagcaattatcata
acagcagtgatcggcctaattgattatcaagctgcattccgtttatggaaagttgacaaactagatttttgtggcttgcttgctcttccttttcg
gtgtccttttcatctcagtgcctcttggcctagcaatagcagtaatcttctcctcataaatctgacatactctcggatgccttgaaatttctac
ttctcatgtttaataatatattctaattttgttcatgaaaaaaatttcaggttggtgttcagttttcaagatcctattgcatgttacaaggcc
aaatactaatgttttgggctacattcctggcactcaatcatttcaagacagtatagcgcagctgttaggattccttcttttccttatc
atagctgttgaggctccttctactttgcaaattctacctacctacaagaaagtaagtttaactttctacaataataagtgaagtagtaaagt
tgttaaatttgtgttacatcacagttgtatcaagcaattgtaattacaggacattgagatggattcgggaagaggaagaggatagaagtcaa
aaaagaaactgcaatcaaatgtgtaattcttgacatgacaggttggttgaaaagaaaacacatcttctcatgttttctttcactagtaatcta
cacgtctagtaacgaaattatggggttatccttctgcagctgtgacagctataggccaattgtgactggcattgattaaaatatgtgaactcagaaggat
acttgagaaaagatcacttaaggtaaacattctgtcaattatattgtgtcaagcttttatttgcagaatcgcgctaatcgttctttgcttgctc
gtttatgctttgatgtatactgcttcagctcgtgctggcaaatccagttggaaacgttatgggaaaagctgcataactcgcatgctcttgaggcc
tttggattagacggattatatctaacagtttctgaagctgtggccgatatttcatcttcttggaagactgaaccatga SEQ ID NO: 24: Polypeptide sequence of NtSULTR3; 4B-T
MTLNSIKVEDSSCNATETEAVTSSSMQSSGVHKVCLPPYRTTFQKLRQRLSEIFFPDDPLHKFKNQTGLRKFVLGLQFFFPVFEWGPLYSFKLV
RSDIISGLTIASLAIPQGISYAKLANLPPIIGLYSSFVPPLIYSILGSSRHLAVGPVSIASLVMGTMLSQAVSYSQEPILYLQLAFTATLFAGL
LQASLGFFRLGFIIDFLSKATLLGFMAGAAVIVSLQQLKGLLGISHFTNQMQIVPVLSSVFTHKDEWSWQTIVMGVSFLIFLLATRQISTRKPK
LFWISAAAPLVSVILSTIIVFLLKSKTIQTIGHLPKGINPPSLNMLHFSGPHLALAIKTGIVTGVLSLTEGIAVGRTFAAMQNYQVDGNKEMIA
IGLMNMAGSCASCFVTTGSFSRSAVNYNAGAKT SEQ ID NO: 25: Polynucleotide sequence of NtSULTR3; 5-S
atgacgagctctcccagtctttgcataggtgaactatgcagcgccacgaagctttgggacattactaaaagcaaacctaaaagagaccctttt
tcccagatgatccattccatgaaatcaagaacgagccaatttcacgcagattttaaggggggctcaatatttgttccaatttcgaatggct
gccaaagtataatttcaagctcttcaagtatgatcttcttgctggaatcactattgctagccttgccattcctcaagggataagctatgccaaa
ctcgctaacattcctccaatcattggactctgtaagctacttataagagtattgtattgtttttcctatatatatattgacacgtcgtaccaa
aagatgtatgtgttcatggctttcttggcttttgattcgaagtaggtacaactaacaattttttgattaaaagatgtatgagttgcatgcatgc
agattcgagcttttgttcctcctctttattatgcggttttttggaagtttcaaagcaccttgctgtggggacggtggctgcttgctcattgcttatt
gctgcaatcattgaaggaaagtgaacgctagcgataatgccgctgtatcttagttggtgttcacggccactctttcctctggttggttc
agactgctctgggtttgctaaggtacacaccaccacctgtccttccctaagctagctagctcttgattaattagtactagtagaaatatataa
gtacaatttatttggttgtgcagacttgggattttgtagatttcctatcacattcaaccataactggatttatggggagaacagcaataatt
atttgcttgcagcaactgaagggcagttggttgaagcattcactacctcagtgtggttctgttctacgcgctatcttccacaaca
gaaaagaggttgtcattctatactcctaattgtatctattagattaattaagtgaatagccatgcattgggatctctcatgcacaatatata
ttcacataccttagctttgatactgacatatcatttagaaatattatttatagatccatatatatatatcaccaaggataaaaaatgaggaatt
gccttttattattggattatgagtaaagttggtcaatttggcaatttaattcctgttatttgatttttttgtgtgtgtgtgtattcgaacagtg
gaagtgggagagtgcagttgttggaataatcttccttactttcctgcaattcactagatttgtggtgagtgtttcctattaatgtgaaaata
agtgttctcgatcgcaagtcatgtatacaagaaaaaatgcttctttgcagaaaaacaaagctatttttgggtttcagccatagctcc
aatggtcactgtaattgtcggctgcctttcgcttacttcgcccatgctgagaaacatggcatccaaatcgtaagccttaattcctctccc
cccacccaaaatgaatttatattaagtgcggtagagatatataaaagctgacaaaatgggccgactaggaaaggaagaatagaagagatc
aatcacgaaaatatagagtgatttcaattagctagttgccgtaaaatatttagtagaaatcgagttaaaaacttctttatgacacatgtat
ctcacacaaatatatacatgtatatacgtggatatagtgtatactcgacgggttcaattgaacccataatttcgacgcgaagtaaaaatttat
atgtaaaaattcattaaagttttagtagtcataaatctaataactttataaatataataggttcgatgttaaaaaatctaaaagttgaaccca
```

SEQUENCE LISTING

```
tagggtttaaatcctgagggctgcttgttaagtattttgcttcggtttgtcaaacgaaatagtttgagaacaggaagagacgcataaggagaga
caaaaattacagaatttgcaactgttagagtcaagtttggaaaagattgataagatcttttgaattctctttaagggttgttggagaatgact
attgagggtgtgtatggctacgtttcactaatttatcattgagacaaaccctttttacaacacttatctaagtggacttccacctaactagcag
gaagagccaatttttgacatttcgagaattagacttaaagtatgcaagtaattatgtccaccgacggatatggacaagatcactaataatccttgt
agaaaacgcaacactaacttttttcttttctgtggtcacagcactaagtccgatccgtattttaatttgtctcatctaatgtaacagtaggtctt
tttgtctcatactttggactgaatatatacaggttggacatttgagtaaaggaataaatccttcttccattcatcttttaaatttcgatcccaa
gtatatatcagcacctataaaagcaggagtcatcgcagcaatgatgatctctagctgtaagtacactcttttaatttatccatacatacgaagagt
ttctgatttgtcaatcatcaaaaatgtacgtgtttactaagtttgtatggaatattttctaggagggaatagccatcggacggagtttcgccat
tatcagaaatgaacaaattgatggcaacaaggaaatgattgccattggcctcatgaacattttggatctttcacttcatgctacttgaccact
ggtaatttgtggtggcaaaatggttaaaagaaaacagttcatattattcgttaaatataggctggataatgaacttttataaaaatgggtcaatt
aatatagataataatcatattatccatttagaaaatggataagcaatgaataattaatggttcaactttttacatttgtaaaactttcaaattgg
gggttcctcaagtttgggatactaggaattctcccaaaagtgatcatattcaagaaacattaaatatactcatattatccattgattaacctat
tttttatccacattaaatatgggtcgagtcggataatttatccattttttcattatccattttttacctgacccgacccgacccgcccatttt
ccaccctactggtaattattcactaaaatcaagagtaaatttaccaagatatagggtatgtttggtatagatcaattttctcatgtttggttg
gcttaaatattttagagaatatttttctcatgaacttattttcctcccattggagaaaattgatttccctaccaaaaggaggaaagatattttt
caaactcttttttaaccttccatacccttattcctcactccctccctccaagaaaaatataaatacaccgtagttttggtgaagaaaattttttta
ttcatcacctaactattacatgcttttcctcagtacttcttcctttttctcctatttctttctatatatatacattaactatgtacttcttgtc
attaaaaacattagtagttctatctatctaatcttctatttctgcattagcttttcaatccagtctctttcttgaacacttgtcttgctcttcaa
ataggtaatgttcctcagtctgcattcttgtttaatctgacttagtatgtatgtagttgtgggtaatcggaagtcccatacaacgatgttccta
gccttccatatccagtatatcagggcagccaatatagcagtagcaactccctgcatctcttttccttttgagtagcctggtcactctctttcata
tccatgtctatatatgtcagttgtatttccatgcacatccagtttttacaccccctcttaagcattgctgtgagaatacacattcaaagaacaaatg
ttggatagttcctctgttattccacatattgggtacctatcatcttgattaatgcacatacgatgcaatatggttttgtcagcagtctttga
tgcatagtgagctagcaaacaaaactgtgcttgggtaggttcatattgttccatacccatcttctccatgcccagttttccttttctcccattc
tccatagatatccctcaattgtgtatttgtccattagcatttctccacaaattctgattatatccaggagcaaatattctctgatcttgcatat
tttcttccagtaccagcaagcatcattggggcatttgtactgccaccaatcctctccttttaagtagacagtgttgatccatttcacccataga
ttatcagttttttgagcggacattccatacatattttgcaatagcaacttcattccatttattatgtctgttacgcccaagcctccttcatgat
ttgtcctacacactaagtctcatgccactaatggtggcttatgtgtgatagctttcccatcccatatgaaatttctacacatagcagttatccc
ttttcagcacttgcttttggaagcaagaacatagttgaccagtaactatggatatgtagtagtactgaattcactaactgcactcttcctgcata
agatagatgtcttgtactccaacctttgattctagctgctatcttgtctatgagtatttcacattccattttagatatcctcttagctatatag
gcacaccaagataccaagatacctgaatggtagacttcctttctggtatcctgccatttccatcaaatccttctagctctggattggcatattg
acactgaatatatttgacttgcttgcattagcagttagacctgagctttctgagaatgttttcaagcccctcaataagagcagcacagattgaa
aagtcccttactgaacaatagaacatcatctgcaattgaaattttgctttttcctcccaacaatgtatatatatgaaaaatagttactccctc
tattctacttttcgtgaacctattattatttgaggagtcaataataaaaattttaaccacggttttggtaaaactttttaaatattttcaatta
ttaactatgacataataattttatgtagtttctagttatgtaaattttatttcaaaattgatatccgaatttgtattgaaaatcagtcaat
ttcaccctcttactccgagtaatatatgtaataagatctctcaacctaaccccatttattttagattctagattcatctcacaatacttaatgaa
catgcttctgggagaaaagtataaaataaaattaaaaacctgtagtagtacataactaataatgatggatgttgtatttttcagggccattttcaa
aaactgcagtgaacttcaacgctggatgcaagactgcaatgtcaaacgtggtaatgtcaatatgcatgatgctaaccttctgttcttggctcc
tctgtttagttacacaccattggtctctctctccgccatcatcatgtccgcaatgcttggcttaattgactatgcaaggcatatcacctcttc
aagacagacaagtttgatttctgtatttgtatggctgccttttttggtgtttccttcataagcatggacattggcctaatgttatccgtaagca
ctacacttctcgacaaaatattaataacaaaaatttgctattagagatgatttttccggggcttttccaggttggacttgccttaatcagagc
acttctatatatagcaaggccagctacttgcaaacttggtctcatatcagaaactggattgtatcgcgatgtggagcagtatcctgatgcaaat
ggaattgcagggtttctgattctgaagcttggttctcctatatactttgcaaattgcaattacgtcagagaaaggttttttaatttgttctattt
tctctcatacacatcaaacaagtgcttctagtaatagtcttcttttgatggattgcgcaggattcttagatggatcagagatgagcgttctcat
accatttctaaaggaaatgaaattgaattcttattacttgaattaggaggtactcctataaattagcaagaaggagaaatttggatgtttcctt
cttttctactataataatgcaatttaatggtaatgtaactgaatcacaaccttatgccaacaaggtatcctgatgcaaat
aacattattagaaattagaaggtgcgtacaagcaaaagggatcaaggtaaaatcaaactctcatttttttttcctatttacttttgggcacg
gtataggaagtccacaagtttctaaatacttacatttcttctctggccttttcaattcttttaatttgtagatgattttggttaatccgaggttg
ggagtcttggaaaagttgatggtgacagagtcaatagacaccattacaaaagaatctgtcttcttaaccattgaagacgcaattgatgcttgca
gattttcactcaaatgttcggatcacattaaaacagaaaaccttgcaatagtttag
```

SEQ ID NO 26: Polypeptide sequence of NtSULTR3; 5-S
MTSSPQSLHRVNYAAPRSFGTLLKANLKETLFPDDPFHEIKNEPISRRFLKGAQYFVPIFEWLPKYNFKLFKYDLLAGITIASLAIPQGISYAK
LANIPPIIGLYSSFVPPLIYAVFGSSKHLAVGTVAACSLLIAAIIEGKVNASDNMPLYLSLVFTATLFSGLVQTALGLLRLGILVDFLSHSTIT
GFMGGTAIIICLQQLKGMLGLKHFTTHTDVVSVLRAIFHNRKEWKWESAVVGIIFLTFLQFTRFVKNKKPKLFWVSAIAPMVTVIVGCLFAYFA
HAEKHGIQIVGHLSKGINPSSIHLLNFDPKYISAPIKAGVIAAMISLAEGIAIGRSFAIIRNEQIDGNKEMIAIGLMNIFGSFTSCYLTTGPFS
KTAVNFNAGCKTAMSNVVMSICMMLTLLFLAPLFSYTPLVSLSAIIMSAMLGLIDYDKAYHLFKTDKFDFCICMAAFFGVSFISMDIGLMLSVG
LALIRALLYIARPATCKLGLISETGLYRDVEQYPDANGIAGFLILKLGSPIYFANCNYVRERILRWIRDERSHTISKGNEIEFLLLELGGITSI
DITGVETLLEIRRCVQAKGIKMILVNPRLGVLEKLMVTESIDTITKESVFLTIEDAIDACRFSLKCSDHIKTENLAIV SEQ ID NO 27: Polynucleotide sequence of NtSULTR3; 5-T
```
atgacgagctctccccagtctttgcataggtgaactatgcagcgccacgaagctttgggacgttactaaaagcaaacctaaaagagacccttt
tcccagatgatccattccatgaaatcaagaacgagccaatttcacgcagatttttaaaggggctcaatattttgttccaattttgaatggct
gccaaagtacagtttcaagctcttcaagtatgatcttcttgctggaatcactattgtctagccttgccattcctcaaggagtaagctatgccaaa
ctcgctaacattcctccaatcatcggactctgtaagctacttataagagtattgtattgttttttcctatatattgacacgtcgtaccaaaaga
tgtatgtgttgataactttcttggcttttgattcgaagtaggtacaactaacaatattttgattaaaagattgagtctaaatatttctgttatt
aattaaacacgggagttgcatgcatgcagattcgagctttgttcctcctcttatttatgctgttttttggaagttcaaagcacctttgctgtgggg
acggtggctgcttgctcattgcttattgctgcaatcattgaaggaaaagtgaacgctaacgataatatgccgctgtatctttagtttggtgttca
cggccactctttttctctggtttggttcagactgctctgggtttgctaaggtatatataaatgaccgaagttacgtacacatgaccaccaccttc
tctaaactagctagctcttgattaattagtactagtataaatatataagtgcaattatttggtttgtgcagacttgggattttggtagattt
tctatcacattcaaccataactggatttatgggagggacagcaataatttatttgcttgcagcaactgaagggcatgcttggtttgaagcatttc
accacccatactgatgtggcttctgtcttacgtgctatcttccacaacagaaagaggttgtcattctatactccttgtatctatttgattaat
taagtgaatagccatgcattggggatacttctacgcacaataatatcatcatccttagcttggacactgacatatcattttagaaatattatt
ttatagatccatatatgtcaccaaaggataaaaaatgaggaatataattgccttttattattgaaagttacacatgattttggtcaattgggca
atttaatttctgttattgatttttttgtgtgtgtattcgaacagtggaagtgggagagtgcagttgttggaataatcttccttactttcctgc
aattcactagatttgtggtgagtgtttcctattggtatgtgaaaataagtgttctcgcagatcatgtatacaagaaaaaataatgcttcttgc
agaaaaacaagaaaccaaagctattttgggtttcagccatagctccaatggtcactgtaattgtcggctgccttttcgcttacttcgcccatgc
tgacaaacatggcatccaaatcgtaagcctttaatttcttctcccccaacccaaatgaatttatattaagtgcggtacaacatatagaaaag
```

SEQUENCE LISTING

```
ctgacaaatatgggccgactaggaaaggaagaatagaacagagaatcacggaaatatacaaaatttgagaaagatgaaggtgatttgaattaac
tagtttgccataaaatattttagtagaaatcgaattaaaaacttcctttatgacacatgtaattcacacatatatatacatgtgtgtatacata
tatacgggaatactaataattaagtctgggcggatgtagtatatactcgacaggttcaattgaacccataaccttttcgacgctgagtaaaaaat
attatatgtaaaaattcattaaaatttcaaaaatagtatatatgaactaaataacttttataaatataatgagttcaatgctaaaaaatttaaaa
attgaacccataggatttaaattctgaatccgttagtttttttgcttagggttatcaaacgaaatagtttgagaacaggaagagacgcattagg
agagacaaaaattaaagaatttgcaactgttaagattgctaagatcttttttgaattctctttaagggttgttggagaatgactattgaggtgtg
tatggcaacgtttgaattctctttaagggttgttggagaatgactattgaggtgtgtatggcaacgtttcaataatttatcattaagacaaacc
cctttacaacacttatctaagtggacttccacctaactagctaggaagagccaattttgaccttcgagaattagacttaaagtatgcaagtt
atgtccaccgacgcatatggacaagatcactaataatcttgtagaaaactcaacactaactctttctttcctgtggtcacagcactaggtccgt
attttaatttgtctcatctaatgtaacagtaggtcctttgtctcatattttggactgaatatatacaggttggacatttgagtaaaggaataa
atccctcttccattcatcttttaaatttcgatcccaagtatatatcagcacctataaaagcaggagtcatcgcagcaatgatatctctagctgt
aagtacacccttatccatacatacgagctccgtttatgacaaagaatttctgatttgtcaatcatcaaaaacgtacgtgtttactaagtttgt
atggaatattttctaggagggaatagccatcggacggagtttcgccatcatcagaaatgaacaaattgatggcaacaaggaaatgattgctatt
ggcctcatgaacattttttggatctttcgcttcatgctacttgacaactggtaattagcggcggcaaacaattaatcatccatattattcactaa
aagatgggctgaataataaacttttaaaaacggatcaaatatggataagaaccatattatccatttaactttttacatttgtaaaacttcaaat
cggtggttcctcaagtttagaagactaagaattttttccaaaagtgatcatattcaagaaggaattaaatacacacatattatccatcgattaacc
catatttttatccacattaaatatggctcggatcggataatttatccgttttgcattacccattttcgacccgacccgaccgtttgccacccta
ctggtaattattcactaaaatcaagagtaaaatttaccaagatagggtgtgtttggtaaggattaattttctcatgtttgattggcttaaat
atttagagaatagttttcttatgaacttatttttttttcaatcggagaaaaatgactttcctaccaaaatgaggcaagatatttttcaaaact
cttttttcaaccttccctaccttattctccaccaaaaactgtcaccaaatacaccatagttgtcaagaccactctcgtgatggaaactgtaccta
ctggataagaaaactaattagattattagcatccgtcgatttacgacaggcttggattcaactgaatctcttgctttcctcccaaacaaaatat
atatatatatatatatatatatatatatataaaatagttactccctctattctacttcaggtgaacctattactgtttgaggagtcaaataaaa
tttttttttgaccaggttttataaaactttttaaatattttcgattattaactatgacatataataattttatgtagtttctaattatataaa
tttatttcaaaatttttgaaaatcttattatccgaatttgtattaaaaattagttaatttaaccctctgactccgaaaagattctaataaacta
gaacgaaaagattcatctctgacagacaataactttaatgaacatgcttctaggaaaagtatatttacaccataaaataaagttaaaacatgtgg
tagtacataactaataatgatggatgttgtatttttcagggccattttctaaaactgcagtgaacttcaacgctggatgcaagactgcaatgtca
aacgtggtaatgtcaatatgcatgatgctaacccttctgttcttggctcctctgtttagttacacaccattggtctctctctccgccatcatca
tgtctgcaatgcttggcttaattgactatgacaaggcatatcacctcttcaagacagacaagtttgatttctgtatttgtatggctgccttttt
tggtgtttccttcataagcatggacattggcctaatgttatctgtaagcactacacttttcaataaaatattaataacaaaattttgctattag
agatgattatttgcttaaattgtttccggggcttttccaggttggacttgccttaatcagagcacttctatatatagcaaggccggctacttgc
aagcttggactcatatcagaaactggattgtatcgcgatgtggagcagtatcctgatgcaaatgaattgcagggattctgattctgaagcttg
gttctcctatatacttttgcaaattgtaattacatcagagaaaggtttttgttctattttctctcatacacatcaaacaagtgcttctactacat
attctgatagtgaacttgatctttctttgatggattgcgcaggattcttagatggatcagagatggagcgtttctcttaccatttctgaaggaaat
gaaattgaattcttattacttgaattaggaggtactcctataaaattagcaagaagaagaaatttggatgtttccttcttttttctattataataa
tgcaatggtaatgtaactgaatcagaaccttatgccaacaggtattacatccattgacataacgggtgttgaaacgttattagaaattcgaagg
tgcgtagaagcaaaagggatcaaggtaaaatcaaactctcattgttttttccatttacttttttgggcatggtataggaagtccataaggttctaa
atacttacatttcttctcttgcctttttcaattctttaatttgtagatgattttggttaatccgaggttgggagtcttggaaaagttgatggtga
cagagtcaatagacaccgttacaaaagaatctgtgttcttaaccattgaagacgcaattgatgcttgcagattttcactcaaatgttcagatca
aatgaaaagagaaaaccttgcaatagtttag
```

SEQ ID NO 28: Polypeptide sequence of NtSULTR3; 5-T
MTSSPQSLHRVNYAAPRSFGTLLKANLKETLFPDDDPFHEIKNEPISRRFLKGAQYFVPIFEWLPKYSFKLFKYDLLAGITIASLAIPQGISYAK
LANIPPIIGLYSSFVPPLIYAVFGSSKHLAVGTVAACSLLIAAIIEGKVNANDNMPLYLSLVFTATLFSGLVQTALGLLRLGILVDFLSHSTIT
GFMGGTAIIICLQQLKGMLGLKHFTTHTDVASVLRAIFHNRKEWKWESAVVGIIFLTFLQFTRFVKNKKPKLFWVSAISPMVTVIVGCLFAYFA
HADKHGIQIVGHLSKGINPSSIHLLNFDPKYIESAPIKAGVIAAMISLAEGIAIGRSFAIIRNEQIDGNKEMIAIGLMNIFGSFASCYLTTGPFS
KTAVNFNAGCKTAMSNVVMSICMMLTLLFLAPLFSYTPLVSLSAIIMSAMLGLIDYDKAYHLFKTDKFDFCICMAAFFGVSFISMDIGLMLSVG
LALIRALLYIARPATCKLGLISETGLYRDVEQYPDANGIAGILILKLGSPIYFANCNYIRERILRWIRDERSLTISEGNEIEFLLLELGGITSI
DITGVETLLEIRRCVEAKGIKMILVNPRLGVLEKLMVTESIDTVTKESVFLTIEDAIDACRFSLKCSDQMKRENLAIV SEQ ID NO 29: Nucleotide sequence used for silencing NtSULTR3:1A-S and NtSULTR3: 1A-T
gtaggcaacattgatactagcggaattagcatgctagaaggtcaagaagaatcttgatagaagagatctcaagcttgtgctggcaaatccag
gggcagaggtaatgaagaagctgaacaagtccaa SEQ ID NO: 30: Polynucleotide sequence of NtSUS1-S
atggcagctagtggtcttagcattaagaaagtttggaggaatccattttggctcatccagatgaaattttggctctcaagtcaaggtacatta
ctacatataatgatattaagaactagaggcttatccaaggttttgttacattttttgaaattataagtttagaacctaatagtacttggtagcac
ttgtttccttattatctagctgttgttactgcttgttgctactgcttttctgttcatctttccttgagcccggtctatcggaaacaacctctcta
ttctcaaagtataaggttttgcgtacatactacctccccagactctacttgtggaatttactgttttttgttgtgttgttgtaatctaatatttat
tagaattttactgatttttcacatatatatatctatgtccccctgtcgaaaattctatagctcatgttagctaaatacattagtaccattgtttt
taattgttttggttttggcacaggattgaaactgaagggaaaggggtaatgaaaccacttgatctcttgaaccatttggtttctgttactagta
agacaaatggagtaaatattgtaccagtgcacttgtggaagttctcagttgcagccaagaagctgtgattgtaccaccaaaactagcactagc
tgtacgtccgaggccccggtgtatgggagtacttgtcactgaatcttaagacaaagaaagtggctgaattaagcattcctgaatacctttcaattg
aaagagaacactgttgatgaaaggtaaagtattagtctgcgatttcgcttttgtgaaattgaagttttttgtttgattcataatgttttgtgtat
caattatgttaccagtggaaacatattggagttggattttgagccatttacaacagttacaccaccaaaaacacttttctgactctattggcaat
ggtttggagtttcttaatcgccacattgcttcgaaaatgtttcatgataaggagattccagatgcctccttgacttcctcagaaaccataact
acaaaggaaaggtaataaaaaaagtgttcttaaacaagttgtatgattatgtgtatatttctaagtatgttaacttgaaaacagtcattga
tggtgaaagaaagcattcaaagcctagagagttccaacttgtctgaaaaaagcagaggaacatttgtgcacattgaatccagaaactccata
ctccaattttgaatcaaagtttgaagagattggcttggaaagagggtggggaaacaccgctgaacgcgtgcaagacactatcagtcatcttttg
catctccttgaggctcctaacgcgtcttcttttggaaaattccttggtagaatcccattggttttcaatgttgtgattctaactccacatggtt
attttgctcaagataatgtcttgggctatcctgacactggtggccaggtttgtgtccaatattttgcattcttgatcaagttctttataccatt
tgaaccaacaatcttnaacattctttttttggttgtgaaatgttgaataggttgtttacattcttgatcaagttccagctatggagcgtgagat
gcttcatcgtatgaagcttcaaggactcgatgatatcatccctcgcaatcctttgttgtaagtggcctttaatttttccctagtttcattacacctct
aaatgaaatttgatcttttttgttgttttatatcaggtaacaaggctgctgcctgatgcagtaggaacccacctgtggcgagcggatggagaaagt
atatggggcagaacattctcatataattcgtgttccatttagaactgagaagggaatgttgcgcaaatggatctcacgattcgaagtctggcca
tacatggaaactttcactgaggttggaacataaaaacaaataaatccattggaatgttccttctgcaattgaaatgtcttgctaactgaaga
cccattttaaattgatcatcaggatgttgcagaagaacttgtcaaagaattgcaagctaaaccagacttgatcattggaaactacagtgaggg
aaatcttgctgcctcttgcttgcgaagaaatttggggctactcagtgtactattgctcatgccttggaaaaaactaagtatccaaactctgac
```

```
cttaattggaagaagtttgatgacaagtatcatttctcaagtcagttcactgctgatctctttgccatgaatcacactgatttcatcatcacca
gcactttccaagaaattgctggaaggtaaaagcaaatgcacaccatcatagtatttcatatttttacccttgtttatactatttccattcaccg
accccgacttgtttaggattgagccatagttgttgttgttgtttgtttatactatttccatttgccgaccacaacttgtttaggactgaggtat
agttgttgttgttggtttgttcatatttattttcattcgctaaccctaacttgtttgggactgaggcatagtagtagtagtagttgttgctatta
gtttatactatttccatttgccaaccccaacttgtttggtactgagacatagtagttgttgttgttgttgttgttgttatactatttccatttgccga
ccccaacttgtttaggactgaggtatagttgttgttgttggtttgttcatatttattttcattcgctaaccccaacttgtttgggactgaggcat
agtagtagtagtagttgttgctattagtttatactatttccatttgccaaccccaacttgtttggtactgagacatagttgttgttgttgt
ttgtttatactatttcaatttgtcgaccccaatttgtttgggaccaaggcatggttgttgttgttgttgtttttgttttttactgtttccattgat
attggaacatttgttatttgcagcaaaaacactgtaggacagtatgagagtcatactgcttttaccatgcctggattgtaccgagtagtccatg
gaatcgattcgtttgatccaaagttcaacattgtctccctgggctgatatgtcaatctacttcccttacactgagaaggagaaaaggctaac
caacttccacccggaaattgaagaactcctctacagtcctgttgagaataaggaccacttgttagtctccttaatttgcttttatttcatccca
tttatgatcgctttatcccaacagatcgattaatcatttgttatcaacataacagatgtgtgttgaaggaccggaacaagccaattctctt
accatggcaaggctagatcgcgtgaagaatctaacagggctcgtggaatggtatgctaagaatgcaaggctgagggagctgttaaccttgtgg
ttgtaggcggagacagaaggaaagaatccaaagatttagaagagcaagcagagatgaagaagatgtatgatcttatcgaaacctataacctgaa
cggccaattcaggtggatttcttcccaaatgaatcgtgtgaggaacggagaactctatcgttacattgcagacacgaggggtgctttcgttcaa
ccagcattctacgaggcttttggtttgacagttgtagagtctatgacttgtggtttgccaacttttgctacttgtaatggtggaccatttgaga
ttatagtgaatggaaaatctggttttccatattgatcctaatcaaggtgacaaggctgctgatatgttggtaaatttcttttgaaaaatctaaaga
agatccaagtcattgggatgctatttccaagggaggtctgcaacgtattcttgaaaagtaagcttttgcatttgattagcacaagtgcacaacc
aagatttaacttttgaacaaactaaaactaacccttttttgtattttcttttgctaggtatacatggcaaatttattcacagaaagtgatcaca
ctatctcgggatttatggattctggaagtatgcaaccaagaatgataaagttgctagtgcaaagaagcgctatctttgagatgtttatgaacttg
gatttaagaaatcagtaagtgtcaatttttaaagggaaccttggatcaacggttaagttgtctttgtcaacctataggtcaggggtttgagcc
gtagaagtagccactaatatttacattaggtagactgtgtacatatcaccccttggggtacggccctctcctggatcctgtatgaacgcgg
gatgccttgtgcaccggctgtatttttttttttagtgtcacttctgtatttgtttgagcttgtttataaagtttggaaatctgctgctaatt
tgtatatttgttggttgtgtatttcaggctgagaaagttccattggctattgatgaatag SEQ ID NO: 31: Polypeptide sequence of NtSUS1-S
MAASGLSIKKSLEESILAHPDEILALKSRIETEGKGVMKPLDLLNHLVSVTSKTNGVNIVPSALVEVLSCSQEAVIVPPKLALAVRPRPGVWEY
LSLNLKTKKVAELSIPEYLQLKENTVDESGNILELDFEPFTTVTPPKTLSDSIGNGLEFLNRHIASKMFHDKEISRCLLDFLRNHNYKGKSLMV
KESIQSLESFQLVLKKAEEHLCTLNPETPYSNFESKFEEIGLERGWGNTAERVQDTISHLLHLLEAPNASSLENFLGRIPLVFNVVILTPHGYF
AQDNVLGYPDTGGQVVYILDQVPAMEREMLHRMKLQGLDDIIPRILVVTRLLPDAVGTTCGERMEKVYGAEHSHIIRVPFRTEKGMLRKWISRF
EVWPYMETFTEDVAEELVKELQAKPDLIIGNYSEGNLAASLLAKKFGATQCTIAHALEKTKYPNSDLNWKKFDDKYHFSSQFTADLFAMNHTDF
IITSTFQEIAGSKNTVGQYESHTAFTMPGLYRVVHGIDSFDPKFNIVSPGADMSIYPPYTEKEKRLTNFHPEIEELLYSPVENKDHLCVLKDRN
KPILFTMARLDRVKNLTGLVEWYAKNARLRELVNLVVVGGDRRKESKDLEEQAEMKKMYDLIETYNLNGQFRWISSQMNRVRNGELYRYIADTR
GAFVQPAFYEAFGLTVVESMTCGLPTFATCNGGPFEIIVNGKSGFHIDPNQGDKAADMLVNFFEKSKEDPSYWDAISKGGLQRILEKYTWQIYS
QKVITLSGIYGFWKYATKNDKVASAKKRYLEMFYELGFKKSAEKVPLAIDE SEQ ID NO: 32: Polynucleotide sequence of NtSUS1-T
atggcaggcagtggtcttagcattaaggaaagtttggaggaatccattttggctcatccagatgaaattttggctctcaagtcaaggtacatta
ctgcataatgatattaagacctagaagcggatccaagattttgttacattttgaaattataagtttagaatctaatatttgttatcgcttgtt
tccttattatcttgctgttgttactgcctgttgctactagttctgttcatcctccttgagctgagtttctatcggaaacaacctctctactc
tcaaagtaggaataagttatgcgtacacactaccctccccagactccacttgtgtagttttactgagtttgttgttgttgttgttgttaatctaat
acttgttagaatttactgatttttcacatatatatctatgacccatgtcgaaaatactatagtctcatgtgctaaatacattagtaccattgtt
ttgtaattgttttggtttggaacaggattgaaactgaagggaaaggggtaatgaaaccagttgatctcttgaaccatttggttttctgttacta
gtaaaacaaatggagtaaatgttgtacctagtgcacttgtggaagttctcagttgcagccaagaagctgtgattgtaccaccaaaactagcact
agctgtacgtccgaggcccggtgtatgggagtacttgtcactgaatcttaagacaaagaagtggctgaattgagcattcctgagtaccttcaa
ttgaaagagaatactgtttgatgaaaggtaaagtaatagtctgcgatttcgctttgtgaaattgaagttttttgtttgattcttaatgttttgtg
tatcaattatgttaccagtggaaacatcttggagttggattttgagccatttacaactgttacaacaccaaaaacactttctgactctattggc
aatggtttggagtttcttaatcgccacattgcttcgaaatgtttcttgataaggagattgccaagtgcctccttgactttctcagaaaccata
actacaaaggaaaggtagtaaaaaaagtgtttctttaaacaagttgtaagttatatgttgtattttctaaatatgtcaatttgaaaacagtcatt
gatggtgaaagaaagcattcaaagcctggagagttttccaacttgttctgaaaaaagcagaggaatatttgcacacactgaatccagaaactcca
tactccaaatttgaatccaagtttgaagagattggcttggaaagagggtggggaaacaccgctgaacgcgtgcaagacaccattagtcatcttt
tgcatctccttgaggctcctaacgcgtcttccttggaaaatttccttggtagaatcccattggttttcaatgttgtgattctcacccccacatgg
ttattttgctcaagataatgtcttgggctatcctgacactggtgtgtccgatataacatatcaagaaattttgcattcttgatc
atgttcttataccatttgaaccacattcttttttggttgtgaaatgttgaatggttgtttacattcttgatcaagttccagctatggagc
gtgagatgcttcatcgtatgaagcttcaaggactcgacgatatcatccctcgcatccttgttgtaagtgccctaatttcctggtttggttta
cctctaaatgaaattgattttctggcttttctaacttttttggattgatctttttgttgttttatatcaggtaactaggctgctgcctgatgctg
taggaaccacttgtggcgagtggatggagaaagtatatggggcagaacttctcatataatttcgtgttccatttagaactgagaaaggaatgtt
gcgcaaatggatctcacgattcgaagtctggccatacatggaaactttcactgaggttggaacataaaaacaaataaaaatcattggaatgttc
ttctgcatttgaaaatgtcttgctaactaaagactcatttttaaattaatcatcaggatgttgcagaagaacttgtcaaagaattgcaagctaa
accagacttgataattggaaactacagtgagggaaatcttgctgcctcattgcttgctaagaaatttggggctactcagtgtactattgctcat
gccttggaaaaaactaagtatccaaactctgaccttaattggaagaagtttgatgacaagtatcatttctcaagtcagttcactgctgatctttt
ttgccatgaatcacactgatttcattcaccaccgacctttccaaggtgatggagaagtaaaagccacatcatatttcatat
tttttaccctagttttatactatttccatttgtcaactccaacttgtttgggattgaacatagttgttgtttgttatactatttccattcgccg
accccaacttatttgggactgagacataattgttgttattattgtttgtttgtttatactatttccattctcagaccccaacttctttgggact
gagccgtagattgttgttgttgttgttgttgtttgtttatgctatttccgttcaccgaccccaacttatttgggactgaggtgtagaagta
gtcgttgttgttgtttatacgacttccaattgatattcgaatgttttatttttgcagcaagaacatgtaggacagtatgagagtcatactg
ctttttaccatgcctggattgtatcgagttcatgaatcaattcgtttgatccaaagttcaacattgtctccctgggctgatatgtcaat
ctacttcccttacactgagaaggagaaaagactaaccaacttccacccggaaattgaagaactcctctacagtcctgttgagaataaggaccac
ttgttagtctcttttatttcattcatttttttctacaccttttttttttcaacagttgattgattggttcttatcaacgtaaacagatgtgtgttga
aggaccagaacaagccaattctctttaccatggcaaggctagatcgcgtgaagaatctaacagggctcgtggaatggtatgcaaagaatgcaag
gctaaggagctcgttaaccttgtggttgtaggcggagacagaaggaaagaatccaaagatttagaagagcaagcagagatgaagaagatgtat
gatcttatcgaaacataccaacctgaatggccaattcaggtggatttcttcccaaatgaatcgtgtgaggaacggagaactctatcgttacattg
cagacacgagggggtgcttctgtcaaccagcattttatgaggcattttgggttttgacagttgtgagtctatgacttgtggtttgccaacttttgc
tacttgtaatggtggaccatttgagattatagtgaatggaaaatctggtttccatattgatcctaatcaaggtgacaaggctgctgatatgttg
gttaaatttcttcgaaaatctaaagaagatccaagtcattgggatactatttccaagggggtctgcagcgtattcttgaaaagtaagcttttg
catttgattagcacaagtgtacaaccaagatttaacttatgaacaaactaaaactaacccttttttattttcttttgctaggtatacatggca
aatttattcacagaaagtgatcacattatctgggatttatggattctggaaatatgcaaccaagaatgacaaagttgctagtgcgaagaagcgc
```

```
tatcttgaaatgttttatgaatttgggtttaagaaatcagtaagtgtcacttctgtattttgtttgagcttgtttgtaaagtttggcaatcttc
tgctaatttgtactatatttgttgacttgtgcatttcaggctgagaaagttccattggctattgatgaatag
```

SEQ ID NO: 33: Polypeptide sequence of NtSUS1-T
```
MAGSGLSIKESLEESILAHPDEILALKSRIETEGKGVMKPVDLLNHLVSVTSKTNGVNVVPSALVEVLSCSQEAVIVPPKLALAVRPRPGVWEY
LSLNLKTKKVAELSIPEYLQLKENTVDESGNILELDFEPFTTVTTPKTLSDSIGNGLEFLNRHIASKMFLDKEIAKCLLDFLRNHNYKGKSLMV
KESIQSLESFQLVLKKAEEYLHTLNPETPYSKFESKFEEIGLERGWGNTAERVQDTISHLLHLLEAPNASSLENFLGRIPLVFNVVILTPHGYF
AQDNVLGYPDTGGQVVYILDQVPAMEREMLHRMKLQGLDDIIPRILVVTRLLPDAVGTTCGEWMEKVYGAEHSHIIRVPFRTEKGMLRKWISRF
EVVWPYMETFTEDVAEELVKELQAKPDLIIGNYSEGNLAASLLAKKFGATQCTIAHALEKTKYPNSDLNWKKFDDKYHFSSQFTADLFAMNHTDF
IITSTFQEIAGSKNTVGQYESHTAFTMPGLYRVVHGINSFDPKFNIVSPGADMSIYFPYTEKEKRLTNFHPEIEELLYSPVENKDHLCVLKDQN
KPILFTMARLDRVKNLTGLVEWYAKNARLRELVNLVVVGGDRRKESKDLEEQAEMKKMYDLIETYNLNGQFRWISSQMNRVRNGELYRYIADTR
GAFVQPAFYEAFGLTVVESMTCGLPTFATCNGGPFEIIVNGKSGFHIDPNQGDKAADMLVNFFEKSKEDPSYWDTISKGGLQRILEKYTWQIYS
QKVITLSGIYGFWKYATKNDKVASAKKRYLEMFYEFGFKKSAEKVPLAIDE
```

SEQ ID NO: 34: Polynucleotide sequence of NtSUS2-S
```
atggctgaacgtgctctgactcgtgttcacagccttcgtgaacgtcttgatgccactttggctgcacatcgcaatgagatattgctgtttcttt
caaggtattgcctaagtagtgttcttgtttcctacaaaagattcagttggtgttcaaaaaacgatatgtgatttgatttatctgcctaagtctt
ggtagtcataattatccggtacctgtgctggtgcgagttagtcggttcggaaactactcttatgaaaacgagagatttagttggtgttgtctgc
aattctgtagtatggactattaagcagatagatcatgtttgatatcgaaaaggaatgtatatgtgatgttacttgaactggttttggttattac
aggattgaaagccatggaaaagggatcttgaaacctcaccagctatgtggctggagttcgatgcaattcgccaagatgacaaaaagaagctgaatg
atcatgcatttgaagaactcctgaaatctactcaggtaattttgattttggctaaatgtgttaccaagctgaatgatcatgcattttgagtttgt
gtccgactactacaatgatatgttataccaggaagcgattgttctgccaccttgggttgcacttgccattcgtttgaggcctggtgtgtgggaa
tatgtccgtgtgaatgttaatgctctagtcgttgaggagctgaccgtccctgagtatttgcattttaaggaagaacttgttgatggaacgtaag
ttttagtctcttatttgatactatgtttagagaataggcagtggattcaatttatcagtgttgttttttacctaatgcagctccaatggaaattt
cgttctcgagttggattttgagccccttcactgcatccttttcctaaaccgaccctccaccaaatctattgggaatggagttgaattcctcaatagg
cacctttctgcgaaaatgttccatgacaaggaaagcatgaccccgcttcttgaatttcttcgggttcacaattataagggcaaggtaacttttgt
tattcccattcatatatatgttcagtttgtgcttatcatgcgcccaatgatgtatgaatatgtactaaaggatagatgtacgatttcgtttgca
gacaatgatgctgaatgacagaatacagaatttaaccactcctgcaaaatgtcctaaggaaggcagaggaataccttattatgcttcccctgaa
actccattttccgaattcgaacacaagttccaagaaattggattggagaaagggatggggcgacactgcggagccgctgctagagatgatatgca
tgcttcttgatctacttgaggctcccgactcctgtactcttgagaagttcctaggagaattcctatggtgttcaacgtggttatcctttcccc
ccatggatatttcgcccaggaaaatgtcttgggttatcccgacactggtggccaggtgcattacttagtctttgtccgtgagtctatgttgct
cagatcctctacaatgccactgtaccgtgtaggatactccaaatataatgcattttgggaggatctgtcaccggtgcaatggcattttggagg
toggagcaacaaacaactgctagtatgcttctaaagcttgcttccataaatgctaaggtccttcaccgtaatgtgcaggttgtctacatatta
gatcaagttccagccttggagcgtgaaatgcttaaacgcctaaaggagcaaggacttgatataacaccgcgtattcttattgttagtatttctt
gtacttgtaattgctgcggattacacaaaattttctctttattggcaacttatcttgatattattcccaggttactcgtctgctgcctgatgca
gttggaacaacttgtggtcagcggcttgagaaggtgtatggagccgagcactcacatattcttagggtccccttaggaccgagaagggcattg
ttcgcaaatggatatctcgctttgaagtgtggccatacatggagactttcactgaggtgacactaagcttccttgtatttgtctatcttctaat
tggtattaggaacaatttgctaattattaacgctttggcttttcgtacatcaggatgttgcaaaagaacttgctgcagaactgcaggccaagcc
agatttgataattggcaactatagcgagggaaatcttgtggcttcattgctggctcacaagttaggcgtaacgcaggtctgtgttatttttcac
ctcttataaatctgattgtatttccattagtctggaactaaaagtactaaaattttcttttcttcgctgtgttatttgccttctgcagtgcacc
attgcccatgcattggagaaaacaaagtatcctgattctgacattctactggaaaaaattgaagaaaataccatttctcgtcccagtttaccg
ctgatcttattgcaatgaatcacaccgattttatcatcaccagcacttccaggagatagcaggaaggtataacatcaattgctaattcggttg
cagtaacattttgttcgatttcttcccccttatgcttaacctaataccctaatgaattttccagcaaggacactgtcggacagtacgagagtcac
caggcattcacaatgcctggattgtacagagtcgttcacggcattgatgtgttcgatcccaaattcaacattgtctcacctggagctgatataa
acctgtattttcccatattccgagaaggaaaagagattgacagcacttcacccagaaattgcagtagggagctcctgtacagtgatgttgagaacgagga
acatctgtaagtttctaacttactcgtaccgtcagtggcagagccagaatttcattaaaatgggtgtcaaaatataaagacataaattcacaaa
gaagccaagggtgtcaatatgtagtataaatatattaaaaaaaaattacctagctacacaatgtaattttccgacaaagggggatcggttgcact
tcttgaatacatgtggctctgccactgggtacagttacaaagtcctgttacctatgtagatgagcttgtgctgaacatgttgtgattttggtag
gtgtgtgctaaaggacaggaataagtgccaatcttattcacaatggcgagattggatcgtgtgaagaacttaaccggacttgttgagtggtacgcc
aagaacgcacggctcaaggagttggttaacccttgttgtcgttggtgggagaccgaaggaaggaatccaaagatttggaagggcaagcagagatga
agaagatgtatgagctaataaaagactcacaacttaaatggccaattcagatggattttcttcacagatgaaccgatgaaggaacggcgaactcta
ccgatacattgccgacactaggggagctttcgtgcagcctgcattctatgaggctttcggttttgactgttgttgaggccatgacctgtggtttg
cctacatttgcaactaatcatggcggtccagctgagatcatcgttaacgaaaatccggcttccatatcgatccatatcacggtgagcaagctg
ctgatctgctagctgattcttttgagaaatgtaagacggaaccttctcattgggaaactatttcaaccggttggcctgaagcgcatccaagagaa
gtaagcaactctttcttgactctagtcattcaaatttaacttgtaaagtctcaaggtttgaggcatagttgattgataaattttatcgcgtctctactactatatac
aggtacacgtggcaaatctactcggagagattattgacgttggctgctgtttacggtttctggaaacatgtttctaagcttgatcgtctagaaa
tccgtcgatatctagaaatgttttatgctctcaaataccggaagatggtgagttcttctgcttcctgctcttctcatagtgtttaatatacact
tgattgattgcattcacttagactaagttgctcggacacgggtgtggatgtccgacacgagtgcggatctagagttcagatccttcaagatgta
aattataagattcggggatatggatcctagtacggatacgggtgcgagaatccggctaaaaataattttaaaaaaaattatctctaaattatga
gatattatgtggaatacttacgtataacttgtaaagttagattttttttaattctcaagttgtagattagtgaaatgattgattttcctagataa
gtatgctatttttcttcaaatttactcttctgatttcgaaaatcaaattgtatctcgtctcgaatttttccgtccgttatgtcaaagtacccaa
aatcgtttgaccaaatcggtacggatcccatacccacacccacactagtgtcgtattgacacgggtgccgcacctaaactgctatgtcggagca
acttagcacttagagaatcattgatgttaaattttcttaattcttgaatctgctaatgaagattttatcttggttttttgtttaggctgaagctg
ttccattggctgctgaatga
```

SEQ ID NO: 35: Polypeptide sequence of NtSUS2-S
```
MAERALTRVHSLRERLDATLAAHRNEILLFLSRIESHGKGILKPHQLLAEFDAIRQDDKKKLNDHAFEELLKSTQEAIVLPPWVALAIRLRPGV
WEYVRVNVNALVVEELTVPEYLHFKEELVDGTSNGNFVLELDFEPFTASFPKPTLTKSIGNGVEFLNRHLSAKMFHDKESMTPLLEFLRVHNYK
GKTMMLNDRIQNLTTLQNVLRKAEEYLIMLPPETPFSEFEHKFQEIGLEKGWGDTAERVLEMICMLLDLLEAPDSCTLEKFLGRIPMVFNVVIL
SPHGYFAQENVLGYPDTGGQVVYILDQVPALEREMLKRLKEQGLDITPRILIVTRLLPDAVGTTCGQRLEKVYGAEHSHILRVPFRTEKGIVRK
WISRFEVVWPYMETFTEDVAKELAAELQAKPDLIIGNYSEGNLVASLLAHKLGVTQCTIAHALEKTKYPDSDIYWKKFDEKYHFSSQFTADLIAM
NHTDFIITSTFQEIAGSKDTVGQYESHQAFTMPGLYRVVHGIDVFDPKFNIVSPGADINLYFPYSEKEKRLTALHPEIEELLYSDVENEEHLCV
LKDRNKPILFTMARLDRVKNLTGLVEWYAKNARLRELVNLVVVGGDRRKESKDLEEQAEMKKMYELIKTHNLNGQFRWISSQMNRVRNGELYRY
IADTRGAFVQPAFYEAFGLTVVEAMTCGLPTFATNHGGPAEIIVNGKSGFHIDPYHGEQAADLLADFFEKCKTEPSHWETISTGGLKRIQEKYT
WQIYSERLLTLAAVYGFWKHVSKLDRLEIRRYLEMFYALKYRKMAEAVPLAAE
```

SEQUENCE LISTING

SEQ ID NO: 36: Polynucleotide sequence of NtSUS2-T
atgcttttatgggagtaaatttatggccggtcattcaactttgtgttcattacgcaaagtcattttcttggtgtttattacgcaagtcat
ttttctttttttttgttacgtaaaaatcattcaactatgtgtttattatctaaaattcaattttttttttccttttgttacacaaaaatcatt
ttactttactctatttatcacaaaagtcaccttggccagatttttataataggcttttatctttttgttacacaaaaattattttacttactcta
tttatcacaaaagtcaccttggccagatttttataataggcttttatctttttgttacacaaaaattattttacttactctatttatcacaaaag
tcaccttggccagatttttacaatacttttaccttaaaagactattatgccttgacattataaatcctctcatttatataatacttctatatg
atacactatataatatattttacctaggtattttacttataattaaaataatattaaattattttatttatctattttataatatattcatac
atttaatttttttcatggcaaatcactttgtttaatcatatttaaacatgaacaaatttttaaatatcaaaaaaataaaaaaataaaaaaatatt
tatttgaaataataacaaacagatttgtttaacaaatgatagttttttttttatagtcaataaaattttaaaaaaattcaaagatatttgtttt
taatattaatattttttaaagctttatctgttaatattatttttattttgaaagtattaatctgatgtgtcattgtgttaaatgtgagtattttattt
attggattaatgagtatggcttggctgataaaaagctttgatttttataatttttcattaaaaatattttattaagctagtacctgacaaatttaa
tatcttgaaaattaacgttaagaaaaaattaaatataaaaatatattataaaaataataaataaataatatcaagttattttaattataaataa
aatacatggttaaaaatatattatatagcatataatatagaaggtattacataaatgagatgatttaaagggcataatagacttttcaggtgaa
tgatttgtaaaatatggttaaagtgattattgtgataattagagcatagtaaaataattttatgtaacaaaagaaaaaaaaaatgactttttgg
gtaatgaacataaaatttgaataactttttacgtaacaaaagaataaaaagatttggataataaacataaaattgaatgaccacctataaaatt
tattattttttttgggctcttcttgatttgatttttttagtttagccttttgcagtaatcttggttgtcacgcgtagcgttgtgcttttcgccacata
agtatttagtagacttaattaatgtcattatatcggttggtgtggttttaattacttaactgtactattatattaggtggaaggtttgaaaatt
tatagtagtaacattctagatcattgaaaatattggtgtttcagtgacttttttagtatgtcattttcattttctaagtggttgtactaatatag
tatattaaaattttgattggttgagaaacaatctctctcacctcacacggtacgggtaaggtatgcgtatacgcttatcctccctacactccatt
tgtgggactattgttgttattttggataagctgaggtatccatcttctactaactgcactagttttatttttttgctgtttacagttgaaacaa
ttgtctgaggatttctccctgctgaatcaactgcaatggctgaacgtgtgctgactcgtgttcacagccttcgtgaacgtcttgatgctactt
tggctgctcatcgcaatgagatattactgtttctttcaaggtatagccaaagatagtattcttgttaactaaaaaagattcagttggtgttcaa
aaaacgatacgtttatctgcctaagtcttggtagtcagaattatccggtacctatgctggtgtgagttagctggctaggaaaccactcttatga
aaacaagagatttagttagagttgtctgtaattctgtagtatggactatgtatgtgatgctatttgaactggttttggttattataggattgaa
agccatggaaaaggaggcttgaaaccgcatcagctattgcgctgagttgatgcaattcgccaagatgacaaaaagaaactgaaatgatcatgcat
ttgaagaactcctgaagtccactcaggtaatatggttttggctatatttgtcgccaacgccaagctcatattttatattttttgagcttgtg
tctgaatacgacgatgatatgttatactaggaagcaattgttctgccaccttgggttgcacttgcgattcgtttgaggcctggtgtgtgggaat
atgtccgtgtgaatgtcaatgcgctagtcgttgaggagctgactgtccctgagtatttgcatttcaaggaagaacttgtcgatgaacgtaagt
gttagtcttcaatttgatgctatgttagagaataggctgtggaatttattgatcaatgctgtgctttgtcctgatacagctccaatggaattt
cgttctcgagttggattttgagcccttcaccgcatcctttcctaaaccaaccctcaccaaatctatcggaaatggagttgaattcctcaatagg
cacctctctgcgaaaatgttccatgacaaggaaagcatgaccccgcttcttgaattttcttcgggttcacaattataagggcaaggtgacttgct
atttccatttatctctataggttcggtttgtgctttatcatgcgcccaatgacatatgaatatgcgctaaaggatagatatatgatttcctttgcag
acaatgatgctgaacgacagaatacagaatttaaccacactgcaaaatgtcctaaggaaggcagaggaatacctcattatgcttcccctgaaa
ctccattttccgaattcgaacacaagttccaagaaattggattggagaagggatggggcgacactgcagagcgcgtgctggagatgatatgcat
gcttcttgatctcctcgaggctcccgattcctgtactcttgagaagtcttggggagaattcctatggtgttcaatgtggttatccttttccccc
cacggatatttcgcccaggaaaatgtcttgggttatcccgacactggtggccaggtgcattactttaatctttatccgtgagtctatgtttgtt
cgaatcctctagaaatgtcactgtacctatgtaggatactccaaatataatgcattttgggggatctgttatgggtgcgatggcattttgaa
ggtcggagcaacaaacaattgctatgtattcttctaaagcttgctttcataaatgctaaggtccttcaccttaatgtgcaggttgtctatata
ttagatcaagttccagcctttggagcgtgaaatgcttaagcgcctaaaggagcaaggacttgatatcacaccgcgtattcttattgttagtattt
cctgtacttgtaattactgcggattacacaaaatttcctttttatcttcttaacaacttatcttgatggtattcccaggttactcgtctgctac
ctgatgcagttggaacgacttgtggtcagcggcttgaaggtgtatggagccgagcactcacatattctgagggtcccctttaggactgagaa
gggcattgttcgtaaatggatctctcgctttgaagtgtggccatatatggagactttcactgaggtgacactaaaacttccttatatttgtcta
tcttctaattggtattaggaataattttgttaattgttaactctttgtcttttcgtacatcaggatgtcgcaaaagaacttgctgcagaattgca
ggccaagccagatttgataataggcaactatagcgagggaaatcttgtggcttcattgctcgctcataagttaggcgtaacacaggtctgtgtt
gttttttcactctcttaaagatctgattgcatttccattagtctggaactagaagtactaaaaagttcttttcttcactgtgttatttgccgtcg
gcagtgcaccatagctcatgcattggagaaaacaaagtatcctgattctgacatctactggaaaaaattcgataaaaataccatttctcgtcc
cagtttaccgctgatccttattgcaatgaatcacaccgattttatcatcaccagcactttccaggagatagcaggaaggtataacatcaatttgc
tacttcgactgcaacagcattgtgttcccatttctttcccttatgcttaacctaataccgtcatgaattttccagcaaggacactgtcggacag
tacgagagtcatcaggcattcacaatgcccggattgtacagagttgttcacggcattgatgtgttcgaccccaaattcaacattgtctcacctg
gagctgacataaacctctatttcccatattccgagaaggaaaagagactgacagcttcacccctgaaatgcgaggagctgctagtacagtgacat
tgagaacgaggaacatctgtaagtttctaccttactcgtacagtcagtggcggagccagaatttcactaaaataaggtcaaaatataaagaca
taaatccacaaagaagccaagggtgtcaatatatagtataaatacattaaaaaaattacctatctacacagtgtaattttccgacaaaggggtg
tcggttgacactccttgaatacatgtggctctgccactgggtacagttacaaagttctgttacctatgtagatgagcttgtgctgaacatgttg
tgattttggcaggtgtgtgctaaaggacaggaataagccaatcttattcacaatggcgagattggatcgtgtgaagaatttaaccggacttgtt
gagtggtatgccaagaacgcacggctaagggagttggttaaccttgttgtggttggtggagatcgaaggaaagaatccaaagatttggaagagc
aaacagaaatgaaaagatgtatgagctaataaagactcacaatttaaatggccaattcagatggatttcttcacagatgaaccgagtgaggaa
cggtgaactctaccgatacattgctgacactagaggagcttttcgtgcagcctttcgctttgactgttgttgaggccatg
acctgtggttgcctacatttgcaactaatcatggcggtccagctgagatcatcgttaacggaaaatctggcttccacatcgatccatatcacg
gtgagcaagctgctgatctgctagctgatttcttgagaaatgtaagacagaaccttctcattgggaaaccatttcaacgggtggcctgaagcg
catccaagagaagtaagcaactctttcttgactctagtcattgaaattaactttcttgactctagtcattgaaattaactcgggatttgaggcg
tagttgattgatattttatcgcgtctctactactgatatacaggtacacgtggcaaatctactcggagaggctattgacattggctgctgtt
tacggggtctgaaacatgttctaagcttgatcgtctagaaatccgtcgatatcttgaaatgttttatgctctcaaatccgcaagatggtga
gttcctcttcttccttgccttctcctagtgtttaagatacaatataattgattgcattatcttagagaatcattaatgttaaattttcttaat
tcttgaatctgttaatgaagttttttctcttggttttttgtttaggctgaagctgttccattggctgctgagtga SEQ ID NO: 37: Polypeptide sequence of NtSUS2-T
MLFMGLKQLSEDFSPAESTAMAERVLTRVHSLRERLDATLAAHRNEILLFLSRIESHGKGILKPHQLLAEFDAIRQDDKKKLNDHAFEELLKST
QEAIVLPPWVALAIRLRPGVWEYVRVNVNALVVEELTVPEYLHFKEELVDGTSNGNFVLELDFEPFTASFPKPTLTKSIGNGVEFLNRHLSAKM
FHDKESMTPLLEFLRVHNYKGKTMMLNDRIQNLTTLQNVLRKAEEYLIMLPPETPFSEFEHKFQEIGLEKGWGDTAERVLEMICMLLDLLEAPD
SCTLEKFLGRIPMVFNVVILSPHGYFAQENVGYPDTGGQVVYILDQVPALEREMLKRLKEQGLDITPRILIVTRLLPDAVGTTCGQRLEKVYG
AEHSILRVPFRTEKGIVRKWISRFEVWPYMETFTEDVAKELAAELQAKPDLIIGNYSEGNLVASLLAHKLGVTQCTIAHALEKTKYPDSDIYW

```
KKFDEKYHFSSQFTADLIAMNHTDFIITSTFQEIAGSKDTVGQYESHQAFTMPGLYRVVHGIDVFDPKFNIVSPGADINLYFPYSEKEKRLTAL
HPEIEELLYSDIENEEHLCVLKDRNKPILFTMARLDRVKNLTGLVEWYAKNARLRELVNLVVVGGDRRKESKDLEEQTEMKKMYELIKTHNLNG
QFRWISSQMNRVRNGELYRYIADTRGAFVQPAFYEAFGLTVVEAMTCGLPTFATNHGGPAEIIVNGKSGFHIDPYHGEQAADLLADFFEKCKTE
PSHWETISTGGLKRIQEKYTWQIYSERLLTLAAVYGFWKHVSKLDRLEIRRYLEMFYALKYRKMAEAVPLAAE

SEQ ID NO: 38: Polynucleotide sequence of NtSUS3-S
atggcgaatccaaagttcacaagagtacctagcatgagggagagagttgaggatactctctctgctcaccgtaaccagcttgttgctcctct
ccaggtatattaataaactctatatacttgttattttcttatttttttgtctttactgataaatttaactgttttcttctttaaatcttgctt
tcgatgcatgatttctgttgtgttaaattgcgtaaccatttatctaaaagtttatgctgataaacacttttaaattttaatatgtaaattata
ttatgtctcaacatcaacatgtggatggccaaaaatataaagcttaattttcgttattttgaatgattttctctgcgagtgttacggtttgcg
tacacattacctaaacctcctccctagtccccacttgtgggaatttaattttttttttctttgttttttttttgttgttgttgttgtctgagttc
aattcctaccatgttagcttggcaaaaataagttggtaaagcttgacccccaactagttttagttgatcgatttatttggtgatttatagttcaa
taataataattactattagagaaagttccagcagcttttctgttttgtttttccagttttagtgattgatatatgtgtatatatattctttgttt
cttttaagatacgtggcgcaggggaagggatattgcaacctcaccacttgatcgatgagttcaacaacgctgtatgtgatgacactgcttgtg
agaagctcaaagatggtcccttagtgaagtcttgaaagctactcaggtatattcactaatccatgggaatcaagatgatactgtatatcttta
ttatggtgtcttcagaaatttgacgatgatgaaatgcaacttttctctgtttgtcacccttatccagactgttttttttattttttattttcat
ttttaaacttgaaatgctcttaatttcctttgttatcgataagaccggatttacaatgtatgaacggagcatcttaagaaccttctggaatga
agatataagatataaaacatggtgtccgtttctcctttgtggaatcagtgtacatatagactgttattttggtcccactttctggatcttctg
atcacaccttctcatgcagaggcgagcttgatggtttcaacctttaaattcttactattgaatccatttcactttcgaaattatgagttcgaaa
tctaatatttgttgaaatttttgcaaatgttcacatataagttaagctttgtgtgaagaatactgggctcaatggattccaatagaccaggct
gtatccgcctctgtctccactctccctgcatccacttctttcgtgtgactaataatgcttaatgagctagaactcgttttaatgtttgaataag
ttgcttatatcagagcagcttttgatgtttcaatcttaacgggttatgcagtaccagcattctgcggctgaaaaacaggaatctgagatttac
ttgtctctggctgaatttcttgttcattttgctaacaagtactttggagttaatgcttgctctctgttgtcaaaataggaagccattgtgctgc
caccatttgttgccatagcagttcgtccaaggccaggtgttgggagtatgtcgtgttaatgtatatgatttgagcgttgaacaattgactgt
tcctgaatatcttcatttcaaggaagaacttgtggatggagagtaagctcttctttatttcaatacgaaacataaaaatttacagaagttgaat
aattaacaaatttgttgatttttaatgtatgccaggggtaataatcactttgtgcttgagctggattttgagccatttaatgcatcagttcctc
gtccatctcgatcgtcatccattggcaatggagtccaattcctcaatcgtcatctttcctcaattatgtttcgcagcaaagactctctggaccc
cttacttgatttccttagaggacactgtcataaagggaatgtaagtaccaaaagcagttttcccttttgtaaatgtctgctttgtccctgattatc
tactaaatctttcaacacgcgcaaccattataagaaatgtacaatacttctagttagaatttcatcatcgacaaactatctgctttactttta
tttttcccatttgatggatgatagtttagtttatataacagatgatattttggttgaagggtaccatgaactttttcacaaccacttaatggat
acatagttgtaatagttgacattttggaataatattgtctcacttggaaatgtttaagaagtattactacttctatttgtaagatggattgttt
atctatgcaggtcttgatgttgaatgatcgtatacagcgaatctccaggctggagtctgctcttttctaaagcagaggattatctctccaagcta
tcaccagatacatcctataatgagttcgaatacgcgtgagcttgtacacatttgttttgtttttcttcaagcatatgtaattctcaagaaaag
ggaaatctataggagttgaaacattctttatggaaccatgtgcatgcagattgcaagaaatgggctttgagagaggttggggtgatactgccag
acgtgtttggagacgatgcatcttcttctgacattcttcaggctccggatccatcaacctggagacatttcttggtagactacctatggtg
ttcaatgtcgtcatattatcccctcatggatattttggccaagcaaatgtcttgggtttgcccgacactggtggccaggtaataacaaggagaa
tgaggtcttgtattatgtactccctccgttccaatctatatgaacctatttgactgggtatggaaagaaatgaagactttgtaaaacttgtggtt
ctttagaaattccaaacattacatttggtttttccctcttcctggaaattatactactgaatcatctctagatgttccagtttaacttgagac
gtaagggtaaataacggaccattactctgtccttcttgcagtaggcttggtacaatgaatatagttcgcatagttgccggaagctagagctgt
gttagaaaactcaggaacattaattggcgatgctaatcactgctaatgttactgaagcatccatggttttccttgatgttattctccttttgg
ttgcttcacaggttgtctatatactggatcaagtgcgtgccttggaggccgaaatgcttcttagaataaagcacaaggacttaacttcaagcc
tagaatccttgtcgtgagtacatatatattgtcaagctcttatttggttttgtgggattgcagttgacatcaatttgcttactctgattactaa
aggtcacacggctgatacctgatgctaaaggaaccatgtgcaaccagaggttggagaggattagtggaactgaatactcgcatattttacgtgt
cccttttaggacagagaagggaatccttcataaatggatatctaggtttgatgtatggccttacctggagaagttcactgaggtaacctcttttg
tccccttggaaattgcctttttgttgctgatgttttctgctagtgtgcttaaatacggagtgttaactagtcacttgctagcgtttgcaatagcaac
gggaaaagaaaggattttttgctagtttgaagtctgcctccaagaaaaattatattaaaagtttatggctagtggaaacatcagtcattcatga
ccttattctatgcccaagttgtttaagttgaaagtaatttggccaactatgcaaatgggagaacgtgtagccaactattgtgtttgccgaca
tgttgatatacttttttggtcctgatttatatttgttggtttgtcatactggatgaagcaattctcatgtttttctgcttatatatattggaaga
agagatacttgtcgtttcatcattttttctcgacctctctattaccaacacttttgccaatttaattcagatttcattatcaccagtacttatcaagagat
gcaagtgaaatgaccgctgagctccagggaaagccagatctgattattggcaactacagtgatggaaatttagttgcctccctttggcatata
aaatgggtgtcacacaggtaggaaatacatgattctttatcttgctagcactaagtcttgaggttatgtatctgaatagaaattttacgctttt
gccttcatttctttttaattatttttccagtgtaccattgctcatgcttggaaaaaacaaagtatcctgattctgacatctactggaaaaagt
ttgagggagaaatatcattttttcatgtcagtttactgctgatctactggcaatgcaaattcagattttcattatcaccagtacttatcaagagat
tgcaggaacgtaagtcattttaatctggtcgtttaaatctgatatttcttcccttagtagtctattcaatccgaatttcagttcagtatatgatg
tcatcggttgaggaactgtgattggtaaccttatcaaatccgtagctgctctataatttatttcgtaattggagaaacaattttttttattattg
agcttgtagtctgagctagaatttggttctttatctatcaagtagcataatactacaactattttttatgtgtggcaatttgcaatttcaattt
tctatttctataagttgcagcttttcttcctgttctgatcatatttacatggctgaaactcaatagaaaactaggctagttgatcaaaagtagt
tggatgcttaaaattagtagacgttttgctaaatgagtgaccaatgttattaaaaaacgttcatgtttctcaaccctttgcaacctttgaccactttga
ccactgcccaagattttggataagtacatgcagtgcttataattataaagcattttatcccaccttgttttcattatgaaaattaagtaattt
acgagtatttgtataagttacttcataaattagaagtaaatctggattgtgtaaagttattcgcccgtatatactgaaagctacttgaacaag
caaaaaaacagacaaacgtaacattctccatggattaatgagacttgtatatatatatatatatgtaaagagagagagagagagatttgg
cttgtaaccacatgtatattatgccatatggatgtgacattgatttgtgactagacctaaatgtttttgtttcaatgtccacgggagtttacgtag
agttaagaggagaagagagtgaggaatactaatgttttgatgtaccccttggcttcttgacctggatactcagtgttcttattcatgcctatac
tttggtcctgattttcattctccctttttctagctttgagctgcatcaaagaaattccactgtaaaaaaaataatgctcaccatattggtgcaaca
tggcaaacatgtatcctatttgatgatcaatcaacttatttttctcctgttaattgacctcagtgtgtaactctctatgtatgatagcattgt
aacttgtgtcatgattcataaatagggtactagaattggatggttgacatagtaaatggtcaattgatgatccacaaaatatgcacctactgat
taaaatgtgatagggcaggtttattttttgttgtggttaacacagtcttaacccctatatttaatacaatttggcttatctacaatcttttctt
cagtgtttatgcgaattccttattgcacaacaatattgtctttctgagttctattctgttgttgcttacactttattattccagtaacataga
tgtgaagacattagattggttgcttgcaaattgatagccacttgtttcaggaagaatactgttggtcagtacgagagccatactgcattcaccc
tcccgggactatatcgcgtcgttcatggcattgatgttttcgatcccaaattcaatagtgtcctggagctgacatgacaatttattccc
atattctgacaaggaaaaagactaacgtctttgcatggctcgattgaaaagttgttatttgatcctgcgcagaatgaagagcatatgtaagtg
gcatccgtttgtactaatttttttgaatagatgacatatttttgcatgaatatgaaaaggagggtctgatatgatttttctatagataaact
accaatgatatttttaaaaactcctggatactgtattaggaagaagaagaaccaggggtagatggcattagaatccttaaatcttgaagag
tcgtcactaacgctcccaacacttctgcctcagacccctcaactaaatactattattgttgatttctttggagaagctataagaatctctctc
cttatggtgaaaattttacttggctttatacttaacttccaaggctccctcttataaaatgcaaaaactgtctgtattcactctcttggttaac
aattgatccaatcaaatgcatatgaacatctttctttacgtttcttctaaagttcgtttgaggataaggagtagaatctgagaagatagacta
gtaggtaaccttagggacggatgtggaaattaacatatggctcagctttctgccgagtgcagaccatgtatatgcgttaaaaaattcactaa
```

```
                                    SEQUENCE LISTING acaagtaaatgtttgattttgaacccagtaaatcaaatgagttgtggtagaatctcgaactcgaaccgataaagttcaaatccaggatccgctt
ttaggtaaactctaccttgggaagtgttatatatatgtccctgattatttcttttccgtttccttttctattttaatttttaaagttattttta
gatggttttattttttgataagtggtaagttgttaatattccaaattaaatgccattgtcataactatatacatttataaagaatgattgatcc
tagtttctcattcctaagatccaaataaggcaataaacaatgtcttagtaattggacctgcttctggtgatcaacgcttgatcgcgtagttagt
tatagatgactgtaaaaactttaaccatttaatggttttgtcaaagaacaaatatcggacatatatagagaatggactattgtactttgctt
ctgattggtcattttattgtgatccgtaaattggctgtgactgatgtcatatctttgcttacagaggtaatctgaatgataaatcaaacccat
aattttttcaatggcaaggctagaccatgttaagaacattacgggactagttgagtgctatgctaaaaatgccacattgagggaattggcgaac
cttgttgtagtagctggatacaacgatgtaaagaaatccagtgatagagaagaaataacagaaattgagaagatgcatgctcttattaaggagc
ataaattggatgggcaattcagatgggtatcagcccaaacaaaccgggcacgtaatggtgagctctatcgctatatagctgaccagagaggtat
atttgttcaggtatgctatttgtattgtattagtccaatttcatttttgcaccaaaagaaaggttgttattgtgacgtatatgtttgtttag
cctgcattttatgaagcatttggactaacggtggttgaagctatgacttgtggtcttccaacatttgcaacttgccatggtggtcctaatgaga
tcattgaaccggtgtatctgggttccatattgatccttatcatcccgataaagctgctgaactcatgtcagaattcttcaacgctgcaaaca
agatcctactcactgggaaaaaatatctgcatctggtctccgaaggattcttgagaggtctgtagttgtgtacatgtatagaagattaaagaat
gctacctgatatttatttgaatcaaaaataacaggaacatctcttttttgaacatcactcaagttcttatattaaataattttaggtatacg
tggaagatttactccgagaggctgatgactttatctggcgtatatggttctggaagcttgtttcaaaacttgagaggcgtgaaactagacgat
accttgagatgttctacattctcaaattccgcgagttggtgagtgccttttagctccttttcagttccaataaactatatatgtggtttaagta
agtattaagcataaacatgtccgtgcttggggctgtcgaaaatgctatggacatatcctgagctaaggattttcaagaaaattgatgttagct
ttactctatttacaggcaaaatctgtacctctagcaattgatgacaagtga SEQ ID NO: 39: Polypeptide sequence of NtSUS3-S
MANPKFTRVPSMRERVEDTLSAHRNQLVALLSRYVAQGKGILQPHHLIDEFNNAVCDDTACEKLKDGPFSEVLKATQEAIVLPPFVAIAVRPRP
GVWEYVRVNVYDLSVEQLTVPEYLHFKEELVDGEGNNHFVLELDFEPFNASVPRPSRSSSIGNGVQFLNRHLSSIMFRSKDSLDPLLDFLRGHC
HKGNVLMLNDRIQRISRLESALSKAEDYLSKLSPDTSYNEFEYALQEMGFERGWGDTARRVLETMHLLSDILQAPDPSTLETFLGRLPMVFNVV
ILSPHGYFGQANVLGLPDTGGQVVYILDQVRALEAEMLLRIKQQGLNFKPRILVVTRLIPDAKGTMCNQRLERISGTEYSHILRVPFRTEKGIL
HKWISRFDVWPYLEKFTEDVASEMTAELQGKPDLIIGNYSDGNLVASLLAYKMGVTQCTIAHALEKTKYPDSDIYWKKFEEKYHFSCQFTADLL
AMNNSDFIITSTYQEIAGTKNTVGQYESHTAFTLPGLYRVVHGIDVFDPKFNIVSPGADMTIYFPYSDKEKRLTSLHGSIEKLLFDPAQNEEHI
GNLNDKSKPIIFSMARLDHVKNITGLVECYAKNATLRELANLVVVAGYNDVKKSSDREEITEIEKMHALIKEHKLDGQFRWVSAQTNRARNGEL
YRYIADQRGIFVQPAFYEAFGLTVVEAMTCGLPTFATCHGGPNEIIEPGVSGFHIDPYHPDKAAELMSEFFQRCKQDPTHWEKISASGLRRILE
RYTWKIYSERLMTLSGVYGFWKLVSKLERRETRRYLEMFYILKFRELAKSVPLAIDDK SEQ ID NO: 40: Polynucleotide sequence of NtSUS3-T
atgtttacatggctgaaactcaatataaaaaacaagggtaggtagtcaaaatcgttggatgcttaaaatcagtagacgttttgctaaatgagc
gaccaatgttattgaaaacgttcatgttttcaaccctttggcatacattttgagcattgcccaagattttggataagtagatgcagtgcttata
attttaaagcattgtatcctgccttgtttttcattgtcaaaattaattaacttacaagtatttctataagttgcttcataaattagaagtaaat
ctggattgtgtaatgttattcgcctcgtaaatactgaaagctgcttgaacaagtgaaaaaacacagacaaacgtaacattctccatggattgat
gagacttgtaaaatacatatatagaaatttggcttgtaaccacatgtatattatgccatatggatgtgacattgatgtgactagacctaaatgt
tttgtttccatgtccactggagtttacgtatagttaagagggaaaagactgaggaataatgtatgatgctaccccttcgtcttgacc
tggatacccagtgttcctattcatgcctataacttggtccttgatttcactctcccttttctaacttgagctgcatcaaagaaatttccactgt
aaaaaaataaataatgctcaccatatctctgcaacattgcaaacatgtatcccatatgattgatattggtgcgacatggcaaacatgtatccta
tttgatgatcaatcaaatttattttttcccctgtcaaaatgacctcagtgtgtaattcctatgtatttgatagcattgtaactcgtgtcatgat
tcatgaataggggtactagaattgcatggttgacaaatattaactggtgatgatcccacaaaacatgcacttactgactaaaatgtgatgg
gacagatttattttttgtttgtgattaacacagtacttaacccctatacttaatacaattttggcctagctacaatctttttcttcagtgcaaattcc
ttgttacacgaccaatattgtctttctgagttctattctgttgttacttacactttttattattcgaataagacatttagattgcttgcatgcaaa
ttgatagccacttgttcaggaagaatactgttggtcagtacgagagccatactgcattcaccctcccaggactatatcgcgtcgttcatggca
ttgatgttttcgatcccaaattcaatatagtgctctcctggagctgacatgacaatttacttcccatattctgacaaggaaaaaagactaacgtc
tttgcatggctcgattgagaagtgttatttgatcctgcgcagaatgaagacatatgtaagtgacatccatttgtacttatttttaattggaa
tagatgacatacttatttgcatgaatataaactgacaacccagagatttcctacattagaaaaggagggtctgatatgatttctacaaataaa
ttcccagtgatattgttcaaaaagtcctggatactttattgagagaaccagggatagatggcactagaatcccttaatcttgagaagtcgcc
acttatcgctcccaacactttctgagacccctcaagtaactactattgtttgataacttggagaagctataagaatcttttttctccttattg
taatttttttacgtgactttaaacttaacttccaagctccttctgataaaatgcaaaaactgtctgtattcactgtcttggtttattaacaat
tgatccaatcaaatgcatatggaacatctttcttttttgttcttcaaaagttcgtttgaggataaggagtagaatctgagaagatagactagta
ggtaaccttaggggcggatgtagaaatcaacgtatggttcagctttgttgcagaccctgtatatgcattaaaaaaatcactaaataagtaaat
aattgattttgaacccagtaaatcaaaatgagttgtagtagaatctcgaactcgaaccgataaagttggatccactaccgggtaaactctacct
tgagaagtgtttatatatgtccctaattattttctttttctgtttccttttctattttaatttttaagttccttttttagatggtttatttttga
caagtggtaagtgttagtattccaaattaaatgccattgccataactatatacatttataaagattgattgacccagtttctcattcctaag
atccaaataaggcaataaacaatgtcttagtacttgaacctgcttctggtggtcaacacttgatcgcgtagttagttatagatgactgtaaa
aaccttaatcattttaatggttttgtcaaagaacaaatatcggacatatatagagaatggactattgtactttgcttctgattggtcattttta
ttgtgatccgtaagttggctgtgagactgatgtcatatctttgcttacagaggtaatctgaatgataaatcaaacccataatttttttcaatgca
aggctagaccatgttaagaacattacgggactagttgagtgctatgctaaaaatgccacattgagggaattggctaaccttgttgttgtagctg
gatacaacgatgtaaagaaatccagtgatagagaagaaatagcagaaattgagaagatgcatgctcttattaaggagcataaattggatgggca
attcagatggatagcagcccaaacaaaccgggcacgtaatggtgagctctatcgctatatagctgacaagagaggtatatttgttcaggtacgc
tgtttgtattgtatttgtccacatttcctttttttgcaccgaaaagaaaggttgttattgtgacatatatgttttttagcctgcatttttatgaa
gcatttggactcacggtggttgaagctatgacttgtggtcttccaacatttgcaacttgccatggtggtcctgaacggatcattgaacacggtg
tatctgggttccatattgatccttatcatcccgataaagctgctgaactcatggcagaattcttcaacgctgcaaacaagatcctactcactg
ggaaaaaatatctgcatctggtctccgaaggattcttgagaggtttgtagttgtgtacatatatagaagattaaagattgttcccttgatatta
tttgaatgaaaataacagtaacatctcttttttgaacatcgctcaagttcttgtgttaaataattgttaggtatacgtggaaaatttactccga
gaggctgatgactttgtctggtgtatatggtttctggaagcttgtttcaaaacttgagaggcgtgaaactagacgatacccttgagatgttctac
attctcaaattccgcgagttgtgagtgccttttgcctcatttttcagttacaatcaactatatatgtggtttaaatacgtattaagcataaaca
tgtccgtgattgcgctgtcgaaaatgctatggacatatcctgagctaaggagttttcaagagaattgatttggcttactctgtttacaggcaa
aatctgttcctctggcaattgatgacaagtga SEQ ID NO: 41: Polypeptide sequence of NtSUS3-T
MFTWLKLNIKNKGRKNTVGQYESHTAFTLPGLYRVVHGIDVFDPKFNIVSPGADMTIYFPYSDKEKRLTSLHGSIEKLLFDPAQNEEHIGNLND
KSKPIIFSMARLDHVKNITGLVECYAKNATLRELANLVVVAGYNDVKKSSDREEIAEIEKMHALIKEHKLDGQFRWIAAQTNRARNGELYRYIA
DKRGIFVQPAFYEAFGLTVVEAMTCGLPTFATCHGGPNEIIEHGVSGFHIDPYHPDKAAELMAEFFQRCKQDPTHWEKISASGLRRILERYTWK
IYSERLMTLSGVYGFWKLVSKLERRETRRYLEMFYILKFRELAKSVPLAIDDK
```

SEQUENCE LISTING

SEQ ID NO: 42: Polynucleotide sequence of NtSUS4-S
atggcggaacgtgtgctgactcgtgttcatagccttcgtgaacgtcttgatgctactttggctgctcatcgcaatgagattttgctgtttcttt
caaggtatagtcttagcagattgttctttgatttagttgttattgccagttctaatgtatgggcttatatataaacaaagtgttgaagtatgca
accatataaactgacagcttaaaatgcttgagagaacacacttttatttatttaattatgccttcagcacaagaagtggaacttgacgcaatgg
aaccataggtcacgggttcaagtcttggaacagcctgcaatctaaggctgcgtgtagtagacccctagtggtccggcccttccacatatctcgct
tagtgtaccgggcccattgagtacgggttcggccgaacccagtcgctttggtccaatccatatatttgtcttaaaaatatattgaatatataca
aattgttaatttagtttaaatatgtgtatcatgggttattcatgctggtttttggctgttgcaggattgaaagccatggaaaagggatactgaaa
cctcaccagttgctggctgaatttgattcaattcacaaagaagacaaaaacaaactgaatgatcatgcttttgaagaagtcctgaaatccactc
aggtatttgtggttttagtgttaggtgatggatagcatttattgttttactaagatcacatatgtgtcagtttgtggctagtatttaaaatctg
gtgtatttttgtcatactaggaagcaattgttttgtcccttgggttgcgcttgccattcgtctgaggcctggtgtgtgggaatacgttcgtgtg
aatgtcaacgctcttgttgttgaggagcttaccgtgcctgagtgtttgcaattcaaggaagaacttgttaatggaacgtaagttttaggttcga
atttgttgatttgttagataacatgttctgaactttttgattaaagttgtgttttttgactgatgcagctcgcacgataacttttgttcttgagtt
ggattttgagcccttcactgcatcatttccaaaaccaaccctcaccaaatcaattggaaatggagttgaattccttaaccgacacctctctgcc
aaaatgttccatgacaaggaaagcatgacccctcttctcgagtttcttcgagttcaccactacaagggcaagtaaacttgtttttcctgtttg
tctatgaatttagtttagttgtttttgctccgcgaaaatttcagtggaaactgatttatgcaaccactgagtgattaatatgttcaaacttaccg
acttctggttttctgtgtagacaatgatgctgaatgacagaattcaggacttaaatactctccaaaatgtcctaaggaaagctgaggaataccct
cactaccctttcccctgaaacttcatactcggcatttgagcacaagttccaagaaattggcttggagaggggttgggggtgacactgcggagcgt
gttctagagatgatctgcatgctcctggatctcctcgaggctcctgactcgtgcacgcttgagaagttccttggtagaattccaatggttttta
atgtggtcatactttcaccccatggttatttcgcccaggaaaatgtcttgggttaccccgacactggtggccaggtgcactgcttatctgtgtt
cggtcttattatctctcttaaaccctactgccacaagtgctgagatgaaccctctttaatttgcaggttgtctatattttggatcaagttcctgc
tttggagcgtgagatgctcaagcgcataaaggagcaaggacttgacatcaaaccgcgtattcttattgttcgtattcccagtaattgtgtttaa
acttatgattatgcaggattttatctgttctaatacagcactcttgcttaaattctcaggttactcggctgctgcctgatgcggttggtaccac
ttgtggtcagaggcttgagaaagtgtttggaacagagcactcacacattcttagggtcccctttaggaccgagaagggcattgttcgcaaatgg
atctctcgcttgaagtctggccatacatggagacattcactgaggtgaagcaagcttttctctattcattttcaatcttccaattggttttg
cagcaatttctgcttgctttgacttccgctaaaacttcggatttttattgcattaggatgtggcgaaagaaattgctgcagaattgcaggctaa
gccagatcttatcattggcaattatagtgagggcaaccttgctgcctccttgttggctcacaaattaggtgtaacacaggtcggcaatgtttgt
gacatgtaatttcatctttgcatttcctttcgtttgcaactaaaagatttaagagttctctctctcttttttttttccgtctactttgccttat
gcagtgcacgatagctcatgctttggagaaaacaaaatatcctgattctgatatctacttgagaaatttgatgaaaaataccatttctcagcc
cagtttactgccgatcttattgcaatgaatcacaccgatttcatcatcaccagtcacttccaggagatagcgggaaggtatttttacatcagtt
tcccactctgattaaattacaatgtatttccctatatgattaaatactgtgtttgatcctaaatcatttctaaattttccagcaaggacactgt
tggacagtacgagagccacatggccgttcacaatgcctggactgtatagagttgttcacggcattgatgtgtttgaccccaaatttaacattgtg
tcaccaggagctgatatgaatctctattttcccatactacgagaaggaaaaagagattgacagcatatcaccctgaaattgaggagctgctgttta
gtgatgttgagaatgacgaacacatgtatgttactaaactagcaatcctgctgcaaaattatggctaattatgtaaacaagtttgtactgaata
gatttgttattcgatcaggtgtgtgctgaagaacaggaataagcctatcatattcactatggtcagattggatcgagtgaagaacttaactgga
cttgtcgagctgtacgccaagaacccacggctaagggagttggttaaccttgtcgtggttggaggagaccgaaggaaagaatccaaagacttgg
aagaacaggcagagatgaagaagatgtacgaacttataaagactcacaatttgaacggccaattccgatggatttcttcccagatgaaccgcgt
gaggaatggcgaactctacaggtacattgccgatactaggggagcttcgtgcagcctgcatttttacgaggctttggtttgactgttgttgag
gccatgacctgtggtttgcctacatttgcaactaatcacggtggtccagctgagatcatcgttcacggggaaatctggtttccacattgatccat
accacggggatcaggcagctgaacttctcgctgatttctttgagaaatgtaagaaagaaccttcgcactgggaagccatttccgagggcggcct
taagcgtatacaggagaagtaagcaaactgctactctttttcatttttgcaaaacctactatgatcattattaagtcatttttgcaaaacctac
ttgctgttgtattgtttgttgcttccttttcactgttctttgagctgaaggtctatcagaaacagtctctctacctttcacaaggtaggggtaa
gatctgcgtgcacgttaccctcctcaaactctacttaattgtgagattacactaggtttgttgttgttgattcttttgctaattaattaaaaggt
acacatggcaaatactcggatcggttgttgacactggctgctgtatatgatttctggaagcatgtttccaagcttgatcgtcttgaaattcg
ccgttatcttgaaatgttctatgctctcaaattccgcaagctggtgagttcattgcttctgcactcctgcaattgatag SEQ ID NO: 43: Polypeptide sequence of NtSUS4-S
MAERVLTRVHSLRERLDATLAAHRNEILLFLSRIESHGKGILKPHQLLAEFDSIHKEDKNKLNDHAFEEVLKSTQEAIVLSPWVALAIRLRPGV
WEYVRVNVNALVVEELTVPEYLQFKEELVNGTSHDNFVLELDFEPFTASFPKPTLTKSIGNGVEFLNRHLSAKMFHDKESMTPLLEFLRVHHYK
GKTMMLNDRIQDLNTLQNVLRKAEEYLTTLSPETSYSAFEHKFQEIGLERGWGDTAERVLEMICMLLDLLEAPDSCTLEKFLGRIPMVFNVVIL
SPHGYFAQENVLGYPDTGGQVVYILDQVPALEREMLKRIKEQGLDIKPRILIVTRLLPDAVGTTCGQRLEKVFGTEHSHILRVPFRTEKGIVRK
WISRFEVWPYMETFTEDVAKEIAAELQAKPDLIIGNYSEGNLAASLLAHKLGVTQCTIAHALEKTKYPDSDIYLKKFDEKYHFSAQFTADLIAM
NHTDFIITSTFQEIAGSKDTVGQYESHMAFTMPGLYRVVHGIDVFDPKFNIVSPGADMNLYFPYYEKEKRLTAYHPEIEELLFSDVENDEHMCV
LKNRNKPIIFTMARLDRVKNLTGLVELYAKNPRLRELVNLVVVGGDRRKESKDLEEQAEMKKMYELIKTHNLNGQFRWISSQMNRVRNGELYRY
IADTRGAFVQPAFYEAFGLTVVEAMTCGLPTFATNHGGPAEIIVHGKSGFHIDPYHGDQAAELLADFFEKCKKEPSHWEAISEGGLKRIQEKYT
WQIYSDRLLTLAAVYGFWKHVSKLDRLEIRRYLEMFYALKFRKLVSFIAFCTPAIV SEQ ID NO: 44: Polynucleotide sequence of NtSUS4-T
atggccgaacgtgtgctaactcgtgttcacagccttcgcgaacgtcttgatgctactttggctgctcatcgcaatgagattttgctgtttcttt
caaggtatagtcttagcagattgttctttgatttagttggtgttatttgccagttctaatgtatggactaatatatgaacaaagtgcgaccatt
tcaactgacaacttaaaatgtttgagagaatacacgttttatttacttaattatggcttgagcataggaagtgtatccttggcgtaactcgtaaag
ttgacctcatgtgacaaggaggtcacggtttcgagccgtggaaacagcctcttgcagaaatgcaggtaaggctgcgtgcaatagatcgcccttc
cacggacccgcgcatagcgggaacttagtgcaccggttgggctgtccttttttatgctcttcagcacaaaaatttagttttaaacatgtgtatcat
ggattattcatgctggttttgccggttgcaggattgaaagccacggaaaaggcgatattgaaacctcaccagttgctggctgagtttgaatcaat
tcacaaagaagacaaaaacaaactgaatgatcatgcttttgaagaagtcctgaaatctactcaggtaatttgtggttttagtgttaggtgatgg
atagcatttattgtcttactaagatcacatatgtgtcagtttgtggctagtatttgaaaagtctggtgtggtttgtcatactaggaagcaattg
tcttgtcccttgggttgcgcttgccattcgtctgcggcctggtgtgtgggaatatgttcgtgtgaatgtcaatgcacttattgtcgaggagct
gactgtgcctgaatattgcaattcaaggaagaacttgttaatggaacgtaagttttaggttcgaaatgatgattttgttaaataatatgttctg
aacttttttgattaatgttgtgtttttccctgatgcagctcgaacgataacttgttcttgagctggattttgagcccttcactgcatcatttcc
caaaccaaccctcaccaaatcaattggaaatggagttgaattccttaaccgacacctctctgccaaaatgttccatgacaaggaaagcatgacc
cctcttctcgagtttcttcgagttcatcactacaagggcaagtaaacttgttttcctgtttgtctatgaatttagtttctgaaagttgcttt
gcttcgtgaattttttagtggcaactgattctatgattttctgtgcagacaatgatgctgaatgacagagttcaggacttaaaacactctccaaaa
tgtcctaaggaaggctgaggaatatctcactaccctttcccctgaaacttcatactcggtatttgagcacaagttccaagaaattggcctagag
aggggctggggtgacaatgctgagcgtgttctagagatgatctgcatgctcctggatctcctcgaggctccagactcatgcactcttgagaagt
tccttggtagaattcctatggtttttaatgtggtcattctttcacctcacggatatttcgcccaggaaaatgtcttgggttaccccgatactgg
tggccaggtgcactgcttatttgtaacaccttacgcttttccctctgaaacttatttgcggcaagttctaaggtcctcctcttaatttgcag
gttgtctatattttggatcaagttccggccttggagcgtgagatgctcaagcgcataaaggagcaaggacttgatatcaaaccgcgtattctta
ttgttcgtatctccaataattgcgtttaaacttatgattgtgcaggatttgatctgttcaaatctaatgactgattttcttttttttttttttt

SEQUENCE LISTING

```
tccctcaggttactcggctgctgcctgatgcggttggtaccacttgtggtcagcggcttgagaaagtgtttggaacagagcattcacatattct
tagggtccccttaggaccgagaagggcatcgttcgcaaatggatctctcgctttgaagtctggccttacatggagacattcactgaggtgaag
caagctttctctattcatttttcaatcttccaatctgttttggcagcaattttttcacttactaacactttggctttcgctaaaacttcggattt
tattacattaggatgtggcaaaagaaattgctgcagaactgcaggcaaagccagatcttataatcggcaactacagcgagggcaaccttgctgc
ctccttgttggctcacaagttaggtgtaactcaggtctgtaatgtttgtcacctgttatttcaactttgcatttcctttcatttgcaactagaa
gttaagagttctctctcttttatcttttccgtctattttgccttctgcagtgcaccatagctcatgcgttggagaaaacaaaatatcctgattc
tgatatctacttgaagaaatttgatgaaaaataccatttctcagcccagtttactgccgatcttattgcaatgaatcacaccgatttcataatc
accagcacttttccaggagatagcgggaaggtattacatcacaatggatttccgatatgattaaattagttaattttaatcctacttcattgtgtt
tgatcctaaaacttttctaaatttcccagcaaggacactgttggacagtacgagagccacatggcttcacgatgcctggattgtatagagttg
ttcacggcattgatgtgttcgatcccaaattcaacattgtgtcaccaggagctgatatgaatctctatttcccctacttcgagaaggaaaagcg
attgacagcatatcaccctgaaattgaggagctgctgtttagcgatgttgagaatgacgaacacatgtatgttactaaactagcaatcctgctg
caaaattgtggctaattatgtaaaaaagttttttactgaatagattttgtgcttctatcaggtgtgtgctgaaggacaggaataagccaattatat
tcaccatggctagattggatcgagtgaagaacttaactggacttgtggagttgtacgccaagaacccacggctaagggagttggttaaccttgt
cgtggttggtggagaccgaaggaaggaatccaaagatttggaagaacaggcagagatgaagaagatgtatgaacttataaagacgcacaattta
aacggccaattccgatggatttcttcccagatgaaccgcgtgaggaatggcgaactctacaggtacattgccgatactagggggagcttttgtgc
agcctgcattttacgaggcttttggtttgactgttgactgccctgtggtttgcctacgtttgcaactaatcacggtggtccagctga
gatcatcgttcacgggaagtctggttttcacattgatccataccacgcgagcaggcagctgaacttctagctgatttcttttgagagatgtaag
aaagaaccttcacactgggaagccattccgagggcggccttaagcgtacaggagaagtaagcaagctgctactcttttcatttttgcaaaa
cctaccatgatcattattaagctcatttttgcaaaacctacttgttattcttgttgcttccttttccctgtttttgagccgaggttttatcg
aaaacatgcttctaccttcacaaggtagggggtaaggtctgcgtttgttattattgttgttgttgattcttcgcgaattaattaaaaggtacac
atggcaaatctactcggatcggttgttgacactggctgctgtttatggattctggaagcatgtttccaaacttgatcgtcttgaaattcgtcgt
tatcttgaaatgttctatgctctaaaattccgcaaactggtgagtttcactgcttttctgcactcttccaattgttagttgagtgcactcattta
aactgtagctaaagctgttgtaaatcttcagttaagcagctgctaatgaagtttttatcttttgtttttggttcaggctgaagctgtcccgttg
gctgttgagtaa
```

SEQ ID NO: 45: Polypeptide sequence of NtSUS4-T
MAERVLTRVHSLRERLDATLAAHRNEILLFLSRIESHGKGILKPHQLLAEFESIHKEDKNKLNDHAFEEVLKSTQEAIVLSPWVALAIRLRPGV
WEYVRVNVNALIVEELTVPEYLQFKEELVNGTSNDNFVLELDFEPFTASFPKPTLTKSIGNGVEFLNRHLSAKMFHDKESMTPLLEFLRVHHYK
GKTMMLNDRVQDLNTLQNVLRKAEEYLTTLSPETSYSVFEHKFQEIGLERGWGDNAERVLEMICMLLDLLEAPDSCTLEKFLGRIPMVFNVVIL
SPHGYFAQENVLGYPDTGGQVVYILDQVPALEREMLKRIKEQGLDIKPRILIVTRLLPDAVGTTCGQRLEKVFGTEHSHILRVPFRTEKGIVRK
WISRFEVWPYMETFTEDVAKEIAAELQAKPDLIIGNYSEGNLAASLLAHKLGVTQCTIAHALEKTKYPDSDIYLKKFDEKYHFSAQFTADLIAM
NHTDFIITSTFQEIAGSKDTVGQYESHMAFTMPGLYRVVHGIDVFDPKFNIVSPGADMNLYFPYFEKEKRLTAYHPEIEELLFSDVENDEHMCV
LKDRNKPIIFTMARLDRVKNLTGLVELYAKNPRLRELVNLVVVGGDRRKESKDLEEQAEMKKMYELIKTHNLNGQFRWISSQMNRVRNGELYRY
IADTRGAFVQPAFYEAFGLTVVEAMTCGLPTFATNHGGPAEIIVHGKSGFHIDPYHGEQAAELLADFFERCKKEPSHWEAISEGGLKRIQEKYT
WQIYSDRLLTLAAVYGFWKHVSKLDRLEIRRYLEMFYALKFRKLAEAVPLAVE SEQ ID NO: 46: Polynucleotide sequence of NtSUS5-S
```
atggcctcaacagttgctgatagcatgcctgatgctttgaaacaaagccggtatcatatgaagagatgcttcgctaggtgaacacccttctttt
atgttttttcccctctacgtgtttatgtcaaatttccatgcataatgctaactacttttcttcttttgacttcaaaattggatgtgaaaggtt
cattgcaatgggaaggaggctaatgaagttgaaacatttaacagaagaaatagaagaaactattgaagacaaggcagaaagaaccaggatttg
gagggttcacttggaaaaattatgagttccacacaggtcagcaccatttaaccaacttagttgaacaggaaaaaagaaaaagcaaaagaagtta
ttgcaaggcgtaacgattttctttgaaattttcaggaggcagctgttgttccacctatgttgctttgtcagtaaggcacaatcctggcttctg
ggattatgtcaaagttaacgctgaaactctctctgtggaagctatttcagccagggaatatctcaaattcaaagagatgatctttgacgaagac
tggtaagtggaaaattgtatcattttaaagagaaacaattttgtaacatacaagaatagttttgatggttgaatgtgcaagcagggcaaaggat
gataatgcactggaagtagattttggtgcttttgactactctaatcctcggttccttcctcttctgtcgggaaatggggtcaactttatct
caaaagttctgtcttcaaagtttggtggaaagccagagttacgcccagcctttgcttgattacttactagctcttaatcatcaaggagaggtatg
aaaatggactacctttgttttcttaaaggtattatataatgatgcgcgttataaagttccttttttaaattgaaacttcagaatctaatgatca
atgagaatctgaatggtgttgctaagcttcaagcagcattgatagtagctgaagttttgtatcttcctttccaaagacacaccttataaga
ctttgagcataagtaagcttctcatatgcttccattgtcatatgcagcatgctaccgaaaagttgtttatgtttgtgacttga
ttatgaaaactctaggctcaaagaatggggcttttgataaagggtggggtcacaatgcaggaagagtaagagagacaatgagactgcttccgag
ataatccaagcaccagatcccataaaatgggagtcctttttcagcaagcttcctactacattcaacattgttatcttctccattcatggttact
ttggccaagcagatgtcctcggtctgcccgatactggaggccaggtctacatatacagcaatttatctccttttgcctcatattgcttattagc
gacacttgcatcattgaaatcagacttttactcacaggttgtttatattctgatcaagtaagggcttagaggaggaaatgttacaaagaat
caagcagcaagggctaaacgtgaagcccaagattcttgtggtgagttttgcaaaaatatgcttagacaggttttgagattgatcggagaaggga
ttaagatgatcaagatctttgtttcctgctttcatgatgtaaacaggtatctcgtctcataccagatgctcgagggacaacatgcaatcaggag
atggaacctattcttaactcatcccattctcacatcctgagaattccattcaggactgagaaaggagttcttcgccaatgggtttctcggtttg
atatctatccttacttggagaactatgccaaggcaagtcttctaacaaaattaccacctattcatacactttatttacttttcttgaactaatcg
tttggtttgtgacgtatatcattaggatgcttctgctaagatacttgagctcatggaaggtaaaccagacctcataattgggaactacactgt
ggaaatttagtggcatctctattggccaacaaacttggagttactcaggttccgtagctgatcatatgatcatatttttctacattgtttcttga
taattaaatggaaatcttattggatgataacattttagggaaccattgctcatgcattagagaaaactaagtatgaagattctgatgtgaagtg
gaagcagtttgatcccaagtaccacttttcttgccaatttactgccgatttattggcaatgaatgctgctgatttatcattaccagcacatat
caagaaatcgctggaaggttagcactgactctctcagtatatttggcaacttaatgaatttactgatggccaacactaaaagctatcattcg
tccttcagcgaaactaggcctggacaataatgaaagtcacacagcatttaccatgccggggcttcatagagctgtttcaggcatcaatgtatttg
atccaaagttcaacattgctgctcctggggctgaacagtctacctatttcccttcactgagaaacagaaacgattcagcacatttcgtcctgc
tattaacgaattacttttacagtaatgaggaaaacaatgagcacatgtaagtctaattgcccatttcctaatctaaccattgcttaaatcgttc
tgttttaccggatgtgtggtacttatcagtaacattttttttggatcagtggatttcttgcagaccggaaaaaaccaattatattttcaatg
gcgagatttgatacagtgaagaacctgtcaggcttgactgagtggtatggggaagaataagaagttgcggaacttgtaaaccttgttattgttg
ggggattcttcgatccatcaaaatcaaaagaccgggaggaagcagctgaaatcaagaagtgcatgaattgattgagaaataccagctcaaggg
acaaatgagatggataagcagctcaaactgataaatatcgaaatagtgagctataccgaactattgctgacactaagggagcttttgtccaacg
gctttatatgaagctttggactaaccgttattgaagcaatggattgtgattgcctacgtttgcaactaatcaaggtggacctgcagaaatca
ttgttgatgggtttcaggtttccatattgatccttacaatggggacgaatcaagcaagaaaatagctgatttcttgagaagtgtaaggttga
ttctaaatattggaacaggatatctggaggaggtctcaagcgcattgaagatgtgaaaaatagttccaagtttaaaaatgaaaaatgc
ttatcatgttatattttcgtgtttaagttctgcttcgatgcagttatacgtggaagatttatgcaaacaaagtgttgaatatggatcaatc
tatgattttggagacaattcaatgtggggcaaaagcaggctaagcaaagatactttgagatgttttacaatcctctcttcaggaaattggtag
gttgtatatgttgaatacaatttactaagatcctcaaaatgaccaagaaatatacattgactatgctacttttgtaatttcacaggccaaagc
gtgccgatcccacatgaagagccattgccacttgcaacatcagactctactcaatcccaagaattaaaaactaccactaccagttccagcagcag
tagctaaagttctgccattaacaaggcatgcttttaacttaattacttctctacctagagtaactggtaaagtggatgtcaagtga
```

SEQUENCE LISTING

SEQ ID NO: 47: Polypeptide sequence of NtSUS5-S
MASTVADSMPDALKQSRYHMKRCFARFIAMGRRLMKLKHLTEEIEETIEDKAERTRILEGSLGKIMSSTQEAAVVPPYVAFAVRHNPGFWDYVK
VNAETLSVEAISAREYLKFKEMIFDEDWAKDDNALEVDFGAFDYSNPRLALSSSVGNGLNFISKVLSSKFGGKPEDAQPLLDYLLALNHQGENL
MINENLNGVAKLQAALIVAEVFVSSPPKDTPYKDFEHKLKEWGFDKGWGHNAGRVRETMRLLSEIIQAPDPINMESFFSKLPTTFNIVIFSIHG
YFGQADVLGLPDTGGQVVYILDQVRALEEEMLQRIKQQGLNVKPKILVVSRLIPDARGTTCNQEMEPILNSSHSHILRIPFRTEKGVLRQWDAS
AKILELMEGKPDLIIGNYTDGNLVASLLANKLGVTQGTIAHALEKTKYEDSDVKWKQFDPKYHFSCQFTADLLAMNAADFIITSTYQEIAGSET
RPGQYESHTAFTMPGLYRAVSGINVFDPKFNIAAPGAEQSTYFPFTEKQKRFSTFRPAINELLYSNEENNEHIGFLADRKKPIIFSMARFDTVK
NLSGLTEWYGKNKKLRNLVNLVIVGGFFDPSKSKDREEAAEIKKMHELIEKYQLKGQMRWIAAQTDKYRNSELYRTIADTKGAFVQPALYEAFG
LTVIEAMDCGLPTFATNQGGPAEIIVDGVSGFHIDPYNGDESSKKIADFFEKCKVDSKYWNRISEGGLKRIEECYTWKIYANKVLNMGSIYGFW
RQFNVGQKQAKQRYFEMFYNPLFRKLAKSVPIPHEEPLPLATSDSTQSQELKLPLPVPAAVAKVLPLTRHAFNLITSLPRVTGKVDVK SEQ ID NO: 48: Polynucleotide sequence of NtSUS5-T
atggcctcaactgttgctggtagcatgcctgatgctttgaaacaaagccgatatcatatgaagagatgcttcgctaggtgaacaccttcttgt
tctttttgtttttccctctaccatttatgtcaaatttcaatgcataatgctaactacttttttttcttttttgacttcaaaattggacgtgaaag
gttcattgcaatgggaaggaggttgatgaagctgaaacattaacagaagaaatattgaagacaaggcagaaagaaccaagatt
ttggagggttcacttggaaaaattatgagttccacacaggtcagcaccatttaaccaacttaattgaataggaagaaaaaaaagcaaaagag
ttattgcaaggcgtaacgatttcctttgaaattttcaggaggcagctgttgtcccacctatgttgcttttgcagtaaggcacaatcctggctt
ctgggattatgtcaaagttgacgctgaaactctctctgtggaagctatttcagccagggactatctcaaattcaaagagatgatctttgatgaa
gattggtaactggaagattgtcattttaaagaaacaattttttaatattagttttgatggttgaatgtgcaacgcagggcaaagga
tgaaatgcactcgaagtagatttttggtgcttttgactactctaatcatcggttagccctttcctcttctgtcggaaatgggctaaacttcatc
tcgaaagttttgtcttcaaagtttggtggaaaggcagaagatgcccagcctttgcttgattacttactagctcttaatcatcaaggagaggtat
ggaaatggactaccttcctttcttaaggaattatataatgatgtatgttataaagatcctttttaaacattgacactttgcagaatctaatgat
caatgagaatctgaatggcgtctctaagcttcaagcagccattgataagtagctgaagttttttgtatcttccttccccaaagacacactttataaa
gactttgagcataagtaagcttttcaaacgcttctgttatcatatgcaatataccaagaatatgttgcctttgaaaagttgtttatgtttatg
acttgataatgaaaatactaggctcaaagaatggggctttgagaaagggtgggtcacaatgcaggaagagtaagagagacaatgagactgctt
tccgagataatccaagcgccagatcccataaatatggagtccttttttcagcaggcttcctactacattcaacattgttatcttctccattcatg
gttactttggccaagcagatgtccttggttttgcccgatactggaggccaggtttacatacacagccaatttatctccttttgcctcatatttact
tattagcgacacttgcattattgaaatcacattttgtatttaacaggttgtttatattctggatcaagtaagagccttagaggaggaaatgttac
aaagaatcaagcagcaagggttaaatgtgaagcccaagatcttgtggtgagttatgcaaaaatatgcgtagcaaggtttttgaaattgttcag
agggattaagatgatcgagatatttgtttccttcttccattgatgtgtacaggtcactcgtctcattccagatgctcgagggactacatgcaa
tcaggagatggaacctatacttaactcgtcccattctcacatcctgagaattccanttcaggacagagaaaggagttcttcgccaatgggtttct
cggtttgatatctatccttacttggagaactcatgccaaggcaagtctcctaccaaaattaccacctattcatacactttattcagttttttgag
ctaatcattctcatttgtcacgtatgtgattaggatgcttctgctcaagatacttgagctcatggaaggtaaaccagacctcattattgggaact
acactgatgaaatttagtggcatctctattggccaacaaacttggagttactcaggttctacagctgatcatttatctgatcagattttctac
attgttttcttgataattaaacggaaatcttatgagattgtaacattttagggaaccattgctcatgcattagagaaaccaagtatgaagatt
ctgatgtcaagtggaagcagtttgattccaagtaccacttttcttgccaagtcactgccgattattggcaatgaatgctgctgattttatcat
taccagcacatatcaagaaatcgcaggaaggttagcactgactctctcagtatatttggcaacttaatgaatgtactgcttgtggcaacacta
aaagctattactcgtccttcagcgaaactaggcctggacaatatgaaagtcacacagcatttaccatgccggggctttatagagctgtttcagg
catcaatgtatttgatccaaagttcaacattgctgctcctggggctgaacagtctgcctatttcccccttcactgagaaacagaaacgattcagc
gcgtttcgtcctgctattgaggaactacttttacagtaagtgacaaaacaacgacgtaagtctaattcactgccgcattttcctaatctaacca
ttgcttaaatgttctgttttttacttgatatgtggtacttatcagtgatatttttttattggaacagtgatttcttgcagaccgtaaaaaccaa
ttatatttcaatggcaagatttgatacggtgaagaacttgtcaggcttgactgagtggtatgggaagaataagaagttgcggaacttggttaa
cctcgttatcgttggggggattcttcgatccatcaaaatcaaaagaccgggaggaagcagctgaaatcaagaagatgcatgaattgattgagaaa
tacaagctcaaggggacaaatgagatggatagcagctcaaactgataaatatcaaaacagtgagctatatcgaactattgctgacactaaaggag
ctttcgtccaaccggctttatatgaagctttcggactaactgttattgaagcaatgaattgtggactgcctacatttgctactaatcaaggcgg
acctgcagaaatcattgttgatggggtttcaggcttccatattgatccttacaatggggatgaatcgagcaagaaaatagctgatttctttgag
aagtgtaaggttgattctaaatattggaacaagatatgtggaggaggtctcaagcgcattgaagaatggtaa SEQ ID NO: 49: Polypeptide sequence of NtSUS5-T
MASTVAGSMPDALKQSRYHMKRCFARFIAMGRRLMKLKHLTEEIEKTIEDKAERTKILEGSLGKIMSSTQEAAVVPPYVAFAVRHNPGFWDYVK
VDAETLSVEAISARDYLKFKEMIFDEDWAKDENALEVDFGAFDYSNHRLALSSSVGNGLNFISKVLSSKFGGKAEDAQPLLDYLLALNHQGENL
MINENLNGVSKLQAALIVAEVFVSSPPKDTPYKDFEHKLKEWGFKGWGHNAGRVRETMRLLSEIIQAPDPINMESFFSRLPTTFNIVIFSIHG
YFGQADVLGLPDTGGQVVYILDQVRALEEEMLQRIKQQGLNVKPKILVVTRLIPDARGTTCNQEMEPILNSSHSHILRIPFRTEKGVLRQWDAS
AKILELMEGKPDLIIGNYTDGNLVASLLANKLGVTQGTIAHALEKTKYEDSDVKWKQFDSKYHFSCQFTADLLAMNAADFIITSTYQEIAGSET
RPGQYESHTAFTMPGLYRAVSGINVFDPKFNIAAPGAEQSAYFPFTEKQKRFSAFRPAIEELLYSNEQNNEHIGFLADRKKPIIFSMARFDTVK
NLSGLTEWYGKNKKLRNLVNLVIVGGFFDPSKSKDREEAAEIKKMHELIEKYKLKGQMRWIAAQTDKYQNSELYRTIADTKGAFVQPALYEAFG
LTVIEAMNCGLPTFATNQGGPAEIIVDGVSGFHIDPYNGDESSKKIADFFEKCKVDSKYWNKICGGGLKRIEEW SEQ ID NO: 50: Polynucleotide sequence of NtSUS6-S
atggctactgcaccagccctaaatagatcagagtccatagctgatagcatgccagaggccttaaggcaaagccggtaccacatgaagaaatgtt
ttgccaagtacatagagcaaggaaagaggatgatgaaacttcataacttgatggatgagttggagaaagtaattgatgatcctgctgaaaggaa
ccatgttttggaaggcttacttggctacatattatgcactacaatggtatagctagattcatatgtacttatgatgcccttatattgtttcctg
atgtattactcttaaaaccttctttgatcaaatttacaggaggctgcagttgttcctcccctacattgcctttgccacagacagaatcctggat
tctgggaatatgtgaaagtgaatgctaatgatctttctgttgagggtattacagctacagaatacttgaaattcaaggaaatgatagttgatga
atgctggtatagtatacgttgcagcttatcatacctttttgtggttttataacttcaatcagaaaactcatcagagttaccttctggtgaacatg
aaatgcagggcaaaagataaatcgactcggaaattgatttttggagcagtagactctcaacgcctcgactgaccctatcctcaattggca
atggtctcagttatgtttccaagttctaacttcaaagctaaaatgctacctccgcgagtgcacagtgtctggttgactacttgctcacttgaa
tcatcaaggagatgtacgtcaacaaaaatcaaactccataagtaaacttgtcaactctaagaagaaaaataggaaaagaagattcacgtaaca
aattttcttttatgttcaactgcagaaactgatgatcaatgagacactcagcactgtctcaaagcttcaggctgcactggttgtagcagaagcat
ctatttcctctttaccaacagatacaccatatgagagctttgagctaaggtgatttgtttttttcctctacttccctccacttgtgccatgctac
gtagtactaagtaacttccattcttgtaaagattcaaacagtgggttttgagaaagatgtggggtgatacagctgaaaggtcagcgacaccat
gagaacactgtctgagggctcaggcaccagatccattgaacattcagaagttcttttggaagggttccaactgttttcaatattgtattgttc
tctgtccatggatacttggccaagcagatgttcttggcttgccagacactggtggtcaggtaagcatttaatagcttttacatttaacttcta
tgcattgacaataaaataatttttaacagtttgaccacttctgctcttgttcaacaggtagtttatgttttggatcaagttgtagcttttgaag
aagaaatgctacaaagaatttaaacagcaggggctcaatattaagcctcaaattcttgtggtgagttcctagacaatcgacgtgactatgcaatt
atgtagaggctgtttagaaaagttaatatcatatgttgattgcacagttaacccgactgattccggatgcaaaaggaacaaagtgcaaccagga

SEQUENCE LISTING

```
actagaaccaatcaagaatacaaaacattcacacatcctcagagttccatttaggacagaaaaaggagtgcttaatcaatgggtttcacgattt
gatatctatccatatctggagagatatactcaggtatgtattttttatatcaaccttgctcatcaaagatgtgttgtttcctcaattccatttt
cccctggcaaaaggatgctgctgacaaaatcgtcgagctaatggaaggcaaacctgatctaatcattggtaactacactgatgggaatctagt
ggcttcactaatggctagaaaacttgggataactctggtaactttcttaatcatatttgatgttgcttcttctccaagttagttcttaatctc
cactgacctagaccatcttgcaacagggaactattgctcatgctttggagaagacaaaatatgaagactctgcataaaattgaaggaactcg
atccgaagtaccacttctcttgccaattcacagctgatttgattgcaatgaattcagcagatttcattatcactagcacataccaagaaatagc
tggaaggtaagaattagagctaataagtaatgcattcatatgtatttcagcatcgctcttttcaccatcatcgaatacacaccactactcagtaa
atgtatttgctcaaaagttttgcaacttaatggatctcattcttgaatgcttcaacatatgcagcaaagataaaccaggacagtatgagagccat
agtgcatttaccccttccagggctttacagagttgcttcaggtatcaatgtctttgatccaaaatttaatattgctgcacctgggcagaccagt
cggtgtatttcccttacacagaaaagcagaagcgtttgactgctttccgccctgccattgaggaactgctttttagtaaagtggacaatgacga
gcacgtgtaagtctaagtgttaaacttcagcttagtgcctagaacatcccactgctctatgtattgatgtttcacttgtttcaaacagtggata
tttagaagacagaaagaaacctatcctgtttaccatggcaaggctggacacagtggacaagtctggactaacagaatggtatggcaagaac
aagaggctcagaagcttagttaaccttgttgtggttggtggttcctttgatcctacaaaatccaaggataggaagaagcagctgaaataaaaa
agatgcacatgctgatagagaaataccagcttaagggtcagattagatggatagcagctcagactgacagatacagaaatagtgaactctaccg
cacaatagcagattccaaaggagcttttgtgcagcctgcattgtatgaagcatttggtctaacagtcattgaggcaatgaactgtggattacca
acctttgctaccaaccaaggtggccctgctgagattattgttagtggggtctcaggctttcatattgatccaaataatgggatgaatcaagca
acaaaattgccaacttttttccaaaaatgcagggaggatcctgagtattggaacaggatttcagtccagggtctaaaccgtatatatgaatggta
actcacagataagccattcaaattgcaaagaggcacatatcttgcagaaaatttcttaatcctaaatcctaatttttgcagttacacatgga
agatctatgcaaacaaggtattgaatatggggtccatctatactttttggaggacattgtacagagatcagaaacaagcaaagcaaagatacat
cgagactttctacaatcttgagtttaggaactggtatagtgctgcatgacatttgacagtataccacaaacatctttatgagatgaattacttt
taataaaaattgtttttaaccttgctccttaatggcacttattgcaggtaaaaaatgtgcctatcagaaaggacgaaacaccacaaggaccaa
aggagagggagaaagttaagccacagatatcacaaaggcatgctctaaagcttttgcctacagttttcaagagaccctagtatatctagtac
taaattagaattatacagcatgcagctttgctgttcacctttctaaatcaccagttgtgtcaatcaagttgacaaaatcaataaattgggatt
ttcccttcctatgcttgattgttattactcctactttgtttatggtagtcttccttcattgttttctcctgtacttcttttactacaactgta
ctgacatactaattttctgtgtgtaccaggcgctcacaatcaaggttgcagaagtaagattagataaaattgctactgcatga
```

SEQ ID NO: 51: Polypeptide sequence of NtSUS6-S
MATAPALNRSESIADSMPEALRQSRYHMKKCFAKYIEQGKRMMKLHNLMDELEKVIDDPAERNHVLEGLLGYILCTTMEAAVVPPYIAFATRQN
PGFWEYVKVNANDLSVEGITATEYLKFKEMIVDECWAKDEYALEIDFGAVDFSTPRLTLSSSIGNGLSYVSKFLTSKLNATSASAQCLVDYLLT
LNHQGDKLMINETLSTVSKLQAALVVAEASISSLPTDTPYESFELRFKQWGFEKGWGDTAERVSDTMRTLSEVLQAPDPLNIQKFFGRVPTVFN
IVLFSVHGYFGQADVLGLPDTGGQVVYVLDQVVAFEEEMLQRIKQQGLNIKPQILVLTRLIPDAKGTKCNQELEPIKNTKHSHILRVPFRTEKG
VLNQWVSRFDIYPYLERYTQDAADKIVELMEGKPDLIIGNYTDGNLVASLMARKLGITLGTIAHALEKTKYEDSDIKLKELDPKYHFSCQFTAD
LIAMNSADFIITSTYQEIAGSKDKPGQYESHSAFTLPGLYRVASGINVFDPKFNIAAPGADQSVYFPYTEKQKRLTAFRPAIEELLFSKVDNDE
HVGYLEDRKKPILFTMARLDTVKNTSGLTEWYGKNKRLRSLVNLVVVGGSFDPTKSKDREEAAEIKKMHMLIEKYQLKGQIRWIAAQTDRYRNS
ELYRTIADSKGAFVQPALYEAFGLTVIEAMNCGLPTFATNQGGPAEIIVDGVSGFHIDPNNGDESSNKIANFFQKCREDPEYWNRISVQGLNRI
YECYTWKIYANKVLNMGSIYTFWRTLYRDQKQAKQRYIETFYNLEFRNLVKNVPIRKDETPQGPKEREKVKPQISQRHALKLLPTVFQETLALT
IKVAEVRLDKIATA SEQ ID NO: 52: Polynucleotide sequence of NtSUS6-T
```
atggctactgcaccagccctgaaaagatcagagtccatagctgatagcatgccagaggcctcaaggcaaagccggtaccacatgaagaaatgtt
ttgccaagtacatagagcaaggcaagaggatgatgaaacttcataacttgatggatgaattggagaaagtaattgatgatcctgctgaaaggaa
ccatgttttggaaggcttacttggctacatattatgtactacaatggtatagctagattcatatgtacttatgatgtccttatattgtttccgg
aggcattattcttaaatcctctttgatcaaatttgtaggaggctgcagttgttcctccctatattgccttcgccacagacagaatcctggat
tctgggaatatgtgaaagtcaatgctaatgatctttctgttgagggtattacagctacagattacttgaaattcaaggaaatgatagttgatga
aagctggtatagaatactttgcagcttatcatacctttgtggttttcaatttcaatcagaaaactcatcagagttacctttgtgtgaacatg
acatgcagggcaaaagatgaatatgcactggaaattgatttggagcagtagacttctcaacgcctcgactgacccatcctcttcaattggaa
atggtctcagttatgtttccaagtttctaacttcaaagctaaatgctacctcagcgagtgcacagtgtctggttgactacttgctcactttgaa
tcaccaaggagatgtacgtcaacaaaaatcaaactccataagtaaacttgtcaactctaagaagtaaaaataggaaaagaagattcatgtaaca
aattttctttatgttcaactgtagaaactgatgatcaaatgagacactcggcactgtctcaaagtttcaggctgcactggttgtagcagaagcat
ctatttcctccttaccaacagatacaccataccagagcttttgagctaaggtgatttgttttttcctctacttccttccacttttggtgtgctac
atagtactaagtaacttcaattcttgtaaagattcaaacagtgggggttttgagaaaggatgggtgatacagctgaaagggtccgcgacaccat
gagaacactttctgaggtacttcaggcgccagatccattgaacattgagaagttctttggggagggttccaactgttttcaatattgtattgttc
tctgttcatggatactttggccaagcaaatgttcttggcttgccagacacaggtggtcaggtaagcatctaatagcttttacatttaacttcta
tgcattgacaataaaattaacttctacactaccaaatatttttgaaagtttgaccacttcggctcttgttcaacaggtggtttatgttttggat
caagttgtagcttttgaagaagaaatgctccaaagaattaaacagcaggggctcaatattaagcctcaaattcttgtggtgagctcctagacaa
tgacgtgactatgcaattaagtagaggctgtttagaaaagttaatatcatatgttgattgcacagttaacccgactgattccggacgccaaagg
aacaaagtgcaaccaggaactagaaccaatcaagaatacaaaacattcacacatcctcagagttccatttaggacagaaaaaggagtgcttaat
caatgggtttcacgatttgatatctatccatatctggagagatatactcaggtgtatttttatatcaacctgtctcatcaaagatgtgttgt
ttcctcaattccattttcgccttgacaaaaggacgctgctgacaaaatcatcgagctaatggaaggcaaacctgatctaatcattgtaacta
cactgatgggaatctagtggcttctctaatggctagaaaagctgggataactctggtaactttttcttatcatatttgatgttgtttcttctcca
agttggttcttaatgtcaactaaccccagaccatctttgtaacagggaactattgctcatgctctggagaagacaaaatatgaagactctgacat
caaattgaaggaactcgatccgaagtaccacttttgccgccaattcacagctgatttgattgcaatgaattcagcagatttcattatcacaagc
acatatcaagaaatagccgaggtaagaattggaactacgggaagcagagagctaataagtagtgcactcatatattcagcatcgctcttcg
cataatcgaatacacaccactactcagtaaatatgcttgctcaaaagttttacaagtttatggatcttattcttgaatgcttcaacatatgcagc
aaagataggccaggacagtatgagagccatagtgcatttaccccttccagggctttacagagttgcttcaggcatcaatgtctttgatcctaaat
ttaatattgctgcacctgggcagaccagtcggtgtatttcccttacacagaaaagcagacgcgtttgactgctttccgccctgccattgagga
actgcttttagtaaagtgggacaatgacgagcacgtaagtctaagtgttaaacttcagcttagtgcctagaacattcccactggct
ctatgtattaatgtttcacttgtttcaaacagtggatatttagaagacagaaagaaacctatcctgtttaccatggcaaggctggacacagt
gaagaacacatctggactaacagaatggtatggcaagaacaagaggctcagaagcttagttaaccttgttgtggttggtggttcctttgatcct
acaaaatccaaggatagagaagaagcagctgaaataaaaaagatgcacatgctgatagagaaataccagcttaagggtcagatcagatggatag
cagctcagactgacagatatagaaacagtgaactctaccgcacaatagcagattccaaaggagcttttgtgcagcctgcattgtatgaagcatt
tggtctaacagtcattgaggcaatgaactgtggattaccaacctttgctaccaaccaaggtggccctgctgagattattgttgatggggtctca
ggctttcatattgatccaaataatgggatgaatcaacaacaaaagttgccaacttttttccaaaaatgcagggaggatcctgagtattggaaca
ggatttcagtccagggtctaaaccgtatatatgaatggtaactcacagataagccattcaaattgcaaagaggcacatatcttgctgaaaattt
cttaatcctttaatcctaaaattttgcagttacacatggaagatctatgcaaacaaggtattgaatatggggtccatctatactttttggagga
cattgtacagagatcagaaacaagcaaagcaaagatacatcgagactttctacaatcttgagtttaggaactggtatagtgctgcatgacatt
gacagtataccacaaacatctttatgagatgaattactttaataaaaattgtttttaaccttgctccttaatgacacttattgcaggtaaaa
```

```
aatgtgcctatcagacaggacgaaacaccacaaggaccaaaggagaggagggagaaagttaagccacagatatcacaaaggcatgctctaaagc
ttttgcctatagttttcaggagaccctagtatattctagtactaaattagaattatacagcatgcagcttgcttctgctgttcacctttctaa
atcaccagttatgtcaatcaagttgacaaaatcaataaattcggcttttcccttcctatgcttgattgttattactcctacttcgtttatggt
agtcttccttcattgttttctcctgtacttcttttactacaactgtactga SEQ ID NO: 53: Polypeptide sequence of NtSUS6-T
MATAPALKRSESIADSMPEALRQSRYHMKKCFAKYIEQGKRMMKLHNLMDELEKVIDDPAERNHVLEGLLGYILCTTMEAAVVPPYIAFATRQN
PGFWEYVKVNANDLSVEGITATDYLKFKEMIVDESWAKDEYALEIDFGAVDFSTPRLTLSSSIGNGLSYVSKFLTSKLNATSASAQCLVDYLLT
LNHQGDKLMINETLGTVSKLQAALVVAEASISSLPTDTPYQSFELRFKQWGFEKGWGDTAERVRDTMRTLSEVLQAPDPLNIEKFFGRVPTVFN
IVLFSVHGYFGQANVLGLPDTGGQVVYVLDQVVAFEEEMLQRIKQQGLNIKPQILVLTRLIPDAKGTKCNQELEPIKNTKHSHILRVPFRTEKG
VLNQWVSRFDIYPYLERYTQDAADKIIELMEGKPDLIIGNYTDGNLVASLMARKLGITLGTIAHALEKTKYEDSDIKLKELDPKYHFSCQFTAD
LIAMNSADFIITSTYQEIAGSKDRPGQYESHSAFTLPGLYRVASGINVFDPKFNIAAPGADQSVYFPYTEKQTRLTAFRPAIEELLFSKVDNDE
HIGYLEDRKKPILFTMARLDTVKNTSGLTEWYGKNKRLRSLVNLVVVGGSFDPTKSKDREEAAEIKKMHMLIEKYQLKGQIRWIAAQTDRYRNS
ELYRTIADSKGAFVQPALYEAFGLTVIEAMNCGLPTFATNQGGPAEIIVDGVSGFHIDPNNGDESSNKVANFFQKCREDPEYWNRISVQGLNRI
YECYTWKIYANKVLNMGSIYTFWRTLYRDQKQAKQRYIETFYNLEFRNLVKNVPIRQDETPQGPKERREKVKPQISQRHALKLLPIVFQETLVY
SSTKLELYSMQLASAVHLSKSPVMSIKLTKSINSAFPFPMLDCYYSYFVYGSLPSLFSPVLLLLQLY
```

The invention claimed is:

1. A plant cell comprising:
   (i) a polynucleotide comprising a sequence having at least 90 sequence identity to SEQ ID NO: 1 (NtSULTR3; 1A-S) or SEQ ID NO: 3 (NtSULTR3;1A-T);
   (ii) a polypeptide encoded by the polynucleotide set forth in (i);
   (iii) a polypeptide comprising a sequence having at least 90% sequence identity to SEQ ID NO: 2 (NtSULTR3; 1A-S) or at least 90% sequence identity to SEQ ID NO: 4 (NtSULTR3;1A-T); or
   (iv) a construct, vector or expression vector comprising the isolated polynucleotide set forth in (i),
   wherein said plant cell comprises at least one modification which reduces (a) the expression or activity of the polynucleotide or (b) the expression or activity of the polypeptide, as compared to a control plant cell in which the expression or activity of the polynucleotide or polypeptide has not been modified.

2. The plant cell according to claim 1, wherein the reduced expression or reduced activity reduced the levels of glucose, fructose and sucrose in cured leaf of a plant comprising the plant cell as compared to the levels of glucose, fructose and sucrose in a control cured leaf.

3. The plant cell according to claim 2, wherein the level of glucose is reduced at least about 60% as compared to a control cured leaf; or
   wherein the level of fructose is reduced at least about 60% as compared to a control cured leaf; or
   wherein the level of sucrose is reduced at least about 60% as compared to a control cured leaf; or
   wherein the levels of glucose, fructose and sucrose are reduced at least about 60% as compared to a control cured leaf.

4. The plant cell according to claim 1, wherein the reduced expression or reduced activity increases the levels of free amino acids, glutamine, glutamate and aspartate in cured leaf of a plant comprising the plant cell as compared to the levels of free amino acids, glutamine, glutamate and aspartate in a control cured leaf.

5. The plant cell according to claim 4, wherein the level of free amino acids is increased by at least about 1.5 times as compared to a control cured leaf; or
   wherein the level of glutamine is increased by at least about 1.5 times as compared to a control cured leaf; or
   wherein the level of glutamate is increased by at least about 1.5 times as compared to a control cured leaf; or
   wherein the level of aspartate is increased by at least about 1.5 times as compared to a control cured leaf; or
   wherein the levels of free amino acids, glutamine, glutamate and aspartate are increased by at least about 1.5 times as compared to a control cured leaf.

6. The plant cell according to claim 1, wherein the at least one modification is a genetic mutation in the polynucleotide and the plant is *Nicotiana tabacum*.

7. The plant cell according to claim 1, further comprising:
   (i) at least one modification in a NtSUS polynucleotide or polypeptide encoded thereby,
   suitably, wherein the NtSUS polynucleotide or polypeptide encoded thereby is selected from the group consisting of NtSUS2-T, NtSUS3-S, NtSUS3-T, NtSUS4-S, NtSUS4-T or a combination of two or more thereof,
   more suitably, wherein the NtSUS polynucleotide or polypeptide encoded thereby is selected from the group consisting of NtSUS2-S, NtSUS3-S, NtSUS3-T and NtSUS4-S or a combination of two or more thereof; or
   (ii) further comprising at least one modification in a CLC-Nt2 polynucleotide or polypeptide encoded thereby or a NtCLCe polynucleotide or polypeptide encoded thereby, or a combination thereof; or
(iii) a combination of (i) and (ii).

8. A plant or part thereof comprising the plant cell according to claim 1.

9. Plant material, cured plant material, or homogenized plant material, derived or obtained from the plant or part thereof of claim 8; suitably,
wherein the plant material is selected from the group consisting of biomass, seed, stem, flowers, or leaves or a combination of two or more thereof; optionally,
wherein the cured plant material is selected from the group consisting of flue-cured plant material, sun-cured plant material or air-cured plant material or a combination of two or more thereof.

10. A tobacco product comprising the plant cell of claim 1.

11. A method for producing the plant of claim 8, comprising the steps of:
(a) providing the plant cell comprising at least one modification; and
(b) propagating the plant cell into a plant.

12. The method according to claim 11, wherein in step (a) the at least one modification is introduced by genome editing; suitably,
wherein the genome editing is selected from CRISPR-mediated genome editing, zinc finger nuclease-mediated mutagenesis, chemical or radiation mutagenesis, homologous recombination, oligonucleotide-directed mutagenesis and meganuclease-mediated mutagenesis; or
wherein in step (a) the at least one modification is introduced using an interference polynucleotide or by introducing at least one mutation or a combination thereof.

13. A method for producing cured plant material with altered levels of glucose, fructose and sucrose and altered levels of free amino acids, glutamine, glutamate and aspartate as compared to control plant material, comprising the steps of:
(a) providing a plant or part thereof according to claim 8;
(b) harvesting plant material therefrom; and
(c) curing the plant material.

14. A method of producing a liquid tobacco extract, the method comprising the steps of:
(a) preparing a first tobacco starting material from a plant or part thereof containing a plant cell according to claim 1;
(b) preparing a second tobacco starting material from a plant or part thereof containing a plant cell comprising:
(i) at least one modification in a NtSUS polynucleotide or polypeptide encoded thereby, suitably, wherein the NtSUS polynucleotide or polypeptide encoded thereby is selected from the group consisting of NtSUS2-T, NtSUS3-S, NtSUS3-T, NtSUS4-S, NtSUS4-T or a combination of two or more thereof, more suitably, wherein the NtSUS polynucleotide or polypeptide encoded thereby is selected from the group consisting of NtSUS2-S, NtSUS3-S, NtSUS3-T and NtSUS4-S or a combination of two or more thereof; or
(ii) comprising at least one modification in a CLC-Nt2 polynucleotide or polypeptide encoded thereby or a NtCLCe polynucleotide or polypeptide encoded thereby, or a combination thereof; or
(iii) a combination of (i) and (ii);
(c) heating the first tobacco starting material at a first extraction temperature;
(d) heating the second tobacco starting material at a second extraction temperature;
(e) collecting the volatile compounds released from the first tobacco starting materials and second tobacco starting materials during heating; and
(f) combining the collected volatile compounds released from the first and second tobacco starting materials and forming a liquid tobacco extract from the combined volatile compounds.

15. The plant cell according to claim 1 wherein the plant cell is a tobacco plant cell.

16. The plant cell according to claim 1 wherein comprising a polynucleotide comprising a sequence having at least 95% sequence identity to SEQ ID NO: 1 (NtSULTR3;1A-S) or SEQ ID NO: 3 (NtSULTR3;1A-T) and a polypeptide comprising a sequence having at least 95% sequence identity to SEQ ID NO: 2 (NtSULTR3;1A-S) or at least 95% sequence identity to SEQ ID NO: 4 (NtSULTR3;1A-T).

17. The plant cell according to claim 1 wherein comprising a polynucleotide comprising a sequence having at least 99% sequence identity to SEQ ID NO: 1 (NtSULTR3;1A-S) or SEQ ID NO: 3 (NtSULTR3;1A-T) and a polypeptide comprising a sequence having at least 99% sequence identity to SEQ ID NO: 2 (NtSULTR3;1A-S) or at least 99% sequence identity to SEQ ID NO: 4 (NtSULTR3;1A-T).

18. The plant cell according to claim 1 wherein comprising a polynucleotide comprising a sequence having 100% sequence identity to SEQ ID NO: 1 (NtSULTR3;1A-S) or SEQ ID NO: 3 (NtSULTR3;1A-T) and a polypeptide comprising a sequence having 100% sequence identity to SEQ ID NO: 2 (NtSULTR3;1A-S) or 100% sequence identity to SEQ ID NO: 4 (NtSULTR3;1A-T).

19. A tobacco plant cell having a modified genome, wherein the genome is modified to alter expression of a NtSLTR3; 1A-S or a NtSLRT3;1A-T gene relative to a control plant cell in which the genome is not modified.

* * * * *

SEQUENCE LISTING

<160> NUMBER OF SEQ ID NOS: 53

<210> SEQ ID NO 1
<211> LENGTH: 7405
<212> TYPE: DNA
<213> ORGANISM: Nicotiana tabacum

<400> SEQUENCE: 1

| | | | | | |
|---|---|---|---|---|---|
| atgggtaaca | aggactatga | gtacccagca | tcaatgaatg | gggagagcag | aaaaacacag | 60 |
| ccagtggaaa | tcccaccacc | acaacctttt | tttaagtctc | taaaaaacac | agttaaagaa | 120 |
| actttgtttc | ctgatgatcc | acttagacaa | ttcaagaatc | agccaccacg | caagaaattc | 180 |
| atacttggac | ttcagtattt | gtttccaatc | tttgaatggg | gtcctcgtta | caccttggat | 240 |
| ttcttcaaat | cggaccttat | tgctgggatc | actatagcca | gtctcgccat | tcctcaggga | 300 |
| attagctatg | caaaacttgc | caatttgcca | cctatacttg | gcctctgtaa | gtcacaacgt | 360 |
| tactctatgt | tttatatata | ttataatggt | ggtgtacgtg | agtgcacctc | aattactttc | 420 |
| cataatcatt | atagagatga | attcaaactt | taaatttgat | gggtttaatt | aatctttacg | 480 |
| tgctcactac | tgaacctggt | gcactcttgc | aattatggat | tcagatttta | aaaactttag | 540 |
| caatttttt | aatttgtact | ttgctacatg | aaaaaggtat | gaggtcgatt | tgaacccact | 600 |
| gactatatac | attacaattt | acatgtgctt | ccgcttacta | gcacaagtac | aggataacta | 660 |
| tgtcaagaat | ttccttaatg | tgtgaggcgt | ggttaattag | ttaattacgt | gataacttat | 720 |
| gggtttgttg | gttattctga | tgacagattc | cagctttgtt | ccgccattag | tctacgcagt | 780 |
| aatgggcagt | tcaagagatt | tagcagttgg | gacagttgct | gtagcatcac | ttctcattag | 840 |
| ttcaatgtta | ggggacgaag | ttaatccaat | tgagaatcca | acactttatc | ttcatcttgc | 900 |
| gttcacggcc | acattctttt | ccggaatgtt | tgaagcagct | cttggaattt | tcaggttagt | 960 |
| atatatatac | agtagaataa | tatactataa | atgaaagggt | gtactacata | aattgggtca | 1020 |
| tcagatgaac | tatgttttaa | tcgtttgatt | atgactatgt | cttttttgtta | gaataaggaa | 1080 |
| cgattaaggt | aagttgatgg | taacgttaat | tggggaaata | attttttgcat | gcaggcttgg | 1140 |
| atttatagtg | gattttctat | ctcatgcaac | aatagttggg | ttcatgggtg | gagcagccac | 1200 |
| agttgtgata | cttcagcagc | taaaggggat | acttggtctt | gaccatttta | ctcagtccac | 1260 |
| cgatgtcatt | tccgtcttgc | gttctgtttt | tacccaaacg | cacgaggtat | atatataaat | 1320 |
| gttagtgtta | aaatggccca | aatatgataa | tataatgtga | tattatccgc | tttgcgataa | 1380 |

```
gtccgtattt tttctcaaaa ggaaattcaa ctcgttataa gtattttttt ttctactttg    1440
catattattg gactttgttc acatacacgt acccaacaaa ccggctcata gacaggctaa    1500
gacaataagc cgggctccca catcacactc cgtatttcca cataatatga tattgtcgct    1560
ttagttaagc ctgcacggtt ttcacaccat taagaattcc aagctcctta taatagtttt    1620
tctctacttt ttatgtgata ctttgttcgc acacaccaac aataacttat tattgatgta    1680
ttttaatttg ttgtaacata taacttatct tattttttcac gtgttctctt cccgccccccc   1740 aacccccttac aacatctgcg actattttcc gtgcaaggct atagccttgt tttcttgaat   1800
attaattttg aaaagcaagt attattgttc gattctcatt aacttctctt ttcgttttag    1860
ttgaatcttc aagaggatta gttttttttta attttaatta attaatatgg tttatgactt   1920
tgcttatggt taatgacaaa aataattgca gtggcgatgg gaaagtgcgg tgctgggttt    1980
ctgtttcctt ttctacctgc tgggttctag attccttgta agttacaacc aactttgatc    2040
tattcaaact tgaatagtac cataaaatca atttattaaa gagtctaaat tttatgcatg    2100
tgatataaga atatttttata aaatcgagtt atttattaaa ataaataagg agttgggtca   2160
tatatacaat aaatctctgc actataactg ctgctcttaa ttttagttat aatgaaatgc    2220
atgcatgcag agccaaaaga gaccgaagtt gttctggata tcagcaatgg ctccattgat    2280
gtccgtcata ctgggaacca ttttttgtcta tttcacgcac gctgaaaaac atggcgttca   2340
agtggtatgt cctttaatta attatgtttt cttaatttct agaaggtgta taatagaagt    2400
tacaatccta tttggcttaa agatttcaat ttgactggtg agctactata ctaaattaga    2460
ccactgttca caacataaac actatggtgg ggtggggtga tgtgatattt ctgctatttg    2520
gattactgca tttgtgagtg tttaatttgg gttgtgattc ttgtggtttg agtattgcac    2580
acgttcgttt gatatagacg acctaccaat gccatgattg actgataatt aaatgtttca    2640
aggacactgg cccagcgtat ttgctgttgg cattatcttt gcccatttaa aaatagacat    2700
ttctagatga tggttttctt cgtcctagaa gttactcaat tttacattaa acactatatg    2760
acaatgaaat tgagatagaa caaagtttga attactgtag tcgatgattc atttgttgaa    2820
atatattatg gtattaatgt tagaccgggt ttagttatgg aaaattttca ttactgaata    2880
ccatctggca tatatcttac tcccaccgtt cactttcact tgtgagccaa aatacatttt    2940
cacttttact tgtccaatat accaaattaa gagaaagacg gtctttttttt tttcgtttta    3000 cccttattat taattacaca tttcccaaat catttctcaa aacttttttga aatgttatta   3060 ttattatgga taaaattaca aaatacatac ttcatttgtt tttttcttaa agagagtgca    3120
aagtcaaaag cgaacgacta aaaatgaatg gatggagtag ttaaagtcca aaaacatgat    3180
gtcggaatta aaaatgtaac ctaatggtta catatagagg tggcaaaatg gttaaaagaa    3240
aacagttatc cacccatatt atccatcaaa atatgggttg gataatgaac catttaaaaa    3300
cgggtcgaat atgactattg aaccatatta tgcacttagg aaatggttaa ccaaatggat    3360
aaccaatgga taataatgta tttaactttt acatttgtaa agcctcaaat tggagttcct    3420
caagtttgga aaattaggaa ttctctcata agtgatcata tttaagaagc cgtagataat    3480
atggatatca atattacccc ccggataaac ccgttttat tcgtctcaaa tacggatcgg     3540
gtcggataat ttatccattt tttaaattac ccgttttgac ccgctcgtat ccgacccgcg    3600
catttgccac cccagttaca tataaccttta ttccacgtaa ctttggtgta gtttcaatcc   3660
aattaatggt ttgatacaat tcggaagtcc tcttcttttt gtaatttttt ctttctacta    3720
```

```
ctccctccgt ttcatattaa atgagttact ttccttttta gtctgttcca aaacaaatga    3780
catatttcta aattaggaaa taattcaaac tttaaactct ttcattttac ccatttacca    3840
ttaatgagaa gcttttatag ccacacaaat gtcatggccc ccacaaacct tttaccccett  3900 aagcttttaa gaccacaagt ttcaaaaatc tttttctttt ttcgtaaact tcgtgcggag    3960
tcaaactacc tcatctcatc taatatgaaa cggagggagt attatatata tgagccatcc    4020
ccaccaaaaa tagttatgtg ataatttatt tgtaactgca cacataatta gacataatgt    4080
gaaaaacatg actaattgga tggttaatta tgaaaatatt atgaacagat tggaaagctg    4140
aagaaagggc taaatccagt gtcaataatg gatttgtcat ttggagcacc ttatgtttca    4200
acatctatca aaactggcat aatcacgggt gtcgtatctc ttgctgtaag ctttcacttt    4260
tcccatactt gacccttttgt catgaagata tgatctcata tgtcgagaga caatgtaatt   4320
aaatgtataa gtacacatac aagtagtgca atttaaccta gtgtaagttt aagtcattca    4380
taaaattact ttgattgggg acatgatagg aaggaatagc agtggggaga agctttgcaa    4440
tgttcaagaa ttaccatata gatggcaaca aagagatgat cgcttttgga atgatgaaca    4500
tcgttggctc ttgcacttcc tgctacctca ctactggtat atattttcct tattctcttt    4560
caaatttgtc tttctaatta cctgaaacag cgggaaaaac aatggcccat tagttggatt    4620
agtcaacatc tgattgtatg gaccatcatg tcgggacaca cataaaggta gcaaataaat    4680
gcagaaagag acggaatatc tacataacaa agtagtggtt aatagatgca gagtaacaac    4740
ttaaaaaaga cagaaaaaaa aaaggtttca tgatttgttg tcagatttga ccagctatac    4800
agtgtttagt taactaaaac atattaatgt taataatata agattattaa ttcgcaacca    4860
tagcagagaa gaagacacaa tcataaatat aatgtagagt taaaagtaa ggaagcgtac    4920 cattcaattc cactgacaca ataacgatag cgattgacga ttaagcctga tgccaacttc    4980
cacgatccac tagctacacg ctctcacact cgaagaactt gacttatggg acgtctacca    5040
ttaccacata ttcaagagac agaatacgat agggttttct aatgcctagg taacgggggg    5100
ttggcctcta tttataaata ttgcatatcc atcacaggtc aattgttatt gggtctcact    5160
tatccacaca catagtattt aatattagac atttttattta tccatcattt gggtcacgtc   5220
accatccttt caggctataa ccaattaata taagttcaaa ttccaacaaa taacactata    5280
ttttcagata atttatatgc taggatttaa gttatacaca cttgcaatgt aaatagtgtt    5340
gttctatcaa tgtatttga ctgtttggtg tattacttgc caattgtttc atgttactca     5400
tatagtctta ccttttaatga tcttttaaag tggttaatgc aaatatttt atattgtcag    5460 tacataaaat ttgaagtcat ttttatattt cctgaacaag gtgctaatca gaaaagtgaa    5520
agtgcaggtc cattttcgcg atcagcagtg aacttcaacg caggatgtaa acagcagta    5580 tcaaacatag taatggcgct ggcagtaatg gtgacactgt tggtgctgac gccattgttc    5640
cattacactc cattagtggt cttatcatcc attataattt ctgcaatgct cggactcatc    5700
gactataatg ctgcaattca cctctggcac gtcgacaaat ttgatttcct ggtgtgcata    5760
agtgcatacc ttggcgtcgt ctttgccagt gtcgaaattg gcttagtcat tgctgtacgt    5820 atccctaat ttctagtaac tactattatt tccattctgt tcggaataaa tacaaggaga    5880
ttcgaaagca atataatgtt gcaccaataa tttgacccctt tagccaaatt aacttttgaa   5940
cccttttgtc acacactaga attttttttt cttatattaa aggggatcca acatttata    6000 tataacacaa aaaaattatt ttttatttat ttgcacaata taattttttcc acaaggata    6060 ttcaattgaa tcccttatt tctatctagc tccgcccttg tcggttcctt ctaaattgtc     6120
```

```
ttttaaagtt tctgcacaat tcatttaata gccttaatca taaaagtatt tatctaaaat   6180
actatttata tctccgttaa tgttttttga ttaaattaac actctactaa ctggagcgga   6240
atggtggatt ccgtaaaaat aacttttat ttttctaaga tatcaaatat tttgatacaa    6300
attcagtttg gatacaacaa ctaaaattat atattggaaa aatccacttt gttattacta   6360
atggactagt agtaactagg aagctaagca ggtggtttcc aattaattaa tcaagattta   6420
gctcttaatg caggttggtt tatcgttgct aagggtattg ctatttgtag caaggccaag   6480
aacgttagta cttggtaaca taccagattc taagatctat agaaatgttg agcaatacac   6540
aaacacagac actgttccgg gtgttctcat acttgacctt ggtgcaccca tttactttgc   6600
caatgctagc tacttaagag agaggtaatt taaattgtat actatatatc taactacaca   6660
aatatgtata tatactaata attaagcgct aattatgtgc tctgcttcac tttttatagg   6720
atctcaagat ggatcgacga cgaggaagac aagttaaatt cttccggaga gacattgcaa   6780 tatgtaaatac ttgatatggg aggtcagtta acttctccta tgtctacaat cttatagttt   6840
gacaaggaca tgctaaaacg attttttgtaa tttaactagt tatagtaggt tttcattctc   6900
ttttcgaggt gactacatca tggttgatat gaagaattat atggtgctaa atatttgtat   6960
attatcagta cgtacgtata actaaaactc gtgctaaaat tctatatatg atgggcagct   7020
gtaggcaaca ttgatactag cggaattagc atgctagaag aggtcaagaa gaatcttgat   7080
agaagagatc tcaaggtttg ccctaactat tatatatcct acacgttaaa tgatatattg   7140
gaagttatga agtgataatt aatccttaa tttgcaacaa catagtaata tggtgtgctt    7200
taattcttgt ggggtattgt agcttgtgct ggcaaatcca ggggcagagg taatgaagaa   7260
gctgaacaag tccaaattca tagagacaat aggacaggaa tggatatttc taactgtggg   7320
ggaggcagtg gaatcatgca attatatgct tcactcctgc aaaccaaaat ctgccataga   7380
tggttcattt agcaataacg tttga                                         7405
```

<210> SEQ ID NO 2
<211> LENGTH: 665
<212> TYPE: PRT
<213> ORGANISM: Nicotiana tabacum

<400> SEQUENCE: 2

Met Gly Asn Lys Asp Tyr Glu Tyr Pro Ala Ser Met Asn Gly Glu Ser
1               5                   10                  15

Arg Lys Thr Gln Pro Val Glu Ile Pro Pro Gln Pro Phe Phe Lys
            20                  25                  30

Ser Leu Lys Asn Thr Val Lys Glu Thr Leu Phe Pro Asp Asp Pro Leu
        35                  40                  45

Arg Gln Phe Lys Asn Gln Pro Pro Arg Lys Lys Phe Ile Leu Gly Leu
    50                  55                  60

Gln Tyr Leu Phe Pro Ile Phe Glu Trp Gly Pro Arg Tyr Thr Leu Asp
65                  70                  75                  80

Phe Phe Lys Ser Asp Leu Ile Ala Gly Ile Thr Ile Ala Ser Leu Ala
                85                  90                  95

Ile Pro Gln Gly Ile Ser Tyr Ala Lys Leu Ala Asn Leu Pro Pro Ile
            100                 105                 110

Leu Gly Leu Tyr Ser Ser Phe Val Pro Pro Leu Val Tyr Ala Val Met
        115                 120                 125

Gly Ser Ser Arg Asp Leu Ala Val Gly Thr Val Ala Val Ala Ser Leu
    130                 135                 140

-continued

```
Leu Ile Ser Ser Met Leu Gly Asp Glu Val Asn Pro Ile Glu Asn Pro
145                 150                 155                 160

Thr Leu Tyr Leu His Leu Ala Phe Thr Ala Thr Phe Phe Ser Gly Met
            165                 170                 175

Phe Glu Ala Ala Leu Gly Ile Phe Arg Leu Gly Phe Ile Val Asp Phe
        180                 185                 190

Leu Ser His Ala Thr Ile Val Gly Phe Met Gly Gly Ala Ala Thr Val
        195                 200                 205

Val Ile Leu Gln Gln Leu Lys Gly Ile Leu Gly Leu Asp His Phe Thr
    210                 215                 220

Gln Ser Thr Asp Val Ile Ser Val Leu Arg Ser Val Phe Thr Gln Thr
225                 230                 235                 240

His Glu Trp Arg Trp Glu Ser Ala Val Leu Gly Phe Cys Phe Leu Phe
            245                 250                 255

Tyr Leu Leu Gly Ser Arg Phe Leu Ser Gln Lys Arg Pro Lys Leu Phe
            260                 265                 270

Trp Ile Ser Ala Met Ala Pro Leu Met Ser Val Ile Leu Gly Thr Ile
            275                 280                 285

Phe Val Tyr Phe Thr His Ala Glu Lys His Gly Val Gln Val Ile Gly
    290                 295                 300

Lys Leu Lys Lys Gly Leu Asn Pro Val Ser Ile Met Asp Leu Ser Phe
305                 310                 315                 320

Gly Ala Pro Tyr Val Ser Thr Ser Ile Lys Thr Gly Ile Ile Thr Gly
                325                 330                 335

Val Val Ser Leu Ala Glu Gly Ile Ala Val Gly Arg Ser Phe Ala Met
            340                 345                 350

Phe Lys Asn Tyr His Ile Asp Gly Asn Lys Glu Met Ile Ala Phe Gly
            355                 360                 365

Met Met Asn Ile Val Gly Ser Cys Thr Ser Cys Tyr Leu Thr Thr Gly
    370                 375                 380

Ala Asn Gln Lys Ser Glu Ser Ala Gly Pro Phe Ser Arg Ser Ala Val
385                 390                 395                 400

Asn Phe Asn Ala Gly Cys Lys Thr Ala Val Ser Asn Ile Val Met Ala
                405                 410                 415

Leu Ala Val Met Val Thr Leu Leu Val Leu Thr Pro Leu Phe His Tyr
            420                 425                 430

Thr Pro Leu Val Val Leu Ser Ser Ile Ile Ser Ala Met Leu Gly
            435                 440                 445

Leu Ile Asp Tyr Asn Ala Ala Ile His Leu Trp His Val Asp Lys Phe
    450                 455                 460

Asp Phe Leu Val Cys Ile Ser Ala Tyr Leu Gly Val Val Phe Ala Ser
465                 470                 475                 480

Val Glu Ile Gly Leu Val Ile Ala Val Gly Leu Ser Leu Leu Arg Val
                485                 490                 495

Leu Leu Phe Val Ala Arg Pro Arg Thr Leu Val Leu Gly Asn Ile Pro
            500                 505                 510

Asp Ser Lys Ile Tyr Arg Asn Val Glu Gln Tyr Thr Asn Thr Asp Thr
            515                 520                 525

Val Pro Gly Val Leu Ile Leu Asp Leu Gly Ala Pro Ile Tyr Phe Ala
    530                 535                 540

Asn Ala Ser Tyr Leu Arg Glu Arg Ile Ser Arg Trp Ile Asp Asp Glu
545                 550                 555                 560
```

```
Glu Asp Lys Leu Asn Ser Ser Gly Glu Thr Leu Gln Tyr Val Ile Leu
                565                 570                 575

Asp Met Gly Ala Val Gly Asn Ile Asp Thr Ser Gly Ile Ser Met Leu
            580                 585                 590

Glu Glu Val Lys Lys Asn Leu Asp Arg Arg Asp Leu Lys Leu Val Leu
        595                 600                 605

Ala Asn Pro Gly Ala Glu Val Met Lys Lys Leu Asn Lys Ser Lys Phe
    610                 615                 620

Ile Glu Thr Ile Gly Gln Glu Trp Ile Phe Leu Thr Val Gly Glu Ala
625                 630                 635                 640

Val Glu Ser Cys Asn Tyr Met Leu His Ser Cys Lys Pro Lys Ser Ala
                645                 650                 655

Ile Asp Gly Ser Phe Ser Asn Asn Val
            660                 665

<210> SEQ ID NO 3
<211> LENGTH: 6846
<212> TYPE: DNA
<213> ORGANISM: Nicotiana tabacum

<400> SEQUENCE: 3
```

| | |
|---|---:|
| atgggtaaca aggactatga gtacccatca tcaatgaatg gggagagcag aaaaacacac | 60 |
| gcagtggaaa tcccaccacc acaacctttt ttcaagtctc taagaacac agttaaagaa | 120 |
| actttgttcc ctgatgatcc acttaggcaa ttcaagaatc agccacctcg caagaaattc | 180 |
| atacttggac ttcagtatat cttctccaatc tttgaatggg gtcctcgtta caccttggat | 240 |
| ttcttcaagt cggaccttat tgctgggatc actatagcca gtctcgccat tcctcaggga | 300 |
| attagctatg caaaacttgc caatttgcca cctatacttg gcctctgtaa gtcacagtat | 360 |
| aacgttattc tgtgttttat tataatggtg gtgtacgtga gtgagtgcac ctcaattagt | 420 |
| tcgttggata tcattatgta gacgaattta aaatttaaat ttggcgggtt caattttac | 480 |
| ttgctcacca ctgaacctgg tgcactcttg caattatgaa ctatacatta caatttacat | 540 |
| gtgcttccgc ttaccagcac aagtacatga taactatgtc aggaatttcc ttaatgtttg | 600 |
| tatcttaatc tcccaaaatc ctaacaagct ttctagtagg gattgagcag tgtgaggcgt | 660 |
| agctagttac gtgataactt atgggtttgt tggttattct gatgacagat tccagctttg | 720 |
| ttccgccact agtctacgca gtaatgggga gttcaagaga cttagcagtt gggacagttg | 780 |
| ctgttgcgtc acttctaatt agttcaatgc tagggacga agtaaatcca actgataatc | 840 |
| caacacttta tcttcatctt gccttcacag ccacattctt ttccggaata tttgaagcag | 900 |
| ctcttggaat tttcaggtta gtatatacag tagaatatac tataattaaa tgaaagtgtg | 960 |
| ctacatatat aaattgggtc agatgaacta gtatgtttta atcgtttgat gattatgact | 1020 |
| gtctttttgt tagaataagt tgatggtaat gctagttggg taaataattt ttacatgcag | 1080 |
| gctgggattc atagtggatt ttctatcaca tgcaacaata gttgggttca tgggtggagc | 1140 |
| agccacagtt gttatacttc agcagctaaa agggatactt ggtcttcacc atttactca | 1200 |
| gtccactgat gtcatttccg tcttgcgttc tgttttttacc caaacgcatg aggtatatat | 1260 |
| aaatgtgatt cgctttgtgt taagtttgca cgattttttcc ttaaagaaaa tccaactcat | 1320 |
| tataagtagt ttttttttac attttgtgtt ggactttgtt cacatgtacg cccaacaacc | 1380 |
| tggctcgtat acaggctaag acaataagtc gggcccccca cttcatacct cgttatctcc | 1440 |
| acatagtatg atattgtcgt tttaggttaa gccttacaat tttcacccta ttaaaattat | 1500 |

```
tcaacttttt acaagtaatt tttttctact tttctcatgt gagactttga ttacatacac    1560
caacaatagc ttatcatgga tgtatttaa tttgtcgtaa catataactt atcttatttt    1620
ttacgtgtgc tctccgcccc caagcccta caattctgcg actctttcga taatggatat    1680
gtattttcc gtgcaagact atagtcttgt tttcttgaat atatttattt ttaaaaagca    1740
aatattattg ttcgattctc actaacttct tttcttttt tttccttgag aataaaaatt    1800
ctactgttac cgtacaattt tagttgaacc ttcacgagga ttagtttatt ctattttatt    1860
ttattttaat taattaatgt ggtttctgac tttgcttatg gttaatgata aaaataattg    1920
cagtggcgat ggcaaagtgc ggtgctgggt ttctgtttcc ttttctacct gctggggtct    1980
agattccttg taagttacaa ccaactttga cctattcaaa catatatgaa tagtaccatg    2040
aaagcaaatt tttaaggagt ataaatttta tgcatggtgt taaaagaaat atttatatgt    2100
tcgagttata atttattatt aaagtaatta ggatttgagt tatataccaa tttaaagaat    2160
ttttacacta taactattgc tcgttgtaat ggaaatgcat gcatgcagag ccaaaaaaga    2220
ccaaagttgt tttggatatc agcaatggct ccattgatgt ccgtcatact gggaactatt    2280
tttgtctatt tcacgcacgc tgaaaaacac ggcgttcaag tggtatgtcc tttaattaat    2340
tttgttttct taatttcaag aaggtgtata attaaattac atctatttgg cttaaaagat    2400
ttcaatatga ctggtgagct actaaattag tctactgttc acaacacaaa cactatggtg    2460
gggtgatgtg atatttctgc tatttggatt actgcatttg gagtgtttaa tttgggtttt    2520
gattcttgtg gtttgagtat tgcacacgtt cgtttgatat agacagacct accaatgcca    2580
tgattgactg acaatttaat gtttcaagga cactggccca gcaaatttgc tgttggcatt    2640
atctttgccc atttaaggag acatttctag gtgatagttt tcttcgtcct agaagttact    2700
caatttaaca ttaaacaaat atgacaatga aattgagata gaacaaagtt tgaattattg    2760
tagtcgatga ttcattttgt tgaaatatat tatggtagtt ttagactggg ttaagttata    2820
gaaaattttc attactgaat accatctggc atatatgtta cttgtcacat ctactaaaaa    2880
tacatttttca cttttacttg tttactatac caaatcaaga caaagataat cttttttttct    2940
tttttgtttt acccttatca ttaattactc atttcctaaa ttatttctca agacttttg    3000
aaatgttatt attattatga gtaaaattat aaaatacata cttcatacat tttttcttaa    3060
aggaggtaca aaattaaaag tgaacaacta aaaatgaaca aatggaatat ttcaagtcca    3120
aaaacatgat gtcggaatta aaaatgcaac ctaatggtta catataactt tattcaacgt    3180
aactttagtg tagtttcaat ccaattaatg gtttgataca atcgaaagtc gtcttcttt    3240
tgtaatttt tctttctact attatatatg agccatcccc accaaaatag gcatgtgata    3300
agttatttgt gactgcacat ataattagac atcatgtgaa aaacatgact aaatggatgg    3360
ttaattatgt ggattatgaa cagattggag agctgaagaa agggttaaat ccagtgtcaa    3420
taatggattt gtcatttgga gcaccttatc tttcaacagc tatcaaaact ggcatagtca    3480
cgggtgttgt atctcttgct gtaagctttc actattccca tacttgacct tttgcgcaaa    3540
actaatttct ctttacggc tctataagca agcaccttag acatgaaatt gtttcaagta    3600
atggagattt tcttaggttc aaatctagtg atttaaata tgattaatat gacttataat    3660
gtcccgagtt tataattcaa taatctttca actacattac cattcaatta ccattcaacc    3720
gccattaact actaagctga taaagttgaa gattttctta gacttatcat gaagatatct    3780
catgtccagt gacaatgtaa atgtataagt agacaattag tgcaatttaa cctactgtaa    3840
cttaactcat tcataaaact ttgatttggg gacgtgacag gaaggaatag cagtggggag    3900
```

```
aagctttgca atgttcaaga actaccatat agatggcaac aaagagatga tcgcttttgg    3960
aatgatgaac atcgtcggct cgtgcacttc ctgctacctc actactggta tatattttcc    4020
ttattctctt tcaaatttgt ttttgaatta cctgaaacag cgggaaaaac aatgccccat    4080
taattggatt aatcaacatc tgtccatcat gtccggagca cccagtatac acacataaaa    4140
gtagcaaata aagtagtggt taatacatgc agattaacag cttaaaaaag aaaaagaaaa    4200
aaaaaggttt catgatttgt tgtcagatta gaccagctac agtgtttaat taactaaaat    4260
ataataatgt taactatact atatttcaga taatttatat actaggattt aaattataca    4320
cactcagttt tatttattct atcaatgtat tttggctgtt tgggcatgac atatctactc    4380
cagcttacag aggatatgat ccttgatagg caggtttgtg ggttgggaat taggatagaa    4440
ggttagtagc tagacatgcg tgtctccttc tcatgcgggt agcattaata ttaatctctt    4500
atcttcgtag cttcttatcc gcagatttct tttgctatac tatgttgttt ctttcgcttt    4560
gattattcta tcaccttatc cctttatctg gctgttatta ctatttgttg tgtctgcctc    4620
ttttaaattt tctttgagcc cggggtgatc tatcgaaaac aacctctcaa cttttcacaaa    4680
ggtcagggta aggtttgcgt atattctacc ttccccaaac cctacttggt gggattacac    4740
tgggtatgtt gtcgtagtat tttggccgtt tggtgtatta cttgccaatt gtttcatgtt    4800
actaatatag acttatcttc aattgtcttt ttaagtgatt ttattgagta aatacttta    4860
cattgccatt atacaaaatt taagctcatt tatatatcat gaacaagctg gtaatcagaa    4920
aagtgaaagt gcaggtccat tttcgcgatc ggcagtgaac ttcaacgcag gatgcaaaac    4980
agcagtatca aacatagtaa tggcgctggc agtaatggtg acactgttgg tgctaactcc    5040
attgttccat tacactccat tagtggtctt atcatccatt ataatttctg caatgttcgg    5100
actcatcgac tataatgctg caattcacct ctggcacgtc gacaaatttg atttcttggt    5160
ctgcattagt gcttactttg gcgtcgtctt tgccagtgtc gaaattggct tagtcattgc    5220
tgtacgtatc ccttaatttc tagtaactaa tatttcattc gattcaggtg gggagtcagg    5280
aatttatatg atgagattca gaaagatact taaatattat acctagaatt tgaccctgtg    5340
accaaaatca acttttgaac ccccctttgcc attaattata ttccttatat taagggattc    5400
aaccatttat atataacata aaaactcttt ttaatttgca catcatagtt ttgggcaaaa    5460
gaaattcaat tgaatcccct tatttctacc tagctccacc cttgtcagtc cgtattaact    5520
gtctttaag gttttgcac aattcttaag aaaagaattt aatagcctta atcataacgt    5580
ttcataattt aatcaacact ctactaacta gagcagaagt ggtagattcc aaaaaaaaaa    5640
aaaaatactt tttgcgtttc taaaatatca aacatttga agcaaattca gtttggatag    5700
aacaattaaa aattatacat tggaaaaatc cgttctgtta ttactaatag actagtagta    5760
actaggaagg gggaagaaac gagtacttgt caactaagca ggtggtttcc aattaatcaa    5820
gatttaatag cgtaaacttt taatgcaaat gcaggttgct ttatcgttgc taagggtgtt    5880
gctatttgta gcaagaccaa gaatgttagt gcttggtaac atccccgatt ctaagatcta    5940
cagaaatgtt gagcaataca caaacacaga cactgttccg ggcgttctca tacttgacct    6000
tggtgcaccc atttactttg ccaatgcaag ctacttaaga gagaggtaat ttgaaactgt    6060
actacatatg taactacaca tcttcgaaca tgtagatgca aagttaacac taattctgag    6120
ttctgtttca cttttatag gatctcaaga tggatcgacg acgaggaaga caagttaaat    6180
tcttcaggag agacgttgca atatgttata cttgatatgg gaggtcagtt aacttgtcct    6240
```

-continued

```
atatatgttt atgatcttga aatttgacaa tttcttatcc aagtaaaaaa gaaacaagga   6300
tgtgctaaaa agatttaagt tatatatacg tataaataat gtttacatta tcagtgttta   6360
ttacgttctc attctatttt ataggttacc aattgttgtg ttgattttac ctgatagtgc   6420
taatatagta cttagaactt aaactcagtg ctaaaattct ttatatgatg ggcagccgta   6480
ggcaacattg atactagcgg aattagcatg ctagaagagg tcaagaagaa tcttgataga   6540
agagatctca aggtttgact cttattaata tcctcagtac atgttaaaaa tctattggaa   6600
gttatcaagt gctaataaat tctttgcaac aaaactgtaa catatattat tgtgggattg   6660
tagcttgtgc tggcaaatcc aggggcagag gtaatgaaga agctgaacaa gtccaatttc   6720
atagagacaa taggacagga atggatattt ctaactgtgg gggaggctgt ggaatcatgc   6780
aattacatgc ttcactcctg caaaccaaag tcttccacag atggttcatt tagcaacaac   6840
gtttga                                                             6846
```

<210> SEQ ID NO 4
<211> LENGTH: 639
<212> TYPE: PRT
<213> ORGANISM: Nicotiana tabacum

<400> SEQUENCE: 4

```
Met Gly Asn Lys Asp Tyr Glu Tyr Pro Ser Ser Met Asn Gly Glu Ser
1               5                   10                  15

Arg Lys Thr His Ala Val Glu Ile Pro Pro Gln Pro Phe Phe Lys
            20                  25                  30

Ser Leu Lys Asn Thr Val Lys Glu Thr Leu Phe Pro Asp Asp Pro Leu
        35                  40                  45

Arg Gln Phe Lys Asn Gln Pro Pro Arg Lys Lys Phe Ile Leu Gly Leu
    50                  55                  60

Gln Tyr Ile Phe Pro Ile Phe Glu Trp Gly Pro Arg Tyr Thr Leu Asp
65                  70                  75                  80

Phe Phe Lys Ser Asp Leu Ile Ala Gly Ile Thr Ile Ala Ser Leu Ala
                85                  90                  95

Ile Pro Gln Gly Ile Ser Tyr Ala Lys Leu Ala Asn Leu Pro Pro Ile
            100                 105                 110

Leu Gly Leu Tyr Ser Ser Phe Val Pro Pro Leu Val Tyr Ala Val Met
        115                 120                 125

Gly Ser Ser Arg Asp Leu Ala Val Gly Thr Val Ala Val Ala Ser Leu
    130                 135                 140

Leu Ile Ser Ser Met Leu Gly Asp Glu Val Asn Pro Thr Asp Asn Pro
145                 150                 155                 160

Thr Leu Tyr Leu His Leu Ala Phe Thr Ala Thr Phe Phe Ser Gly Ile
                165                 170                 175

Phe Glu Ala Ala Leu Gly Ile Phe Arg Leu Gly Phe Ile Val Asp Phe
            180                 185                 190

Leu Ser His Ala Thr Ile Val Gly Phe Met Gly Gly Ala Ala Thr Val
        195                 200                 205

Val Ile Leu Gln Gln Leu Lys Gly Ile Leu Gly Leu His His Phe Thr
    210                 215                 220

Gln Ser Thr Asp Val Ile Ser Val Leu Arg Ser Val Phe Thr Gln Thr
225                 230                 235                 240

His Glu Ser Gln Lys Arg Pro Lys Leu Phe Trp Ile Ser Ala Met Ala
                245                 250                 255

Pro Leu Met Ser Val Ile Leu Gly Thr Ile Phe Val Tyr Phe Thr His
```

```
                    260                 265                 270
Ala Glu Lys His Gly Val Gln Val Ile Gly Glu Leu Lys Lys Gly Leu
            275                 280                 285

Asn Pro Val Ser Ile Met Asp Leu Ser Phe Gly Ala Pro Tyr Leu Ser
            290                 295                 300

Thr Ala Ile Lys Thr Gly Ile Val Thr Gly Val Val Ser Leu Ala Glu
305                 310                 315                 320

Gly Ile Ala Val Gly Arg Ser Phe Ala Met Phe Lys Asn Tyr His Ile
                325                 330                 335

Asp Gly Asn Lys Glu Met Ile Ala Phe Gly Met Met Asn Ile Val Gly
            340                 345                 350

Ser Cys Thr Ser Cys Tyr Leu Thr Thr Glu Asp Met Ile Leu Asp Arg
            355                 360                 365

Gln Val Cys Gly Leu Gly Ile Arg Ile Glu Gly Cys Lys Thr Ala Val
            370                 375                 380

Ser Asn Ile Val Met Ala Leu Ala Val Met Val Thr Leu Leu Val Leu
385                 390                 395                 400

Thr Pro Leu Phe His Tyr Thr Pro Leu Val Val Leu Ser Ser Ile Ile
                405                 410                 415

Ile Ser Ala Met Phe Gly Leu Ile Asp Tyr Asn Ala Ala Ile His Leu
                420                 425                 430

Trp His Val Asp Lys Phe Asp Phe Leu Val Cys Ile Ser Ala Tyr Phe
            435                 440                 445

Gly Val Val Phe Ala Ser Val Glu Ile Gly Leu Val Ile Ala Val Ala
            450                 455                 460

Leu Ser Leu Leu Arg Val Leu Leu Phe Val Ala Arg Pro Arg Met Leu
465                 470                 475                 480

Val Leu Gly Asn Ile Pro Asp Ser Lys Ile Tyr Arg Asn Val Glu Gln
                485                 490                 495

Tyr Thr Asn Thr Asp Thr Val Pro Gly Val Leu Ile Leu Asp Leu Gly
            500                 505                 510

Ala Pro Ile Tyr Phe Ala Asn Ala Ser Tyr Leu Arg Glu Arg Ile Ser
            515                 520                 525

Arg Trp Ile Asp Asp Glu Glu Asp Lys Leu Asn Ser Ser Gly Glu Thr
            530                 535                 540

Leu Gln Tyr Val Ile Leu Asp Met Gly Ala Val Gly Asn Ile Asp Thr
545                 550                 555                 560

Ser Gly Ile Ser Met Leu Glu Glu Val Lys Lys Asn Leu Asp Arg Arg
                565                 570                 575

Asp Leu Lys Leu Val Leu Ala Asn Pro Gly Ala Glu Val Met Lys Lys
            580                 585                 590

Leu Asn Lys Ser Asn Phe Ile Glu Thr Ile Gly Gln Glu Trp Ile Phe
            595                 600                 605

Leu Thr Val Gly Glu Ala Val Glu Ser Cys Asn Tyr Met Leu His Ser
            610                 615                 620

Cys Lys Pro Lys Ser Ser Thr Asp Gly Ser Phe Ser Asn Asn Val
625                 630                 635
```

<210> SEQ ID NO 5
<211> LENGTH: 9584
<212> TYPE: DNA
<213> ORGANISM: Nicotiana tabacum

<400> SEQUENCE: 5

-continued

```
atgggtaatg cagattatga gtacccatca ataatgaatg gagagagcac aggcataggc    60
atacatagag tggaaatccc accaccacag cctttttcca aatcactaaa gaatacagtg   120
aaagaaactt tatttccaga tgatcccctt aggcaattca agaaccaaac accccttaga   180
aaattcatac ttggtgtgca gtatttcttt ccaattttg aatggggttc tcgttacaat    240
tttgggttct tcaaatctga tcttattgct ggaattacca tagctagtct tgctattcct   300
cagggaataa gctatgcaaa acttgccaac ttgccaccta ttcttggact atgtaagtct   360
tgataattta ttcagtcaac tctcatatca tgttgaagtg tacatgcgat catttcatct   420
aaaacaaatg atgtgtatat acacagttca aaaccttaaa cacagcaact catatcttta   480
gtagttttg cagtagccga tgttgcatat atatagttaa cgggttcaac tgcaccgtta    540
acaacaacaa gaaccaagt atagttcaca agtggggtct ggggagggta gcatatacgt    600
agaccttacc cttagcttga aggtagtgag gttgtttccc atagactttt ggctcaagca   660
actgcaccgt taacaacaac aagaaaccca atatagtcct gcaagtgggg tctggggaag   720
gtggcgtgac cttacctcta gcttgaaggt agtgaggttg tttcccgtag accctcagct   780
caagcaactg caccgttaac taaagtgaaa aacactaaaa tttaaaaaga tattgaagtt   840
tgaacgtaaa atttcaaaaa tgaaatatgt ttaataataa gaatctaaag gttgaattca   900
tctaatttaa atcctggatt cgctattttt gtgttttgca gattcaagct ttgttccacc   960
tttagtttat gcaataatgg gcagttcaag agatttggca gtgggcacag ttgctgttgg  1020
atcgcttcta atggcttcta tgataggaaa tgaagtaaat gcaactgaga atccagcact  1080
gtatcttcat cttgcgttta ctgccacatt cttcgctgga ctatttgaat tagctcttgg  1140
attttttcagg tcattgtctc tatttcttgt tagtacgttc ttagtttaca atatcgctta  1200
tactaaaata gtttgagccg aagaagcaag cagcagtgca ttactttagg gtaagctgtc  1260
tacgtcacac tccttggaat gcggcctttt cccgaatccg gcatgaacgc ggaatggctt  1320
ttacaccggg ctgtctcagt ttgagcttaa ttaatttatg gttaattaat tttgtaggct  1380
gggatttatt gtggattttc tatcacatgc aaccatagta ggatttatgg gaggagcagc  1440
tacagtggtg atactacagc agctaaaggg aatacttggt cttgaacatt ttacacatgc  1500
tacagatgtt gtctctgtct tgcgttctgt ctttacccaa attcaccagg taatttttt   1560
ttttactcta tcaagttact tgaaaatcta ttaaataata ttctgtaaca agtatgcttt  1620
gttaacctac ataaattata gtaacacctt aagtaacctg ttatagctag taaaactata  1680
catatagtat aaataaattt aaatctagtg aaagctccca ttcttttcga cagaatagat  1740
ggtaaatatt tttcagttac tgattgattc ttaatttgtt ccttttttcgg ttaaagtttg  1800
aagagaaatg ttttttttgt ttgtaatagt aactttctga tgctaaactt tattattatt  1860
ttatttttt acatttact tttttggttc gtttcgtttt ctccacccct ttttagcccg    1920
tggaaaaaac ttgtatagtg tacaaatcat gagattgagt tgaactaaag ttattattga  1980
agagtaaaat ttttggattt agttacacac ttttatccct tttgatttat ttgtttgttt  2040
attactccga gtacttatat ttgttacttt ctttaaatat actctaatga tggttaattg  2100
gttaaaataa ctgcagtggc gatgggaaag tgcggtgcta ggattttgtt tccttttcta  2160
cctgatgatg gcaaaatttt tgtaagtat acacactgac tttgaccttt tgaaatgcga   2220
atagtatcca caagtcaaaa gcagtctact atcaaaagtg datacccttt agacttataa  2280
tgctcaatta agctttccta tctttcctca aataatttca tacctaacct caacttttgt  2340
taatttctta ctctttcgaa attattatgg actgatattg actttgctcc tcgatttaac  2400
```

```
ctaccccact ccgaaaatgc caacaaatta aagcaatgtc ttctatttaa agtttatgaa    2460
ttatggattt atcacataat cgatattatt actgagttcg taattagata tttatactta    2520
tttaaaaaaa ttctaatata aatataatat ttaagtaaaa gtgattgggt ccggcccatc    2580
ctacgagaat aagctagctc catttctgct cgtcagaggg aaaatttata tatttttctc    2640
gtgagaaaag aaaattaact tttatatttt gttaatagaa aactactagt agtattctac    2700 aactttata  gaaagaatag agagagtgta gtttaaaaaa gttgctaata tatgcatgca    2760
tgcagagcca aaagagaccg aagctgtttt ggatttcagc aatggcgcca ttgacgtccg    2820
tcatattggg aactattctt gtttatctca cccacgctga aaaacacggt gttgcagtgg    2880
taagaaaaaa attcattaat agtaaattta atctattata gcaagtaaac tgtcttattt    2940
ttcatcttac taatatagaa gttaaattcg cgtgttagct taagctctta aattcaagga    3000
cttcattcaa cttctgaatt actcctacta gtttactaca gtataagaac ataaatccta    3060
cctagctcca acaatctcat atttctaccc attgaattct cttttagac  atactatata    3120 ctcctatcta gtaacttgcg gtttaagtac cctagatgtt tgtttgggca acaacggca    3180 acaataacgg tccagtaaaa tctcactaat aaggtctggg gagtatagtg tgtacgcaga    3240
ctttacccta ccgctatgag gtagagaggc tattccgaaa gacactcggc tcaagaagac    3300 gaaaaagaa  tatatcagca ccatcaataa aaagtatgga acaaataaca acgtcaccag    3360
acagggacaa acaacctact agtgccaaaa ttggttatcc atgatattct acgtttatta    3420
gctgttcata ttccttattg gtgaatttta aagagacact tttgattgat agcttcattt    3480
gtcttaataa aatttgggtc aagttgacac ttaaagacaa acaagacaac gaaggtgaaa    3540
tgaaaaaaag ttttatttg  tgttatacgt actttgtcgg tcacggaaaa aaagtagta    3600 gtgctatgag aactttagca taacaagact tttgtgaata gtttagacct acacagtata    3660
aaagaatttt caccgcattt aattactaca aaaataacta taggcaacta tccataacaa    3720
cttagatttg taacctcaaa acataaagca tgtcacatgc atactcaaca agctaagttt    3780
agcgcataat ttttcttaca ctgtcagtgc gcgtatgacc tatagatcac gggttcgaat    3840
tataaaatca ttcattaata tttatatcag agtagattgt ctgcatcaat aacccattaa    3900
gatgcggccc tttcccgaac cttgcgagaa cgcgtgatta ctttgtgcac cggattgccc    3960
tttagtacac ataagtaaag tcgtatgcag aagatggttg tatcttagga gagattgttg    4020
tgataattgt ggatgcttta tattatccat caatcattgg attcttataa ttatgtgaat    4080
gaaaaattgg aacagatagg ggagctgaag aaagggttaa atcctccgtc aataatggat    4140
ctgtcatttg ggtcggccta tatgacaact gctatcaaaa caggaatagt cacgggtgtc    4200
atttctcttg ctgtaagcac tcgatctgct ttccaatctc aacctttgtc ctctttctgc    4260
tgcaattcct gctacttgca ttactttttct ctagctaatg ttcttttttt ttacaatttc    4320
aagaacaagc atacaaaaca tgtgtgcatg acggatctt  gataatgttc accgctttga    4380
atacaatatt agagtacaga acttatattt atttcttcgt ccccttcattt ttacttatcc    4440 actataaagt ataatttcat ttttacttgt ccgtttagca aagaaagaga aagcaacatct    4500 ttttttttcaa tgtgattagg aggtcacggg ttcgagccgc gaaatagct  tcttgcagaa    4560 atgtagggta aagttggtac gatagaccct tgtgttccgg gccttacccg gacccgcgc     4620 atacgagaat ttagtgcact gggttgctct ttacttttca tatcattaac tgctcattcc    4680
ccaaattatt tttccagatt ttttgaaatg ctataattat tataggtaaa atagtagaac    4740
```

```
acatatttta attattttt tcttaaagaa agtacaacgt taaaagtgga caactaataa    4800
aattgaacgg agaaagtcat taatttgtaa ctatatcata attggatgct tattgggact    4860
tctttggcga cgatatataa atcactagag aatttggccg cgcttcgcgc gattatataa    4920
aagaactata ataaattttg tgattttata ataaaactaa attcaatctg atcaaataaa    4980
caaccaaaaa tagataaata taatttagga agtcatggtc tactcttgag gtaaccccta    5040
gagcaaaaat tacaaagaat catcctcaag gttgatttta tatatataca cacacgtgtg    5100
tgtgcacgac gcagatgttt ttcaaatatt ttttcttagt ttataatatt ttactttta    5160 gaactgcggt taattattta aattgtacaa tggttagttt actttgttgt ttaatataca    5220
tatatattta tctagataaa tatatcttgg cgaaataatt tttcttctac tcatttgata    5280
tatgtattgt ttaaatcctt aattagagag tcgaatatta ttttgcgaaa ggtttctcca    5340
ttgttcttta tttccttgtt ctctcttcct tcctttcttg ttcatttctt ccctcttttt    5400 gttctttct acatttcac ccactaacca ctacttcatc tagaacttt gaaaatgtta    5460 cttttttgtaa aataatcaag tcaattcctc ttttgcttcc tcttaattt ctgcgaaaca    5520 ataatagatt ctctttttc ctgaaatagc tcctccgaac aatcataat gcaatcattt    5580 cattttcgaa tatattcagc aaaaattttt ggggcaattt taattgccac ctattgtcat    5640
tattacaatc atttcactct tccttttgga cagaagaaaa catacatata tagaaaattg    5700
atatggaaaa gaaataaaaa agaaataaag tatacaaatg ttcgtatcac tgcatatctc    5760
tgaatgaact cttttttta aatactataa cctcattttt actttgtaat gaggcatacg    5820
aagcacaaaa ccttcataat tatatagtaa tacacaagta agttgtatgc atttattata    5880
cgtttcaaaa tacaactgca ataaagcaga attgctcact gaaattaact tcattttcaa    5940
gaaaatcata ttatatataa aaatactcac tacagatatt agtgtcattc ccttacaaga    6000
atatataaat ataaataacg taagaatcat tatgtaatat aattatgagt gtgctttgaa    6060
aaactgaact tttgtagaga tcaaagatta aagagtccct taaaaagata gagtaagtcc    6120
atatccgaga aatttagatg gaaagaaaga agccaaaaag aagaaccata ttaagagaaa    6180
atttgaaaac tttattttca tgcaaccatt taaagtagga atgtgaaagc tcattttcca    6240
aaccatattc tttacgttca tgctctgctg ggcgttacgt tatttccatt cttcaaaagc    6300
accactttga aattcttccc atctcaatga gtttctgttt cttccagcac taaagtagtt    6360
gctttgtttc tccttttggg aatcaagcca acgtacatct tttaatggaa aggagaagtg    6420
gagaagtaat atgagtagac tgaggataag ggaataaact tggctgagaa gccattgttg    6480
gaagcatgtg tatatcgatc tgacgtgatg tgtaaccttt agtaaaagac aatttctttt    6540
tacacatttt gaattgttgc acaactatat ttgttattta taaactgcag tgattgcgag    6600
gctccataaa tgaggaatat ggatggctga aacggtaaca tccattcatt tgacagtttc    6660
ttttattaat tgacatgaag agacacgact tttgggcttt ttaaagcaaa ataaataaag    6720
taaaaattga gaaagtatga aaaggcccca aaaatttgag aaaataaata aatatgattc    6780
ttggctttag agaagtgcca agtcatctct tctatcccct cttttataga tatatagatt    6840
agtaaaattg caatgatagt ataacatttt atacaatatc agtgtacata actccttgtc    6900
acatgtatga atcaaaattc tataaaattg tgtatgaact ttgaaggcaa ctttcaatga    6960
cactgtaaac ttacaagatt atagacaata agtgtatttc gtatacttat aattgcatta    7020
tgtggcaaag aattttttta gtggatttga aactctctat aacacactgc actaaaatta    7080
aatccttaat ttattgatat ggacaggaag gaatagcagt agggagaagt tttgcaatgt    7140
```

```
tcaagaatta ccatatagat ggaaacaaag agatgattgc ttttggaatg atgaatattg     7200
ttggctcctg cacctcctgc tacctcacta ctggtacgtt cctacatact actatagtat     7260
atcatatttg acttggttat tatttctctt ttctctttta tttcctttat gggccgaaag     7320
ttgatgtgga ttactctcat ttcccatttg ggcccatacc acgtgattgt atgtctccgc     7380
atacctacta acaataaaag aagaaaaaga aaagcaaaa aaaaaaaaga gagaaagaga     7440
gaaagaaaag cttaaaatta atgggataga gactggaaaa gaggaaacgt aattatacta     7500
tattatatgg gaaggaaaat actaaaaaat ggaggggtgg aaggtaagaa aagagtgggg     7560
ttggctaggt tgatgaaatg catatatttt caacaaagtg taacgagttt gagtcgtatt     7620
atgtgtaaat aaagggtat tatgttattg ataattcctt gtcgataaaa aaaaaatgaa     7680
aataagaaag aatgaggaat tgacaataag gacatttcaa gttttagca aattaacatt     7740 acattaaacg taaatttatg gagtagttta gtcaaataag ttttaaaaga gcaaatgtga     7800
ataggtcagt gttttcgaaa agactaacac tactacatta cctaaaaaat aattacatac     7860
aactgtccac aatatgtggc attagaaact tgaaaaataa gacagttaac ctataataag     7920
aagtaaaaat atactgatag tgtaaaaatt atttatactg cagggccatt ctcgcgatca     7980
gcagtgaact ttaacgcagg atgcaaaact gcagtatcaa acattgtcat ggcgttggca     8040
gtgatggtga cattgttgtt gctaacgcca ttgttccact tcactcccct cgtcgtcctg     8100
tcctccatta tcatctccgc catgctcggc ctcattgatt ataatgcagc cattcatctc     8160
tggcatgtcg acaaattcga cttcttggtc tgcatcagtg cttacattgg cgttgtcttt     8220
gccaacattg agattggctt agtcttagcc gtaagtatcc cttatgttct atgcactaac     8280
agtgtaaaaa aaaattacag tatcaaattt gaccgataat tatatggttt gacttataaa     8340
aatgttgttt aatggaaatg caggtaggat tatcgttgct aagggtgtta cttttttatag     8400 caaggccaag gacgttagta cttggtaata tcccagattc tatgatatac agaaatgttg     8460
agcattaccc aaatacaaac aacgttccag gcgttctcat tcttgacatt ggagcccta     8520 tttacttcgc taattctagc tatttaagag aacggtaatt agtatttga taactgtagt     8580 gtctatatca gtttgcagac acctcgacta attatggtta actcaattct tgttatagga     8640
tctcaaggtg gattgacgaa gaggaagaca agttaaaatc ttcaggagaa acaacattgc     8700
agtatgttat acttgatatg ggaggttagt taatttatgc agtctctata atttctttca     8760
tcactcagtt tattttttga aaataacaat aaaaacattt aaacgtagca caagaacata     8820
taagactgag tttgagcatt gacagctaaa attctttgat tggcagctgt gggaaatatc     8880
gatacaagtg gaattagcat gcttgaagaa gtcaagaaaa atcttgatag aagagattac     8940
aaggttgggc tcttgttttc caatttcttt cttcgaaaca atttcactat atcactgatg     9000
ttactgctag ttgatactgc tcctttcat tttgtccttg ggccgagggt atccaaaaaa     9060
tagcctctct acctttacag gcaaggtagg gataaggtct gcgtacatat taccctcccc     9120
aaattatgct gggtatgtta ttgttgttgt cattccaagt tataaagaca gactgcacca     9180
taaagtacat ctataagata ggatttaaat tacatacact aaaagtactg taaaaaaaat     9240
tccaacgatc agtgttttat aacttattat agcaggtaac ttgccttatt tttcagatta     9300
ctaatcctgc ttttttatggc cagtcagtgt atagaagtta aacttgtgta acatatggtg     9360
gttttttttt ttttttttttt gtggcaatgc agcttgtgtt ggcaaatcca ggagcagagg     9420
tgatgaaaaa gttgaacaag tccaaattta ttgagacatt aggacaagaa tggatctttc     9480
```

```
taacagtagg ggaagctgtg ggagcatgca atttcatgct tcattcctgc aaaccaaaat    9540
ctacaacaga tgaggcatcc caaaaatgga gcaacaacgt ttga                    9584
```

<210> SEQ ID NO 6
<211> LENGTH: 662
<212> TYPE: PRT
<213> ORGANISM: Nicotiana tabacum

<400> SEQUENCE: 6

```
Met Gly Asn Ala Asp Tyr Glu Tyr Pro Ser Ile Met Asn Gly Glu Ser
1               5                   10                  15

Thr Gly Ile Gly Ile His Arg Val Glu Ile Pro Pro Gln Pro Phe
            20                  25                  30

Phe Lys Ser Leu Lys Asn Thr Val Lys Glu Thr Leu Phe Pro Asp Asp
        35                  40                  45

Pro Leu Arg Gln Phe Lys Asn Gln Thr Pro Leu Arg Lys Phe Ile Leu
    50                  55                  60

Gly Val Gln Tyr Phe Phe Pro Ile Phe Glu Trp Gly Ser Arg Tyr Asn
65                  70                  75                  80

Phe Gly Phe Phe Lys Ser Asp Leu Ile Ala Gly Ile Thr Ile Ala Ser
                85                  90                  95

Leu Ala Ile Pro Gln Gly Ile Ser Tyr Ala Lys Leu Ala Asn Leu Pro
            100                 105                 110

Pro Ile Leu Gly Leu Tyr Ser Ser Phe Val Pro Pro Leu Val Tyr Ala
        115                 120                 125

Ile Met Gly Ser Ser Arg Asp Leu Ala Val Gly Thr Val Ala Val Gly
    130                 135                 140

Ser Leu Leu Met Ala Ser Met Ile Gly Asn Glu Val Asn Ala Thr Glu
145                 150                 155                 160

Asn Pro Ala Leu Tyr Leu His Leu Ala Phe Thr Ala Thr Phe Phe Ala
                165                 170                 175

Gly Leu Phe Glu Leu Ala Leu Gly Phe Phe Arg Leu Gly Phe Ile Val
            180                 185                 190

Asp Phe Leu Ser His Ala Thr Ile Val Gly Phe Met Gly Gly Ala Ala
        195                 200                 205

Thr Val Val Ile Leu Gln Gln Leu Lys Gly Ile Leu Gly Leu Glu His
    210                 215                 220

Phe Thr His Ala Thr Asp Val Val Ser Val Leu Arg Ser Val Phe Thr
225                 230                 235                 240

Gln Ile His Gln Trp Arg Trp Glu Ser Ala Val Leu Gly Phe Cys Phe
                245                 250                 255

Leu Phe Tyr Leu Met Met Ala Lys Phe Phe Ser Gln Lys Arg Pro Lys
            260                 265                 270

Leu Phe Trp Ile Ser Ala Met Ala Pro Leu Thr Ser Val Ile Leu Gly
        275                 280                 285

Thr Ile Leu Val Tyr Leu Thr His Ala Glu Lys His Gly Val Ala Val
    290                 295                 300

Ile Gly Glu Leu Lys Lys Gly Leu Asn Pro Pro Ser Ile Met Asp Leu
305                 310                 315                 320

Ser Phe Gly Ser Ala Tyr Met Thr Thr Ala Ile Lys Thr Gly Ile Val
                325                 330                 335

Thr Gly Val Ile Ser Leu Ala Glu Gly Ile Ala Val Gly Arg Ser Phe
            340                 345                 350

Ala Met Phe Lys Asn Tyr His Ile Asp Gly Asn Lys Glu Met Ile Ala
```

| | | | | | | 355 | | | 360 | | | | 365 | | |
|---|---|---|---|---|---|---|---|---|---|---|---|---|---|---|---|

Phe Gly Met Met Asn Ile Val Gly Ser Cys Thr Ser Cys Tyr Leu Thr
370           375           380

Thr Gly Pro Phe Ser Arg Ser Ala Val Asn Phe Asn Ala Gly Cys Lys
385           390           395           400

Thr Ala Val Ser Asn Ile Val Met Ala Leu Ala Val Met Val Thr Leu
        405           410           415

Leu Leu Leu Thr Pro Leu Phe His Phe Thr Pro Leu Val Leu Ser
        420           425           430

Ser Ile Ile Ile Ser Ala Met Leu Gly Leu Ile Asp Tyr Asn Ala Ala
        435           440           445

Ile His Leu Trp His Val Asp Lys Phe Asp Phe Leu Val Cys Ile Ser
        450           455           460

Ala Tyr Ile Gly Val Val Phe Ala Asn Ile Glu Ile Gly Leu Val Leu
465           470           475           480

Ala Val Gly Leu Ser Leu Leu Arg Val Leu Leu Phe Ile Ala Arg Pro
        485           490           495

Arg Thr Leu Val Leu Gly Asn Ile Pro Asp Ser Met Ile Tyr Arg Asn
        500           505           510

Val Glu His Tyr Pro Asn Thr Asn Asn Val Pro Gly Val Leu Ile Leu
        515           520           525

Asp Ile Gly Ala Pro Ile Tyr Phe Ala Asn Ser Ser Tyr Leu Arg Glu
        530           535           540

Arg Ile Ser Arg Trp Ile Asp Glu Glu Asp Lys Leu Lys Ser Ser
545           550           555           560

Gly Glu Thr Thr Leu Gln Tyr Val Ile Leu Asp Met Gly Ala Val Gly
        565           570           575

Asn Ile Asp Thr Ser Gly Ile Ser Met Leu Glu Glu Val Lys Lys Asn
        580           585           590

Leu Asp Arg Arg Asp Tyr Lys Leu Val Leu Ala Asn Pro Gly Ala Glu
        595           600           605

Val Met Lys Lys Leu Asn Lys Ser Lys Phe Ile Glu Thr Leu Gly Gln
610           615           620

Glu Trp Ile Phe Leu Thr Val Gly Glu Ala Val Gly Ala Cys Asn Phe
625           630           635           640

Met Leu His Ser Cys Lys Pro Lys Ser Thr Thr Asp Glu Ala Ser Gln
        645           650           655

Lys Trp Ser Asn Asn Val
        660

<210> SEQ ID NO 7
<211> LENGTH: 8192
<212> TYPE: DNA
<213> ORGANISM: Nicotiana tabacum

<400> SEQUENCE: 7
atgaatggag aaagcgcagg acaggcata catagagtgg aaatcccacc accacaacct      60
tttttcaagt cactaaagaa tacagtgaag gaaactttat ttccagatga tccccttagg    120
caattcaaga accaaacacc ccttcgaaaa ttcatacttg gtcttcagta tttcttccca    180
atttttgaat ggggttctcg ttacaatttt gggttcttca atctgatct tattgctgga    240 attaccatag ctagtcttgc tattcctcag ggaataagct atgcaaaact tgccaacttg    300
ccacctattc ttggcctatg tgagtcttga tataattatt tttgtcggct ctaatatcat    360

```
gttaaagtgt gtaatcattt catccaaaac ttatgaggtg atatacacag ttcaacacct      420
taaatacaac aactcatgtc tttagtagtt ttggagtagc gcatgttgca tatagttaac      480
gggttcaagt gcactaaaac tttaaaaaaa aatattagac ttttgaacgt aaaattttaa      540
aaataaaata tgttcaataa tatgaatcta agggttgaat ccatctaatt tacatagatc      600
cgctattttt gtgttttgca gattcaagct ttgttccacc attagtgtac gcaataatgg      660
gcagttcaag agatttggca gtggggacag ttgctgttgg atcgcttcta atggcttcta      720
tgataggaaa tgaagttaat gcaactgaga atccagcact ttatcttcat cttgctttca      780
ctgccacatt ctttgctgga ttatttgaat tagctcttgg atttttcagg ttagtgtctc      840
tatttcatgt tagtacgttc ttaatttact atatcgcctg tactaaaata gtttgagcca      900
aggaagcagc tatcgatgct ggcattaggg taggttggtc tacgtcacac tcgttgggtg      960
cgacccttcc cgaactctac gtgaatgcgg gatgccttgt gcatcgggat gctcaatttt     1020
agcttaatta atttatggtt aattaatctt tcaggctggg atttatagtg gatttttctat    1080 cacatgcaac catagtagga tttatgggag gagcagctac agtggtgata ctacagcagc     1140
taaagggaat acttggtctt gaacatttta ctcatgccac agatgttgtc tctgtcttac     1200
gttctgtctt tacccaaact cagcaggtaa atttttttta ctctatcatg ttacttgaaa     1260
atctattata aataattatt ctgtaacaag tatgctttgt taacctatat aaattatgga     1320
gtaatatcat aagtaatttg ttatggcaag taaattaaac tatattataa tataaaagaa     1380
attaaatcta gtaaaagctt ctattctttt cgacaaaata aatggtaatt gttttcagta     1440
cttgttattt ctttctttct ttctcttttc ggttaaaagt taaatagaag tgcttttttc     1500
gtgttcaaaa gtaattcttg ctgatacaag acctttttt aattactttt tttttgttca      1560
tttcgttttc ccgttgaaga atcaaacttg tatagtgtcc aaatgagctt gagttggatt     1620
agtgttactc acttttatcc atttagtatt tgtttattta ttactccaag tacttatatt     1680
tgtaactttc tttaaatata ctctaatgat agccaattgg ttataaataa ctgcagtggc     1740
gatgggaaag tgcggtgcta ggattttgtt tccttttcta cctgatgatg gctaaatttt     1800
ttgtaagtat acacactgac tttgaccttt tgaaatgtga atagtatcca caagtcaaaa     1860
gcagtctact ataaaagtgg ataccctta gacttataat ggccaattgt gctttcctat      1920
ctttcctcat ataatttcat acctaacctc aacttttgtt aatttcttac tctttccaaa     1980
tatctttgat ggacactgac tttgctcctc gatttaacct actcccactc cgaaagttcc     2040
aacaaattaa agccaatgtc ttctatttct tgccccccc ccccaaaaaa aaacccggtg      2100
cacaaggcat tctgttttca tgcagggtcc gggaagggag gcatcccaag ggatgtgata     2160
tagacagcct accctatgca agcattaatg actacttcta cggcatgaac ccgtgatcta     2220
taggtcacat ggagataact tcatcctggc tccaaaactc ccttcacgtg gaaagaatat     2280
tgctccaaaa ctccccttt acataatttt tatatttttt tgatagaaaa ctactagtag      2340
tattctagta cttttataga aaaaattaca gagagtgtag tttaagaaag ttgctaatat     2400
atgcatgcat gcagagccaa aagagaccga agctgttctg gatttcagca atggcgccat     2460
tgacgtccgt catattggga actattctcg tttatgtcac ccacgctgaa aaacacggtg     2520
ttgcagtggt aagaaaaaaa tcacttataa taatgtattt aataaactgt cttatttaa      2580 tattgctaat taatcccatt gattatatag aagttaaact cgcgtgttag cttaagctct     2640
taaattcaag gacttcattt gactttagaa ttactcctac tagttactac cagtataaga     2700
acataaatcc tacctagctc caacgatttc ataattctac ccatcgaatt ccctttttag     2760
```

```
acatactata tactccaaca gacgtttgtt tgggacaatt ggacaaacaa cctactactg    2820
ccaaaattgg ttagccctga tacttctacg tttattagct gttcatattc attattggtg    2880
cattttaaag agacactttt gattgatagc ttcatttgtc ttaataaaaa ttggtcaagt    2940
tgacatttaa agacaaacaa gacaacgaaa atgaaatgaa aaaaagtttg tatttgtgtt    3000
tacatacttt gtcggtcacg ggaaaaaaaa agtaggtagt accatgaaaa ctttagcatg    3060
gcaggatttt tgtgaatgtt taattctaca cattataaaa taattttcac cccatttgat    3120
tactataaaa ataaatataa gcaactaccc acaataactg agatttataa cctgaaacat    3180
actcaacaat ttaaattaaa ctttagcgca ttaatataag taaagtttgt gcaaaggatt    3240
gttgtaataa ttgtggttgc tttatattat tgatcaatca ttggattctt attatgtgaa    3300
aatgaaaaat tggaacagat aggggagctg aagaaagggt taaatcctcc gtcaataatg    3360
gatctgtcat ttgggtcggc ctatatgaca actgctatca aaacaggaat agtcacgggt    3420
gtcatttctc ttgctgtaag cactcgatct gctttccaat ctcaaccttt gtcctctctc    3480
tgctgcaatt cctcctactt gcattacttt tcactatcta atgttctttt tttacgtcta    3540
tttacaattt caagaacaag catacaaaac atgtgtgcat ggacggatct tgataatgtt    3600
ccccgctttg aatttgaata caatattaga gtataaaact taaatttatt ttcattttta    3660
cttgtctatt atattaaaaa tatattttca ttttttacttg tccatttttag ctaatcaaga    3720 taaagacaat ctcttgcaaa aatacagggt aaggctgcgt acgatagacc cttgtggtcc    3780
ggtccttcct tggacctcgc gcataacgga ggcttagtgc accaggatgc cctttacttt    3840
acccgtatca ttaactgttc attccccgaa tcatttttca agactttttg aaatgttatc    3900
attattatgg gtaaaacagt aaaacaaact ttatttattt tttcttaaaa agagtgcaaa    3960
gtcaaaattg gataactgaa agtgaatgga gggagtaatt aatttgtaac tattccataa    4020
tttgttgctt cttgaggctt ctttggcgac caaaagtcac tagtaaaatt gcaattatag    4080 tataacatt tatacaatat cagtgtatat aacttcttgt catatatgta tgaatcaaaa    4140
ttctataaat tgtgtgcgaa ctttgaaggc cactttcagt gacaccgtaa acttacaagg    4200
ttatagacaa taagtgtatt tcgtatactt ataattgcat tatgtggcat agaatttttt    4260
taatatattt gaggctcttt ataacacact acactaaaat taaaacettt aatttattga    4320 tatggacagg aaggaatagc agtagggaga agctttgcaa tgttcaagaa ttaccatata    4380
gatggaaaca aagagatgat tgcttttggg atgatgaata ttgttggctc ctgcacctcc    4440
tgctacctca ctactggtat gttcctccat actactatgg ggccgtttgg cagaaggtat    4500
taaaaaaaat aatgcaagca ttagctttgt acattactaa actttgtttt ggtatatttt    4560
ttcaacatat gtataactaa tacttgtatt agttatacat catacttggt attagcctat    4620
gtataagtaa tgcatagaaa accatgacat tagtaatacc aaggctatta atgcaatgca    4680
ttagtatggt taaagacaaa attgtcctta agtcccctta aagctagaga atatggaggg    4740 cattttgta aacaactatt tttcttaaaa ttatgcaatg cattataatt tttaatacac    4800
cacaccaaac agtttataag aaataatatc tgcataacta atgcttgcat tactaactca    4860
tgcattacta atccttgcat tactaataca ctgtattctg cactattctt atactcctac    4920
caaacgaccc ctatatcata tatgacttgg ttattattgg gtattatcac ttttagcgcg    4980
gctatacagt gttattttct cgttattatt tccctttttct cttttatttc ctttatgggc    5040
cgaaagttga aatggattat tctcacttct tgtccattac tcaggaaaac gaacatccca    5100
```

```
tttgggccca taccacgtga ttgtatgtct ccacatgcct accaacaaaa ggaagaaaaa    5160
aaaagagaga gagagagaga gagagagaga gagagagaga gagagagaaa gaaagcctta    5220
agattaatgg gacagagatt ggaaaagagg aaacataatt acaccatatt atatgggaag    5280
gaatatatta aaaattggag gggtgaaagg taagaaacga gtggggttgt ctaggtttga    5340
gtcgtaatat gcgtaactta agggatatta tgttattgac aattccttgt aggaaaaaaa    5400
aaatagacaa attaaaagaa gaaagaatga ggaatgtagt aaggacattt caatttctta    5460
gcaaattaac attacattta acgtaaattt atggagtagt ttagtcaaat aagtttaaat    5520
ggagcaaaat gtgaacaggt ctgtgttttt taaaagacta agagcccgtt tggattggct    5580
taaaataagt ggcttttaag ttaattgctt gaaagcattt tataagtgct gaaacttatt    5640
ttataaataa acagttacgt gtttggataa aagtgctgaa actgaaaaaa aagctgatga    5700
agtgtttggt aaagaagtgc tcgtaagcac ttttttcttgt aaaatgact gaattatcct    5760 taaagttgtt aacattataa acaagatgat tactataata ttatatttttt tgttcatagc    5820 ttcaaacaga tgattgtttc attttttgtct tgtgtgtttg ctatttttttg ctgggttagt    5880 aaatgggaag atagatgagc tattgagcca attatttgta aaagttttcc tctttctcat    5940
tccaataaat caaccttttc tttaaactaa taaatcgacc acccaaaaat aaaaaattaa    6000
aaatagatcg caactaattc atctgcccctt taatttttttc cccacttaga ttgataaaag    6060
ttcttcgaat atgtaaaaat atttttactga aaaatatgag gggtgcgaaa agaaagaaat    6120
gaaaggaaaa gaaaagagg ggaaaataat gaatgaaagt gtaaagaaag aaacgaaagg    6180
aaaagagagg aaagttatgg aagaagacga agaagaaagc gagggtaatt tcgggattaa    6240
gaaaaattat aagggataag aatgtaatat atttggtcaa agcaatatgg cttttaagcc    6300
aatttcgaaa aaattgggtt ttccaactta ctggttttgg cttttttta agcagatttt    6360 aatttttttta aaccttttttt ttttgttgcc aaacacttcc acagattaaa aagtgctttt    6420
taccaacttt taagctcatc caaacaggct ctaacactac tgctttccct aaaaaataat    6480
tacatacaac tgtccacaat atgtggcatt agtaacttga aaaataagac agtcaacctt    6540
ctataagaag ttaaaatata ctgatagtgt aaatatatt tatgttgtag ggccattctc    6600
gcgatcagca gtgaacttta acgcaggatg caaaactgca gtatcaaaca tcgtcatggc    6660
gttggcagta atggtgacat tgttgttgct aacgccattg ttccacttca ctcccctcgt    6720
cgtcctgtcc tccattatca tctccgctat gctcggcctc attgattata atgctgccat    6780
tcatctctgg catgtcgaca aattcgactt cttggtctgc atcagtgctt atattggcgt    6840
tgtctttgcc aacattgaga ttggcttagt cttagccgta agtatcccctt atgttctatg    6900 cactaagtgt taaaaaaaat tacagtgtta aacttgaccg ataatgatat ggtttgactt    6960
ataaatatgt tgtttaatgg aaatgcaggt aggattatcg ttgctaaggg tgttacttttt    7020 tatagcaagg ccaaggacgt tggtacttgg taatatccca gattctatga tctacagaaa    7080
tgttgagcat taccccaaata caaacaacgt tccaggcgtt tcattcttg atattggagc    7140 ccctattttac ttcgctaatt ctagctatttt aagggagagg taattatttt ttgataaccg    7200
tgacgtctga atcagcttgc acacgtctcg actaattatg gttaattcaa atcttgttat    7260
aggatctcaa ggtggattga cgaagaggaa gacaagttaa aatttcagg agaaacaaca    7320 ttgcagtatg ttatacttga tatgggaggt tagttaattt atgcagtcta taatttcttt    7380
catcactcag tttatctttt tgaaataata gcaaaatcat taaaacgtag cacaagaaaa    7440
tttaaaactg aatttgagca ttgacagcta aaacattctt tgattggcag ctgtaggaaa    7500
```

```
cattgataca agtggaatta gcatgctcga agaagttaag aaaaatcttg atagaagaga    7560
ttacaaggtt ggcctcttat tttccgaata ttatttttt tccgcaacaa atatgttata    7620
aagataaatt gtgcaccata aagtagatct atcacgtagg atttaactta catacactaa    7680
aagtactacc gtcaggcctc tctataacag cggtcactat aaaagccaag ttttctcgc    7740 aactgatttt tatattatgt tatagtatat atcctctata acagcacttc actataacag    7800 ccaaaaaat atcagaacaa gcgagactgt tatagaaag tttgaccatt tttatacaat    7860
cagtgtttta taacttatta tagcaggtaa cctacattat aattcaggtt actaatcctg    7920
atcctgcttt ttatggacag tctgtgcata gaagataaat ttgtgtaaca tatggctttt    7980 tttttttgt ggcaatgcag cttgtgttgg caaatccagg agcagaggtg atgaaaaagt    8040
tgaacaagtc caaattcata gagacattag gacaagaatg gatctttcta acagtagggg    8100
aagctgtggg agcatgcaat tcatgcttc attcctgcaa accaaaatct acaacagatg    8160
atgcatccca aaatggagc aacaacgttt ga                                  8192
```

<210> SEQ ID NO 8
<211> LENGTH: 640
<212> TYPE: PRT
<213> ORGANISM: Nicotiana tabacum

<400> SEQUENCE: 8

```
Met Gly Asn Ala Asp Tyr Glu Tyr Pro Ser Ile Met Asn Gly Glu Ser
1               5                   10                  15

Ala Gly Thr Gly Ile His Arg Val Glu Ile Pro Pro Gln Pro Phe
            20                  25                  30

Phe Lys Ser Leu Lys Asn Thr Val Lys Glu Thr Leu Phe Pro Asp Asp
        35                  40                  45

Pro Leu Arg Gln Phe Lys Asn Gln Thr Pro Leu Arg Lys Phe Ile Leu
    50                  55                  60

Gly Leu Gln Tyr Phe Phe Pro Ile Phe Glu Trp Gly Ser Arg Tyr Asn
65                  70                  75                  80

Phe Gly Phe Phe Lys Ser Asp Leu Ile Ala Gly Ile Thr Ile Ala Ser
                85                  90                  95

Leu Ala Ile Pro Gln Gly Ile Ser Tyr Ala Lys Leu Ala Asn Leu Pro
            100                 105                 110

Pro Ile Leu Gly Leu Tyr Ser Ser Phe Val Pro Leu Val Tyr Ala
        115                 120                 125

Ile Met Gly Ser Ser Arg Asp Leu Ala Val Gly Thr Val Ala Val Gly
    130                 135                 140

Ser Leu Leu Met Ala Ser Met Ile Gly Asn Glu Val Asn Ala Thr Glu
145                 150                 155                 160

Asn Pro Ala Leu Tyr Leu His Leu Ala Phe Thr Ala Thr Phe Phe Ala
                165                 170                 175

Gly Leu Phe Glu Leu Ala Leu Gly Phe Phe Arg Leu Gly Phe Ile Val
            180                 185                 190

Asp Phe Leu Ser His Ala Thr Ile Val Gly Phe Met Gly Gly Ala Ala
        195                 200                 205

Thr Val Val Ile Leu Gln Gln Leu Lys Gly Ile Leu Gly Leu Glu His
    210                 215                 220

Phe Thr His Ala Thr Asp Val Val Ser Val Leu Arg Ser Val Phe Thr
225                 230                 235                 240

Gln Thr Gln Gln Ser Gln Lys Arg Pro Lys Leu Phe Trp Ile Ser Ala
```

```
                    245                 250                 255
Met Ala Pro Leu Thr Ser Val Ile Leu Gly Thr Ile Leu Tyr Val
            260                 265                 270

Thr His Ala Glu Lys His Gly Val Ala Val Ile Gly Glu Leu Lys Lys
            275                 280                 285

Gly Leu Asn Pro Pro Ser Ile Met Asp Leu Ser Phe Gly Ser Ala Tyr
            290                 295                 300

Met Thr Thr Ala Ile Lys Thr Gly Ile Val Thr Gly Val Ile Ser Leu
305                 310                 315                 320

Ala Glu Gly Ile Ala Val Gly Arg Ser Phe Ala Met Phe Lys Asn Tyr
                325                 330                 335

His Ile Asp Gly Asn Lys Glu Met Ile Ala Phe Gly Met Met Asn Ile
                340                 345                 350

Val Gly Ser Cys Thr Ser Cys Tyr Leu Thr Thr Gly Pro Phe Ser Arg
                355                 360                 365

Ser Ala Val Asn Phe Asn Ala Gly Cys Lys Thr Ala Val Ser Asn Ile
            370                 375                 380

Val Met Ala Leu Ala Val Met Val Thr Leu Leu Leu Leu Thr Pro Leu
385                 390                 395                 400

Phe His Phe Thr Pro Leu Val Val Leu Ser Ile Ile Ser Ala
                    405                 410                 415

Met Leu Gly Leu Ile Asp Tyr Asn Ala Ala Ile His Leu Trp His Val
                420                 425                 430

Asp Lys Phe Asp Phe Leu Val Cys Ile Ser Ala Tyr Ile Gly Val Val
            435                 440                 445

Phe Ala Asn Ile Glu Ile Gly Leu Val Leu Ala Val Gly Leu Ser Leu
    450                 455                 460

Leu Arg Val Leu Leu Phe Ile Ala Arg Pro Arg Thr Leu Val Leu Gly
465                 470                 475                 480

Asn Ile Pro Asp Ser Met Ile Tyr Arg Asn Val Glu His Tyr Pro Asn
                485                 490                 495

Thr Asn Asn Val Pro Gly Val Leu Ile Leu Asp Ile Gly Ala Pro Ile
            500                 505                 510

Tyr Phe Ala Asn Ser Ser Tyr Leu Arg Glu Arg Ile Ser Arg Trp Ile
    515                 520                 525

Asp Glu Glu Glu Asp Lys Leu Lys Phe Ser Gly Glu Thr Thr Leu Gln
    530                 535                 540

Tyr Val Ile Leu Asp Met Gly Ala Val Gly Asn Ile Asp Thr Ser Gly
545                 550                 555                 560

Ile Ser Met Leu Glu Glu Val Lys Lys Asn Leu Asp Arg Arg Asp Tyr
                565                 570                 575

Lys Leu Val Leu Ala Asn Pro Gly Ala Glu Val Met Lys Lys Leu Asn
                580                 585                 590

Lys Ser Lys Phe Ile Glu Thr Leu Gly Gln Glu Trp Ile Phe Leu Thr
            595                 600                 605

Val Gly Glu Ala Val Gly Ala Cys Asn Phe Met Leu His Ser Cys Lys
610                 615                 620

Pro Lys Ser Thr Thr Asp Asp Ala Ser Gln Lys Trp Ser Asn Asn Val
625                 630                 635                 640

<210> SEQ ID NO 9
<211> LENGTH: 4769
<212> TYPE: DNA
<213> ORGANISM: Nicotiana tabacum
```

<400> SEQUENCE: 9

```
atgggtaatg ctcactttga tgatcaatat tcacatcaaa aggtagaaat cccagcacca    60
aagccattct tgaagacact caaatcttgt gtgaaagaaa cactatttcc tgatgacccc   120
tttaggaaat tcaagaacca gtcacttacc aagaaacttg ctttgggttt gcagtatttt   180
gtccccatcc tcgattgggc tcctcgctat acgtttcaac ttttcaaagc tgattttatt   240
gctggaatca caattgctag tcttgctgtt cctcaaggga taagctatgc tggtttggct   300
aacttgcctc cagttattgg actttgtaag ttactattta tataaatata catgaattaa   360
tccatcaaat atctttgaaa tatactcgaa atcatgcatc tagctttgga catggaacta   420
gtacatacac aaggctagcc tctttccaac taactctagt cttttaaaata tactatatga   480
atttgacttt tatgcacctg caatgtcaag caaattaggc agataactcc tgcaggtcta   540
ggtaaaaaaa attatatcgt atcagtatat tttacaagtt aaacacttaa aatatacata   600
actataattg tgattataaa ggtattacgt gtcttgatat gtaagttaca aatgatacgt   660
acgtcgagtc catagcctga gcgcacgtac atggcacaat aaagttacta gtccagattt   720
agttaaaatag aagttttcat tgtggttgat ctgataaata tattttggaa atgcagattc   780
aagctttgtg ccaccgatgg tatatgcgat gttgggaagt tcgaagcatt tggcaatagg   840
gaatgtggca gttccatcgc ttctcatttc tgcaatgctt ggccgagtcg ttaatcctca   900
cgataatccc aagctttatc ttcagttggt atttactgct actttctttg ctggagtttt   960
ccaagcttcc ttaggcttgt taaggtcaga agtcttcatt ttttcgtta gatttagtgt  1020
cgagtcaaat tgcaacggca gtagacctaa ttaatttgta ttttatctga tggtgatata  1080
ggctaggatt catagtggac tttctatcgc atgcaacaat attagggttc atgggaggag  1140
cagccacagt agtgtgctta cagcagctga aaggaattct tggacttgtt catttcaccc  1200
atgaaactga tattgtcagt gtcatgcgct ccatctttag ccaattacac caggttcctt  1260
cactatctca tttttatttt taaatctttt ttctcaaaat aataagttat acttagcctc  1320
caatatttta cgtacggtct tttcttttc tttcttatac gttttgtta attatttgct  1380
acagtggaga tgggaaagtg gagtcctagg ttgttgtttt ctcttcttcc tcttgttgac  1440
cagatatttt gtaagtaaat taattaattt taaatttata ctcgctttcg gcagatttgt  1500
tacgtattta tagtttataa ataaatatgt cactattgtg ttatatccgt aaattaatca  1560
tgatactatc cattaagcat gtgatacaat tgtagacttc cttcaccttta agattaactc  1620
atactcgtgt ataacatatt tctaatgatt cctagaattg ttttcaccat atttcaattg  1680
ctaataacct cattaattat ttcataccat tatcttcagt tcaagttcac tagattaatt  1740
tactaatgga cttgtttatt tattgtgtgg tgtaattcct ataccagagc aaaaagaagc  1800
cagctttctt ctggataagt tgtatggcgc ctctaacatc tgtgatcttg ggaagtgttc  1860
ttgtttattt cacccatgct gaaaaaaatg gggttcaagt ggtaattaat ttctccacag  1920
tcgaaattaa atttatatct ttatatttca ctgccaaatt ttattttttta tttctataca  1980
tgatgtgaat ataatttatg gtgagtgacc agtgacgtcc acatgttggt cccttagtat  2040
gatatcgatt aacttttttct agcgatgttt gtattaatta aagacagta cgtacatgcg  2100
gctaacctgt gaatatgttt ggacttttgt tggatttaat tttctcagat tgggcacttg  2160
aaaaaaggga taaatccacc atcgtattct gaactggcat ttagctcgca gtatcttaca  2220
actgccatta agactggaat cgtcactggt gtcatcgcca tggctgtaag tacaatatgt  2280
```

```
ctccaattgt taatttattt ttatttactt tttatctgtc atactaattc ggattcggtc    2340
ttagactttc tgatttatat aagattctca tgacctcatt ctatagtctg aagatactt     2400 gggtcaaaaa ggttagaaaa gaaaaaaaat agacgggaat aaatgttcat aaattatgct    2460
tgaagaaact aattaaaata gtgatatact tcttgtctct ttgtcatttt atcgtacaca    2520
cggcaatata ttggtgacta gctcatagac tacaactagc agcttttagt taaagaatta    2580
actatataca taaatttatt cttacattat tgatgtacat aagttaaact ctttaaattc    2640
ctctttgtgc ttttttttgat tctgaatttt atataaatgt ggtatatgtc agacacacca   2700
acttgtttag gactgcgaag ttgtgcttgt tatatatata tatatatata tatatatata    2760
tatatatata tatatatata tatatatcac acatgaagga ataacagttg gcgtatatta    2820
tttattgctt acctatttta accgatgaaa ttaaacaata caggaaggaa tagcagttgg    2880
aaggagtttc gccatagtgg agaactatca cattgatgga aacaaagaaa tgattgcctt    2940
tgggatgatg aacattgctg gttcttgcac ctcttgctac ttaaccacag gtactctttc    3000
actcaaaact aacatctctc agtccactca attacttaaa ttaaaattag ttggtgaatg    3060
tatagtatat gtaaattta tattaatata tgtgttatta gtgtataatc taattatacc     3120
ggctagaaaa agtgacactg aaactaaaca gctatttgtg taaagatccc atttttttc     3180 cttcaagttt ctagagatgg gagtgaacaa ttgaaaacat aattaagtaa ataagaattt    3240 gcttttagt aggttaagtt tgtaaatgag atggtcatat aattcaacat aatcatgagt     3300
tctcgtctca ccaccacaca ttacgagaat tttcacgaaa aaagaattag gctcacaact   3360 aggggggtgtg ctgaacacat tctttaattt agttgtctgt ttgcgtaatt tttcttctaa   3420
tattaacatc tttttttcc tttttcagga ccattttcac gtacggcagt gaatttcaat     3480
gcaggatgca agacagcagt gtccaacata gtaatggcaa cagcagtgat gataacattg    3540
ttgttgctaa caccattgtt ccattacaca ccccttgttg tgctttcctc cattataatt    3600
tcagccatgc taggcatcat tgactataat gctgctatcc acctttggaa agttgacaaa    3660
tacgatttcc tcgtttgcat tagttccttc attggagttg tctttggtag cgttgaagtt    3720 ggcctaaatag tcgcggtaag tagcatacat ttttaatagg atttaaaaat ctttctgcgc   3780
actcagctta atttaatttt tatgataact atgttttcgt gtgtgattca ggtggcaatg    3840 tcttttacttta ggatacttct ctttgtagca aggccaaaga catttgtctt aggtaaaata  3900
ccaaactcca tgacctatag aaacactgaa caatattcag cagcaagcag tgttcctgga    3960
attctcatca tacacattga tgccccaatc tattttgcaa atgcaagtta tttgagggaa    4020
aggtaactac aacacccaca ttttcatctc aatttagtga ttgatgactt caacacaata    4080
gttagtcact tttatatcga tgggttcttg aaatatctta ggatttcaag atggatagat    4140
gaagaagaag agaagcaaag gactttatct gagattgagc tgcaatatgt catattggat    4200
atgagtggta agtgttaatt caagataaaa aaaacttcgg ttttttttt cttttttaat    4260 agttaatgtt ttactgctga catcaatcct cttaaatgca gctgttggaa acatcgatac    4320
aagtggaatt agtatgcttg aggaagtgaa gagaaatgca gataggcgat gtctaaaggt    4380
acaaatatct gacaaattat tagtagtgaa acatcatatt accatttata gttgtctcta    4440
cgggaacagt tcagtgatta ataaaccaca actcgaactt tagtatcacg agcttgaatt    4500
cagtgacatc ttgtccacta ctacccagtt gattttcctt tttctttct tttttattc     4560 aattgttcaa tttgtagctt ttattggcaa atcctgaggg ggaagtgatg aagaagctgg    4620
ataagtcaaa tttcattgac acaattggga aggaatggat ctatttaaca gttggggagg    4680
```

-continued

```
ctgttaatgc atgcaattat attcttcaca cttgcaagtt tcaatccaag agaattgaat    4740
cttcaacaat cccagacgat aacgtatga                                      4769
```

<210> SEQ ID NO 10
<211> LENGTH: 653
<212> TYPE: PRT
<213> ORGANISM: Nicotiana tabacum

<400> SEQUENCE: 10

```
Met Gly Asn Ala His Phe Asp Asp Gln Tyr Ser His Gln Lys Val Glu
1               5                   10                  15

Ile Pro Ala Pro Lys Pro Phe Leu Lys Thr Leu Lys Ser Cys Val Lys
            20                  25                  30

Glu Thr Leu Phe Pro Asp Asp Pro Phe Arg Lys Phe Lys Asn Gln Ser
        35                  40                  45

Leu Thr Lys Lys Leu Ala Leu Gly Leu Gln Tyr Phe Val Pro Ile Leu
    50                  55                  60

Asp Trp Ala Pro Arg Tyr Thr Phe Gln Leu Phe Lys Ala Asp Phe Ile
65                  70                  75                  80

Ala Gly Ile Thr Ile Ala Ser Leu Ala Val Pro Gln Gly Ile Ser Tyr
                85                  90                  95

Ala Gly Leu Ala Asn Leu Pro Pro Val Ile Gly Leu Tyr Ser Ser Phe
            100                 105                 110

Val Pro Pro Met Val Tyr Ala Met Leu Gly Ser Ser Lys His Leu Ala
        115                 120                 125

Ile Gly Asn Val Ala Val Pro Ser Leu Leu Ile Ser Ala Met Leu Gly
    130                 135                 140

Arg Val Val Asn Pro His Asp Asn Pro Lys Leu Tyr Leu Gln Leu Val
145                 150                 155                 160

Phe Thr Ala Thr Phe Phe Ala Gly Val Phe Gln Ala Ser Leu Gly Leu
                165                 170                 175

Leu Arg Leu Gly Phe Ile Val Asp Phe Leu Ser His Ala Thr Ile Leu
            180                 185                 190

Gly Phe Met Gly Gly Ala Ala Thr Val Val Cys Leu Gln Gln Leu Lys
        195                 200                 205

Gly Ile Leu Gly Leu Val His Phe Thr His Glu Thr Asp Ile Val Ser
    210                 215                 220

Val Met Arg Ser Ile Phe Ser Gln Leu His Gln Trp Arg Trp Glu Ser
225                 230                 235                 240

Gly Val Leu Gly Cys Cys Phe Leu Phe Leu Leu Thr Arg Tyr
                245                 250                 255

Phe Ser Lys Lys Lys Pro Ala Phe Trp Ile Ser Cys Met Ala Pro
            260                 265                 270

Leu Thr Ser Val Ile Leu Gly Ser Val Leu Val Tyr Phe Thr His Ala
        275                 280                 285

Glu Lys Asn Gly Val Gln Val Ile Gly His Leu Lys Lys Gly Ile Asn
    290                 295                 300

Pro Pro Ser Tyr Ser Glu Leu Ala Phe Ser Ser Gln Tyr Leu Thr Thr
305                 310                 315                 320

Ala Ile Lys Thr Gly Ile Val Thr Gly Val Ile Ala Met Ala Glu Gly
                325                 330                 335

Ile Ala Val Gly Arg Ser Phe Ala Ile Val Glu Asn Tyr His Ile Asp
            340                 345                 350
```

```
Gly Asn Lys Glu Met Ile Ala Phe Gly Met Met Asn Ile Ala Gly Ser
            355                 360                 365

Cys Thr Ser Cys Tyr Leu Thr Thr Gly Pro Phe Ser Arg Thr Ala Val
        370                 375                 380

Asn Phe Asn Ala Gly Cys Lys Thr Ala Val Ser Asn Ile Val Met Ala
385                 390                 395                 400

Thr Ala Val Met Ile Thr Leu Leu Leu Thr Pro Leu Phe His Tyr
                405                 410                 415

Thr Pro Leu Val Val Leu Ser Ser Ile Ile Ser Ala Met Leu Gly
            420                 425                 430

Ile Ile Asp Tyr Asn Ala Ala Ile His Leu Trp Lys Val Asp Lys Tyr
        435                 440                 445

Asp Phe Leu Val Cys Ile Ser Ser Phe Ile Gly Val Val Phe Gly Ser
        450                 455                 460

Val Glu Val Gly Leu Ile Val Ala Val Ala Met Ser Leu Leu Arg Ile
465                 470                 475                 480

Leu Leu Phe Val Ala Arg Pro Lys Thr Phe Val Leu Gly Lys Ile Pro
            485                 490                 495

Asn Ser Met Thr Tyr Arg Asn Thr Glu Gln Tyr Ser Ala Ala Ser Ser
            500                 505                 510

Val Pro Gly Ile Leu Ile Ile His Ile Asp Ala Pro Ile Tyr Phe Ala
        515                 520                 525

Asn Ala Ser Tyr Leu Arg Glu Arg Ile Ser Arg Trp Ile Asp Glu Glu
        530                 535                 540

Glu Glu Lys Gln Arg Thr Leu Ser Glu Ile Glu Leu Gln Tyr Val Ile
545                 550                 555                 560

Leu Asp Met Ser Ala Val Gly Asn Ile Asp Thr Ser Gly Ile Ser Met
            565                 570                 575

Leu Glu Glu Val Lys Arg Asn Ala Asp Arg Arg Cys Leu Lys Leu Leu
            580                 585                 590

Leu Ala Asn Pro Gly Gly Glu Val Met Lys Lys Leu Asp Lys Ser Asn
            595                 600                 605

Phe Ile Asp Thr Ile Gly Lys Glu Trp Ile Tyr Leu Thr Val Gly Glu
610                 615                 620

Ala Val Asn Ala Cys Asn Tyr Ile Leu His Thr Cys Lys Phe Gln Ser
625                 630                 635                 640

Lys Arg Ile Glu Ser Ser Thr Ile Pro Asp Asp Asn Val
            645                 650

<210> SEQ ID NO 11
<211> LENGTH: 6063
<212> TYPE: DNA
<213> ORGANISM: Nicotiana tabacum

<400> SEQUENCE: 11
atcactttat ctaaaactat ccctctgaaa ctctgagtac tcttcattta taatcttgac      60
ccttactcta tatttattgt ataaatttca taaccttctt agagaagtgc acccttccat     120
ttaatgaaat ttctctatta attttctcat tttcccattt cacatattta cttggatacg     180
tacctatcac aaaatctcac cttattttca tcagaatctt atccaacttc actttctcca     240
tcttttggac agtaacactt actgtcacct tccatcaaat tccaagtcat tagtaagttt     300
acttgtttga tattaagtag attttgtgat ctccttttta gattatatat gtccatattt     360
tacctataaa tttagtcagc ccaaagtctc tagtcaagga aaatattca acacaagtac      420
```

```
tgttacatttt ccatttcatt ctctcttctt agaagttatt cttttcattt caactcaatt    480
accaagtgga gtagtactag tttgtttggt agctgtcttt ttgaaagttg atggaaacat    540
aaataggagg aaaggaacca cagacatttt gcattccaaa ccattctcat taattagacc    600
aaaatggaac caaataatga gaacagagtt atagacataa cagcaatgga ggtacacaaa    660
gttgtttctc cacctcatag aagcaccttt caaaaactca aaaacaggct taaggaaacc    720
ttttttcctg atgacccttt acgtcaattc aaaggtcagc cattgaaaca gaagctaatt    780
cttggtgctc agtatgtttt tcccatacta gaatgggtc ctaattacag cttcaagttg     840
ttcaaatctg atataatctc tggcctcacc attgctagcc ttgcaattcc tcaggttggt    900
tctttttttg tctcaggcct aaccctttc ttgattttgt cttttaaagt tatggtaatt     960
tcctctttta ctattgccac tttgctaact cttttccttt tttctttttg cagggaatt    1020 agctatgcaa aactagctaa cttacctcca attgttggcc tttgtacgtg ttttcattgt   1080
catcgtgcaa ttatttttc atttttaat ttgttggggg tacttaagta actttttttt    1140
ttcttttcat ttgcttttgg agtgtagatt caagttttgt tcctcctctt gtttatgctg   1200
ttcttggaag ctcaagggat cttgcagtag ggccagtttc aattgcatca cttgttttag   1260
gatcaatgct aagagaagtg gtgtccccaa ctaaagatcc aatcttgttc cttcaacttg   1320 cttttctcttc tacttctttt gctggccttt tccaagcttc tttaggcttt ttgaggtaat   1380
tcccactttt tttatttcat tcttctcaat tacaaattac aaaggaggtg cacaaggttc   1440
gaggacgagc tgcaccccag ggtgtaatgc atatagccca cgctaataca agtattagtg   1500
cttgtttcca cggctcgaat tcgtgactta taggtcacgc ggagacaaac atatcgttgt   1560
tcccaggctt cccttctact attacctaaa aagaaaaag ggtaattaca agtgtaagat    1620
ccattttagt aatctatttt ttttgatatt tttgggaaat tgcagactcg gttttattat   1680
tgattttctt tcaaaagcaa cactgattgg attcatggct ggagctgctg ttatagtgtc   1740
actgcagcaa cttaagagtc ttcttggaat cacaaatttt accaagcaaa tggcgatagt   1800
ccctgtttta agttctgttt tccatagaac taatgaggtt actactgtct ttttaaccct   1860
ctcttatgta ctattgtatg taaatgtaac tgataattat actttaattt tccttcttg    1920 gcattatata aaactaaatt tgtctttagt cttcagcttt ttggagcaaa ttcagagaat   1980
tgtatttgtc tgtgtctttt ctacatttgg attataagaa tattcacgtg ctgacttggc   2040
tttcgatgcc atcatgtgaa ttcaagattc ttaaaatcaa gtactaattt tctccccatt   2100
tgttgatttg ttttacaaa ttttgatgtg gataagttca ttataatgta aaatcgtcta    2160
aaaaggtgat tacgatctga taataattga ttgtagaaaa acaaataata gcaatttaat   2220
ggtgttgtag aatgagaaac atgtagtcaa caagaaaaaa tgttgaccaa tctagcatat   2280
tataagctag taatgcaccg aattttttta aatttcttc caaaatagtt tgacaaaaat    2340
taattcttta ttaactattg aaactttata atagacatcc acacacacct tctaattttc   2400
aatttgagtt agactacatt caagtcaagg cagccaaggg tttgagtgtt tgaccttatg   2460
atgttatgtt tttttttttt ttaccccgtc acttttggat cttactaatt tgggagtaac   2520
atgcttcctc ttaaaggcga ctctattttc aagactacaa acccgagagc atgtttatca   2580
ctttgagggg cttaactgaa atagtaacat tttatatggt atatatgcag tggtcttggc   2640
aaactatact aatggcattc tgcttcttgg tgttcctcct attgaccaga cacattgtaa   2700
gtgctctttt ccagttttgt ttttctttct tcacttttaa aatgtaagga aaagtcatat   2760
ttagttgacg taatttactg aattctaaat gcaaaagtca ttatatagtt cacaattaag   2820
```

```
tacgtaataa tgtattgact gtggtttcaa agttttgttg cacaatagat aagttcgaat    2880
ttcttaaatt ccttaccaat tagtagaaag gaaagatgtc ctatactata ttacctttcg    2940
ggagacattt ctaagttcta accatttttc gaatctgcaa actgtgcatt tttcatgttc    3000
tttgtaaatc tctatatatt tttgaatgaa aatttaataa taactttaaa aattggttaa    3060
ctagataatc tgaaataaag aaacataacc ataatcttaa gaaaatttgt aactgatatc    3120
atagactcat gagagaaaaa tacttaatac ttttgactta caaacatttt ctttctgttt    3180
ttgggatgaa catttttttat acagtcaaac atctctataa tagtcttatt tgtaccgaat    3240
tgttttagct cttatcgcgc aatgatgtta tagtgaacat atattataac atagcatgaa    3300
aattagttcc ataaaaaaag ttgaattttta tagtgaatgg ttgttatata gtgatattgt    3360
tatagaaaaa tctcactgta tatcttgtta ttaacatgac aaacttttgg gtgcagagca    3420
tgagaaagcc aaagctattt tgggtttcag caggagcccc tcttctttct gtcattatct    3480
ctacacttct ggtctttgca atgaaaggtc aaaagcatgg tatcagcatt gtatgtttct    3540
aaacccaaga aaatttatct atacttctaa gttctaatat ctattactac tatatttcta    3600
aatctttata tttatgtaat tatttttcctt ttgtcttttg gtagattggc aaattacaag    3660
aagggttgaa ccctccttca tggaacatgt tacatttcag tggaagctac ttgggacttg    3720
taatcaaaac tggaattgtc actggcatcc tttcacttac tgtaattttt ttctcttttta    3780 cctatctttt tatgaaaaag gaaagaact caaattatga ttttggaata taacatctat    3840
aaataatgac tataaagctc atagcaggca ctaatatctt tagacacaaa gaaaacttag    3900
gacccgtttg tccataaatc ttttttttccg aattttaaaa aaaaatatg tttatccata    3960 aaattttgaa agtttttgaa gattttttga aaatgagttt ttccaaattt ttgggagaaa    4020
cttttttccc cactcacaaa actgcaatat tttttcaagt gaaatgtatg ttcaaacata    4080
attttcaaat ttcaaatacc atttttcaac ttaactccaa atagtatttg ttttcaaaat    4140 tacaatttttt atatccaaac ggctacttaa tgtgttgtgt aaaaaaaaaa ttaggaagga    4200
attgcagtgg ggaggacttt tgctgcttta aagaactacc aagtggatgg aaacaaagag    4260
atgattgcta ttggggtcat gaacatagtt ggttcctcaa cttcctgcta tgtcacaact    4320
ggtacaataa acctttcaac agtttagaat ttctaaaact gtttgttgct ttattttcac    4380
tgtttcttga gccaagggtc tatcggaaac aatctctcta cctttaaaag gtaggggtaa    4440
ggtctatgtg cacattacct tccccagaca tcacttgtgg aattacactg ggtttgtttg    4500
ttgttgatgt agaatctcta aaactgcaga atcctttaaa tgtaactcta cattttcagg    4560
tgcattctct aggtcagcag tgaatcacaa tgcaggaagc aaaactgcag tttctaacat    4620
agtaatggca gtgacagtaa tggtgacact ccttttccta atgcccctct tccaatatac    4680
tcccaatgtt gtgctcggag ccataatcgt cactgctgtc gttggcctaa tcgacatccc    4740
agctgcttac caaatctgga agatcgataa attcgatttc ctagtcttgt tatgtgcatt    4800
cttcggagtc atcttcattt ctgttcagaa tggtcttgcc attgcagtaa gctccctctc    4860
aagttccttt cctttttttct taacagtctc tccacctgca caaggtaggg gtaagactgc    4920
gtacacacta ccctccccac cccacttgtg ggattatact gggtatgttg ttgttgttac    4980
gttacttggt ttttgacttt cttttataat gaatttcaga ttggaatatc aatttttaaag    5040 gtgttgctgc aaattacaag gcccaaaaca gtaatgttag gaaatatacc tggtactggg    5100
atttatagaa atcttgatca ttataaggag gctatgagtg ttcctggttt tctcattttta    5160
```

-continued

```
agtattgaag ctccaatcaa ctttgccaat gcaacttatc ttaaagaaag gttagtatta    5220
gttgaactgc tgcattgacc attctatctt tcattttttct tcttttttc ttctttccat    5280 atttatttag gtcttttttat ttgccccgaa aaaaaggat ttcaagatgg atagaagact    5340
acgatgcaga gggagaaaaa aacaagaaag agtcggggct tagatttgtg gtccttgatt    5400
tgtctggtaa gttcatagag acgttctcaa tattgtcatt tattcccaat ttggcataac    5460
tggcaaagtt gttgtcatgt gaccaggagg tcacaggttc gagccgtgaa aataatatct    5520
tgcagaaatg caggataaga ttgcgtacaa taaatcattg tggtccggct cttctccggg    5580
tcccgcgcat agtggaagtt tagtgcaccg ggctgcccct accctactt ttagataata     5640 ccaagaaaca gtcaggacat caagaaattc ccataaataa aacaaattaa tttcaacttg    5700
aaaagtgatt gtggcttgtt ttttattctt cagctgtgac tgccattgat acaagtggag    5760
tctcattgtt caaggatttg agtatggcaa tggaaaagaa aggccttgag gcaagtgtac    5820
tttagctttt agaagaccat tttgtttct atttattctg atattatgtg agtatttatt     5880
tccttaatga ttttggcatt gcagtttgta ttggtgaatc caataggaga agtactggaa    5940
aaattacaga gggctgatga aactaaagat atgatgagac cagattgcct ttttttaaca    6000
gtcgaagaag cagtagcttc actttcctca acaataaaat atcaaatacc agacaatgtt    6060
tga                                                                 6063
```

<210> SEQ ID NO 12
<211> LENGTH: 658
<212> TYPE: PRT
<213> ORGANISM: Nicotiana tabacum

<400> SEQUENCE: 12

```
Met Gly Asn Ala Asp Phe Asp Asp Gln Tyr Ser His Gln Lys Val Glu
1               5                   10                  15

Ile Pro Pro Lys Pro Phe Leu Lys Thr Leu Lys Ser Cys Val Lys
            20                  25                  30

Glu Thr Leu Phe Pro Asp Asp Pro Phe Arg Lys Phe Lys Lys Gln Pro
            35                  40                  45

Leu Thr Lys Lys Leu Thr Leu Gly Leu Gln Tyr Phe Val Pro Ile Leu
        50                  55                  60

Asp Trp Ala Pro Arg Tyr Thr Phe Gln Leu Phe Lys Ala Asp Phe Ile
65                  70                  75                  80

Ala Gly Ile Thr Ile Ala Ser Leu Ala Val Pro Gln Gly Ile Ser Tyr
                85                  90                  95

Ala Gly Leu Ala Asn Leu Pro Pro Val Ile Gly Leu Tyr Ser Ser Phe
            100                 105                 110

Val Pro Pro Met Val Tyr Ala Met Leu Gly Ser Ser Lys His Leu Ala
            115                 120                 125

Ile Gly Asn Val Ala Val Pro Ser Leu Leu Ile Ser Ala Met Leu Gly
        130                 135                 140

Arg Val Val Asn Pro His Asp Asn Pro Lys Leu Tyr Leu Gln Leu Val
145                 150                 155                 160

Phe Thr Ala Thr Phe Phe Ala Gly Val Phe Gln Ala Ser Leu Gly Leu
                165                 170                 175

Leu Arg Leu Gly Phe Ile Val Asp Phe Leu Ser His Ala Thr Ile Leu
            180                 185                 190

Gly Phe Met Gly Gly Ala Ala Thr Val Val Cys Leu Gln Gln Leu Lys
        195                 200                 205
```

```
Gly Ile Leu Gly Leu Val His Phe Thr His Glu Thr Asp Ile Val Ser
        210                 215                 220

Val Met Arg Ser Ile Phe Ser Gln Leu His Gln Trp Arg Trp Glu Ser
225                 230                 235                 240

Gly Val Leu Gly Cys Cys Phe Leu Phe Phe Leu Leu Leu Thr Arg Tyr
                245                 250                 255

Phe Ser Lys Lys Lys Pro Ala Phe Phe Trp Ile Ser Cys Met Ala Pro
                260                 265                 270

Leu Thr Ser Val Ile Leu Gly Ser Val Leu Val Tyr Phe Thr His Ala
            275                 280                 285

Glu Lys Asn Gly Val Gln Val Ile Gly His Leu Lys Lys Gly Ile Asn
290                 295                 300

Pro Pro Ser Tyr Ser Glu Leu Ala Phe Ser Ser Gln Tyr Leu Thr Thr
305                 310                 315                 320

Ala Ile Lys Thr Gly Ile Val Thr Gly Val Ile Ala Met Ala Glu Gly
                325                 330                 335

Ile Ala Val Gly Arg Ser Phe Ala Ile Val Glu Asn Tyr His Ile Asp
                340                 345                 350

Gly Asn Lys Glu Met Ile Ala Phe Gly Met Met Asn Ile Ala Gly Ser
            355                 360                 365

Cys Thr Ser Cys Tyr Leu Thr Thr Gly Pro Phe Ser Arg Thr Ala Val
    370                 375                 380

Asn Phe Asn Ala Gly Cys Lys Thr Ala Ala Ser Asn Ile Val Met Ala
385                 390                 395                 400

Thr Ala Val Met Ile Thr Leu Leu Leu Leu Thr Pro Leu Phe His Tyr
                405                 410                 415

Thr Pro Leu Val Val Leu Ser Ser Ile Ile Ser Ala Met Leu Gly
                420                 425                 430

Ile Ile Asp Tyr Asn Ala Ala Ile His Leu Trp Lys Val Asp Lys Tyr
        435                 440                 445

Asp Phe Leu Val Cys Ile Cys Ser Phe Ile Gly Val Val Phe Ser Ser
    450                 455                 460

Val Glu Val Gly Leu Ile Val Ala Val Ala Met Ser Leu Leu Arg Ile
465                 470                 475                 480

Leu Leu Phe Val Ala Arg Pro Lys Thr Phe Val Leu Gly Lys Ile Pro
                485                 490                 495

Asn Ser Met Thr Tyr Arg Asn Thr Glu Gln Tyr Ser Ala Ala Ser Arg
                500                 505                 510

Val Pro Gly Val Leu Ile Ile His Ile Asp Ala Pro Ile Tyr Phe Ala
            515                 520                 525

Asn Ala Ser Tyr Leu Arg Glu Arg Ile Ser Arg Trp Ile Glu Glu Glu
530                 535                 540

Glu Glu Glu Glu Glu Glu Lys Gln Arg Thr Ser Thr Glu Ile Glu
545                 550                 555                 560

Leu Gln Tyr Val Ile Leu Asp Met Ser Ala Val Gly Asn Ile Asp Thr
                565                 570                 575

Ser Gly Ile Ser Met Leu Glu Glu Val Lys Arg Asn Ala Asp Arg Arg
            580                 585                 590

Cys Leu Lys Leu Val Leu Ala Asn Pro Gly Gly Glu Val Met Lys Lys
        595                 600                 605

Leu Asp Lys Ser Asn Phe Ile Asp Lys Ile Gly Lys Glu Trp Ile Tyr
610                 615                 620

Leu Thr Val Gly Glu Ala Val Asn Ala Cys Asn Tyr Ile Leu His Thr
```

Cys Lys Phe Gln Ser Glu Arg Ile Glu Ser Ser Thr Ile Pro Asp Asp
625                 630                 635                 640

Asn Val

<210> SEQ ID NO 13
<211> LENGTH: 5935
<212> TYPE: DNA
<213> ORGANISM: Nicotiana tabacum

<400> SEQUENCE: 13

| | | | | | |
|---|---|---|---|---|---|
| atggaaccaa | ataatgagaa | tagagttata | gacataacag | caatggaggt | acacaaagtt | 60 |
| gtttctccac | cccatagaag | cactttccaa | aaactcaaaa | ataggcttaa | agaaaccttt | 120 |
| ttccctgatg | acccttttacg | tcaattcaaa | ggtcagccat | taaaacagaa | gctagttctt | 180 |
| ggtgctcagt | atgttttttcc | tatactagaa | tggggtccta | attacagctt | caagttgttc | 240 |
| aaatctgata | tagtctctgg | cctcaccatt | gctagccttg | caattcctca | ggttggttct | 300 |
| ttttttttgta | tcttattgat | ggtactgtta | tattgcctct | tttcctcctc | ttgagtcgag | 360 |
| ggttttttcgg | aaacagcctc | tctatcgctc | gggtaggggt | aaagtttgtg | tacacactaa | 420 |
| cctccccaca | ccccattagt | tagatttcac | tggtcgtcgt | tgttgttggt | tcttttatcg | 480 |
| tctcaggcct | aaccattttc | ttgattttgt | cttctaaagt | tatggtaatt | ttcttttttca | 540 |
| ctattgttac | tttgctaact | ctttccttct | tttcttttct | tcttttttggc | agggaattag | 600 |
| ctatgcaaaa | ctagctaact | tacctccaat | tgttggtctt | tgtgagtgtt | ttcattgtca | 660 |
| tcatgcattt | ttttttgttg | gggtacttaa | gtaattaact | tttttttttta | atttgctttt | 720 |
| tggaaagtag | attcaagttt | tgttcctcct | cttgtttatg | ctgttcttgg | aagttcaagg | 780 |
| gatcttgcag | tagggccagt | ttcaattgca | tcacttgttt | taggatcaat | gttgagagaa | 840 |
| gtggtgtccc | caactaaaga | tccaatcttg | ttccttcaac | ttgctttctc | ttctactttc | 900 |
| tttgctggcc | ttttccaagc | ctctttaggc | tttttgaggt | attcccactt | tttttatttc | 960 |
| attcttctga | agtacaaatt | ccctaaaagg | aaaaaaaaat | ggacagttcg | gtgcacaagg | 1020 |
| tatcatgtgt | tcacccaggg | cccggaaaag | ggtcgaactc | caagggggtgt | gatgtatata | 1080 |
| cagaggcgta | cccaggattt | gaaggtcgct | ggtgcacttt | tggttcaac | caaaatctgc | 1140 |
| tttgtatata | gggtatccac | actatttttct | aaagacatat | acatgtatac | atggagtttt | 1200 |
| tgccgaactt | tagtgtgccg | gtgaccccctc | tacctattgt | ataggtccgc | ctctgtgtat | 1260 |
| atagcctact | cttatacaag | tattagtggt | tacgtccacg | gctcgaactc | gcgacatacg | 1320 |
| aatcacacgg | agaccatttt | atccttactc | caaggcttcc | tactatgatt | acctaaaaag | 1380 |
| aaaaaggaca | attacaagtg | tagatattgg | ttttggttag | taatctattt | ttttttaatat | 1440 |
| ttttgggaaa | ttgcagactg | gttttatta | ttgatttct | ttcaaaagca | acactgattg | 1500 |
| gattcatggc | tggagctgct | gttatagtgt | cactgcagca | actcaagagt | cttcttggta | 1560 |
| tcacaaattt | taccaagcaa | atggcgatag | tccctgttct | aagttctgtt | ttccacagaa | 1620 |
| ctaatgaggt | tattactgtc | ttttttacccct | cttcttatct | actattgtat | gtaaatgtaa | 1680 |
| ctgataatta | ctttttttct | ttcttggaat | tatataaaac | taaatttgtc | tttagttttc | 1740 |
| agcttttttgg | agcaaattca | gagaattgta | tttgtctgtg | tcttttctac | atttggatta | 1800 |
| taagaatatt | cacgtgctga | cttggctttc | gattgccatc | atgtgaattc | aagattctta | 1860 |
| aaatcaagta | ctaattgtct | ccccatttgt | tattattttta | ttttaattta | attttacaaa | 1920 |

```
ttttgatgtg gataagttca ttatcatgca aaatcgtcta aaaagttgat tagaatctga    1980
aaataattga ttgtagaaaa acaaataata gcaatttaat ggtgttgtag aatgagaaac    2040
atgtagtcaa caagaaaaaa tgttgaccag tgtagcatat atattataag ctagtaatgc    2100
accgaatttt taaaaatttc ttccaaaatt gtttgacaaa aattaattct ttattaagta    2160
tggaaacttt ataaaataca tccccacaaa ccttctaatt ctcaatttga gttgactaca    2220
ttcaagtcaa ggcagtcaag ggcttgagtg tttgacctca tgatgtccaa aaagttttta    2280
aagcaattcg gagagaaaaa aaaaggtgc ttcactttaa tgtttatttt ttatatttca    2340
tcatgtccga cttgtgagtt cgagtcttcc caagagcaag gtgggaagtt cttggaggga    2400
aggatgccgg gggtctattt ggaaacagtc tctctaccct agggtagggg taaggtctgc    2460
gtacacacta tcctccccag accacactaa atgggattat actgggttgt tgttgttgtt    2520
gttgtatact ccctctaaag atgactccat ttacaagact acaaatccaa aagcatattt    2580
atctctttga ggggcttaac tgaaataata aggaaaatg acattatata atcgctttta    2640
aaataataat aataaaaata atgtatattt ttttttttg tatatataac attttatatg    2700
gtatatatgc agtggtcttg gcaaactata ctaatggcat tctgcttctt ggggtttctc    2760
ctattgacca gacacattgt aagtgctctt ttccactttt gttttttcct tttatttttc    2820
tttcttcact tttgttatag tgaatatatt ataacatagc atgaatattc gttacacaaa    2880
agctctgacc tttatagaaa atgattgtta tataacgata ctattataaa aatgtctaac    2940
ggtatatctt ggtattatca tgataaattt gggtgcagag catgagaaag ccaaaactat    3000
tttggatatc agcaggagcc cctcttcttt ctgtcattat ctctacactt ctggtatttg    3060
caatgaaagg tcagaagcat ggtatcagca ttgtaagttt ctaaacccaa ggaaattcat    3120
ctatactttt aatatctatt atatttctaa accttgatat ttatgtaatt attttccttt    3180
tgtcatttgg tagattggca aattacaaga agggttgaac cctccttcat ggaacatgtt    3240
acatttcagt ggaagctact tgggacttgt aatcaaaact ggaattatca ctggcatcct    3300
ttcacttact gtaattttt tttttctct tttacctatc tttttatgaa aaaggaaaag    3360
aactcaaatt atgagttttt ggaatataac atccataaat aatgactata agctctatag    3420
caggctctaa tatctttaga cacagaaaac ttaggacctg tttgtccata tccttttttt    3480 ccttctttt ttcggaactt tttaaaaaaa atgtgtttgt ccataaaatt ttggaagttt    3540
ttggaaattt ttcgaaaata aattttttcaa aaaccaataa gttttttccc gctttcaaaa    3600
ctgcaatatt ttattcaaac ataattttaa tttcaaatat tatttttcaa cttaactcca    3660
atattattat tattattatt attattatta ttttcaaaac ttacagtttt tatgtccaaa    3720
cgcctactta atgtgttgtg ttaaaaaaaa aaaaaaatag gaaggaattg cagtggggag    3780
gacttttgct gctttaaaga actaccaagt ggatggaaac aaagagatga ttgctattgg    3840
ggtcatgaac atagttggtt cctcaacttc ctgctatgtc acaactggta cataaatctt    3900
tcaacatttt agaattccta aaactgtttg tttgcttat tttcactgtt tcttgagccg    3960
atggtctatc ggaaacaatc tctctacgtt tagaaggtag gagtaaagtc tgcgtacaca    4020
ttaccctccc caacccccac ttgtgtgatt acactgggtt tgttattgtt acagtagaat    4080
ttctaaaact gcaaacatg tgttaaatgt aactctaaat tttcaggtgc attctctagg    4140
tcagcagtga atcataatgc aggaagcaaa actgcagttt ctaacatagt aatggcagtg    4200
acagtgatgg tgacactcct tttcctaatg cctctcttcc aatatactcc caatgttgtg    4260
ctcggagcca tcatcgtcac tgctgttgtt ggcctgatcg acgtcccagc tgcttaccaa    4320
```

```
atctggaaga tcgataaatt cgatttccta gtcttgttat gtgcattctt cggagtcatc    4380
ttcatctctg ttcaaaatgg tcttgccatt gcagtaagct ccctctcaag ttccttttcg    4440
tttttttctta acagtctctc cgcttgcaca aggtaggggt aagggtgcgt acacaccact   4500
ctcctcagat cccacttgtg gaattatacg gggtatattg ttgttacgtt acttggtttt    4560
tgactttctt ttataatgaa tttcagattg gaatatcaat tttaaaggtg ttgctgcaaa    4620
ttacaaggcc aaaaacagta atgttaggaa atatacctgg gactggaatt tatagaaatc    4680
ttgatcatta taaagaggct atgagtgttc ctggttttct cattttaagt attgaagctc    4740
caatcaactt tgccaatgca acttatctta agaaaggtt agtactagtt gaactgctgc     4800
attgaccatt ctgtcattca tttttttttt ttttttttc ttccttccat atttatttag     4860
gtatttttat ttgccaaaaa aaggatttca agatggatag aagactatga tgcagaggga   4920
ggaaaaaaca agaaacagtc agggcttaga tttgtggtcc ttgatttgtc tggtaagttc    4980
atagagacat ggttctcaat attgtcattt aatcccaatt tggcgtaatt ggtaaagttg    5040
ctgccatgtg actaagtggt cacgggttcg agccatggaa acagcctcct gcagaaatgc    5100
agcgtaaggt tgtgtacaat aaacctctgt ggtccggctc ttccctggac cttgcgcata    5160
gcgggagctt agtgcaccgg gctgcccttc cccctactt ttggataata ccaagaaaca     5220
gtcaggacat caagaaattc ccacaaataa aacaaattaa tttaccaaga aacagtcagg    5280
acatcaagaa attcccacaa ataaaacaaa ctaatttcaa cttgacaagt aattgtggat    5340
tgttttttta atcttcagct gtgactgcca ttgatacaag tggagtctca ttgttcaagg    5400
atttgagtat ggcaatggaa aagaaaggct ttgaggtaag tgtactttag cttttagagt    5460
cactatttct ttccaacaac aacaacaaca acaacccagt ataatcccac ttagtggggt    5520
ctggggagcg tagtgtgtac gcagaccta ccctaccct agggtagaga gactgttcc        5580
aaatagaccc ccggcatcct tccctccaag aacttcccac cttgctcttg gagagactcg    5640
aactcacagc ctttccttcc ctccaacaat ccactatttc tttccaaatg aagtcaaaat    5700
cctcaagacc attttgtttt ctatttattc tgatattatg tgagtattta tttccttaat    5760
gattttggca ttgcagtttg tattggtgaa tccaatagga gaagtactgg aaaaattaca    5820
gagggctgat gaaactaaag atatgatgag accagattgc ctctttttaa cagtcgaaga    5880
agcagtagct tcactttcct caacaataaa ataccaaata ccagacaatg tttga         5935
```

<210> SEQ ID NO 14
<211> LENGTH: 648
<212> TYPE: PRT
<213> ORGANISM: Nicotiana tabacum

<400> SEQUENCE: 14

Met Glu Pro Asn Asn Glu Asn Arg Val Ile Asp Ile Thr Ala Met Glu
1               5                   10                  15

Val His Lys Val Val Ser Pro His Arg Ser Thr Phe Gln Lys Leu
            20                  25                  30

Lys Asn Arg Leu Lys Glu Thr Phe Phe Pro Asp Asp Pro Leu Arg Gln
        35                  40                  45

Phe Lys Gly Gln Pro Leu Lys Gln Lys Leu Val Leu Gly Ala Gln Tyr
    50                  55                  60

Val Phe Pro Ile Leu Glu Trp Gly Pro Asn Tyr Ser Phe Lys Leu Phe
65                  70                  75                  80

Lys Ser Asp Ile Val Ser Gly Leu Thr Ile Ala Ser Leu Ala Ile Pro

```
                    85                  90                  95
Gln Gly Ile Ser Tyr Ala Lys Leu Ala Asn Leu Pro Pro Ile Val Gly
                100                 105                 110
Leu Tyr Ser Ser Phe Val Pro Pro Leu Val Tyr Ala Val Leu Gly Ser
                115                 120                 125
Ser Arg Asp Leu Ala Val Gly Pro Val Ser Ile Ala Ser Leu Val Leu
                130                 135                 140
Gly Ser Met Leu Arg Glu Val Val Ser Pro Thr Lys Asp Pro Ile Leu
145                 150                 155                 160
Phe Leu Gln Leu Ala Phe Ser Ser Thr Phe Phe Ala Gly Leu Phe Gln
                165                 170                 175
Ala Ser Leu Gly Phe Leu Arg Leu Gly Phe Ile Ile Asp Phe Leu Ser
                180                 185                 190
Lys Ala Thr Leu Ile Gly Phe Met Ala Gly Ala Ala Val Ile Val Ser
                195                 200                 205
Leu Gln Gln Leu Lys Ser Leu Leu Gly Ile Thr Asn Phe Thr Lys Gln
                210                 215                 220
Met Ala Ile Val Pro Val Leu Ser Ser Val Phe His Arg Thr Asn Glu
225                 230                 235                 240
Trp Ser Trp Gln Thr Ile Leu Met Ala Phe Cys Phe Leu Gly Phe Leu
                245                 250                 255
Leu Leu Thr Arg His Ile Ser Met Arg Lys Pro Lys Leu Phe Trp Ile
                260                 265                 270
Ser Ala Gly Ala Pro Leu Leu Ser Val Ile Ile Ser Thr Leu Leu Val
                275                 280                 285
Phe Ala Met Lys Gly Gln Lys His Gly Ile Ser Ile Ile Gly Lys Leu
                290                 295                 300
Gln Glu Gly Leu Asn Pro Pro Ser Trp Asn Met Leu His Phe Ser Gly
305                 310                 315                 320
Ser Tyr Leu Gly Leu Val Ile Lys Thr Gly Ile Ile Thr Gly Ile Leu
                325                 330                 335
Ser Leu Thr Glu Gly Ile Ala Val Gly Arg Thr Phe Ala Ala Leu Lys
                340                 345                 350
Asn Tyr Gln Val Asp Gly Asn Lys Glu Met Ile Ala Ile Gly Val Met
                355                 360                 365
Asn Ile Val Gly Ser Ser Thr Ser Cys Tyr Val Thr Thr Gly Ala Phe
                370                 375                 380
Ser Arg Ser Ala Val Asn His Asn Ala Gly Ser Lys Thr Ala Val Ser
385                 390                 395                 400
Asn Ile Val Met Ala Val Thr Val Met Val Thr Leu Leu Phe Leu Met
                405                 410                 415
Pro Leu Phe Gln Tyr Thr Pro Asn Val Val Leu Gly Ala Ile Ile Val
                420                 425                 430
Thr Ala Val Val Gly Leu Ile Asp Val Pro Ala Ala Tyr Gln Ile Trp
                435                 440                 445
Lys Ile Asp Lys Phe Asp Phe Leu Val Leu Leu Cys Ala Phe Phe Gly
                450                 455                 460
Val Ile Phe Ile Ser Val Gln Asn Gly Leu Ala Ile Ala Ile Gly Ile
465                 470                 475                 480
Ser Ile Leu Lys Val Leu Leu Gln Ile Thr Arg Pro Lys Thr Val Met
                485                 490                 495
Leu Gly Asn Ile Pro Gly Thr Gly Ile Tyr Arg Asn Leu Asp His Tyr
                500                 505                 510
```

```
Lys Glu Ala Met Ser Val Pro Gly Phe Leu Ile Leu Ser Ile Glu Ala
            515                 520                 525

Pro Ile Asn Phe Ala Asn Ala Thr Tyr Leu Lys Glu Arg Ile Ser Arg
        530                 535                 540

Trp Ile Glu Asp Tyr Asp Ala Glu Gly Gly Lys Asn Lys Lys Gln Ser
545                 550                 555                 560

Gly Leu Arg Phe Val Val Leu Asp Leu Ser Ala Val Thr Ala Ile Asp
                565                 570                 575

Thr Ser Gly Val Ser Leu Phe Lys Asp Leu Ser Met Ala Met Glu Lys
            580                 585                 590

Lys Gly Phe Glu Phe Val Leu Val Asn Pro Ile Gly Glu Val Leu Glu
        595                 600                 605

Lys Leu Gln Arg Ala Asp Glu Thr Lys Asp Met Met Arg Pro Asp Cys
    610                 615                 620

Leu Phe Leu Thr Val Glu Glu Ala Val Ala Ser Leu Ser Ser Thr Ile
625                 630                 635                 640

Lys Tyr Gln Ile Pro Asp Asn Val
                645

<210> SEQ ID NO 15
<211> LENGTH: 5460
<212> TYPE: DNA
<213> ORGANISM: Nicotiana tabacum

<400> SEQUENCE: 15
```

| | |
|---|---|
| atggaaccaa ataatgagaa cagagttata gacataacag caatggaggt acacaaagtt | 60 |
| gtttctccac ctcatagaag cacctttcaa aaactcaaaa acaggcttaa ggaaaccttt | 120 |
| tttcctgatg acccttacg tcaattcaaa ggtcagccat tgaaacagaa gctaattctt | 180 |
| ggtgctcagt atgtttttcc catactagaa tggggtccta attcagctt caagttgttc | 240 |
| aaatctgata taatctctgg cctcaccatt gctagcctg caattcctca ggttggttct | 300 |
| ttttttgtct caggcctaac cctttcttg attttgtctt ttaaagttat ggtaatttcc | 360 |
| tcttttacta ttgccactt gctaactctt tccttttttt cttttggca gggaattagc | 420 |
| tatgcaaaac tagctaactt acctccaatt gttggccttt gtacgtgttt tcattgtcat | 480 |
| cgtgcaatta ttttttcatt ttttaatttg ttggggggta cttaagtaact tttttttttc | 540 |
| ttttcatttg cttttggagt gtagattcaa gttttgttcc tcctcttgtt tatgctgttc | 600 |
| ttggaagctc aagggatctt gcagtagggc cagtttcaat tgcatcactt gttttaggat | 660 |
| caatgctaag agaagtggtg tccccaacta agatccaat cttgttcctt caacttgctt | 720 |
| tctcttctac tttctttgct ggccttttcc aagcttcttt aggcttttg aggtaattcc | 780 |
| cacttttttt atttcattct tctcaattac aaattacaaa ggaggtgcac aaggttcgag | 840 |
| gacgagctgc accccagggt gtaatgcata tagcccacgc taatacaagt attagtgctt | 900 |
| gtttccacgg ctcgaattcg tgacttatag gtcacgcgga gacaaacata tcgttgttcc | 960 |
| caggcttccc ttctactatt acctaaaaaa gaaaagggt aattacaagt gtaagatcca | 1020 |
| ttttagtaat ctattttttt tgatatttt gggaaattgc agactcggtt ttattattga | 1080 |
| ttttctttca aaagcaacac tgattggatt catggctgga gctgctgtta gtgtcact | 1140 |
| gcagcaactt aagagtcttc ttggaatcac aaatttttacc aagcaaatgg cgatagtccc | 1200 |
| tgttttaagt tctgttttcc atagaactaa tgaggttact actgtctttt taaccctctc | 1260 |
| ttatgtacta ttgtatgtaa atgtaactga taattatact ttaattttcc tttcttggca | 1320 |

```
ttatataaaa ctaaatttgt ctttagtctt cagcttttg gagcaaattc agagaattgt    1380
atttgtctgt gtcttttcta catttggatt ataagaatat tcacgtgctg acttggcttt    1440
cgatgccatc atgtgaattc aagattctta aaatcaagta ctaattttct ccccatttgt    1500
tgatttgttt ttacaaattt tgatgtggat aagttcatta taatgtaaaa tcgtctaaaa    1560
aggtgattac gatctgataa taattgattg tagaaaaaca ataatagca atttaatggt     1620 gttgtagaat gagaaacatg tagtcaacaa gaaaaaatgt tgaccaatct agcatattat    1680
aagctagtaa tgcaccgaat ttttttataa tttcttccaa aatagtttga caaaaattaa    1740
ttctttatta actattgaaa ctttataata gacatccaca cacaccttct aattttcaat    1800
ttgagttaga ctacattcaa gtcaaggcag ccaagggttt gagtgtttga ccttatgatg    1860
ttatgttttt ttttttttta ccccgtcact tttggatctt actaatttgg gagtaacatg    1920
cttcctctta aaggcgactc tattttcaag actacaaacc cgagagcatg tttatcactt    1980
tgagggcctt aactgaaata gtaacatttt atatggtata tatgcagtgg tcttggcaaa    2040
ctatactaat ggcattctgc ttcttggtgt tcctcctatt gaccagacac attgtaagtg    2100 ctctttttcca gtttttgtttt tctttcttca cttttaaaat gtaaggaaaa gtcatattta   2160
gttgacgtaa tttactgaat tctaaatgca aaagtcatta tatagttcac aattaagtac    2220
gtaataatgt attgactgtg gtttcaaagt tttgttgcac aatagataag ttcgaatttc    2280
ttaaattcct taccaattag tagaaaggaa agatgtccta tactatatta cctttcggga    2340
gacatttcta agttctaacc atttttcgaa tctgcaaact gtgcattttt catgttcttt    2400
gtaaatctct atatatttt gaatgaaaat ttaataataa ctttaaaaat tggttaacta    2460
gataatctga aataaagaaa cataaccata atcttaagaa aatttgtaac tgatatcata    2520
gactcatgag agaaaaatac ttaatacttt tgacttacaa acatttttctt tctgttttg    2580 ggatgaacat tttttataca gtcaaacatc tctataatag tcttatttgt accgaattgt    2640
tttagctctt atcgcgcaat gatgttatag tgaacatata ttataacata gcatgaaaat    2700
tagttccata aaaaaagttg aattttatag tgaatggttg ttatatagtg atattgttat    2760
agaaaaatct cactgtatat cttgttatta acatgacaaa cttttgggtg cagagcatga    2820
gaaagccaaa gctatttgg gtttcagcag gagcccctct tctttctgtc attatctcta    2880
cacttctggt ctttgcaatg aaaggtcaaa agcatggtat cagcattgta tgttctaaa    2940 cccaagaaaa tttatctata cttctaagtt ctaatatcta ttactactat atttctaaat    3000
cttatatttt atgtaattat tttccttttg tcttttggta gattggcaaa ttacaagaag    3060
ggttgaaccc tccttcatgg aacatgttac atttcagtgg aagctacttg ggacttgtaa    3120
tcaaaactgg aattgtcact ggcatccttt cacttactgt aatttttttc tcttttacct    3180 atcttttat gaaaaggaa aagaactcaa attatgattt tggaatataa catctataaa    3240
taatgactat aaagctcata gcaggcacta atatctttag acacaaagaa aacttaggac    3300
ccgtttgtcc ataaatcttt ttttccgaat tttaaaaaaa aatatgtttt atccataaaa   3360
ttttgaaagt ttttgaagat tttttgaaaa tgagttttc caattttgt ggagaaactt     3420 ttttccccac tcacaaaact gcaatatttt ttcagtgaa atgtatgttc aaacataatt    3480
ttcaaatttc aaataccatt tttcaactta actccaaata gtatttgttt tcaaaattac    3540 aattttata tccaaacggc tacttaatgt gttgtgtaaa aaaaaaatta ggaaggaatt    3600
gcagtgggga ggacttttgc tgctttaaag aactaccaag tggatggaaa caagagatg    3660
```

```
attgctattg gggtcatgaa catagttggt tcctcaactt cctgctatgt cacaactggt    3720
acaataaacc tttcaacagt ttagaatttc taaaactgtt tgttgcttta ttttcactgt    3780
ttcttgagcc aagggtctat cggaaacaat ctctctacct ttaaaaggta ggggtaaggt    3840
ctatgtgcac attccttcc ccagacatca cttgtggaat tacactgggt ttgtttgttg     3900
ttgatgtaga atctctaaaa ctgcagaatc ctttaaatgt aactctacat tttcaggtgc    3960
attctctagg tcagcagtga atcacaatgc aggaagcaaa actgcagttt ctaacatagt    4020
aatggcagtg acagtaatgg tgacactcct tttcctaatg cccctcttcc aatatactcc    4080
caatgttgtg ctcggagcca taatcgtcac tgctgtcgtt ggcctaatcg acatcccagc    4140
tgcttaccaa atctggaaga tcgataaatt cgatttccta gtcttgttat gtgcattctt    4200
cggagtcatc ttcatttctg ttcagaatgg tcttgccatt gcagtaagct ccctctcaag    4260
ttccttttcct tttttcttaa cagtctctcc acctgcacaa ggtaggggta agactgcgta    4320
cacactaccc tccccacccc acttgtggga ttatactggg tatgttgttg ttgttacgtt    4380
acttggtttt tgactttctt ttataatgaa tttcagattg gaatatcaat tttaaaggtg    4440
ttgctgcaaa ttacaaggcc caaaacagta atgttaggaa atatacctgg tactgggatt    4500
tatagaaatc ttgatcatta taaggaggct atgagtgttc ctggttttct cattttaagt    4560
attgaagctc caatcaactt tgccaatgca acttatctta agaaaggtt agtattagtt      4620
gaactgctgc attgaccatt ctatctttca ttttcttct tttttcttc tttccatatt       4680
tatttaggtc ttttatttg ccccgaaaaa aaggatttc aagatggata aagactacg        4740
atgcagaggg agaaaaaaac aagaaagagt cggggcttag atttgtggtc cttgatttgt    4800
ctggtaagtt catagagacg ttctcaatat tgtcatttat tcccaatttg gcataactgg    4860
caaagttgtt gtcatgtgac caggaggtca caggttcgag ccgtgaaaat aatatccttgc   4920
agaaatgcag ataagattg cgtacaataa atcattgtgg tccggctctt ctccgggtcc     4980
cgcgcatagt ggaagtttag tgcaccgggc tgcccttacc cctactttta gataatacca    5040
agaaacagtc aggacatcaa gaaattccca taaataaaac aaattaattt caacttgaaa    5100
agtgattgtg gcttgttttt tattcttcag ctgtgactgc cattgataca agtggagtct    5160
cattgttcaa ggatttgagt atggcaatgg aaaagaaagg ccttgaggca agtgtacttt    5220
agcttttaga agaccatttt gttttctatt tattctgata ttatgtgagt atttatttcc    5280
ttaatgattt tggcattgca gtttgtattg gtgaatccaa taggagaagt actggaaaaa    5340
ttacagaggg ctgatgaaac taagatatg atgagaccag attgccttt tttaacagtc      5400
gaagaagcag tagcttcact ttcctcaaca ataaaatatc aaataccaga caatgtttga    5460
```

<210> SEQ ID NO 16
<211> LENGTH: 648
<212> TYPE: PRT
<213> ORGANISM: Nicotiana tabacum

<400> SEQUENCE: 16

```
Met Glu Pro Asn Asn Glu Asn Arg Val Ile Asp Ile Thr Ala Met Glu
1               5                   10                  15

Val His Lys Val Val Ser Pro Pro His Arg Ser Thr Phe Gln Lys Leu
            20                  25                  30

Lys Asn Arg Leu Lys Glu Thr Phe Phe Pro Asp Asp Pro Leu Arg Gln
        35                  40                  45

Phe Lys Gly Gln Pro Leu Lys Gln Lys Leu Ile Leu Gly Ala Gln Tyr
    50                  55                  60
```

```
Val Phe Pro Ile Leu Glu Trp Gly Pro Asn Tyr Ser Phe Lys Leu Phe
 65                  70                  75                  80

Lys Ser Asp Ile Ile Ser Gly Leu Thr Ile Ala Ser Leu Ala Ile Pro
                 85                  90                  95

Gln Gly Ile Ser Tyr Ala Lys Leu Ala Asn Leu Pro Pro Ile Val Gly
            100                 105                 110

Leu Tyr Ser Ser Phe Val Pro Pro Leu Val Tyr Ala Val Leu Gly Ser
            115                 120                 125

Ser Arg Asp Leu Ala Val Gly Pro Val Ser Ile Ala Ser Leu Val Leu
130                 135                 140

Gly Ser Met Leu Arg Glu Val Val Ser Pro Thr Lys Asp Pro Ile Leu
145                 150                 155                 160

Phe Leu Gln Leu Ala Phe Ser Ser Thr Phe Phe Ala Gly Leu Phe Gln
                165                 170                 175

Ala Ser Leu Gly Phe Leu Arg Leu Gly Phe Ile Ile Asp Phe Leu Ser
            180                 185                 190

Lys Ala Thr Leu Ile Gly Phe Met Ala Gly Ala Ala Val Ile Val Ser
            195                 200                 205

Leu Gln Gln Leu Lys Ser Leu Leu Gly Ile Thr Asn Phe Thr Lys Gln
210                 215                 220

Met Ala Ile Val Pro Val Leu Ser Ser Val Phe His Arg Thr Asn Glu
225                 230                 235                 240

Trp Ser Trp Gln Thr Ile Leu Met Ala Phe Cys Phe Leu Val Phe Leu
                245                 250                 255

Leu Leu Thr Arg His Ile Ser Met Arg Lys Pro Lys Leu Phe Trp Val
            260                 265                 270

Ser Ala Gly Ala Pro Leu Leu Ser Val Ile Ile Ser Thr Leu Leu Val
            275                 280                 285

Phe Ala Met Lys Gly Gln Lys His Gly Ile Ser Ile Ile Gly Lys Leu
290                 295                 300

Gln Glu Gly Leu Asn Pro Pro Ser Trp Asn Met Leu His Phe Ser Gly
305                 310                 315                 320

Ser Tyr Leu Gly Leu Val Ile Lys Thr Gly Ile Val Thr Gly Ile Leu
                325                 330                 335

Ser Leu Thr Glu Gly Ile Ala Val Gly Arg Thr Phe Ala Ala Leu Lys
            340                 345                 350

Asn Tyr Gln Val Asp Gly Asn Lys Glu Met Ile Ala Ile Gly Val Met
            355                 360                 365

Asn Ile Val Gly Ser Ser Thr Ser Cys Tyr Val Thr Thr Gly Ala Phe
            370                 375                 380

Ser Arg Ser Ala Val Asn His Asn Ala Gly Ser Lys Thr Ala Val Ser
385                 390                 395                 400

Asn Ile Val Met Ala Val Thr Val Met Val Thr Leu Leu Phe Leu Met
                405                 410                 415

Pro Leu Phe Gln Tyr Thr Pro Asn Val Val Leu Gly Ala Ile Ile Val
            420                 425                 430

Thr Ala Val Val Gly Leu Ile Asp Ile Pro Ala Ala Tyr Gln Ile Trp
            435                 440                 445

Lys Ile Asp Lys Phe Asp Phe Leu Val Leu Cys Ala Phe Phe Gly
            450                 455                 460

Val Ile Phe Ile Ser Val Gln Asn Gly Leu Ala Ile Ala Ile Gly Ile
465                 470                 475                 480
```

```
Ser Ile Leu Lys Val Leu Leu Gln Ile Thr Arg Pro Lys Thr Val Met
                485                 490                 495

Leu Gly Asn Ile Pro Gly Thr Gly Ile Tyr Arg Asn Leu Asp His Tyr
            500                 505                 510

Lys Glu Ala Met Ser Val Pro Gly Phe Leu Ile Leu Ser Ile Glu Ala
        515                 520                 525

Pro Ile Asn Phe Ala Asn Ala Thr Tyr Leu Lys Glu Arg Ile Ser Arg
    530                 535                 540

Trp Ile Glu Asp Tyr Asp Ala Glu Gly Glu Lys Asn Lys Lys Glu Ser
545                 550                 555                 560

Gly Leu Arg Phe Val Leu Asp Leu Ser Ala Val Thr Ala Ile Asp
                565                 570                 575

Thr Ser Gly Val Ser Leu Phe Lys Asp Leu Ser Met Ala Met Glu Lys
            580                 585                 590

Lys Gly Leu Glu Phe Val Leu Val Asn Pro Ile Gly Glu Val Leu Glu
        595                 600                 605

Lys Leu Gln Arg Ala Asp Glu Thr Lys Asp Met Met Arg Pro Asp Cys
    610                 615                 620

Leu Phe Leu Thr Val Glu Glu Ala Val Ala Ser Leu Ser Ser Thr Ile
625                 630                 635                 640

Lys Tyr Gln Ile Pro Asp Asn Val
                645

<210> SEQ ID NO 17
<211> LENGTH: 4249
<212> TYPE: DNA
<213> ORGANISM: Nicotiana tabacum

<400> SEQUENCE: 17
atgggattaa gttcaaacag ggtagaagat ttatcaggcc atgcatgcaa tgaaacaatt      60
gtcacaatct ctactactac tactactaca gaattacaaa tatcaagtaa tccaccattt     120
gaagtacaca gagtttgctt accaccacac aaaaccaccc ttcaaaaact taggcaaagg     180
ttgttggaag tatttttccc agatgatcca ctgcacaaat tcaagaacca aacatggtta     240
atgaagttgg ttttgggtct tcagtttttc ttccctgttt ttgagtgggg tcctcagtat     300
aatcttaaac tactaagggc tgatataatt tctgggctca caattgctag ccttgctatc     360
ccacaaggaa ttagctatgc aaaacttgct aatttgccac ctattgttgg cttatgtaag     420
taaataacca cacttgtcat tttcttcttt aaaatctaat ttgcttttga tcccttaatt     480
ttagaatatg aatttgattt ttaagtgata gaattgttcg ttttttatcat ttactaacaa     540 ttttttgtca gttgtattgg aatgaaatgg ggcagaatag agctgaattg atgtaaaata     600
catatagcca actccaactc gtttggggtt gaagcataat tattgaataa ggttttttcc     660
atagttaaaa ccagttgtta attaatcaat atttgataat taattttaat tcttaagttt     720
aaaaatcggt taagattatg aaaatttatc tggggtctac tggtctattc attgaaggca     780
gaggtgcatg caagattata agatcagtgg atatgaatat tgttgtcttt tgtgaattgc     840
gacatgcagt tcagacttc ctataaatac ataatttcta gaaatttccg catatatatg     900
taatttgagt aaaaaatgat gcacccgctg tttgtaaagt atacagtcta tgttgaagag     960
taaatgtgtg cttaatcgaa tacggtactt tacttatttt gtaaataaaa atcacactat    1020
attcaatata gttatttact aatctaagag tggaaatatt aatggatatg atgatgcaga    1080
ttcaagcttt gtgccaccat tgatctattc agttttgggg agttcgaaac acttagcagt    1140
```

```
tggtccggtc tcgatagctt cacttgttat gggcacaatg ctgagtgaag cagtttctta    1200
cactgaagag cctgttcttt accttcagtt ggcttttaca gctacccttt ttgccggact    1260
gtttcaggct tcactagggt ttttcaggta ttaattctct tgaagcaaga aacacttaca    1320
caattaggtc acttaaaagg tagttaatat actgccatta actctggata acctggaata    1380
aattataagt aaccttctat gaaatgttaa attacattga ccctgtcagt tgatataact    1440
taagtccata tgttagtcgt tctcatccac ttgaaaattg gtgcaaaagt tgttaagtcg    1500
actttctaat ggactcgtta ttatttattc aactaaaaag agaggaataa tttataattc    1560
tagcataaca ttccccattc caccatcaaa gttaccgtta attaagtaat ggactacagt    1620
agctaagtgg aaacaaactt ttggaaagat atcccaaaag aatcatttag aaacattggg    1680
cacttccact aaaaacagca agaaaacaga gaagaaacat ggaaagggac agaggatttt    1740
tacgcgccat ataaaactgg actctagatt tttatgcaca atatgaaact aacaaatata    1800
gctggtgaaa agaaaaaaga tttcaaggtt gacataatga cttttgttac tcttattttg    1860
tttgatcact cccaaagctt tcgactttac aattctaatg tttatgtaat aacttgacca    1920
agagtatgca tctctgtctt tagccatata accacagtgt taaacttttta aagatgtcac    1980 atgacccata agtcaagaga gaatttgaat tttgcatagc attcaaatgc ttacatttcc    2040
ggactatcct tcttggccac acttgatcgc tattattgac ttttatgtat caatattgcg    2100
ttacttctaa attagttggg tcggctatat taatcctgta tacccactcc attttatgcg    2160
agtccatttc attctatctt tatgttttta agtaatctaa ggtcctcaaa gatttacttt    2220
caagaattaa aacttttgc catgtgttta tatttatttt agagctcggt tagttcaaat    2280
gtcaagcgac ttaaagttta tggtttgcag gttaggattt atcattgatt ttctgtcgaa    2340
ggcgactttg gttggcttca tggctggtgc agcagtcatt gtttcattgc aacaactgaa    2400
agggttgtta gggatagtcc acttcacaag ccagatgcaa ataattcctg ttttgtcttc    2460
tgttttccag cacaaagatg aagtaagaaa agcttctttt tcaatattga actcctctaa    2520
gatataagat tgtggaaaaa ttaactatgt tgtgcactg atgcaaatca ttatttagta    2580
atttaactct tctatatctc taccttaccc ggtaggggta aggtctttat atgcactacc    2640
ctccccaaac tccacatgtg ggattagact gggtcttttg ttgttgttgt tgttgtaact    2700
cttctatatc tatttgcagt ggtccttgca aaccattgtt atgggtgtct gttttctcgc    2760
cttcctactg accactcggc aaattgtaag tgtttggttt atttcagaac ataatattct    2820
gactaatatt catctctgtg ttcatttttct aactaaagat ttgaattttc tgctgtgatt    2880
acagagcacc aggaacccaa aacttttctg gctttcagca gcatctccgt tggcctcggt    2940
tattctctca actctggtag tcgcgctcct taagtcgaat gctcatggca ttcaaactgt    3000
aagtaaaatt catcagcttt acctccattc gtagtttta gctatgttgc tcggactctc    3060
cgaaaatgtc gtcgggtgta tgttggatcc tccaaaatta gtgtatttt aaaggatcca    3120 acacgggtgt ggcagtattt tggagagtcc gccaacatag gttttttgac agaataaaac    3180
tgaaaatatc tttggtttat tgcagattgg acacctgcaa aagggtctaa atccaccctc    3240
attgaacatg ttatatctaa gtggtcctta tctgcctctt gccatcaaaa ctggcattgt    3300
ttccggaatc ttagcgctaa cagtaagtca cttgagacta ttacaagcaa ttggccgtag    3360
aaatataaag aagcgctttg ggtttgacat tttcattgac ctgcaggaag ggattgcagt    3420
aggaagaaca tttgctgctt taaggaatta ccaaattgac ggcaacaaag aaatgatggc    3480
gattggactt atgaacatgg ctggctcttg ttcttcgtgc tatgttacaa caggtacccg    3540
```

```
cctcattggc ctgttttcc cgataagtaa gattaactct tttttaacc agctaatatt    3600 tgatttacag ggtcattttc tcgatcagca gtaaattaca acgctggggc acaaacagtc    3660
ttttcaaaca taataatggc aacagctgtg ctaatcactt tgttatttct aatgccactg    3720
ttctattaca cccccattgt catcttggct gcaattatta taacagcagt tattggccta    3780
attgattatc aagctgcttt ccggttatgg aaagttgaca agctcgactt cttggcttgc    3840
ttgtgttcat tttttggtgt tcttttcatc tcagtgcctc tcggcctagc catagcagta    3900
agcatctcct caaaaatcac atcttatagt acgactttct tgatgtctc ctccttgtac    3960 ctaacatttt ctacttctgc ttgtgaaact ttaggttgga gtttcggttt ttaagatcct    4020
cttgcatgta acaaggccaa atactagtgt cctgggcaat attcctggaa ctcaagtata    4080
tcaaaactta agcagatata gaacagctgt tagaattcct tctttcctta tcctcgctgt    4140
tgaggctcct atctactttg caaattctac ctacctaaaa gagaggttag ttcaaacttc    4200
aaacacagag tgcagattca gtattttgct tttcgccaac ttcaattaa                4249
```

<210> SEQ ID NO 18
<211> LENGTH: 586
<212> TYPE: PRT
<213> ORGANISM: Nicotiana tabacum

<400> SEQUENCE: 18

```
Met Gly Leu Ser Ser Asn Arg Val Glu Asp Leu Ser Gly His Ala Cys
1               5                   10                  15

Asn Glu Thr Ile Val Thr Ile Ser Thr Thr Thr Thr Thr Thr Glu Leu
            20                  25                  30

Gln Ile Ser Ser Asn Pro Pro Phe Glu Val His Arg Val Cys Leu Pro
        35                  40                  45

Pro His Lys Thr Thr Leu Gln Lys Leu Arg Gln Arg Leu Leu Glu Val
    50                  55                  60

Phe Phe Pro Asp Asp Pro Leu His Lys Phe Lys Asn Gln Thr Trp Leu
65                  70                  75                  80

Met Lys Leu Val Leu Gly Leu Gln Phe Phe Pro Val Phe Glu Trp
                85                  90                  95

Gly Pro Gln Tyr Asn Leu Lys Leu Leu Arg Ala Asp Ile Ile Ser Gly
            100                 105                 110

Leu Thr Ile Ala Ser Leu Ala Ile Pro Gln Gly Ile Ser Tyr Ala Lys
        115                 120                 125

Leu Ala Asn Leu Pro Pro Ile Val Gly Leu Tyr Ser Ser Phe Val Pro
    130                 135                 140

Pro Leu Ile Tyr Ser Val Leu Gly Ser Ser Lys His Leu Ala Val Gly
145                 150                 155                 160

Pro Val Ser Ile Ala Ser Leu Val Met Gly Thr Met Leu Ser Glu Ala
                165                 170                 175

Val Ser Tyr Thr Glu Glu Pro Leu Tyr Leu Gln Leu Ala Phe Thr
            180                 185                 190

Ala Thr Leu Phe Ala Gly Leu Phe Gln Ala Ser Leu Gly Phe Phe Arg
        195                 200                 205

Leu Gly Phe Ile Ile Asp Phe Leu Ser Lys Ala Thr Leu Val Gly Phe
    210                 215                 220

Met Ala Gly Ala Ala Val Ile Val Ser Leu Gln Gln Leu Lys Gly Leu
225                 230                 235                 240

Leu Gly Ile Val His Phe Thr Ser Gln Met Gln Ile Ile Pro Val Leu
```

```
            245                 250                 255
Ser Ser Val Phe Gln His Lys Asp Glu Trp Ser Trp Gln Thr Ile Val
            260                 265                 270
Met Gly Val Cys Phe Leu Ala Phe Leu Leu Thr Thr Arg Gln Ile Ser
            275                 280                 285
Thr Arg Asn Pro Lys Leu Phe Trp Leu Ser Ala Ala Ser Pro Leu Ala
        290                 295                 300
Ser Val Ile Leu Ser Thr Leu Val Val Ala Leu Leu Lys Ser Asn Ala
305                 310                 315                 320
His Gly Ile Gln Thr Ile Gly His Leu Gln Lys Gly Leu Asn Pro Pro
                325                 330                 335
Ser Leu Asn Met Leu Tyr Leu Ser Gly Pro Tyr Leu Pro Leu Ala Ile
                340                 345                 350
Lys Thr Gly Ile Val Ser Gly Ile Leu Ala Leu Thr Glu Gly Ile Ala
                355                 360                 365
Val Gly Arg Thr Phe Ala Ala Leu Arg Asn Tyr Gln Ile Asp Gly Asn
        370                 375                 380
Lys Glu Met Met Ala Ile Gly Leu Met Asn Met Ala Gly Ser Cys Ser
385                 390                 395                 400
Ser Cys Tyr Val Thr Thr Gly Ser Phe Ser Arg Ser Ala Val Asn Tyr
                405                 410                 415
Asn Ala Gly Ala Gln Thr Val Phe Ser Asn Ile Ile Met Ala Thr Ala
                420                 425                 430
Val Leu Ile Thr Leu Leu Phe Leu Met Pro Leu Phe Tyr Tyr Thr Pro
            435                 440                 445
Ile Val Ile Leu Ala Ala Ile Ile Ile Thr Ala Val Ile Gly Leu Ile
        450                 455                 460
Asp Tyr Gln Ala Ala Phe Arg Leu Trp Lys Val Asp Lys Leu Asp Phe
465                 470                 475                 480
Leu Ala Cys Leu Cys Ser Phe Phe Gly Val Leu Phe Ile Ser Val Pro
                485                 490                 495
Leu Gly Leu Ala Ile Ala Val Gly Val Ser Val Phe Lys Ile Leu Leu
                500                 505                 510
His Val Thr Arg Pro Asn Thr Ser Val Leu Gly Asn Ile Pro Gly Thr
            515                 520                 525
Gln Val Tyr Gln Asn Leu Ser Arg Tyr Arg Thr Ala Val Arg Ile Pro
        530                 535                 540
Ser Phe Leu Ile Leu Ala Val Glu Ala Pro Ile Tyr Phe Ala Asn Ser
545                 550                 555                 560
Thr Tyr Leu Lys Glu Arg Leu Val Gln Thr Ser Asn Thr Glu Cys Arg
                565                 570                 575
Phe Ser Ile Leu Leu Phe Ala Asn Phe Asn
            580                 585

<210> SEQ ID NO 19
<211> LENGTH: 5012
<212> TYPE: DNA
<213> ORGANISM: Nicotiana tabacum

<400> SEQUENCE: 19
atgggactaa gttcaaacag agtagaagat ttatctggcc atgcatgcaa tgaaacaatt      60
atcacaatct ctactactag tacagaatta cacatatcaa ataatcaacc atttgaagta     120
cacagagttt gcttaccacc acacaaaact acccttcaaa aactcaggca aaggctattg     180
```

```
gaaatattt  tcccagatga  tccacttcac  aaattcaaga  accaaacatg  gttaatgaag    240
ttggttttgg  gtcttcaatt  tttcttccca  gtttttgagt  ggggtcctca  gtataatctt    300
aaactactaa  gggcagatgt  aatttctgga  ctcacaattg  ctagccttgc  tatcccacag    360
ggaattagct  atgcaaagct  tgctaatttg  ccacctattg  ttgggctatg  taagtaaatg    420
atcacacttg  ttattttctt  ctttaaaatc  taatttgctt  ttgatcccct  aatttagaat    480
atgaatttgt  tttttaagtg  atagaattgt  tcgttttat  cggttactaa  caatcttttt    540
ctgttgtatt  ggcttaaccg  gtgaaaacag  cctcttgcaa  agatttaggc  taaggttgcg    600
tacaaatata  cctttgtgtt  ccggctcttc  ccggacccgc  gcatagcgga  agcttagtgc    660
acggctgcct  ttttcctatt  ggaatgaaat  ggtgcagaat  agagctgaat  tgatataaaa    720
tgcatatagc  caactccaag  tagtttcggg  ttgaagcata  attattgatt  gataaggggt    780
ttctcattgt  taaaaccagt  tgttaatcag  tcaatatttg  gtaatttatt  ttaagtttaa    840
agatccgtta  agttaatgga  aatttatcaa  gggtctactg  gtctattaat  tgaaggtaga    900
ggcgcatgca  agcttataaa  atccgtgggt  atgaaatatt  gttgtaccta  catattcttt    960
tgcgaattgt  cacagtgcat  tttcagactt  cctataaata  tataatttat  ggaaatttct    1020
gtatatatat  atatatatat  atatatatgt  aattttagta  aaaaatgatt  tcgctgtttg    1080
taaagtatac  attctatgtt  gaagagtaaa  tgtgtgctta  atcgactacg  gtgatttact    1140
aattttcttg  tgctttgcaa  tatctttttg  taaataaaaa  tcaaactaca  tccaatctag    1200
atatctacta  atctaagagt  tgaaatatta  atggatatga  tgatgcagat  tcaagctttg    1260
tgccaccatt  gatctattca  gtattgggga  gttcgaaaca  cttagcagtt  ggtccggtct    1320
cgatagcttc  acttgttatg  ggcacaatgc  tgagtgaagc  agtttcttat  actgaagaac    1380 ctgttctta  ccttcagttg  gcttttacag  ctacccttt  tgccggactg  tttcagtctt    1440
cactcggttt  tttcaggtat  attctattaa  aactttaagt  tctatgcacc  gacatgtcac    1500
ttaaaaagta  attcaactg  attctataga  ataaacgtta  ttgttaatct  agtaacatcc    1560
tataacaagt  taaattgcac  tgaaatatat  ttttagggtg  tcagtgtata  aacttaaat    1620 tctttgacgt  aatggttctc  attcactcga  aaattcgtgc  agcgttttaa  tttgactttc    1680
taatatttaa  agagaaagta  aaagaggagg  aataatctta  gcttaacatt  ccccattcca    1740
ccatcaacgt  taccgttaat  ttagtaatgg  actacagtag  ctaagtggaa  acaaactttt    1800
ggaaagatat  ccaaaagaat  catttagaaa  catgggcac  ttccactaaa  aacagcaaga    1860
aaacagagaa  aaatgcatgg  aaagggacag  aggatgttat  gcaccatata  aaactggact    1920
ctggcttttt  atgcacagta  tgaaactaac  aaatacagct  ggagaaaaag  aataaaaatt    1980
caaggttaca  taatgtaatt  acagaaattt  gcttttcaaa  atcttccttg  agccgaggat    2040
ctatcagaaa  gaagatctat  tgttgttgtt  gttgctgctt  ttcaaaatct  ccgcattcct    2100
atattaaact  atttgttcta  agtataatct  tatgcctgta  gcctagtatt  cagattttg    2160 caactctatt  ttgtttaca  aatcccatta  tttcaacttt  acaactgaat  tttgcagagt    2220
attcaaatgc  atatatttca  ggactatcct  tcttggccac  actagatcaa  ttttcattgc    2280
aaaattattg  acttctattt  atcaatcgtg  catggatata  tcaattctag  caaatttgaa    2340
atagatcagg  atcgctggat  ggctgaaatg  tagtaggtga  atctgctaat  tctaaattag    2400
ttgggtcggc  tatatgaatc  ttgtatatca  tttcaattga  atgcgagtcc  atttcattct    2460
aactttgtgt  tttagagtaa  actatggttc  tcaaaacttt  actttcaaga  aataaaattt    2520
gcttccaagt  gctcactgat  tcggtttatt  ttagaactca  gttagttcaa  atggaaatgc    2580
```

```
actaaaagtt catggtttgc aggttaggat ttatcattga ttttctgtcg aaggcgactt      2640
tggttgggtt catggctggt gcagcagtca ttgtttcatt gcaacaactg aaagggttgt      2700
tagggatagt ccacttcaca agccagatgc aaatagttcc tgttttgtct tctgttttcc      2760
agcacaaaaa tgaggtaaaa agaagcttct ttgtcgatat tgaacttctt tgagatataa      2820
gatagtggaa aaaacaacta tctttgtcaa ctgatgcaaa tcattattta gtagttttac      2880
tcctctatat ctatttgcag tggtcttggc aaaccattgt tatgggcgtt tgttttctcg      2940
cctttctgct gacgactagg caaattgtaa gtgtttgttt tatggcagaa cataatattc      3000
tgattaatat tcatctcttt tgttcatttt ctaactaaag atttgaattt tcttctgtaa      3060
ttacagagca ccaggaaccc aaaacttttc tggctttcag cagcatctcc gttggcctcg      3120
gttattctct caactctcgt agtgaccctc cttaagtcca aggctcatgg tattcaaact      3180
gtaagtaaaa ttcatcagct ttacctccat ccatagtttt tagctatgtt gctcggactc      3240
tctgaaaatg tcgccgggtg catgctggat cctccaaaat agtatatttt taaaggatcc      3300
aacacgggta cggcagtatt ttggagagtc cgccaacata ggttttttaga cagaatgaaa      3360 ctgaaaatat ctttggtttg cagattggac acctgcaaaa gggtctaaat ccgccctcat      3420
tgaacatgtt gtatctaagt ggtccttatc tgcctcttgc cattaaaact ggcattgttt      3480
ccggaatctt agcgttaaca gtaagtcact tgagacgatt acaagcaatt ggccgtagaa      3540
atataacgaa gcgctttgtg tttgacattt tcattgacct gcaggaaggg attgcagtag      3600
gaagaacatt tgctgcttta aagaattacc aagttgatgg caacaaagaa atgatggcga      3660
ttggactcat gaatatggct ggctcttgtt cttcctgcta tgttacaaca ggtacccgcc      3720
tcattggcct gttgttcgcg ataagattaa ctcttttta accagcaaat atttgattta      3780
caggttcatt ttctcgatca gcagtaaatt acaacgctgg ggcacaaacg gtcgtttcaa      3840
acataataat ggcaacagct gtgttaatca ccttgttgtt tctaatgcca ctgttctatt      3900 acaccccccat tgtcatcttg gctgcaatta ttataacagc agttattggc ctaattgatt      3960
atcaagctgc tttccggtta tggaaagttg acaagctcga tttcttggct tgcttgtgtt      4020
cgttttttgg tgttcttttc atctcagtgc ctctcggcct agccattgca gtaagcatct      4080
cctcaaatat cacatcttat agtaccactt actttgatat ctcctccttg tacctaacat      4140
tttctacttc tgctcgtgaa atttcaggtt ggagtttcgg ttttttaagat cctattgcat      4200 gttacaaggc ccaatactag tgtcctgggc aatattcctg gaactcaagt atatcaaaac      4260
ttaagtagat atagaacagc tgttagaatt ccttctttcc ttatccttgc tgttgaggct      4320
cctatctact ttgcaaattc tacctactta aagaaaggt tagttcaaac atagggtaca      4380
gattttgtat tttgctttta gccaacttca actaatttgt taagattatt acacagtttt      4440
atttactcaa aattcacatt ttgtaactgt aggatattga gatggattcg cgaagaggaa      4500
gagtggatag tagccaacaa agaaactgca atcaaatgtg taataatcga catgacaggt      4560
cagttgaaaa aaaaaagtga catttactca tcttctgttt tactggcagt tctcaacatg      4620
ttgagtaaca aaattatgtc ttgcttcacc agctgtgtcg tccatagact caagtggcat      4680
cgacacaata tgtgaactac gaaagacact ggataaacga tctcttaagg taaatccgtc      4740
agccacataa aagatgtttc tttgtttttcc ttcactagtc aaaatatttc ttacaaaatt      4800
tgttttcctt ttttctttttc ctttcacgtg aaatctttga ttttttgttg gtgtagcttg      4860
tgatggcaaa tccaggtggg aatgttatgg aaaaactgca tcaatctaac actctcgacg      4920
```

```
cctttggatt aaatggaata tatctaacag tttctgaagc tgtggctgat atctcatctt    4980
tgtggaagtc tgaacctgaa tcatcaatat aa                                  5012
```

<210> SEQ ID NO 20
<211> LENGTH: 669
<212> TYPE: PRT
<213> ORGANISM: Nicotiana tabacum

<400> SEQUENCE: 20

```
Met Gly Leu Ser Ser Asn Arg Val Glu Asp Leu Ser Gly His Ala Cys
1               5                   10                  15

Asn Glu Thr Ile Ile Thr Ile Ser Thr Thr Ser Thr Glu Leu His Ile
            20                  25                  30

Ser Asn Asn Gln Pro Phe Glu Val His Arg Val Cys Leu Pro Pro His
        35                  40                  45

Lys Thr Thr Leu Gln Lys Leu Arg Gln Arg Leu Leu Glu Ile Phe Phe
    50                  55                  60

Pro Asp Asp Pro Leu His Lys Phe Lys Asn Gln Thr Trp Leu Met Lys
65                  70                  75                  80

Leu Val Leu Gly Leu Gln Phe Phe Pro Val Phe Glu Trp Gly Pro
                85                  90                  95

Gln Tyr Asn Leu Lys Leu Leu Arg Ala Asp Val Ile Ser Gly Leu Thr
            100                 105                 110

Ile Ala Ser Leu Ala Ile Pro Gln Gly Ile Ser Tyr Ala Lys Leu Ala
        115                 120                 125

Asn Leu Pro Pro Ile Val Gly Leu Tyr Ser Ser Phe Val Pro Pro Leu
    130                 135                 140

Ile Tyr Ser Val Leu Gly Ser Ser Lys His Leu Ala Val Gly Pro Val
145                 150                 155                 160

Ser Ile Ala Ser Leu Val Met Gly Thr Met Leu Ser Glu Ala Val Ser
                165                 170                 175

Tyr Thr Glu Glu Pro Val Leu Tyr Leu Gln Leu Ala Phe Thr Ala Thr
            180                 185                 190

Leu Phe Ala Gly Leu Phe Gln Ser Ser Leu Gly Phe Phe Arg Leu Gly
        195                 200                 205

Phe Ile Ile Asp Phe Leu Ser Lys Ala Thr Leu Val Gly Phe Met Ala
    210                 215                 220

Gly Ala Ala Val Ile Val Ser Leu Gln Gln Leu Lys Gly Leu Leu Gly
225                 230                 235                 240

Ile Val His Phe Thr Ser Gln Met Gln Ile Val Pro Val Leu Ser Ser
                245                 250                 255

Val Phe Gln His Lys Asn Glu Trp Ser Trp Gln Thr Ile Val Met Gly
            260                 265                 270

Val Cys Phe Leu Ala Phe Leu Leu Thr Thr Arg Gln Ile Ser Thr Arg
        275                 280                 285

Asn Pro Lys Leu Phe Trp Leu Ser Ala Ala Ser Pro Leu Ala Ser Val
    290                 295                 300

Ile Leu Ser Thr Leu Val Val Thr Leu Leu Ser Lys Ala His Gly
305                 310                 315                 320

Ile Gln Thr Ile Gly His Leu Gln Lys Gly Leu Asn Pro Pro Ser Leu
                325                 330                 335

Asn Met Leu Tyr Leu Ser Gly Pro Tyr Leu Pro Leu Ala Ile Lys Thr
            340                 345                 350

Gly Ile Val Ser Gly Ile Leu Ala Leu Thr Glu Gly Ile Ala Val Gly
```

```
         355                 360                 365
Arg Thr Phe Ala Ala Leu Lys Asn Tyr Gln Val Asp Gly Asn Lys Glu
370                 375                 380

Met Met Ala Ile Gly Leu Met Asn Met Ala Gly Ser Cys Ser Ser Cys
385                 390                 395                 400

Tyr Val Thr Thr Gly Ser Phe Ser Arg Ser Ala Val Asn Tyr Asn Ala
                405                 410                 415

Gly Ala Gln Thr Val Val Ser Asn Ile Ile Met Ala Thr Ala Val Leu
            420                 425                 430

Ile Thr Leu Leu Phe Leu Met Pro Leu Phe Tyr Tyr Thr Pro Ile Val
        435                 440                 445

Ile Leu Ala Ala Ile Ile Ile Thr Ala Val Ile Gly Leu Ile Asp Tyr
    450                 455                 460

Gln Ala Ala Phe Arg Leu Trp Lys Val Asp Lys Leu Asp Phe Leu Ala
465                 470                 475                 480

Cys Leu Cys Ser Phe Phe Gly Val Leu Phe Ile Ser Val Pro Leu Gly
                485                 490                 495

Leu Ala Ile Ala Val Gly Val Ser Val Phe Lys Ile Leu Leu His Val
            500                 505                 510

Thr Arg Pro Asn Thr Ser Val Leu Gly Asn Ile Pro Gly Thr Gln Val
        515                 520                 525

Tyr Gln Asn Leu Ser Arg Tyr Arg Thr Ala Val Arg Ile Pro Ser Phe
    530                 535                 540

Leu Ile Leu Ala Val Glu Ala Pro Ile Tyr Phe Ala Asn Ser Thr Tyr
545                 550                 555                 560

Leu Lys Glu Arg Ile Leu Arg Trp Ile Arg Glu Glu Glu Trp Ile
                565                 570                 575

Val Ala Asn Lys Glu Thr Ala Ile Lys Cys Val Ile Ile Asp Met Thr
            580                 585                 590

Ala Val Ser Ser Ile Asp Ser Ser Gly Ile Asp Thr Ile Cys Glu Leu
        595                 600                 605

Arg Lys Thr Leu Asp Lys Arg Ser Leu Lys Leu Val Met Ala Asn Pro
    610                 615                 620

Gly Gly Asn Val Met Glu Lys Leu His Gln Ser Asn Thr Leu Asp Ala
625                 630                 635                 640

Phe Gly Leu Asn Gly Ile Tyr Leu Thr Val Ser Glu Ala Val Ala Asp
                645                 650                 655

Ile Ser Ser Leu Trp Lys Ser Glu Pro Glu Ser Ser Ile
            660                 665

<210> SEQ ID NO 21
<211> LENGTH: 4050
<212> TYPE: DNA
<213> ORGANISM: Nicotiana tabacum

<400> SEQUENCE: 21
atgacattaa attcaattaa agtggaagat tcgtcatgca atgcaacaga aggagagtcg    60
gcaacgtcgt cgtcaatgca atcctcaggt gtacataagg tttgtttgcc gccgtacaga   120 accactttc agaaactccg gcaacggttg tcggagattt tctttcccga cgatccactt   180
cataagttca agaagcaaac agggttgagg aaatttgttt tgggtcttca gttttttcttc   240 cctgttttg aatgggtcc tctgtacagt ttcaaacttt taaggtctga tataatctct   300
ggcctcacca ttgctagcct tgctatccct caaggaatta gttatgctaa acttgccaat   360
```

```
ttgcctccca ttattgggtt atgtaagtgc cactctttt  atctttcttt  ttcttcttc    420 cctgtgatgg tcgccactaa aaccgtcgag gggtgtcaat taaacagcct tctctccaaa    480
gttacacggt atatatatat atatatgcca aatattactt cttgtacgtt caccccttaac   540 gaaattcctt tggttcgcca acccttactt tttgtgacga ctaaggtgat ggtcgcataa    600
agtcaccatg aaaagttctc atttctagta gtgttaccgc aaatgattgc cactaaatct    660
atcactattt gcaaccatta ggtagtaaat tcactgaaaa attatattgt atatatatat    720
gtcaaagatg actatttata tatgtatata taaaatcttg attaccttta gtggaattcc    780
ttcttttgct cgtgtacttt ttgtggcaac taaggttagt ggaattcctt cttttgctcg    840 tgtactttt  gtggcaacta aggttattga cacgtagagt catcactaaa aatttcattt    900
tgtagagtta actaaattat ggagtagtaa ttaattaaag gtgatatgga ttttttgtgac    960 acagattcaa gctttgtgcc accattaatc tattcaattt tgggaagttc aagacactta   1020
gcagttggtc cagtatctat agcctcacta gtgatgggaa caatgttaag ccaagcagtt   1080
tcatacagcc aagagccaat tctataccct caacttgctt tcacagcaac acttttttgct  1140 ggattgttgc aagcttcatt ggggttttc aggtataata ctctgttcat gaactttttt   1200
gtattactta cattttttc aacttctttt tctcattatt cataaagaat agaatagaat   1260
tattccagca aattttttcat tccactatca atgtttctgt taattaaagt taatgctgta   1320
atgtagcata tagcaaagtg gaaacaaact tttagaaaaa gatataccaa caaattcatt   1380
tagaaacact gagacctttt gctgaaaaaa atggtgcttt atcgaaaaag aaaagaatag   1440
aaaggaaaag gttgttcact ccaaggtaga caaactgaaa ctaaagatat ttacctacac   1500
ttttcagaat cttatggtta aagcagtaag tatatttga aaaatatttt cctcaaattt    1560
tacctcacca agaattatca gcatatgaaa cctatgcact aatgtcatat agccttggtg   1620
gtaaaaaaat tcaagttatt aattaattca taattcaaga gatttgaatt ccatctgagg   1680
aggtcacgaa actcattttt gtttgtcata acaatctata tgtgtaaagt aattacttga   1740
ttgtcacaca taagattaga tcaacatgct caaactgatc tgctcttatg atttacaaat   1800
tattggcttc tgctgaattt cagcagttta atcgcaagga aattgactta aattccatga   1860
cttgcaggtt aggattcatc attgattttc tctcaaaggc gactctacta gggttcatgg   1920
ctggtgcagc ggtcattgtc tctttgcaac aactgaaagg attgctaggg atatctcact   1980
tcacaaacca gatgcaaata gttcctgttt tgtcttctgt tttcacgcac aaagatgagg   2040
ttagaagttt cctccaatgt tgtgctcttt tgaggtaata ttgaaggcat aaaattgccg   2100
ttgtaactct gcaacatctt ttcgcagtgg tcttggcaaa ccattgttat gggtgttagt   2160
tttctcatct tcttgctggc gacaaggcaa atcgtaagtt tttggtttat gtggatgaga   2220 aagtttttc ttcatgttca tctccttatt gatcattttc taattaatgt cagagtacta   2280
ggaaaccgaa acttttctgg atttcagcag cagctccgtt agtatccgtt attctctcaa   2340
ctatcatagt tttcctactt aaatccaaga ctattcagac tgtgagtaac atgcatcgtt   2400
tctagtttca tcccttaaat ttagacggaa aagactaaag attctttat tgtagattgg    2460 acacctacca aagggggatta atccaccatc attgaacatg ttacatttta gtggccctca   2520
tatcgctctt gctatcaaaa ttggcattat aactggagtc ttatctctca cagtaagtga   2580
atactaacta ctactaccag cattttattc ctcaaagaaa gaaaaggagg agatttgtga   2640
tcgacatagc tctgcaggaa gggatagcgg taggaaggac atttgctgct atgcaaaatt   2700
accaagttga cggtaacaaa gaaatgatag ctatcggact tatgaacatg gctggctctt   2760
```

```
gtgcttcctg ctttgtcact acaggtacga cctaagcaat actcttattc ttagttgtaa    2820
ctaaagcttg ctaagtttcc tctttctctt attccatgtg aaattcaatt ttgcagggtc    2880
attttctcga tctgctgtaa attacaatgc tggagcaaaa actgtcgttt caaatataat    2940
aatggcggca actgtgctta tcaccctgct gtttctcatg ccgttgttcc attacacccc    3000
taacctcatc ttggcagcaa ttatcataac agcagtgatc ggcctaattg attatcaagc    3060
tgcattccgt ttatggaaag ttgacaaact agattttgtg gcttgcttgt cttcctttt    3120
tggtgtcctt ttcatctcag tgcctcttgg cctagcaatt gcagtaagct tctcctcata    3180
aatctcaatc ctctcatgcc ttgaaatatc tacttctcat gtctaatata ttctaatatt    3240
ttgttgttca tgaaaaaatt tcaggttggt gtttcagttt tcaagatcct attgcacgtt    3300
acacggccaa atactaatgt cttgggctac attcctggta ctcaatcatt tcaaagccta    3360
agcagatata gcacagctgt tagggttcct tctttcctta tcatagctgt tgaggctcct    3420
ttctattttg caaattctac ctacctacaa gaaaggtaag ttaggtttaa ctttcatcga    3480
taacaagtga aattgtaaag tttttaaata tttgctacat cagagttgta tcaagcaatt    3540
gtaattacag gacattgaga tggattcggg aagaggaaga gaggatagaa gtcaaaagag    3600
aaactgcaat caaatgtgta attcttgaca tgacaggttg gttgaaaaag aaaacaacat    3660
cctctcatgt tttctttcct tagtaatcta ctcgtctagt aacgaaataa tggggttttc    3720
cttctgcagc tgtgacagct atagacacta gtggcattga taacaatatgt gaactcagaa    3780
ggatacttga gaaagatca ctgaaggtaa atatactgtc aattatattg tgtcaagctt    3840
ttatttgcag aattgcgtta tcctttcctt tcttgctcgt ttatgctttg atgtattctg    3900
cttcagctcg tgctggcaaa tccggttgga aacgttatgg aaaagctgca taactcgcat    3960
gctcttgagg cctttggatt agacggatta tatctaacag tttctgaagc tgtggcggat    4020
atttcatctt cttggaagcc tgaagcctga                                     4050
```

<210> SEQ ID NO 22
<211> LENGTH: 654
<212> TYPE: PRT
<213> ORGANISM: Nicotiana tabacum

<400> SEQUENCE: 22

```
Met Thr Leu Asn Ser Ile Lys Val Glu Asp Ser Ser Cys Asn Ala Thr
1               5                  10                  15

Glu Gly Glu Ser Ala Thr Ser Ser Ser Met Gln Ser Ser Gly Val His
            20                  25                  30

Lys Val Cys Leu Pro Pro Tyr Arg Thr Thr Phe Gln Lys Leu Arg Gln
        35                  40                  45

Arg Leu Ser Glu Ile Phe Phe Pro Asp Asp Pro Leu His Lys Phe Lys
    50                  55                  60

Lys Gln Thr Gly Leu Arg Lys Phe Val Leu Gly Leu Gln Phe Phe
65                  70                  75                  80

Pro Val Phe Glu Trp Gly Pro Leu Tyr Ser Phe Lys Leu Leu Arg Ser
                85                  90                  95

Asp Ile Ile Ser Gly Leu Thr Ile Ala Ser Leu Ala Ile Pro Gln Gly
            100                 105                 110

Ile Ser Tyr Ala Lys Leu Ala Asn Leu Pro Pro Ile Ile Gly Leu Tyr
        115                 120                 125

Ser Ser Phe Val Pro Pro Leu Ile Tyr Ser Ile Leu Gly Ser Ser Arg
    130                 135                 140
```

```
His Leu Ala Val Gly Pro Val Ser Ile Ala Ser Leu Val Met Gly Thr
145                 150                 155                 160

Met Leu Ser Gln Ala Val Ser Tyr Ser Gln Glu Pro Ile Leu Tyr Leu
            165                 170                 175

Gln Leu Ala Phe Thr Ala Thr Leu Phe Ala Gly Leu Leu Gln Ala Ser
            180                 185                 190

Leu Gly Phe Phe Arg Leu Gly Phe Ile Ile Asp Phe Leu Ser Lys Ala
            195                 200                 205

Thr Leu Leu Gly Phe Met Ala Gly Ala Val Ile Val Ser Leu Gln
210                 215                 220

Gln Leu Lys Gly Leu Leu Gly Ile Ser His Phe Thr Asn Gln Met Gln
225                 230                 235                 240

Ile Val Pro Val Leu Ser Ser Val Phe Thr His Lys Asp Glu Trp Ser
            245                 250                 255

Trp Gln Thr Ile Val Met Gly Val Ser Phe Leu Ile Phe Leu Leu Ala
            260                 265                 270

Thr Arg Gln Ile Ser Thr Arg Lys Pro Lys Leu Phe Trp Ile Ser Ala
            275                 280                 285

Ala Ala Pro Leu Val Ser Val Ile Leu Ser Thr Ile Ile Val Phe Leu
290                 295                 300

Leu Lys Ser Lys Thr Ile Gln Thr Ile Gly His Leu Pro Lys Gly Ile
305                 310                 315                 320

Asn Pro Pro Ser Leu Asn Met Leu His Phe Ser Gly Pro His Ile Ala
            325                 330                 335

Leu Ala Ile Lys Ile Gly Ile Ile Thr Gly Val Leu Ser Leu Thr Glu
            340                 345                 350

Gly Ile Ala Val Gly Arg Thr Phe Ala Ala Met Gln Asn Tyr Gln Val
            355                 360                 365

Asp Gly Asn Lys Glu Met Ile Ala Ile Gly Leu Met Asn Met Ala Gly
            370                 375                 380

Ser Cys Ala Ser Cys Phe Val Thr Thr Gly Ser Phe Ser Arg Ser Ala
385                 390                 395                 400

Val Asn Tyr Asn Ala Gly Ala Lys Thr Val Val Ser Asn Ile Ile Met
            405                 410                 415

Ala Ala Thr Val Leu Ile Thr Leu Leu Phe Leu Met Pro Leu Phe His
            420                 425                 430

Tyr Thr Pro Asn Leu Ile Leu Ala Ala Ile Ile Thr Ala Val Ile
            435                 440                 445

Gly Leu Ile Asp Tyr Gln Ala Ala Phe Arg Leu Trp Lys Val Asp Lys
            450                 455                 460

Leu Asp Phe Val Ala Cys Leu Ser Ser Phe Phe Gly Val Leu Phe Ile
465                 470                 475                 480

Ser Val Pro Leu Gly Leu Ala Ile Ala Val Gly Val Ser Val Phe Lys
            485                 490                 495

Ile Leu Leu His Val Thr Arg Pro Asn Thr Asn Val Leu Gly Tyr Ile
            500                 505                 510

Pro Gly Thr Gln Ser Phe Gln Ser Leu Ser Arg Tyr Ser Thr Ala Val
            515                 520                 525

Arg Val Pro Ser Phe Leu Ile Ile Ala Val Glu Ala Pro Phe Tyr Phe
            530                 535                 540

Ala Asn Ser Thr Tyr Leu Gln Glu Arg Thr Leu Arg Trp Ile Arg Glu
545                 550                 555                 560
```

```
Glu Glu Glu Arg Ile Glu Val Lys Arg Glu Thr Ala Ile Lys Cys Val
                565                 570                 575

Ile Leu Asp Met Thr Ala Val Thr Ala Ile Asp Thr Ser Gly Ile Asp
            580                 585                 590

Thr Ile Cys Glu Leu Arg Arg Ile Leu Glu Lys Arg Ser Leu Lys Leu
        595                 600                 605

Val Leu Ala Asn Pro Val Gly Asn Val Met Glu Lys Leu His Asn Ser
    610                 615                 620

His Ala Leu Glu Ala Phe Gly Leu Asp Gly Leu Tyr Leu Thr Val Ser
625                 630                 635                 640

Glu Ala Val Ala Asp Ile Ser Ser Ser Trp Lys Pro Glu Ala
                645                 650
```

<210> SEQ ID NO 23
<211> LENGTH: 4026
<212> TYPE: DNA
<213> ORGANISM: Nicotiana tabacum

<400> SEQUENCE: 23

```
atgacattaa attcaattaa agtggaagat tcgtcatgca atgcaacaga aacagaagcg      60
gtaacgtctt cgtcaatgca atcctcaggt gtacataagg tttgtttgcc gccgtacaga     120
accactttc agaaactccg gcaacggttg tcggagattt ctttcccga cgatccactt       180
cacaagttca agaaccaaac gggggttgagg aaatttgttt gggtcttca gttttcttc     240
cctgttttg aatggggtcc tctgtacagt ttcaacttg taaggtctga tataatctct      300
ggcctcacca ttgctagcct tgctattcct caaggaatta gttatgctaa acttgccaat    360
ttgcctccca ttattgggtt atgtaagtgc cactcttttt atctttcttt ttcttctttc    420
tctattttaa catgatagtc gccactaaaa ccggggagta acagctttag ctgaaaaatt    480
atactatata tatatatatg ccaaatatta ccttttgtac gttcacccctt aacgaaattc   540
ctttggttcg ccaaccccta ctctttgtga cgactaaggc aatggtcgca taagtcgcc    600
atgaaatatt ctcatttctg gtcaagaggt agtaaattga acaacattca ccgaaaaatt   660
atactgtgta tatatatgtc aaatatgact atttatacat gtatatataa aatctttgaa  720
tacctttaac aaaattcctt cttttgctcg tgcgtggaac ccttactttt gtggcgacta   780
aggttattga cgcgtagagt cgtcactaaa aatttcattt cttgtagtgt taactaaatt   840
atggagtaag taattaatta aaggtggaat ggattttgt gaaacagatt caagctttgt   900
gccgccatta atattcaa ttttgggaag ttcaagacac ttagcagttg gtccagtatc     960
tatagcatca ctagtgatgg gaacaatgtt aagccaagca gtttcataca gccaagagcc  1020
aattctatac cttcaacttg ctttcacagc aacactttttt gctggattgt tgcaagcttc 1080
attgggggtttt ttcaggtata gtactctgtt catgaacttt ttgtattaca tttttattg   1140
tgtataaaca gtgttacact aagttctttt tttcctcatt ttctttactt catgaagaat   1200
agaattgctc tagcaaactt tcccattccc aatatcaatg ttactgttaa ttaaagttaa   1260
tgctataatg tagcagatag caaagtagaa acaaactttt agaaaagat ataccaacag    1320
aatcatttaa aaacattggg aacatttgct gagaattcga aaaaaaaaaa gaagaaaag    1380
gtacagatga ttttggaaa aagaatagaa aggaaaaggt tgttgattcc aaggttgaca    1440
aaatgaaact aaatatattt acctgcactt ttcagaatct caattaacca gtaaggcagt   1500
aatcatattt tgaaaatat tttcctcaaa ttttacctga ccaagaatta tcaacatatg    1560
agacctatgc actaatgtca tatagccttg atggtaaaaa tttcaagtta gtaactcata  1620
```

```
aatcaggagt atttgttttc ccccggggga gatcatgaaa ctgtttgatt ttcacttgtg    1680
actttgtatg tcataacaat ctatacttgt aaagtaatca cttgattttc acacataaga    1740
ttagctcctc aaactgattt gctcttatga tttacgaatt attgggttct gctgaattta    1800
ctgcagttta atcataagga aattgactta aattccatga cttgcaggtt aggattcatc    1860
attgattttc tctcgaaggc gactctacta gggttcatgg ctggtgcagc ggtcattgtc    1920
tctttgcaac aactgaaagg attgctaggg atatcccact ttacaaacca gatgcaaata    1980
gttcctgttt tgtcttctgt tttcacgcac aaagatgagg ttagaagttt cctccaacat    2040
tgtgctcttc tgagataata ttgaaggcat aaaattgtca ttgtaactct gcaacatctg    2100
tttgcagtgg tcttggcaaa ccattgttat gggtgttagt tttctcatct tcttgctggc    2160
tacaaggcaa atcgtaagtt tttggtttat gtgaatgaga agttttttgc ttcatgttca    2220
tctccttatt gatcattttc taattaatga cagagtacta ggaaaccgaa acttttctgg    2280
atttcagcag cagctccgtt agtatccgtt attctctcaa ctatcatagt tttcctactt    2340
aaatccaaga ctattcagac tgtgagtaac atgcatcatt tctagtttca tcccttaaat    2400
ttaggcggaa aagactaaag attcttttgt tgtagattgg acacctacca aagggataa     2460 atccaccatc attgaacatg ttacatttta gtggccctca tctcgctctt gctatcaaaa    2520
ctggcattgt aactggagtc ttatcgctca cagtaagtga atactaacta ctactaccag    2580 catttattc ctcaaagaaa gaaaagagg agatttgtga tcgacatagc cctgcaggaa      2640
gggatagcgg taggaaggac atttgctgct atgcaaaatt accaagttga cggtaacaaa    2700
gaaatgatag ctatcggact tatgaacatg gctggctctt gtgcttcctg ctttgtcact    2760
acaggtacaa cccaagcaac actcttattc ttagttgtaa ctaaagcttg ctaagttttcc   2820 tcttactctt attccaacta aaattcaatt ttgcaggatc attttctcga tctgctgtaa    2880
attacaatgc tggagcaaaa actgtcgttt caaatataat aatggcggca actgtgctta    2940
tcaccctgct gtttctcatg ccgctgttcc attcaccccc taacctcatc ttggcagcaa    3000
ttatcataac agcagtgatc ggcctaattg attatcaagc tgcattccgt ttatggaaag    3060
ttgacaaact agattttgtg gcttgcttgt cttccttttt cggtgtcctt ttcatctcag    3120
tgcctcttgg cctagcaata gcagtaatct tctcctcata aatctgacat actctcggat    3180
gccttgaaat ttctacttct catgtttaat aatatattct aattttgttc atgaaaaaaa    3240
tttcaggttg gtgtttcagt tttcaagatc ctattgcatg ttacaaggcc aaatactaat    3300
gttttgggct acattcctgg cactcaatca tttcaaagcc taagcagata tagcgcagct    3360
gttaggattc cttctttcct tatcatagct gttgaggctc ctttctactt tgcaaattct    3420
acctacctac aagaaggta agtttaactt tctacaataa taagtgaagt agtaaagttg    3480
ttaaatttgt gttacatcac agttgtatca agcaattgta attacaggac attgagatgg    3540
attcgggaag aggaagagag gatagaagtc aaaaagaaa ctgcaatcaa atgtgtaatt     3600
cttgacatga caggttggtt gaaaagaaa acacatcttc tcatgttttc tttcactagt     3660
aatctacacg tctagtaacg aaattatggg gttatccttc tgcagctgtg acagctatag    3720
acactagtgg cattgataca atatgtgaac tcagaaggat acttgagaaa agatcactta    3780
aggtaaacat tctgtcaatt atattgtgtc aagcttttat ttgcagaatc gcgctatccg    3840
ttctttgctt gctcgtttat gctttgatgt atactgcttc agctcgtgct ggcaaatcca    3900
gttggaaacg ttatggaaaa gctgcataac tcgcatgctc ttgaggcctt tggattagac    3960
```

```
ggattatatc taacagtttc tgaagctgtg gccgatattt catcttcttg gaagactgaa    4020
ccatga                                                              4026
```

<210> SEQ ID NO 24
<211> LENGTH: 409
<212> TYPE: PRT
<213> ORGANISM: Nicotiana tabacum

<400> SEQUENCE: 24

```
Met Thr Leu Asn Ser Ile Lys Val Glu Asp Ser Ser Cys Asn Ala Thr
1               5                   10                  15

Glu Thr Glu Ala Val Thr Ser Ser Met Gln Ser Ser Gly Val His
            20                  25                  30

Lys Val Cys Leu Pro Pro Tyr Arg Thr Thr Phe Gln Lys Leu Arg Gln
        35                  40                  45

Arg Leu Ser Glu Ile Phe Phe Pro Asp Asp Pro Leu His Lys Phe Lys
    50                  55                  60

Asn Gln Thr Gly Leu Arg Lys Phe Val Leu Gly Leu Gln Phe Phe
65                  70                  75                  80

Pro Val Phe Glu Trp Gly Pro Leu Tyr Ser Phe Lys Leu Val Arg Ser
                85                  90                  95

Asp Ile Ile Ser Gly Leu Thr Ile Ala Ser Leu Ala Ile Pro Gln Gly
            100                 105                 110

Ile Ser Tyr Ala Lys Leu Ala Asn Leu Pro Pro Ile Gly Leu Tyr
        115                 120                 125

Ser Ser Phe Val Pro Pro Leu Ile Tyr Ser Ile Leu Gly Ser Ser Arg
    130                 135                 140

His Leu Ala Val Gly Pro Val Ser Ile Ala Ser Leu Val Met Gly Thr
145                 150                 155                 160

Met Leu Ser Gln Ala Val Ser Tyr Ser Gln Glu Pro Ile Leu Tyr Leu
                165                 170                 175

Gln Leu Ala Phe Thr Ala Thr Leu Phe Ala Gly Leu Leu Gln Ala Ser
            180                 185                 190

Leu Gly Phe Phe Arg Leu Gly Phe Ile Ile Asp Phe Leu Ser Lys Ala
        195                 200                 205

Thr Leu Leu Gly Phe Met Ala Gly Ala Ala Val Ile Val Ser Leu Gln
    210                 215                 220

Gln Leu Lys Gly Leu Leu Gly Ile Ser His Phe Thr Asn Gln Met Gln
225                 230                 235                 240

Ile Val Pro Val Leu Ser Ser Val Phe Thr His Lys Asp Glu Trp Ser
                245                 250                 255

Trp Gln Thr Ile Val Met Gly Val Ser Phe Leu Ile Phe Leu Leu Ala
            260                 265                 270

Thr Arg Gln Ile Ser Thr Arg Lys Pro Lys Leu Phe Trp Ile Ser Ala
        275                 280                 285

Ala Ala Pro Leu Val Ser Val Ile Leu Ser Thr Ile Ile Val Phe Leu
    290                 295                 300

Leu Lys Ser Lys Thr Ile Gln Thr Ile Gly His Leu Pro Lys Gly Ile
305                 310                 315                 320

Asn Pro Pro Ser Leu Asn Met Leu His Phe Ser Gly Pro His Leu Ala
                325                 330                 335

Leu Ala Ile Lys Thr Gly Ile Val Thr Gly Val Leu Ser Leu Thr Glu
            340                 345                 350

Gly Ile Ala Val Gly Arg Thr Phe Ala Ala Met Gln Asn Tyr Gln Val
```

```
                355              360              365
Asp Gly Asn Lys Glu Met Ile Ala Ile Gly Leu Met Asn Met Ala Gly
        370              375              380

Ser Cys Ala Ser Cys Phe Val Thr Thr Gly Ser Phe Ser Arg Ser Ala
385              390              395              400

Val Asn Tyr Asn Ala Gly Ala Lys Thr
            405

<210> SEQ ID NO 25
<211> LENGTH: 6448
<212> TYPE: DNA
<213> ORGANISM: Nicotiana tabacum

<400> SEQUENCE: 25
```

| | | | | | |
|---|---|---|---|---|---|
| atgacgagct | ctccccagtc | tttgcatagg | gtgaactatg | cagcgccacg | aagctttggg | 60 |
| acattactaa | aagcaaacct | aaaagagacc | cttttcccag | atgatccatt | ccatgaaatc | 120 |
| aagaacgagc | caatttcacg | cagattttta | aggggggctc | aatattttgt | tccaattttc | 180 |
| gaatggctgc | caaagtataa | tttcaagctc | ttcaagtatg | atcttcttgc | tggaatcact | 240 |
| attgctagcc | ttgccattcc | tcaagggata | agctatgcca | aactcgctaa | cattcctcca | 300 |
| atcattggac | tctgtaagct | acttataaga | gtattgtatt | gttttttcct | atatatatat | 360 |
| tgacacgtcg | taccaaaaga | tgtatgtgtt | catggctttc | ttggcttttg | attcgaagta | 420 |
| ggtacaacta | acaatttttt | gattaaaaga | tgtatgagtt | gcatgcatgc | agattcgagc | 480 |
| tttgttcctc | ctcttattta | tgcggttttt | ggaagttcaa | agcaccttgc | tgtggggacg | 540 |
| gtggctgctt | gctcattgct | tattgctgca | atcattgaag | gaaaagtgaa | cgctagcgat | 600 |
| aatatgccgc | tgtatcttag | tttggtgttc | acggccactc | ttttctctgg | tttggttcag | 660 |
| actgctctgg | gtttgctaag | gtacacacca | ccacctgtcc | ttccctaagc | tagctagctc | 720 |
| tttgattaat | tagtactagt | agaaatatat | aagtacaatt | tatttggttt | gtgcagactt | 780 |
| gggattttgg | tagatttcct | atcacattca | accataactg | gatttatggg | aggaacagca | 840 |
| ataattattt | gcttgcagca | actgaagggc | atgcttggtt | tgaagcattt | cactacccat | 900 |
| actgatgtgg | tttctgtctt | acgcgctatc | ttccacaaca | gaaaagaggt | tgtcattcta | 960 |
| tactcctaat | tgtatctatt | agattaatta | agtgaatagc | catgcattgg | ggatacttct | 1020 |
| atgcacaata | tatattcaca | taccttagct | ttgatactga | catatcattt | agaaatatta | 1080 |
| ttttatagat | ccatatatat | atcaccaaag | gataaaaaat | gaggaattgc | cttttattat | 1140 |
| tggattatga | gtaaagttgg | tcaatttggc | aatttaattt | ctgttattga | ttttttttgt | 1200 |
| gtgtgtgtgt | attcgaacag | tggaagtggg | agagtgcagt | tgttggaata | atcttcctta | 1260 |
| cttttcctgca | attcactaga | tttgtggtga | gtgtttccta | ttaatatgtg | aaaataagtg | 1320 |
| ttctcgatcg | cagatcatgt | atacaagaaa | aaatgcttct | ttgcagaaaa | acaagaaacc | 1380 |
| aaagctattt | tgggtttcag | ccatagctcc | aatggtcact | gtaattgtcg | gctgcctttt | 1440 |
| cgcttacttc | gcccatgctg | agaaacatgg | catccaaatc | gtaagccttt | aatttccttc | 1500 |
| tcccccacc | ccaaaatgaa | tttatattaa | gtgcggtaga | agatatataa | aagctgacaa | 1560 |
| aatatgggcc | gactaggaaa | ggaagaatag | aagagatcaa | tcacgaaaat | atagagtgat | 1620 |
| ttcaattagc | tagtttgccg | taaaatattt | tagtagaaat | cgagttaaaa | actttcttta | 1680 |
| tgacacatgt | atctcacaca | aatatataca | tgtatatacg | tggatatagt | gtatactcga | 1740 |
| cgggttcaat | tgaacccata | attttcgacg | cgaagtaaaa | atttatatgt | aaaaattcat | 1800 |

-continued

```
taaagttttt agtagtcata aatctaataa ctttataaat ataataggtt cgatgttaaa    1860
aaatctaaaa gttgaacccca tagggtttaa atcctgaggg ctgcttgtta agtattttgc   1920
ttcggtttgt caaacgaaat agtttgagaa caggaagaga cgcataagga gagacaaaaa   1980
ttacagaatt tgcaactgtt agagtcaagt ttggaaaaga ttgataagat cttttttgaat  2040 tctctttaag ggttgttgga gaatgactat tgaggtgtgt atggctacgt ttcactaatt   2100
tatcattgag acaaacccctt tttacaacac ttatctaagt ggacttccac ctaactagcg  2160
aggaagagcc aattttgaca tttcgagaat tagacttaaa gtatgcaagt aattatgtcc   2220
accgacggat atggacaaga tcactaataa tcttgtagaa aacgcaacac taacttttttc 2280 ttttctgtgg tcacagcact aagtccgatc cgtattttaa tttgtctcat ctaatgtaac   2340
agtaggtctt tttgtctcat actttggact gaatatatac aggttggaca tttgagtaaa   2400
ggaataaatc cttcttccat tcatcttttta aatttcgatc ccaagtatat atcagcacct  2460
ataaaagcag gagtcatcgc agcaatgata tctctagctg taagtacact ctttaattta   2520
tccatacata cgaagagttt ctgatttgtc aatcatcaaa aatgtacgtg tttactaagt   2580
ttgtatggaa tatttttctag gagggaatag ccatcggacg gagtttcgcc attatcagaa  2640
atgaacaaat tgatggcaac aaggaaatga ttgccattgg cctcatgaac atttttggat  2700 cttttcacttc atgctacttg accactggta atttgtggtg gcaaaatggt taaaagaaaa 2760
cagttcatat tattcgttaa ataggctg gataatgaac tttataaaaa tgggtcaatt    2820
aatatagata taatcatat tatccattta gaaaatggat aagcaatgaa taattaatgg   2880
gttcaacttt tacatttgta aaacttcaaa ttgggggttc ctcaagtttg ggatactagg   2940
aattctccca aaagtgatca tattcaagaa acattaaata tactcatatt atccattgat   3000 taacctatt tttatccac attaaatatg ggtcgagtcg gataatttat ccatttttc     3060 attatccatt ttttacctga cccgacccga cccgcccatt ttccacccct actggtaatt   3120
attcactaaa atcaagagta aatttaccaa gatataggt atgtttggta tagatcaatt   3180
ttctcatgtt tggttggctt aaatatttta gagaatattt ttctcatgaa cttatttttc 3240
tcccattgga gaaaattgat ttccctacca aaaggaggaa agatattttt caaactctt   3300 tttaaccttc catacctat tcctcactcc ctcccctcaag aaaaatataa atacaccgta   3360
gttttggtga agaaaattttt tttattcatc acctaactat tacatgcttt ttcctcagta  3420 cttttctcctt ttctcctatt tctttctata tatatacatt aactatgtac ttcttgtcat  3480
taaaacatta gtagttctat ctatctaatc ttctattct gcattagctt ttcaatccag   3540
tctctttctt gaacacttgt cttgctcttc aaataggtaa tgttcctcag tctgcattct   3600
tgtttaatct gacttagtat gtatgtagtt gtgggtaatc ggaagtccca tacaacgatg   3660
ttcctagcct tccatatcca gtatatcagg gcagccaata tagcagtagc aactcccctg   3720
catctctttc ctttgagtag cctggtcact ctctttcata tccatgttat atatgtcagt   3780
tgtatttcca tgcacatcca gttttacacc cctcttaagc attgctgtga gaatacacat   3840
tcaaagaaca aatgttggat agtttcctct gttattccac atattgggta cctatcatct   3900
tgattaatgc acatacgatg caatatggtt tttgtcagca gtctttgatg catagtgagc   3960
tagcaaacaa aactgtgctt gggtaggttc atattgttcc atacccatct tctccatgcc   4020
cagttttcct tttctcccat tctccataga tatccctcaa ttgtgtattg tccattagca   4080
tttctccaca aattctgatt atatccagga gcaaatattt ctctgatctt gcatattttc   4140
ttccagtacc agcaagcatc attggggcat ttgtactgcc accaatcctt ctcctttaag   4200
```

```
tagacagtgt tgatccattt cacccataga ttatcagttt tttgagcgac attccataca    4260
tattttgcaa tagcaacttc attccatttt attatgtctg ttacgcccaa gcctccttca    4320
tgatttgtcc tacacactaa gtctcatgcc actaatggtg gcttatgtgt gatagctttc    4380
ccatcccata tgaaatttct acacatagca gttatccctt ttcagcactt gctttggaag    4440
caagaacata gttgaccagt aactatggat atgtagtagt actgaattca ctaactgcac    4500
tcttcctgca taagatagat gtcttgtact ccaacctttg attctagctg ctatcttgtc    4560
tatgagtatt tcacattcca ttttagatat cctcttagct atataggcac accaagatac    4620
caagatacct gaatggtaga cttccttct ggtatcctgc catttccatc aaatccttct      4680
agctctggat tggcatattg acactgaata tatttgactt gcttgcatta gcagttagac    4740
ctgagctttc tgagaatgtt ttcaagcccc tcaataagag cagcacagat tgaaaagtcc    4800
ctttactgaa caatagaaca tcatctgcaa ttgaaacttt tgctttcctc cccaacaatg    4860
tatatatatg aaaaatagtt actccctcta ttctactttt cgtgaaccta ttattatttg    4920
aggagtcaat aataaaaatt ttaaccacgg ttttggtaaa acttttaaa tattttcaat      4980 tattaactat gacatataat aatttttatg tagtttctag ttatgtaaat tttatttcaa    5040
aattgatatc cgaatttgta ttgaaaatca gtcaatttca ccctcttact ccgagtaata    5100
tatgtaataa gatctctcaa cctaacccat ttatttaga ttctagattc atctcacaat      5160
acttaatgaa catgcttctg ggagaaaagt ataaaataaa attaaaaccct gtagtagtac    5220 ataactaata atgatggatg ttgtattttc agggccattt tcaaaaactg cagtgaactt    5280
caacgctgga tgcaagactg caatgtcaaa cgtggtaatg tcaatatgca tgatgctaac    5340
ccttctgttc ttggctcctc tgtttagtta cacaccattg gtctctctct ccgccatcat    5400
catgtccgca atgcttggct taattgacta tgacaaggca tatcacctct tcaagacaga    5460
caagtttgat ttctgtattt gtatggctgc ctttttttggt gtttccttca taagcatgga    5520
cattggccta atgttatccg taagcactac acttctcgac aaaatattaa taacaaaaat    5580
ttgctattag agatgatttt ttccggggct tttccaggtt ggacttgcct taatcagagc    5640
acttctatat atagcaaggc cagctacttg caaacttggt ctcatatcag aaactggatt    5700
gtatcgcgat gtggagcagt atcctgatgc aaatggaatt gcagggtttc tgattctgaa    5760
gcttggttct cctatatact ttgcaaattg caattacgtc agagaaaggt ttttaatttg    5820
ttctattttc tctcatacac atcaaacaag tgcttctagt aatagtcttt ctttgatgga    5880
ttgcgcagga ttcttagatg gatcagagat gagcgttctc ataccatttc taaggaaat     5940 gaaattgaat tcttattact tgaattagga ggtactccta taaattagca agaaggagaa    6000
atttggatgt ttccttcttt ttctactata ataatgcaat taatggtaat gtaactgaat    6060
cacaacctta tgccaacagg tattacatcc attgacataa cgggtgttga aacattatta    6120
gaaattagaa ggtgcgtaca agcaaaaggg atcaaggtaa aatcaaactc tcatttttt     6180 tttcctatttt acttttttggg cacggtatag gaagtccaca gtttctaaa tacttacatt    6240 tcttctctgg cctttttcaat tctttaattt gtagatgatt ttggttaatc cgaggttggg    6300
agtcttggaa aagttgatgg tgacagagtc aatagacacc attacaaaag aatctgtctt    6360
cttaaccatt gaagacgcaa ttgatgcttg cagattttca ctcaaatgtt cggatcacat    6420
taaaacagaa aaccttgcaa tagttttag                                      6448
```

<210> SEQ ID NO 26

```
<211> LENGTH: 642
<212> TYPE: PRT
<213> ORGANISM: Nicotiana tabacum

<400> SEQUENCE: 26

Met Thr Ser Ser Pro Gln Ser Leu His Arg Val Asn Tyr Ala Ala Pro
1               5                   10                  15

Arg Ser Phe Gly Thr Leu Leu Lys Ala Asn Leu Lys Glu Thr Leu Phe
            20                  25                  30

Pro Asp Asp Pro Phe His Glu Ile Lys Asn Glu Pro Ile Ser Arg Arg
        35                  40                  45

Phe Leu Lys Gly Ala Gln Tyr Phe Val Pro Ile Phe Glu Trp Leu Pro
    50                  55                  60

Lys Tyr Asn Phe Lys Leu Phe Lys Tyr Asp Leu Leu Ala Gly Ile Thr
65                  70                  75                  80

Ile Ala Ser Leu Ala Ile Pro Gln Gly Ile Ser Tyr Ala Lys Leu Ala
                85                  90                  95

Asn Ile Pro Pro Ile Ile Gly Leu Tyr Ser Ser Phe Val Pro Pro Leu
            100                 105                 110

Ile Tyr Ala Val Phe Gly Ser Ser Lys His Leu Ala Val Gly Thr Val
        115                 120                 125

Ala Ala Cys Ser Leu Leu Ile Ala Ala Ile Ile Glu Gly Lys Val Asn
    130                 135                 140

Ala Ser Asp Asn Met Pro Leu Tyr Leu Ser Leu Val Phe Thr Ala Thr
145                 150                 155                 160

Leu Phe Ser Gly Leu Val Gln Thr Ala Leu Gly Leu Leu Arg Leu Gly
                165                 170                 175

Ile Leu Val Asp Phe Leu Ser His Ser Thr Ile Thr Gly Phe Met Gly
            180                 185                 190

Gly Thr Ala Ile Ile Ile Cys Leu Gln Gln Leu Lys Gly Met Leu Gly
        195                 200                 205

Leu Lys His Phe Thr Thr His Thr Asp Val Val Ser Val Leu Arg Ala
    210                 215                 220

Ile Phe His Asn Arg Lys Glu Trp Lys Trp Glu Ser Ala Val Val Gly
225                 230                 235                 240

Ile Ile Phe Leu Thr Phe Leu Gln Phe Thr Arg Phe Val Lys Asn Lys
                245                 250                 255

Lys Pro Lys Leu Phe Trp Val Ser Ala Ile Ala Pro Met Val Thr Val
            260                 265                 270

Ile Val Gly Cys Leu Phe Ala Tyr Phe Ala His Ala Glu Lys His Gly
        275                 280                 285

Ile Gln Ile Val Gly His Leu Ser Lys Gly Ile Asn Pro Ser Ser Ile
    290                 295                 300

His Leu Leu Asn Phe Asp Pro Lys Tyr Ile Ser Ala Pro Ile Lys Ala
305                 310                 315                 320

Gly Val Ile Ala Ala Met Ile Ser Leu Ala Glu Gly Ile Ala Ile Gly
                325                 330                 335

Arg Ser Phe Ala Ile Ile Arg Asn Glu Gln Ile Asp Gly Asn Lys Glu
            340                 345                 350

Met Ile Ala Ile Gly Leu Met Asn Ile Phe Gly Ser Phe Thr Ser Cys
        355                 360                 365

Tyr Leu Thr Thr Gly Pro Phe Ser Lys Thr Ala Val Asn Phe Asn Ala
    370                 375                 380

Gly Cys Lys Thr Ala Met Ser Asn Val Val Met Ser Ile Cys Met Met
```

|   |   |   |   |   | 385 |   |   |   |   | 390 |   |   |   |   | 395 |   |   |   |   | 400 |
|---|---|---|---|---|---|---|---|---|---|---|---|---|---|---|---|---|---|---|---|---|

Leu Thr Leu Leu Phe Leu Ala Pro Leu Phe Ser Tyr Thr Pro Leu Val
                        405                    410                        415

Ser Leu Ser Ala Ile Ile Met Ser Ala Met Leu Gly Leu Ile Asp Tyr
                  420                    425                    430

Asp Lys Ala Tyr His Leu Phe Lys Thr Asp Lys Phe Asp Phe Cys Ile
            435                    440                    445

Cys Met Ala Ala Phe Phe Gly Val Ser Phe Ile Ser Met Asp Ile Gly
450                              455                    460

Leu Met Leu Ser Val Gly Leu Ala Leu Ile Arg Ala Leu Leu Tyr Ile
465                    470                  475                  480

Ala Arg Pro Ala Thr Cys Lys Leu Gly Leu Ile Ser Glu Thr Gly Leu
            485                    490                    495

Tyr Arg Asp Val Glu Gln Tyr Pro Asp Ala Asn Gly Ile Ala Gly Phe
                  500                    505                    510

Leu Ile Leu Lys Leu Gly Ser Pro Ile Tyr Phe Ala Asn Cys Asn Tyr
            515                    520                    525

Val Arg Glu Arg Ile Leu Arg Trp Ile Arg Asp Glu Arg Ser His Thr
530                          535                  540

Ile Ser Lys Gly Asn Glu Ile Glu Phe Leu Leu Glu Leu Gly Gly
545                    550                  555                  560

Ile Thr Ser Ile Asp Ile Thr Gly Val Glu Thr Leu Leu Glu Ile Arg
                565                    570                575

Arg Cys Val Gln Ala Lys Gly Ile Lys Met Ile Leu Val Asn Pro Arg
            580                    585                    590

Leu Gly Val Leu Glu Lys Leu Met Val Thr Glu Ser Ile Asp Thr Ile
            595                    600                    605

Thr Lys Glu Ser Val Phe Leu Thr Ile Glu Asp Ala Ile Asp Ala Cys
            610                    615                    620

Arg Phe Ser Leu Lys Cys Ser Asp His Ile Lys Thr Glu Asn Leu Ala
625                              630                    635                  640

Ile Val

<210> SEQ ID NO 27
<211> LENGTH: 5201
<212> TYPE: DNA
<213> ORGANISM: Nicotiana tabacum

<400> SEQUENCE: 27

| | | | |
|---|---|---|---|
| atgacgagct ctccccagtc tttgcatagg gtgaactatg cagcgccacg aagctttggg | 60 |
| acgttactaa aagcaaacct aaaagagacc cttttcccag atgatccatt ccatgaaatc | 120 |
| aagaacgagc caatttcacg cagattttta aggggggctc aatattttgt tccaattttt | 180 |
| gaatggctgc caaagtacag tttcaagctc ttcaagtatg atcttcttgc tggaatcact | 240 |
| attgctagcc ttgccattcc tcaagggata agctatgcca aactcgctaa cattcctcca | 300 |
| atcatcggac tctgtaagct acttataaga gtattgtatt gttttttcct atatattgac | 360 |
| acgtcgtacc aaaagatgta tgtgttgata actttcttgg cttttgattc gaagtaggta | 420 |
| caactaacaa tattttgatt aaaagattga gtctaaatat ttctgttatt aattaaacac | 480 |
| gggagttgca tgcatgcaga ttcgagcttt gttcctcctc ttatttatgc tgttttggga | 540 |
| agttcaaagc accttgctgt ggggacggtg gctgcttgct cattgctat tgctgcaatc | 600 |
| attgaaggaa aagtgaacgc taacgataat atgccgctgt atcttagttt ggtgttcacg | 660 |

```
gccactcttt tctctggttt ggttcagact gctctgggtt tgctaaggta tatataaatg    720
accgaagtta cgtacacatg accaccacct tctctaaact agctagctct ttgattaatt    780
agtactagta taaatatata agtgcaattt atttggtttg tgcagacttg ggattttggt    840
agattttcta tcacattcaa ccataactgg atttatggga gggacagcaa taattatttg    900
cttgcagcaa ctgaagggca tgcttggttt gaagcatttc accacccata ctgatgtggc    960
ttctgtctta cgtgctatct tccacaacag aaaagaggtt gtcattctat actccttgta   1020
tctatttgat taattaagtg aatagccatg cattggggat acttctacgc acaatatata   1080
ttcacatacc ttagcttgga cactgacata tcatttagaa atattatttt atagatccat   1140
atatgtcacc aaaggataaa aaatgaggaa tataattgcc ttttattatt gaaagttaca   1200
catggttttg gtcaatgggg caatttaatt tctgttattg atttttttttg tgtgtgtatt   1260 cgaacagtgg aagtgggaga gtgcagttgt tggaataatc ttccttactt tcctgcaatt   1320
cactagattt gtggtgagtg tttcctattg gtatgtgaaa ataagtgttc tcgcagatca   1380
tgtatacaag aaaaaataat gcttcttttgc agaaaaacaa gaaaccaaag ctattttggg   1440
tttcagccat agctccaatg gtcactgtaa ttgtcggctg ccttttcgct tacttcgccc   1500
atgctgacaa acatggcatc caaatcgtaa gcctttaatt tccttctccc ccaccccaaa   1560
atgaatttat attaagtgcg gtacaacata tagaaaagct gacaaatatg gccgactag   1620 gaaaggaaga atagaacaga gaatcacgga aatatacaaa atttgagaaa gatgaaggtg   1680
atttgaatta actagtttgc cataaaatat tttagtagaa atcgaattaa aaacttcctt   1740
tatgacacat gtaattcaca catatatata catgtgtgta tacatatata cggggaatac   1800
taataattaa gtctgggcgg atgtagtata tactcgacag gttcaattga acccataact   1860
ttcgacgctg agtaaaaaat attatatgta aaaattcatt aaaatttcaa aaatagtata   1920
tatgaactaa ataactttat aaatataatg agttcaatgc taaaaaattt aaaaattgaa   1980
cccataggat ttaaattctg aatccgttag tttttttgct tagggttatc aaacgaaata   2040
gtttgagaac aggaagagac gcattaggag agacaaaaat taaagaattt gcaactgtta   2100
agattgctaa gatcttttttg aattctcttt aagggttgtt ggagaatgac tattgaggtg   2160
tgtatggcaa cgtttgaatt ctctttaagg gttgttggag aatgactatt gaggtgtgta   2220
tggcaacgtt tcaataattt atcattaaga caaaccccctt ttacaacact tatctaagtg   2280
gacttccacc taactagcta ggaagagcca attttgacct ttcgagaatt agacttaaag   2340
tatgcaagtt atgtccaccg acgcatatgg acaagatcac taataatctt gtagaaaact   2400
caacactaac tctttctttt ctgtggtcac agcactaggt ccgtatttta atttgtctca   2460
tctaatgtaa cagtaggtcc ttttgtctca tattttggac tgaatatata caggttggac   2520
atttgagtaa aggaataaat ccctcttcca ttcatctttt aaatttcgat cccaagtata   2580
tatcagcacc tataaaagca ggagtcatcg cagcaatgat atctctagct gtaagtacac   2640
cctttatcca tacatacgag ctccgtttat gacaaagaat ttctgatttg tcaatcatca   2700
aaaacgtacg tgtttactaa gtttgtatgg aatattttct aggagggaat agccatcgga   2760
cggagtttcg ccatcatcag aaatgaacaa attgatggca acaaggaaat gattgctatt   2820
ggcctcatga acattttttgg atctttcgct tcatgctact tgacaactgg taattagcgg   2880
cggcaaacaa ttaatcatcc atattattca ctaaaagatg ggctgaataa taaacttttt   2940
aaaaacggat caaatatgga taagaaccat attatccatt taacttttac atttgtaaaa   3000
cttcaaatcg gtggttcctc aagtttagaa gactaagaat tttttccaaaa gtgatcatat   3060
```

```
tcaagaagaa ttaaatacac acatattatc catcgattaa cccatatttt atccacatta    3120
aatatggctc ggatcggata atttatccgt tttgcattac ccattttcga cccgacccga    3180
ccgtttgcca cccctactgg taattattca ctaaaatcaa gagtaaaatt taccaagata    3240
tagggtgtgt ttggtaagga ttaattttct catgtttgat tggcttaaat atttagagaa    3300
tagttttctt atgaacttat ttttttttc aatcggagaa aaatgacttt cctaccaaaa     3360
tgaggcaaga tattttttcaa aactctttttt caaccttccc taccttattc tccacccaaa   3420
aactgtacca atacaccat agttgtcaag accactctcg tgatggaaac tgtacctact    3480
ggataagaaa actaattaga ttattagcat ccgtcgattt acgacaggct tggattcaac    3540
tgaatctctt gctttcctcc caaacaaaat atatatatat atatatatat atatatatat    3600
ataaaatagt tactccctct attctacttc aggtgaacct attactgttt gaggagtcaa    3660
ataaaatttt ttttgaccag gttttttataa aacttttttaa atattttcga ttattaacta    3720
tgacatataa taatttttat gtagtttcta attatataaa tttttatttca aaattttttga    3780
aaatcttata tccgaatttg tattaaaaat tagttaatttt aaccctcgta ctccgaaaag   3840
attctaataa actagaacga aaagattcat ctctgacaga caatacttta atgaacatgc    3900
ttctaggaaa agtatatttta caccataaaa taaagttaaa acatgtggta gtacataact    3960
aataatgatg gatgttgtat tttcagggcc attttctaaa actgcagtga acttcaacgc    4020
tggatgcaag actgcaatgt caaacgtggt aatgtcaata tgcatgatgc taaccctttct    4080
gttcttggct cctctgtttta gttacacacc attggtctct ctctccgcca tcatcatgtc    4140
tgcaatgctt ggcttaattg actatgacaa ggcatatcac ctcttcaaga cagacaagtt    4200
tgatttctgt atttgtatgg ctgcctttttt tggtgtttcc ttcataagca tggacattgg    4260
cctaatgtta tctgtaagca ctacactttt caataaaata ttaataacaa aatttttgcta    4320
ttagagatga ttatttgctt aaattgtttc cggggcttttt ccaggttgga cttgccttaa    4380
tcagagcact tctatatata gcaaggccgg ctacttgcaa gcttggactc atatcagaaa    4440
ctggattgta tcgcgatgtg gagcagtatc ctgatgcaaa tggaattgca gggattctga    4500
ttctgaagct tggttctcct atatactttg caaattgtaa ttcatcaga gaaaggtttt     4560
tgttctatttt tctctcatac acatcaaaca agtgcttcta ctacatattc tgatagtgaa    4620
cttgatcttt ctttgatgga ttgcgcagga ttcttagatg gatcagagat gagcgttctc    4680
ttaccatttc tgaaggaaat gaaattgaat tcttattact tgaattagga ggtactccta    4740
taaattagca agaagaagaa atttggatgt ttccttctttt ttctattata ataatgcaat    4800
ggtaatgtaa ctgaatcaga accttatgcc aacaggtatt acatccattg acataacggg    4860
tgttgaaacg ttattagaaa ttcgaaggtg cgtagaagca aaaggggatca aggtaaaatc    4920
aaactctcat tgttttttcca tttactttttt gggcatggta taggaagtcc ataaggttct    4980
aaatacttac atttcttctc ttgcctttttc aattctttaa tttgtagatg atttttggtta    5040
atccgaggtt gggagtcttg gaaaagttga tggtgacaga gtcaatagac accgttacaa    5100
aagaatctgt gttcttaacc attgaagacg caattgatgc ttgcagatttt tcactcaaat    5160
gttcagatca aatgaaaaga gaaaaccttg caatagttta g                       5201
```

<210> SEQ ID NO 28
<211> LENGTH: 642
<212> TYPE: PRT
<213> ORGANISM: Nicotiana tabacum

```
<400> SEQUENCE: 28

Met Thr Ser Ser Pro Gln Ser Leu His Arg Val Asn Tyr Ala Ala Pro
1               5                   10                  15

Arg Ser Phe Gly Thr Leu Leu Lys Ala Asn Leu Lys Glu Thr Leu Phe
            20                  25                  30

Pro Asp Asp Pro Phe His Glu Ile Lys Asn Glu Pro Ile Ser Arg Arg
            35                  40                  45

Phe Leu Lys Gly Ala Gln Tyr Phe Val Pro Ile Phe Glu Trp Leu Pro
        50                  55                  60

Lys Tyr Ser Phe Lys Leu Phe Lys Tyr Asp Leu Leu Ala Gly Ile Thr
65                  70                  75                  80

Ile Ala Ser Leu Ala Ile Pro Gln Gly Ile Ser Tyr Ala Lys Leu Ala
                85                  90                  95

Asn Ile Pro Pro Ile Ile Gly Leu Tyr Ser Ser Phe Val Pro Pro Leu
            100                 105                 110

Ile Tyr Ala Val Phe Gly Ser Ser Lys His Leu Ala Val Gly Thr Val
        115                 120                 125

Ala Ala Cys Ser Leu Leu Ile Ala Ala Ile Ile Glu Gly Lys Val Asn
    130                 135                 140

Ala Asn Asp Asn Met Pro Leu Tyr Leu Ser Leu Val Phe Thr Ala Thr
145                 150                 155                 160

Leu Phe Ser Gly Leu Val Gln Thr Ala Leu Gly Leu Leu Arg Leu Gly
                165                 170                 175

Ile Leu Val Asp Phe Leu Ser His Ser Thr Ile Thr Gly Phe Met Gly
            180                 185                 190

Gly Thr Ala Ile Ile Ile Cys Leu Gln Gln Leu Lys Gly Met Leu Gly
        195                 200                 205

Leu Lys His Phe Thr Thr His Thr Asp Val Ala Ser Val Leu Arg Ala
210                 215                 220

Ile Phe His Asn Arg Lys Glu Trp Lys Trp Glu Ser Ala Val Val Gly
225                 230                 235                 240

Ile Ile Phe Leu Thr Phe Leu Gln Phe Thr Arg Phe Val Lys Asn Lys
                245                 250                 255

Lys Pro Lys Leu Phe Trp Val Ser Ala Ile Ala Pro Met Val Thr Val
            260                 265                 270

Ile Val Gly Cys Leu Phe Ala Tyr Phe Ala His Ala Asp Lys His Gly
        275                 280                 285

Ile Gln Ile Val Gly His Leu Ser Lys Gly Ile Asn Pro Ser Ser Ile
    290                 295                 300

His Leu Leu Asn Phe Asp Pro Lys Tyr Ile Ser Ala Pro Ile Lys Ala
305                 310                 315                 320

Gly Val Ile Ala Ala Met Ile Ser Leu Ala Glu Gly Ile Ala Ile Gly
                325                 330                 335

Arg Ser Phe Ala Ile Ile Arg Asn Glu Gln Ile Asp Gly Asn Lys Glu
            340                 345                 350

Met Ile Ala Ile Gly Leu Met Asn Ile Phe Gly Ser Phe Ala Ser Cys
        355                 360                 365

Tyr Leu Thr Thr Gly Pro Phe Ser Lys Thr Ala Val Asn Phe Asn Ala
    370                 375                 380

Gly Cys Lys Thr Ala Met Ser Asn Val Val Met Ser Ile Cys Met Met
385                 390                 395                 400

Leu Thr Leu Leu Phe Leu Ala Pro Leu Phe Ser Tyr Thr Pro Leu Val
                405                 410                 415
```

Ser Leu Ser Ala Ile Ile Met Ser Ala Met Leu Gly Leu Ile Asp Tyr
                420                 425                 430

Asp Lys Ala Tyr His Leu Phe Lys Thr Asp Lys Phe Asp Phe Cys Ile
            435                 440                 445

Cys Met Ala Ala Phe Phe Gly Val Ser Phe Ile Ser Met Asp Ile Gly
450                 455                 460

Leu Met Leu Ser Val Gly Leu Ala Leu Ile Arg Ala Leu Leu Tyr Ile
465                 470                 475                 480

Ala Arg Pro Ala Thr Cys Lys Leu Gly Leu Ile Ser Glu Thr Gly Leu
                485                 490                 495

Tyr Arg Asp Val Glu Gln Tyr Pro Asp Ala Asn Gly Ile Ala Gly Ile
                500                 505                 510

Leu Ile Leu Lys Leu Gly Ser Pro Ile Tyr Phe Ala Asn Cys Asn Tyr
            515                 520                 525

Ile Arg Glu Arg Ile Leu Arg Trp Ile Arg Asp Glu Arg Ser Leu Thr
            530                 535                 540

Ile Ser Glu Gly Asn Glu Ile Glu Phe Leu Leu Glu Leu Gly Gly
545                 550                 555                 560

Ile Thr Ser Ile Asp Ile Thr Gly Val Glu Thr Leu Leu Glu Ile Arg
                565                 570                 575

Arg Cys Val Glu Ala Lys Gly Ile Lys Met Ile Leu Val Asn Pro Arg
                580                 585                 590

Leu Gly Val Leu Glu Lys Leu Met Val Thr Glu Ser Ile Asp Thr Val
            595                 600                 605

Thr Lys Glu Ser Val Phe Leu Thr Ile Glu Asp Ala Ile Asp Ala Cys
610                 615                 620

Arg Phe Ser Leu Lys Cys Ser Asp Gln Met Lys Arg Glu Asn Leu Ala
625                 630                 635                 640

Ile Val

<210> SEQ ID NO 29
<211> LENGTH: 128
<212> TYPE: DNA
<213> ORGANISM: Artificial Sequence
<220> FEATURE:
<223> OTHER INFORMATION: Nucleotide sequence used for silencing
      NtSULTR3:1A-S and NtSULTR3:1A-T

<400> SEQUENCE: 29
gtaggcaaca ttgatactag cggaattagc atgctagaag aggtcaagaa gaatcttgat      60
agaagagatc tcaagcttgt gctggcaaat ccaggggcag aggtaatgaa gaagctgaac     120
aagtccaa                                                              128

<210> SEQ ID NO 30
<211> LENGTH: 4384
<212> TYPE: DNA
<213> ORGANISM: Nicotiana tabacum
<220> FEATURE:
<221> NAME/KEY: misc_feature
<222> LOCATION: (1520)..(1520)
<223> OTHER INFORMATION: n is a, c, g, or t

<400> SEQUENCE: 30
atggcagcta gtggtcttag cattaagaaa agtttggagg aatccatttt ggctcatcca      60
gatgaaattt tggctctcaa gtcaaggtac attactacat ataatgatat taagaactag     120
aggcttatcc aaggttttgt tacatttttg aaattataag tttagaacct aatagtactt     180

```
ggtagcactt gtttccttat tatctagctg ttgttactgc ttgttgctac tgctttctgt    240
tcatctttcc ttgagcccgg tctatcggaa acaacctctc tattctcaaa gtataaggtt    300
tgcgtacata ctacctcccc agactctact tgtggaattt actgttttg ttgtgttgtt     360 gtaatctaat atttattaga attttactga tttttcacat atatatatct atgtcccctg    420
tcgaaaattc tatagctcat gttagctaaa tacattagta ccattgtttt taattgtttt    480
ggttttggca caggattgaa actgaaggga aaggggtaat gaaaccactt gatctcttga    540
accatttggt ttctgttact agtaagacaa atggagtaaa tattgtacct agtgcacttg    600
tggaagttct cagttgcagc caagaagctg tgattgtacc accaaaacta gcactagctg    660
tacgtccgag gcccggtgta tgggagtact tgtcactgaa tcttaagaca agaaagtgg     720 ctgaattaag cattcctgaa taccttcaat tgaaagagaa cactgttgat gaaaggtaaa    780
gtattagtct gcgatttcgc tttgtgaaat tgaagttttt gttttgattc ataatgtttt    840
gtgtatcaat tatgttacca gtggaaacat attggagttg gattttgagc catttacaac    900
agttacacca ccaaaaacac tttctgactc tattggcaat ggtttggagt ttcttaatcg    960
ccacattgct tcgaaaatgt ttcatgataa ggagatttcc agatgcctcc ttgacttcct    1020
cagaaaccat aactacaaag gaaaggtaat aaaaaaaagt gtttctttaa caagttgta    1080 tgattatgtg tatatttcta agtatgttaa cttgaaaaca gtcattgatg gtgaaagaaa    1140
gcattcaaag cctagagagt ttccaacttg ttctgaaaaa agcagaggaa catttgtgca    1200
cattgaatcc agaaactcca tactccaatt ttgaatcaaa gtttgaagag attggcttgg    1260
aaagagggtg gggaaacacc gctgaacgcg tgcaagacac tatcagtcat cttttgcatc    1320
tccttgaggc tcctaacgcg tcttctttgg aaaatttcct tggtagaatc ccattggttt    1380
tcaatgttgt gattctaact ccacatggtt attttgctca agataatgtc ttgggctatc    1440
ctgacactgg tggccaggtt tgtgtccaat attttgcatt cttgatcaag ttctttatac    1500
catttgaacc aacaatcttn aacattcttt ttttggttgt gaaatgttga ataggttgtt    1560
tacattcttg atcaagttcc agctatggag cgtgagatgc ttcatcgtat gaagcttcaa    1620
ggactcgatg atatcatccc tcgcatcctt gttgtaagtg gccttaattt tcctagtttc    1680
atttacacct ctaaatgaaa ttgatctttt ttgttgtttt atatcaggta acaaggctgc    1740
tgcctgatgc agtaggaacc acctgtggcg agcggatgga gaaagtatat ggggcagaac    1800
attctcatat aattcgtgtt ccatttagaa ctgagaaggg aatgttgcgc aaatggatct    1860
cacgattcga agtctggcca tacatggaaa cttttcactga ggttggaaca taaaaacaaa    1920
taaaatccat tggaatgttc cttctgcaat tgaaaatgtc ttgctaactg aagacccatt    1980
tttaaattga tcatcaggat gttgcagaag aacttgtcaa agaattgcaa gctaaaccag    2040
acttgatcat tggaaactac agtgagggaa atcttgctgc ctctttgctt gcgaagaaat    2100
ttggggctac tcagtgtact attgctcatg ccttggaaaa aactaagtat ccaaactctg    2160
accttaattg gaagaagttt gatgacaagt atcatttctc aagtcagttc actgctgatc    2220
tctttgccat gaatcacact gatttcatca tcaccagcac tttccaagaa attgctggaa    2280
ggtaaaagca aatgcacacc atcatagtat ttcatatttt tacccttgtt tatactattt    2340
ccattcaccg accccgactt gtttaggatt gagccatagt tgttgttgtt gtttgtttat    2400
actatttcca tttgccgacc acaacttgtt taggactgag gtatagttgt tgttgttggt    2460
ttgttcatat tattttcatt cgctaacct aacttgtttg ggactgaggc atagtagtag    2520
```

```
tagtagttgt tgctattagt ttatactatt tccatttgcc aaccccaact tgtttggtac      2580
tgagacatag ttgttgttgt tgttgtttgt ttatactatt tccatttgcc gaccccaact      2640
tgtttaggac tgaggtatag ttgttgttgt tggtttgttc atattatttt cattcgctaa      2700
ccccaacttg tttgggactg aggcatagta gtagtagtag tagttgttgc tattagttta      2760
tactatttcc atttgccaac cccaacttgt ttggtactga gacatagttg ttgttgttgt      2820
ttgtttatac tatttcaatt tgtcgacccc aatttgtttg ggaccaaggc atggttgttg      2880
ttgttgtttg tttgtttttta ctgtttccat tgatattgga acatttgtta tttgcagcaa      2940
aaacactgta ggacagtatg agagtcatac tgcttttacc atgcctggat tgtaccgagt      3000
agtccatgga atcgattcgt ttgatccaaa gttcaacatt gtctccctg gggctgatat        3060
gtcaatctac ttcccttaca ctgagaagga gaaaaggcta accaacttcc acccggaaat      3120
tgaagaactc ctctacagtc ctgttgagaa taaggaccac ttgttagtct ccttaatttg      3180
cttttatttc atcccattta tgatcgcttt tatcccaaca gatcgattaa tcatttgtta      3240
tcaacataaa cagatgtgtg ttgaaggacc ggaacaagcc aattctcttt accatggcaa      3300
ggctagatcg cgtgaagaat ctaacagggc tcgtggaatg gtatgctaag aatgcaaggc      3360
tgagggagct tgttaacctt gtggttgtag gcggagacag aaggaaagaa tccaaagatt      3420
tagaagagca agcagagatg aagaagatgt atgatcttat cgaaacctat aacctgaacg      3480
gccaattcag gtggatttct tcccaaatga atcgtgtgag gaacgagaa ctctatcgtt        3540
acattgcaga cacgaggggt gctttcgttc aaccagcatt ctacgaggct tttggttttga     3600
cagttgtaga gtctatgact tgtggttttgc caacttttgc tacttgtaat ggtggaccat      3660
ttgagattat agtgaatgga aaatctggtt tccatattga tcctaatcaa ggtgacaagg      3720
ctgctgatat gttggtaaat ttctttgaaa aatctaaaga agatccaagt tattgggatg      3780
ctatttccaa gggaggtctg caacgtattc ttgaaaagta agcttttgca tttgattagc      3840
acaagtgcac aaccaagatt taacttttga acaaactaaa actaacccctt ttttgtattt      3900
tcttttgcta ggtatacatg gcaaatttat tcacagaaag tgatcacact atctgggatt      3960
tatggattct ggaagtatgc aaccaagaat gataaagttg ctagtgcaaa gaagcgctat      4020
cttgagatgt tttatgaact tggatttaag aaatcagtaa gtgtcaattt taaaggggaa      4080
ccttggatca acggttaagt tgtctttgtg caacctatag gtcagggggtt tgagccgtag     4140
aagtagccac taatatttac attagggtag actgtgtaca tatcacaccc cttggggtac      4200
ggcccttttcc tggatcctgt atgaacgcgg gatgccttgt gcaccgggct gtatttttttt    4260
ttttagtgtc acttctgtat tttgtttgag cttgtttata aagtttggaa atctgctgct       4320
aatttgtata tttgttggtt gtgtatttca ggctgagaaa gttccattgg ctattgatga      4380
atag                                                                   4384
```

<210> SEQ ID NO 31  
<211> LENGTH: 803  
<212> TYPE: PRT  
<213> ORGANISM: Nicotiana tabacum

<400> SEQUENCE: 31

Met Ala Ala Ser Gly Leu Ser Ile Lys Lys Ser Leu Glu Glu Ser Ile  
1               5                   10                  15

Leu Ala His Pro Asp Glu Ile Leu Ala Leu Lys Ser Arg Ile Glu Thr  
            20                  25                  30

Glu Gly Lys Gly Val Met Lys Pro Leu Asp Leu Leu Asn His Leu Val

```
            35                  40                  45
Ser Val Thr Ser Lys Thr Asn Gly Val Asn Ile Val Pro Ser Ala Leu
 50                  55                  60

Val Glu Val Leu Ser Cys Ser Gln Glu Ala Val Ile Val Pro Pro Lys
 65                  70                  75                  80

Leu Ala Leu Ala Val Arg Pro Arg Pro Gly Val Trp Glu Tyr Leu Ser
                 85                  90                  95

Leu Asn Leu Lys Thr Lys Lys Val Ala Glu Leu Ser Ile Pro Glu Tyr
                100                 105                 110

Leu Gln Leu Lys Glu Asn Thr Val Asp Glu Ser Gly Asn Ile Leu Glu
            115                 120                 125

Leu Asp Phe Glu Pro Phe Thr Thr Val Thr Pro Pro Lys Thr Leu Ser
        130                 135                 140

Asp Ser Ile Gly Asn Gly Leu Glu Phe Leu Asn Arg His Ile Ala Ser
145                 150                 155                 160

Lys Met Phe His Asp Lys Glu Ile Ser Arg Cys Leu Leu Asp Phe Leu
                165                 170                 175

Arg Asn His Asn Tyr Lys Gly Lys Ser Leu Met Val Lys Glu Ser Ile
            180                 185                 190

Gln Ser Leu Glu Ser Phe Gln Leu Val Leu Lys Lys Ala Glu Glu His
        195                 200                 205

Leu Cys Thr Leu Asn Pro Glu Thr Pro Tyr Ser Asn Phe Glu Ser Lys
    210                 215                 220

Phe Glu Glu Ile Gly Leu Glu Arg Gly Trp Gly Asn Thr Ala Glu Arg
225                 230                 235                 240

Val Gln Asp Thr Ile Ser His Leu Leu His Leu Leu Glu Ala Pro Asn
                245                 250                 255

Ala Ser Ser Leu Glu Asn Phe Leu Gly Arg Ile Pro Leu Val Phe Asn
            260                 265                 270

Val Val Ile Leu Thr Pro His Gly Tyr Phe Ala Gln Asp Asn Val Leu
        275                 280                 285

Gly Tyr Pro Asp Thr Gly Gly Gln Val Val Tyr Ile Leu Asp Gln Val
    290                 295                 300

Pro Ala Met Glu Arg Glu Met Leu His Arg Met Lys Leu Gln Gly Leu
305                 310                 315                 320

Asp Asp Ile Ile Pro Arg Ile Leu Val Val Thr Arg Leu Leu Pro Asp
                325                 330                 335

Ala Val Gly Thr Thr Cys Gly Glu Arg Met Glu Lys Val Tyr Gly Ala
            340                 345                 350

Glu His Ser His Ile Ile Arg Val Pro Phe Arg Thr Glu Lys Gly Met
        355                 360                 365

Leu Arg Lys Trp Ile Ser Arg Phe Glu Val Trp Pro Tyr Met Glu Thr
    370                 375                 380

Phe Thr Glu Asp Val Ala Glu Glu Leu Val Lys Glu Leu Gln Ala Lys
385                 390                 395                 400

Pro Asp Leu Ile Ile Gly Asn Tyr Ser Glu Gly Asn Leu Ala Ala Ser
                405                 410                 415

Leu Leu Ala Lys Lys Phe Gly Ala Thr Gln Cys Thr Ile Ala His Ala
            420                 425                 430

Leu Glu Lys Thr Lys Tyr Pro Asn Ser Asp Leu Asn Trp Lys Lys Phe
        435                 440                 445

Asp Asp Lys Tyr His Phe Ser Ser Gln Phe Thr Ala Asp Leu Phe Ala
    450                 455                 460
```

Met Asn His Thr Asp Phe Ile Ile Thr Ser Thr Phe Gln Glu Ile Ala
465                 470                 475                 480

Gly Ser Lys Asn Thr Val Gly Gln Tyr Glu Ser His Thr Ala Phe Thr
            485                 490                 495

Met Pro Gly Leu Tyr Arg Val Val His Gly Ile Asp Ser Phe Asp Pro
        500                 505                 510

Lys Phe Asn Ile Val Ser Pro Gly Ala Asp Met Ser Ile Tyr Phe Pro
            515                 520                 525

Tyr Thr Glu Lys Glu Lys Arg Leu Thr Asn Phe His Pro Glu Ile Glu
530                 535                 540

Glu Leu Leu Tyr Ser Pro Val Glu Asn Lys Asp His Leu Cys Val Leu
545                 550                 555                 560

Lys Asp Arg Asn Lys Pro Ile Leu Phe Thr Met Ala Arg Leu Asp Arg
                565                 570                 575

Val Lys Asn Leu Thr Gly Leu Val Glu Trp Tyr Ala Lys Asn Ala Arg
            580                 585                 590

Leu Arg Glu Leu Val Asn Leu Val Val Gly Asp Arg Arg Lys
        595                 600                 605

Glu Ser Lys Asp Leu Glu Glu Gln Ala Glu Met Lys Lys Met Tyr Asp
610                 615                 620

Leu Ile Glu Thr Tyr Asn Leu Asn Gly Gln Phe Arg Trp Ile Ser Ser
625                 630                 635                 640

Gln Met Asn Arg Val Arg Asn Gly Glu Leu Tyr Arg Tyr Ile Ala Asp
                645                 650                 655

Thr Arg Gly Ala Phe Val Gln Pro Ala Phe Tyr Glu Ala Phe Gly Leu
            660                 665                 670

Thr Val Val Glu Ser Met Thr Cys Gly Leu Pro Thr Phe Ala Thr Cys
        675                 680                 685

Asn Gly Gly Pro Phe Glu Ile Ile Val Asn Gly Lys Ser Gly Phe His
690                 695                 700

Ile Asp Pro Asn Gln Gly Asp Lys Ala Ala Asp Met Leu Val Asn Phe
705                 710                 715                 720

Phe Glu Lys Ser Lys Glu Asp Pro Ser Tyr Trp Asp Ala Ile Ser Lys
                725                 730                 735

Gly Gly Leu Gln Arg Ile Leu Glu Lys Tyr Thr Trp Gln Ile Tyr Ser
            740                 745                 750

Gln Lys Val Ile Thr Leu Ser Gly Ile Tyr Gly Phe Trp Lys Tyr Ala
        755                 760                 765

Thr Lys Asn Asp Lys Val Ala Ser Ala Lys Lys Arg Tyr Leu Glu Met
        770                 775                 780

Phe Tyr Glu Leu Gly Phe Lys Lys Ser Ala Lys Val Pro Leu Ala
785                 790                 795                 800

Ile Asp Glu

<210> SEQ ID NO 32
<211> LENGTH: 3926
<212> TYPE: DNA
<213> ORGANISM: Nicotiana tabacum

<400> SEQUENCE: 32
atggcaggca gtggtcttag cattaaggaa agtttggagg aatccatttt ggctcatcca      60
gatgaaattt tggctctcaa gtcaaggtac attactgcat aatgatatta agacctagaa     120
gcggatccaa gatttgtta cattttgaa attataagtt tagaatctaa tatttgttat     180

```
cgcttgtttc cttattatct tgctgttgtt actgcctgtt gctactagtt tctgttcatc        240
cttccttgag ctgagtttct atcggaaaca acctctctac tctcaaagta ggaataagtt        300
atgcgtacac actaccctcc ccagactcca cttgtgtaat ttactgagtt tgttgttgtt        360
gttgttgtaa tctaatactt gttagaattt tactgatttt tcacatatat atctatgacc        420
catgtcgaaa atactatagc tcatgtgcta aatacattag taccattgtt ttgtaattgt        480
tttggttttg aacaggatt gaaactgaag ggaaaggggt aatgaaacca gttgatctct         540
tgaaccattt ggtttctgtt actagtaaaa caaatggagt aaatgttgta cctagtgcac        600
ttgtggaagt tctcagttgc agccaagaag ctgtgattgt accaccaaaa ctagcactag        660
ctgtacgtcc gaggcccggt gtatgggagt acttgtcact gaatcttaag acaaagaaag        720
tggctgaatt gagcattcct gagtaccttc aattgaaaga gaatactgtt gatgaaaggt        780
aaagtaatag tctgcgattt cgctttgtga aattgaagtt ttttgtttga ttcttaatgt        840
tttgtgtatc aattatgtta ccagtggaaa catcttggag ttggattttg agccatttac        900
aactgttaca acaccaaaaa cactttctga ctctattggc aatggtttgg agtttcttaa        960
tcgccacatt gcttcgaaaa tgtttcttga taaggagatt gccaagtgcc tccttgactt       1020
tctcagaaac cataactaca aaggaaaggt agtaaaaaaa gtgtttcttt aaacaagttg       1080
tatgattatg tgtgtatttc taaatatgtc aatttgaaaa cagtcattga tggtgaaaga       1140
aagcattcaa agcctggaga gtttccaact tgttctgaaa aaagcagagg aatatttgca       1200
cacactgaat ccagaaactc catactccaa atttgaatcc aagtttgaag agattggctt       1260
ggaagagggg tggggaaaca ccgctgaacg cgtgcaagac accattagtc atcttttgca       1320
tctccttgag gctcctaacg cgtcttcctt ggaaaatttc cttggtagaa tcccattggt       1380
tttcaatgtt gtgattctca ccccacatgg ttattttgct caagataatg tcttgggcta       1440
tcctgacact ggtggccagg tttgtgtccg atataacata tcaagaaatt ttgcattctt       1500
gatcatgttc tttataccat ttgaaccaac attctttttt tggttgtgaa atgttgaata       1560
ggttgtttac attcttgatc aagttccagc tatggagcgt gagatgcttc atcgtatgaa       1620
gcttcaagga ctcgacgata tcatccctcg catccttgtt gtaagtgccc ttaattttcc       1680
tggtttggtt tacctctaaa tgaaattgat tttctggctt tctaactttt ttggattgat       1740 cttttttgttg ttttatatca ggtaactagg ctgctgcctg atgctgtagg aaccacttgt       1800
ggcgagtgga tggagaaagt atatggggca gaacattctc atataattcg tgttccattt       1860
agaactgaga aaggaatgtt gcgcaaatgg atctcacgat tcgaagtctg gccatacatg       1920
gaaactttca ctgaggttgg aacataaaaa caaataaaaa tcattggaat gttcttctgc       1980
atttgaaaat gtcttgctaa ctaaagactc attttttaaat taatcatcag gatgttgcag       2040
aagaacttgt caaagaattg caagctaaac cagacttgat aattggaaac tacagtgagg       2100
gaaatcttgc tgcctcattg cttgctaaga aatttggggc tactcagtgt actattgctc       2160
atgccttgga aaaaactaag tatccaaact ctgaccttaa ttggaagaag tttgatgaca       2220
agtatcattt ctcaagtcag ttcactgctg atcttttgc catgaatcac actgatttca       2280
ttatcaccag cactttccaa gaaattgctg aaggtaaaa gcaaatgcac accatcatag       2340
tatttcatat ttttacccta gtttatacta tttccatttg tcaactccaa cttgtttggg       2400
attgaaccat agttgttgtt tgtttatact atttccattc gccgacccca acttatttgg       2460
gactgagaca taattgttgt tattattgtt tgtttgttta tactatttcc attctcagac       2520
```

```
cccaacttct ttgggactga gccgtagatt gttgttgttg ttgttgttgt tgtttgttta    2580
tgctatttcc gttcaccgac cccaacttat ttgggactga ggtgtagaag tagtcgttgt    2640
tgtttgttta tacgacttcc aattgatatt cgaatgtttt tattttttgca gcaagaacac   2700
tgtaggacag tatgagagtc atactgcttt taccatgcct ggattgtatc gagtagtcca    2760
tggaatcaat tcgtttgatc caaagttcaa cattgtctcc cctggggctg atatgtcaat    2820
ctacttccct tacactgaga aggagaaaag actaaccaac ttccacccgg aaattgaaga    2880
actcctctac agtcctgttg agaataagga ccacttgtta gtcttcttta tttcattcat    2940
ttttctacac cttttttttc aacagattga ttgattggtt cttatcaacg taaacagatg    3000
tgtgttgaag gaccagaaca agccaattct ctttaccatg gcaaggctag atcgcgtgaa    3060
gaatctaaca gggctcgtgg aatggtatgc aaagaatgca aggctaaggg agctcgttaa    3120
ccttgtggtt gtaggcggag acagaaggaa agaatccaaa gatttagaag agcaagcaga   3180
gatgaagaag atgtatgatc ttatcgaaac atacaacctg aatggccaat tcaggtggat    3240
ttcttcccaa atgaatcgtg tgaggaacgg agaactttat cgatacattg cagacacgag    3300
gggtgctttc gttcaaccag cattttatga ggcatttggt ttgacagttg ttgagtctat    3360
gacttgtggt ttgccaactt ttgctacttg taatggtgga ccatttgaga ttatagtgaa    3420
tggaaaatct ggtttccata ttgatcctaa tcaaggtgac aaggctgctg atatgttggt    3480
taatttcttc gaaaaatcta agaagatcc aagttattgg gatactattt ccaagggtgg    3540
tctgcagcgt attcttgaaa gtaagctttt tgcatttgat tagcacaagt gtacaaccaa    3600
gatttaactt atgaacaaac taaaactaac ccttttttta ttttcttttg ctaggtatac    3660
atggcaaatt tattcacaga aagtgatcac attatctggg atttatggat tctggaaata    3720
tgcaaccaag aatgacaaag ttgctagtgc gaagaagcgc tatcttgaaa tgttttatga    3780
atttgggttt aagaaatcag taagtgtcac ttctgtattt tgtttgagct tgtttgtaaa    3840
gtttggcaat cttctgctaa tttgtactat atttgttgac ttgtgcattt caggctgaga    3900
aagttccatt ggctattgat gaatag                                         3926
```

<210> SEQ ID NO 33
<211> LENGTH: 803
<212> TYPE: PRT
<213> ORGANISM: Nicotiana tabacum

<400> SEQUENCE: 33

```
Met Ala Gly Ser Gly Leu Ser Ile Lys Glu Ser Leu Glu Ser Ile
1               5                  10                  15

Leu Ala His Pro Asp Glu Ile Leu Ala Leu Lys Ser Arg Ile Glu Thr
                20                  25                  30

Glu Gly Lys Gly Val Met Lys Pro Val Asp Leu Leu Asn His Leu Val
            35                  40                  45

Ser Val Thr Ser Lys Thr Asn Gly Val Asn Val Pro Ser Ala Leu
        50                  55                  60

Val Glu Val Leu Ser Cys Ser Gln Glu Ala Val Ile Val Pro Pro Lys
65                  70                  75                  80

Leu Ala Leu Ala Val Arg Pro Arg Pro Gly Val Trp Glu Tyr Leu Ser
                85                  90                  95

Leu Asn Leu Lys Thr Lys Lys Val Ala Glu Leu Ser Ile Pro Glu Tyr
            100                 105                 110

Leu Gln Leu Lys Glu Asn Thr Val Asp Glu Ser Gly Asn Ile Leu Glu
        115                 120                 125
```

```
Leu Asp Phe Glu Pro Phe Thr Thr Val Thr Thr Pro Lys Thr Leu Ser
    130                 135                 140

Asp Ser Ile Gly Asn Gly Leu Glu Phe Leu Asn Arg His Ile Ala Ser
145                 150                 155                 160

Lys Met Phe Leu Asp Lys Glu Ile Ala Lys Cys Leu Leu Asp Phe Leu
                165                 170                 175

Arg Asn His Asn Tyr Lys Gly Lys Ser Leu Met Val Lys Glu Ser Ile
                180                 185                 190

Gln Ser Leu Glu Ser Phe Gln Leu Val Leu Lys Lys Ala Glu Glu Tyr
            195                 200                 205

Leu His Thr Leu Asn Pro Glu Thr Pro Tyr Ser Lys Phe Glu Ser Lys
    210                 215                 220

Phe Glu Glu Ile Gly Leu Glu Arg Gly Trp Gly Asn Thr Ala Glu Arg
225                 230                 235                 240

Val Gln Asp Thr Ile Ser His Leu Leu His Leu Leu Glu Ala Pro Asn
                245                 250                 255

Ala Ser Ser Leu Glu Asn Phe Leu Gly Arg Ile Pro Leu Val Phe Asn
                260                 265                 270

Val Val Ile Leu Thr Pro His Gly Tyr Phe Ala Gln Asp Asn Val Leu
            275                 280                 285

Gly Tyr Pro Asp Thr Gly Gly Gln Val Val Tyr Ile Leu Asp Gln Val
    290                 295                 300

Pro Ala Met Glu Arg Glu Met Leu His Arg Met Lys Leu Gln Gly Leu
305                 310                 315                 320

Asp Asp Ile Ile Pro Arg Ile Leu Val Val Thr Arg Leu Leu Pro Asp
                325                 330                 335

Ala Val Gly Thr Thr Cys Gly Glu Trp Met Glu Lys Val Tyr Gly Ala
                340                 345                 350

Glu His Ser His Ile Ile Arg Val Pro Phe Arg Thr Glu Lys Gly Met
            355                 360                 365

Leu Arg Lys Trp Ile Ser Arg Phe Glu Val Trp Pro Tyr Met Glu Thr
    370                 375                 380

Phe Thr Glu Asp Val Ala Glu Glu Leu Val Lys Glu Leu Gln Ala Lys
385                 390                 395                 400

Pro Asp Leu Ile Ile Gly Asn Tyr Ser Glu Gly Asn Leu Ala Ala Ser
                405                 410                 415

Leu Leu Ala Lys Lys Phe Gly Ala Thr Gln Cys Thr Ile Ala His Ala
                420                 425                 430

Leu Glu Lys Thr Lys Tyr Pro Asn Ser Asp Leu Asn Trp Lys Lys Phe
            435                 440                 445

Asp Asp Lys Tyr His Phe Ser Ser Gln Phe Thr Ala Asp Leu Phe Ala
    450                 455                 460

Met Asn His Thr Asp Phe Ile Ile Thr Ser Thr Phe Gln Glu Ile Ala
465                 470                 475                 480

Gly Ser Lys Asn Thr Val Gly Gln Tyr Glu Ser His Thr Ala Phe Thr
                485                 490                 495

Met Pro Gly Leu Tyr Arg Val Val His Gly Ile Asn Ser Phe Asp Pro
                500                 505                 510

Lys Phe Asn Ile Val Ser Pro Gly Ala Asp Met Ser Ile Tyr Phe Pro
            515                 520                 525

Tyr Thr Glu Lys Glu Lys Arg Leu Thr Asn Phe His Pro Glu Ile Glu
    530                 535                 540
```

| | | | | | | | | | | | | | | | |
|---|---|---|---|---|---|---|---|---|---|---|---|---|---|---|---|
|Glu|Leu|Leu|Tyr|Ser|Pro|Val|Glu|Asn|Lys|Asp|His|Leu|Cys|Val|Leu|
|545| | | | |550| | | |555| | | | |560| |

Lys Asp Gln Asn Lys Pro Ile Leu Phe Thr Met Ala Arg Leu Asp Arg
                 565                    570                    575

Val Lys Asn Leu Thr Gly Leu Val Glu Trp Tyr Ala Lys Asn Ala Arg
              580                    585                    590

Leu Arg Glu Leu Val Asn Leu Val Val Gly Gly Asp Arg Lys
    595                  600                605

Glu Ser Lys Asp Leu Glu Gln Ala Glu Met Lys Met Tyr Asp
610                  615                  620

Leu Ile Glu Thr Tyr Asn Leu Asn Gly Gln Phe Arg Trp Ile Ser Ser
625                  630                  635                  640

Gln Met Asn Arg Val Arg Asn Gly Glu Leu Tyr Arg Tyr Ile Ala Asp
              645                    650                    655

Thr Arg Gly Ala Phe Val Gln Pro Ala Phe Tyr Glu Ala Phe Gly Leu
             660                    665                    670

Thr Val Val Glu Ser Met Thr Cys Gly Leu Pro Thr Phe Ala Thr Cys
            675                    680                    685

Asn Gly Gly Pro Phe Glu Ile Ile Val Asn Gly Lys Ser Gly Phe His
690                  695                  700

Ile Asp Pro Asn Gln Gly Asp Lys Ala Ala Asp Met Leu Val Asn Phe
705                  710                  715                  720

Phe Glu Lys Ser Lys Glu Asp Pro Ser Tyr Trp Asp Thr Ile Ser Lys
              725                    730                735

Gly Gly Leu Gln Arg Ile Leu Glu Lys Tyr Thr Trp Gln Ile Tyr Ser
           740                    745                    750

Gln Lys Val Ile Thr Leu Ser Gly Ile Tyr Gly Phe Trp Lys Tyr Ala
             755                    760                  765

Thr Lys Asn Asp Lys Val Ala Ser Ala Lys Lys Arg Tyr Leu Glu Met
    770                  775                  780

Phe Tyr Glu Phe Gly Phe Lys Lys Ser Ala Glu Lys Val Pro Leu Ala
785                  790                  795                  800

Ile Asp Glu

<210> SEQ ID NO 34
<211> LENGTH: 4532
<212> TYPE: DNA
<213> ORGANISM: Nicotiana tabacum

<400> SEQUENCE: 34

```
atggctgaac gtgctctgac tcgtgttcac agccttcgtg aacgtcttga tgccactttg      60
gctgcacatc gcaatgagat attgctgttt ctttcaaggt attgcctaag tagtgttctt     120
gtttcctaca aaagattcag ttggtgttca aaaaacgata tgtgatttga tttatctgcc     180
taagtcttgg tagtcataat tatccggtac ctgtgctggt gcgagttagc tggttcggaa     240
actactctta tgaaaacgag agatttagtt ggtgttgtct gcaattctgt agtatggact     300
attaagcaga tagatcatgt ttgatatcga aaaggaatgt atatgtgatg ttacttgaac     360
tggttttggt tattacagga ttgaaagcca tggaaaaggg atcttgaaac ctcaccagct     420
attggctgag ttcgatgcaa ttcgccaaga tgacaaaaag aagctgaatg atcatgcatt     480
tgaagaactc ctgaaatcta ctcaggtaat tttgatttg gctaaatgtg ttaccaagct     540
gaatgatcat gcatttgagt ttgtgtccga ctactacaat gatatgttat accaggaagc     600
gattgttctg ccaccttggg ttgcacttgc cattcgtttg aggcctggtg tgtgggaata     660
```

```
tgtccgtgtg aatgttaatg ctctagtcgt tgaggagctg accgtccctg agtatttgca      720
ttttaaggaa gaacttgttg atggaacgta agttttagtc tcttatttga tactatgtta      780
gagaataggc agtggattca atttatcagt gttgtttttt acctaatgca gctccaatgg      840
aaatttcgtt ctcgagttgg attttgagcc cttcactgca tccttttccta aaccgaccct    900 caccaaatct attgggaatg gagttgaatt cctcaatagg caccttttctg cgaaaatgtt    960 ccatgacaag gaaagcatga ccccgcttct tgaatttctt cgggttcaca attataaggg     1020
caaggtaact ttgttattcc cattcatata tatgttcagt ttgtgcttat catgcgccca     1080
atgatgtatg aatatgtact aaaggataga tgtacgattt cgtttgcaga caatgatgct     1140
gaatgacaga atacagaatt taaccactct gcaaaatgtc ctaaggaagg cagaggaata     1200
ccttattatg cttcccctg aaactccatt ttccgaattc gaacacaagt tccaagaaat      1260
tggattggag aagggatggg gcgacactgc ggagcgcgtg ctagagatga tatgcatgct     1320
tcttgatcta cttgaggctc ccgactcctg tactcttgag aagttcctag ggagaattcc    1380
tatggtgttc aacgtggtta cctttcccc ccatggatat ttcgcccagg aaaatgtctt     1440
gggttatccc gacactggtg gccaggtgca ttactttagt ctttgtccgt gagtctatgt     1500
tgctcagatc ctctacaatg ccactgtacc cgtgtaggat actccaaata taatgcattt    1560
ttggaggatc tgtcaccggt gcaatggcat tttggaggtc ggagcaacaa acaactgcta     1620
gtatgcttct aaagcttgct tccataaatg ctaaggtcct tcacccgtaa tgtgcaggtt     1680
gtctacatat tagatcaagt tccagccttg gagcgtgaaa tgcttaaacg cctaaaggag    1740
caaggacttg atataacacc gcgtattctt attgttagta tttcttgtac ttgtaattgc     1800
tgcggattac acaaaatttt ctcttttatg gcaacttatc ttgatattat tcccaggtta    1860
ctcgtctgct gcctgatgca gttggaacaa cttgtggtca gcggcttgag aaggtgtatg    1920
gagccgagca ctcacatatt cttagggtcc cctttaggac cgagaagggc attgttcgca    1980
aatggatatc tcgctttgaa gtgtggccat acatggagac tttcactgag gtgacactaa     2040
gcttccttgt atttgtctat cttctaattg gtattaggaa caatttgcta attattaacg    2100 cttttggcttt tcgtacatca ggatgttgca aaagaacttg ctgcagaact gcaggccaag    2160
ccagatttga taattggcaa ctatagcgag ggaaatcttg tggcttcatt gctggctcac     2220
aagttaggcg taacgcaggt ctgtgttatt tttcacctct tataaatctg attgtatttc     2280
cattagtctg gaactaaaag tactaaaatt ttcttttctt cgctgtgtta tttgccttct     2340
gcagtgcacc attgcccatg cattggagaa acaaagtat cctgattctg acatctactg     2400 gaaaaatt gacgaaaaat accatttctc gtcccagttt accgctgatc ttattgcaat      2460
gaatcacacc gattttatca tcaccagcac tttccaggag atagcaggaa ggtataacat    2520
caattgctaa ttcggttgca gtaacatttt gttcgatttc ttccccttat gcttaaccta    2580
ataccctaat gaatttttcca gcaaggacac tgtcggacag tacgagagtc accaggcatt   2640
cacaatgcct ggattgtaca gagtcgttca cggcattgat gtgttcgatc ccaaattcaa     2700
cattgtctca cctggagctg atataaacct gtatttccca tattccgaga aggaaaagag    2760
attgacagca cttcacccag aaattgagga gcttctgtac agtgatgttg agaacgagga    2820
acatctgtaa gtttctaact tactcgtacc gtcagtggca gagccagaat tttcattaaa    2880
atggggtcaa aatataaaga cataaattca caaagaagcc aagggggtgtc aatatgtagt    2940 ataaatatat taaaaaaatt acctagctac acaatgtaat tttccgacaa aggggtatcg    3000
```

```
gttgcacttc ttgaatacat gtggctctgc cactgggtac agttacaaag tcctgttacc    3060
tatgtagatg agcttgtgct gaacatgttg tgattttggt aggtgtgtgc taaaggacag    3120
gaataagcca atcttattca caatggcgag attggatcgt gtgaagaact taaccggact    3180
tgttgagtgg tacgccaaga acgcacggct aagggagttg gttaaccttg ttgtcgttgg    3240
tggagaccga aggaaggaat ccaaagattt ggaagagcaa gcagagatga agaagatgta    3300
tgagctaata aagactcaca acttaaatgg ccaattcaga tggatttctt cacagatgaa    3360
ccgagtaagg aacggcgaac tctaccgata cattgccgac actaggggag ctttcgtgca    3420
gcctgcattc tatgaggctt tcggtttgac tgttgttgag ccatgacct gtggtttgcc     3480 tacatttgca actaatcatg gcggtccagc tgagatcatc gttaacggaa atccggctt     3540 ccatatcgat ccatatcacg gtgagcaagc tgctgatctg ctagctgatt tctttgagaa    3600
atgtaagacg gaaccttctc attgggaaac tatttcaacc ggtggcctga gcgcatcca    3660 agagaagtaa gcaactcttt cttgactcta gtcattcaaa ttaacttggg atttgaggca    3720
tagttgattg ataatttatc gcgtctctac tactatatac aggtacacgt ggcaaatcta    3780
ctcggagaga ttattgacgt tggctgctgt ttacggtttc tggaaacatg tttctaagct    3840
tgatcgtcta gaaatccgtc gatatctaga aatgttttat gctctcaaat accgaagat    3900 ggtgagttct tctgcttcct gctcttctca tagtgtttaa tatacacttg attgattgca    3960
ttcacttaga ctaagttgct cggacacggg tgtggatgtc cgacacgagt gcggatctag    4020
agttcagatc cttcaagatg taaattataa gattcgggga tatggatcct agtacggata    4080
cgggtgcgag aatccggcta aaataattt taaaaaaaat tatctctaaa ttatgagata     4140
ttatgtggaa tacttacgta taacttgtaa agtgtagatt tttttttaatt ctcaagttgt    4200 agattagtaa atgattgatt tcctagataa gtatgctatt tcttcaaat ttactcttct     4260 gatttcgaaa atcaaattgt atctcgtctc gaattttttcc gtccgttatg gtcaaagtac    4320
ccaaaatcgt ttgaccaaat cggtacggat cccatacca cacccacact agtgtcgtat     4380
tgacacgggt gccgcaccta aactgctatg tcggagcaac ttagcactta gagaatcatt    4440
gatgttaaat tttcttaatt cttgaatctg ctaatgaaga ttttatcttg gttttgttt     4500 aggctgaagc tgttccattg gctgctgaat ga                                  4532
```

<210> SEQ ID NO 35
<211> LENGTH: 805
<212> TYPE: PRT
<213> ORGANISM: Nicotiana tabacum

<400> SEQUENCE: 35

```
Met Ala Glu Arg Ala Leu Thr Arg Val His Ser Leu Arg Glu Arg Leu
1               5                   10                  15

Asp Ala Thr Leu Ala Ala His Arg Asn Glu Ile Leu Leu Phe Leu Ser
                20                  25                  30

Arg Ile Glu Ser His Gly Lys Gly Ile Leu Lys Pro His Gln Leu Leu
            35                  40                  45

Ala Glu Phe Asp Ala Ile Arg Gln Asp Asp Lys Lys Lys Leu Asn Asp
        50                  55                  60

His Ala Phe Glu Glu Leu Leu Lys Ser Thr Gln Glu Ala Ile Val Leu
65                  70                  75                  80

Pro Pro Trp Val Ala Leu Ala Ile Arg Leu Arg Pro Gly Val Trp Glu
                85                  90                  95

Tyr Val Arg Val Asn Val Asn Ala Leu Val Val Glu Glu Leu Thr Val
```

-continued

```
                100                 105                 110
Pro Glu Tyr Leu His Phe Lys Glu Glu Leu Val Asp Gly Thr Ser Asn
            115                 120                 125
Gly Asn Phe Val Leu Glu Leu Asp Phe Glu Pro Phe Thr Ala Ser Phe
            130                 135                 140
Pro Lys Pro Thr Leu Thr Lys Ser Ile Gly Asn Gly Val Glu Phe Leu
145                 150                 155                 160
Asn Arg His Leu Ser Ala Lys Met Phe His Asp Lys Glu Ser Met Thr
                165                 170                 175
Pro Leu Leu Glu Phe Leu Arg Val His Asn Tyr Lys Gly Lys Thr Met
            180                 185                 190
Met Leu Asn Asp Arg Ile Gln Asn Leu Thr Thr Leu Gln Asn Val Leu
            195                 200                 205
Arg Lys Ala Glu Glu Tyr Leu Ile Met Leu Pro Pro Glu Thr Pro Phe
210                 215                 220
Ser Glu Phe Glu His Lys Phe Gln Glu Ile Gly Leu Glu Lys Gly Trp
225                 230                 235                 240
Gly Asp Thr Ala Glu Arg Val Leu Glu Met Ile Cys Met Leu Leu Asp
                245                 250                 255
Leu Leu Glu Ala Pro Asp Ser Cys Thr Leu Glu Lys Phe Leu Gly Arg
            260                 265                 270
Ile Pro Met Val Phe Asn Val Val Ile Leu Ser Pro His Gly Tyr Phe
            275                 280                 285
Ala Gln Glu Asn Val Leu Gly Tyr Pro Asp Thr Gly Gly Gln Val Val
            290                 295                 300
Tyr Ile Leu Asp Gln Val Pro Ala Leu Glu Arg Glu Met Leu Lys Arg
305                 310                 315                 320
Leu Lys Glu Gln Gly Leu Asp Ile Thr Pro Arg Ile Leu Ile Val Thr
                325                 330                 335
Arg Leu Leu Pro Asp Ala Val Gly Thr Thr Cys Gly Gln Arg Leu Glu
            340                 345                 350
Lys Val Tyr Gly Ala Glu His Ser His Ile Leu Arg Val Pro Phe Arg
            355                 360                 365
Thr Glu Lys Gly Ile Val Arg Lys Trp Ile Ser Arg Phe Glu Val Trp
370                 375                 380
Pro Tyr Met Glu Thr Phe Thr Glu Asp Val Ala Lys Glu Leu Ala Ala
385                 390                 395                 400
Glu Leu Gln Ala Lys Pro Asp Leu Ile Ile Gly Asn Tyr Ser Glu Gly
                405                 410                 415
Asn Leu Val Ala Ser Leu Leu Ala His Lys Leu Gly Val Thr Gln Cys
            420                 425                 430
Thr Ile Ala His Ala Leu Glu Lys Thr Lys Tyr Pro Asp Ser Asp Ile
            435                 440                 445
Tyr Trp Lys Lys Phe Asp Glu Lys Tyr His Phe Ser Ser Gln Phe Thr
450                 455                 460
Ala Asp Leu Ile Ala Met Asn His Thr Asp Phe Ile Ile Thr Ser Thr
465                 470                 475                 480
Phe Gln Glu Ile Ala Gly Ser Lys Asp Thr Val Gly Gln Tyr Glu Ser
                485                 490                 495
His Gln Ala Phe Thr Met Pro Gly Leu Tyr Arg Val Val His Gly Ile
            500                 505                 510
Asp Val Phe Asp Pro Lys Phe Asn Ile Val Ser Pro Gly Ala Asp Ile
            515                 520                 525
```

```
Asn Leu Tyr Phe Pro Tyr Ser Glu Lys Glu Lys Arg Leu Thr Ala Leu
        530                 535                 540

His Pro Glu Ile Glu Glu Leu Leu Tyr Ser Asp Val Glu Asn Glu Glu
545                 550                 555                 560

His Leu Cys Val Leu Lys Asp Arg Asn Lys Pro Ile Leu Phe Thr Met
                565                 570                 575

Ala Arg Leu Asp Arg Val Lys Asn Leu Thr Gly Leu Val Glu Trp Tyr
            580                 585                 590

Ala Lys Asn Ala Arg Leu Arg Glu Leu Val Asn Leu Val Val Gly
        595                 600                 605

Gly Asp Arg Arg Lys Glu Ser Lys Asp Leu Glu Glu Gln Ala Glu Met
    610                 615                 620

Lys Lys Met Tyr Glu Leu Ile Lys Thr His Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Arg Gly Ala Phe Val Gln Pro Ala Phe Tyr
            660                 665                 670

Glu Ala Phe Gly Leu Thr Val Val Glu Ala Met Thr Cys Gly Leu Pro
        675                 680                 685

Thr Phe Ala Thr Asn His Gly Gly Pro Ala Glu Ile Ile Val Asn Gly
    690                 695                 700

Lys Ser Gly Phe His Ile Asp Pro Tyr His Gly Glu Gln Ala Ala Asp
705                 710                 715                 720

Leu Leu Ala Asp Phe Phe Glu Lys Cys Lys Thr Glu Pro Ser His Trp
                725                 730                 735

Glu Thr Ile Ser Thr Gly Gly Leu Lys Arg Ile Gln Glu Lys Tyr Thr
            740                 745                 750

Trp Gln Ile Tyr Ser Glu Arg Leu Leu Thr Leu Ala Ala Val Tyr Gly
        755                 760                 765

Phe Trp Lys His Val Ser Lys Leu Asp Arg Leu Glu Ile Arg Arg Tyr
    770                 775                 780

Leu Glu Met Phe Tyr Ala Leu Lys Tyr Arg Lys Met Ala Glu Ala Val
785                 790                 795                 800

Pro Leu Ala Ala Glu
            805

<210> SEQ ID NO 36
<211> LENGTH: 5901
<212> TYPE: DNA
<213> ORGANISM: Nicotiana tabacum

<400> SEQUENCE: 36
atgcttttta tgggagtaaa ttttatggcc ggtcattcaa ctttgtgttc attacgcaaa      60
agtcattttt cttggtgttt attacgcaag tcatttttct ttttttttg ttacgtaaaa     120 atcattcaac tatgtgttta ttatctaaaa ttcaattttt ttttccttt tgttacacaa     180 aaatcatttt actttactct atttatcaca aaagtcacct tggccagatt ttataatagg     240
cttttatctt ttgttacaca aaaattattt tactttactc tatttatcac aaaagtcacc     300
ttggccagat tttataatag cttttatct tttgttacac aaaaattatt ttactttact     360
ctatttatca caaagtcac cttggccaga ttttacaata cttttacctt aaaagactat     420
tatgcccttg acattataaa tcctctcatt tatataatac cttctatatg atacactata     480
```

```
taatatattt ttacctaggt attttactta taattaaaat aatattaaat tattttattt    540
atctatttta taatatattc atacatttaa ttttttcatg gcaaatcact ttgtttaatc    600
atatttaaac atgaacaaat tttaaatatc aaaaaaataa aaaaataaaa aaaatattta    660
tttgaaataa taacaaacag atttgtttaa caaatgatag tttttttttta tagtcaataa    720
aattttttaaa aaaattcaaa gatatttgtt tttaatatta atatttttaa agctttatct   780
gttaatatta tttatttgaa agtattaatc tgatgtgtca ttgtgttaaa tgtgagtatt    840
ttatttattg gattaatgag tatggcttgg ctgataaaaa gctttgattt tataattttc    900
attaaaaata ttttattaag ctagtacctg acaaatttaa tatcttgaaa attaacgtta    960
agaaaaaatt aaatataaaa atatattata aaaataataa ataaataata tcaagttatt   1020
ttaattataa ataaaataca tggttaaaaa tatattatat agcatataat atagaaggta   1080
ttacataaat gagatgattt aaagggcata atagactttt caggtgaatg atttgtaaaa   1140
tatggttaaa gtgattattg tgataattag agcatagtaa aataattttt atgtaacaaa   1200
agaaaaaaaa aatgactttt gggtaatgaa cataaatttg aataacttttt acgtaacaaa   1260
agaataaaat aaattttgga taataaacat aaaattgaat gaccacctat aaaatttatt   1320
atttttttgg gctcttcttg atttgatttt ttagtttagc ctttgcagta atcttggttg   1380
tcacgcgtag cgttgtgctt tcgccacata agtatttagt agacttaatt aatgtcatta   1440
tatcggttgg tgtggtttta attacttaac tgtactatta tattaggtgg aaggtttgaa   1500
aatttatagt agtaacattc tagatcattg aaaatattgg tgtttcagtg acttttttagt  1560
atgtcatttt cattttctaa gtggttgtac taatatagta tattaaaatt ttgattggtt   1620
gagaaacaat ctctctcacc tacacggtac gggtaaggta tgcgtatacg cttatcctcc   1680
ctacactcca tttgtgggac tattgttgtt attttggata agctgaggta tccatcttct   1740
actaactgca ctagtttatt ttttttgctg tttacagttg aaacaattgt ctgaggattt   1800
ctcacctgct gaatcaactg caatggctga acgtgtgctg actcgtgttc acagccttcg   1860
tgaacgtctt gatgctactt tggctgctca tcgcaatgag atattactgt ttctttcaag   1920
gtatagccaa agatagtatt cttgttaact aaaaaagatt cagttggtgt tcaaaaaacg   1980
atacgtttat ctgcctaagt cttggtagtc agaattatcc ggtacctatg ctggtgtgag   2040
ttagctggct aggaaaccac tcttatgaaa acaagagatt tagttagagt tgtctgtaat   2100
tctgtagtat ggactatgta tgtgatgcta tttgaactgg ttttggttat tataggattg   2160
aaagccatgg aaaagggatc ttgaaaccgc atcagctatt ggctgagttt gatgcaattc   2220
gccaagatga caaaaagaaa ctgaatgatc atgcatttga agaactcctg aagtccactc   2280
aggtaatatg gttttggcta tatttgtcgc caacgccaag ctcatatttt tatattattt   2340
tgagcttgtg tctgaatacg acgatgatat gttatactag gaagcaattg ttctgccacc   2400
ttgggttgca cttgcgattc gtttgaggcc tggtgtgtgg gaatatgtcc gtgtgaatgt   2460
caatgcgcta gtcgttgagg agctgactgt ccctgagtat ttgcatttca aggaagaact   2520
tgtcgatgga acgtaagtgt tagtcttcaa tttgatgcta tgttagagaa taggctgtgg   2580
aatttattga tcaatgctgt gctttgtcct gatacagctc caatggaaat ttcgttctcg   2640
agttggattt tgagcccttc accgcatcct ttcctaaacc aaccctcacc aaatctatcg   2700
gaaatggagt tgaattcctc aataggcacc tctctgcgaa aatgttccat gacaaggaaa   2760
gcatgacccc gcttcttgaa tttcttcggg ttcacaatta taagggcaag gtgacttgct   2820
atttccatttt atctataggt tcggtttgtg cttatcatgc gcccaatgac atatgaatat  2880
```

```
gcgctaaagg atagatatat gatttccttt gcagacaatg atgctgaacg acagaataca      2940
gaatttaacc acactgcaaa atgtcctaag gaaggcagag gaatacctca ttatgcttcc      3000
ccctgaaact ccattttccg aattcgaaca caagttccaa gaaattggat tggagaaggg      3060
atggggcgac actgcagagc gcgtgctgga gatgatatgc atgcttcttg atctcctcga      3120
ggctcccgat tcctgtactc ttgagaagtt cttggggaga attcctatgg tgttcaatgt      3180
ggttatcctt tcccccacg gatatttcgc ccaggaaaat gtcttgggtt atcccgacac       3240
tggtggccag gtgcattact ttaatcttta tccgtgagtc tatgtttgtt cgaatcctct      3300
agaaatgtca ctgtacctat gtaggatact ccaaatataa tgcattttgg ggggatctgt      3360
tatgggtgcg atggcatttt tggaggtcgg agcaacaaac aattgctatg tattcttcta      3420
aagcttgctt tcataaatgc taaggtcctt caccccttaat gtgcaggttg tctatatatt     3480
agatcaagtt ccagccttgg agcgtgaaat gcttaagcgc ctaaaggagc aaggacttga      3540
tatcacaccg cgtattctta ttgttagtat ttcctgtact tgtaattact gcggattaca      3600
caaaatttcc tttttatctt cttaacaact tatcttgatg gtattcccag gttactcgtc      3660
tgctacctga tgcagttgga acgacttgtg gtcagcggct tgagaaggtg tatggagccg      3720
agcactcaca tattctgagg gtccccttta ggactgagaa gggcattgtt cgtaaatgga      3780
tctctcgctt tgaagtgtgg ccatatatgg agactttcac tgaggtgaca ctaaaacttc      3840
cttatatttg tctatcttct aattggtatt aggaataatt tgttaattgt taactctttg      3900
tcttttcgta catcaggatg tcgcaaaaga acttgctgca gaattgcagg ccaagccaga      3960
tttgataata ggcaactata gcgagggaaa tcttgtggct tcattgctcg ctcataagtt      4020
aggcgtaaca caggtctgtg ttgttttca ctctcttaaa gatctgattg catttccatt       4080
agtctggaac tagaagtact aaaaagttct tttcttcact gtgttatttg ccgtcggcag      4140
tgcaccatag ctcatgcatt ggagaaaaca aagtatcctg attctgacat ctactggaaa      4200
aaattcgatg aaaaatacca tttctcgtcc cagtttaccg ctgatcttat tgcaatgaat      4260
cacaccgatt ttatcatcac cagcactttc caggagatag caggaaggta taacatcaat      4320
ttgctacttc gactgcaaca gcattgtgtt cccattcctt tcccttatgc ttaacctaat      4380
accgtcatga attttccagc aaggacactg tcggacagta cgagagtcat caggcattca      4440
caatgcccgg attgtacaga gttgttcacg gcattgatgt gttcgacccc aaattcaaca      4500
ttgtctcacc tggagctgac ataaacctct atttcccata ttccgagaag gaaaagagac      4560
tgacagcact tcaccctgaa atcgaggagc tgctgtacag tgacattgag aacgaggaac      4620
atctgtaagt ttctacctta ctcgtacagt cagtggcgga gccagaattt tcactaaaat      4680
aaggtcaaaa tataaagaca taaatccaca agaagccaa gggtgtcaat atatagtata       4740
aatacattaa aaaaattacc tatctacaca gtgtaatttt ccgacaaagg ggtgtcggtt      4800
gacactcctt gaatacatgt ggctctgcca ctgggtacag ttacaaagtt ctgttaccta      4860
tgtagatgag cttgtgctga acatgttgtg atttttggcag gtgtgtgcta aaggacagga     4920
ataagccaat cttattccaca atggcgagat tggatcgtgt gaagaattta accggacttg     4980
ttgagtggta tgccaagaac gcacggctaa gggagttggt taaccttgtt gtggttggtg     5040
gagatcgaag gaaagaatcc aaagatttgg aagagcaaac agaaatgaaa aagatgtatg     5100
agctaataaa gactcacaat ttaaatggcc aattcagatg gatttcttca cagatgaacc      5160
gagtgaggaa cggtgaactc taccgataca ttgctgacac tagaggagct ttcgtgcagc      5220
```

-continued

```
ctgcattcta cgaggctttc ggtttgactg ttgttgaggc catgacctgt ggtttgccta    5280
catttgcaac taatcatggc ggtccagctg agatcatcgt taacggaaaa tctggcttcc    5340
acatcgatcc atatcacggt gagcaagctg ctgatctgct agctgatttc tttgagaaat    5400
gtaagacaga accttctcat tgggaaacca tttcaacggg tggcctgaag cgcatccaag    5460
agaagtaagc aactctttct tgactctagt cattgaaatt aactttcttg actctagtca    5520
ttgaaattaa ctcgggattt gaggcgtagt tgattgatat tttatcgcgt ctctactact    5580
gatatataca ggtacacgtg gcaaatctac tcggagaggc tattgacatt ggctgctgtt    5640
tacgggttct ggaaacatgt ttctaagctt gatcgtctag aaatccgtcg atatcttgaa    5700
atgttttatg ctctcaaata ccgcaagatg gtgagttcct cttcttcctt gcccttctcc    5760
tagtgtttaa gatacaatat aattgattgc attatcttag agaatcatta atgttaaatt    5820
ttcttaattc ttgaatctgt taatgaagtt tttctcttgg tttttgttta ggctgaagct    5880
gttccattgg ctgctgagtg a                                              5901
```

<210> SEQ ID NO 37
<211> LENGTH: 825
<212> TYPE: PRT
<213> ORGANISM: Nicotiana tabacum

<400> SEQUENCE: 37

```
Met Leu Phe Met Gly Leu Lys Gln Leu Ser Glu Asp Phe Ser Pro Ala
1               5                   10                  15

Glu Ser Thr Ala Met Ala Glu Arg Val Leu Thr Arg Val His Ser Leu
            20                  25                  30

Arg Glu Arg Leu Asp Ala Thr Leu Ala Ala His Arg Asn Glu Ile Leu
        35                  40                  45

Leu Phe Leu Ser Arg Ile Glu Ser His Gly Lys Gly Ile Leu Lys Pro
    50                  55                  60

His Gln Leu Leu Ala Glu Phe Asp Ala Ile Arg Gln Asp Asp Lys Lys
65                  70                  75                  80

Lys Leu Asn Asp His Ala Phe Glu Glu Leu Leu Lys Ser Thr Gln Glu
                85                  90                  95

Ala Ile Val Leu Pro Pro Trp Val Ala Leu Ala Ile Arg Leu Arg Pro
            100                 105                 110

Gly Val Trp Glu Tyr Val Arg Val Asn Val Asn Ala Leu Val Val Glu
        115                 120                 125

Glu Leu Thr Val Pro Glu Tyr Leu His Phe Lys Glu Glu Leu Val Asp
    130                 135                 140

Gly Thr Ser Asn Gly Asn Phe Val Leu Glu Leu Asp Phe Glu Pro Phe
145                 150                 155                 160

Thr Ala Ser Phe Pro Lys Pro Thr Leu Thr Lys Ser Ile Gly Asn Gly
                165                 170                 175

Val Glu Phe Leu Asn Arg His Leu Ser Ala Lys Met Phe His Asp Lys
            180                 185                 190

Glu Ser Met Thr Pro Leu Leu Glu Phe Leu Arg Val His Asn Tyr Lys
        195                 200                 205

Gly Lys Thr Met Met Leu Asn Asp Arg Ile Gln Asn Leu Thr Thr Leu
    210                 215                 220

Gln Asn Val Leu Arg Lys Ala Glu Glu Tyr Leu Ile Met Leu Pro Pro
225                 230                 235                 240

Glu Thr Pro Phe Ser Glu Phe Glu His Lys Phe Gln Glu Ile Gly Leu
                245                 250                 255
```

```
Glu Lys Gly Trp Gly Asp Thr Ala Glu Arg Val Leu Glu Met Ile Cys
            260                 265                 270

Met Leu Leu Asp Leu Leu Glu Ala Pro Asp Ser Cys Thr Leu Glu Lys
        275                 280                 285

Phe Leu Gly Arg Ile Pro Met Val Phe Asn Val Ile Leu Ser Pro
        290                 295                 300

His Gly Tyr Phe Ala Gln Glu Asn Val Leu Gly Tyr Pro Asp Thr Gly
305                 310                 315                 320

Gly Gln Val Val Tyr Ile Leu Asp Gln Val Pro Ala Leu Glu Arg Glu
                325                 330                 335

Met Leu Lys Arg Leu Lys Glu Gln Gly Leu Asp Ile Thr Pro Arg Ile
            340                 345                 350

Leu Ile Val Thr Arg Leu Leu Pro Asp Ala Val Gly Thr Thr Cys Gly
                355                 360                 365

Gln Arg Leu Glu Lys Val Tyr Gly Ala Glu His Ser His Ile Leu Arg
    370                 375                 380

Val Pro Phe Arg Thr Glu Lys Gly Ile Val Arg Lys Trp Ile Ser Arg
385                 390                 395                 400

Phe Glu Val Trp Pro Tyr Met Glu Thr Phe Thr Glu Asp Val Ala Lys
                405                 410                 415

Glu Leu Ala Ala Glu Leu Gln Ala Lys Pro Asp Leu Ile Ile Gly Asn
            420                 425                 430

Tyr Ser Glu Gly Asn Leu Val Ala Ser Leu Leu Ala His Lys Leu Gly
                435                 440                 445

Val Thr Gln Cys Thr Ile Ala His Ala Leu Glu Lys Thr Lys Tyr Pro
            450                 455                 460

Asp Ser Asp Ile Tyr Trp Lys Lys Phe Asp Glu Lys Tyr His Phe Ser
465                 470                 475                 480

Ser Gln Phe Thr Ala Asp Leu Ile Ala Met Asn His Thr Asp Phe Ile
                485                 490                 495

Ile Thr Ser Thr Phe Gln Glu Ile Ala Gly Ser Lys Asp Thr Val Gly
                500                 505                 510

Gln Tyr Glu Ser His Gln Ala Phe Thr Met Pro Gly Leu Tyr Arg Val
            515                 520                 525

Val His Gly Ile Asp Val Phe Asp Pro Lys Phe Asn Ile Val Ser Pro
            530                 535                 540

Gly Ala Asp Ile Asn Leu Tyr Phe Pro Tyr Ser Glu Lys Glu Lys Arg
545                 550                 555                 560

Leu Thr Ala Leu His Pro Glu Ile Glu Glu Leu Leu Tyr Ser Asp Ile
                565                 570                 575

Glu Asn Glu Glu His Leu Cys Val Leu Lys Asp Arg Asn Lys Pro Ile
            580                 585                 590

Leu Phe Thr Met Ala Arg Leu Asp Arg Val Lys Asn Leu Thr Gly Leu
        595                 600                 605

Val Glu Trp Tyr Ala Lys Asn Ala Arg Leu Arg Glu Leu Val Asn Leu
            610                 615                 620

Val Val Val Gly Gly Asp Arg Arg Lys Glu Ser Lys Asp Leu Glu Glu
625                 630                 635                 640

Gln Thr Glu Met Lys Lys Met Tyr Glu Leu Ile Lys Thr His Asn Leu
                645                 650                 655

Asn Gly Gln Phe Arg Trp Ile Ser Ser Gln Met Asn Arg Val Arg Asn
                660                 665                 670
```

```
Gly Glu Leu Tyr Arg Tyr Ile Ala Asp Thr Arg Gly Ala Phe Val Gln
            675                 680                 685

Pro Ala Phe Tyr Glu Ala Phe Gly Leu Thr Val Glu Ala Met Thr
        690                 695                 700

Cys Gly Leu Pro Thr Phe Ala Thr Asn His Gly Gly Pro Ala Glu Ile
705                 710                 715                 720

Ile Val Asn Gly Lys Ser Gly Phe His Ile Asp Pro Tyr His Gly Glu
                725                 730                 735

Gln Ala Ala Asp Leu Leu Ala Asp Phe Glu Lys Cys Lys Thr Glu
            740                 745                 750

Pro Ser His Trp Glu Thr Ile Ser Thr Gly Gly Leu Lys Arg Ile Gln
        755                 760                 765

Glu Lys Tyr Thr Trp Gln Ile Tyr Ser Glu Arg Leu Leu Thr Leu Ala
    770                 775                 780

Ala Val Tyr Gly Phe Trp Lys His Val Ser Lys Leu Asp Arg Leu Glu
785                 790                 795                 800

Ile Arg Arg Tyr Leu Glu Met Phe Tyr Ala Leu Lys Tyr Arg Lys Met
                805                 810                 815

Ala Glu Ala Val Pro Leu Ala Ala Glu
            820                 825

<210> SEQ ID NO 38
<211> LENGTH: 8323
<212> TYPE: DNA
<213> ORGANISM: Nicotiana tabacum

<400> SEQUENCE: 38
atggcgaatc caaagttcac aagagtacct agcatgaggg agagagttga ggatactctc      60
tctgctcacc gtaaccagct tgttgctctc ctctccaggt atattaataa actctatata     120
cttgttattt tctttatttt tttgtcttta ctgataaatt taactgtttt cttctttaaa     180
tcttgctttc gatgcatgat ttctgttgtg ttaaattgcg taaccatttt atctaaaagt     240
ttatgctgat aaacactttt aaatttaat atgtaaatta tattatgtct caacatcaac     300
atgtggatgg ccaaaaatat aaagcttaat tttcgttatt ttgaatgatt tttctctgcg     360
agtgttacgg tttgcgtaca cattacctaa acctcctccc tagtccccac tgtgggaat      420
ttaattttt ttttctttgt ttttttttgt tgttgttgtt gtctgagttc aattcctacc     480
atgttagctt ggcaaaaata agttggtaaa gcttgacccc aactagtttt agttgatcga     540
tttatttggt gatttatagt tcaataataa taattactat tagagaaagt tccagcagct     600
tttctgtttg tttttccagt tttagtgatt gatatatgtg tatatatatt ctttgtttct     660
tttaagatac gtggcgcagg ggaaggggat attgcaacct caccacttga tcgatgagtt     720
caacaacgct gtatgtgatg acactgcttg tgagaagctc aaagatggtc cctttagtga     780
agtcttgaaa gctactcagg tatattcact aatccatggg aatcaagatg atactgtata     840
tctttattat ggtgtctttc agaaatttga cgatgatgaa atgcaacttt tctctgtttg     900
tcaccttatc cagactgttt ttttattttt tattttttcat tttttaactt gaaatgctct     960
taatttcctt tgtttatcga taagaccgga tttacaatgt atgaacggag catcttaaga    1020
accttctgga atgaagatat aagatataaa acatggtgtc cgttttctcc tttgtggaat    1080
cagtgtacat atagactgtt attttggtcc cactttctgg atcttctgat cacaccttct    1140
catgcagagg cgagcttgat ggtttcaacc tttaaattct tactattgaa tccatttcac    1200
tttcgaaatt atgagttcga aatctaatat ttgttgaaat ttttgcaaat gttcacatat    1260
```

```
aagtttaagc tttgtgtcaa gaatactggg ctcaatggat tccaatagac caggctgtat    1320
ccgcctctgt ctccactctc cctgcatcca cttctttcgt gtgactaata atgcttaatg    1380
agctagaact cgttttaatg tttgaataag ttgcttatat cagagcagct tttgatgttt    1440
caatctttaa cgggttatgc agtaccagca ttctgcggct gaaaaacagg aatctgagat    1500
ttacttgtct ctggctgaat ttcttgttca ttttgctaac aagtactttg gagttaatgc    1560
ttgctctctg ttgtcaaaat aggaagccat tgtgctgcca ccatttgttg ccatagcagt    1620
tcgtccaagg ccaggtgttt gggagtatgt tcgtgttaat gtatatgatt tgagcgttga    1680
acaattgact gttcctgaat atcttcattt caaggaagaa cttgtggatg gagagtaagc    1740
tctttcttat ttcaatacga aacataaaaa tttacagaag ttgaataatt aacaaatttg    1800
ttgattttta atgtatgcca ggggtaataa tcactttgtg cttgagctgg attttgagcc    1860
atttaatgca tcagttcctc gtccatctcg atcgtcatcc attggcaatg gagtccaatt    1920
cctcaatcgt catctttcct caattatgtt tcgcagcaaa gactctctgg accccttact    1980
tgatttcctt agaggacact gtcataaagg gaatgtaagt accaaaagca gttttccctt    2040
tgtaaatgtc tgcttgtccc tgattatcta ctaaatcttt caacacgcgc aaccattata    2100
agaaatgtac aatacttcta gttagaattt catcatcgac aaactatctg ctttacttt    2160 tattttccc atttgatgga tgatagttta gtttatataa cagatgatat tttggttgaa    2220
gggtaccatg aacttttca caaccactta atggatacat agttgtaata gttgacattt    2280
tggaataata ttgtctcact tggaaatgtt taagaagtat tactacttct atttgtaaga    2340
tggattgttt atctatgcag gtcttgatgt tgaatgatcg tatacagcga atctccaggc    2400
tggagtctgc tctttctaaa gcagaggatt atctctccaa gctatcacca gatacatcct    2460
ataatgagtt cgaatacgcg tgagcttgta cacatttgtt ttgttttctt tcaagcatat    2520
gtaatttctc aagaaaaggg aaatctatag gagttgaaac attctttatg gaaccatgtg    2580
catgcagatt gcaagaaatg ggctttgaga gaggttgggg tgatactgcc agacgtgttt    2640
tggagacgat gcatcttctt tctgacattc ttcaggctcc ggatccatca accttggaga    2700
catttcttgg tagactacct atggtgttca atgtcgtcat attatcccct catggatatt    2760
ttggccaagc aaatgtcttg ggtttgcccg acactggtgg ccaggtaata acaaggagaa    2820
tgaggtcttg tattatgtac tccctccgtt ccaatctata tgaacctatt tgactgggta    2880
tggaaagaaa tgaagacttg taaaacttgt ggttctttag aaattccaaa cattacattt    2940 ggtttttcc ctcttcctgg aaattatact actgaatcat ctctagatgt tccagtttaa    3000
cttgagacgt aagggtaaat aacggaccat tactctgtcc tttcttgcag taggcttggt    3060
acaatgaata tagttcgcat agttgccgga agctagagct gtgttagaaa actcaggaac    3120
attaatttgg cgatgctaat cactgctaat gttactgaag catccatggt tttccttgat    3180
gttattctcc ttttggttgc ttcacaggtt gtctatatac tggatcaagt gcgtgccttg    3240
gaggccgaaa tgcttcttag aataaagcaa caaggactta acttcaagcc tagaatcctt    3300
gtcgtgagta catatatatt atgcaagctc ttatttggtt tgtgggattg cagttgacat    3360
caatttgctt actctgatta ctaaaggtca cacggctgat acctgatgct aaaggaacca    3420
tgtgcaacca gaggttggag aggattagtg gaactgaata ctcgcatatt ttacgtgtcc    3480
cttttaggac agagaaggga atccttcata aatggatatc taggtttgat gtatggcctt    3540
acctggagaa gttcactgag gtaacctctt tgtcccttgg aaattgcctt tgttgctga    3600
```

```
tgtttctgct agtgtgctta aatgacggat gttaactagt cacttgctag cgtttgcaat    3660
agcaacggga aaagaaagga tttttgctag tttgaagtct gcctccaaga aaaattatat    3720
taaaagttta tggctagtgg aaacatcagt cattcatgta ccttatttct atgcccaagt    3780
tgtttaagtt gaaagtaatt tggccaacta tgcaaattgg gagaacgtgt agccaactat    3840
tgtgtttgcc gacatgttga tatacttttt ggtcctgatt tatatttgtt ggtttgtcat    3900
actggatgaa gcaattctca tgttttctg cttatatata ttggaagaag agatacttgt     3960
cgtttcatca ttttctcga cctctctatt accaacactt tgccaattta atgtttggaa    4020
atgtcttctt gaccaggatg tggcaagtga aatgaccgct gagctccagg gaaagccaga    4080
tctgattatt ggcaactaca gtgatggaaa tttagttgcc tccctttgg catataaaat     4140 gggtgtcaca caggtaggaa atacatgatt ctttatcttg ctagcactaa gtcttgaggt    4200
tatgtatctg caatagaaat tttacgcttt gccttcattt cttttaatt attttttccag    4260 tgtaccattg ctcatgcctt ggaaaaaaca aagtatcctg attctgacat ctactggaaa    4320
aagtttgagg agaaatatca ttttcatgt cagtttactc ctgatctact ggcaatgaat     4380
aattcagatt tcattatcac cagtacttat caagagattg caggaacgta agtcatttta    4440
atctggtcgt ttaaatctga tatttcttcc ctagtagtct attcaatccg aatttcagtt    4500
cagtatatga tgtcatcggt tgaggaactg tgattggtaa ccttatcaaa tccgtagctg    4560
ctctataatt ttatttcgta attggagaaa caatttttta ttattgagct tgtagtctga    4620
gctagaattt ggttctttat ctatcaagta gcataatact acaactattt tttatgtgtg    4680
gcaatttgca atttcaattt tctatttcta taagttgcag ctttttcttcc tgttctgatc    4740 atatttacat ggctgaaact caatagaaaa ctaggctagt tgatcaaaag tagttggatg    4800
ctttaaaatt agtagacgtt ttgctaaatg agtgaccaat gttattaaaa aaacgttcat    4860
gttttcaacc cttttggcat acatttgacc actgcccaag attttggata agtacatgca    4920
gtgcttataa ttataaagca ttttatccca ccttgttttt cattatgaaa attaagtaat    4980
ttacgagtat ttgtataagt tacttcataa attagaagta aatctggatt gtgtaaagtt    5040
attcgccccg tatatactga aagctacttg aacaagcaaa aaaacagaca aacgtaacat    5100
tctccatgga ttaatgagac ttgtatatat atatatatat atatgtaaag agagagagag    5160
agagatttgg cttgtaacca catgtatatt atgccatatg gatgtgacat tgatgtgact    5220
agacctaaat gttttgtttc aatgtccacg ggagttttac gtagagttaa gaggagaaga    5280
gagtgaggaa tactaatgtt tgatggtacc ccttggcttc ttgacctgga tactcagtgt    5340
tcttattcat gcctatactt tggtccttga tttcattctc ccttttctag cttgagctgc    5400
atcaaagaaa ttccactgta aaaaaataa tgctcaccat attggtgcaa catggcaaac    5460
atgtatccta tttgatgatc aatcaacttt atttttctcc tgttaattga cctcagtgtg    5520
taactctcta tgtatgatag cattgtaact tgtgtcatga ttcataaata gggtactaga    5580
attggatggt tgacatagta aatggtcaat tgatgatcca caaatatgc acctactgat    5640 taaaatgtga tagggcaggt ttatttttgt ttgtggttaa cacagtactt aaccctatat    5700
ttaatacaat ttggcttatc tacaatcttt tcttcagtgt ttatgcgaat tccttattgc    5760
acaacaatat tgtctttctg agttctattc tgttgttgct tacactttta ttattccagt    5820
aacatagatg tgaagacatt agattggttg cttgcaaatt gatagccact tgtttcagga    5880
agaatactgt tggtcagtac gagagccata ctgcattcac cctcccggga ctatatcgcg    5940
tcgttcatgg cattgatgtt ttcgatccca aattcaatat agtgtctcct ggagctgaca    6000
```

-continued

```
tgacaattta tttcccatat tctgacaagg aaaaaagact aacgtctttg catggctcga    6060
ttgaaaagtt gttatttgat cctgcgcaga atgaagagca tatgtaagtg gcatccgttt    6120
gtacttaatt tttttggaat agatgacata ttatttgcat gaatatgaaa aggagggtct    6180
gatatgattt tctatagata aactaccaat gatattattt aaaaactcct ggatactgta    6240
ttaggagaag aagagaacca ggggtagatg gcattagaat cccttaaatc ttgaagagtc    6300
gtcactaacg ctcccaacac ttctgcctca gaccctcaac taaatactat tattgttgat    6360
ttctttggag aagctataag aatctctctc tccttatggt gaaaatttta cttggcttta    6420
tacttaactt ccaaggctcc ctcttataaa atgcaaaaac tgtctgtatt cactctcttg    6480
gttaacaatt gatccaatca aatgcatatg gaacatcttt ctttacgttt cttctaaagt    6540
tcgtttgagg ataaggagta gaatctgaga agatagacta gtaggtaacc ttagggacgg    6600
atgtggaaat taacatatgg gctcagcttt tctgccgagt gcagaccatg tatatgcgtt    6660
aaaaaattca ctaaacaagt aaatgtttga ttttgaaccc agtaaatcaa atgagttgtg    6720
gtagaatctc gaactcgaac cgataaagtt caaatccagg atccgctttt aggtaaactc    6780
taccttggga agtgttatat atatgtccct gattatttct ttttccgttt cctttctatt    6840
ttaatttta aagttatttt tagatggttt tattttttga taagtggtaa gttgttaata    6900
ttccaaatta aatgccattg tcataactat atacatttat aaagaatgat tgatcctagt    6960
ttctcattcc taagatccaa ataaggcaat aaacaatgtc ttagtaattg gacctgcttc    7020
tggtgatcaa cgcttgatcg cgtagttagt tatagatgac tgtaaaaact ttaaccattt    7080
taatggtttt gtcaaagaac aaatatcgga catattatag agaatggact attgtacttt    7140
gcttctgatt ggtcatttta ttgtgatccg taaattggct gtgactgatg tcatatcttt    7200
gcttacagag gtaatctgaa tgataaatca aaacccataa ttttttcaat ggcaaggcta    7260
gaccatgtta agaacattac gggactagtt gagtgctatg ctaaaaatgc cacattgagg    7320
gaattggcga accttgttgt agtagctgga tacaacgatg taaagaaatc cagtgataga    7380
gaagaaataa cagaaattga gaagatgcat gctcttatta aggagcataa attggatggg    7440
caattcagat gggtatcagc ccaaacaaac cgggcacgta atggtgagct ctatcgctat    7500
atagctgacc agagaggtat atttgttcag gtatgctatt tgtattgtat tagtccaatt    7560
tcatttttg caccaaaaga aaggttgtta ttgtgacgta tatgtttgtt ttagcctgca    7620
ttttatgaag catttggact aacggtggtt gaagctatga cttgtggtct tccaacattt    7680
gcaacttgcc atggtggtcc taatgagatc attgaacccg gtgtatctgg gttccatatt    7740
gatccttatc atcccgataa agctgctgaa ctcatgtcag aattctttca acgctgcaaa    7800
caagatccta ctcactggga aaaaatatct gcatctggtc tccgaaggat tcttgagagg    7860
tctgtagttg tgtacatgta tagaagatta aagaatgcta ccttgatatt tatttgaatc    7920
aaaaataaca ggaacatctc ttttttgaac atcactcaag ttcttatatt aaataattt     7980
taggtatacg tggaagattt actccgagag gctgatgact ttatctggcg tatatggttt    8040
ctggaagctt gtttcaaaac ttgagaggcg tgaaactaga cgataccttg agatgttcta    8100
cattctcaaa ttccgcgagt tggtgagtgc cttttagctc cttttcagtt ccaataaact    8160
atatatgtgg tttaagtaag tattaagcat aaacatgtcc gtgcttgggg ctgtcgaaaa    8220
tgctatggac atatcctgag ctaaggattt ttcaagaaaa ttgatgttag ctttactcta    8280
tttacaggca aaatctgtac ctctagcaat tgatgacaag tga                      8323
```

```
<210> SEQ ID NO 39
<211> LENGTH: 810
<212> TYPE: PRT
<213> ORGANISM: Nicotiana tabacum

<400> SEQUENCE: 39

Met Ala Asn Pro Lys Phe Thr Arg Val Pro Ser Met Arg Glu Arg Val
1               5                   10                  15

Glu Asp Thr Leu Ser Ala His Arg Asn Gln Leu Val Ala Leu Leu Ser
            20                  25                  30

Arg Tyr Val Ala Gln Gly Lys Gly Ile Leu Gln Pro His His Leu Ile
        35                  40                  45

Asp Glu Phe Asn Asn Ala Val Cys Asp Asp Thr Ala Cys Glu Lys Leu
    50                  55                  60

Lys Asp Gly Pro Phe Ser Glu Val Leu Lys Ala Thr Gln Glu Ala Ile
65                  70                  75                  80

Val Leu Pro Pro Phe Val Ala Ile Ala Val Arg Pro Arg Pro Gly Val
                85                  90                  95

Trp Glu Tyr Val Arg Val Asn Val Tyr Asp Leu Ser Val Glu Gln Leu
            100                 105                 110

Thr Val Pro Glu Tyr Leu His Phe Lys Glu Glu Leu Val Asp Gly Glu
        115                 120                 125

Gly Asn Asn His Phe Val Leu Glu Leu Asp Phe Glu Pro Phe Asn Ala
    130                 135                 140

Ser Val Pro Arg Pro Ser Arg Ser Ser Ile Gly Asn Gly Val Gln Phe
145                 150                 155                 160

Phe Leu Asn Arg His Leu Ser Ser Ile Met Phe Arg Ser Lys Asp Ser
                165                 170                 175

Leu Asp Pro Leu Leu Asp Phe Leu Arg Gly His Cys His Lys Gly Asn
            180                 185                 190

Val Leu Met Leu Asn Asp Arg Ile Gln Arg Ile Ser Arg Leu Glu Ser
        195                 200                 205

Ala Leu Ser Lys Ala Glu Asp Tyr Leu Ser Lys Leu Ser Pro Asp Thr
    210                 215                 220

Ser Tyr Asn Glu Phe Glu Tyr Ala Leu Gln Glu Met Gly Phe Glu Arg
225                 230                 235                 240

Gly Trp Gly Asp Thr Ala Arg Arg Val Leu Glu Thr Met His Leu Leu
                245                 250                 255

Ser Asp Ile Leu Gln Ala Pro Asp Pro Ser Thr Leu Glu Thr Phe Leu
            260                 265                 270

Gly Arg Leu Pro Met Val Phe Asn Val Val Ile Leu Ser Pro His Gly
        275                 280                 285

Tyr Phe Gly Gln Ala Asn Val Leu Gly Leu Pro Asp Thr Gly Gly Gln
    290                 295                 300

Val Val Tyr Ile Leu Asp Gln Val Arg Ala Leu Glu Ala Glu Met Leu
305                 310                 315                 320

Leu Arg Ile Lys Gln Gln Gly Leu Asn Phe Lys Pro Arg Ile Leu Val
                325                 330                 335

Val Thr Arg Leu Ile Pro Asp Ala Lys Gly Thr Met Cys Asn Gln Arg
            340                 345                 350

Leu Glu Arg Ile Ser Gly Thr Glu Tyr Ser His Ile Leu Arg Val Pro
        355                 360                 365

Phe Arg Thr Glu Lys Gly Ile Leu His Lys Trp Ile Ser Arg Phe Asp
    370                 375                 380
```

```
Val Trp Pro Tyr Leu Glu Lys Phe Thr Glu Asp Val Ala Ser Glu Met
385                 390                 395                 400

Thr Ala Glu Leu Gln Gly Lys Pro Asp Leu Ile Ile Gly Asn Tyr Ser
            405                 410                 415

Asp Gly Asn Leu Val Ala Ser Leu Leu Ala Tyr Lys Met Gly Val Thr
        420                 425                 430

Gln Cys Thr Ile Ala His Ala Leu Glu Lys Thr Lys Tyr Pro Asp Ser
    435                 440                 445

Asp Ile Tyr Trp Lys Lys Phe Glu Glu Lys Tyr His Phe Ser Cys Gln
450                 455                 460

Phe Thr Ala Asp Leu Leu Ala Met Asn Asn Ser Asp Phe Ile Ile Thr
465                 470                 475                 480

Ser Thr Tyr Gln Glu Ile Ala Gly Thr Lys Asn Thr Val Gly Gln Tyr
            485                 490                 495

Glu Ser His Thr Ala Phe Thr Leu Pro Gly Leu Tyr Arg Val Val His
        500                 505                 510

Gly Ile Asp Val Phe Asp Pro Lys Phe Asn Ile Val Ser Pro Gly Ala
    515                 520                 525

Asp Met Thr Ile Tyr Phe Pro Tyr Ser Asp Lys Glu Lys Arg Leu Thr
530                 535                 540

Ser Leu His Gly Ser Ile Glu Lys Leu Leu Phe Asp Pro Ala Gln Asn
545                 550                 555                 560

Glu Glu His Ile Gly Asn Leu Asn Asp Lys Ser Lys Pro Ile Ile Phe
            565                 570                 575

Ser Met Ala Arg Leu Asp His Val Lys Asn Ile Thr Gly Leu Val Glu
        580                 585                 590

Cys Tyr Ala Lys Asn Ala Thr Leu Arg Glu Leu Ala Asn Leu Val Val
    595                 600                 605

Val Ala Gly Tyr Asn Asp Val Lys Lys Ser Ser Asp Arg Glu Glu Ile
    610                 615                 620

Thr Glu Ile Glu Lys Met His Ala Leu Ile Lys Glu His Lys Leu Asp
625                 630                 635                 640

Gly Gln Phe Arg Trp Val Ser Ala Gln Thr Asn Arg Ala Arg Asn Gly
            645                 650                 655

Glu Leu Tyr Arg Tyr Ile Ala Asp Gln Arg Gly Ile Phe Val Gln Pro
        660                 665                 670

Ala Phe Tyr Glu Ala Phe Gly Leu Thr Val Val Glu Ala Met Thr Cys
    675                 680                 685

Gly Leu Pro Thr Phe Ala Thr Cys His Gly Gly Pro Asn Glu Ile Ile
    690                 695                 700

Glu Pro Gly Val Ser Gly Phe His Ile Asp Pro Tyr His Pro Asp Lys
705                 710                 715                 720

Ala Ala Glu Leu Met Ser Glu Phe Phe Gln Arg Cys Lys Gln Asp Pro
            725                 730                 735

Thr His Trp Glu Lys Ile Ser Ala Ser Gly Leu Arg Arg Ile Leu Glu
        740                 745                 750

Arg Tyr Thr Trp Lys Ile Tyr Ser Glu Arg Leu Met Thr Leu Ser Gly
    755                 760                 765

Val Tyr Gly Phe Trp Lys Leu Val Ser Lys Leu Glu Arg Arg Glu Thr
    770                 775                 780

Arg Arg Tyr Leu Glu Met Phe Tyr Ile Leu Lys Phe Arg Glu Leu Ala
785                 790                 795                 800
```

Lys Ser Val Pro Leu Ala Ile Asp Asp Lys
                805                 810

<210> SEQ ID NO 40
<211> LENGTH: 3604
<212> TYPE: DNA
<213> ORGANISM: Nicotiana tabacum

<400> SEQUENCE: 40

| | | | | | |
|---|---|---|---|---|---|
| atgtttacat | ggctgaaact | caatataaaa | aacaaggta | ggtgatcaaa | atcgttgga | 60 |
| tgcttaaaat | cagtagacgt | tttgctaaat | gagcgaccaa | tgttattgaa | acgttcatg | 120 |
| ttttcaaccc | ttttggcata | catttgagca | ttgcccaaga | ttttggataa | gtagatgcag | 180 |
| tgcttataat | tttaaagcat | tgtatcctgc | cttgttttc | attgtcaaaa | ttaattaact | 240 |
| tacaagtatt | tctataagtt | gcttcataaa | ttagaagtaa | atctggattg | tgtaatgtta | 300 |
| ttcgcctcgt | aaatactgaa | agctgcttga | acaagtgaaa | aaacacagac | aaacgtaaca | 360 |
| ttctccatgg | attgatgaga | cttgtaaaat | acatatatag | aaatttggct | tgtaaccaca | 420 |
| tgtatattat | gccatatgga | tgtgacattg | atgtgactag | acctaaatgt | tttgtttcca | 480 |
| tgtccactgg | agttttacgt | atagttaaga | ggagaaaaga | ctgaggaata | ctaatgtatg | 540 |
| atggtacccc | tttgcttctt | gacctggata | cccagtgttc | ctattcatgc | ctatactttg | 600 |
| gtccttgatt | tcactctccc | ttttctaact | tgagctgcat | caaagaaatt | tccactgtaa | 660 |
| aaaaataaat | aatgctcacc | atatctctgc | aacattgcaa | acatgtatcc | catatgattg | 720 |
| atattggtgc | gacatggcaa | acatgtatcc | tatttgatga | tcaatcaaat | ttatttttcc | 780 |
| cctgtcaaaa | tgacctcagt | gtgtaattcc | ctatgtattt | gatagcattg | taactcgtgt | 840 |
| catgattcat | gaatagggta | ctagaattgc | atggttgaca | atattaact | ggtcgattga | 900 |
| tgatccacaa | acatgcact | tactgactaa | aatgtgatgg | gacagattta | ttttgttg | 960 |
| tgattaacac | agtacttaac | cctatactta | atacaatttg | gcctagctac | aatctttct | 1020 |
| tcagtgcaaa | ttccttgtta | cacgaccaat | attgtctttc | tgagttctat | tctgttgtta | 1080 |
| cttacacttt | tattattcga | ataagacatt | agattgcttg | catgcaaatt | gatagccact | 1140 |
| tgtttcagga | agaatactgt | tggtcagtac | gagagccata | ctgcattcac | cctcccagga | 1200 |
| ctatatcgcg | tcgttcatgg | cattgatgtt | ttcgatccca | aattcaatat | agtgtctcct | 1260 |
| ggagctgaca | tgcaatta | cttcccatat | tctgacaagg | aaaaaagact | aacgtctttg | 1320 |
| catggctcga | ttgagaagtt | gttatttgat | cctgcgcaga | atgaagagca | tatgtaagtg | 1380 |
| acatccattt | gtacttattt | taatttggaa | tagatgacat | acttatttgc | atgaatataa | 1440 |
| actgacaacc | cagagatttc | ctacattaga | aaaggagggt | ctgatatgat | tttctacaaa | 1500 |
| taaattccca | gtgatattgt | tcaaaaagtc | ctggatactt | tattatgaga | gaaccaggga | 1560 |
| tagatggcac | tagaatccct | aatcttgag | aagtcgccac | ttatcgctcc | caacactttc | 1620 |
| tgagaccctc | aagtaactac | tattattgtt | tgatatcttg | gagaagctat | aagaatcttt | 1680 |
| ttctccttat | tgtaattttt | tttacgtgac | tttaaactta | acttccaagc | tccttctgat | 1740 |
| aaaatgcaaa | aactgtctgt | attcactgtc | ttggttatt | aacaattgat | ccaatcaaat | 1800 |
| gcatatggaa | catctttctt | tttgtttctt | caaaagttcg | tttgaggata | aggagtagaa | 1860 |
| tctgagaaga | tagactagta | ggtaaccta | ggggcggatg | tagaaatcaa | cgtatgggtt | 1920 |
| cagctttgtt | gcagaccctg | tatatgcatt | aaaaaaatca | ctaaataagt | aaataattga | 1980 |
| ttttgaaccc | agtaaatcaa | aatgagttgt | agtagaatcc | tgaactcgaa | ccgataaagt | 2040 |

-continued

```
tggatccact accgggtaaa ctctaccttg agaagtgttt atatatgtcc ctaattattt    2100
cttttctgtt tcctttctat tttaattttt taagttcctt tttagatggt tttatttttt    2160
gacaagtggt aagttgttag tattccaaat taaatgccat tgccataact atatacattt    2220
ataaagattg attgaccctta gtttctcatt cctaagatcc aaataaggca ataaacaata    2280
tgtcttagta cttgaacctg cttctggtgg tcaacacttg atcgcgtagt tagttataga    2340
tgactgtaaa aaccttaatc attttaatgg ttttgtcaaa gaacaaatat cggacatatt    2400
atagcgaatg gactattgta cttttcttct gattggtcat tttattgtga tccgtaagtt    2460
ggctgagact gatgtcatat ctttgcttac agaggtaatc tgaatgataa atcaaaaccc    2520 ataattttt caatggcaag gctagaccat gttaagaaca ttacgggact agttgagtgc    2580
tatgctaaaa atgccacatt gagggaattg ctaaccttg ttgttgtagc tggatacaac    2640
gatgtaaaga aatccagtga tagagaagaa atagcagaaa ttgagaagat gcatgctctt    2700
attaaggagc ataaattgga tgggcaattc agatggatag cagcccaaac aaaccgggca    2760
cgtaatggtg agctctatcg ctatatagct gacaagagag gtatatttgt tcaggtacgc    2820
tgtttgtatt gtatttgtcc acattccttt ttttgcaccg aaagaaaggt tgttattgtg    2880
acaaatatgt ttgttttagc ctgcatttta tgaagcattt ggactcacgg tggttgaagc    2940
tatgacttgt ggtcttccaa catttgcaac ttgccatggt ggtccgaacg agatcattga    3000
acacggtgta tctgggttcc atattgatcc ttatcatccc gataaagctg ctgaactcat    3060
ggcagaattc tttcaacgct gcaaacaaga tcctactcac tgggaaaaaa tatctgcatc    3120
tggtctccga aggattcttg agaggtttgt agttgtgtac atatatagaa gattaaagat    3180
tgttcccttg atattatttg aatgaaaaat aacagtaaca tctcttttg aacatcgctc     3240 aagttcttgt gttaaataat tgttaggtat acgtggaaaa tttactccga gaggctgatg    3300
actttgtctg gtgtatatgg tttctggaag cttgtttcaa aacttgagag gcgcgaaact    3360
agacgatacc ttgagatgtt ctacattctc aaattccgcg agttggtgag tgcctttttg    3420
ctcattttca gttacaatca actatatatg tggtttaaat acgtattaag cataaacatg    3480
tccgtgattg cggctgtcga aaatgctatg gacatatcct gagctaagga gttttcaaga    3540
gaattgattt ggcttactct gtttacaggc aaaatctgtt cctctggcaa ttgatgacaa    3600
gtga                                                                 3604
```

<210> SEQ ID NO 41
<211> LENGTH: 335
<212> TYPE: PRT
<213> ORGANISM: Nicotiana tabacum

<400> SEQUENCE: 41

```
Met Phe Thr Trp Leu Lys Leu Asn Ile Lys Asn Lys Gly Arg Lys Asn
1               5                   10                  15

Thr Val Gly Gln Tyr Glu Ser His Thr Ala Phe Thr Leu Pro Gly Leu
            20                  25                  30

Tyr Arg Val Val His Gly Ile Asp Val Phe Asp Pro Lys Phe Asn Ile
        35                  40                  45

Val Ser Pro Gly Ala Asp Met Thr Ile Tyr Phe Pro Tyr Ser Asp Lys
    50                  55                  60

Glu Lys Arg Leu Thr Ser Leu His Gly Ser Ile Glu Lys Leu Leu Phe
65                  70                  75                  80

Asp Pro Ala Gln Asn Glu Glu His Ile Gly Asn Leu Asn Asp Lys Ser
                85                  90                  95
```

Lys Pro Ile Ile Phe Ser Met Ala Arg Leu Asp His Val Lys Asn Ile
            100                 105                 110

Thr Gly Leu Val Glu Cys Tyr Ala Lys Asn Ala Thr Leu Arg Glu Leu
        115                 120                 125

Ala Asn Leu Val Val Val Ala Gly Tyr Asn Asp Val Lys Lys Ser Ser
    130                 135                 140

Asp Arg Glu Glu Ile Ala Glu Ile Glu Lys Met His Ala Leu Ile Lys
145                 150                 155                 160

Glu His Lys Leu Asp Gly Gln Phe Arg Trp Ile Ala Ala Gln Thr Asn
                165                 170                 175

Arg Ala Arg Asn Gly Glu Leu Tyr Arg Tyr Ile Ala Asp Lys Arg Gly
            180                 185                 190

Ile Phe Val Gln Pro Ala Phe Tyr Glu Ala Phe Gly Leu Thr Val Val
        195                 200                 205

Glu Ala Met Thr Cys Gly Leu Pro Thr Phe Ala Thr Cys His Gly Gly
    210                 215                 220

Pro Asn Glu Ile Ile Glu His Gly Val Ser Gly Phe His Ile Asp Pro
225                 230                 235                 240

Tyr His Pro Asp Lys Ala Ala Glu Leu Met Ala Glu Phe Phe Gln Arg
                245                 250                 255

Cys Lys Gln Asp Pro Thr His Trp Glu Lys Ile Ser Ala Ser Gly Leu
            260                 265                 270

Arg Arg Ile Leu Glu Arg Tyr Thr Trp Lys Ile Tyr Ser Glu Arg Leu
        275                 280                 285

Met Thr Leu Ser Gly Val Tyr Gly Phe Trp Lys Leu Val Ser Lys Leu
    290                 295                 300

Glu Arg Arg Glu Thr Arg Arg Tyr Leu Glu Met Phe Tyr Ile Leu Lys
305                 310                 315                 320

Phe Arg Glu Leu Ala Lys Ser Val Pro Leu Ala Ile Asp Asp Lys
                325                 330                 335

<210> SEQ ID NO 42
<211> LENGTH: 4030
<212> TYPE: DNA
<213> ORGANISM: Nicotiana tabacum

<400> SEQUENCE: 42
atggcggaac gtgtgctgac tcgtgttcat agccttcgtg aacgtcttga tgctactttg      60
gctgctcatc gcaatgagat tttgctgttt ctttcaaggt atagtcttag cagattgttc     120
tttgatttag ttgttattgc cagttctaat gtatgggctt atatataaac aaagtgttga     180
agtatgcaac catataaact gacagcttaa aatgcttgag agaacacact tttatttatt     240
taattatgcc ttcagcacaa gaagtggaac ttgacgcaat ggaaccatag gtcacgggtt     300
caagtcttgg aacagcctgc aatctaaggc tgcgtgtagt agaccctagt ggtccggccc     360
ttccacatat ctcgcttagt gtaccgggcc cattgagtac gggttcggcc gaacccagtc     420
gctttggtcc aatccatata tttgtcttaa aaatatattg aatatataca aattgttaat     480
ttagtttaaa tatgtgtatc atgggttatt catgctggtt ttggctgttg caggattgaa     540
agccatggaa aagggatact gaaacctcac cagttgctgg ctgaatttga ttcaattcac     600
aaagaagaca aaaacaaact gaatgatcat gcttttgaag aagtcctgaa atccactcag     660
gtatttgtgg ttttagtgtt aggtgatgga tagcattat tgttttacta agatcacata      720
tgtgtcagtt tgtggctagt atttaaaatc tggtgtattt tgtcatacta ggaagcaatt     780

```
gttttgtccc cttgggttgc gcttgccatt cgtctgaggc ctggtgtgtg ggaatacgtt   840
cgtgtgaatg tcaacgctct tgttgttgag gagcttaccg tgcctgagta tttgcaattc   900
aaggaagaac ttgttaatgg aacgtaagtt ttaggttcga atttgttgat tgttagata    960 acatgttctg aacttttga ttaaagttgt gtttttgact gatgcagctc gcacgataac  1020
tttgttcttg agttggattt tgagcccttc actgcatcat ttccaaaacc aaccctcacc  1080
aaatcaattg gaaatggagt tgaattcctt aaccgacacc tctctgccaa aatgttccat  1140
gacaaggaaa gcatgacccc tcttctcgag tttcttcgag ttcaccacta caagggcaag  1200
gtaaacttgt ttttcctgtt tgtctatgaa tttagtttag ttgttttgct ccgcgaaaat  1260
ttcagtggaa actgatttat gcaaccactg agtgattaat atgttcaaac ttaccgactt  1320
ctggttttct gtgtagacaa tgatgctgaa tgacagaatt caggacttaa atactctcca  1380
aaatgtccta aggaaagctg aggaatacct cactacccct tcccctgaaa cttcatactc  1440
ggcatttgag cacaagttcc aagaaattgg cttggagagg ggttggggtg acactgcgga  1500
gcgtgttcta gagatgatct gcatgctcct ggatctcctc gaggctcctg actcgtgcac  1560
gcttgagaag ttccttggta gaattccaat ggttttaat gtggtcatac tttcaccca  1620 tggttatttc gcccaggaaa atgtcttggg ttaccccgac actggtggcc aggtgcactg  1680
cttatctgtg ttcggtctta ttatctcttt aaaccctact gccacaagtg ctgagatgaa  1740 cctccttaa tttgcaggtt gtctatattt tggatcaagt tcctgctttg gagcgtgaga  1800
tgctcaagcg cataaaggag caaggacttg acatcaaacc gcgtattctt attgttcgta  1860
ttcccagtaa ttgtgtttaa acttatgatt atgcaggatt ttatctgttc taatacagca  1920
ctcttgctta aattctcagg ttactcggct gctgcctgat gcggttggta ccacttgtgg  1980
tcagaggctt gagaaagtgt ttggaacaga gcactcacac attcttaggg tcccctttag  2040
gaccgagaag ggcattgttc gcaaatggat ctctcgcttt gaagtctggc catacatgga  2100
gacattcact gaggtgaagc aagctttctc tattcatttt tcaatcttcc aattggtttt  2160
ggcagcaatt ttctgcttgc tttgacttcc gctaaaactt cggattttat tgcattagga  2220
tgtggcgaaa gaaattgctg cagaattgca ggctaagcca gatcttatca ttggcaatta  2280
tagtgagggc aaccttgctg cctccttgtt ggctcacaaa ttaggtgtaa cacaggtcgg  2340 caatgttgt gacatgtaat tcatctttg catttccttt cgtttgcaac taaaagattt  2400
aagagttctc tctctcttt ttttttccgt ctactttgcc ttatgcagtg cacgatagct  2460
catgctttgg agaaaacaaa atatcctgat tctgatatct acttgaagaa atttgatgaa  2520
aaataccatt tctcagccca gtttactgcc gatcttattg caatgaatca caccgatttc  2580
atcatcacca gcactttcca ggagatagcg ggaaggtatt tttacatcag tttcccactc  2640
tgattaaatt acaatgtatt tccctatatg attaaatact gtgtttgatc ctaaatcatt  2700
tctaaatttt ccagcaagga cactgttgga cagtacgaga gccacatggc gttcacaatg  2760
cctggactgt atagagttgt tcacggcatt gatgtgtttg accccaaatt taacattgtg  2820
tcaccaggag ctgatatgaa tctctatttc ccatactacg agaaggaaaa gagattgaca  2880
gcatatcacc ctgaaattga ggagctgctg tttagtgatg ttgagaatga cgaacacatg  2940
tatgttacta aactagcaat cctgctgcaa aattatggct aattatgtaa acaagtttgt  3000
actgaataga tttgttattc gatcaggtgt gtgctgaaga acaggaataa gcctatcata  3060
ttcactatgg ctagattgga tcgagtgaag aacttaactg gacttgtcga gctgtacgcc  3120
```

```
aagaacccac ggctaaggga gttggttaac cttgtcgtgg ttggaggaga ccgaaggaaa    3180
gaatccaaag acttggaaga acaggcagag atgaagaaga tgtacgaact tataaagact    3240
cacaatttga acggccaatt ccgatggatt tcttcccaga tgaaccgcgt gaggaatggc    3300
gaactctaca ggtacattgc cgatactagg ggagctttcg tgcagcctgc attttacgag    3360
gcttttggtt tgactgttgt tgaggccatg acctgtggtt tgcctacatt tgcaactaat    3420
cacggtggtc cagctgagat catcgttcac gggaaatctg gtttccacat tgatccatac    3480
cacggggatc aggcagctga acttctcgct gatttctttg agaaatgtaa gaaagaacct    3540
tcgcactggg aagccatttc cgagggcggc cttaagcgta tacaggagaa gtaagcaaac    3600
tgctactctt ttcattttg caaaacctac tatgatcatt attaagctca tttttgcaaa     3660
acctacttgc tgttgttatt gtttgttgct tccttttcac tgttctttga gctgaaggtc    3720
tatcagaaac agtctctcta ccttcacaag gtaggggtaa gatctgcgtg cacgttaccc    3780
tcctcaaact ctacttaatt gtgagattac actaggtttg ttgttgttga ttctttgcta    3840
attaattaaa aggtacacat ggcaaatata ctcggatcgg ttgttgacac tggctgctgt    3900
atatggattc tggaagcatg tttccaagct tgatcgtctt gaaattcgcc gttatcttga    3960
aatgttctat gctctcaaat ccgcaagct ggtgagtttc attgctttct gcactcctgc      4020
aattgtatag                                                           4030
```

<210> SEQ ID NO 43
<211> LENGTH: 808
<212> TYPE: PRT
<213> ORGANISM: Nicotiana tabacum

<400> SEQUENCE: 43

Met Ala Glu Arg Val Leu Thr Arg Val His Ser Leu Arg Glu Arg Leu
1               5                   10                  15

Asp Ala Thr Leu Ala Ala His Arg Asn Glu Ile Leu Leu Phe Leu Ser
                20                  25                  30

Arg Ile Glu Ser His Gly Lys Gly Ile Leu Lys Pro His Gln Leu Leu
            35                  40                  45

Ala Glu Phe Asp Ser Ile His Lys Glu Asp Lys Asn Lys Leu Asn Asp
        50                  55                  60

His Ala Phe Glu Glu Val Leu Lys Ser Thr Gln Glu Ala Ile Val Leu
65                  70                  75                  80

Ser Pro Trp Val Ala Leu Ala Ile Arg Leu Arg Pro Gly Val Trp Glu
                85                  90                  95

Tyr Val Arg Val Asn Val Asn Ala Leu Val Val Glu Glu Leu Thr Val
                100                 105                 110

Pro Glu Tyr Leu Gln Phe Lys Glu Glu Leu Val Asn Gly Thr Ser His
            115                 120                 125

Asp Asn Phe Val Leu Glu Leu Asp Phe Glu Pro Phe Thr Ala Ser Phe
        130                 135                 140

Pro Lys Pro Thr Leu Thr Lys Ser Ile Gly Asn Gly Val Glu Phe Leu
145                 150                 155                 160

Asn Arg His Leu Ser Ala Lys Met Phe His Asp Lys Glu Ser Met Thr
                165                 170                 175

Pro Leu Leu Glu Phe Leu Arg Val His His Tyr Lys Gly Lys Thr Met
            180                 185                 190

Met Leu Asn Asp Arg Ile Gln Asp Leu Asn Thr Leu Gln Asn Val Leu
        195                 200                 205

-continued

Arg Lys Ala Glu Glu Tyr Leu Thr Leu Ser Pro Glu Thr Ser Tyr
210             215                 220

Ser Ala Phe Glu His Lys Phe Gln Glu Ile Gly Leu Glu Arg Gly Trp
225                 230                 235                 240

Gly Asp Thr Ala Glu Arg Val Leu Glu Met Ile Cys Met Leu Leu Asp
                245                 250                 255

Leu Leu Glu Ala Pro Asp Ser Cys Thr Leu Glu Lys Phe Leu Gly Arg
        260                 265                 270

Ile Pro Met Val Phe Asn Val Ile Leu Ser Pro His Gly Tyr Phe
    275                 280                 285

Ala Gln Glu Asn Val Leu Gly Tyr Pro Asp Thr Gly Gly Gln Val Val
    290                 295                 300

Tyr Ile Leu Asp Gln Val Pro Ala Leu Glu Arg Glu Met Leu Lys Arg
305                 310                 315                 320

Ile Lys Glu Gln Gly Leu Asp Ile Lys Pro Arg Ile Leu Ile Val Thr
                325                 330                 335

Arg Leu Leu Pro Asp Ala Val Gly Thr Thr Cys Gly Gln Arg Leu Glu
            340                 345                 350

Lys Val Phe Gly Thr Glu His Ser His Ile Leu Arg Val Pro Phe Arg
        355                 360                 365

Thr Glu Lys Gly Ile Val Arg Lys Trp Ile Ser Arg Phe Glu Val Trp
370                 375                 380

Pro Tyr Met Glu Thr Phe Thr Glu Asp Val Ala Lys Glu Ile Ala Ala
385                 390                 395                 400

Glu Leu Gln Ala Lys Pro Asp Leu Ile Ile Gly Asn Tyr Ser Glu Gly
                405                 410                 415

Asn Leu Ala Ala Ser Leu Leu Ala His Lys Leu Gly Val Thr Gln Cys
            420                 425                 430

Thr Ile Ala His Ala Leu Glu Lys Thr Lys Tyr Pro Asp Ser Asp Ile
        435                 440                 445

Tyr Leu Lys Lys Phe Asp Glu Lys Tyr His Phe Ser Ala Gln Phe Thr
    450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Met Ala Phe Thr Met Pro Gly Leu Tyr Arg Val Val His Gly Ile
            500                 505                 510

Asp Val Phe Asp Pro Lys Phe Asn Ile Val Ser Pro Gly Ala Asp Met
        515                 520                 525

Asn Leu Tyr Phe Pro Tyr Tyr Glu Lys Glu Lys Arg Leu Thr Ala Tyr
    530                 535                 540

His Pro Glu Ile Glu Glu Leu Leu Phe Ser Asp Val Glu Asn Asp Glu
545                 550                 555                 560

His Met Cys Val Leu Lys Asn Arg Asn Lys Pro Ile Ile Phe Thr Met
                565                 570                 575

Ala Arg Leu Asp Arg Val Lys Asn Leu Thr Gly Leu Val Glu Leu Tyr
            580                 585                 590

Ala Lys Asn Pro Arg Leu Arg Glu Leu Val Asn Leu Val Val Val Gly
        595                 600                 605

Gly Asp Arg Arg Lys Glu Ser Lys Asp Leu Glu Glu Gln Ala Glu Met
    610                 615                 620

Lys Lys Met Tyr Glu Leu Ile Lys Thr His Asn Leu Asn Gly Gln Phe

```
                625                 630                 635                 640
Arg Trp Ile Ser Ser Gln Met Asn Arg Val Arg Asn Gly Glu Leu Tyr
                    645                 650                 655
Arg Tyr Ile Ala Asp Thr Arg Gly Ala Phe Val Gln Pro Ala Phe Tyr
                660                 665                 670
Glu Ala Phe Gly Leu Thr Val Val Glu Ala Met Thr Cys Gly Leu Pro
            675                 680                 685
Thr Phe Ala Thr Asn His Gly Gly Pro Ala Glu Ile Ile Val His Gly
        690                 695                 700
Lys Ser Gly Phe His Ile Asp Pro Tyr His Gly Asp Gln Ala Ala Glu
705                 710                 715                 720
Leu Leu Ala Asp Phe Phe Glu Lys Cys Lys Lys Glu Pro Ser His Trp
                    725                 730                 735
Glu Ala Ile Ser Glu Gly Gly Leu Lys Arg Ile Gln Glu Lys Tyr Thr
                740                 745                 750
Trp Gln Ile Tyr Ser Asp Arg Leu Leu Thr Leu Ala Ala Val Tyr Gly
            755                 760                 765
Phe Trp Lys His Val Ser Lys Leu Asp Arg Leu Glu Ile Arg Arg Tyr
        770                 775                 780
Leu Glu Met Phe Tyr Ala Leu Lys Phe Arg Lys Leu Val Ser Phe Ile
785                 790                 795                 800
Ala Phe Cys Thr Pro Ala Ile Val
                805
```

<210> SEQ ID NO 44
<211> LENGTH: 4054
<212> TYPE: DNA
<213> ORGANISM: Nicotiana tabacum

<400> SEQUENCE: 44

```
atggccgaac gtgtgctaac tcgtgttcac agccttcgcg aacgtcttga tgctactttg      60
gctgctcatc gcaatgagat tttgctgttt ctttcaaggt atagtcttag cagattgttc     120
tttgatttag ttggtgttat ttgccagttc taatgtatgg actaatatat gaacaaagtg     180
cgaccatttc aactgacaac ttaaaatgtt tgagagaata cacgtttatt tacttaatta     240
tggcttgagc ataggaagtg tatcttggcg taactcgtaa agttgacctc atgtgacaag     300
gaggtcacgg tttcgagccg tggaaacagc ctcttgcaga aatgcaggta aggctgcgtg     360
caatagatcg cccttccacg gacccgcgca tagcgggaac ttagtgcacc ggttgggctg     420
tccttttta tgtcttcagc acaaaaattt agtttaaaca tgtgtatcat ggattattca     480
tgctggtttt gccggttgca ggattgaaag ccacggaaaa gggatattga aacctcacca     540
gttgctggct gagtttgaat caattcacaa agaagacaaa aacaaactga atgatcatgc     600
ttttgaagaa gtcctgaaat ctactcaggt aatttgtggt tttagtgtta ggtgatggat     660
agcatttatt gtcttactaa gatcatatat gtgtcagttt gtggctagta tttgaaaagt     720
ctggtgtggt ttgtcatact aggaagcaat tgtcttgtcc ccttgggttg cgcttgccat     780
tcgtctgcgg cctggtgtgt gggaatatgt tcgtgtgaat gtcaatgcac ttattgtcga     840
ggagctgact gtgcctgaat atttgcaatt caaggaagaa cttgttaatg aacgtaagt      900
tttaggttcg aaatgatgat ttgttaaata atatgttctg aacttttga ttaatgttgt      960
gttttcccct gatgcagctc gaacgataac tttgttcttg agctggattt tgagcccttc    1020
actgcatcat ttcccaaacc aaccctcacc aaatcaattg gaaatggagt tgaattcctc    1080
```

```
aaccgacacc tctctgccaa aatgttccat gacaaggaaa gcatgacccc tcttctcgag    1140
tttcttcgag ttcatcacta caagggcaag gtaaacttgt ttttcctgtt tgtctatgaa    1200
tttagtttct gaaagttgct tgcttcgtg aattttttag tggcaactga tttatgattt     1260
tctgtgcaga caatgatgct gaatgacaga gttcaggact taaacactct ccaaaatgtc    1320
ctaaggaagg ctgaggaata tctcactacc cttcccctg aaacttcata ctcggtattt     1380
gagcacaagt tccaagaaat tggcctagag aggggctggg gtgacaatgc tgagcgtgtt   1440
ctagagatga tctgcatgct cctggatctc ctcgaggctc cagactcatg cactcttgag    1500 aagttcctg gtagaattcc tatggttttt aatgtggtca ttctttcacc tcacggatat     1560
ttcgcccagg aaaatgtctt gggttacccc gatactggtg gccaggtgca ctgcttattt    1620
gtaacacctt acgcttttcc ctctgaaact tatttgcggc aagttctaag gtcctccttc    1680
cttaatttgc aggttgtcta tattttggat caagttccgg ccttggagcg tgagatgctc    1740
aagcgcataa aggagcaagg acttgatatc aaaccgcgta ttcttattgt tcgtatctcc    1800
aataattgcg tttaaactta tgattgtgca ggatttgatc tgttcaaatc taatgactga    1860 ttttctttt ttttttttt tccctcaggt tactcggctg ctgcctgatg cggttggtac      1920
cacttgtggt cagcggcttg agaaagtgtt tggaacagag cattcacata ttcttagggt    1980
cccctttagg accgagaagg gcatcgttcg caaatggatc tctcgctttg aagtctggcc   2040
ttacatggag acattcactg aggtgaagca agctttctct attcattttt caatcttcca    2100
atctgttttg gcagcaattt ttcacttact aacactttgg ctttcgctaa aacttcggat    2160
tttattacat taggatgtgg caaaagaaat tgctgcagaa ctgcaggcaa agccagatct   2220
tataatcggc aactacagcg agggcaacct tgctgcctcc ttgttggctc acaagttagg   2280
tgtaactcag gtctgtaatg tttgtcacct gttatttcaa ctttgcattt cctttcattt    2340
gcaactagaa gttaagagtt ctctctcttt tatcttttcc gtctattttg ccttctgcag    2400
tgcaccatag ctcatgcgtt ggagaaaaca aaatatcctg attctgatat ctacttgaag    2460
aaatttgatg aaaaatacca tttctcagcc cagtttactg ccgatcttat tgcaatgaat   2520
cacaccgatt tcataatcac cagcactttc caggagatag cgggaaggta ttacatcaca    2580
atggatttcc gatatgatta aattagttaa tttaatccta cttcattgtg tttgatccta    2640
aaacttttct aaatttccca gcaaggacac tgttggacag tacgagagcc acatggcttt    2700
cacgatgcct ggattgtata gagttgttca cggcattgat gtgttcgatc ccaaattcaa    2760
cattgtgtca ccaggagctg atatgaatct ctatttcccc tacttcgaga aggaaaagcg    2820
attgacagca tatcaccctg aaattgagga gctgctgttt agcgatgttg agaatgacga    2880
acacatgtat gttactaaac tagcaatcct gctgcaaaat tgtggctaat tatgtaaaaa    2940 agttttact gaatagattt gtgcttctat caggtgtgtg ctgaaggaca ggaataagcc     3000
aattatattc accatggcta gattggatcg agtgaagaac ttaactggac ttgtggagtt    3060
gtacgccaag aacccacggc taagggagtt ggttaacctt gtcgtggttg gtggagaccg   3120
aaggaaggaa tccaaagatt tggaagaaca ggcagagatg aagaagatgt atgaacttat    3180
aaagacgcac aatttaaacg gccaattccg atggatttct ccagatgaa accgcgtgag     3240 gaatggcgaa ctctacaggt acattgccga tactagggga gcttttgtgc agcctgcatt    3300
ttacgaggct tttggtttga ctgttgttga ggccatgacc tgtggtttgc ctacgtttgc    3360
aactaatcac ggtggtccag ctgagatcat cgttcacggg aagtctggtt tcacattga    3420 tccataccac ggcgagcagg cagctgaact tctagctgat ttctttgaga gatgtaagaa    3480
```

-continued

```
agaaccttca cactgggaag ccatttccga gggcggcctt aagcgtatac aggagaagta    3540
agcaagctgc tactcttttc attttttgcaa aacctaccat gatcattatt aagctcattt    3600
ttgcaaaacc tacttgttat tctttgttgc ttccttttcc ctgttttttg agccgaggtt    3660
ttatcgaaaa catgctttct accttcacaa ggtaggggta aggtctgcgt ttgttattat    3720
tgttgttgtt gattctctgc gaattaatta aaaggtacac atggcaaatc tactcggatc    3780
ggttgttgac actggctgct gtttatggat tctggaagca tgtttccaaa cttgatcgtc    3840
ttgaaattcg tcgttatctt gaaatgttct atgctctaaa attccgcaaa ctggtgagtt    3900
tcactgcttt ctgcactctt ccaattgtta gttgagtgca ctcatttaaa ctgtagctaa    3960
agctgttgta aatcttcagt taagcagctg ctaatgaagt ttttatcttt tgttttttggt    4020 tcaggctgaa gctgtcccgt tggctgttga gtaa                                4054
```

<210> SEQ ID NO 45
<211> LENGTH: 805
<212> TYPE: PRT
<213> ORGANISM: Nicotiana tabacum

<400> SEQUENCE: 45

```
Met Ala Glu Arg Val Leu Thr Arg Val His Ser Leu Arg Glu Arg Leu
1               5                   10                  15

Asp Ala Thr Leu Ala Ala His Arg Asn Glu Ile Leu Leu Phe Leu Ser
            20                  25                  30

Arg Ile Glu Ser His Gly Lys Gly Ile Leu Lys Pro His Gln Leu Leu
        35                  40                  45

Ala Glu Phe Glu Ser Ile His Lys Glu Asp Lys Asn Lys Leu Asn Asp
    50                  55                  60

His Ala Phe Glu Glu Val Leu Lys Ser Thr Gln Glu Ala Ile Val Leu
65                  70                  75                  80

Ser Pro Trp Val Ala Leu Ala Ile Arg Leu Arg Pro Gly Val Trp Glu
                85                  90                  95

Tyr Val Arg Val Asn Val Asn Ala Leu Ile Val Glu Glu Leu Thr Val
            100                 105                 110

Pro Glu Tyr Leu Gln Phe Lys Glu Glu Leu Val Asn Gly Thr Ser Asn
        115                 120                 125

Asp Asn Phe Val Leu Glu Leu Asp Phe Glu Pro Phe Thr Ala Ser Phe
    130                 135                 140

Pro Lys Pro Thr Leu Thr Lys Ser Ile Gly Asn Gly Val Glu Phe Leu
145                 150                 155                 160

Asn Arg His Leu Ser Ala Lys Met Phe His Asp Lys Glu Ser Met Thr
                165                 170                 175

Pro Leu Leu Glu Phe Leu Arg Val His His Tyr Lys Gly Lys Thr Met
            180                 185                 190

Met Leu Asn Asp Arg Val Gln Asp Leu Asn Thr Leu Gln Asn Val Leu
        195                 200                 205

Arg Lys Ala Glu Glu Tyr Leu Thr Thr Leu Ser Pro Glu Thr Ser Tyr
    210                 215                 220

Ser Val Phe Glu His Lys Phe Gln Glu Ile Gly Leu Glu Arg Gly Trp
225                 230                 235                 240

Gly Asp Asn Ala Glu Arg Val Leu Glu Met Ile Cys Met Leu Leu Asp
                245                 250                 255

Leu Leu Glu Ala Pro Asp Ser Cys Thr Leu Glu Lys Phe Leu Gly Arg
            260                 265                 270
```

```
Ile Pro Met Val Phe Asn Val Ile Leu Ser Pro His Gly Tyr Phe
            275                 280                 285

Ala Gln Glu Asn Val Leu Gly Tyr Pro Asp Thr Gly Gly Gln Val Val
290                 295                 300

Tyr Ile Leu Asp Gln Val Pro Ala Leu Glu Arg Glu Met Leu Lys Arg
305                 310                 315                 320

Ile Lys Glu Gln Gly Leu Asp Ile Lys Pro Arg Ile Leu Ile Val Thr
                325                 330                 335

Arg Leu Leu Pro Asp Ala Val Gly Thr Thr Cys Gly Gln Arg Leu Glu
                340                 345                 350

Lys Val Phe Gly Thr Glu His Ser His Ile Leu Arg Val Pro Phe Arg
                355                 360                 365

Thr Glu Lys Gly Ile Val Arg Lys Trp Ile Ser Arg Phe Glu Val Trp
                370                 375                 380

Pro Tyr Met Glu Thr Phe Thr Glu Asp Val Ala Lys Glu Ile Ala Ala
385                 390                 395                 400

Glu Leu Gln Ala Lys Pro Asp Leu Ile Ile Gly Asn Tyr Ser Glu Gly
                405                 410                 415

Asn Leu Ala Ala Ser Leu Leu Ala His Lys Leu Gly Val Thr Gln Cys
                420                 425                 430

Thr Ile Ala His Ala Leu Glu Lys Thr Lys Tyr Pro Asp Ser Asp Ile
                435                 440                 445

Tyr Leu Lys Lys Phe Asp Glu Lys Tyr His Phe Ser Ala Gln Phe Thr
450                 455                 460

Ala Asp Leu Ile Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Met Ala Phe Thr Met Pro Gly Leu Tyr Arg Val Val His Gly Ile
                500                 505                 510

Asp Val Phe Asp Pro Lys Phe Asn Ile Val Ser Pro Gly Ala Asp Met
                515                 520                 525

Asn Leu Tyr Phe Pro Tyr Phe Glu Lys Glu Lys Arg Leu Thr Ala Tyr
                530                 535                 540

His Pro Glu Ile Glu Glu Leu Leu Phe Ser Asp Val Glu Asn Asp Glu
545                 550                 555                 560

His Met Cys Val Leu Lys Asp Arg Asn Lys Pro Ile Ile Phe Thr Met
                565                 570                 575

Ala Arg Leu Asp Arg Val Lys Asn Leu Thr Gly Leu Val Glu Leu Tyr
                580                 585                 590

Ala Lys Asn Pro Arg Leu Arg Glu Leu Val Asn Leu Val Val Val Gly
                595                 600                 605

Gly Asp Arg Arg Lys Glu Ser Lys Asp Leu Glu Glu Gln Ala Glu Met
610                 615                 620

Lys Lys Met Tyr Glu Leu Ile Lys Thr His Asn Leu Asn Gly Gln Phe
625                 630                 635                 640

Arg Trp Ile Ser Ser Gln Met Asn Arg Val Arg Asn Gly Glu Leu Tyr
                645                 650                 655

Arg Tyr Ile Ala Asp Thr Arg Gly Ala Phe Val Gln Pro Ala Phe Tyr
                660                 665                 670

Glu Ala Phe Gly Leu Thr Val Val Glu Ala Met Thr Cys Gly Leu Pro
                675                 680                 685
```

```
Thr Phe Ala Thr Asn His Gly Gly Pro Ala Glu Ile Ile Val His Gly
    690                 695                 700
Lys Ser Gly Phe His Ile Asp Pro Tyr His Gly Glu Gln Ala Ala Glu
705                 710                 715                 720
Leu Leu Ala Asp Phe Phe Glu Arg Cys Lys Lys Glu Pro Ser His Trp
                725                 730                 735
Glu Ala Ile Ser Glu Gly Gly Leu Lys Arg Ile Gln Glu Lys Tyr Thr
                740                 745                 750
Trp Gln Ile Tyr Ser Asp Arg Leu Leu Thr Leu Ala Ala Val Tyr Gly
            755                 760                 765
Phe Trp Lys His Val Ser Lys Leu Asp Arg Leu Glu Ile Arg Arg Tyr
770                 775                 780
Leu Glu Met Phe Tyr Ala Leu Lys Phe Arg Lys Leu Ala Glu Ala Val
785                 790                 795                 800
Pro Leu Ala Val Glu
            805

<210> SEQ ID NO 46
<211> LENGTH: 3752
<212> TYPE: DNA
<213> ORGANISM: Nicotiana tabacum

<400> SEQUENCE: 46
atggcctcaa cagttgctga tagcatgcct gatgctttga acaaagccg gtatcatatg      60 aagagatgct tcgctaggtg aacacccttc ttttatgttt tttcccctct acgtgtttat    120
gtcaaatttc catgcataat gctaactact tttcttcttt ttgacttcaa aattggatgt    180
gaaaggttca ttgcaatggg aaggaggcta atgaagttga acatttaac agaagaaata    240 gaagaaacta ttgaagacaa ggcagaaaga accaggattt tggagggttc acttggaaaa    300
attatgagtt ccacacaggt cagcaccatt taaccaactt agttgaacag gaaaaaaaga    360
aaaagcaaaa gagttattgc aaggcgtaac gattttcttt gaaattttca ggaggcagct    420
gttgttccac cttatgttgc ttttgcagta aggcacaatc ctggcttctg ggattatgtc    480
aaagttaacg ctgaaactct ctctgtggaa gctatttcag ccagggaata tctcaaattc    540
aaagagatga tctttgacga agactggtaa gtggaaaatt gtatcatttt aaagagaaac    600
aattttgtaa catacaagaa tagttttgat ggttgaatgt gcaagcaggg caaggatga    660 taatgcactg gaagtagatt ttggtgcttt tgactactct aatcctcggt tagcccttc    720 ctcttctgtc ggaaatgggc tcaactttat ctcaaaagtt ctgtcttcaa agtttggtgg    780
aaagccagag gacgcccagc ctttgcttga ttacttacta gctcttaatc atcaaggaga    840
ggtatgaaaa tggactacct tgtttctta aaggtattat ataatgatgc gcgttataaa    900 gttcctttt aaattgaaac tttgcagaat ctaatgatca atgagaatct gaatggtgtt    960
gctaagcttc aagcagcatt gatagtagct gaagttttg tatcttcctt tcccaaagac   1020 acacccttata aagactttga gcataagtaa gcttctcata tgcttccatt gtcatatgca   1080
gtataccaat gacatgctac cgaaaagttg tttatgtttg tgacttgatt atgaaaactc   1140
taggctcaaa gaatggggct ttgataaagg gtggggtcac aatgcaggaa gagtaagaga   1200
gacaatgaga ctgctttccg agataatcca agcaccagat cccataaata tggagtcctt   1260
tttcagcaag cttcctacta cattcaacat tgttatcttc tccattcatg gttactttgg   1320
ccaagcagat gtccttggtc tgcccgatac tggaggccag gtctacatat acagcaattt   1380 atctccttt gcctcatatt gcttattagc gacacttgca tcattgaaat cagacttta   1440
```

```
cttcacaggt tgtttatatt ctggatcaag taagggcttt agaggaggaa atgttacaaa    1500
gaatcaagca gcaagggcta aacgtgaagc ccaagattct tgtggtgagt tttgcaaaaa    1560
tatgcttaga caggttttga gattgatcgg agaagggatt aagatgatca agatctttgt    1620
ttcctgcttt catgatgtaa acaggtatct cgtctcatac cagatgctcg agggacaaca    1680
tgcaatcagg agatggaacc tattcttaac tcatcccatt ctcacatcct gagaattcca    1740
ttcaggactg agaaaggagt tcttcgccaa tgggtttctc ggtttgatat ctatccttac    1800
ttggagaact atgccaaggc aagtcttcta acaaaattac cacctattca tacactttat    1860
ttactttctt gaactaatcg tttggtttgt gacgtatatc attaggatgc ttctgctaag    1920
atacttgagc tcatggaagg taaaccagac ctcataattg ggaactacac tgatggaaat    1980
ttagtggcat ctctattggc caacaaactt ggagttactc aggttccgta gctgatcata    2040
tgatcatatt ttctacattg tttcttgata attaaatgga aatcttattg gatgataaca    2100
ttttagggaa ccattgctca tgcattagag aaaactaagt atgaagattc tgatgtgaag    2160
tggaagcagt ttgatcccaa gtaccacttt tcttgccaat ttactgccga tttattggca    2220
atgaatgctg ctgattttat cattaccagc acatatcaag aaatcgctgg aaggttagca    2280
ctgactctct cagtatattt ggcaacttaa tgaatttact gcagtggcca cactaaaag     2340 ctatcattcg tccttcagcg aaactaggcc tggacaatat gaaagtcaca cagcatttac    2400
catgccgggg ctttatagag ctgtttcagg catcaatgta tttgatccaa agttcaacat    2460
tgctgctcct ggggctgaac agtctaccta tttcccttc actgagaaac agaaacgatt      2520
cagcacattt cgtcctgcta ttaacgaatt actttacagt aatgaggaaa acaatgagca    2580
catgtaagtc taattgccca ttttcctaat ctaaccattg cttaaatcgt tctgttttta    2640
ccggatgtgt ggtacttatc agtaacattt ttttttggat cagtggattt cttgcagacc    2700
ggaaaaaacc aattatattt tcaatggcga gatttgatac agtgaagaac ctgtcaggct    2760
tgactgagtg gtatgggaag aataagaagt tgcggaactt ggtaaacctt gttattgttg    2820
ggggattctt cgatccatca aaatcaaaag accgggagga agcagctgaa atcaagaaga    2880
tgcatgaatt gattgagaaa taccagctca agggacaaat gagatggata gcagctcaaa    2940
ctgataaata tcgaaatagt gagctatacc gaactattgc tgacactaag ggagcttttg    3000
tccaaccggc tttatatgaa gcttttggac taaccgttat tgaagcaatg gattgtggat    3060
tgcctacgtt tgcaactaat caaggtggac ctgcagaaat cattgttgat ggggtttcag    3120
gtttccatat tgatccttac aatggggacg aatcaagcaa gaaaatagct gatttctttg    3180
agaagtgtaa ggttgattct aaatattgga acaggatatc tgagggaggt ctcaagcgca    3240
ttgaagaatg gtaacaaact agttccaagt ttaaaaatg gaaaaaatgc ttatcatgtt      3300
atattttcgt ggttttaagt tctgcttcga tgcagttata cgtggaagat ttatgcaaac    3360
aaagtgttga atatgggatc aatctatgga ttttggagac aattcaatgt ggggcaaaag    3420
caggctaagc aaagatactt tgagatgttt tacaatcctc tcttcaggaa attggtaggt    3480
tgtatatgtt gaatacaatt tactaagatc ctcaaaatga ccaagaaata tacattgact    3540
atgctacttt tgtaatttca caggccaaaa gcgtgccgat cccacatgaa gagccattgc    3600
cacttgcaac atcagactct actcaatccc aagaattaaa actaccacta ccagttccag    3660
cagcagtagc taaagttctg ccattaacaa ggcatgcttt taacttaatt acttctctac    3720
ctagagtaac tggtaaagtg gatgtcaagt ga                                   3752
```

<210> SEQ ID NO 47
<211> LENGTH: 840
<212> TYPE: PRT
<213> ORGANISM: Nicotiana tabacum

<400> SEQUENCE: 47

```
Met Ala Ser Thr Val Ala Asp Ser Met Pro Asp Ala Leu Lys Gln Ser
1               5                   10                  15

Arg Tyr His Met Lys Arg Cys Phe Ala Arg Phe Ile Ala Met Gly Arg
                20                  25                  30

Arg Leu Met Lys Leu Lys His Leu Thr Glu Glu Ile Glu Glu Thr Ile
            35                  40                  45

Glu Asp Lys Ala Glu Arg Thr Arg Ile Leu Glu Gly Ser Leu Gly Lys
    50                  55                  60

Ile Met Ser Ser Thr Gln Glu Ala Ala Val Val Pro Pro Tyr Val Ala
65                  70                  75                  80

Phe Ala Val Arg His Asn Pro Gly Phe Trp Asp Tyr Val Lys Val Asn
                85                  90                  95

Ala Glu Thr Leu Ser Val Glu Ala Ile Ser Ala Arg Glu Tyr Leu Lys
                100                 105                 110

Phe Lys Glu Met Ile Phe Asp Glu Asp Trp Ala Lys Asp Asn Ala
                115                 120                 125

Leu Glu Val Asp Phe Gly Ala Phe Asp Tyr Ser Asn Pro Arg Leu Ala
    130                 135                 140

Leu Ser Ser Ser Val Gly Asn Gly Leu Asn Phe Ile Ser Lys Val Leu
145                 150                 155                 160

Ser Ser Lys Phe Gly Gly Lys Pro Glu Asp Ala Gln Pro Leu Leu Asp
                165                 170                 175

Tyr Leu Leu Ala Leu Asn His Gln Gly Glu Asn Leu Met Ile Asn Glu
                180                 185                 190

Asn Leu Asn Gly Val Ala Lys Leu Gln Ala Ala Leu Ile Val Ala Glu
            195                 200                 205

Val Phe Val Ser Ser Phe Pro Lys Asp Thr Pro Tyr Lys Asp Phe Glu
    210                 215                 220

His Lys Leu Lys Glu Trp Gly Phe Asp Lys Gly Trp Gly His Asn Ala
225                 230                 235                 240

Gly Arg Val Arg Glu Thr Met Arg Leu Leu Ser Glu Ile Ile Gln Ala
                245                 250                 255

Pro Asp Pro Ile Asn Met Glu Ser Phe Phe Ser Lys Leu Pro Thr Thr
                260                 265                 270

Phe Asn Ile Val Ile Phe Ser Ile His Gly Tyr Phe Gly Gln Ala Asp
            275                 280                 285

Val Leu Gly Leu Pro Asp Thr Gly Gly Gln Val Val Tyr Ile Leu Asp
    290                 295                 300

Gln Val Arg Ala Leu Glu Glu Glu Met Leu Gln Arg Ile Lys Gln Gln
305                 310                 315                 320

Gly Leu Asn Val Lys Pro Lys Ile Leu Val Val Ser Arg Leu Ile Pro
                325                 330                 335

Asp Ala Arg Gly Thr Thr Cys Asn Gln Glu Met Glu Pro Ile Leu Asn
                340                 345                 350

Ser Ser His Ser His Ile Leu Arg Ile Pro Phe Arg Thr Glu Lys Gly
            355                 360                 365

Val Leu Arg Gln Trp Asp Ala Ser Ala Lys Ile Leu Glu Leu Met Glu
    370                 375                 380
```

```
Gly Lys Pro Asp Leu Ile Ile Gly Asn Tyr Thr Asp Gly Asn Leu Val
385                 390                 395                 400

Ala Ser Leu Leu Ala Asn Lys Leu Gly Val Thr Gln Gly Thr Ile Ala
                405                 410                 415

His Ala Leu Glu Lys Thr Lys Tyr Glu Asp Ser Asp Val Lys Trp Lys
            420                 425                 430

Gln Phe Asp Pro Lys Tyr His Phe Ser Cys Gln Phe Thr Ala Asp Leu
        435                 440                 445

Leu Ala Met Asn Ala Ala Asp Phe Ile Ile Thr Ser Thr Tyr Gln Glu
    450                 455                 460

Ile Ala Gly Ser Glu Thr Arg Pro Gly Gln Tyr Glu Ser His Thr Ala
465                 470                 475                 480

Phe Thr Met Pro Gly Leu Tyr Arg Ala Val Ser Gly Ile Asn Val Phe
                485                 490                 495

Asp Pro Lys Phe Asn Ile Ala Ala Pro Gly Ala Glu Gln Ser Thr Tyr
            500                 505                 510

Phe Pro Phe Thr Glu Lys Gln Lys Arg Phe Ser Thr Phe Arg Pro Ala
        515                 520                 525

Ile Asn Glu Leu Leu Tyr Ser Asn Glu Glu Asn Asn Glu His Ile Gly
    530                 535                 540

Phe Leu Ala Asp Arg Lys Lys Pro Ile Ile Phe Ser Met Ala Arg Phe
545                 550                 555                 560

Asp Thr Val Lys Asn Leu Ser Gly Leu Thr Glu Trp Tyr Gly Lys Asn
                565                 570                 575

Lys Lys Leu Arg Asn Leu Val Asn Leu Val Ile Val Gly Gly Phe Phe
            580                 585                 590

Asp Pro Ser Lys Ser Lys Asp Arg Glu Glu Ala Ala Glu Ile Lys Lys
        595                 600                 605

Met His Glu Leu Ile Glu Lys Tyr Gln Leu Lys Gly Gln Met Arg Trp
    610                 615                 620

Ile Ala Ala Gln Thr Asp Lys Tyr Arg Asn Ser Glu Leu Tyr Arg Thr
625                 630                 635                 640

Ile Ala Asp Thr Lys Gly Ala Phe Val Gln Pro Ala Leu Tyr Glu Ala
                645                 650                 655

Phe Gly Leu Thr Val Ile Glu Ala Met Asp Cys Gly Leu Pro Thr Phe
            660                 665                 670

Ala Thr Asn Gln Gly Gly Pro Ala Glu Ile Ile Val Asp Gly Val Ser
        675                 680                 685

Gly Phe His Ile Asp Pro Tyr Asn Gly Asp Glu Ser Ser Lys Lys Ile
    690                 695                 700

Ala Asp Phe Phe Glu Lys Cys Lys Val Asp Ser Lys Tyr Trp Asn Arg
705                 710                 715                 720

Ile Ser Glu Gly Gly Leu Lys Arg Ile Glu Glu Cys Tyr Thr Trp Lys
                725                 730                 735

Ile Tyr Ala Asn Lys Val Leu Asn Met Gly Ser Ile Tyr Gly Phe Trp
            740                 745                 750

Arg Gln Phe Asn Val Gly Gln Lys Gln Ala Lys Gln Arg Tyr Phe Glu
        755                 760                 765

Met Phe Tyr Asn Pro Leu Phe Arg Lys Leu Ala Lys Ser Val Pro Ile
    770                 775                 780

Pro His Glu Glu Pro Leu Pro Leu Ala Thr Ser Asp Ser Thr Gln Ser
785                 790                 795                 800
```

```
Gln Glu Leu Lys Leu Pro Leu Pro Val Pro Ala Ala Val Ala Lys Val
            805                 810                 815

Leu Pro Leu Thr Arg His Ala Phe Asn Leu Ile Thr Ser Leu Pro Arg
            820                 825                 830

Val Thr Gly Lys Val Asp Val Lys
            835                 840

<210> SEQ ID NO 48
<211> LENGTH: 3268
<212> TYPE: DNA
<213> ORGANISM: Nicotiana tabacum

<400> SEQUENCE: 48
atggcctcaa ctgttgctgg tagcatgcct gatgctttga acaaagccg atatcatatg      60 aagagatgct cgctaggtg aacacccttc ttgttctttt tgttttttcc ctctaccatt     120
tatgtcaaat ttcaatgcat aatgctaact acttttttc tttttgactt caaaattgga    180
cgtgaaaggt tcattgcaat gggaaggagg ttgatgaagc tgaaacattt aacagaagaa    240
atagaaaaaa ctattgaaga caaggcagaa agaaccaaga ttttggaggg ttcacttgga    300
aaaattatga gttccacaca ggtcagcacc atttaaccaa cttaattgaa taggaagaaa    360
aaaaaaagca aagagttat tgcaaggcgt aacgatttcc tttgaaattt tcaggaggca     420
gctgttgtcc caccttatgt tgcttttgca gtaaggcaca atcctggctt ctgggattat    480
gtcaaagttg acgctgaaac tctctctgtg gaagctattt cagccaggga ctatctcaaa    540
ttcaaagaga tgatctttga tgaagattgg taactggaag attgtatcat tttaaagaaa    600 caattttta atattcaaga ttagttttga tggttgaatg tgcaagcagg gcaaaggatg     660
aaaatgcact cgaagtagat tttggtgctt ttgactactc taatcatcgg ttagcccttt    720
cctcttctgt cggaaatggg ctaaacttca tctcgaaagt tttgtcttca aagtttggtg    780
gaaaggcaga agatgcccag cctttgcttg attacttact agctcttaat catcaaggag    840
aggtatggaa atggactacc ttcctttctt aaggaattat ataatgatgt atgttataaa    900
gatccttttt aaacattgac actttgcaga atctaatgat caatgagaat ctgaatggcg    960
tctctaagct tcaagcagca ttgatagtag ctgaagtttt tgtatcttcc tttcccaaag   1020 acacaccta taaagacttt gagcataagt aagcttttca aacgcttctg ttatcatatg    1080
caatatacca agaatatgtt gccttttgaa aagttgttta tgtttatgac ttgataatga   1140
aaatactagg ctcaaagaat ggggctttga gaaagggtgg ggtcacaatg caggaagagt   1200
aagagagaca atgagactgc tttccgagat aatccaagcg ccagatccca taaatatgga   1260 gtccttttc agcaggcttc ctactacatt caacattgtt atcttctcca ttcatggtta    1320
ctttggccaa gcagatgtcc ttggtttgcc cgatactgga ggccaggttt acatacacag   1380
caatttatct cctttgcct catatttact tattagcgac acttgcatta ttgaaatcac    1440
atttgtattt aacaggttgt ttatattctg atcaagtaa gagccttaga ggaggaaatg    1500
ttacaaagaa tcaagcagca agggttaaat gtgaagccca agattcttgt ggtgagttat   1560
gcaaaaatat gcgtagccaa ggttttgaaa ttgttcagag gggattaaga tgatcgagat   1620
atttgtttcc ttcttccatt gatgtgtaca ggtcactcgt ctcattccag atgctcgagg   1680
gactacatgc aatcaggaga tggaacctat acttaactcg tcccattctc acatcctgag   1740
aattccattc aggacagaga aaggagttct tcgccaatgg gtttctcggt ttgatatcta   1800
tccttacttg gagaactatg ccaaggcaag tctcctacca aaattaccac ctattcatac   1860
```

| | |
|---|---|
| actttattca gttttttgag ctaatcattc tcatttgtca cgtatgtgat taggatgctt | 1920 |
| ctgctaagat acttgagctc atggaaggta aaccagacct cattattggg aactacactg | 1980 |
| atggaaattt agtggcatct ctattggcca acaaacttgg agttactcag gttctacagc | 2040 |
| tgatcattta tctgatcaga ttttctacat tgttttcttg ataattaaac ggaaatctta | 2100 |
| tgagattgta acattttagg gaaccattgc tcatgcatta gagaaaacca gtatgaaga | 2160 |
| ttctgatgtc aagtggaagc agtttgattc caagtaccac ttttcttgcc aattcactgc | 2220 |
| cgatttattg gcaatgaatg ctgctgattt tatcattacc agcacatatc aagaaatcgc | 2280 |
| aggaaggtta gcactgactc tctcagtata tttggcaact taatgaatgt actgcttgtg | 2340 |
| gccaacacta aaagctatta ctcgtccttc agcgaaacta ggcctggaca atatgaaagt | 2400 |
| cacacagcat ttaccatgcc ggggctttat agagctgttt caggcatcaa tgtatttgat | 2460 |
| ccaaagttca acattgctgc tcctggggct gaacagtctg cctatttccc cttcactgag | 2520 |
| aaacagaaac gattcagcgc gtttcgtcct gctattgagg aactacttta cagtaatgag | 2580 |
| caaaacaacg agcacatgta agtctaattg ccccattttc ctaatctaac cattgcttaa | 2640 |
| atgttctgtt tttacttgat atgtggtact tatcagtgat attttttatt ggaacagtgg | 2700 |
| atttcttgca gaccgtaaaa aaccaattat attttcaatg gcaagatttg atacggtgaa | 2760 |
| gaacttgtca ggcttgactg agtggtatgg gaagaataag aagttgcgga acttggttaa | 2820 |
| cctcgttatc gttgggggat tcttcgatcc atcaaaatca aaagaccggg aggaagcagc | 2880 |
| tgaaatcaag aagatgcatg aattgattga gaaatacaag ctcaagggac aaatgagatg | 2940 |
| gatagcagct caaactgata aatatcaaaa cagtgagcta tcgaactga ttgctgacac | 3000 |
| taaaggagct ttcgtccaac cggctttata tgaagctttt ggactaactg ttattgaagc | 3060 |
| aatgaattgt ggactgccta catttgctac taatcaaggc ggacctgcag aaatcattgt | 3120 |
| tgatggggtt tcaggcttcc atattgatcc ttacaatggg gatgaatcga gcaagaaaat | 3180 |
| agctgatttc tttgagaagt gtaaggttga ttctaaatat tggaacaaga tatgtggagg | 3240 |
| aggtctcaag cgcattgaag aatggtaa | 3268 |

<210> SEQ ID NO 49
<211> LENGTH: 732
<212> TYPE: PRT
<213> ORGANISM: Nicotiana tabacum

<400> SEQUENCE: 49

```
Met Ala Ser Thr Val Ala Gly Ser Met Pro Asp Ala Leu Lys Gln Ser
1               5                   10                  15

Arg Tyr His Met Lys Arg Cys Phe Ala Arg Phe Ile Ala Met Gly Arg
                20                  25                  30

Arg Leu Met Lys Leu Lys His Leu Thr Glu Glu Ile Glu Lys Thr Ile
            35                  40                  45

Glu Asp Lys Ala Glu Arg Thr Lys Ile Leu Glu Gly Ser Leu Gly Lys
        50                  55                  60

Ile Met Ser Ser Thr Gln Glu Ala Ala Val Val Pro Pro Tyr Val Ala
65                  70                  75                  80

Phe Ala Val Arg His Asn Pro Gly Phe Trp Asp Tyr Lys Val Asp
                85                  90                  95

Ala Glu Thr Leu Ser Val Glu Ala Ile Ser Ala Arg Asp Tyr Leu Lys
                100                 105                 110

Phe Lys Glu Met Ile Phe Asp Glu Asp Trp Ala Lys Asp Glu Asn Ala
            115                 120                 125
```

```
Leu Glu Val Asp Phe Gly Ala Phe Asp Tyr Ser Asn His Arg Leu Ala
    130                 135                 140

Leu Ser Ser Ser Val Gly Asn Gly Leu Asn Phe Ile Ser Lys Val Leu
145                 150                 155                 160

Ser Ser Lys Phe Gly Gly Lys Ala Glu Asp Ala Gln Pro Leu Leu Asp
                165                 170                 175

Tyr Leu Ala Leu Asn His Gln Gly Glu Asn Leu Met Ile Asn Glu
        180                 185                 190

Asn Leu Asn Gly Val Ser Lys Leu Gln Ala Ala Leu Ile Val Ala Glu
        195                 200                 205

Val Phe Val Ser Ser Phe Pro Lys Asp Thr Pro Tyr Lys Asp Phe Glu
210                 215                 220

His Lys Leu Lys Glu Trp Gly Phe Glu Lys Gly Trp Gly His Asn Ala
225                 230                 235                 240

Gly Arg Val Arg Glu Thr Met Arg Leu Leu Ser Glu Ile Ile Gln Ala
                245                 250                 255

Pro Asp Pro Ile Asn Met Glu Ser Phe Ser Arg Leu Pro Thr Thr
                260                 265                 270

Phe Asn Ile Val Ile Phe Ser Ile His Gly Tyr Phe Gly Gln Ala Asp
        275                 280                 285

Val Leu Gly Leu Pro Asp Thr Gly Gly Gln Val Val Tyr Ile Leu Asp
290                 295                 300

Gln Val Arg Ala Leu Glu Glu Met Leu Gln Arg Ile Lys Gln Gln
305                 310                 315                 320

Gly Leu Asn Val Lys Pro Lys Ile Leu Val Val Thr Arg Leu Ile Pro
                325                 330                 335

Asp Ala Arg Gly Thr Thr Cys Asn Gln Glu Met Glu Pro Ile Leu Asn
                340                 345                 350

Ser Ser His Ser His Ile Leu Arg Ile Pro Phe Arg Thr Glu Lys Gly
        355                 360                 365

Val Leu Arg Gln Trp Asp Ala Ser Ala Lys Ile Leu Glu Leu Met Glu
        370                 375                 380

Gly Lys Pro Asp Leu Ile Ile Gly Asn Tyr Thr Asp Gly Asn Leu Val
385                 390                 395                 400

Ala Ser Leu Leu Ala Asn Lys Leu Gly Val Thr Gln Gly Thr Ile Ala
                405                 410                 415

His Ala Leu Glu Lys Thr Lys Tyr Glu Asp Ser Asp Val Lys Trp Lys
            420                 425                 430

Gln Phe Asp Ser Lys Tyr His Phe Ser Cys Gln Phe Thr Ala Asp Leu
        435                 440                 445

Leu Ala Met Asn Ala Ala Asp Phe Ile Ile Thr Ser Thr Tyr Gln Glu
450                 455                 460

Ile Ala Gly Ser Glu Thr Arg Pro Gly Gln Tyr Glu Ser His Thr Ala
465                 470                 475                 480

Phe Thr Met Pro Gly Leu Tyr Arg Ala Val Ser Gly Ile Asn Val Phe
                485                 490                 495

Asp Pro Lys Phe Asn Ile Ala Ala Pro Gly Ala Glu Gln Ser Ala Tyr
                500                 505                 510

Phe Pro Phe Thr Glu Lys Gln Lys Arg Phe Ser Ala Phe Arg Pro Ala
        515                 520                 525

Ile Glu Glu Leu Leu Tyr Ser Asn Glu Gln Asn Asn Glu His Ile Gly
530                 535                 540
```

```
Phe Leu Ala Asp Arg Lys Lys Pro Ile Ile Phe Ser Met Ala Arg Phe
545                 550                 555                 560

Asp Thr Val Lys Asn Leu Ser Gly Leu Thr Glu Trp Tyr Gly Lys Asn
            565                 570                 575

Lys Lys Leu Arg Asn Leu Val Asn Leu Val Ile Val Gly Gly Phe Phe
        580                 585                 590

Asp Pro Ser Lys Ser Lys Asp Arg Glu Glu Ala Ala Glu Ile Lys Lys
    595                 600                 605

Met His Glu Leu Ile Glu Lys Tyr Lys Leu Lys Gly Gln Met Arg Trp
610                 615                 620

Ile Ala Ala Gln Thr Asp Lys Tyr Gln Asn Ser Glu Leu Tyr Arg Thr
625                 630                 635                 640

Ile Ala Asp Thr Lys Gly Ala Phe Val Gln Pro Ala Leu Tyr Glu Ala
            645                 650                 655

Phe Gly Leu Thr Val Ile Glu Ala Met Asn Cys Gly Leu Pro Thr Phe
            660                 665                 670

Ala Thr Asn Gln Gly Gly Pro Ala Glu Ile Ile Val Asp Gly Val Ser
        675                 680                 685

Gly Phe His Ile Asp Pro Tyr Asn Gly Asp Glu Ser Ser Lys Lys Ile
    690                 695                 700

Ala Asp Phe Phe Glu Lys Cys Lys Val Asp Ser Lys Tyr Trp Asn Lys
705                 710                 715                 720

Ile Cys Gly Gly Gly Leu Lys Arg Ile Glu Glu Trp
            725                 730

<210> SEQ ID NO 50
<211> LENGTH: 3937
<212> TYPE: DNA
<213> ORGANISM: Nicotiana tabacum

<400> SEQUENCE: 50
atggctactg caccagccct aaatagatca gagtccatag ctgatagcat gccagaggcc      60
ttaaggcaaa gccggtacca catgaagaaa tgttttgcca agtacataga gcaaggaaag     120
aggatgatga aacttcataa cttgatggat gagttggaga agtaattga tgatcctgct     180
gaaaggaacc atgttttgga aggcttactt ggctacatat tatgcactac aatggtatag     240
ctagattcat atgtacttat gatgccctta tattgtttcc tgatgtatta ctcttaaaac     300
cttctttgat caaatttaca ggaggctgca gttgttcctc cctacattgc ctttgccacg     360
agacagaatc ctggattctg gaatatgtg aaagtgaatg ctaatgatct ttctgttgag      420
ggtattacag ctacagaata cttgaaattc aaggaaatga tagttgatga atgctggtat     480
agtatacgtt gcagcttatc ataccttttg tggttttata acttcaatca gaaaactcat     540
cagagttacc tttgtgtgaa catgaaatgc agggcaaaag atgaatatgc actggaaatt     600
gattttggag cagtagactt ctcaacgcct cgactgaccc tatcctcttc aattggcaat     660
ggtctcagtt atgtttccaa gtttctaact tcaaagctaa atgctacctc cgcgagtgca     720
cagtgtctgg ttgactactt gctcactttg aatcatcaag agatgtacg tcaacaaaaa     780
tcaaactcca taagtaaact tgtcaactct aagaagaaaa aataggaaaa gaagattcac     840
gtaacaaatt ttctttatgt tcaactgcag aaactgatga tcaatgagac actcagcact     900
gtctcaaagc ttcaggctgc actggttgta gcagaagcat ctatttcctc tttaccaaca     960
gatacaccat atgagagctt tgagctaagg tgatttgttt tttcctctac ttccctccac    1020
ttgtgccatg ctacgtagta ctaagtaact tcaattcttg taaagattca aacagtgggg    1080
```

```
tttgagaaa ggatggggtg atacagctga aagggtcagc gacaccatga gaacactgtc    1140
tgaggtgctt caggcaccag atccattgaa cattcagaag ttctttggaa gggttccaac    1200
tgttttcaat attgtattgt tctctgtcca tggatacttt ggccaagcag atgttcttgg    1260
cttgccagac actggtggtc aggtaagcat ttaatagctt ttacatttaa cttctatgca    1320
ttgacaataa aataattttt aacagtttga ccacttctgc tcttgttcaa caggtagttt    1380
atgttttgga tcaagttgta gcttttgaag aagaaatgct acaaagaatt aaacagcagg    1440
ggctcaatat taagcctcaa attcttgtgg tgagttccta gacaatcgac gtgactatgc    1500
aattatgtag aggctgttta gaaaagttaa tatcatatgt tgattgcaca gttaacccga    1560
ctgattccgg atgcaaaagg aacaaagtgc aaccaggaac tagaaccaat caagaataca    1620
aaacattcac acatcctcag agttccattt aggacagaaa aaggagtgct taatcaatgg    1680
gtttcacgat ttgatatcta tccatatctg gagagatata ctcaggtatg tatttttata    1740
tcaaccttgc tcatcaaaga tgtgttgttt cctcaattcc atttttcccc ttggcaaaag    1800
gatgctgctg acaaaatcgt cgagctaatg gaaggcaaac ctgatctaat cattggtaac    1860
tacactgatg ggaatctagt ggcttcacta atggctagaa acttgggat aactctggta    1920 acttttctta atcatatttg atgttgcttc ttctccaagt tagttcttaa tctccactga    1980
cctagaccat ctttgcaaca gggaactatt gctcatgctt tggagaagac aaaatatgaa    2040
gactctgaca taaaattgaa ggaactcgat ccgaagtacc acttctcttg ccaattcaca    2100
gctgatttga ttgcaatgaa ttcagcagat tcattatca ctagcacata ccaagaaata    2160
gctggaaggt aagaattaga gctaataagt aatgcattca tatgtatttc agcatcgctc    2220
tttcaccatc atcgaataca caccactact cagtaaatgt atttgctcaa agtttgcaa    2280 cttaatggat ctcattcttg aatgcttcaa catatgcagc aaagataaac caggacagta    2340
tgagagccat agtgcattta cccttccagg gctttacaga gttgcttcag gtatcaatgt    2400
ctttgatcca aaatttaata ttgctgcacc tggggcagac cagtcggtgt atttcccta    2460 cacagaaaag cagaagcgtt tgactgcttt ccgccctgcc attgaggaac tgcttttag    2520 taaagtggac aatgacgagc acgtgtaagt ctaagtgtta aacttcagct tagtgcctag    2580
aacatcccac tgctctatgt attgatgttt cacttgtttc aaacagtgga tatttagaag    2640
acagaaagaa acctatcctg tttaccatgg caaggctgga cacagtgaag aacacatctg    2700
gactaacaga atggtatggc aagaacaaga ggctcagaag cttagttaac cttgttgtgg    2760
ttggtggttc ctttgatcct acaaaatcca aggatagga agaagcagct gaaataaaaa    2820
agatgcacat gctgatagag aaataccagc ttaagggtca gattagatgg atagcagctc    2880 agactgcacag atacagaaat agtgaactct accgcacaat agcagattcc aaaggagctt    2940
ttgtgcagcc tgcattgtat gaagcatttg gtctaacagt cattgaggca atgaactgtg    3000
gattaccaac ctttgctacc aaccaaggtg gccctgctga gattattgtt gatgggtct    3060 caggctttca tattgatcca aataatgggg atgaatcaag caacaaaatt gccaactttt    3120
tccaaaaatg cagggaggat cctgagtatt ggacaggat tcagtccag ggtctaaacc    3180 gtatatatga atggtaactc acagataagc cattcaaatt gcaaagaggc acatatcttg    3240
cagaaaattt cttaatcctt aaatcctaat tttttgcagt tacacatgga agatctatgc    3300
aaacaaggta ttgaatatgg ggtccatcta ctttttgg aggacattgt acagagatca    3360
gaaacaagca aagcaaagat acatcgagac tttctacaat cttgagttta ggaacttggt    3420
```

-continued

| | |
|---|---|
| atagtgctgc atgacattga cagtataccaa caaacatctt tatgagatga attacttttta | 3480 |
| ataaaattgt ttttaaccctt tgcttcctta atggcactta ttgcaggtaa aaaatgtgcc | 3540 |
| tatcagaaag gacgaaacac cacaaggacc aaaggagagg gagaaagtta agccacagat | 3600 |
| atcacaaagg catgctctaa agcttttgcc tacagttttt caagagaccc tagtatattc | 3660 |
| tagtactaaa ttagaattat acagcatgca gcttttgctg ttcacctttc taaatcacca | 3720 |
| gttgtgtcaa tcaagttgac aaaatcaata aattgggatt ttcccttttcc tatgcttgat | 3780 |
| tgttattact cctactttgt ttatggtagt cttccttcat tgttttctcc tgtacttctt | 3840 |
| ttactacaac tgtactgaca tactaattat ttctgtgtac caggcgctca caatcaaggt | 3900 |
| tgcagaagta agattagata aaattgctac tgcatga | 3937 |

<210> SEQ ID NO 51
<211> LENGTH: 860
<212> TYPE: PRT
<213> ORGANISM: Nicotiana tabacum

<400> SEQUENCE: 51

```
Met Ala Thr Ala Pro Ala Leu Asn Arg Ser Glu Ser Ile Ala Asp Ser
1               5                   10                  15

Met Pro Glu Ala Leu Arg Gln Ser Arg Tyr His Met Lys Lys Cys Phe
            20                  25                  30

Ala Lys Tyr Ile Glu Gln Gly Lys Arg Met Met Lys Leu His Asn Leu
        35                  40                  45

Met Asp Glu Leu Glu Lys Val Ile Asp Asp Pro Ala Glu Arg Asn His
    50                  55                  60

Val Leu Glu Gly Leu Leu Gly Tyr Ile Leu Cys Thr Thr Met Glu Ala
65                  70                  75                  80

Ala Val Val Pro Pro Tyr Ile Ala Phe Ala Thr Arg Gln Asn Pro Gly
                85                  90                  95

Phe Trp Glu Tyr Val Lys Val Asn Ala Asn Asp Leu Ser Val Glu Gly
            100                 105                 110

Ile Thr Ala Thr Glu Tyr Leu Lys Phe Lys Glu Met Ile Val Asp Glu
        115                 120                 125

Cys Trp Ala Lys Asp Glu Tyr Ala Leu Glu Ile Asp Phe Gly Ala Val
    130                 135                 140

Asp Phe Ser Thr Pro Arg Leu Thr Leu Ser Ser Ile Gly Asn Gly
145                 150                 155                 160

Leu Ser Tyr Val Ser Lys Phe Leu Thr Ser Lys Leu Asn Ala Thr Ser
                165                 170                 175

Ala Ser Ala Gln Cys Leu Val Asp Tyr Leu Leu Thr Leu Asn His Gln
            180                 185                 190

Gly Asp Lys Leu Met Ile Asn Glu Thr Leu Ser Thr Val Ser Lys Leu
        195                 200                 205

Gln Ala Ala Leu Val Val Ala Glu Ala Ser Ile Ser Ser Leu Pro Thr
    210                 215                 220

Asp Thr Pro Tyr Glu Ser Phe Glu Leu Arg Phe Lys Gln Trp Gly Phe
225                 230                 235                 240

Glu Lys Gly Trp Gly Asp Thr Ala Glu Arg Val Ser Asp Thr Met Arg
                245                 250                 255

Thr Leu Ser Glu Val Leu Gln Ala Pro Asp Pro Leu Asn Ile Gln Lys
            260                 265                 270

Phe Phe Gly Arg Val Pro Thr Val Phe Asn Ile Val Leu Phe Ser Val
        275                 280                 285
```

```
His Gly Tyr Phe Gly Gln Ala Asp Val Leu Gly Leu Pro Asp Thr Gly
    290                 295                 300

Gly Gln Val Val Tyr Val Leu Asp Gln Val Val Ala Phe Glu Glu Glu
305                 310                 315                 320

Met Leu Gln Arg Ile Lys Gln Gln Gly Leu Asn Ile Lys Pro Gln Ile
                325                 330                 335

Leu Val Leu Thr Arg Leu Ile Pro Asp Ala Lys Gly Thr Lys Cys Asn
            340                 345                 350

Gln Glu Leu Glu Pro Ile Lys Asn Thr Lys His Ser His Ile Leu Arg
        355                 360                 365

Val Pro Phe Arg Thr Glu Lys Gly Val Leu Asn Gln Trp Val Ser Arg
    370                 375                 380

Phe Asp Ile Tyr Pro Tyr Leu Glu Arg Tyr Thr Gln Asp Ala Ala Asp
385                 390                 395                 400

Lys Ile Val Glu Leu Met Glu Gly Lys Pro Asp Leu Ile Ile Gly Asn
                405                 410                 415

Tyr Thr Asp Gly Asn Leu Val Ala Ser Leu Met Ala Arg Lys Leu Gly
            420                 425                 430

Ile Thr Leu Gly Thr Ile Ala His Ala Leu Glu Lys Thr Lys Tyr Glu
        435                 440                 445

Asp Ser Asp Ile Lys Leu Lys Glu Leu Asp Pro Lys Tyr His Phe Ser
    450                 455                 460

Cys Gln Phe Thr Ala Asp Leu Ile Ala Met Asn Ser Ala Asp Phe Ile
465                 470                 475                 480

Ile Thr Ser Thr Tyr Gln Glu Ile Ala Gly Ser Lys Asp Lys Pro Gly
                485                 490                 495

Gln Tyr Glu Ser His Ser Ala Phe Thr Leu Pro Gly Leu Tyr Arg Val
            500                 505                 510

Ala Ser Gly Ile Asn Val Phe Asp Pro Lys Phe Asn Ile Ala Ala Pro
        515                 520                 525

Gly Ala Asp Gln Ser Val Tyr Phe Pro Tyr Thr Glu Lys Gln Lys Arg
    530                 535                 540

Leu Thr Ala Phe Arg Pro Ala Ile Glu Glu Leu Leu Phe Ser Lys Val
545                 550                 555                 560

Asp Asn Asp Glu His Val Gly Tyr Leu Glu Asp Arg Lys Lys Pro Ile
                565                 570                 575

Leu Phe Thr Met Ala Arg Leu Asp Thr Val Lys Asn Thr Ser Gly Leu
            580                 585                 590

Thr Glu Trp Tyr Gly Lys Asn Lys Arg Leu Arg Ser Leu Val Asn Leu
        595                 600                 605

Val Val Val Gly Gly Ser Phe Asp Pro Thr Lys Ser Lys Asp Arg Glu
    610                 615                 620

Glu Ala Ala Glu Ile Lys Lys Met His Met Leu Ile Glu Lys Tyr Gln
625                 630                 635                 640

Leu Lys Gly Gln Ile Arg Trp Ile Ala Ala Gln Thr Asp Arg Tyr Arg
                645                 650                 655

Asn Ser Glu Leu Tyr Arg Thr Ile Ala Asp Ser Lys Gly Ala Phe Val
            660                 665                 670

Gln Pro Ala Leu Tyr Glu Ala Phe Gly Leu Thr Val Ile Glu Ala Met
        675                 680                 685

Asn Cys Gly Leu Pro Thr Phe Ala Thr Asn Gln Gly Gly Pro Ala Glu
    690                 695                 700
```

```
Ile Ile Val Asp Gly Val Ser Gly Phe His Ile Asp Pro Asn Asn Gly
705                 710                 715                 720

Asp Glu Ser Ser Asn Lys Ile Ala Asn Phe Phe Gln Lys Cys Arg Glu
                725                 730                 735

Asp Pro Glu Tyr Trp Asn Arg Ile Ser Val Gln Gly Leu Asn Arg Ile
            740                 745                 750

Tyr Glu Cys Tyr Thr Trp Lys Ile Tyr Ala Asn Lys Val Leu Asn Met
        755                 760                 765

Gly Ser Ile Tyr Thr Phe Trp Arg Thr Leu Tyr Arg Asp Gln Lys Gln
    770                 775                 780

Ala Lys Gln Arg Tyr Ile Glu Thr Phe Tyr Asn Leu Glu Phe Arg Asn
785                 790                 795                 800

Leu Val Lys Asn Val Pro Ile Arg Lys Asp Glu Thr Pro Gln Gly Pro
                805                 810                 815

Lys Glu Arg Glu Lys Val Lys Pro Gln Ile Ser Gln Arg His Ala Leu
            820                 825                 830

Lys Leu Leu Pro Thr Val Phe Gln Glu Thr Leu Ala Leu Thr Ile Lys
        835                 840                 845

Val Ala Glu Val Arg Leu Asp Lys Ile Ala Thr Ala
    850                 855                 860

<210> SEQ ID NO 52
<211> LENGTH: 3905
<212> TYPE: DNA
<213> ORGANISM: Nicotiana tabacum

<400> SEQUENCE: 52
atggctactg caccagccct gaaaagatca gagtccatag ctgatagcat gccagaggcc      60
ttaaggcaaa gccggtacca catgaagaaa tgttttgcca agtacataga gcaaggcaag     120
aggatgatga aacttcataa cttgatggat gaattggaga agtaattga tgatcctgct      180 gaaaggaacc atgttttgga aggcttactt ggctacatat tatgtactac aatggtatag     240
ctagattcat atgtacttat gatgtcctta tattgtttcc ggaggcatta ttcttaaatc     300
cttctttgat caaatttgta ggaggctgca gttgttcctc cctatattgc cttcgccacg     360
agacagaatc ctggattctg gaatatgtgt aaagtcaatg ctaatgatct ttctgttgag     420
ggtattacag ctacagatta cttgaaattc aaggaaatga tagttgatga agctggtat      480 agaatacttt gcagcttatc ataccttttg tggttttata atttcaatca gaaaactcat     540
cagagttacc tttgtgtgaa catgacatgc agggcaaaag atgaatatgc actggaaatt     600
gattttggag cagtagactt ctcaacgcct cgactgaccc tatcctcttc aattggaaat     660
ggtctcagtt atgtttccaa gtttctaact tcaaagctaa atgctacctc agcgagtgca     720
cagtgtctgg ttgactactt gctcactttg aatcaccaag gagatgtacg tcaacaaaaa     780
tcaaactcca taagtaaact tgtcaactct aagaagtaaa aataggaaaa gaagattcat     840
gtaacaaatt ttctttatgt tcaactgtag aaactgatga tcaatgagac actcggcact     900
gtctcaaagc ttcaggctgc actggttgta gcagaagcat ctatttcctc cttaccaaca     960
gatacaccat accagagctt tgagctaagg tgatttgttt tttcctctac ttccttccac    1020
ttttggtgtg ctacatagta ctaagtaact tcaattcttg taaagattca aacagtgggg    1080
ttttgagaaa ggatggggtg atacagctga aagggtccgc gacaccatga gaacactttc    1140
tgaggtactt caggcgccag atccattgaa cattgagaag ttcttggga gggttccaac     1200 tgttttcaat attgtattgt tctctgttca tggatacttt ggccaagcaa atgttcttgg    1260
```

-continued

```
cttgccagac acaggtggtc aggtaagcat ctaatagctt ttacatttaa cttctatgca    1320
ttgacaataa aataacttct acactaccaa ataattttg aaagtttgac cacttcggct     1380
cttgttcaac aggtggttta tgttttggat caagttgtag cttttgaaga agaaatgctc    1440
caaagaatta aacagcaggg gctcaatatt aagcctcaaa ttcttgtggt gagctcctag    1500
acaatgacgt gactatgcaa ttaagtagag gctgtttaga aaagttaata tcatatgttg    1560
attgcacagt taacccgact gattccggac gccaaaggaa caaagtgcaa ccaggaacta    1620
gaaccaatca agaatacaaa acattcacac atcctcagag ttccatttag gacagaaaaa    1680
ggagtgctta atcaatgggt ttcacgattt gatatctatc catatctgga gagatatact    1740
caggtgtgta ttttatatc aaccctgctc atcaaagatg tgttgtttcc tcaattccat     1800
ttttcgcctt gacaaaagga cgctgctgac aaaatcatcg agctaatgga aggcaaacct    1860
gatctaatca ttggtaacta cactgatggg aatctagtgg cttctctaat ggctagaaag    1920
cttgggataa ctctggtaac ttttcttatc atatttgatg ttgtttcttc tccaagttgg    1980
ttcttaatgt caactaaccc agaccatctt tgtaacaggg aactattgct catgctctgg    2040
agaagacaaa atatgaagac tctgacatca aattgaagga actcgatccg aagtaccact    2100
tttcttgcca attcacagct gatttgattg caatgaattc agcagatttc attatcacaa    2160
gcacatatca agaaatagcc ggaaggtaag aattggaact acggaagcag agagctaata    2220
agtagtgcac tcatatattt cagcatcgct cttttcgcata atcgaataca caccactact    2280
cagtaaatgt acttgctcaa aagtttacaa gtttatggat cttattcttg aatgcttcaa    2340
catatgcagc aaagataggc caggacagta tgagagccat agtgcattta cccttccagg    2400
gctttacaga gttgcttcag gcatcaatgt ctttgatcct aaatttaata ttgctgcacc    2460
tggggcagac caatcggtgt atttcccta cacagaaaag cagacgcgtt tgactgcttt     2520
ccgccctgcc attgaggaac tgcttttag taaagtggac aatgacgagc acatgtaagt    2580
cttagtgtta aacttcagct ttcagcttag tgcctagaac attccactgg ctctatgtat    2640
taatgtttca cttgtttcaa acacagtgga tatttagaag acagaaagaa acctatcctg    2700
tttaccatgg caaggctgga cacagtgaag aacacatctg gactaacaga atggtatggc    2760
aagaacaaga ggctcagaag cttagttaac cttgttgtgg ttggtggttc ctttgatcct    2820
acaaaatcca aggatagaga agaagcagct gaaataaaaa agatgcacat gctgatagag    2880
aaataccagc ttaagggtca gatcagatgg atagcagctc agactgacag atatagaaac    2940
agtgaactct accgcacaat agcagattcc aaggagctt ttgtgcagcc tgcattatat     3000
gaagcatttg gtctaacagt cattgaggca atgaactgtg gattaccaac ctttgctacc    3060
aaccaaggtg gccctgctga gattattgtt gatgggtct caggctttca tattgatcca     3120
aataatgggg atgaatcaag caacaaagtt gccaactttt tccaaaaatg cagggaggat    3180
cctgagtatt ggaacaggat ttcagtccag ggtctaaacc gtatatatga atggtaactc    3240
acagataagc cattcaaatt gcaaagaggc acatatcttg ctgaaaattt cttaatcctt    3300
taatcctaaa attttgcagt tacacatgga agatctatgc aaacaaggta ttgaatatgg    3360
ggtccatcta acttttttgg aggacattgt acagagatca gaaacaagca aagcaaagat    3420
acatcgagac tttctacaat cttgagttta ggaacttggt atagtgctgc atgacattga    3480
cagtatacca caaacatctt tatgagatga attactttta ataaaattgt ttttaacctt    3540
tgcctcctta atgacactta ttgcaggtaa aaaatgtgcc tatcagacag gacgaaacac    3600
```

-continued

```
cacaaggacc aaaggagagg agggagaaag ttaagccaca gatatcacaa aggcatgctc    3660
taaagctttt gcctatagtt tttcaggaga ccctagtata ttctagtact aaattagaat    3720
tatacagcat gcagcttgct tctgctgttc acctttctaa atcaccagtt atgtcaatca    3780
agttgacaaa atcaataaat tcggcttttc cctttcctat gcttgattgt tattactcct    3840
acttcgttta tggtagtctt ccttcattgt tttctcctgt acttctttta ctacaactgt    3900
actga                                                                3905
```

<210> SEQ ID NO 53
<211> LENGTH: 913
<212> TYPE: PRT
<213> ORGANISM: Nicotiana tabacum

<400> SEQUENCE: 53

```
Met Ala Thr Ala Pro Ala Leu Lys Arg Ser Glu Ser Ile Ala Asp Ser
 1               5                  10                  15

Met Pro Glu Ala Leu Arg Gln Ser Arg Tyr His Met Lys Lys Cys Phe
                20                  25                  30

Ala Lys Tyr Ile Glu Gln Gly Lys Arg Met Met Lys Leu His Asn Leu
            35                  40                  45

Met Asp Glu Leu Glu Lys Val Ile Asp Pro Ala Glu Arg Asn His
        50                  55                  60

Val Leu Glu Gly Leu Leu Gly Tyr Ile Leu Cys Thr Thr Met Glu Ala
 65                  70                  75                  80

Ala Val Val Pro Pro Tyr Ile Ala Phe Ala Thr Arg Gln Asn Pro Gly
                 85                  90                  95

Phe Trp Glu Tyr Val Lys Val Asn Ala Asn Asp Leu Ser Val Glu Gly
                100                 105                 110

Ile Thr Ala Thr Asp Tyr Leu Lys Phe Lys Glu Met Ile Val Asp Glu
            115                 120                 125

Ser Trp Ala Lys Asp Glu Tyr Ala Leu Glu Ile Asp Phe Gly Ala Val
        130                 135                 140

Asp Phe Ser Thr Pro Arg Leu Thr Leu Ser Ser Ser Ile Gly Asn Gly
145                 150                 155                 160

Leu Ser Tyr Val Ser Lys Phe Leu Thr Ser Lys Leu Asn Ala Thr Ser
                165                 170                 175

Ala Ser Ala Gln Cys Leu Val Asp Tyr Leu Leu Thr Leu Asn His Gln
            180                 185                 190

Gly Asp Lys Leu Met Ile Asn Glu Thr Leu Gly Thr Val Ser Lys Leu
        195                 200                 205

Gln Ala Ala Leu Val Val Ala Glu Ala Ser Ile Ser Ser Leu Pro Thr
    210                 215                 220

Asp Thr Pro Tyr Gln Ser Phe Glu Leu Arg Phe Lys Gln Trp Gly Phe
225                 230                 235                 240

Glu Lys Gly Trp Gly Asp Thr Ala Glu Arg Val Arg Asp Thr Met Arg
                245                 250                 255

Thr Leu Ser Glu Val Leu Gln Ala Pro Asp Pro Leu Asn Ile Glu Lys
            260                 265                 270

Phe Phe Gly Arg Val Pro Thr Val Phe Asn Ile Val Leu Phe Ser Val
        275                 280                 285

His Gly Tyr Phe Gly Gln Ala Asn Val Leu Gly Leu Pro Asp Thr Gly
    290                 295                 300

Gly Gln Val Val Tyr Val Leu Asp Gln Val Val Ala Phe Glu Glu Glu
305                 310                 315                 320
```

Met Leu Gln Arg Ile Lys Gln Gln Gly Leu Asn Ile Lys Pro Gln Ile
                325                 330                 335

Leu Val Leu Thr Arg Leu Ile Pro Asp Ala Lys Gly Thr Lys Cys Asn
                340                 345                 350

Gln Glu Leu Glu Pro Ile Lys Asn Thr Lys His Ser His Ile Leu Arg
                355                 360                 365

Val Pro Phe Arg Thr Glu Lys Gly Val Leu Asn Gln Trp Val Ser Arg
                370                 375                 380

Phe Asp Ile Tyr Pro Tyr Leu Glu Arg Tyr Thr Gln Asp Ala Ala Asp
385                 390                 395                 400

Lys Ile Ile Glu Leu Met Glu Gly Lys Pro Asp Leu Ile Ile Gly Asn
                405                 410                 415

Tyr Thr Asp Gly Asn Leu Val Ala Ser Leu Met Ala Arg Lys Leu Gly
                420                 425                 430

Ile Thr Leu Gly Thr Ile Ala His Ala Leu Glu Lys Thr Lys Tyr Glu
                435                 440                 445

Asp Ser Asp Ile Lys Leu Lys Glu Leu Asp Pro Lys Tyr His Phe Ser
                450                 455                 460

Cys Gln Phe Thr Ala Asp Leu Ile Ala Met Asn Ser Ala Asp Phe Ile
465                 470                 475                 480

Ile Thr Ser Thr Tyr Gln Glu Ile Ala Gly Ser Lys Asp Arg Pro Gly
                485                 490                 495

Gln Tyr Glu Ser His Ser Ala Phe Thr Leu Pro Gly Leu Tyr Arg Val
                500                 505                 510

Ala Ser Gly Ile Asn Val Phe Asp Pro Lys Phe Asn Ile Ala Ala Pro
                515                 520                 525

Gly Ala Asp Gln Ser Val Tyr Phe Pro Tyr Thr Glu Lys Gln Thr Arg
                530                 535                 540

Leu Thr Ala Phe Arg Pro Ala Ile Glu Glu Leu Leu Phe Ser Lys Val
545                 550                 555                 560

Asp Asn Asp Glu His Ile Gly Tyr Leu Glu Asp Arg Lys Lys Pro Ile
                565                 570                 575

Leu Phe Thr Met Ala Arg Leu Asp Thr Val Lys Asn Thr Ser Gly Leu
                580                 585                 590

Thr Glu Trp Tyr Gly Lys Asn Lys Arg Leu Arg Ser Leu Val Asn Leu
                595                 600                 605

Val Val Val Gly Gly Ser Phe Asp Pro Thr Lys Ser Lys Asp Arg Glu
                610                 615                 620

Glu Ala Ala Glu Ile Lys Lys Met His Met Leu Ile Glu Lys Tyr Gln
625                 630                 635                 640

Leu Lys Gly Gln Ile Arg Trp Ile Ala Ala Gln Thr Asp Arg Tyr Arg
                645                 650                 655

Asn Ser Glu Leu Tyr Arg Thr Ile Ala Asp Ser Lys Gly Ala Phe Val
                660                 665                 670

Gln Pro Ala Leu Tyr Glu Ala Phe Gly Leu Thr Val Ile Glu Ala Met
                675                 680                 685

Asn Cys Gly Leu Pro Thr Phe Ala Thr Asn Gln Gly Gly Pro Ala Glu
                690                 695                 700

Ile Ile Val Asp Gly Val Ser Gly Phe His Ile Asp Pro Asn Asn Gly
705                 710                 715                 720

Asp Glu Ser Ser Asn Lys Val Ala Asn Phe Phe Gln Lys Cys Arg Glu
                725                 730                 735

```
Asp Pro Glu Tyr Trp Asn Arg Ile Ser Val Gln Gly Leu Asn Arg Ile
            740                 745                 750

Tyr Glu Cys Tyr Thr Trp Lys Ile Tyr Ala Asn Lys Val Leu Asn Met
        755                 760                 765

Gly Ser Ile Tyr Thr Phe Trp Arg Thr Leu Tyr Arg Asp Gln Lys Gln
        770                 775                 780

Ala Lys Gln Arg Tyr Ile Glu Thr Phe Tyr Asn Leu Glu Phe Arg Asn
785                 790                 795                 800

Leu Val Lys Asn Val Pro Ile Arg Gln Asp Glu Thr Pro Gln Gly Pro
                805                 810                 815

Lys Glu Arg Arg Glu Lys Val Lys Pro Gln Ile Ser Gln Arg His Ala
            820                 825                 830

Leu Lys Leu Leu Pro Ile Val Phe Gln Glu Thr Leu Val Tyr Ser Ser
            835                 840                 845

Thr Lys Leu Glu Leu Tyr Ser Met Gln Leu Ala Ser Ala Val His Leu
        850                 855                 860

Ser Lys Ser Pro Val Met Ser Ile Lys Leu Thr Lys Ser Ile Asn Ser
865                 870                 875                 880

Ala Phe Pro Phe Pro Met Leu Asp Cys Tyr Tyr Ser Tyr Phe Val Tyr
                885                 890                 895

Gly Ser Leu Pro Ser Leu Phe Ser Pro Val Leu Leu Leu Leu Gln Leu
            900                 905                 910

Tyr
```